United States Patent
Achab et al.

(10) Patent No.: US 11,274,111 B2
(45) Date of Patent: Mar. 15, 2022

(54) ARGINASE INHIBITORS AND METHODS OF USE

(71) Applicant: Merck Sharp & Dohme Corp., Rahway, NJ (US)

(72) Inventors: Abdelghani Abe Achab, Melrose, MA (US); Jared N. Cumming, Winchester, MA (US); Christian Fischer, Natick, MA (US); Symon Gathiaka, Waltham, MA (US); Charles A. Lesburg, Newton, MA (US); Derun Li, West Roxbury, MA (US); Min Lu, Brookline, MA (US); Matthew J. Mitcheltree, Boston, MA (US); Anandan Palani, Needham, MA (US); Rachel L. Palte, Melrose, MA (US); David L. Sloman, Brookline, MA (US); Hongjun Zhang, Boston, MA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 16/973,623

(22) PCT Filed: Jun. 14, 2019

(86) PCT No.: PCT/US2019/037140
§ 371 (c)(1),
(2) Date: Dec. 9, 2020

(87) PCT Pub. No.: WO2019/245890
PCT Pub. Date: Dec. 26, 2019

(65) Prior Publication Data
US 2021/0163505 A1  Jun. 3, 2021

Related U.S. Application Data

(60) Provisional application No. 62/687,304, filed on Jun. 20, 2018.

(51) Int. Cl.
C07F 5/02 (2006.01)
C07K 16/28 (2006.01)

(52) U.S. Cl.
CPC .......... C07F 5/025 (2013.01); C07K 16/2818 (2013.01)

(58) Field of Classification Search
CPC .................................................... C07F 5/025
See application file for complete search history.

(56) References Cited

U.S. PATENT DOCUMENTS

| | | |
|---|---|---|
| 8,894,970 B2 | 11/2014 | Tomczuk et al. |
| 9,233,985 B2 | 1/2016 | Van Zandt et al. |
| 9,592,221 B2 | 3/2017 | Ebright et al. |
| 10,391,077 B2 * | 8/2019 | Blaszczyk .............. A61K 31/33 |
| 2014/0371175 A1 | 12/2014 | Van Zandt et al. |
| 2017/0319536 A1 | 11/2017 | Blaszczyk et al. |

FOREIGN PATENT DOCUMENTS

| | | |
|---|---|---|
| WO | 2011133653 A1 | 10/2011 |
| WO | 2012058065 A1 | 5/2012 |
| WO | 2016108707 A1 | 7/2016 |
| WO | 2017075363 A1 | 5/2017 |
| WO | 2017189386 A1 | 11/2017 |
| WO | 2017191130 A2 | 11/2017 |
| WO | 2019173188 A1 | 9/2019 |
| WO | 2019177873 A1 | 9/2019 |
| WO | 2019245890 A1 | 12/2019 |
| WO | 2020131598 A1 | 6/2020 |

OTHER PUBLICATIONS

Development of OAT-1746: A Novel Arginase 1 and 2 Inhibitor for Cancer Immunotherapy, ESMO 2017 Poster, 2017, 1-1.
Marciniec, Bogdan et al., Ruthenium(II) Complex Catalyzed O-Borylation of Alcohols with Vinylboronates, Synlett, 2009, 2433-2436, 15.
Papadopoulos et al., CX-1158-101: A First-in-Human Phase 1 Study of CB-1158, a Small Molecule Inhibitor of Arginase, as Monotherapy and in Combination with an anti-PD-1 Checkpoint Inhibitor in Patients with Solid Tumors, ASCO Annual Meeting '17, 2017, 1-22.
PubChem CID 67513622.
Public presentation by Calithera: https://www.calithera.com/wp-content/uploads/2017/06/CB-1158-101-ASCO-2017-FINAL.pdf (22 pages).
Public presentation by OncoArendi: ESMO 2017 poster (1 page).
Pubmed Comound Summary for CID 65165396, 2-(Oxolan-2-yl)ethylboronic acid, U.S. National Library of Medicine, Oct. 23, 2019 (Oct. 23, 2012), p. 1-11; p. 2 (https://pubchem.ncbi.nlm.nih.gov/compound/65165396).
Pubmed Compound Summary for CID 10654176, 5-Methyl-4-oxaspiro[2,3]hexane, U.S. National Library of Medicine, Oct. 25, 2006 (Oct. 25, 2006), p. 1-12; p. 2 (https://pubchem.ncbi.nlm.nih.gov/compound/10654176).

* cited by examiner

Primary Examiner — Golam M Shameem
(74) Attorney, Agent, or Firm — Janet E. Fair; Alysia Finnegan

(57) ABSTRACT

Described herein are compounds of Formula (I) or a pharmaceutically acceptable salt thereof. The compounds of Formula (I) act as arginase inhibitors and can be useful in preventing, treating or acting as a remedial agent for arginase-related diseases.

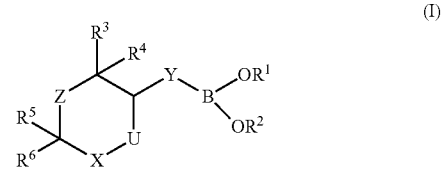

19 Claims, No Drawings

ARGINASE INHIBITORS AND METHODS OF USE

CROSS-REFERENCE TO RELATED APPLICATIONS

This application is a U.S. National Phase application under 35 U.S.C. § 371 of PCT Application No. PCT/US2019/037140, filed Jun. 14, 2019, which published as WO2019/245890 A1 on Dec. 26, 2019 and claims priority under 35 U.S.C. § 365(b) from U.S. provisional patent application No. 62/687,304, filed Jun. 20, 2018.

TECHNICAL FIELD

The present invention is directed to arginase inhibitors. Specifically, the arginase inhibitors described herein can be useful in preventing, treating or acting as a remedial agent for arginase-related diseases.

BACKGROUND

Arginase is an enzyme that metabolizes L-arginine to L-ornithine and urea. There are two types of arginase, and they are both products of distinct genes that are regulated independently and located on different chromosomes. Arginase I is a cytosolic protein (34.7 kDa) and is dominant in the liver, but also expressed extrahepatically. Arginase II is a mitochondrial protein and is expressed in kidney, small intestine, brain, monocytes and macrophages.

In addition to its fundamental role in the hepatic urea cycle, arginase also influences the immune systems in humans and mice. Arginase participates in many inflammatory disorders by decreasing the synthesis of nitric oxide and inducing fibrosis and tissue regeneration. L-Arginine deficiency, which is modulated by myeloid cell arginase, suppresses T-cell immune response. This mechanism plays a fundamental role in inflammation-associated immunosuppression.

Arginase expression and L-arginine depletion is also a known immune-suppressive pathway of the mammalian immune system. The depletion of arginine in the tumor microenvironment renders cytotoxic T-cells unable to proliferate and therefore unable to effectively mount an anti-tumor attack. Similarly, M2 macrophages and polymorphonuclear cells (PMNs) express high levels of arginase and may contribute to the local suppression of immune responses. Restoration of arginine levels in the tumor microenvironment via arginase inhibition would be expected to allow T-cell activation and proliferation to occur and result in T-cell mediated anti-tumor responses.

Small-molecule arginase inhibitors are currently described as promising therapeutics for the treatment of several diseases, including allergic asthma, inflammatory bowel disease, ulcerative colitis, cardiovascular diseases (atherosclerosis and hypertension), diseases associated with pathogens (e.g., *Helicobacter pylori, Trypanosoma cruzi, Leishmania, Mycobacterium tuberculosis* and *Salmonella*), cancer and induced or spontaneous immune disorders. Development of potent and specific inhibitors of arginase would be useful for the treatment of diseases where depletion of L-arginine from the microenvironment and/or induction of arginase pathway is involved in the evasion of anti-tumor immunity, especially for immuno-oncology indications.

SUMMARY

A compound of Formula I:

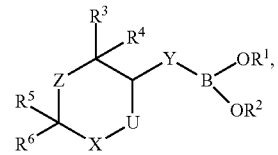

wherein U, X, Y, Z, $R^1$, $R^2$, $R^3$, $R^4$, $R^5$ and $R^6$ are described below.

The compounds described herein are arginase inhibitors, which can be useful in the prevention, treatment or amelioration of diseases where depletion of L-arginine from the microenvironment and/or induction of arginase pathway is involved in the evasion of anti-tumor immunity, especially for immuno-oncology indications.

Also described herein are methods of treating cancer comprising administering to a patient in need thereof a compound described herein, or a pharmaceutically acceptable salt thereof.

Also described herein are methods of treating fibrosis related diseases such as nonalcoholic fatty liver disease comprising administering to a patient in need thereof a compound described herein, or a pharmaceutically acceptable salt thereof.

Also described herein are uses of a compound described herein, or a pharmaceutically acceptable salt thereof, to treat cancer in a patient in need thereof.

Also described herein are pharmaceutical compositions comprising a compound described herein, or a pharmaceutically acceptable salt thereof and a pharmaceutically acceptable carrier. Also described herein are pharmaceutical compositions comprising a compound described herein and a pharmaceutically acceptable carrier.

DETAILED DESCRIPTION

Compounds

Described herein are compounds of Formula I:

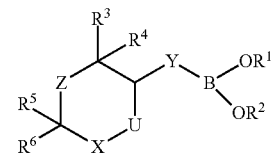

or a pharmaceutically acceptable salt thereof, wherein:
Y is a straight or branched $(C_2-C_5)$alkylene, wherein one or more —$CH_2$— groups in Y are optionally and independently replaced with a moiety selected from the group consisting of O, S and NH;
U is a bond, O, $NR^{15}$ or $CR^7R^8$;
X is O, $NR^{15}$ or $CR^9R^{10}$, wherein U and X cannot be simultaneously O and $NR^{15}$, respectively;
Z is a bond or $CR^{11}R^{12}$;
$R^1$ is hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^2$ is hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^3$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy or COO$C_1$-$C_6$alkyl;

$R^4$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy or COO$C_1$-$C_6$alkyl;

$R^5$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy or COO$C_1$-$C_6$alkyl or when taken with $R^6$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, CO$C_1$-$C_6$alkyl, CO$C_1$-$C_6$alkyN($R^{13}$)($R^{14}$), CO$C_1$-$C_6$alkyl(OH)N($R^{13}$)($R^{14}$), $C_1$-$C_6$alkyCON($R^{13}$)($R^{14}$), CON($R^{13}$)($R^{14}$), SO$_2$$C_1$-$C_6$alkyl, SO$_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and COO$C_1$-$C_6$alkyl;

$R^6$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy or COO$C_1$-$C_6$alkyl or when taken with $R^5$ forms a $C_3$-$C_6$cycloalkyl or heterocycle, or taken with $R^7$ forms a $C_1$-$C_6$alkyl bridge, or taken with $R^{10}$ or $R^{12}$ forms an aryl, heteroaryl, $C_3$-$C_6$cycloalkyl or heterocycle or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, CO$C_1$-$C_6$alkyl, CO$C_1$-$C_6$alkyN($R^{13}$)($R^{14}$), CO$C_1$-$C_6$alkyl(OH)N($R^{13}$)($R^{14}$), $C_1$-$C_6$alkyCON($R^{13}$)($R^{14}$), CON($R^{13}$)($R^{14}$), SO$_2$$C_1$-$C_6$alkyl, SO$_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy or COO$C_1$-$C_6$alkyl;

$R^7$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy or COO$C_1$-$C_6$alkyl or when taken with $R^6$, $R^{11}$ or $R^{12}$ forms a $C_1$-$C_6$alkyl bridge or when taken with $R^8$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, CO$C_1$-$C_6$alkyl, CO$C_1$-$C_6$alkyN($R^{13}$)($R^{14}$), CO$C_1$-$C_6$alkyl(OH)N($R^{13}$)($R^{14}$), $C_1$-$C_6$alkylCON($R^{13}$)($R^{14}$), CON($R^{13}$)($R^{14}$), SO$_2$$C_1$-$C_6$alkyl, SO$_2$N($R^{13}$)($R^{14}$), N($R^{13}$)($R^{14}$), —$C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and COO$C_1$-$C_6$alkyl;

$R^8$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy or COO$C_1$-$C_6$alkyl or when taken with $R^{11}$ or $R^{12}$ forms a $C_1$-$C_6$alkyl bridge or when taken with $R^7$ forms a $C_3$-$C_6$cycloalkyl or heterocycle, or when taken with $R^{10}$ forms an aryl, heteroaryl, $C_3$-$C_6$cycloalkyl or heterocycle or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, CO$C_1$-$C_6$alkyl, CO$C_1$-$C_6$alkylN($R^{13}$)($R^{14}$), CO$C_1$-$C_6$alkyl(OH)N($R^{13}$)($R^{14}$), $C_1$-$C_6$alkyCON($R^{13}$)($R^{14}$), CON($R^{13}$)($R^{14}$), SO$_2$$C_1$-$C_6$alkyl, SO$_2$N($R^{13}$)($R^{14}$), N($R^{13}$)($R^{14}$), —$C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and COO$C_1$-$C_6$alkyl;

$R^9$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy or COO$C_1$-$C_6$alkyl or when taken with $R^{10}$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, CO$C_1$-$C_6$alkyl, CO$C_1$-$C_6$alkylN($R^{13}$)($R^{14}$), CO$C_1$-$C_6$alkyl(OH)N($R^{13}$)($R^{14}$), $C_1$-$C_6$alkylCON($R^{13}$)($R^{14}$), CON($R^{13}$)($R^{14}$), SO$_2$$C_1$-$C_6$alkyl, SO$_2$N($R^{13}$)($R^{14}$), N($R^{13}$)($R^{14}$), $C_1$-$C_6$alkyN($R^{13}$)($R^{14}$), —$C_1$-$C_6$alkylaryl, —$C_1$-$C_6$alkylhaloaryl, C(NH)N($R^{13}$)($R^{14}$), heteroaryl, $C_1$-$C_6$alkoxy and COO$C_1$-$C_6$alkyl;

$R^{10}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkylN($R^{13}$)($R^{14}$), $C_1$-$C_6$alkoxy or COO$C_1$-$C_6$alkyl or when taken with $R^6$ or $R^8$ forms an aryl, heteroaryl, $C_3$-$C_6$cycloalkyl or heterocycle, or taken with $R^9$ forms $C_3$-$C_6$cycloalkyl or heterocycle, or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, CO$C_1$-$C_6$alkyl, CO$C_1$-$C_6$alkylN($R^{13}$)($R^{14}$), CO$C_1$-$C_6$alkyl(OH)N($R^{13}$)($R^{14}$), $C_1$-$C_6$alkylCON($R^{13}$)($R^{14}$), CON($R^{13}$)($R^{14}$), SO$_2$$C_1$-$C_6$alkyl, SO$_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), $C_1$-$C_6$alkoxy and COO$C_1$-$C_6$alkyl;

$R^{11}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy or COO$C_1$-$C_6$alkyl or when taken with $R^7$ or $R^8$ forms a $C_1$-$C_6$alkyl bridge or when taken with $R^{12}$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, CO$C_1$-$C_6$alkyl, CO$C_1$-$C_6$alkylN($R^{13}$)($R^{14}$), CO$C_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, —$C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and COOC$_1$-$C_6$alkyl;

$R^{12}$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, $N(R^{13})(R^{14})$, $C_1$-$C_6$alkyN($R^{13}$)($R^{14}$), $C_1$-$C_6$alkoxy or COOC$_1$-$C_6$alkyl or when taken with $R^7$ or $R^8$ forms a $C_1$-$C_6$alkyl bridge or when taken with $R^6$ forms an aryl, heteroaryl, $C_3$-$C_6$cycloalkyl or heterocycle or when taken with $R^{11}$ forms a $C_3$-$C_6$cycloalkyl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, $C_1$-$C_6$alkylOC$_1$-$C_6$alkyl, oxo, $C_1$-$C_6$alkyl, $C_1$-$C_6$haloalkyl, COC$_1$-$C_6$alkyl, COC$_1$-$C_6$alkylN($R^{13}$)($R^{14}$), COC$_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, —$C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and COOC$_1$-$C_6$alkyl;

$R^{13}$ is hydrogen, $C_3$-$C_6$cycloalkyl, $C_1$-$C_6$alkyl, COC$_1$-$C_6$alkylNH$_2$, COC$_1$-$C_6$alkylNH(C$_1$-$C_6$alkyl), COC$_1$-$C_6$alkylN(C$_1$-$C_6$alkyl)$_2$, $C_1$-$C_6$haloalkyl, $C_1$-$C_6$alkylOH or COC$_1$-$C_6$alkyl;

$R^{14}$ is hydrogen, $C_3$-$C_6$cycloalkyl, $C_1$-$C_6$alkyl, COC$_1$-$C_6$alkylNH$_2$, COC$_1$-$C_6$alkylNH(C$_1$-$C_6$alkyl), COC$_1$-$C_6$alkylN(C$_1$-$C_6$alkyl)$_2$, $C_1$-$C_6$haloalkyl, $C_1$-$C_6$alkylOH or COC$_1$-$C_6$alkyl; and $R^{15}$ is hydrogen, $C_3$-$C_6$cycloalkyl, $C_1$-$C_6$alkyl, COC$_1$-$C_6$alkyN($R^{13}$)($R^{14}$) or COC$_1$-$C_6$alkyl or when taken with $R^6$ or $R^8$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, $C_1$-$C_6$alkylOC$_1$-$C_6$alkyl, oxo, $C_1$-$C_6$alkyl, $C_1$-$C_6$haloalkyl, COC$_1$-$C_6$alkyl, COC$_1$-$C_6$alkylN($R^{13}$)($R^{14}$), COC$_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, —$C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and COOC$_1$-$C_6$alkyl;

wherein the structure of Formula I comprises a bridged ring or multiple rings.

Also described herein are compounds of Formula I:

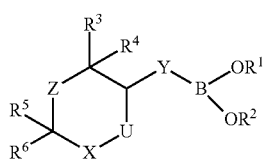

I or a pharmaceutically acceptable salt thereof, wherein:

Y is a straight or branched (C$_2$-C$_5$)alkylene, wherein one or more —CH$_2$— groups in Y are optionally and independently replaced with a moiety selected from the group consisting of O, S and NH;

U is a bond, O, NR$^{15}$ or CR$^7$R$^8$;

X is O, NR$^{15}$ or CR$^9$R$^{10}$, wherein U and X cannot be simultaneously O and NR$^{15}$, respectively;

Z is a bond or CR$^{11}$R$^{12}$;

$R^1$ is hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^2$ is hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^3$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, $N(R^{13})(R^{14})$, $C_1$-$C_6$alkyN($R^{13}$)($R^{14}$), $C_1$-$C_6$alkoxy or COOC$_1$-$C_6$alkyl;

$R^4$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, $N(R^{13})(R^{14})$, $C_1$-$C_6$alkyN($R^{13}$)($R^{14}$), $C_1$-$C_6$alkoxy or COOC$_1$-$C_6$alkyl;

$R^5$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, $N(R^{13})(R^{14})$, $C_1$-$C_6$alkyN($R^{13}$)($R^{14}$), $C_1$-$C_6$alkoxy or COOC$_1$-$C_6$alkyl or when taken with $R^6$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, COC$_1$-$C_6$alkyl, COC$_1$-$C_6$alkylN($R^{13}$)($R^{14}$), COC$_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and COOC$_1$-$C_6$alkyl;

$R^6$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, $N(R^{13})(R^{14})$, $C_1$-$C_6$alkyN($R^{13}$)($R^{14}$), $C_1$-$C_6$alkoxy or COOC$_1$-$C_6$alkyl or when taken with $R^5$ forms a $C_3$-$C_6$cycloalkyl or heterocycle, or taken with $R^{10}$ or $R^{12}$ forms an aryl, heteroaryl, $C_3$-$C_6$cycloalkyl or heterocycle or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, COC$_1$-$C_6$alkyl, COC$_1$-$C_6$alkylN($R^{13}$)($R^{14}$), COC$_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy or COOC$_1$-$C_6$alkyl;

$R^7$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, $N(R^{13})(R^{14})$, $C_1$-$C_6$alkyN($R^{13}$)($R^{14}$), $C_1$-$C_6$alkoxy or COOC$_1$-$C_6$alkyl or when taken with $R^{11}$ or $R^{12}$ forms a $C_1$-$C_6$alkyl bridge or when taken with $R^8$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, COC$_1$-$C_6$alkyl, COC$_1$-$C_6$alkylN($R^{13}$)($R^{14}$), COC$_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, —$C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and COOC$_1$-$C_6$alkyl;

$R^8$ is hydrogen, halogen, $C_3-C_6$cycloalkyl, $C_1-C_6$alkyl, halo$C_1-C_6$alkyl, OH, $C_1-C_6$alkylOH, $C_1-C_6$alkylO$C_1-C_6$alkyl, COOH, $N(R^{13})(R^{14})$, $C_1-C_6$alkyl$N(R^{13})(R^{14})$, $C_1-C_6$alkoxy or COO$C_1-C_6$alkyl or when taken with $R^6$, $R^{11}$ or $R^{12}$ forms a $C_1-C_6$alkyl bridge or when taken with $R^7$ forms a $C_3-C_6$cycloalkyl or heterocycle, or when taken with $R^{10}$ forms an aryl, heteroaryl, $C_3-C_6$cycloalkyl or heterocycle or when taken with $R^{15}$ forms a heteroaryl or heterocycle, wherein the aryl, heteroaryl, $C_3-C_6$cycloalkyl or heterocycle is unsubstituted or substituted with 1 to 3 substituents selected from the group consisting of halogen, OH, $C_1-C_6$alkylOH, $C_3-C_6$cycloalkyl, oxo, $C_1-C_6$alkyl, $C_1-C_6$haloalkyl, COC$_1-C_6$alkyl, COC$_1-C_6$alkyN$(R^{13})(R^{14})$, COC$_1-C_6$alkyl(OH)N$(R^{13})(R^{14})$, $C_1-C_6$alkylCON$(R^{13})(R^{14})$, CON$(R^{13})(R^{14})$, SO$_2C_1-C_6$alkyl, SO$_2$N$(R^{13})(R^{14})$, $N(R^{13})(R^{14})$, —$C_1-C_6$alkylN$(R^{13})(R^{14})$, $C_1-C_6$alkylaryl, $C_1-C_6$alkylhaloaryl, C(NH)N$(R^{13})(R^{14})$, heteroaryl, $C_1-C_6$alkoxy and COO$C_1-C_6$alkyl;

$R^9$ is hydrogen, halogen, $C_3-C_6$cycloalkyl, $C_1-C_6$alkyl, halo$C_1-C_6$alkyl, OH, $C_1-C_6$alkylOH, $C_1-C_6$alkylO$C_1-C_6$alkyl, COOH, $N(R^{13})(R^{14})$, $C_1-C_6$alkyl$N(R^{13})(R^{14})$, $C_1-C_6$alkoxy or COO$C_1-C_6$alkyl or when taken with $R^{10}$ forms a $C_3-C_6$cycloalkyl or heterocycle, wherein the $C_3-C_6$cycloalkyl or heterocycle is unsubstituted or substituted with 1 to 3 substituents selected from the group consisting of halogen, OH, $C_1-C_6$alkylOH, $C_3-C_6$cycloalkyl, $C_1-C_6$alkylO$C_1-C_6$alkyl, oxo, $C_1-C_6$alkyl, $C_1-C_6$haloalkyl, COC$_1-C_6$alkyl, COC$_1-C_6$alkyN$(R^{13})(R^{14})$, COC$_1-C_6$alkyl(OH)N$(R^{13})(R^{14})$, $C_1-C_6$alkylCON$(R^{13})(R^{14})$, CON$(R^{13})(R^{14})$, SO$_2C_1-C_6$alkyl, SO$_2$N$(R^{13})(R^{14})$, $N(R^{13})(R^{14})$, $C_1-C_6$alkylN$(R^{13})(R^{14})$, —$C_1-C_6$alkylaryl, —$C_1-C_6$alkylhaloaryl, C(NH)N$(R^{13})(R^{14})$, heteroaryl, $C_1-C_6$alkoxy and COO$C_1-C_6$alkyl;

$R^{10}$ is hydrogen, halogen, $C_3-C_6$cycloalkyl, $C_1-C_6$alkyl, halo$C_1-C_6$alkyl, OH, $C_1-C_6$alkylOH, $C_1-C_6$alkylO$C_1-C_6$alkyl, COOH, $N(R^{13})(R^{14})$, $C_1-C_6$alkyl$N(R^{13})(R^{14})$, $C_1-C_6$alkoxy or COO$C_1-C_6$alkyl or when taken with $R^6$ or $R^8$ forms an aryl, heteroaryl, $C_3-C_6$cycloalkyl or heterocycle, or taken with $R^9$ forms $C_3-C_6$cycloalkyl or heterocycle, or when taken with $R^{15}$ forms a heteroaryl or heterocycle, wherein the aryl, heteroaryl, $C_3-C_6$cycloalkyl or heterocycle is unsubstituted or substituted with 1 to 3 substituents selected from the group consisting of halogen, OH, $C_1-C_6$alkylOH, $C_3-C_6$cycloalkyl, $C_1-C_6$alkylO$C_1-C_6$alkyl, oxo, $C_1-C_6$alkyl, $C_1-C_6$haloalkyl, COC$_1-C_6$alkyl, COC$_1-C_6$alkyN$(R^{13})(R^{14})$, COC$_1-C_6$alkyl(OH)N$(R^{13})(R^{14})$, $C_1-C_6$alkyCON$(R^{13})(R^{14})$, CON$(R^{13})(R^{14})$, SO$_2C_1-C_6$alkyl, SO$_2$N$(R^{13})(R^{14})$, $N(R^{13})(R^{14})$, $C_1-C_6$alkyN$(R^{13})(R^{14})$, $C_1-C_6$alkylaryl, $C_1-C_6$alkylhaloaryl, C(NH)N$(R^{13})(R^{14})$, $C_1-C_6$alkoxy and COO$C_1-C_6$alkyl;

$R^{11}$ is hydrogen, halogen, $C_3-C_6$cycloalkyl, $C_1-C_6$alkyl, halo$C_1-C_6$alkyl, OH, $C_1-C_6$alkylOH, $C_1-C_6$alkylO$C_1-C_6$alkyl, COOH, $N(R^{13})(R^{14})$, $C_1-C_6$alkyl$N(R^{13})(R^{14})$, $C_1-C_6$alkoxy or COO$C_1-C_6$alkyl or when taken with $R^7$ or $R^8$ forms a $C_1-C_6$alkyl bridge or when taken with $R^{12}$ forms a $C_3-C_6$cycloalkyl or heterocycle, wherein the $C_3-C_6$cycloalkyl or heterocycle is unsubstituted or substituted with 1 to 3 substituents selected from the group consisting of halogen, OH, $C_1-C_6$alkylOH, $C_3-C_6$cycloalkyl, $C_1-C_6$alkylO$C_1-C_6$alkyl, oxo, $C_1-C_6$alkyl, $C_1-C_6$haloalkyl, COC$_1-C_6$alkyl, COC$_1-C_6$alkyN$(R^{13})(R^{14})$, COC$_1-C_6$alkyl(OH)N$(R^{13})(R^{14})$, $C_1-C_6$alkyCON$(R^{13})(R^{14})$, CON$(R^{13})(R^{14})$, SO$_2C_1-C_6$alkyl, SO$_2$N$(R^{13})(R^{14})$, $N(R^{13})(R^{14})$, —$C_1-C_6$alkyN$(R^{13})(R^{14})$, $C_1-C_6$alkylaryl, $C_1-C_6$alkylhaloaryl, C(NH)N$(R^{13})(R^{14})$, heteroaryl, $C_1-C_6$alkoxy and COO$C_1-C_6$alkyl;

$R^{12}$ is hydrogen, halogen, $C_3-C_6$cycloalkyl, $C_1-C_6$alkyl, halo$C_1-C_6$alkyl, OH, $C_1-C_6$alkylOH, $C_1-C_6$alkylO$C_1-C_6$alkyl, COOH, $N(R^{13})(R^{14})$, $C_1-C_6$alkyl$N(R^{13})(R^{14})$, $C_1-C_6$alkoxy or COO$C_1-C_6$alkyl or when taken with $R^7$ or $R^8$ forms a $C_1-C_6$alkyl bridge or when taken with $R^6$ forms an aryl, heteroaryl, $C_3-C_6$cycloalkyl or heterocycle or when taken with $R^{11}$ forms a $C_3-C_6$cycloalkyl or heterocycle, wherein the aryl, heteroaryl, $C_3-C_6$cycloalkyl or heterocycle is unsubstituted or substituted with 1 to 3 substituents selected from the group consisting of halogen, OH, $C_1-C_6$alkylOH, $C_3-C_6$cycloalkyl, $C_1-C_6$alkylO$C_1-C_6$alkyl, oxo, $C_1-C_6$alkyl, $C_1-C_6$haloalkyl, COC$_1-C_6$alkyl, COC$_1-C_6$alkyN$(R^{13})(R^{14})$, COC$_1-C_6$alkyl(OH)N$(R^{13})(R^{14})$, $C_1-C_6$alkyCON$(R^{13})(R^{14})$, CON$(R^{13})(R^{14})$, SO$_2C_1-C_6$alkyl, SO$_2$N$(R^{13})(R^{14})$, $N(R^{13})(R^{14})$, —$C_1-C_6$alkyN$(R^{13})(R^{14})$, $C_1-C_6$alkylaryl, $C_1-C_6$alkylhaloaryl, C(NH)N$(R^{13})(R^{14})$, heteroaryl, $C_1-C_6$alkoxy and COO$C_1-C_6$alkyl;

$R^{13}$ is hydrogen, $C_3-C_6$cycloalkyl, $C_1-C_6$alkyl, COC$_1-C_6$alkylNH$_2$, COC$_1-C_6$alkylNH(C$_1-C_6$alkyl), COC$_1-C_6$alkylN(C$_1-C_6$alkyl)$_2$, $C_1-C_6$haloalkyl, $C_1-C_6$alkylOH or COC$_1-C_6$alkyl;

$R^{14}$ is hydrogen, $C_3-C_6$cycloalkyl, $C_1-C_6$alkyl, COC$_1-C_6$alkylNH$_2$, COC$_1-C_6$alkylNH(C$_1-C_6$alkyl), COC$_1-C_6$alkylN(C$_1-C_6$alkyl)$_2$, $C_1-C_6$haloalkyl, $C_1-C_6$alkylOH or COC$_1-C_6$alkyl; and $R^{15}$ is hydrogen, $C_3-C_6$cycloalkyl, $C_1-C_6$alkyl, COC$_1-C_6$alkyN$(R^{13})(R^{14})$ or COC$_1-C_6$alkyl or when taken with $R^6$ or $R^8$ forms a heteroaryl or heterocycle, wherein the aryl, heteroaryl, $C_3-C_6$cycloalkyl or heterocycle is unsubstituted or substituted with 1 to 3 substituents selected from the group consisting of halogen, OH, $C_1-C_6$alkylOH, $C_3-C_6$cycloalkyl, $C_1-C_6$alkylO$C_1-C_6$alkyl, oxo, $C_1-C_6$alkyl, $C_1-C_6$haloalkyl, COC$_1-C_6$alkyl, COC$_1-C_6$alkyN$(R^{13})(R^{14})$, COC$_1-C_6$alkyl(OH)N$(R^{13})(R^{14})$, $C_1-C_6$alkylCON$(R^{13})(R^{14})$, CON$(R^{13})(R^{14})$, SO$_2C_1-C_6$alkyl, SO$_2$N$(R^{13})(R^{14})$, $N(R^{13})(R^{14})$, —$C_1-C_6$alkylN$(R^{13})(R^{14})$, $C_1-C_6$alkylaryl, $C_1-C_6$alkylhaloaryl, C(NH)N$(R^{13})(R^{14})$, heteroaryl, $C_1-C_6$alkoxy and COO$C_1-C_6$alkyl.

In certain embodiments, the structure of Formula I comprises a bridged ring or multiple rings.

With regard to the compounds described herein, Y is selected from the group consisting of straight or branched $(C_2-C_5)$alkylene, wherein one or more —CH$_2$— groups in Y are optionally and independently replaced with a moiety selected from the group consisting of O, S or NH. In certain embodiments, Y is ethelenyl, propylenyl, butylenyl or pentylenyl. In certain embodiments Y is propylenyl. In other embodiments, one or more —CH$_2$— groups in Y are optionally and independently replaced with a moiety selected from the group consisting of O, S or NH. In certain embodiments, Y is In certain embodiments, Y is $(C_2-C_5)$alkylene or O—$C_1-C_4$alkylene,

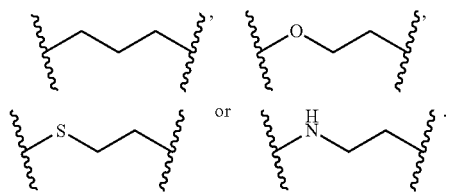

With regard to the compounds described herein, U is a bond, O, NR$^{15}$ or CR$^7$R$^8$. In certain embodiments, U is a bond. In certain embodiments, U is O. In certain embodiments, U is NR$^{15}$. In certain embodiments, U is CR$^7$R$^8$.

With regard to the compounds described herein, X is O, $NR^{15}$ or $CR^9R^{10}$. In certain embodiments, X is O. In certain embodiments, X is $NR^{15}$. In certain embodiments, X is $CR^9R^{10}$.

In embodiments of the compounds described herein, U and X cannot be simultaneously O or $NR^{15}$.

With regard to the compounds described herein, Z is a bond or $CR^{11}R^{12}$. In certain embodiments, Z is a bond. In certain embodiments, Z is $CR^{11}R^{12}$.

With regard to the compounds described herein, $R^1$ is hydrogen, $C_3$-$C_6$cycloalkyl or $C_1$-$C_6$alkyl, or when taken with $R^2$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or —OH. In certain embodiments, $R^1$ is hydrogen. In certain embodiments, $R^1$ is $C_3$-$C_6$cycloalkyl. Suitable cycloalkyl groups include, but are not limited to, cyclopropyl, cyclobutyl, cyclopentyl, cyclohexyl. In certain embodiments, $R^1$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^1$ and $R^2$ taken together form a $C_3$-$C_8$cycloalkyl, wherein the $C_3$-$C_8$cycloalkyl is unsubstituted or substituted with one to four substituents selected from the group consisting of halogen, $C_1$-$C_6$alkyl or —OH. In certain embodiments, the $C_3$-$C_8$cycloalkyl is a six or seven-membered carbon ring. In certain embodiments, the $C_3$-$C_8$cycloalkyl is a six or seven-membered, saturated carbon ring. In certain embodiments, the $C_3$-$C_8$cycloalkyl is a bridged ring. In certain embodiments, the $C_3$-$C_8$cycloalkyl is substituted with one substituent selected from the group consisting of halogen, $C_1$-$C_6$alkyl or —OH. In certain embodiments, the $C_3$-$C_8$cycloalkyl is substituted with two substituents selected from the group consisting of halogen, $C_1$-$C_6$alkyl or —OH. In certain embodiments, the $C_3$-$C_8$cycloalkyl is substituted with three substituents selected from the group consisting of halogen, $C_1$-$C_6$alkyl or —OH. In certain embodiments, the $C_3$-$C_8$cycloalkyl is substituted with four substituents selected from the group consisting of halogen, $C_1$-$C_6$alkyl or —OH. In certain embodiments, the $C_3$-$C_8$cycloalkyl is substituted with three substituents, wherein all the substituents are $C_1$-$C_6$alkyl groups. In certain embodiments, the $C_3$-$C_8$cycloalkyl is substituted with three substituents, wherein all the substituents are methyl. In certain embodiments, the $C_3$-$C_8$cycloalkyl is substituted with four substituents, wherein all the substituents are $C_1$-$C_6$alkyl groups. In certain embodiments, the $C_3$-$C_8$cycloalkyl is substituted with four substituents, wherein all the substituents are methyl.

In certain embodiments, $R^1$ and $R^2$, when taken together form a $C_3$-$C_8$cycloalkyl selected from the group consisting of:

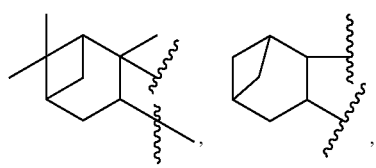

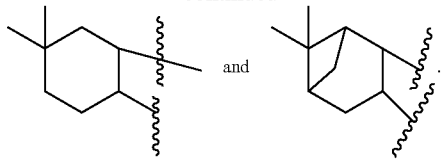

In certain embodiments, $R^1$ and $R^2$ when taken together form the following $C_3$-$C_8$cycloalkyl

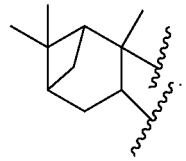 [SMILES: *C1CC2CC(C1(*)C)C2(C)C]

With regard to the compounds described herein, $R^2$ is hydrogen, $C_3$-$C_8$cycloalkyl or $C_1$-$C_6$alkyl, or when taken with $R^1$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or —OH. In certain embodiments, $R^2$ is hydrogen. In certain embodiments, $R^2$ is $C_3$-$C_6$cycloalkyl. Suitable cycloalkyl groups include, but are not limited to, cyclopropyl, cyclobutyl, cyclopentyl, cyclohexyl. In certain embodiments, $R^2$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^2$ when taken with $R^1$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or —OH. In certain embodiments, the $C_3$-$C_8$cycloalkyl is a six or seven carbon ring. In certain embodiments, the $C_3$-$C_8$cycloalkyl is a six or seven-membered saturated carbon ring. In certain embodiments, the $C_3$-$C_8$cycloalkyl is a bridged ring. In certain embodiments, the $C_3$-$C_8$cycloalkyl is substituted with one substituent selected from the group consisting of halogen, $C_1$-$C_6$alkyl or —OH. In certain embodiments, the $C_3$-$C_8$cycloalkyl is substituted with two substituents selected from the group consisting of halogen, $C_1$-$C_6$alkyl or —OH. In certain embodiments, the $C_3$-$C_8$cycloalkyl is substituted with three substituents selected from the group consisting of halogen, $C_1$-$C_6$alkyl or —OH. In certain embodiments, the $C_3$-$C_8$cycloalkyl is substituted with four substituents selected from the group consisting of halogen, $C_1$-$C_6$alkyl or —OH. In certain embodiments, the $C_3$-$C_8$cycloalkyl is substituted with three substituents, wherein all the substituents are $C_1$-$C_6$alkyl groups. In certain embodiments, the $C_3$-$C_8$cycloalkyl is substituted with three substituents, wherein all the substituents are methyl. In certain embodiments, the $C_3$-$C_8$cycloalkyl is substituted with four substituents, wherein all the substituents are $C_1$-$C_6$alkyl groups. In certain embodiments, the $C_3$-$C_8$cycloalkyl is substituted with four substituents, wherein all the substituents are methyl.

In certain embodiments, $R^1$ and $R^2$, when taken together form a $C_3$-$C_8$cycloalkyl selected from the group consisting of:

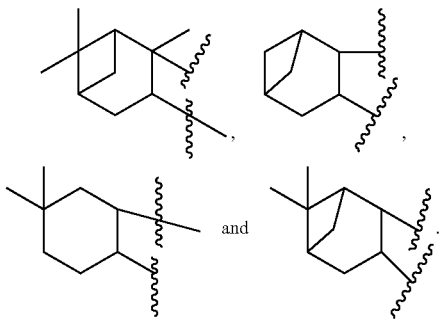

In certain embodiments, $R^1$ and $R^2$ when taken together form the following $C_3$-$C_8$cycloalkyl

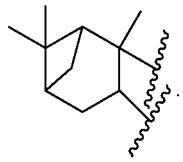

In certain embodiments, $R^1$ and $R^2$ are both hydrogen. In certain embodiments, $R^1$ and $R^2$ are each hydrogen or taken together form a pinane.

With regard to the compounds described herein, $R^3$ is hydrogen, halogen, $C_3$-$C_6$cycloalkyl, $C_1$-$C_6$alkyl, haloC$_1$-C$_6$alkyl, OH, $C_1$-$C_6$alkylOH, $C_1$-$C_6$alkylOC$_1$-$C_6$alkyl, COOH, N(R$^{13}$)(R$^{14}$), $C_1$-$C_6$alkylN(R$^{13}$)(R$^{14}$), $C_1$-$C_6$alkoxy or COOC$_1$-$C_6$alkyl. In certain embodiments, $R^3$ is hydrogen. In certain embodiments described herein, $R^3$ is halogen. Examples of suitable halogens include, but are not limited to, chlorine, bromine, fluorine and iodine. In certain embodiments, $R^3$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^3$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^3$ is haloC$_1$-$C_6$alkyl. Suitable haloC$_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^3$ is OH. In certain embodiments, $R^3$ is $C_1$-$C_6$alkylOH.

Examples of suitable alcohols, include, but are not limited to, methanol, ethanol, propanol, butanol and iso-butanol. In certain embodiments, $R^3$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether. In certain embodiments, $R^3$ is COOH.

In certain embodiments, $R^3$ is N(R$^{13}$)(R$^{14}$). Examples of suitable N(R$^{13}$)(R$^{14}$) groups include, but are not limited to, NH$_2$, NH(CH$_3$), N(CH$_3$)$_2$ and N(CH$_3$)$_2$. In certain embodiments, $R^3$ is $C_1$-$C_6$alkylN(R$^{13}$)(R$^{14}$). Examples of suitable $C_1$-$C_6$alkylN(R$^{13}$)(R$^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^3$ is $C_1$-$C_6$alkoxy. Examples of suitable alkoxys, include but are not limited to, methoxy, ethoxy, butoxy and propoxy. In certain embodiments, $R^3$ is COOC$_1$-$C_6$alkyl. Examples of suitable COOC$_1$-$C_6$alkyl groups include, but are not limited to, methoxycarbonyl, ethoxycarbonyl and butoxycarbonyl. In certain embodiments, $R^3$ is NH$_2$.

With regard to the compounds described herein, $R^4$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, N(R$^{13}$)(R$^{14}$), $C_1$-$C_6$alkylN(R$^{13}$)(R$^{14}$), $C_1$-$C_6$alkoxy or COOC$_1$-$C_6$alkyl. In certain embodiments, $R^4$ is hydrogen. In certain embodiments described herein, $R^4$ is halogen. Examples of suitable halogens include, but are not limited to, chlorine, bromine, fluorine and iodine. In certain embodiments, $R^4$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^4$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^4$ is haloC$_1$-$C_6$alkyl. Suitable haloC$_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^4$ is OH. In certain embodiments, $R^4$ is $C_1$-$C_6$alkylOH. Examples of suitable alcohols, include, but are not limited to, methanol, ethanol, propanol, butanol and iso-butanol. In certain embodiments, $R^4$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether. In certain embodiments, $R^4$ is COOH.

In certain embodiments, $R^4$ is N(R$^{13}$)(R$^{14}$). Examples of suitable N(R$^{13}$)(R$^{14}$) groups include, but are not limited to, NH$_2$, NH(CH$_3$), N(CH$_3$)$_2$ and N(CH$_3$)$_2$. In certain embodiments, $R^4$ is $C_1$-$C_6$alkylN(R$^{13}$)(R$^{14}$). Examples of suitable $C_1$-$C_6$alkylN(R$^{13}$)(R$^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^4$ is $C_1$-$C_6$alkoxy. Examples of suitable alkoxys, include but are not limited to, methoxy, ethoxy, butoxy and propoxy. In certain embodiments, $R^4$ is COOC$_1$-$C_6$alkyl. Examples of suitable COOC$_1$-$C_6$alkyl groups include, but are not limited to, methoxycarbonyl, ethoxycarbonyl and butoxycarbonyl.

With regard to the compounds described herein, $R^5$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, N(R$^{13}$)(R$^{14}$), $C_1$-$C_6$alkylN(R$^{13}$)(R$^{14}$), $C_1$-$C_6$alkoxy or COOC$_1$-$C_6$alkyl or when taken with $R^6$ forms an $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, COC$_1$-$C_6$alkyl, COC$_1$-

$C_6$alkylN($R^{13}$)($R^{14}$), COC$_1$-C$_6$alkyl(OH)N($R^{13}$)($R^{14}$), C$_1$-C$_6$alkylCON($R^{13}$)($R^{14}$), CON($R^{13}$)($R^{14}$), SO$_2$C$_1$-C$_6$alkyl, SO$_2$N($R^{13}$)($R^{14}$), N($R^{13}$)($R^{14}$), C$_1$-C$_6$alkylN($R^{13}$)($R^{14}$), C$_1$-C$_6$alkylaryl, C$_1$-C$_6$alkylhaloaryl, C(NH)N($R^{13}$)($R^{14}$), heteroaryl, C$_1$-C$_6$alkoxy and COOC$_1$-C$_6$alkyl.

In certain embodiments described herein, $R^5$ is hydrogen. In certain embodiments described herein, $R^5$ is halogen. Examples of suitable halogens include, but are not limited to, chlorine, bromine, fluorine and iodine. In certain embodiments, $R^5$ is C$_3$-C$_6$cycloalkyl. Suitable cycloalkyl groups include, but are not limited to, cyclopropyl, cyclobutyl, cyclopentyl, cyclohexyl. In certain embodiments described herein, $R^5$ is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^5$ is haloC$_1$-C$_6$alkyl. Suitable haloC$_1$-C$_6$alkyls include but are not limited to, fluoromethyl, difluoromethyl, trifluoromethyl, 2-fluoroethyl, 1,2-difluoroethyl and 2,2-difluoroethyl. In certain embodiments, $R^5$ is OH. In certain embodiments, $R^5$ is C$_1$-C$_6$alkylOH. Examples of suitable alcohols, include, but are not limited to, methanol, ethanol, propanol, butanol and iso-butanol. In certain embodiments, $R^5$ is C$_1$-C$_6$alkylOC$_1$-C$_6$alkyl. Suitable C$_1$-C$_6$alkylOC$_1$-C$_6$alkyls include but are not limited to, dimethyl ether, ethyl methyl ether, diethyl ether, dipropyl ether, dibutyl ether and diisopropyl ether. In certain embodiments, $R^5$ is COOH.

In certain embodiments, $R^5$ is N($R^{13}$)($R^{14}$). Examples of suitable N($R^{13}$)($R^{14}$) groups include, but are not limited to, NH$_2$, NH(CH$_3$), —N(CH$_3$)$_2$ and N(CH$_3$)$_2$. In certain embodiments, $R^5$ is C$_1$-C$_6$alkylN($R^{13}$)($R^{14}$). Examples of suitable C$_1$-C$_6$alkylN($R^{13}$)($R^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^5$ is C$_1$-C$_6$alkoxy. Examples of suitable alkoxys, include but are not limited to, methoxy, ethoxy, butoxy and propoxy. In certain embodiments, $R^5$ is COOC$_1$-C$_6$alkyl. Examples of suitable COOC$_1$-C$_6$alkyl groups include, but are not limited to, methoxycarbonyl, ethoxycarbonyl and butoxycarbonyl.

In certain embodiments, $R^5$ hydrogen or methyl.

In certain embodiments, when taken with $R^6$, $R^5$ and $R^6$ form a C$_3$-C$_6$cycloalkyl or heterocycle.

In certain embodiments, $R^6$ and $R^5$ form a cycloalkyl group. Suitable cycloalkyl groups include, but are not limited to, cyclopropyl, cyclobutyl, cyclopentyl, cyclohexyl. In certain embodiments, $R^6$ and $R^5$ form a heterocycle group. Suitable heterocycle groups include, but are not limited to, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl and tetrahydropyran.

In certain embodiments, when taken with $R^6$, $R^5$ and $R^6$ form an aryl, heteroaryl, C$_3$-C$_6$cycloalkyl or heterocycle, wherein the aryl, heteroaryl, C$_3$-C$_6$cycloalkyl or heterocycle is unsubstituted or substituted with 1 to 3 substituents selected from the group consisting of halogen, OH, C$_1$-C$_6$alkylOH, C$_3$-C$_6$cycloalkyl, oxo, C$_1$-C$_6$alkyl, C$_1$-C$_6$haloalkyl, COC$_1$-C$_6$alkyl, COC$_1$-C$_6$alkylN($R^{13}$)($R^{14}$), COC$_1$-C$_6$alkyl(OH)N($R^{13}$)($R^{14}$), C$_1$-C$_6$alkylCON($R^{13}$)($R^{14}$), CON($R^{13}$)($R^{14}$), SO$_2$C$_1$-C$_6$alkyl, SO$_2$N($R^{13}$)($R^{14}$), N($R^{13}$)($R^{14}$), C$_1$-C$_6$alkylN($R^{13}$)($R^{14}$), C$_1$-C$_6$alkylaryl, C$_1$-C$_6$alkylhaloaryl, C(NH)N($R^{13}$)($R^{14}$), heteroaryl, C$_1$-C$_6$alkoxy and COOC$_1$-C$_6$alkyl.

In certain embodiments, when taken with $R^6$, $R^5$ and $R^6$ form a C$_3$-C$_6$cycloalkyl or heterocycle, wherein the C$_3$-C$_6$cycloalkyl or heterocycle is unsubstituted or substituted with 1 to 3 substituents selected from the group consisting of OH, C$_1$-C$_6$alkylOH, C$_3$-C$_6$cycloalkyl, C$_1$-C$_6$alkylOC$_1$-C$_6$alkyl, oxo, C$_1$-C$_6$alkyl, C$_1$-C$_6$haloalkyl, COC$_1$-C$_6$alkyl, COC$_1$-C$_6$alkylN($R^{13}$)($R^{14}$), COC$_1$-C$_6$alkyl(OH)N($R^{13}$)($R^{14}$), C$_1$-C$_6$alkylCON($R^{13}$)($R^{14}$), CON($R^{13}$)($R^{14}$), SO$_2$C$_1$-C$_6$alkyl, SO$_2$N($R^{13}$)($R^{14}$), N($R^{13}$)($R^{14}$), C$_1$-C$_6$alkylN($R^{13}$)($R^{14}$), C$_1$-C$_6$alkylaryl, C$_1$-C$_6$alkylhaloaryl, C(NH)N($R^{13}$)($R^{14}$), C$_1$-C$_6$alkoxy or COOC$_1$-C$_6$alkyl.

In certain embodiments, $R^5$, when taken with $R^6$, forms a C$_3$-C$_6$cycloalkyl or heterocycle, wherein the C$_3$-C$_6$cycloalkyl or heterocycle is unsubstituted or substituted with 1 to 3 substituents selected from the group consisting of methyl, ethyl, isopropyl, NH$_2$,

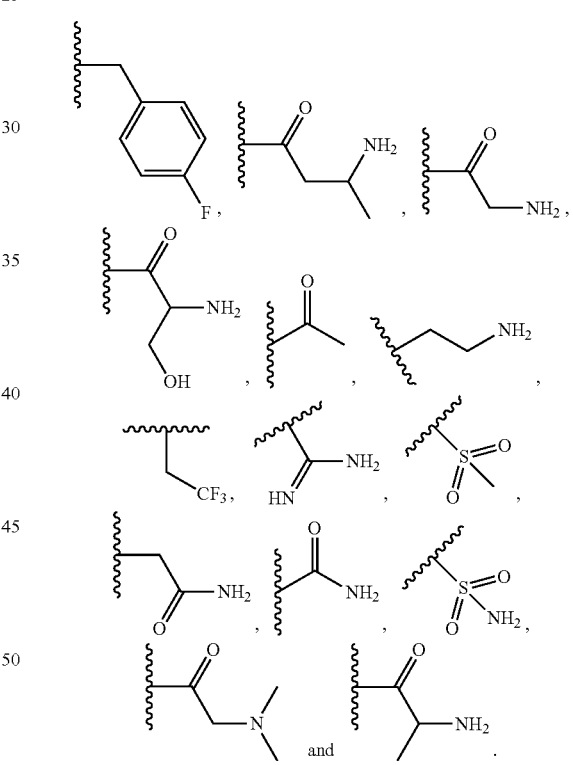

With regard to the compounds described herein, $R^6$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N($R^{13}$)($R^{14}$), C$_1$-C$_6$alkylN($R^{13}$)($R^{14}$), C$_1$-C$_6$alkoxy or COOC$_1$-C$_6$alkyl or when taken with $R^5$ forms a C$_3$-C$_6$cycloalkyl or heterocycle, or taken with $R^7$ forms a C$_1$-C$_6$alkyl bridge, or when taken with $R^{15}$ forms a heteroaryl or heterocycle, or when taken with $R^{10}$ or $R^{12}$ forms an aryl, heteroaryl, C$_3$-C$_6$cycloalkyl or heterocycle, wherein the aryl, heteroaryl, C$_3$-C$_6$cycloalkyl or heterocycle is unsubstituted or substituted with 1 to 3 substituents selected from the group consisting of halogen, OH, C$_1$-C$_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and $COOC_1$-$C_6$alkyl.

In certain embodiments, $R^6$ is hydrogen. In certain embodiments described herein, $R^6$ is halogen. Examples of suitable halogens include, but are not limited to, chlorine, bromine, fluorine and iodine. In certain embodiments, $R^6$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^6$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^6$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^6$ is OH. In certain embodiments, $R^6$ is $C_1$-$C_6$alkylOH. Examples of suitable alcohols, include, but are not limited to, methanol, ethanol, propanol, butanol and iso-butanol. In certain embodiments, $R^6$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^6$ is COOH.

In certain embodiments, $R^6$ is $N(R^{13})(R^{14})$. Examples of suitable $N(R^{13})(R^{14})$ groups include, but are not limited to, $NH_2$, $NH(CH_3)$, $N(CH_3)_2$ and $N(CH_3)_2$. In certain embodiments, $R^6$ is $C_1$-$C_6$alkylN($R^{13}$)($R^{14}$). Examples of suitable $C_1$-$C_6$alkylN($R^{13}$)($R^{14}$) groups include, but are not limited to, $CH_2NH_2$, $CH_2NH(CH_3)$, $CH_2N(CH_3)_2$ and $CH_2CH_2N(CH_3)_2$.

In certain embodiments, $R^6$ is $C_1$-$C_6$alkoxy. Examples of suitable alkoxys, include but are not limited to, methoxy, ethoxy, butoxy and propoxy. In certain embodiments, $R^6$ is $COOC_1$-$C_6$alkyl. Examples of suitable $COOC_1$-$C_6$alkyl groups include, but are not limited to, methoxycarbonyl, ethoxycarbonyl and butoxycarbonyl.

In certain embodiments, $R^6$, when taken with $R^5$ forms a $C_3$-$C_6$cycloalkyl or heterocycle, or when taken with $R^{10}$ or $R^{12}$ forms an aryl, heteroaryl, $C_3$-$C_6$cycloalkyl or heterocycle, or when taken with $R^{15}$ forms a heteroaryl or heterocycle. In certain embodiments, $R^6$, when taken with $R^5$ forms a $C_3$-$C_6$cycloalkyl or heterocycle. In certain embodiments, $R^6$, when taken with $R^7$ forms a $C_1$-$C_6$alkyl bridge. In certain embodiments, $R^6$, when taken with $R^{10}$ forms an aryl, heteroaryl, $C_3$-$C_6$cycloalkyl or heterocycle. In certain embodiments, $R^6$, when taken with $R^{12}$ forms an aryl, heteroaryl, $C_3$-$C_6$cycloalkyl or heterocycle. In certain embodiments, $R^6$, when taken with $R^{15}$ forms a heteroaryl or heterocycle.

In certain embodiments, $R^6$, when taken with $R^{10}$ or $R^{12}$ forms an aryl, heteroaryl, $C_3$-$C_6$cycloalkyl or heterocycle, or when taken with $R^{15}$ forms a heteroaryl or heterocycle. Suitable aryl groups include but are not limited to, benzyl. In certain embodiments, $R^6$, when taken with $R^{10}$, $R^{12}$ or $R^{15}$ forms an heteroaryl group. In certain embodiments, the heteroaryl group is a nitrogen containing heteroaryl group. In certain embodiments the heteroaryl group is an oxygen containing heteroaryl group. In certain embodiments the heteroaryl is a sulfur containing heteroaryl. Suitable heteroaryls include, but are not limited to, pyridyl (pyridinyl), oxazolyl, imidazolyl, triazolyl, furyl, triazinyl, thienyl, pyrimidyl, pyridazinyl, indolizinyl, cinnolinyl, phthalazinyl, quinazolinyl, naphthyridinyl, quinoxalinyl, purinyl, benzimidazolyl, quinolyl and isoquinolyl. In certain embodiments, $R^6$, when taken with $R^{12}$ forms a pyridine. In certain embodiments, $R^6$, when taken with $R^{12}$ forms a cyclopropyl. In certain embodiments, $R^6$, when taken with $R^{12}$ forms a pyrrolidine.

In certain embodiments, $R^6$, when taken with $R^5$, $R^{10}$ or $R^{12}$ forms a cycloalkyl group. Suitable cycloalkyl groups include, but are not limited to, cyclopropyl, cyclobutyl, cyclopentyl, cyclohexyl. In certain embodiments, $R^6$, when taken with $R^{10}$ forms a cyclopentyl ring. In certain embodiments, $R^6$, when taken with $R^5$, $R^{10}$, $R^{12}$ or $R^{15}$ form a heterocycle group. Suitable heterocycle groups include, but are not limited to, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl and tetrahydropyran.

In certain embodiments, $R^6$, when taken with $R^5$ forms a $C_3$-$C_6$cycloalkyl or heterocycle, or when taken with $R^{10}$ or $R^{12}$ forms an aryl, heteroaryl, $C_3$-$C_6$cycloalkyl or heterocycle or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, $C_1$-$C_6$alkyN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and $COOC_1$-$C_6$alkyl.

In certain embodiments, $R^6$, when taken with $R^5$ forms a heterocycle. Suitable heterocycles include but are not limited to, nitrogen-containing heterocycles such as azacyclobutane and azacyclopentane.

In certain embodiments, $R^6$, when taken with $R^5$ forms a $C_3$-$C_6$cycloalkyl or heterocycle, or when taken with $R^{10}$ or $R^{12}$ forms an aryl, heteroaryl, $C_3$-$C_6$cycloalkyl or heterocycle or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, $COC_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), $C_1$-$C_6$alkoxy or $COOC_1$-$C_6$alkyl.

In certain embodiments, $R^6$, when taken with $R^{10}$ forms a cyclopentyl ring, wherein the cyclopentyl is unsubstituted or substituted with 1 to 3 substituents selected from the group consisting of OH or $N(R^{13})(R^{14})$.

In certain embodiments, $R^6$, when taken with $R^5$, forms a $C_3$-$C_6$cycloalkyl or heterocycle, wherein the $C_3$-$C_6$cycloalkyl or heterocycle is unsubstituted or substituted with 1 to 3 substituents selected from the group consisting of methyl, ethyl, isopropyl, $NH_2$,

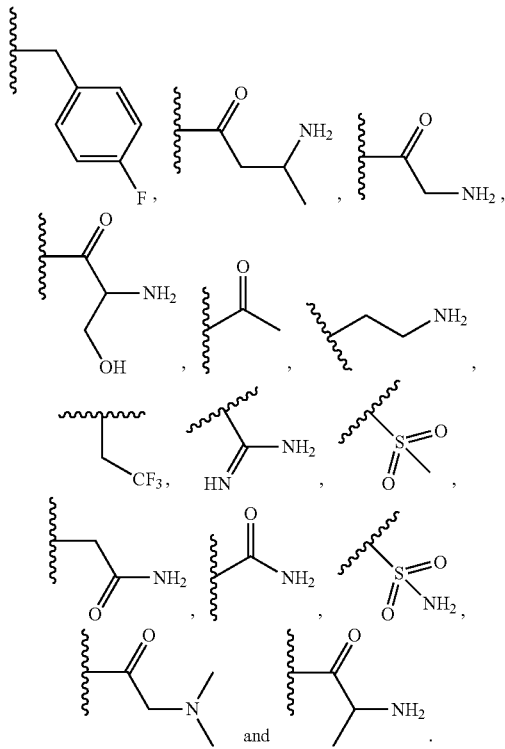

In certain embodiments, $R^5$ is hydrogen and $R^6$, when taken with $R^{10}$ forms a heterocycle. In certain embodiments, $R^5$ is hydrogen and $R^6$, when taken with $R^{10}$ forms a pyrrolidine.

In certain embodiments, $R^6$, when taken with $R^8$ forms a $C_1$-$C_6$alkyl bridge. Examples of suitable bridges include, but are not limited to,

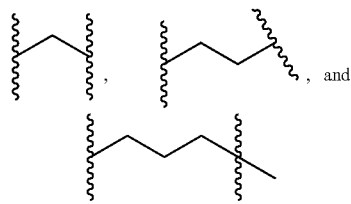

With regard to the compounds described herein, $R^7$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, $N(R^{13})(R^{14})$, $C_1$-$C_6$alkylN$(R^{13})(R^{14})$, $C_1$-$C_6$alkoxy or COOC$_1$-$C_6$alkyl or when taken with $R^{11}$ or $R^{12}$ forms a $C_1$-$C_6$alkyl bridge or when taken with $R^8$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, COC$_1$-$C_6$alkyl, COC$_1$-$C_6$alkyN$(R^{13})(R^{14})$, COC$_1$-$C_6$alkyl(OH)N$(R^{13})(R^{14})$, $C_1$-$C_6$alkylCON$(R^{13})(R^{14})$, CON$(R^{13})(R^{14})$, SO$_2$C$_1$-$C_6$alkyl, SO$_2$N$(R^{13})(R^{14})$, $N(R^{13})(R^{14})$, $C_1$-$C_6$alkylN$(R^{13})$$(R^{14})$, $C_1$-$C_6$alkylaryl, $C_1$-$C_6$alkylhaloaryl, C(NH)N$(R^{13})$$(R^{14})$, heteroaryl, $C_1$-$C_6$alkoxy and COOC$_1$-$C_6$alkyl.

In certain embodiments described herein, $R^7$ is hydrogen. In certain embodiments described herein, $R^7$ is halogen. Examples of suitable halogens include, but are not limited to, chlorine, bromine, fluorine and iodine. In certain embodiments, $R^7$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^7$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^7$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^7$ is OH. In certain embodiments, $R^7$ is $C_1$-$C_6$alkylOH. Examples of suitable alcohols, include, but are not limited to, methanol, ethanol, propanol, butanol and iso-butanol. In certain embodiments, $R^7$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether. In certain embodiments, $R^7$ is COOH.

In certain embodiments, $R^7$ is $N(R^{13})(R^{14})$. Examples of suitable $N(R^{13})(R^{14})$ groups include, but are not limited to, $NH_2$, $NH(CH_3)$, $N(CH_3)_2$ and $N(CH_3)_2$. In certain embodiments, $R^7$ is $C_1$-$C_6$alkylN$(R^{13})(R^{14})$. Examples of suitable $C_1$-$C_6$alkylN$(R^{13})(R^{14})$ groups include, but are not limited to, $CH_2NH_2$, $CH_2NH(CH_3)$, $CH_2N(CH_3)_2$ and $CH_2CH_2N$ $(CH_3)_2$.

In certain embodiments, $R^7$ is $C_1$-$C_6$alkoxy. Examples of suitable alkoxys, include but are not limited to, methoxy, ethoxy, butoxy and propoxy. In certain embodiments, $R^7$ is COOC$_1$-$C_6$alkyl. Examples of suitable COOC$_1$-$C_6$alkyl groups include, but are not limited to, methoxycarbonyl, ethoxycarbonyl and butoxycarbonyl.

In certain embodiments, $R^7$ when taken with $R^{11}$ or $R^{12}$ forms a $C_1$-$C_6$alkyl bridge. In certain embodiments, $R^7$ when taken with $R^{11}$ forms a $C_1$-$C_6$alkyl bridge. In certain embodiments, $R^7$ when taken with $R^{12}$ forms a $C_1$-$C_6$alkyl bridge.

In certain embodiments, $R^7$, when taken with $R^8$ forms a $C_3$-$C_6$cycloalkyl or heterocycle.

In certain embodiments, $R^7$, when taken with $R^8$ forms a cycloalkyl group. Suitable cycloalkyl groups include, but are not limited to, cyclopropyl, cyclobutyl, cyclopentyl, cyclohexyl.

In certain embodiments, $R^7$, when taken with $R^8$ forms a heterocycle group. Suitable heterocycle groups include, but are not limited to, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl and tetrahydropyran.

In certain embodiments, $R^7$, when taken with $R^8$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, COC$_1$-$C_6$alkyl, COC$_1$-

$C_6$alkyN($R^{13}$)($R^{14}$), COC$_1$-C$_6$alkyl(OH)N($R^{13}$)($R^{14}$), $C_1$-$C_6$alkylCON($R^{13}$)($R^{14}$), CON($R^{13}$)($R^{14}$), SO$_2$C$_1$-$C_6$alkyl, SO$_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and COOC$_1$-$C_6$alkyl.

In certain embodiments, $R^7$, when taken with $R^8$ forms a $C_3$-$C_6$cycloalkyl or heterocycle, wherein the $C_3$-$C_6$cycloalkyl or heterocycle is unsubstituted or substituted with 1 to 3 substituents selected from the group consisting of OH, $C_1$-$C_6$alkylOH, $C_3$-$C_6$cycloalkyl, $C_1$-$C_6$alkylOC$_1$-$C_6$alkyl, oxo, $C_1$-$C_6$alkyl, $C_1$-$C_6$haloalkyl, COC$_1$-$C_6$alkyl, COC$_1$-$C_6$alkylN($R^{13}$)($R^{14}$), COC$_1$-$C_6$alkyl(OH)N($R^{13}$)($R^{14}$), $C_1$-$C_6$alkylCON($R^{13}$)($R^{14}$), CON($R^{13}$)($R^{14}$), SO$_2$C$_1$-$C_6$alkyl, SO$_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), $C_1$-$C_6$alkoxy or COOC$_1$-$C_6$alkyl.

In certain embodiments, $R^7$, when taken with $R^8$ forms a $C_3$-$C_6$cycloalkyl or heterocycle, wherein the $C_3$-$C_6$cycloalkyl or heterocycle is unsubstituted or substituted with 1 to 3 substituents selected from the group consisting of methyl, ethyl, isopropyl, NH$_2$,

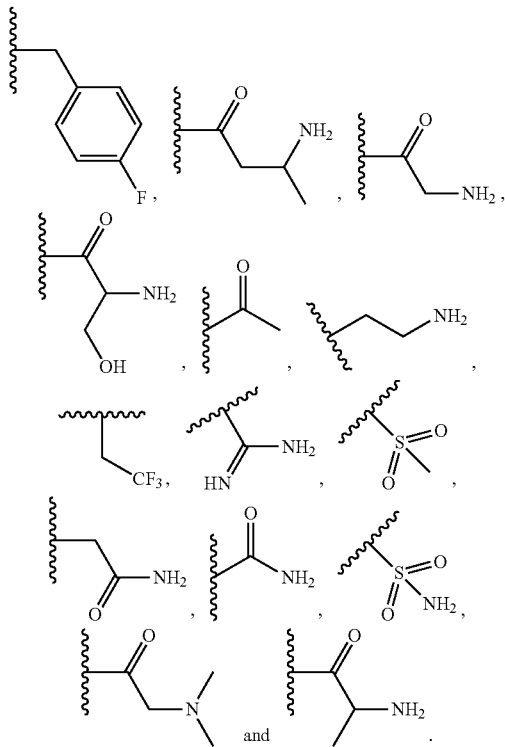

With regard to the compounds described herein, $R^8$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkylN($R^{13}$)($R^{14}$), $C_1$-$C_6$alkoxy or COOC$_1$-$C_6$alkyl or when taken with $R^6$, $R^{11}$ or $R^{12}$ forms a $C_1$-$C_6$alkyl bridge, or when taken with $R^7$ forms a $C_3$-$C_6$cycloalkyl or heterocycle, or when taken with $R^{10}$ forms an aryl, heteroaryl, $C_3$-$C_6$cycloalkyl or heterocycle or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, COC$_1$-$C_6$alkyl, COC$_1$-$C_6$alkylN($R^{13}$)($R^{14}$), COC$_1$-$C_6$alkyl(OH)N($R^{13}$)($R^{14}$), $C_1$-$C_6$alkylCON($R^{13}$)($R^{14}$), CON($R^{13}$)($R^{14}$), SO$_2$C$_1$-$C_6$alkyl, SO$_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and COOC$_1$-$C_6$alkyl.

In certain embodiments described herein, $R^8$ is hydrogen. In certain embodiments described herein, $R^8$ is halogen. Examples of suitable halogens include, but are not limited to, chlorine, bromine, fluorine and iodine. In certain embodiments, $R^8$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^8$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^8$ is haloC$_1$-$C_6$alkyl. Suitable haloC$_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^8$ is OH. In certain embodiments, $R^8$ is $C_1$-$C_6$alkylOH. Examples of suitable alcohols, include, but are not limited to, methanol, ethanol, propanol, butanol and iso-butanol. In certain embodiments, $R^8$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether. In certain embodiments, $R^8$ is COOH.

In certain embodiments, $R^8$ is N($R^{13}$)($R^{14}$). Examples of suitable N($R^{13}$)($R^{14}$) groups include, but are not limited to, NH$_2$, NH(CH$_3$), N(CH$_3$)$_2$ and N(CH$_3$)$_2$. In certain embodiments, $R^8$ is $C_1$-$C_6$alkylN($R^{13}$)($R^{14}$). Examples of suitable $C_1$-$C_6$alkylN($R^{13}$)($R^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^8$ is $C_1$-$C_6$alkoxy. Examples of suitable alkoxys, include but are not limited to, methoxy, ethoxy, butoxy and propoxy. In certain embodiments, $R^8$ is COOC$_1$-$C_6$alkyl. Examples of suitable COOC$_1$-$C_6$alkyl groups include, but are not limited to, methoxycarbonyl, ethoxycarbonyl and butoxycarbonyl.

In certain embodiments, $R^8$, when taken with $R^7$ forms a $C_3$-$C_6$cycloalkyl or heterocycle, or when taken with $R^{10}$ forms an aryl, heteroaryl, $C_3$-$C_6$cycloalkyl or heterocycle, or when taken with $R^{15}$ forms a heteroaryl or heterocycle. In certain embodiments, $R^8$, when taken with $R^7$ forms a $C_3$-$C_6$cycloalkyl or heterocycle. In certain embodiments, $R^8$, when taken with $R^{10}$ forms an aryl, heteroaryl, $C_3$-$C_6$cycloalkyl or heterocycle. In certain embodiments, $R^8$, when taken with $R^{15}$ forms a heteroaryl or heterocycle.

In certain embodiments, $R^8$, when taken with $R^{10}$ forms an aryl group. Suitable aryl groups include but are not limited to, benzyl. In certain embodiments, $R^8$, when taken with $R^{10}$ or $R^{15}$ form an heteroaryl group. In certain embodiments, the heteroaryl group is a nitrogen containing heteroaryl group. In certain embodiments the heteroaryl group is an oxygen containing heteroaryl group. In certain embodiments the heteroaryl is a sulfur containing heteroaryl. Suitable heteroaryls include, but are not limited to, pyridyl (pyridinyl), oxazolyl, imidazolyl, triazolyl, furyl, triazinyl, thienyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl.

In certain embodiments, $R^8$, when taken with $R^7$ or $R^{10}$ form a cycloalkyl group. Suitable cycloalkyl groups include, but are not limited to, cyclopropyl, cyclobutyl, cyclopentyl, cyclohexyl. In certain embodiments, $R^8$, when taken with $R^7$, $R^{10}$ or $R^{15}$ form a heterocycle group. Suitable heterocycle groups include, but are not limited to, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl and tetrahydropyran.

In certain embodiments, $R^8$, when taken with $R^7$ forms a $C_3$-$C_6$cycloalkyl or heterocycle, or when taken with $R^{10}$ forms an aryl, heteroaryl, $C_3$-$C_6$cycloalkyl or heterocycle, or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and $COOC_1$-$C_6$alkyl.

In certain embodiments, $R^8$, when taken with $R^7$ forms a $C_3$-$C_6$cycloalkyl or heterocycle, or when taken with $R^{10}$ forms an aryl, heteroaryl, $C_3$-$C_6$cycloalkyl or heterocycle, or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, $COC_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkyCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), $C_1$-$C_6$alkyN($R^{13}$)($R^{14}$), $C_1$-$C_6$alkylaryl, $C_1$-$C_6$alkylhaloaryl, C(NH)N($R^{13}$)($R^{14}$), $C_1$-$C_6$alkoxy or $COOC_1$-$C_6$alkyl.

In certain embodiments, $R^8$, when taken with $R^7$ forms a $C_3$-$C_6$cycloalkyl or heterocycle, or when taken with $R^{10}$ forms an aryl, heteroaryl, $C_3$-$C_6$cycloalkyl or heterocycle, or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of methyl, ethyl, isopropyl, $NH_2$,

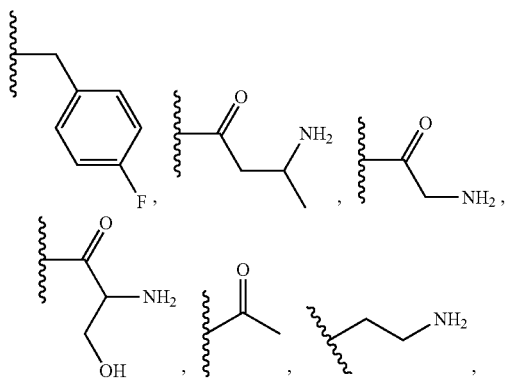

-continued

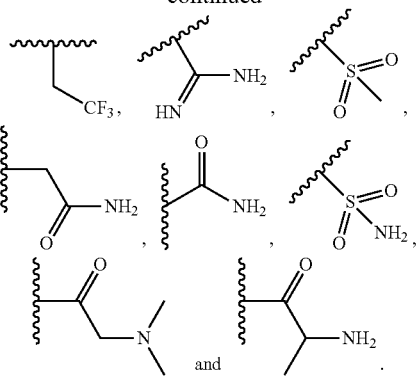

In certain embodiments, $R^8$, when taken with $R^6$, $R^{11}$ or $R^{12}$ forms a $C_1$-$C_6$alkyl bridge. Examples of suitable bridges include, but are not limited to,

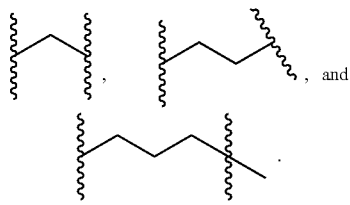

With regard to the compounds described herein, $R^9$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkylN($R^{13}$)($R^{14}$), $C_1$-$C_6$alkoxy or $COOC_1$-$C_6$alkyl or when taken with $R^{10}$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and $COOC_1$-$C_6$alkyl.

In certain embodiments described herein, $R^9$ is hydrogen. In certain embodiments described herein, $R^9$ is halogen. Examples of suitable halogens include, but are not limited to, chlorine, bromine, fluorine and iodine. In certain embodiments, $R^9$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^9$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^9$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^9$ is OH. In certain embodiments, $R^9$ is $C_1$-$C_6$alkylOH.

Examples of suitable alcohols, include, but are not limited to, methanol, ethanol, propanol, butanol and iso-butanol. In certain embodiments, $R^9$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^9$ is COOH.

In certain embodiments, $R^9$ is $N(R^{13})(R^{14})$. Examples of suitable $N(R^{13})(R^{14})$ groups include, but are not limited to, $NH_2$, $NH(CH_3)$, $N(CH_3)_2$ and $N(CH_3)_2$. In certain embodiments, $R^9$ is $C_1$-$C_6$alkyl$N(R^{13})(R^{14})$. Examples of suitable $C_1$-$C_6$alkyl$N(R^{13})(R^{14})$ groups include, but are not limited to, $CH_2NH_2$, $CH_2NH(CH_3)$, $CH_2N(CH_3)_2$ and $CH_2CH_2N(CH_3)_2$.

In certain embodiments, $R^9$ is $C_1$-$C_6$alkoxy. Examples of suitable alkoxys, include but are not limited to, methoxy, ethoxy, butoxy and propoxy. In certain embodiments, $R^9$ is COO$C_1$-$C_6$alkyl. Examples of suitable COO$C_1$-$C_6$alkyl groups include, but are not limited to, methoxycarbonyl, ethoxycarbonyl and butoxycarbonyl.

In certain embodiments, $R^9$, when taken with $R^{10}$ forms a $C_3$-$C_6$cycloalkyl or heterocycle.

In certain embodiments, $R^9$, when taken with $R^{10}$ forms a cycloalkyl group. Suitable cycloalkyl groups include, but are not limited to, cyclopropyl, cyclobutyl, cyclopentyl, cyclohexyl. In certain embodiments, $R^9$, when taken with $R^{10}$ forms a heterocycle group. Suitable heterocycle groups include, but are not limited to, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl and tetrahydropyran.

In certain embodiments, $R^9$, when taken with $R^{10}$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_3$-$C_6$cycloalkyl, oxo, $C_1$-$C_6$alkyl, $C_1$-$C_6$haloalkyl, CO$C_1$-$C_6$alkyl, CO$C_1$-$C_6$alkylN(R^{13})(R^{14})$, CO$C_1$-$C_6$alkyl(OH)N(R^{13})(R^{14})$, $C_1$-$C_6$alkylCON(R^{13})(R^{14})$, CON(R^{13})(R^{14})$, $SO_2C_1$-$C_6$alkyl, $SO_2N(R^{13})(R^{14})$, $N(R^{13})(R^{14})$, $C_1$-$C_6$alkylN(R^{13})(R^{14})$, $C_1$-$C_6$alkylaryl, $C_1$-$C_6$alkylhaloaryl, C(NH)N(R^{13})(R^{14})$, heteroaryl, $C_1$-$C_6$alkoxy and COO$C_1$-$C_6$alkyl.

In certain embodiments, $R^9$, when taken with $R^{10}$ forms a $C_3$-$C_6$cycloalkyl or heterocycle, wherein the $C_3$-$C_6$cycloalkyl or heterocycle is unsubstituted or substituted with 1 to 3 substituents selected from the group consisting of OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, CO$C_1$-$C_6$alkyl, CO$C_1$-$C_6$alkyN(R^{13})(R^{14})$, CO$C_1$-$C_6$alkyl(OH)N(R^{13})(R^{14})$, $C_1$-$C_6$alkylCON(R^{13})(R^{14})$, CON(R^{13})(R^{14})$, $SO_2C_1$-$C_6$alkyl, $SO_2N(R^{13})(R^{14})$, $N(R^{13})(R^{14})$, $C_1$-$C_6$alkylN(R^{13})(R^{14})$, $C_1$-$C_6$alkylaryl, $C_1$-$C_6$alkylhaloaryl, C(NH)N(R^{13})(R^{14})$, $C_1$-$C_6$alkoxy or COO$C_1$-$C_6$alkyl.

In certain embodiments, $R^9$, when taken with $R^{10}$ forms a $C_3$-$C_6$cycloalkyl or heterocycle, wherein the $C_3$-$C_6$cycloalkyl or heterocycle is unsubstituted or substituted with 1 to 3 substituents selected from the group consisting of methyl ethyl isopropyl, $NH_2$,

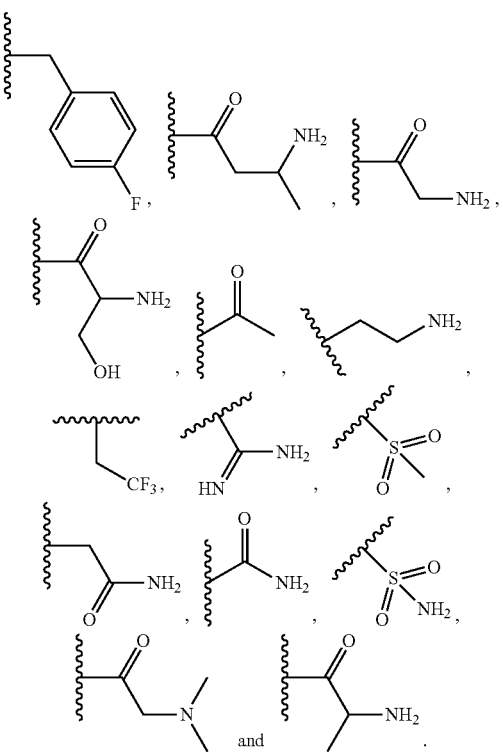

With regard to the compounds described herein, $R^1$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, $N(R^{13})(R^{14})$, $C_1$-$C_6$alkylN(R^{13})(R^{14})$, $C_1$-$C_6$alkoxy or COO$C_1$-$C_6$alkyl or when taken with $R^6$ or $R^8$ form an aryl, heteroaryl, $C_3$-$C_6$cycloalkyl or heterocycle, or when taken with $R^9$ forms a $C_3$-$C_6$cycloalkyl or heterocycle, or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, CO$C_1$-$C_6$alkyl, CO$C_1$-$C_6$alkylN(R^{13})(R^{14})$, CO$C_1$-$C_6$alkyl(OH)N(R^{13})(R^{14})$, $C_1$-$C_6$alkylCON(R^{13})(R^{14})$, CON(R^{13})(R^{14})$, $SO_2C_1$-$C_6$alkyl, $SO_2N(R^{13})(R^{14})$, $N(R^{13})(R^{14})$, $C_1$-$C_6$alkylN(R^{13})(R^{14})$, $C_1$-$C_6$alkylaryl, $C_1$-$C_6$alkylhaloaryl, C(NH)N(R^{13})(R^{14})$, heteroaryl, $C_1$-$C_6$alkoxy and COO$C_1$-$C_6$alkyl.

In certain embodiments described herein, $R^{10}$ is hydrogen. In certain embodiments described herein, $R^{10}$ is halogen. Examples of suitable halogens include, but are not limited to, chlorine, bromine, fluorine and iodine. In certain embodiments, $R^{10}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{10}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{10}$ is haloC$_1$-C$_6$alkyl. Suitable haloC$_1$-C$_6$alkyls include but are not limited to, fluoromethyl, difluoromethyl, trifluoromethyl, 2-fluoroethyl, 1,2-difluoroethyl and 2,2-difluoroethyl. In certain embodiments, $R^{10}$ is OH. In certain embodiments, $R^{10}$ is C$_1$-C$_6$alkylOH. Examples of suitable alcohols, include, but are not limited to, methanol, ethanol, propanol, butanol and iso-butanol. In certain embodiments, $R^{10}$ is C$_1$-C$_6$alkylOC$_1$-C$_6$alkyl. Suitable C$_1$-C$_6$alkylOC$_1$-C$_6$alkyls include but are not limited to, dimethyl ether, ethyl methyl ether, diethyl ether, dipropyl ether, dibutyl ether and diisopropyl ether. In certain embodiments, $R^{10}$ is COOH.

In certain embodiments, $R^{10}$ is N(R$^{13}$)(R$^{14}$). Examples of suitable N(R$^{13}$)(R$^{14}$) groups include, but are not limited to, NH$_2$, NH(CH$_3$), N(CH$_3$)$_2$ and N(CH$_3$)$_2$. In certain embodiments, $R^{10}$ is C$_1$-C$_6$alkylN(R$^{13}$)(R$^{14}$). Examples of suitable C$_1$-C$_6$alkylN(R$^{13}$)(R$^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^{10}$ is C$_1$-C$_6$alkoxy. Examples of suitable alkoxys, include but are not limited to, methoxy, ethoxy, butoxy and propoxy. In certain embodiments, $R^{10}$ is COOC$_1$-C$_6$alkyl. Examples of suitable COOC$_1$-C$_6$alkyl groups include, but are not limited to, methoxycarbonyl, ethoxycarbonyl and butoxycarbonyl.

In certain embodiments, $R^{10}$, when taken with $R^6$ or $R^8$ forms an aryl, heteroaryl, C$_3$-C$_6$cycloalkyl or heterocycle, or when taken with $R^9$ form a C$_3$-C$_6$cycloalkyl or heterocycle, or when taken with $R^{15}$ forms a heteroaryl or heterocycle. In certain embodiments, $R^{10}$, when taken with $R^6$ forms an aryl, heteroaryl, C$_3$-C$_6$cycloalkyl or heterocycle. In certain embodiments, $R^{10}$, when taken with $R^8$ forms an aryl, heteroaryl, C$_3$-C$_6$cycloalkyl or heterocycle. In certain embodiments, $R^{10}$, when taken with $R^9$ forms a C$_3$-C$_6$cycloalkyl or heterocycle. In certain embodiments, $R^{10}$ when taken with $R^{15}$ forms a heteroaryl or heterocycle.

In certain embodiments, $R^{10}$, when taken with $R^6$ or $R^8$ forms an aryl group. Suitable aryl groups include but are not limited to, benzyl. In certain embodiments, $R^{10}$, when taken with $R^6$ or $R^8$ or $R^{15}$ form an heteroaryl group. In certain embodiments, the heteroaryl group is a nitrogen containing heteroaryl group. In certain embodiments the heteroaryl group is an oxygen containing heteroaryl group. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl.

In certain embodiments, $R^1$, when taken with $R^6$, $R^8$ or $R^9$ forms a cycloalkyl group. Suitable cycloalkyl groups include, but are not limited to, cyclopropyl, cyclobutyl, cyclopentyl, cyclohexyl. In certain embodiments, $R^{10}$, when taken with $R^6$, $R^8$, $R^9$ or $R^{15}$ form a heterocycle group. Suitable heterocycle groups include, but are not limited to, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl and tetrahydropyran.

In certain embodiments, $R^{10}$, when taken with $R^6$ or $R^8$ forms an aryl, heteroaryl, C$_3$-C$_6$cycloalkyl or heterocycle, or when taken with $R^9$ forms a C$_3$-C$_6$cycloalkyl or heterocycle, or when taken with $R^{15}$ forms a heteroaryl or heterocycle, wherein the aryl, heteroaryl, C$_3$-C$_6$cycloalkyl or heterocycle is unsubstituted or substituted with 1 to 3 substituents selected from the group consisting of halogen, OH, C$_1$-C$_6$alkylOH, C$_3$-C$_6$cycloalkyl, oxo, C$_1$-C$_6$alkyl, C$_1$-C$_6$haloalkyl, COC$_1$-C$_6$alkyl, COC$_1$-C$_6$alkylN(R$^{13}$)(R$^{14}$), COC$_1$-C$_6$alkyl(OH)N(R$^{13}$)(R$^{14}$), C$_1$-C$_6$alkylCON(R$^{13}$)(R$^{14}$), CON(R$^{13}$)(R$^{14}$), SO$_2$C$_1$-C$_6$alkyl, SO$_2$N(R$^{13}$)(R$^{14}$), N(R$^{13}$)(R$^{14}$), C$_1$-C$_6$alkyN(R$^{13}$)(R$^{14}$), C$_1$-C$_6$alkylaryl, C$_1$-C$_6$alkylhaloaryl, C(NH)N(R$^{13}$)(R$^{14}$), heteroaryl, C$_1$-C$_6$alkoxy and COOC$_1$-C$_6$alkyl.

In certain embodiments, $R^1$, when taken with $R^6$ or $R^8$ forms an aryl, heteroaryl, C$_3$-C$_6$cycloalkyl or heterocycle, or when taken with $R^9$ forms a C$_3$-C$_6$cycloalkyl or heterocycle, or when taken with $R^{15}$ forms a heteroaryl or heterocycle, wherein the aryl, heteroaryl, C$_3$-C$_6$cycloalkyl or heterocycle is unsubstituted or substituted with 1 to 3 substituents selected from the group consisting of OH, C$_1$-C$_6$alkylOH, C$_3$-C$_6$cycloalkyl, C$_1$-C$_6$alkylOC$_1$-C$_6$alkyl, oxo, C$_1$-C$_6$alkyl, C$_1$-C$_6$haloalkyl, COC$_1$-C$_6$alkyl, COC$_1$-C$_6$alkylN(R$^{13}$)(R$^{14}$), COC$_1$-C$_6$alkyl(OH)N(R$^{13}$)(R$^{14}$), C$_1$-C$_6$alkylCON(R$^{13}$)(R$^{14}$), CON(R$^{13}$)(R$^{14}$), SO$_2$C$_1$-C$_6$alkyl, SO$_2$N(R$^{13}$)(R$^{14}$), N(R$^{13}$)(R$^{14}$), C$_1$-C$_6$alkyIN(R$^{13}$)(R$^{14}$), C$_1$-C$_6$alkylaryl, C$_1$-C$_6$alkylhaloaryl, C(NH)N(R$^{13}$)(R$^{14}$), C$_1$-C$_6$alkoxy or COOC$_1$-C$_6$alkyl.

In certain embodiments, $R^1$, when taken with $R^6$ or $R^8$ forms an aryl, heteroaryl, C$_3$-C$_6$cycloalkyl or heterocycle, or when taken with $R^9$ forms a C$_3$-C$_6$cycloalkyl or heterocycle, or when taken with $R^{15}$ forms a heteroaryl or heterocycle, wherein the aryl, heteroaryl, C$_3$-C$_6$cycloalkyl or heterocycle is unsubstituted or substituted with 1 to 3 substituents selected from the group consisting of methyl, ethyl, isopropyl, NH$_2$,

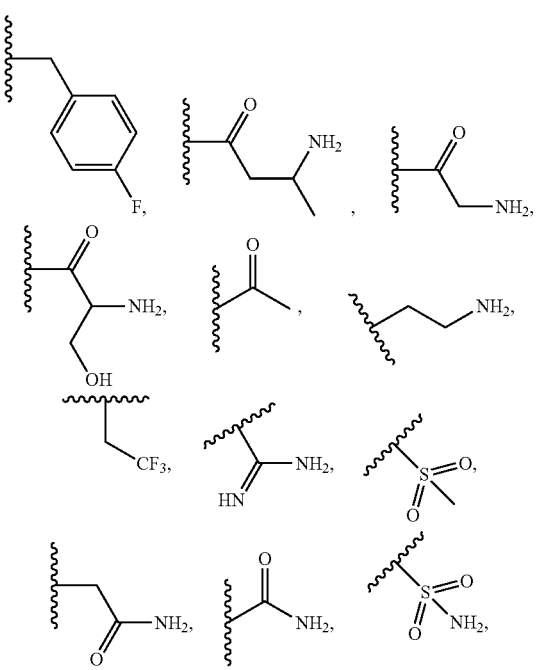

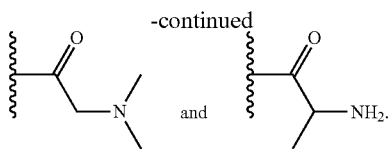

In certain embodiments of the compounds described herein, X is $CR^9R^{10}$, wherein $R^{10}$ when taken with $R^9$ forms a heterocycle. In certain embodiments of the compounds described herein, X is $CR^9R^{10}$, wherein $R^{10}$ when taken with $R^9$ forms a pyrrolidine. In certain embodiments, the heterocycle or pyrrolidine is substituted with a substituent selected from the group consisting of halogen, OH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, $COC_1$-$C_6$alkyl, $COC_1$-$C_6$alkylN$(R^{13})(R^{14})$, $COC_1$-$C_6$alkyl(OH)N$(R^{13})(R^{14})$, $C_1$-$C_6$alkylCON$(R^{13})(R^{14})$, $CON(R^{13})(R^{14})$, $SO_2C_1$-$C_6$alkyl, $SO_2N(R^{13})(R^{14})$, $N(R^{13})(R^{14})$, $C_1$-$C_6$alkyN$(R^{13})(R^{14})$, $C_1$-$C_6$alkylaryl, $C_1$-$C_6$alkylhaloaryl, $C(NH)N(R^{13})(R^{14})$, $C_1$-$C_6$alkoxy or $COOC_1$-$C_6$alkyl.

In certain embodiments of the compounds described herein, X is $CR^9R^{10}$ and $R^9$ is hydrogen and $R^{10}$ when taken with $R^8$ forms a heterocycle. In certain embodiments of the compounds described herein, X is $CR^9R^{10}$ and $R^9$ is hydrogen and $R^{10}$ when taken with $R^8$ forms a pyrrolidine. In certain embodiments the heterocycle or pyrrolidine is substituted with a substituent selected from the group consisting of halogen, OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, $COC_1$-$C_6$alkyl, $COC_1$-$C_6$alkylN$(R^{13})(R^{14})$, $COC_1$-$C_6$alkyl(OH)N$(R^{13})(R^{14})$, $C_1$-$C_6$alkylCON$(R^{13})(R^{14})$, $CON(R^{13})(R^{14})$, $SO_2C_1$-$C_6$alkyl, $SO_2N(R^{13})(R^{14})$, $N(R^{13})(R^{14})$, —$C_1$-$C_6$alkylN$(R^{13})(R^{14})$, $C_1$-$C_6$alkylaryl, $C_1$-$C_6$alkylhaloaryl, $C(NH)N(R^{13})(R^{14})$, $C_1$-$C_6$alkoxy and $COOC_1$-$C_6$alkyl, wherein $R^{13}$ is hydrogen, $C_3$-$C_6$cycloalkyl, $C_1$-$C_6$alkyl or $COC_1$-$C_6$alkyl.

With regard to the compounds described herein, $R^{11}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, $N(R^{13})(R^{14})$, $C_1$-$C_6$alkylN$(R^{13})(R^{14})$, $C_1$-$C_6$alkoxy or $COOC_1$-$C_6$alkyl or when taken with $R^{12}$ form a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkyN$(R^{13})(R^{14})$, $COC_1$-$C_6$alkyl(OH)N$(R^{13})(R^{14})$, $C_1$-$C_6$alkylCON$(R^{13})(R^{14})$, $CON(R^{13})(R^{14})$, $SO_2C_1$-$C_6$alkyl, $SO_2N(R^{13})(R^{14})$, $N(R^{13})(R^{14})$, $C_1$-$C_6$alkylN$(R^{13})(R^{14})$, $C_1$-$C_6$alkylaryl, $C_1$-$C_6$alkylhaloaryl, $C(NH)N(R^{13})(R^{14})$, heteroaryl, $C_1$-$C_6$alkoxy and $COOC_1$-$C_6$alkyl.

In certain embodiments described herein, $R^{11}$ is hydrogen. In certain embodiments described herein, $R^{11}$ is halogen. Examples of suitable halogens include, but are not limited to, chlorine, bromine, fluorine and iodine. In certain embodiments, $R^{11}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{11}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{11}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{11}$ is OH. In certain embodiments, $R^{11}$ is $C_1$-$C_6$alkylOH. Examples of suitable alcohols, include, but are not limited to, methanol, ethanol, propanol, butanol and iso-butanol. In certain embodiments, $R^{11}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^{11}$ is COOH.

In certain embodiments, $R^{11}$ is $N(R^{13})(R^{14})$. Examples of suitable $N(R^{13})(R^{14})$ groups include, but are not limited to, $NH_2$, $NH(CH_3)$, $N(CH_3)_2$ and $N(CH_3)_2$. In certain embodiments, $R^{11}$ is $C_1$-$C_6$alkylN$(R^{13})(R^{14})$. Examples of suitable $C_1$-$C_6$alkylN$(R^{13})(R^{14})$ groups include, but are not limited to, $CH_2NH_2$, $CH_2NH(CH_3)$, $CH_2N(CH_3)_2$ and $CH_2CH_2N(CH_3)_2$.

In certain embodiments, $R^{11}$ is $C_1$-$C_6$alkoxy. Examples of suitable alkoxys, include but are not limited to, methoxy, ethoxy, butoxy and propoxy. In certain embodiments, $R^{11}$ is $COOC_1$-$C_6$alkyl. Examples of suitable $COOC_1$-$C_6$alkyl groups include, but are not limited to, methoxycarbonyl, ethoxycarbonyl and butoxycarbonyl.

In certain embodiments, $R^{11}$, when taken with $R^{12}$ forms a $C_3$-$C_6$cycloalkyl or heterocycle.

In certain embodiments, $R^{11}$, when taken with $R^{12}$ forms a cycloalkyl group. Suitable cycloalkyl groups include, but are not limited to, cyclopropyl, cyclobutyl, cyclopentyl, cyclohexyl.

In certain embodiments, $R^{11}$, when taken with $R^{12}$ forms a heterocycle group. Suitable heterocycle groups include, but are not limited to, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl and tetrahydropyran.

In certain embodiments, $R^{11}$, when taken with $R^{12}$ forms a $C_3$-$C_6$cycloalkyl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkyN$(R^{13})(R^{14})$, $COC_1$-$C_6$alkyl(OH)N$(R^{13})(R^{14})$, $C_1$-$C_6$alkylCON$(R^{13})(R^{14})$, $CON(R^{13})(R^{14})$, $SO_2C_1$-$C_6$alkyl, $SO_2N(R^{13})(R^{14})$, $N(R^{13})(R^{14})$, $C_1$-$C_6$alkylN$(R^{13})(R^{14})$, $C_1$-$C_6$alkylaryl, $C_1$-$C_6$alkylhaloaryl, $C(NH)N(R^{13})(R^{14})$, heteroaryl, $C_1$-$C_6$alkoxy and $COOC_1$-$C_6$alkyl.

In certain embodiments, $R^{11}$, when taken with $R^{12}$ forms a $C_3$-$C_6$cycloalkyl or heterocycle, wherein the $C_3$-$C_6$cycloalkyl or heterocycle is unsubstituted or substituted with 1 to 3 substituents selected from the group consisting of OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, $COC_1$-$C_6$alkyl, $COC_1$-$C_6$alkyN$(R^{13})(R^{14})$, $COC_1$-$C_6$alkyl(OH)N$(R^{13})(R^{14})$, $C_1$-$C_6$alkyCON$(R^{13})(R^{14})$, $CON(R^{13})(R^{14})$, $SO_2C_1$-$C_6$alkyl, $SO_2N(R^{13})(R^{14})$, $N(R^{13})(R^{14})$, $C_1$-$C_6$alkylN$(R^{13})(R^{14})$, $C_1$-$C_6$alkylaryl, $C_1$-$C_6$alkylhaloaryl, $C(NH)N(R^{13})(R^{14})$, $C_1$-$C_6$alkoxy or $COOC_1$-$C_6$alkyl.

In certain embodiments, $R^{11}$, when taken with $R^{12}$ forms a $C_3$-$C_6$cycloalkyl or heterocycle, wherein the $C_3$-$C_6$cycloalkyl or heterocycle is unsubstituted or substituted with 1 to 3 substituents selected from the group consisting of methyl, ethyl, isopropyl, $NH_2$,

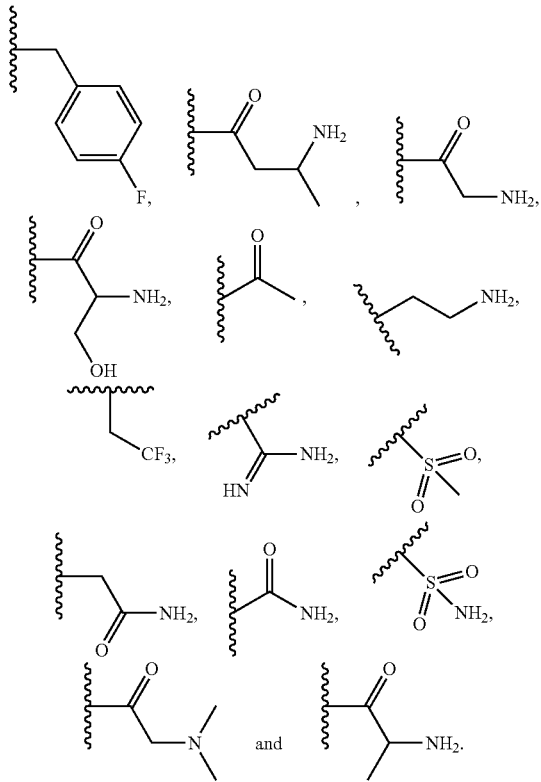

With regard to the compounds described herein, $R^{12}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC_1$-$C_6$alkyl, COOH, $N(R^{13})(R^{14})$, $C_1$-$C_6$alkylN($R^{13}$)($R^{14}$), $C_1$-$C_6$alkoxy or $COOC_1$-$C_6$alkyl or when taken with $R^6$ forms an aryl, heteroaryl, $C_3$-$C_6$cycloalkyl or heterocycle, or when taken with $R^{11}$ forms a $C_3$-$C_6$cycloalkyl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), $CON(R^{13})(R^{14})$, $SO_2C_1$-$C_6$alkyl, $SO_2N(R^{13})(R^{14})$, $N(R^{13})(R^{14})$, $C_1$-$C_6$alkylN($R^{13}$)($R^{14}$), $C_1$-$C_6$alkylaryl, $C_1$-$C_6$alkylhaloaryl, $C(NH)N(R^{13})(R^{14})$, heteroaryl, $C_1$-$C_6$alkoxy and $COOC_1$-$C_6$alkyl.

In certain embodiments described herein, $R^{12}$ is hydrogen. In certain embodiments described herein, $R^{12}$ is halogen. Examples of suitable halogens include, but are not limited to, chlorine, bromine, fluorine and iodine. In certain embodiments, $R^{12}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{12}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{12}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{12}$ is OH. In certain embodiments, $R^{12}$ is $C_1$-$C_6$alkylOH. Examples of suitable alcohols, include, but are not limited to, methanol, ethanol, propanol, butanol and iso-butanol. In certain embodiments, $R^{12}$ is $C_1$-$C_6$alkylOC_1$-$C_6$alkyl. Suitable $C_1$-$C_6$alkylOC_1$-$C_6$alkyls include but are not limited to, dimethyl ether, ethyl methyl ether, diethyl ether, dipropyl ether, dibutyl ether and diisopropyl ether. In certain embodiments, $R^{12}$ is COOH.

In certain embodiments, $R^{12}$ is $N(R^{13})(R^{14})$. Examples of suitable $N(R^{13})(R^{14})$ groups include, but are not limited to, $NH_2$, $NH(CH_3)$, $N(CH_3)_2$ and $N(CH_3)_2$. In certain embodiments, $R^{12}$ is $C_1$-$C_6$alkylN($R^{13}$)($R^{14}$). Examples of suitable $C_1$-$C_6$alkylN($R^{13}$)($R^{14}$) groups include, but are not limited to, $CH_2NH_2$, $CH_2NH(CH_3)$, $CH_2N(CH_3)_2$ and $CH_2CH_2N(CH_3)_2$.

In certain embodiments, $R^{12}$ is $C_1$-$C_6$alkoxy. Examples of suitable alkoxys, include, but are not limited to, methoxy, ethoxy, butoxy and propoxy. In certain embodiments, $R^{12}$ is $COOC_1$-$C_6$alkyl. Examples of suitable $COOC_1$-$C_6$alkyl groups include, but are not limited to, methoxycarbonyl, ethoxycarbonyl and butoxycarbonyl.

In certain embodiments, $R^{12}$, when taken with $R^6$ forms an aryl, heteroaryl, $C_3$-$C_6$cycloalkyl or heterocycle, or when taken with $R^{11}$ forms a $C_3$-$C_6$cycloalkyl or heterocycle. In certain embodiments, $R^{12}$, when taken with $R^6$ forms an aryl, heteroaryl, $C_3$-$C_6$cycloalkyl or heterocycle. In certain embodiments, $R^{12}$, when taken with $R^{11}$ forms a $C_3$-$C_6$cycloalkyl or heterocycle.

In certain embodiments, $R^{12}$, when taken with $R^6$ forms an aryl group. Suitable aryl groups include but are not limited to, benzyl. In certain embodiments, $R^{12}$, when taken with $R^6$ forms an heteroaryl group. In certain embodiments, the heteroaryl group is a nitrogen containing heteroaryl group. In certain embodiments the heteroaryl group is an oxygen containing heteroaryl group. In certain embodiments the heteroaryl is a sulfur containing heteroaryl. Suitable heteroaryls include, but are not limited to, pyridyl (pyridinyl), oxazolyl, imidazolyl, triazolyl, furyl, triazinyl, thienyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl.

In certain embodiments, $R^{12}$, when taken with $R^6$ or $R^{11}$ forms a cycloalkyl group. Suitable cycloalkyl groups include, but are not limited to, cyclopropyl, cyclobutyl, cyclopentyl, cyclohexyl. In certain embodiments, $R^{12}$, when taken with $R^6$ or $R^{11}$ forms a heterocycle group. Suitable heterocycle groups include, but are not limited to, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl and tetrahydroisoquinolinyl, dihydroindolyl and tetrahydropyran.

In certain embodiments, $R^{12}$, when taken with $R^6$ forms an aryl, heteroaryl, $C_3$-$C_6$cycloalkyl or heterocycle, or when taken with $R^{11}$ forms a $C_3$-$C_6$cycloalkyl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkyN($R^{13}$)($R^{14}$), $COC_1$-$C_6$alkyl(OH)N($R^{13}$)($R^{14}$) $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and $COOC_1$-$C_6$alkyl.

In certain embodiments, $R^{12}$, when taken with $R^6$ forms an aryl, heteroaryl, $C_3$-$C_6$cycloalkyl or heterocycle, or when taken with $R^{11}$ forms a $C_3$-$C_6$cycloalkyl or heterocycle, wherein the aryl, heteroaryl, $C_3$-$C_6$cycloalkyl or heterocycle is unsubstituted or substituted with 1 to 3 substituents selected from the group consisting of OH, $C_1$-$C_6$alkylOH, $C_3$-$C_6$cycloalkyl, $C_1$-$C_6$alkylOC_1-$C_6$alkyl, oxo, $C_1$-$C_6$alkyl, $C_1$-$C_6$haloalkyl, $COC_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkyCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), $C_1$-$C_6$alkoxy or $COOC_1$-$C_6$alkyl.

In certain embodiments, $R^{12}$, when taken with $R^6$ forms an aryl, heteroaryl, $C_3$-$C_6$cycloalkyl or heterocycle, or when taken with $R^{11}$ forms a $C_3$-$C_6$cycloalkyl or heterocycle, wherein the aryl, heteroaryl, $C_3$-$C_6$cycloalkyl or heterocycle is unsubstituted or substituted with 1 to 3 substituents selected from the group consisting of methyl, ethyl, isopropyl, $NH_2$,

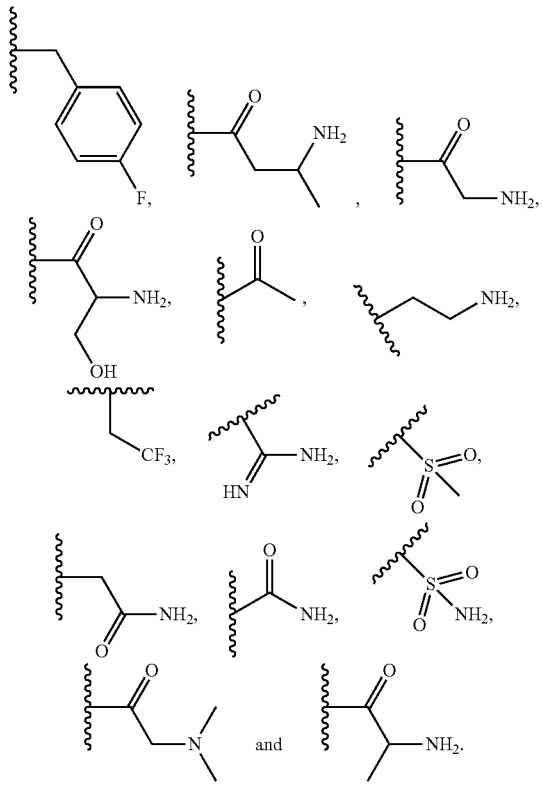

With regard to the compounds described herein, $R^{13}$ is hydrogen, $C_3$-$C_6$cycloalkyl, $C_1$-$C_6$alkyl, $COC_1$-$C_6$alkylNH_2$, $COC_1$-$C_6$alkylNH($C_1$-$C_6$alkyl), $COC_1$-$C_6$alkyN($C_1$-$C_6$alkyl)$_2$, $C_1$-$C_6$haloalkyl, $C_1$-$C_6$alkylOH or $COC_1$-$C_6$alkyl. In certain embodiments, $R^{13}$ is hydrogen. In certain embodiments, $R^{13}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{13}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{13}$ is $COC_1$-$C_6$alkylNH_2$. In certain embodiments, $R^{13}$ is $COC_1$-$C_6$alkylNH($C_1$-$C_6$alkyl). In certain embodiments, $R^{13}$ is $COC_1$-$C_6$alkylN($C_1$-$C_6$alkyl)$_2$.

In certain embodiments, $R^{13}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{13}$ is $C_1$-$C_6$alkylOH. Examples of suitable alcohols, include, but are not limited to, methanol, ethanol, propanol, butanol and iso-butanol.

With regard to the compounds described herein, $R^{14}$ is hydrogen, $C_3$-$C_6$cycloalkyl, $C_1$-$C_6$alkyl, $COC_1$-$C_6$alkylNH_2$, $COC_1$-$C_6$alkylNH($C_1$-$C_6$alkyl), $COC_1$-$C_6$alkylN($C_1$-$C_6$alkyl)$_2$, or $COC_1$-$C_6$alkyl. In certain embodiments, $R^{14}$ is hydrogen. In certain embodiments, $R^{14}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{14}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{14}$ is $COC_1$-$C_6$alkylNH_2$. In certain embodiments, $R^{14}$ is $COC_1$-$C_6$alkylNH($C_1$-$C_6$alkyl). In certain embodiments, $R^{14}$ is $COC_1$-$C_6$alkyN($C_1$-$C_6$alkyl)$_2$.

In certain embodiments, $R^{14}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{14}$ is $C_1$-$C_6$alkylOH. Examples of suitable alcohols, include, but are not limited to, methanol, ethanol, propanol, butanol and iso-butanol.

With regard to the compounds described herein, $R^{15}$ is hydrogen, $C_3$-$C_6$cycloalkyl, $C_1$-$C_6$alkyl, $COC_1$-$C_6$alkylN($R^{13}$)($R^{14}$) or $COC_1$-$C_6$alkyl or when taken with $R^6$ or $R^8$ forms a heteroaryl, or heterocycle, wherein a heteroaryl or heterocycle is unsubstituted or substituted with 1 to 3 substituents selected from the group consisting of halogen, OH, $C_3$-$C_6$cycloalkyl, $C_1$-$C_6$alkylOC_1-$C_6$alkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkyCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), —$C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and $COOC_1$-$C_6$alkyl.

In certain embodiments, $R^{15}$ is hydrogen. In certain embodiments, $R^{15}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{15}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{15}$ is $COC_1$-$C_6$alkyN($R^{13}$)($R^{14}$). Examples of suitable $COC_1$-$C_6$alkylN($R^{13}$)($R^{14}$) groups include, but are not limited to, $COCH_2NH_2$, $COCH_2NH(CH_3)$, $COCH_2N(CH_3)_2$ and $COCH_2CH_2N(CH_3)_2$. In certain embodiments, $R^{15}$ is $COC_1$-$C_6$alkyl. Examples of suitable $COC_1$-$C_6$alkyl groups include, but are not limited to, $COCH_3$, $COCH_2(CH_3)$, $COCH_2(CH_3)_2$ and $COCH_2CH_2(CH_3)_2$.

In certain embodiments, $R^{15}$, when taken with $R^6$ or $R^8$ forms a heteroaryl or heterocycle. In certain embodiments, $R^{15}$, when taken with $R^6$ forms a heteroaryl or heterocycle. In certain embodiments, $R^{15}$, when taken with $R^8$ forms a heteroaryl or heterocycle.

In certain embodiments, $R^{15}$, when taken with $R^6$ or $R^8$ forms an heteroaryl group. In certain embodiments, the heteroaryl group is a nitrogen containing heteroaryl group. In certain embodiments the heteroaryl group is an oxygen containing heteroaryl group. In certain embodiments the heteroaryl is a sulfur containing heteroaryl. Suitable heteroaryls include, but are not limited to, pyridyl (pyridinyl), oxazolyl, imidazolyl, triazolyl, furyl, triazinyl, thienyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl.

In certain embodiments, $R^{15}$, when taken with $R^6$ or $R^8$ forms a heteroaryl or heterocycle, wherein the heteroaryl or heterocycle is unsubstituted or substituted with 1 to 3 substituents selected from the group consisting of halogen, OH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkyCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, $C_1$-$C_6$alkyN($R^{13}$)($R^{14}$), $C_1$-$C_6$alkylaryl, $C_1$-$C_6$alkylhaloaryl, $C(NH)N(R^{13})(R^{14})$, heteroaryl, $C_1$-$C_6$alkoxy and $COOC_1$-$C_6$alkyl.

In certain embodiments, $R^{15}$, when taken with $R^6$ or $R^8$ forms a heteroaryl or heterocycle, wherein the heteroaryl or heterocycle is unsubstituted or substituted with 1 to 3 substituents selected from the group consisting of OH, $C_3$-$C_6$cycloalkyl, $C_1$-$C_6$alkylOC_1$-$C_6$alkyl, oxo, $C_1$-$C_6$alkyl, $C_1$-$C_6$haloalkyl, $COC_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, $C_1$-$C_6$alkyN($R^{13}$)($R^{14}$), $C_1$-$C_6$alkylaryl, $C_1$-$C_6$alkylhaloaryl, $C(NH)N(R^{13})(R^{14})$, $C_1$-$C_6$alkoxy or $COOC_1$-$C_6$alkyl.

In certain embodiments, $R^{15}$, when taken with $R^6$ or $R^8$ forms a heteroaryl or heterocycle, wherein the aryl, heteroaryl, $C_3$-$C_6$cycloalkyl or heterocycle is unsubstituted or substituted with 1 to 3 substituents selected from the group consisting of methyl, ethyl, isopropyl, $NH_2$,

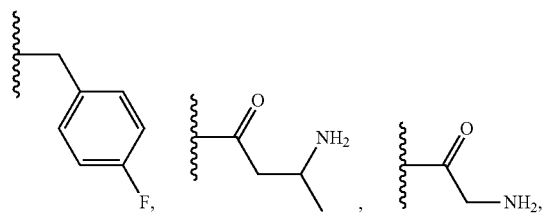

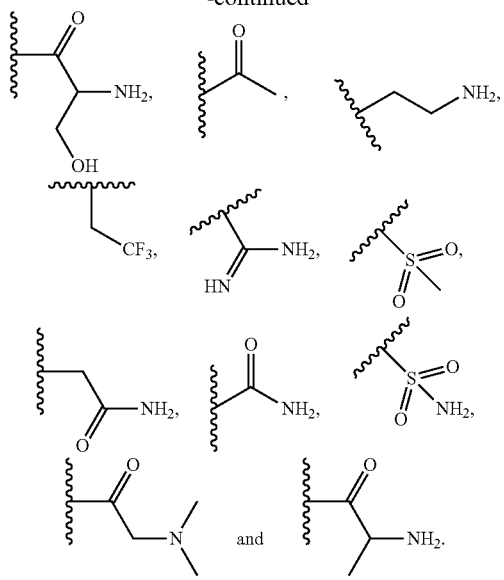

In certain embodiments, $R^6$, when taken with $R^{10}$, forms

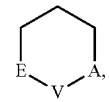

wherein

A is NH or $CH_2$;

E is a bond, NH or $CHR^{21}$;

V is O, $NR^{22}$ or $CHR^{23}$;

$R^{21}$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, $N(R^{13})(R^{14})$, $C_1$-$C_6$alkyN($R^{13}$)($R^{14}$), $C_1$-$C_6$alkoxy, $COOC_1$-$C_6$alkyl, $COC_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $C_1$-$C_6$alkylaryl, $C_1$-$C_6$alkylhaloaryl, $C(NH)N(R^{13})(R^{14})$ or heteroaryl;

$R^{22}$ is hydrogen, $C_3$-$C_6$cycloalkyl, $C_1$-$C_6$alkyl, haloC$_1$-$C_6$alkyl, $C_1$-$C_6$alkylOH, $C_1$-$C_6$alkylOC$_1$-$C_6$alkyl, COOH, $C_1$-$C_6$alkylN($R^{13}$)($R^{14}$), $COOC_1$-$C_6$alkyl, $COC_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $C_1$-$C_6$alkylaryl, $C_1$-$C_6$alkylhaloaryl, $C(NH)N(R^{13})(R^{14})$ or heteroaryl; and $R^{23}$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, $N(R^{13})(R^{14})$, $C_1$-$C_6$alkyN($R^{13}$)($R^{14}$), $C_1$-$C_6$alkoxy, $COOC_1$-$C_6$alkyl, $COC_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2N(R^{13})(R^{14})$, $C_1$-$C_6$alkylaryl, $C_1$-$C_6$alkylhaloaryl, $C(NH)N(R^{13})(R^{14})$ or heteroaryl.

With regard to the compounds described herein, A is NH or $CH_2$. In certain embodiments, A is NH. In other embodiments, A is $CH_2$.

With regard to the compounds described herein, E is a bond, NH or $CHR^{21}$. In certain embodiments, E is a bond. In other embodiments, E is NH. In still other embodiments, E is $CHR^{21}$.

With regard to the compounds described herein, V is O, $NR^{22}$ or $CR^{23}$. In certain embodiments, V is O. In certain embodiments, V is $NR^{22}$. In other embodiments, V is $CHR^{23}$. In certain embodiments, V is $NR^{22}$ or $CHR^{23}$. In certain embodiments, V is $CH(NH_2)$.

In certain embodiments, A and V cannot be simultaneously NH and $NR^{22}$ or E and V cannot be simultaneously NH and $NR^{22}$.

With regard to the compounds described herein, $R^{21}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC_1$-$C_6$alkyl, COOH, $N(R^{13})(R^{14})$, $C_1$-$C_6$alkylN(R^{13})(R^{14})$, $C_1$-$C_6$alkoxy, $COOC_1$-$C_6$alkyl, $COC_1$-$C_6$alkyl, $COC_1$-$C_6$alkyN(R^{13})(R^{14})$, $COC_1$-$C_6$alkyl(OH)N(R^{13})(R^{14})$, $C_1$-$C_6$alkyCON(R^{13})(R^{14})$, $CON(R^{13})(R^{14})$, $SO_2C_1$-$C_6$alkyl, $SO_2N(R^{13})(R^{14})$, $C_1$-$C_6$alkylaryl, $C_1$-$C_6$alkylhaloaryl or $C(NH)N(R^{13})(R^{14})$.

In certain embodiments, $R^{21}$ is hydrogen. In certain embodiments described herein, $R^{21}$ is halogen. Examples of suitable halogens include, but are not limited to, chlorine, bromine, fluorine and iodine. In certain embodiments, $R^{21}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{21}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{21}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{21}$ is OH. In certain embodiments, $R^{21}$ is $C_1$-$C_6$alkylOH. Examples of suitable alcohols, include, but are not limited to, methanol, ethanol, propanol, butanol and iso-butanol. In certain embodiments, $R^{21}$ is $C_1$-$C_6$alkylOC_1$-$C_6$alkyl. Suitable $C_1$-$C_6$alkylOC_1$-$C_6$alkyls include but are not limited to, dimethyl ether, ethyl methyl ether, diethyl ether, dipropyl ether, dibutyl ether and diisopropyl ether. In certain embodiments, $R^{21}$ is COOH.

In certain embodiments, $R^{21}$ is $N(R^{13})(R^{14})$. Examples of suitable $N(R^{13})(R^{14})$ groups include, but are not limited to, $NH_2$, $NH(CH_3)$, $N(CH_3)_2$ and $N(CH_3)_2$. In certain embodiments, $R^{21}$ is $C_1$-$C_6$alkylN(R^{13})(R^{14})$. Examples of suitable $C_1$-$C_6$alkylN(R^{13})(R^{14})$ groups include, but are not limited to, $CH_2NH_2$, $CH_2NH(CH_3)$, $CH_2N(CH_3)_2$ and $CH_2CH_2N(CH_3)_2$.

In certain embodiments, $R^{21}$ is $C_1$-$C_6$alkoxy. Examples of suitable alkoxys, include, but are not limited to, methoxy, ethoxy, butoxy and propoxy. In certain embodiments, $R^{21}$ is $COOC_1$-$C_6$alkyl. Examples of suitable $COOC_1$-$C_6$alkyl groups include, but are not limited to, methoxycarbonyl, ethoxycarbonyl and butoxycarbonyl.

In certain embodiments, $R^{21}$ is $COC_1$-$C_6$alkyl. Suitable $COC_1$-$C_6$alkyl groups include $COCH_3$ and $COCH_2CH_3$. In certain embodiments, $R^{21}$ is $COC_1$-$C_6$alkyN(R^{13})(R^{14})$. Suitable examples of $COC_1$-$C_6$alkyN(R^{13})(R^{14})$ groups include, but are not limited to,

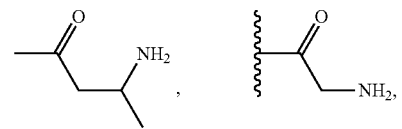

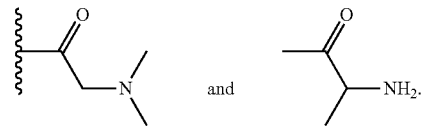

In certain embodiments, $R^{21}$ is $COC_1$-$C_6$alkyl(OH)N(R^{13})(R^{14})$. Suitable examples $COC_1$-$C_6$alkyl(OH)N(R^{13})(R^{14})$ groups include, but are not limited to,

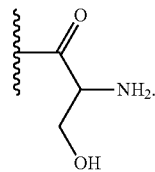 [SMILES: *C(=O)C(N)CO]

In certain embodiments, $R^{21}$ is $C_1$-$C_6$alkylCON(R^{13})(R^{14})$. Suitable groups include but are not to,

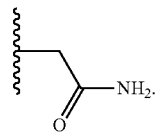

In certain embodiments, $R^{21}$ is $CON(R^{13})(R^{14})$. Suitable $CON(R^{13})(R^{14})$ groups include, but are not limited to, $CONH_2$. In certain embodiments, $R^{21}$ is $SO_2C_1$-$C_6$alkyl. Suitable $SO_2C_1$-$C_6$alkyl groups include, but are not limited to, $SO_2CH_3$. In certain embodiments, $R^{21}$ is $SO_2N(R^{13})(R^{14})$. Suitable $SO_2N(R^{13})(R^{14})$ groups include, but are not limited to, $SO_2NH_2$. In certain embodiments, $R^{21}$ is $C_1$-$C_6$alkylaryl. In certain embodiments, $R^{21}$ is $C_1$-$C_6$alkylhaloaryl. In certain embodiments, $R^{21}$ is $C(NH)N(R^{13})(R^{14})$. In certain embodiments, $R^{21}$ is heteroaryl.

In certain embodiments, $R^{21}$ is selected from the group consisting of methyl, ethyl, isopropyl, $NH_2$,

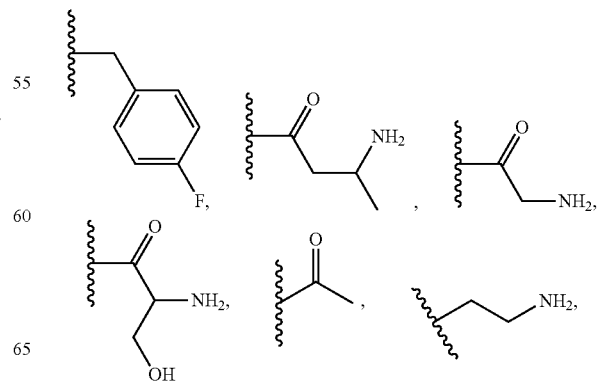

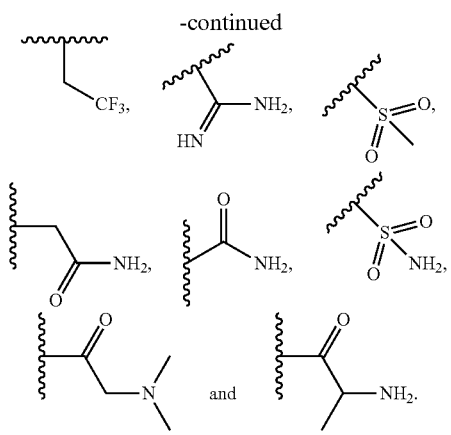

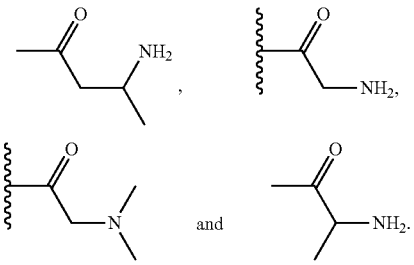

With regard to the compounds described herein, $R^{22}$ hydrogen, $C_3$-$C_6$cycloalkyl, $C_1$-$C_6$alkyl, halo$C_1$-$C_6$alkyl, $C_1$-$C_6$alkylOH, $C_1$-$C_6$alkylO$C_1$-$C_6$alkyl, COOH, $C_1$-$C_6$alkyN($R^{13}$)($R^{14}$), COO$C_1$-$C_6$alkyl, CO$C_1$-$C_6$alkyl, CO$C_1$-$C_6$alkylN($R^{13}$)($R^{14}$), CO$C_1$-$C_6$alkyl(OH)N($R^{13}$)($R^{14}$), $C_1$-$C_6$alkylCON($R^{13}$)($R^{14}$), CON($R^{13}$)($R^{14}$), SO$_2$$C_1$-$C_6$alkyl, SO$_2$N($R^{13}$)($R^{14}$), $C_1$-$C_6$alkylaryl, $C_1$-$C_6$alkylhaloaryl, C(NH)N($R^{13}$)($R^{14}$) or heteroaryl.

In certain embodiments, $R^{22}$ is hydrogen. In certain embodiments, $R^{22}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{22}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{22}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{22}$ is OH. In certain embodiments, $R^{22}$ is $C_1$-$C_6$alkylOH. Examples of suitable alcohols, include, but are not limited to, methanol, ethanol, propanol, butanol and iso-butanol. In certain embodiments, $R^{22}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^{22}$ is COOH.

In certain embodiments, $R^{22}$ is N($R^{13}$)($R^{14}$). Examples of suitable N($R^{13}$)($R^{14}$) groups include, but are not limited to, NH$_2$, NH(CH$_3$), N(CH$_3$)$_2$ and N(CH$_3$)$_2$. In certain embodiments, $R^{22}$ is $C_1$-$C_6$alkylN($R^{13}$)($R^{14}$). Examples of suitable $C_1$-$C_6$alkylN($R^{13}$)($R^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^{22}$ is $C_1$-$C_6$alkoxy. Examples of suitable alkoxys, include but are not limited to, methoxy, ethoxy, butoxy and propoxy. In certain embodiments, $R^{22}$ is COO$C_1$-$C_6$alkyl. Examples of suitable COO$C_1$-$C_6$alkyl groups include, but are not limited to, methoxycarbonyl, ethoxycarbonyl and butoxycarbonyl.

In certain embodiments, $R^{22}$ is CO$C_1$-$C_6$alkyl. Suitable CO$C_1$-$C_6$alkyl groups include COCH$_3$ and COCH$_2$CH$_3$. In certain embodiments, $R^{22}$ is CO$C_1$-$C_6$alkyN($R^{13}$)($R^{14}$). Suitable examples of CO$C_1$-$C_6$alkylN($R^{13}$)($R^{14}$) groups include, but are not limited to,

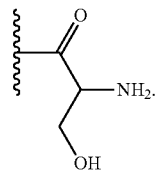

In certain embodiments, $R^{22}$ is CO$C_1$-$C_6$alkyl(OH)N($R^{13}$)($R^{14}$). Suitable examples CO$C_1$-$C_6$alkyl(OH)N($R^{13}$)($R^{14}$) groups include, but are not limited to, In certain embodiments, $R^{22}$ is $C_1$-$C_6$alkylCON($R^{13}$)($R^{14}$). Suitable groups include but are not to,

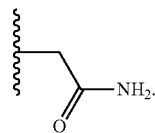 [SMILES: *CC(N)=O]

In certain embodiments, $R^{22}$ is CON($R^{13}$)($R^{14}$). Suitable CON($R^{13}$)($R^{14}$) groups include, but are not limited to, CONH$_2$. In certain embodiments, $R^{22}$ is SO$_2$$C_1$-$C_6$alkyl. Suitable SO$_2$$C_1$-$C_6$alkyl groups include, but are not limited to, SO$_2$CH$_3$. In certain embodiments, $R^{22}$ is SO$_2$N($R^{13}$)($R^{14}$). Suitable SO$_2$N($R^{13}$)($R^{14}$) groups include, but are not limited to, SO$_2$NH$_2$. In certain embodiments, $R^{22}$ is $C_1$-$C_6$alkylaryl. In certain embodiments, $R^{22}$ is $C_1$-$C_6$alkylhaloaryl. In certain embodiments, $R^{22}$ is C(NH)N($R^{13}$)($R^{14}$). In certain embodiments, $R^{22}$ is heteroaryl.

In certain embodiments, $R^{22}$ is selected from the group consisting of methyl, ethyl, isopropyl, NH$_2$,

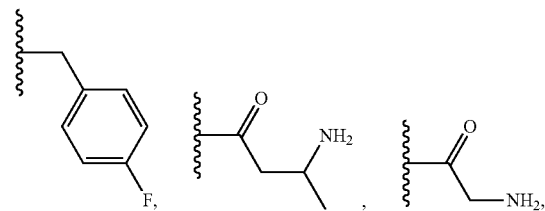

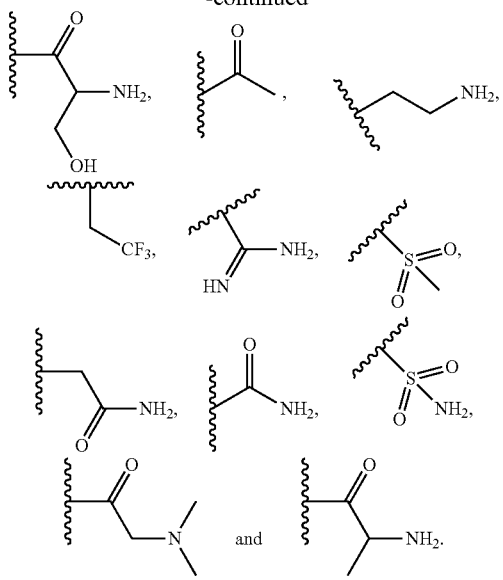

In certain embodiments, V is $NR^{22}$ and $R^{22}$ is $C_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkyCON($R^{13}$)($R^{14}$), CON($R^{13}$)($R^{14}$), $SO_2C_1$-$C_6$alkyl, $SO_2N(R^{13})(R^{14})$, $N(R^{13})(R^{14})$, $C_1$-$C_6$alkylN($R^{13}$)($R^{14}$) or $C_1$-$C_6$alkylhaloaryl or C(NH)N($R^{13}$)($R^{14}$).

With regard to the compounds described herein, $R^{23}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, $N(R^{13})(R^{14})$, $C_1$-$C_6$alkylN($R^{13}$)($R^{14}$), $C_1$-$C_6$alkoxy, $COOC_1$-$C_6$alkyl, $COC_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkyCON($R^{13}$)($R^{14}$), CON($R^{13}$)($R^{14}$), $SO_2C_1$-$C_6$alkyl, $SO_2N(R^{13})(R^{14})$, $C_1$-$C_6$alkylaryl, $C_1$-$C_6$alkylhaloaryl, C(NH)N($R^{13}$)($R^{14}$) or heteroaryl.

In certain embodiments, $R^{23}$ is hydrogen. In certain embodiments described herein, $R^{23}$ is halogen. Examples of suitable halogens include, but are not limited to, chlorine, bromine, fluorine and iodine. In certain embodiments, $R^{23}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{23}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{23}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{23}$ is OH. In certain embodiments, $R^{23}$ is $C_1$-$C_6$alkylOH. Examples of suitable alcohols, include, but are not limited to, methanol, ethanol, propanol, butanol and iso-butanol. In certain embodiments, $R^{23}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^{23}$ is COOH.

In certain embodiments, $R^{23}$ is $N(R^{13})(R^{14})$. Examples of suitable $N(R^{13})(R^{14})$ groups include, but are not limited to, $NH_2$, $NH(CH_3)$, $N(CH_3)_2$ and $N(CH_3)_2$. In certain embodiments, $R^{23}$ is $C_1$-$C_6$alkylN($R^{13}$)($R^{14}$). Examples of suitable $C_1$-$C_6$alkylN($R^{13}$)($R^{14}$) groups include, but are not limited to, $CH_2NH_2$, $CH_2NH(CH_3)$, $CH_2N(CH_3)_2$ and $CH_2CH_2N(CH_3)_2$.

In certain embodiments, $R^{23}$ is $C_1$-$C_6$alkoxy. Examples of suitable alkoxys, include but are not limited to, methoxy, ethoxy, butoxy and propoxy. In certain embodiments, $R^{23}$ is $COOC_1$-$C_6$alkyl. Examples of suitable $COOC_1$-$C_6$alkyl groups include, but are not limited to, methoxycarbonyl, ethoxycarbonyl and butoxycarbonyl.

In certain embodiments, $R^{23}$ is $COC_1$-$C_6$alkyl. Suitable $COC_1$-$C_6$alkyl groups include $COCH_3$ and $COCH_2CH_3$. In certain embodiments, $R^{23}$ is $COC_1$-$C_6$alkyN($R^{13}$)($R^{14}$). Suitable examples of $COC_1$-$C_6$alkyN($R^{13}$)($R^{14}$) groups include, but are not limited to,

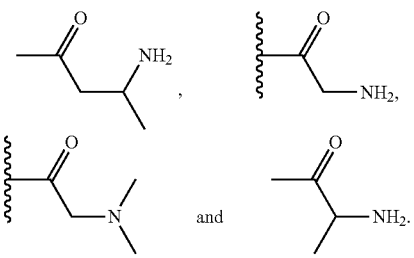

In certain embodiments, $R^{23}$ is $COC_1$-$C_6$alkyl(OH)N($R^{13}$)($R^{14}$). Suitable examples $COC_1$-$C_6$alkyl(OH)N($R^{13}$)($R^{14}$) groups include, but are not limited to,

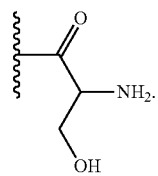

In certain embodiments, $R^{23}$ is $C_1$-$C_6$alkylCON($R^{13}$)($R^{14}$). Suitable groups include but are not to,

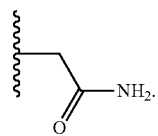 [SMILES: *CC(N)=O]

In certain embodiments, $R^{23}$ is CON($R^{13}$)($R^{14}$). Suitable CON($R^{13}$)($R^{14}$) groups include, but are not limited to, $CONH_2$. In certain embodiments, $R^{23}$ is $SO_2C_1$-$C_6$alkyl. Suitable $SO_2C_1$-$C_6$alkyl groups include, but are not limited to, $SO_2CH_3$. In certain embodiments, $R^{23}$ is $SO_2N(R^{13})(R^{14})$. Suitable $SO_2N(R^{13})(R^{14})$ groups include, but are not limited to, $SO_2NH_2$. In certain embodiments, $R^{22}$ is $C_1$-$C_6$alkylaryl. In certain embodiments, $R^{23}$ is $C_1$-$C_6$alkylhaloaryl. In certain embodiments, $R^{22}$ is C(NH)N($R^{13}$)($R^{14}$). In certain embodiments, $R^{23}$ is heteroaryl.

In certain embodiments, $R^{23}$ is selected from the group consisting of methyl, ethyl, isopropyl, $NH_2$,

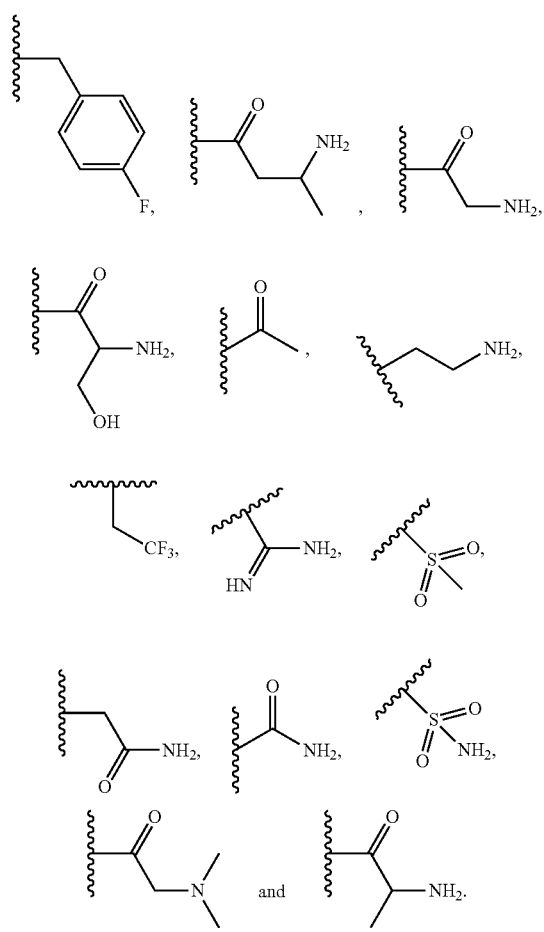

In certain embodiments of the compounds described herein, $R^8$, when taken with $R^{10}$, forms

wherein

V is $NR^{22}$ or $CHR^{23}$;

$R^{22}$ is hydrogen, $C_3$-$C_6$cycloalkyl, $C_1$-$C_6$alkyl, halo$C_1$-$C_6$alkyl, $C_1$-$C_6$alkylOH, $C_1$-$C_6$alkylOC$_1$-$C_6$alkyl, COOH, $C_1$-$C_6$alkylN($R^{13}$)($R^{14}$), COO$C_1$-$C_6$alkyl, CO$C_1$-$C_6$alkyl, CO$C_1$-$C_6$alkylN($R^{13}$)($R^{14}$), CO$C_1$-$C_6$alkyl(OH)N($R^{13}$)($R^{14}$), $C_1$-$C_6$alkylCON($R^{13}$)($R^{14}$), CON($R^{13}$)($R^{14}$), SO$_2$$C_1$-$C_6$alkyl, SO$_2$N($R^{13}$)($R^{14}$), $C_1$-$C_6$alkylaryl, $C_1$-$C_6$alkylhaloaryl, C(NH)N($R^{13}$)($R^{14}$) or heteroaryl; and $R^{23}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl, CO$C_1$-$C_6$alkyl, CO$C_1$-$C_6$alkyN($R^{13}$)($R^{14}$), CO$C_1$-$C_6$alkyl(OH)N($R^{13}$)($R^{14}$), $C_1$-$C_6$alkylCON($R^{13}$)($R^{14}$), CON($R^{13}$)($R^{14}$), SO$_2$$C_1$-$C_6$alkyl, SO$_2$N($R^{13}$)($R^{14}$), $C_1$-$C_6$alkylaryl, $C_1$-$C_6$alkylhaloaryl, C(NH)N($R^{13}$)($R^{14}$) or heteroaryl.

V, $R^{22}$ and $R^{23}$ are further discussed and defined above.

Also described herein are compounds of Formula II:

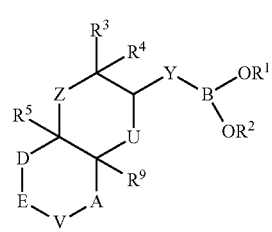

or a pharmaceutically acceptable salt thereof, wherein:

Y is a straight or branched ($C_2$-$C_5$)alkylene, wherein one or more —$CH_2$— groups in Y are optionally and independently replaced with a moiety selected from the group consisting of O, S and NH;

U is a bond or $CR^7R^8$;

Z is a bond or $CR^{11}R^{12}$;

A is a bond, O, $NR^{16}$ or $CR^{17}R^{18}$;

E is a bond, O, $NR^{19}$ or $CR^{20}R^{21}$;

V is O, $NR^{22}$ or $CR^{23}R^{24}$;

D is a bond, O, $NR^{25}$ or $CR^{26}R^{27}$;

$R^1$ is a hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^2$ is a hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^3$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkylN($R^{13}$)($R^{14}$), $C_1$-$C_6$alkoxy or COO$C_1$-$C_6$alkyl;

$R^4$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkyN($R^{13}$)($R^{14}$), $C_1$-$C_6$alkoxy or COO$C_1$-$C_6$alkyl;

$R^5$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkyN($R^{13}$)($R^{14}$), $C_1$-$C_6$alkoxy or COO$C_1$-$C_6$alkyl;

$R^7$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl;

$R^8$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl;

$R^9$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkyN($R^{13}$)($R^{14}$), $C_1$-$C_6$alkoxy or COO$C_1$-$C_6$alkyl;

$R^{11}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl;

$R^{12}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl;

$R^{13}$ is hydrogen, $C_3$-$C_6$cycloalkyl, $C_1$-$C_6$alkyl, $COC_1$-$C_6$alkylNH$_2$, $COC_1$-$C_6$alkylNH($C_1$-$C_6$alkyl), $COC_1$-$C_6$alkylN($C_1$-$C_6$alkyl)$_2$, $C_1$-$C_6$haloalkyl, $C_1$-$C_6$alkylOH or $COC_1$-$C_6$alkyl;

$R^{14}$ is hydrogen, $C_3$-$C_6$cycloalkyl, $C_1$-$C_6$alkyl, $COC_1$-$C_6$alkylNH$_2$, $COC_1$-$C_6$alkylNH($C_1$-$C_6$alkyl), $COC_1$-$C_6$alkylN($C_1$-$C_6$alkyl)$_2$, $C_1$-$C_6$haloalkyl, $C_1$-$C_6$alkylOH or $COC_1$-$C_6$alkyl;

$R^{16}$ is hydrogen, $C_3$-$C_6$cycloalkyl, $C_1$-$C_6$alkyl, $COC_1$-$C_6$alkylNH$_2$, $COC_1$-$C_6$alkylNH($C_1$-$C_6$alkyl), $COC_1$-$C_6$alkylN($C_1$-$C_6$alkyl)$_2$, or $COC_1$-$C_6$alkyl;

$R^{17}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl, CO$C_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), $C_1$-$C_6$alkylaryl, $C_1$-$C_6$alkylhaloaryl, C(NH)N($R^{13}$)($R^{14}$) or heteroaryl or $R^{17}$ and $R^{18}$ combined form an oxo group;

$R^{18}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl, CO$C_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), $C_1$-$C_6$alkylaryl, $C_1$-$C_6$alkylhaloaryl, C(NH)N($R^{13}$)($R^{14}$) or heteroaryl or $R^{17}$ and $R^{18}$ combined form an oxo group;

$R^{19}$ is hydrogen, $C_3$-$C_6$cycloalkyl, $C_1$-$C_6$alkyl, $COC_1$-$C_6$alkylNH$_2$, $COC_1$-$C_6$alkylNH($C_1$-$C_6$alkyl), $COC_1$-$C_6$alkylN($C_1$-$C_6$alkyl)$_2$, or $COC_1$-$C_6$alkyl;

$R^{20}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl, CO$C_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), $C_1$-$C_6$alkylaryl, $C_1$-$C_6$alkylhaloaryl, C(NH)N($R^{13}$)($R^{14}$) or heteroaryl or $R^{20}$ and $R^{21}$ combined form an oxo group;

$R^{21}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl, CO$C_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), $C_1$-$C_6$alkylaryl, $C_1$-$C_6$alkylhaloaryl, C(NH)N($R^{13}$)($R^{14}$) or heteroaryl or $R^{20}$ and $R^{21}$ combined form an oxo group;

$R^{22}$ hydrogen, $C_3$-$C_6$cycloalkyl, $C_1$-$C_6$alkyl, halo$C_1$-$C_6$alkyl, $C_1$-$C_6$alkylOH, $C_1$-$C_6$alkylO$C_1$-$C_6$alkyl, COOH, $C_1$-$C_6$alkyN($R^{13}$)($R^{14}$), COO$C_1$-$C_6$alkyl, CO$C_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkyCON($R^{13}$)($R^{14}$), CON($R^{13}$)($R^{14}$), $SO_2C_1$-$C_6$alkyl, $SO_2$N($R^{13}$)($R^{14}$), $C_1$-$C_6$alkylaryl, $C_1$-$C_6$alkylhaloaryl, C(NH)N($R^{13}$)($R^{14}$) or heteroaryl;

$R^{23}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl, CO$C_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), $C_1$-$C_6$alkylaryl, $C_1$-$C_6$alkylhaloaryl, C(NH)N($R^{13}$)($R^{14}$) or heteroaryl;

$R^{24}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl, CO$C_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), $C_1$-$C_6$alkylaryl, $C_1$-$C_6$alkylhaloaryl, C(NH)N($R^{13}$)($R^{14}$) or heteroaryl or $R^{23}$ and $R^{24}$ combined form an oxo group;

$R^{25}$ hydrogen, $C_3$-$C_6$cycloalkyl, $C_1$-$C_6$alkyl, $COC_1$-$C_6$alkylNH$_2$, $COC_1$-$C_6$alkylNH($C_1$-$C_6$alkyl), $COC_1$-$C_6$alkylN($C_1$-$C_6$alkyl)$_2$, or $COC_1$-$C_6$alkyl;

$R^{26}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl, CO$C_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), $C_1$-$C_6$alkylaryl, $C_1$-$C_6$alkylhaloaryl, C(NH)N($R^{13}$)($R^{14}$) or heteroaryl; and $R^{27}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkyN($R^{13}$)($R^{14}$), $C_1$-$C_6$alkoxy, COO$C_1$-$C_6$alkyl, CO$C_1$-$C_6$alkyl, $COC_1$-$C_6$alkyN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), $C_1$-$C_6$alkylaryl, $C_1$-$C_6$alkylhaloaryl, C(NH)N($R^{13}$)($R^{14}$) or heteroaryl or $R^{26}$ and $R^{27}$ combined form an oxo group.

With regard to the compounds of Formula II, Y, U, Z, V, $R^1$, $R^2$, $R^3$, $R^4$, $R^5$, $R^7$, $R^8$, $R^9$, $R^{11}$, $R^{12}$, $R^{13}$, $R^{14}$, $R^{22}$, $R^{23}$ and $R^{24}$ are discussed above.

With regard to the compounds described herein, A is a bond, O, $NR^{16}$ or $CR^{17}R^{18}$. In certain embodiments, A is a bond. In certain embodiments, A is O. In certain embodiments, A is $NR^{16}$. In certain embodiments, A is $CR^{17}R^{18}$.

With regard to the compounds described herein, E is a bond, O, $NR^{19}$ or $CR^{20}R^{21}$. In certain embodiments, E is a bond. In certain embodiments, E is O. In certain embodiments, E is $NR^{19}$. In certain embodiments, E is $CR^{20}R^{21}$.

With regard to the compounds described herein, D is a bond, O, $NR^{25}$ or $CR^{26}R^{27}$. In certain embodiments, D is a bond. In certain embodiments, D is O. In certain embodiments, D is $NR^{25}$. In certain embodiments, D is $CR^{26}R^{27}$.

In certain embodiments, A and V cannot be simultaneously O. In certain embodiments, A and V cannot be simultaneously $NR^{16}$ and O, respectively. In certain embodiments, A and V cannot be simultaneously O and $NR^{22}$, respectively. In certain embodiments, A and V cannot be simultaneously $NR^{16}$ and $NR^{22}$, respectively. In certain embodiments, E and V cannot be simultaneously O. In certain embodiments, E and V cannot be simultaneously $NR^{19}$ and O, respectively. In certain embodiments, E and V cannot be simultaneously O and $NR^{22}$, respectively. In certain embodiments, E and V cannot be simultaneously $NR^{19}$ and $NR^{22}$, respectively. In certain embodiments, E and D cannot be simultaneously O, respectively. In certain embodiments, E and D cannot be simultaneously $NR^{19}$ and O, respectively. In certain embodiments, E and D cannot be simultaneously O and $NR^{25}$, respectively. In certain embodiments, wherein, if E is a bond, V and D cannot be simultaneously O. In certain embodiments, wherein, if E is a bond, V and D cannot be simultaneously $NR^{22}$ and O, respectively. In certain embodiments, wherein, if E is a bond, V and D cannot be simultaneously O and $NR^{25}$, respectively In certain embodiments, wherein, if E is a bond, V and D cannot be simultaneously $NR^{22}$ and $NR^{25}$, respectively.

With regard to the compounds described herein, $R^{16}$ is hydrogen, $C_3$-$C_6$cycloalkyl, $C_1$-$C_6$alkyl, $COC_1$-$C_6$alkylNH$_2$, $COC_1$-$C_6$alkylNH($C_1$-$C_6$alkyl), $COC_1$-$C_6$alkylN($C_1$-$C_6$alkyl)$_2$, or $COC_1$-$C_6$alkyl. In certain embodiments, $R^{16}$ is hydrogen. In certain embodiments, $R^{16}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{16}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{16}$ is $COC_1$-$C_6$alkylNH$_2$. In certain embodiments, $R^{16}$ is $COC_1$-$C_6$alkylNH($C_1$-$C_6$alkyl). In certain embodiments, $R^{16}$ is $COC_1$-$C_6$alkylN($C_1$-$C_6$alkyl)$_2$.

With regard to the compounds described herein, $R^{17}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, N($R^{13}$)($R^{14}$), $C_1$-$C_6$alkylN($R^{13}$)($R^{14}$), $C_1$-$C_6$alkoxy, COO$C_1$-$C_6$alkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkyCON($R^{13}$)($R^{14}$), CON($R^{13}$)($R^{14}$), SO$_2$$C_1$-$C_6$alkyl, SO$_2$N($R^{13}$)($R^{14}$), $C_1$-$C_6$alkylaryl, $C_1$-$C_6$alkylhaloaryl, C(NH)N($R^{13}$)($R^{14}$) or heteroaryl or $R^{17}$ and $R^{18}$ combined form an oxo group. In certain embodiments, $R^{17}$ is hydrogen. In certain embodiments described herein, $R^{17}$ is halogen. Examples of suitable halogens include, but are not limited to, chlorine, bromine, fluorine and iodine. In certain embodiments, $R^{17}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{17}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{17}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{17}$ is OH. In certain embodiments, $R^{17}$ is $C_1$-$C_6$alkylOH. Examples of suitable alcohols, include, but are not limited to, methanol, ethanol, propanol, butanol and iso-butanol. In certain embodiments, $R^{17}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^{17}$ is COOH.

In certain embodiments, $R^{17}$ is N($R^{13}$)($R^{14}$). Examples of suitable N($R^{13}$)($R^{14}$) groups include, but are not limited to, NH$_2$, NH(CH$_3$), —N(CH$_3$)$_2$ and N(CH$_3$)$_2$. In certain embodiments, $R^{17}$ is $C_1$-$C_6$alkylN($R^{13}$)($R^{14}$). Examples of suitable $C_1$-$C_6$alkylN($R^{13}$)($R^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^{17}$ is $C_1$-$C_6$alkoxy. Examples of suitable alkoxys, include, but are not limited to, methoxy, ethoxy, butoxy and propoxy. In certain embodiments, $R^{17}$ is COO$C_1$-$C_6$alkyl. Examples of suitable COO$C_1$-$C_6$alkyl groups include, but are not limited to, methoxycarbonyl, ethoxycarbonyl and butoxycarbonyl.

In certain embodiments, $R^{17}$ is $COC_1$-$C_6$alkyl. Suitable $COC_1$-$C_6$alkyl groups include COCH$_3$ and COCH$_2$CH$_3$. In certain embodiments, $R^{17}$ is $COC_1$-$C_6$alkylN($R^{13}$)($R^{14}$). Suitable examples of $COC_1$-$C_6$alkylN($R^{13}$)($R^{14}$) groups include, but are not limited to,

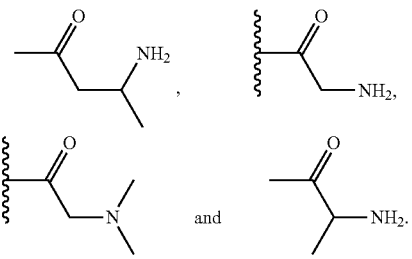

In certain embodiments, $R^{17}$ is $COC_1$-$C_6$alkyl(OH)N($R^{13}$)($R^{14}$). Suitable examples $COC_1$-$C_6$alkyl(OH)N($R^{13}$)($R^{14}$) groups include, but are not limited to,

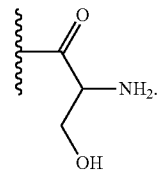 [SMILES: *C(=O)C(N)CO]

In certain embodiments, $R^{17}$ is $C_1$-$C_6$alkylCON($R^{13}$)($R^{14}$). Suitable groups include but are not to,

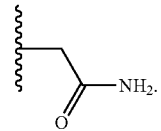

In certain embodiments, $R^{17}$ is CON($R^{13}$)($R^{14}$). Suitable CON($R^{13}$)($R^{14}$) groups include, but are not limited to, CONH$_2$. In certain embodiments, $R^{17}$ is SO$_2$$C_1$-$C_6$alkyl. Suitable SO$_2$$C_1$-$C_6$alkyl groups include, but are not limited to, SO$_2$CH$_3$. In certain embodiments, $R^{17}$ is SO$_2$N($R^{13}$)($R^{14}$). Suitable SO$_2$N($R^{13}$)($R^{14}$) groups include, but are not limited to, SO$_2$NH$_2$. In certain embodiments, $R^{17}$ is $C_1$-$C_6$alkylaryl. In certain embodiments, $R^{17}$ is $C_1$-$C_6$alkylhaloaryl. In certain embodiments, $R^{17}$ is C(NH)N($R^{13}$)($R^{14}$). In certain embodiments, $R^{17}$ is heteroaryl.

In certain embodiments, $R^{17}$ is selected from the group consisting of methyl, ethyl, isopropyl, NH$_2$,

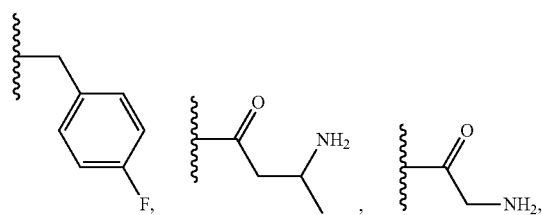

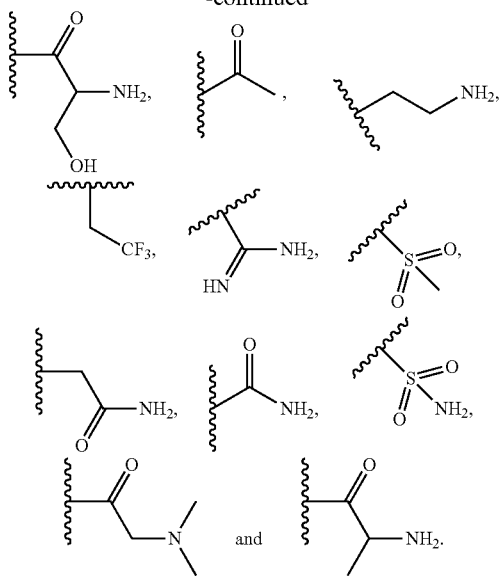

With regard to the compounds described herein, $R^{18}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, $N(R^{13})(R^{14})$, $C_1$-$C_6$alkylN$(R^{13})(R^{14})$, $C_1$-$C_6$alkoxy, COOC$_1$-$C_6$alkyl, COC$_1$-$C_6$alkyl, COC$_1$-$C_6$alkyN$(R^{13})(R^{14})$, COC$_1$-$C_6$alkyl(OH)N$(R^{13})(R^{14})$, $C_1$-$C_6$alkyCON$(R^{13})(R^{14})$, CON$(R^{13})(R^{14})$, SO$_2$C$_1$-$C_6$alkyl, SO$_2$N$(R^{13})(R^{14})$, $C_1$-$C_6$alkylaryl, $C_1$-$C_6$alkylhaloaryl, C(NH)N$(R^{13})(R^{14})$ or heteroaryl or $R^{17}$ and $R^{18}$ combined form an oxo group.

In certain embodiments, $R^{18}$ is hydrogen. In certain embodiments described herein, $R^{18}$ is halogen. Examples of suitable halogens include, but are not limited to, chlorine, bromine, fluorine and iodine. In certain embodiments, $R^{18}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{18}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{18}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{18}$ is OH. In certain embodiments, $R^{18}$ is $C_1$-$C_6$alkylOH. Examples of suitable alcohols, include, but are not limited to, methanol, ethanol, propanol, butanol and iso-butanol. In certain embodiments, $R^{18}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^{18}$ is COOH.

In certain embodiments, $R^{18}$ is $N(R^{13})(R^{14})$. Examples of suitable $N(R^{13})(R^{14})$ groups include, but are not limited to, NH$_2$, NH(CH$_3$), N(CH$_3$)$_2$ and N(CH$_3$)$_2$. In certain embodiments, $R^{18}$ is $C_1$-$C_6$alkylN$(R^{13})(R^{14})$. Examples of suitable $C_1$-$C_6$alkylN$(R^{13})(R^{14})$ groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^{18}$ is $C_1$-$C_6$alkoxy. Examples of suitable alkoxys, include but are not limited to, methoxy, ethoxy, butoxy and propoxy. In certain embodiments, $R^{18}$ is COOC$_1$-$C_6$alkyl. Examples of suitable COOC$_1$-$C_6$alkyl groups include, but are not limited to, methoxycarbonyl, ethoxycarbonyl and butoxycarbonyl.

In certain embodiments, $R^{18}$ is COC$_1$-$C_6$alkyl. Suitable COC$_1$-$C_6$alkyl groups include COCH$_3$ and COCH$_2$CH$_3$. In certain embodiments, $R^{18}$ is COC$_1$-$C_6$alkyN$(R^{13})(R^{14})$. Suitable examples of COC$_1$-$C_6$alkyN$(R^{13})(R^{14})$ groups include, but are not limited to,

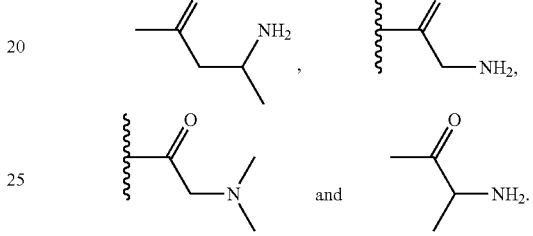

In certain embodiments, $R^{18}$ is COC$_1$-$C_6$alkyl(OH)N$(R^{13})(R^{14})$. Suitable examples COC$_1$-$C_6$alkyl(OH)N$(R^{13})(R^{14})$ groups include, but are not limited to,

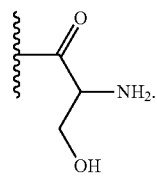 [SMILES: *C(=O)C(N)CO]

In certain embodiments, $R^{18}$ is $C_1$-$C_6$alkylCON$(R^{13})(R^{14})$. Suitable groups include but are not to,

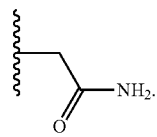 [SMILES: *CC(N)=O]

In certain embodiments, $R^{18}$ is CON$(R^{13})(R^{14})$. Suitable CON$(R^{13})(R^{14})$ groups include, but are not limited to, CONH$_2$. In certain embodiments, $R^{18}$ is SO$_2$C$_1$-$C_6$alkyl. Suitable SO$_2$C$_1$-$C_6$alkyl groups include, but are not limited to, SO$_2$CH$_3$. In certain embodiments, $R^{18}$ is SO$_2$N$(R^{13})(R^{14})$. Suitable SO$_2$N$(R^{13})(R^{14})$ groups include, but are not limited to, SO$_2$NH$_2$. In certain embodiments, $R^{18}$ is $C_1$-$C_6$alkylaryl. In certain embodiments, $R^{18}$ is $C_1$-$C_6$alkylhaloaryl. In certain embodiments, $R^{18}$ is C(NH)N$(R^{13})(R^{14})$. In certain embodiments, $R^{18}$ is heteroaryl.

In certain embodiments, $R^{17}$ and $R^{18}$ combine to form an oxo group.

In certain embodiments, $R^{18}$ is selected from the group consisting of methyl, ethyl, isopropyl, NH$_2$,

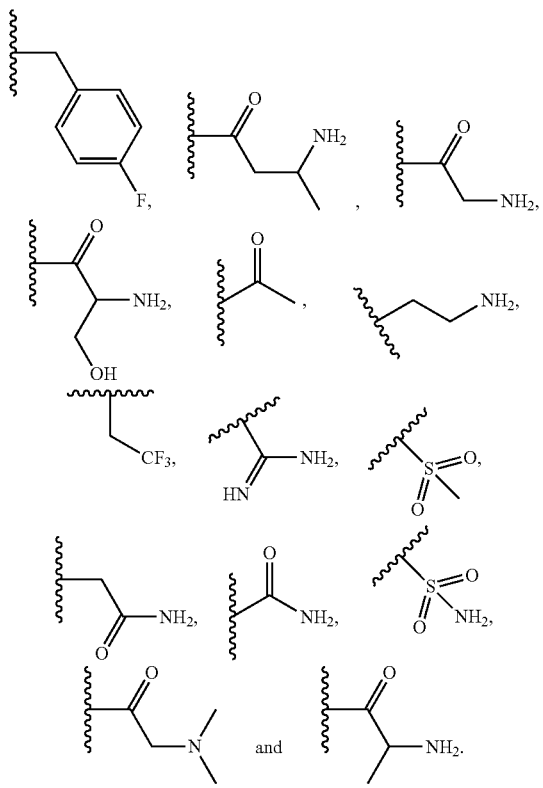

With regard to the compounds described herein, $R^{19}$ is hydrogen, $C_3$-$C_6$cycloalkyl, $C_1$-$C_6$alkyl, $COC_1$-$C_6$alkylNH$_2$, $COC_1$-$C_6$alkylNH($C_1$-$C_6$alkyl), $COC_1$-$C_6$alkylN($C_1$-$C_6$alkyl)$_2$, or $COC_1$-$C_6$alkyl. In certain embodiments, $R^{19}$ is hydrogen. In certain embodiments, $R^{19}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{19}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{19}$ is $COC_1$-$C_6$alkylNH$_2$. In certain embodiments, $R^{19}$ is $COC_1$-$C_6$alkylNH($C_1$-$C_6$alkyl). In certain embodiments, $R^{19}$ is $COC_1$-$C_6$alkyN($C_1$-$C_6$alkyl)$_2$.

With regard to the compounds described herein, $R^2$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkylN($R^{13}$)($R^{14}$), $C_1$-$C_6$alkoxy, COOC$_1$-$C_6$alkyl, COC$_1$-$C_6$alkyl, COC$_1$-$C_6$alkyN($R^{13}$)($R^{14}$), COC$_1$-$C_6$alkyl(OH)N($R^{13}$)($R^{14}$), $C_1$-$C_6$alkyCON($R^{13}$)($R^{14}$), CON($R^{13}$)($R^{14}$), SO$_2$C$_1$-$C_6$alkyl, SO$_2$N($R^{13}$)($R^{14}$), $C_1$-$C_6$alkylaryl, $C_1$-$C_6$alkylhaloaryl, C(NH)N($R^{13}$)($R^{14}$) or heteroaryl or $R^{20}$ and $R^{21}$ combined form an oxo group.

In certain embodiments, $R^{20}$ is hydrogen. In certain embodiments described herein, $R^{20}$ is halogen. Examples of suitable halogens include, but are not limited to, chlorine, bromine, fluorine and iodine. In certain embodiments, $R^{20}$ is $C_3$-$C_6$cycloalkyl. Suitable cycloalkyl groups are not limited to, cyclopropyl, cyclobutyl, cyclopentyl, cyclohexyl. In certain embodiments described herein, $R^{20}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{20}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{20}$ is OH. In certain embodiments, $R^{20}$ is $C_1$-$C_6$alkylOH. Examples of suitable alcohols, include, but are not limited to, methanol, ethanol, propanol, butanol and iso-butanol. In certain embodiments, $R^{20}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether. In certain embodiments, $R^{20}$ is COOH.

In certain embodiments, $R^{20}$ is N($R^{13}$)($R^{14}$). Examples of suitable N($R^{13}$)($R^{14}$) groups include, but are not limited to, NH$_2$, NH(CH$_3$), N(CH$_3$)$_2$ and N(CH$_3$)$_2$. In certain embodiments, $R^{20}$ is $C_1$-$C_6$alkylN($R^{13}$)($R^{14}$). Examples of suitable $C_1$-$C_6$alkylN($R^{13}$)($R^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^{20}$ is $C_1$-$C_6$alkoxy. Examples of suitable alkoxys, include but are not limited to, methoxy, ethoxy, butoxy and propoxy. In certain embodiments, $R^{20}$ is COOC$_1$-$C_6$alkyl. Examples of suitable COOC$_1$-$C_6$alkyl groups include, but are not limited to, methoxycarbonyl, ethoxycarbonyl and butoxycarbonyl.

In certain embodiments, $R^{20}$ is COC$_1$-$C_6$alkyl. Suitable COC$_1$-$C_6$alkyl groups include COCH$_3$ and COCH$_2$CH$_3$. In certain embodiments, $R^{20}$ is COC$_1$-$C_6$alkyN($R^{13}$)($R^{14}$). Suitable examples of COC$_1$-$C_6$alkylN($R^{13}$)($R^{14}$) groups include, but are not limited to,

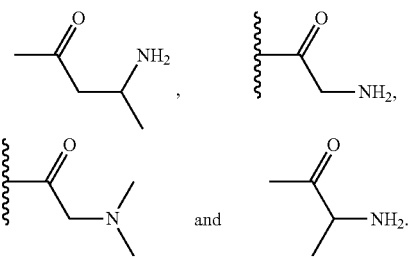

In certain embodiments, $R^{20}$ is COC$_1$-$C_6$alkyl(OH)N($R^{13}$)($R^{14}$). Suitable examples COC$_1$-$C_6$alkyl(OH)N($R^{13}$)($R^{14}$) groups include, but are not limited to,

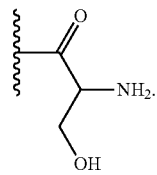 [SMILES: *C(=O)C(N)CO]

In certain embodiments, $R^{20}$ is $C_1$-$C_6$alkylCON($R^{13}$)($R^{14}$). Suitable groups include but are not to,

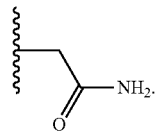 [SMILES: *CC(N)=O]

In certain embodiments, $R^{20}$ is CON($R^{13}$)($R^{14}$). Suitable CON($R^{13}$)($R^{14}$) groups include, but are not limited to, $CONH_2$. In certain embodiments, $R^{20}$ is $SO_2C_1$-$C_6$alkyl. Suitable $SO_2C_1$-$C_6$alkyl groups include, but are not limited to, $SO_2CH_3$. In certain embodiments, $R^{20}$ is $SO_2N(R^{13})(R^{14})$. Suitable $SO_2N(R^{13})(R^{14})$ groups include, but are not limited to, $SO_2NH_2$. In certain embodiments, $R^{20}$ is $C_1$-$C_6$alkylaryl. In certain embodiments, $R^{20}$ is $C_1$-$C_6$alkylhaloaryl. In certain embodiments, $R^{20}$ is C(NH)N($R^{13}$)($R^{14}$). In certain embodiments, $R^{20}$ is heteroaryl.

In certain embodiments, $R^{20}$ is selected from the group consisting of methyl, ethyl, isopropyl, $NH_2$,

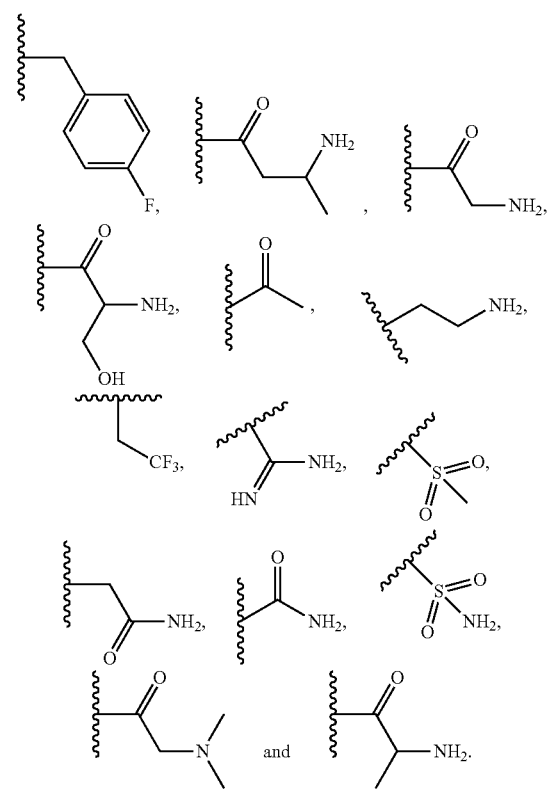

With regard to the compounds described herein, $R^{21}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC_1$-$C_6$alkyl, COOH, N($R^{13}$)($R^{14}$), $C_1$-$C_6$alkylN($R^{13}$)($R^{14}$), $C_1$-$C_6$alkoxy, COOC$_1$-$C_6$alkyl, COC$_1$-$C_6$alkyl, COC$_1$-$C_6$alkyN($R^{13}$)($R^{14}$), COC$_1$-$C_6$alkyl(OH)N($R^{13}$)($R^{14}$), $C_1$-$C_6$alkyCON($R^{13}$)($R^{14}$), CON($R^{13}$)($R^{14}$), $SO_2C_1$-$C_6$alkyl, $SO_2N(R^{13})(R^{14})$, $C_1$-$C_6$alkylaryl, $C_1$-$C_6$alkylhaloaryl, C(NH)N($R^{13}$)($R^{14}$) or heteroaryl.

In certain embodiments, $R^{21}$ is hydrogen. In certain embodiments described herein, $R^{21}$ is halogen. Examples of suitable halogens include, but are not limited to, chlorine, bromine, fluorine and iodine. In certain embodiments, $R^{21}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{21}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{21}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{21}$ is OH. In certain embodiments, $R^{21}$ is $C_1$-$C_6$alkylOH. Examples of suitable alcohols, include, but are not limited to, methanol, ethanol, propanol, butanol and iso-butanol. In certain embodiments, $R^{21}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether. In certain embodiments, $R^{21}$ is COOH.

In certain embodiments, $R^{21}$ is N($R^{13}$)($R^{14}$). Examples of suitable N($R^{13}$)($R^{14}$) groups include, but are not limited to, $NH_2$, $NH(CH_3)$, $N(CH_3)_2$ and $N(CH_3)_2$. In certain embodiments, $R^{21}$ is $C_1$-$C_6$alkylN($R^{13}$)($R^{14}$). Examples of suitable $C_1$-$C_6$alkylN($R^{13}$)($R^{14}$) groups include, but are not limited to, $CH_2NH_2$, $CH_2NH(CH_3)$, $CH_2N(CH_3)_2$ and $CH_2CH_2N(CH_3)_2$.

In certain embodiments, $R^{21}$ is $C_1$-$C_6$alkoxy. Examples of suitable alkoxys, include but are not limited to, methoxy, ethoxy, butoxy and propoxy. In certain embodiments, $R^{21}$ is COOC$_1$-$C_6$alkyl. Examples of suitable COOC$_1$-$C_6$alkyl groups include, but are not limited to, methoxycarbonyl, ethoxycarbonyl and butoxycarbonyl.

In certain embodiments, $R^{21}$ is COC$_1$-$C_6$alkyl. Suitable COC$_1$-$C_6$alkyl groups include $COCH_3$ and $COCH_2CH_3$. In certain embodiments, $R^{21}$ is COC$_1$-$C_6$alkyN($R^{13}$)($R^{14}$). Suitable examples of COC$_1$-$C_6$alkylN($R^{13}$)($R^{14}$) groups include, but are not limited to

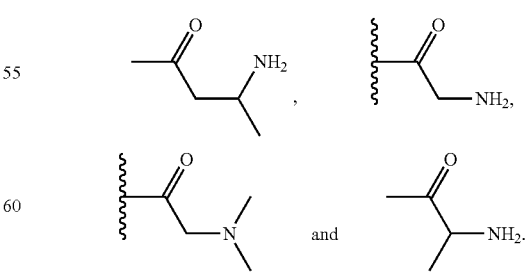

In certain embodiments, $R^{21}$ is COC$_1$-$C_6$alkyl(OH)N($R^{13}$)($R^{14}$). Suitable examples COC$_1$-$C_6$alkyl(OH)N($R^{13}$)($R^{14}$) groups include, but are not limited to,

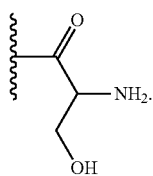 [SMILES: *C(=O)C(N)CO]

In certain embodiments, $R^{21}$ is $C_1$-$C_6$alkylCON($R^{13}$)($R^{14}$). Suitable groups include but are not to,

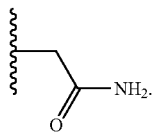 [SMILES: *CC(N)=O]

In certain embodiments, $R^{21}$ is CON($R^{13}$)($R^{14}$). Suitable CON($R^{13}$)($R^{14}$) groups include, but are not limited to, CONH$_2$. In certain embodiments, $R^{21}$ is SO$_2$C$_1$-C$_6$alkyl. Suitable SO$_2$C$_1$-C$_6$alkyl groups include, but are not limited to, SO$_2$CH$_3$. In certain embodiments, $R^{21}$ is SO$_2$N($R^{13}$)($R^{14}$). Suitable SO$_2$N($R^{13}$)($R^{14}$) groups include, but are not limited to, SO$_2$NH$_2$. In certain embodiments, $R^{21}$ is C$_1$-C$_6$alkylaryl. In certain embodiments, $R^{21}$ is C$_1$-C$_6$alkylhaloaryl. In certain embodiments, $R^{21}$ is C(NH)N($R^{13}$)($R^{14}$). In certain embodiments, $R^{21}$ is heteroaryl.

In certain embodiments, $R^{21}$ is selected from the group consisting of methyl, ethyl, isopropyl, NH$_2$,

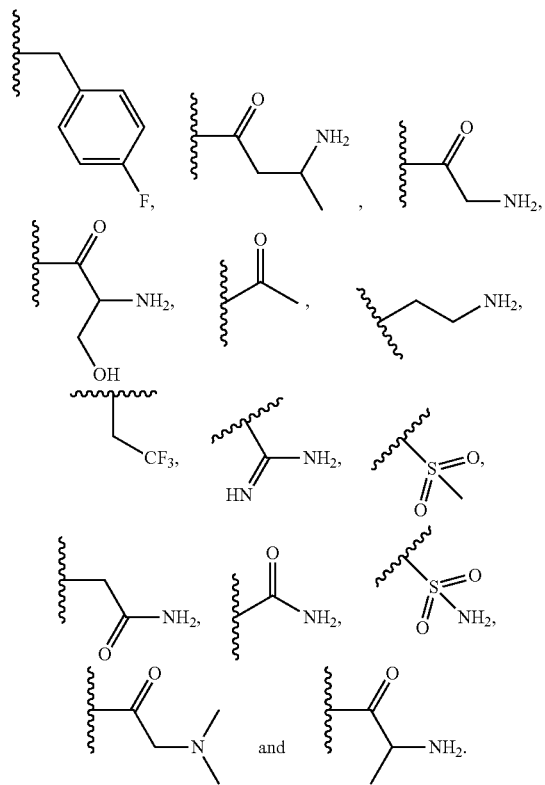

In certain embodiments, $R^{20}$ and $R^{21}$ combined form an oxo group.

With regard to the compounds described herein, $R^{25}$ is hydrogen, C$_3$-C$_6$cycloalkyl, C$_1$-C$_6$alkyl, COC$_1$-C$_6$alkylNH$_2$, COC$_1$-C$_6$alkylNH(C$_1$-C$_6$alkyl), COC$_1$-C$_6$alkylN(C$_1$-C$_6$alkyl)$_2$, or COC$_1$-C$_6$alkyl. In certain embodiments, $R^{25}$ is hydrogen. In certain embodiments, $R^{25}$ is C$_3$-C$_6$cycloalkyl. Suitable cycloalkyl groups include, but are not limited to, cyclopropyl, cyclobutyl, cyclopentyl, cyclohexyl. In certain embodiments described herein, $R^{25}$ is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{25}$ is COC$_1$-C$_6$alkylNH$_2$. In certain embodiments, $R^{25}$ is COC$_1$-C$_6$alkylNH(C$_1$-C$_6$alkyl). In certain embodiments, $R^{25}$ is COC$_1$-C$_6$alkyN(C$_1$-C$_6$alkyl)$_2$.

With regard to the compounds described herein, $R^{26}$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N($R^{13}$)($R^{14}$), C$_1$-C$_6$alkylN($R^{13}$)($R^{14}$), C$_1$-C$_6$alkoxy, COOC$_1$-C$_6$alkyl, COC$_1$-C$_6$alkyl, COC$_1$-C$_6$alkylN($R^{13}$)($R^{14}$), COC$_1$-C$_6$alkyl(OH)N($R^{13}$)($R^{14}$), C$_1$-C$_6$alkyCON($R^{13}$)($R^{14}$), CON($R^{13}$)($R^{14}$), SO$_2$C$_1$-C$_6$alkyl, SO$_2$N($R^{13}$)($R^{14}$), C$_1$-C$_6$alkylaryl, C$_1$-C$_6$alkylhaloaryl, C(NH)N($R^{13}$)($R^{14}$) or heteroaryl.

In certain embodiments, $R^{26}$ is hydrogen. In certain embodiments described herein, $R^{26}$ is halogen. Examples of suitable halogens include, but are not limited to, chlorine, bromine, fluorine and iodine. In certain embodiments, $R^{26}$ is C$_3$-C$_6$cycloalkyl. Suitable cycloalkyl groups include, but are not limited to, cyclopropyl, cyclobutyl, cyclopentyl, cyclohexyl. In certain embodiments described herein, $R^{26}$ is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{26}$ is haloC$_1$-C$_6$alkyl. Suitable haloC$_1$-C$_6$alkyls include but are not limited to, fluoromethyl, difluoromethyl, trifluoromethyl, 2-fluoroethyl, 1,2-difluoroethyl and 2,2-difluoroethyl. In certain embodiments, $R^{26}$ is OH. In certain embodiments, $R^{26}$ is C$_1$-C$_6$alkylOH. Examples of suitable alcohols, include, but are not limited to, methanol, ethanol, propanol, butanol and iso-butanol. In certain embodiments, $R^{26}$ is C$_1$-C$_6$alkylOC$_1$-C$_6$alkyl. Suitable C$_1$-C$_6$alkylOC$_1$-C$_6$alkyls include but are not limited to, dimethyl ether, ethyl methyl ether, diethyl ether, dipropyl ether, dibutyl ether and diisopropyl ether. In certain embodiments, $R^{26}$ is COOH.

In certain embodiments, $R^{26}$ is N($R^{13}$)($R^{14}$). Examples of suitable N($R^{13}$)($R^{14}$) groups include, but are not limited to, NH$_2$, NH(CH$_3$), —N(CH$_3$)$_2$ and N(CH$_3$)$_2$. In certain embodiments, $R^{26}$ is C$_1$-C$_6$alkylN($R^{13}$)($R^{14}$). Examples of suitable C$_1$-C$_6$alkylN($R^{13}$)($R^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^{26}$ is C$_1$-C$_6$alkoxy. Examples of suitable alkoxys, include but are not limited to, methoxy, ethoxy, butoxy and propoxy. In certain embodiments, $R^{26}$ is COOC$_1$-C$_6$alkyl. Examples of suitable COOC$_1$-C$_6$alkyl groups include, but are not limited to, methoxycarbonyl, ethoxycarbonyl and butoxycarbonyl.

In certain embodiments, R$^{26}$ is COC$_1$-C$_6$alkyl. Suitable COC$_1$-C$_6$alkyl groups include COCH$_3$ and COCH$_2$CH$_3$. In certain embodiments, R$^{26}$ is COC$_1$-C$_6$alkyN(R$^{13}$)(R$^{14}$). Suitable examples of COC$_1$-C$_6$alkylN(R$^{13}$)(R$^{14}$ groups include, but are not limited to

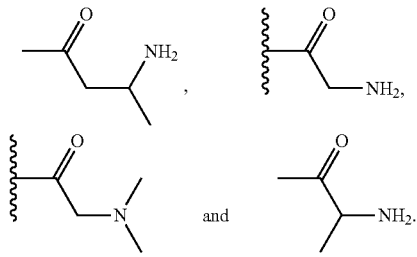

In certain embodiments, R$^{26}$ is COC$_1$-C$_6$alkyl(OH)N(R$^{13}$)(R$^{14}$). Suitable examples COC$_1$-C$_6$alkyl(OH)N(R$^{13}$)(R$^{14}$) groups include, but are not limited to,

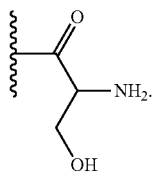 [SMILES: *C(=O)C(N)CO]

In certain embodiments, R$^{26}$ is C$_1$-C$_6$alkylCON(R$^{13}$)(R$^{14}$). Suitable groups include but are not to,

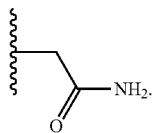 [SMILES: *CC(N)=O]

In certain embodiments, R$^{26}$ is CON(R$^{13}$)(R$^{14}$). Suitable CON(R$^{13}$)(R$^{14}$) groups include, but are not limited to, CONH$_2$. In certain embodiments, R$^{26}$ is SO$_2$C$_1$-C$_6$alkyl. Suitable SO$_2$C$_1$-C$_6$alkyl groups include, but are not limited to, SO$_2$CH$_3$. In certain embodiments, R$^{26}$ is SO$_2$N(R$^{13}$)(R$^{14}$). Suitable SO$_2$N(R$^{13}$)(R$^{14}$) groups include, but are not limited to, SO$_2$NH$_2$. In certain embodiments, R$^{26}$ is C$_1$-C$_6$alkylaryl. In certain embodiments, R$^{26}$ is C$_1$-C$_6$alkylhaloaryl. In certain embodiments, R$^{26}$ is C(NH)N(R$^{13}$)(R$^{14}$). In certain embodiments, R$^{26}$ is heteroaryl.

In certain embodiments, R$^{26}$ is selected from the group consisting of methyl, ethyl, isopropyl, NH$_2$,

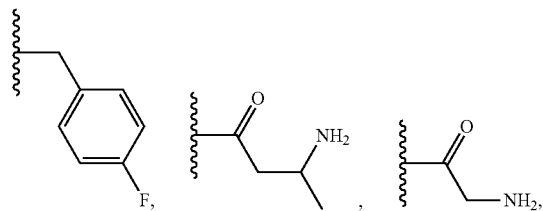

-continued

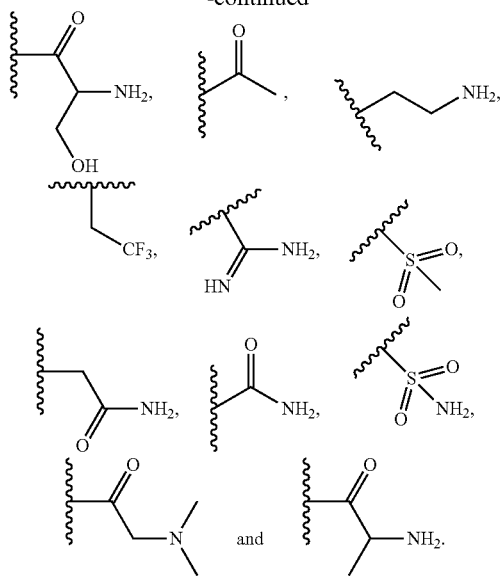

With regard to the compounds described herein, R$^2$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N(R$^{13}$)(R$^{14}$), C$_1$-C$_6$alkylN(R$^{13}$)(R$^{14}$), C$_1$-C$_6$alkoxy, COOC$_1$-C$_6$alkyl, COC$_1$-C$_6$alkyl, COC$_1$-C$_6$alkyN(R$^{13}$)(R$^{14}$), COC$_1$-C$_6$alkyl(OH)N(R$^{13}$)(R$^{14}$), C$_1$-C$_6$alkyCON(R$^{13}$)(R$^{14}$), CON(R$^{13}$)(R$^{14}$), SO$_2$C$_1$-C$_6$alkyl, SO$_2$N(R$^{13}$)(R$^{14}$), C$_1$-C$_6$alkylaryl, C$_1$-C$_6$alkylhaloaryl, C(NH)N(R$^{13}$)(R$^{14}$) or heteroaryl.

In certain embodiments, R$^{27}$ is hydrogen. In certain embodiments described herein, R$^{27}$ is halogen. Examples of suitable halogens include, but are not limited to, chlorine, bromine, fluorine and iodine. In certain embodiments, R$^{27}$ is C$_3$-C$_6$cycloalkyl. Suitable cycloalkyl groups include, but are not limited to, cyclopropyl, cyclobutyl, cyclopentyl, cyclohexyl. In certain embodiments described herein, R$^{27}$ is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, R$^{27}$ is haloC$_1$-C$_6$alkyl. Suitable haloC$_1$-C$_6$alkyls include but are not limited to, fluoromethyl, difluoromethyl, trifluoromethyl, 2-fluoroethyl, 1,2-difluoroethyl and 2,2-difluoroethyl. In certain embodiments, R$^{27}$ is OH. In certain embodiments, R$^{27}$ is C$_1$-C$_6$alkylOH. Examples of suitable alcohols, include, but are not limited to, methanol, ethanol, propanol, butanol and iso-butanol. In certain embodiments, R$^{27}$ is C$_1$-C$_6$alkylOC$_1$-C$_6$alkyl. Suitable C$_1$-C$_6$alkylOC$_1$-C$_6$alkyls include but are not limited to, dimethyl ether, ethyl methyl ether, diethyl ether, dipropyl ether, dibutyl ether and diisopropyl ether. In certain embodiments, R$^{27}$ is COOH.

In certain embodiments, R$^{27}$ is N(R$^{13}$)(R$^{14}$). Examples of suitable N(R$^{13}$)(R$^{14}$) groups include, but are not limited to, NH$_2$, NH(CH$_3$), —N(CH$_3$)$_2$ and N(CH$_3$)$_2$. In certain embodiments, R$^{27}$ is C$_1$-C$_6$alkylN(R$^{13}$)(R$^{14}$). Examples of suitable $C_1$-$C_6$alkylN($R^{13}$)($R^{14}$) groups include, but are not limited to, $CH_2NH_2$, $CH_2NH(CH_3)$, $CH_2N(CH_3)_2$ and $CH_2CH_2N(CH_3)_2$.

In certain embodiments, $R^{27}$ is $C_1$-$C_6$alkoxy. Examples of suitable alkoxys, include but are not limited to, methoxy, ethoxy, butoxy and propoxy. In certain embodiments, $R^{27}$ is COO$C_1$-$C_6$alkyl. Examples of suitable COO$C_1$-$C_6$alkyl groups include, but are not limited to, methoxycarbonyl, ethoxycarbonyl and butoxycarbonyl.

In certain embodiments, $R^{27}$ is CO$C_1$-$C_6$alkyl. Suitable CO$C_1$-$C_6$alkyl groups include $COCH_3$ and $COCH_2CH_3$. In certain embodiments, $R^{27}$ is CO$C_1$-$C_6$alkyN($R^{13}$)($R^{14}$). Suitable examples of CO$C_1$-$C_6$alkylN($R^{13}$)($R^{14}$ groups include, but are not limited to

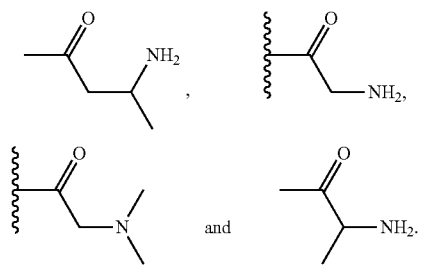

In certain embodiments, $R^{27}$ is CO$C_1$-$C_6$alkyl(OH)N($R^{13}$)($R^{14}$). Suitable examples CO$C_1$-$C_6$alkyl(OH)N($R^{13}$)($R^{14}$) groups include, but are not limited to,

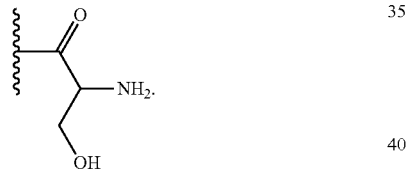

In certain embodiments, $R^{27}$ is $C_1$-$C_6$alkylCON($R^{13}$)($R^{14}$). Suitable groups include but are not to,

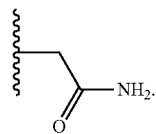 [SMILES: *CC(N)=O]

In certain embodiments, $R^{27}$ is CON($R^{13}$)($R^{14}$). Suitable CON($R^{13}$)($R^{14}$) groups include, but are not limited to, $CONH_2$. In certain embodiments, $R^{27}$ is $SO_2C_1$-$C_6$alkyl. Suitable $SO_2C_1$-$C_6$alkyl groups include, but are not limited to, $SO_2CH_3$. In certain embodiments, $R^{27}$ is $SO_2N(R^{13})(R^{14})$. Suitable $SO_2N(R^{13})(R^{14})$ groups include, but are not limited to, $SO_2NH_2$. In certain embodiments, $R^{27}$ is $C_1$-$C_6$alkylaryl. In certain embodiments, $R^{27}$ is $C_1$-$C_6$alkylhaloaryl. In certain embodiments, $R^{27}$ is C(NH)N($R^{13}$)($R^{14}$). In certain embodiments, $R^{27}$ is heteroaryl.

In certain embodiments, $R^{27}$ is selected from the group consisting of methyl, ethyl, isopropyl, $NH_2$,

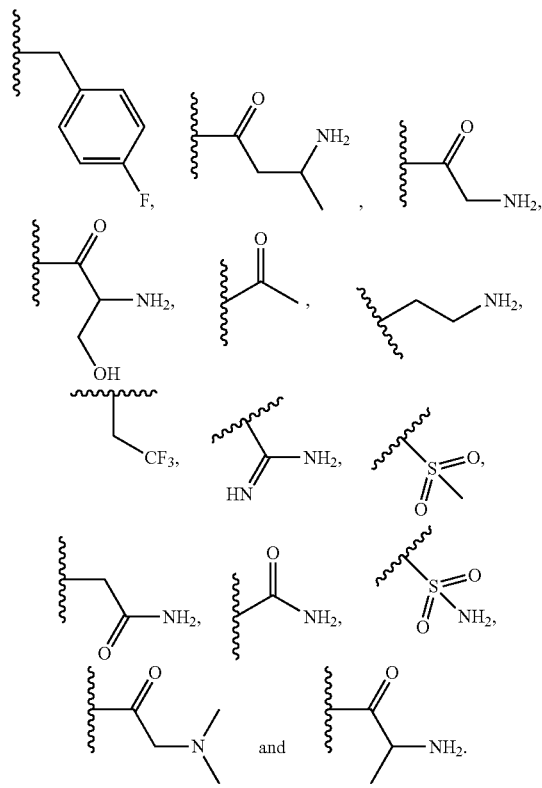

Also described herein are compounds having Formula III:

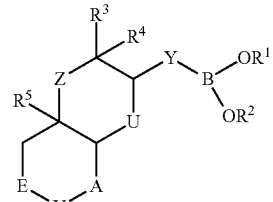

or a pharmaceutically acceptable salt thereof, wherein:
Y is a straight or branched ($C_2$-$C_5$)alkylene, wherein one or more —$CH_2$— groups in Y are optionally and independently replaced with a moiety selected from the group consisting of O, S and NH;
A is NH or $CH_2$;
E is a bond, NH or $CHR^{21}$;
V is $NR^{22}$ or $CHR^{23}$, wherein A and V cannot be simultaneously NH and $NR^{22}$, and wherein E and V cannot be simultaneously NH and $NR^{22}$;
U is a bond or $CR^7R^8$;
Z is a bond or $CR^{11}R^{12}$;
$R^1$ is a hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;
$R^2$ is a hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

R³ is hydrogen, halogen, C₃-C₆cycloalkyl, C₁-C₆alkyl, haloC₁-C₆alkyl, OH, C₁-C₆alkylOH, COOH, N(R¹³)(R¹⁴), C₁-C₆alkylN(R¹³)(R¹⁴), C₁-C₆alkoxy or COOC₁-C₆alkyl;

R⁴ is hydrogen, halogen, C₃-C₆cycloalkyl, C₁-C₆alkyl, haloC₁-C₆alkyl, OH, C₁-C₆alkylOH, COOH, N(R¹³)(R¹⁴), C₁-C₆alkylN(R¹³)(R¹⁴), C₁-C₆alkoxy or COOC₁-C₆alkyl;

R⁵ is hydrogen, halogen, C₃-C₆cycloalkyl, C₁-C₆alkyl, haloC₁-C₆alkyl, OH, C₁-C₆alkylOH, C₁-C₆alkylOC₁-C₆alkyl, COOH, N(R¹³)(R¹⁴), C₁-C₆alkylN(R¹³)(R¹⁴), C₁-C₆alkoxy or COOC₁-C₆alkyl;

R⁷ is hydrogen, halogen, C₃-C₆cycloalkyl, C₁-C₆alkyl, haloC₁-C₆alkyl, OH, C₁-C₆alkylOH, C₁-C₆alkylOC₁-C₆alkyl, COOH, N(R¹³)(R¹⁴), C₁-C₆alkylN(R¹³)(R¹⁴), C₁-C₆alkoxy, COOC₁-C₆alkyl;

R⁸ is hydrogen, halogen, C₃-C₆cycloalkyl, C₁-C₆alkyl, haloC₁-C₆alkyl, OH, C₁-C₆alkylOH, C₁-C₆alkylOC₁-C₆alkyl, COOH, N(R¹³)(R¹⁴), C₁-C₆alkylN(R¹³)(R¹⁴), C₁-C₆alkoxy, COOC₁-C₆alkyl;

R¹¹ is hydrogen, halogen, C₃-C₆cycloalkyl, C₁-C₆alkyl, haloC₁-C₆alkyl, OH, C₁-C₆alkylOH, C₁-C₆alkylOC₁-C₆alkyl, COOH, N(R¹³)(R¹⁴), C₁-C₆alkylN(R¹³)(R¹⁴), C₁-C₆alkoxy, COOC₁-C₆alkyl;

R¹² is hydrogen, halogen, C₃-C₆cycloalkyl, C₁-C₆alkyl, haloC₁-C₆alkyl, OH, C₁-C₆alkylOH, C₁-C₆alkylOC₁-C₆alkyl, COOH, N(R¹³)(R¹⁴), C₁-C₆alkylN(R¹³)(R¹⁴), C₁-C₆alkoxy, COOC₁-C₆alkyl;

R¹³ is hydrogen, C₃-C₆cycloalkyl, C₁-C₆alkyl, COC₁-C₆alkylNH₂, COC₁-C₆alkylNH(C₁-C₆alkyl), COC₁-C₆alkylN(C₁-C₆alkyl)₂, C₁-C₆haloalkyl, C₁-C₆alkylOH or COC₁-C₆alkyl;

R¹⁴ is hydrogen, C₃-C₆cycloalkyl, C₁-C₆alkyl, COC₁-C₆alkylNH₂, COC₁-C₆alkylNH(C₁-C₆alkyl), COC₁-C₆alkylN(C₁-C₆alkyl)₂, C₁-C₆haloalkyl, C₁-C₆alkylOH or COC₁-C₆alkyl;

R²¹ is hydrogen, halogen, C₃-C₆cycloalkyl, C₁-C₆alkyl, haloC₁-C₆alkyl, OH, C₁-C₆alkylOH, C₁-C₆alkylOC₁-C₆alkyl, COOH, N(R¹³)(R¹⁴), C₁-C₆alkylN(R¹³)(R¹⁴), C₁-C₆alkoxy, COOC₁-C₆alkyl, COC₁-C₆alkyl, COC₁-C₆alkyN(R¹³)(R¹⁴), COC₁-C₆alkyl(OH)N(R¹³)(R¹⁴), C₁-C₆alkylCON(R¹³)(R¹⁴), CON(R¹³)(R¹⁴), SO₂C₁-C₆alkyl, SO₂N(R¹³)(R¹⁴), C₁-C₆alkylaryl, C₁-C₆alkylhaloaryl, C(NH)N(R¹³)(R¹⁴) or heteroaryl;

R²² is hydrogen, C₃-C₆cycloalkyl, C₁-C₆alkyl, haloC₁-C₆alkyl, C₁-C₆alkylOH, C₁-C₆alkylOC₁-C₆alkyl, COOH, C₁-C₆alkylN(R¹³)(R¹⁴), COOC₁-C₆alkyl, COC₁-C₆alkyl, COC₁-C₆alkylN(R¹³)(R¹⁴), COC₁-C₆alkyl(OH)N(R¹³)(R¹⁴), C₁-C₆alkylCON(R¹³)(R¹⁴), CON(R¹³)(R¹⁴), SO₂C₁-C₆alkyl, SO₂N(R¹³)(R¹⁴), C₁-C₆alkylaryl, C₁-C₆alkylhaloaryl, C(NH)N(R¹³)(R¹⁴) or heteroaryl; and R²³ is hydrogen, halogen, C₃-C₆cycloalkyl, C₁-C₆alkyl, haloC₁-C₆alkyl, OH, C₁-C₆alkylOH, C₁-C₆alkylOC₁-C₆alkyl, COOH, N(R¹³)(R¹⁴), C₁-C₆alkylN(R¹³)(R¹⁴), C₁-C₆alkoxy, COOC₁-C₆alkyl, COC₁-C₆alkyl, COC₁-C₆alkyN(R¹³)(R¹⁴), COC₁-C₆alkyl(OH)N(R¹³)(R¹⁴), C₁-C₆alkylCON(R¹³)(R¹⁴), CON(R¹³)(R¹⁴), SO₂C₁-C₆alkyl, SO₂N(R¹³)(R¹⁴), C₁-C₆alkylaryl, C₁-C₆alkylhaloaryl, C(NH)N(R¹³)(R¹⁴) or heteroaryl.

With regard to compounds of Formula III, Y, A, E, V, U, Z, R¹, R², R³, R⁴, R⁵, R⁷, R⁸, R¹¹, R¹², R¹³, R¹⁴, R²¹, R²² and R²³ are discussed in detail above.

Also described herein are compounds having Formula IV:

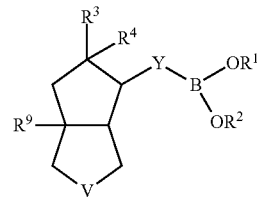

IV or a pharmaceutically acceptable salt thereof, wherein:

Y is a straight or branched (C₂-C₅)alkylene, wherein one or more —CH₂— groups in Y are optionally and independently replaced with a moiety selected from the group consisting of O, S and NH;

V is NR²² or CHR²³;

R¹ is hydrogen or C₁-C₆alkyl or, taken with R² forms a C₃-C₈cycloalkyl, wherein the C₃-C₈cycloalkyl is unsubstituted or substituted with one to four substituents selected from the group consisting of halogen, C₁-C₆alkyl or OH;

R² is hydrogen or C₁-C₆alkyl or, taken with R¹ forms a C₃-C₈cycloalkyl, wherein the C₃-C₈cycloalkyl is unsubstituted or substituted with one to four substituents selected from the group consisting of halogen, C₁-C₆alkyl or OH;

R³ is hydrogen, halogen, C₃-C₆cycloalkyl, C₁-C₆alkyl, haloC₁-C₆alkyl, OH, C₁-C₆alkylOH, COOH, N(R¹³)(R¹⁴), C₁-C₆alkylN(R¹³)(R¹⁴), C₁-C₆alkoxy or COOC₁-C₆alkyl;

R⁴ is hydrogen, halogen, C₃-C₆cycloalkyl, C₁-C₆alkyl, haloC₁-C₆alkyl, OH, C₁-C₆alkylOH, COOH, N(R¹³)(R¹⁴), C₁-C₆alkylN(R¹³)(R¹⁴), C₁-C₆alkoxy or COOC₁-C₆alkyl;

R⁹ is hydrogen, halogen, C₃-C₆cycloalkyl, C₁-C₆alkyl, haloC₁-C₆alkyl, OH, C₁-C₆alkylOH, COOH, N(R¹³)(R¹⁴), C₁-C₆alkylN(R¹³)(R¹⁴), C₁-C₆alkoxy or COOC₁-C₆alkyl;

R¹³ is hydrogen, C₃-C₆cycloalkyl, C₁-C₆alkyl, COC₁-C₆alkylNH₂, COC₁-C₆alkylNH(C₁-C₆alkyl), COC₁-C₆alkylN(C₁-C₆alkyl)₂, C₁-C₆haloalkyl, C₁-C₆alkylOH or COC₁-C₆alkyl;

R¹⁴ is hydrogen, C₃-C₆cycloalkyl, C₁-C₆alkyl, COC₁-C₆alkylNH₂, COC₁-C₆alkylNH(C₁-C₆alkyl), COC₁-C₆alkylN(C₁-C₆alkyl)₂, C₁-C₆haloalkyl, C₁-C₆alkylOH or COC₁-C₆alkyl;

R²² is hydrogen, C₃-C₆cycloalkyl, C₁-C₆alkyl, haloC₁-C₆alkyl, C₁-C₆alkylOH, C₁-C₆alkylOC₁-C₆alkyl, COOH, C₁-C₆alkylN(R¹³)(R¹⁴), COOC₁-C₆alkyl, COC₁-C₆alkyl, COC₁-C₆alkylN(R¹³)(R¹⁴), COC₁-C₆alkyl(OH)N(R¹³)(R¹⁴), C₁-C₆alkylCON(R¹³)(R¹⁴), CON(R¹³)(R¹⁴), SO₂C₁-C₆alkyl, SO₂N(R¹³)(R¹⁴), C₁-C₆alkylaryl, C₁-C₆alkylhaloaryl, C(NH)N(R¹³)(R¹⁴) or heteroaryl; and R²³ is hydrogen, halogen, C₃-C₆cycloalkyl, C₁-C₆alkyl, haloC₁-C₆alkyl, OH, C₁-C₆alkylOH, C₁-C₆alkylOC₁-C₆alkyl, COOH, N(R¹³)(R¹⁴), C₁-C₆alkyN(R¹³)(R¹⁴), C₁-C₆alkoxy, COOC₁-C₆alkyl, COC₁-C₆alkyl, COC₁-C₆alkyN(R¹³)(R¹⁴), COC₁-C₆alkyl(OH)N(R¹³)(R¹⁴), C₁-C₆alkylCON(R¹³)(R¹⁴), CON(R¹³)(R¹⁴), SO₂C₁-C₆alkyl, SO₂N(R¹³)(R¹⁴), C₁-C₆alkylaryl, C₁-C₆alkylhaloaryl, C(NH)N(R¹³)(R¹⁴) or heteroaryl.

With regard to the compounds of Formula IV, Y, V, R¹, R², R³, R⁴, R⁹, R¹³, R¹⁴, R²² and R²³ are discussed in further detail above.

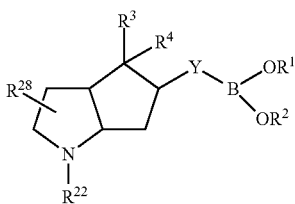

V or a pharmaceutically acceptable salt thereof, wherein:

Y is a straight or branched $(C_2-C_5)$alkylene, wherein one or more —$CH_2$— groups in Y are optionally and independently replaced with a moiety selected from the group consisting of O, S and NH;

$R^1$ is hydrogen or $C_1$-$C_6$alkyl or, taken with $R^2$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^2$ is hydrogen or $C_1$-$C_6$alkyl or, taken with $R^1$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^3$ is hydrogen, halogen, $C_3$-$C_6$cycloalkyl, $C_1$-$C_6$alkyl, halo$C_1$-$C_6$alkyl, OH, $C_1$-$C_6$alkylOH, COOH, N($R^{13}$)($R^{14}$), $C_1$-$C_6$alkylN($R^{13}$)($R^{14}$), $C_1$-$C_6$alkoxy or COO$C_1$-$C_6$alkyl;

$R^4$ is hydrogen, halogen, $C_3$-$C_6$cycloalkyl, $C_1$-$C_6$alkyl, halo$C_1$-$C_6$alkyl, OH, $C_1$-$C_6$alkylOH, COOH, N($R^{13}$)($R^{14}$), $C_1$-$C_6$alkylN($R^{13}$)($R^{14}$), $C_1$-$C_6$alkoxy or COO$C_1$-$C_6$alkyl;

$R^{13}$ is hydrogen, $C_3$-$C_6$cycloalkyl, $C_1$-$C_6$alkyl, CO$C_1$-$C_6$alkylNH$_2$, CO$C_1$-$C_6$alkylNH($C_1$-$C_6$alkyl), CO$C_1$-$C_6$alkylN($C_1$-$C_6$alkyl)$_2$, $C_1$-$C_6$haloalkyl, $C_1$-$C_6$alkylOH or CO$C_1$-$C_6$alkyl;

$R^{14}$ is hydrogen, $C_3$-$C_6$cycloalkyl, $C_1$-$C_6$alkyl, CO$C_1$-$C_6$alkylNH$_2$, CO$C_1$-$C_6$alkylNH($C_1$-$C_6$alkyl), CO$C_1$-$C_6$alkylN($C_1$-$C_6$alkyl)$_2$, $C_1$-$C_6$haloalkyl, $C_1$-$C_6$alkylOH or CO$C_1$-$C_6$alkyl;

$R^{22}$ is hydrogen, $C_1$-$C_6$alkyl, $C_1$-$C_6$haloalkyl, CO$C_1$-$C_6$alkyl, CO$C_1$-$C_6$alkyN($R^{13}$)($R^{14}$), CO$C_1$-$C_6$alkyl(OH)N($R^{13}$)($R^{14}$), $C_1$-$C_6$alkyCON($R^{13}$)($R^{14}$), CON($R^{13}$)($R^{14}$), SO$_2$$C_1$-$C_6$alkyl, SO$_2$N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$) or COO$C_1$-$C_6$alkyl; and $R^{28}$ is hydrogen, halogen, OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, CO$C_1$-$C_6$alkyl, CO$C_1$-$C_6$alkylN($R^{13}$)($R^{14}$), CO$C_1$-$C_6$alkyl(OH)N($R^{13}$)($R^{14}$), $C_1$-$C_6$alkyCON($R^{13}$)($R^{14}$), CON($R^{13}$)($R^{14}$), SO$_2$$C_1$-$C_6$alkyl, SO$_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), $C_1$-$C_6$alkoxy or COO$C_1$-$C_6$alkyl.

With regard to the compounds of Formula V, Y, $R^1$, $R^2$, $R^3$, $R^4$, $R^{13}$, $R^{14}$ and $R^{22}$ are discussed in detail above.

With regard to compounds described herein, $R^{28}$ is hydrogen, halogen, OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, CO$C_1$-$C_6$alkyl, CO$C_1$-$C_6$alkylN($R^{13}$)($R^{14}$), CO$C_1$-$C_6$alkyl(OH)N($R^{13}$)($R^{14}$), $C_1$-$C_6$alkylCON($R^{13}$)($R^{14}$), CON($R^{13}$)($R^{14}$), SO$_2$$C_1$-$C_6$alkyl, SO$_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), $C_1$-$C_6$alkoxy or COO$C_1$-$C_6$alkyl.

In certain embodiments, $R^{28}$ is hydrogen. In certain embodiments described herein, $R^{28}$ is halogen. Examples of suitable halogens include, but are not limited to, chlorine, bromine, fluorine and iodine. In certain embodiments, $R^{28}$ is OH. In certain embodiments, $R^{28}$ is $C_1$-$C_6$alkylOH. Examples of suitable alcohols, include, but are not limited to, methanol, ethanol, propanol, butanol and iso-butanol. In certain embodiments, $R^{28}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{28}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{28}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{28}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^{28}$ is oxo.

In certain embodiments, $R^{28}$ is N($R^{13}$)($R^{14}$). Examples of suitable N($R^{13}$)($R^{14}$) groups include, but are not limited to, NH$_2$, NH(CH$_3$), N(CH$_3$)$_2$ and N(CH$_3$)$_2$. In certain embodiments, $R^{28}$ is $C_1$-$C_6$alkylN($R^{13}$)($R^{14}$). Examples of suitable $C_1$-$C_6$alkylN($R^{13}$)($R^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^{28}$ is $C_1$-$C_6$alkoxy. Examples of suitable alkoxys, include but are not limited to, methoxy, ethoxy, butoxy and propoxy. In certain embodiments, $R^{28}$ is COO$C_1$-$C_6$alkyl. Examples of suitable COO$C_1$-$C_6$alkyl groups include, but are not limited to, methoxycarbonyl, ethoxycarbonyl and butoxycarbonyl.

In certain embodiments, $R^{28}$ is CO$C_1$-$C_6$alkyl. Suitable CO$C_1$-$C_6$alkyl groups include COCH$_3$ and COCH$_2$CH$_3$. In certain embodiments, $R^{28}$ is CO$C_1$-$C_6$alkyN($R^{13}$)($R^{14}$). Suitable examples of CO$C_1$-$C_6$alkyN($R^{13}$)($R^{14}$) groups include, but are not limited to,

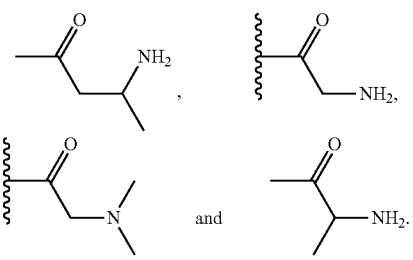

In certain embodiments, $R^{28}$ is CO$C_1$-$C_6$alkyl(OH)N($R^{13}$)($R^{14}$). Suitable examples CO$C_1$-$C_6$alkyl(OH)N($R^{13}$)($R^{14}$) groups include, but are not limited to,

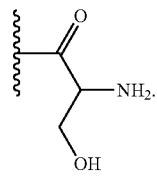

In certain embodiments, $R^{28}$ is $C_1$-$C_6$alkylCON($R^{13}$)($R^{14}$). Suitable groups include but are not to,

[structure: -CH2-C(=O)-NH2]

In certain embodiments, $R^{28}$ is CON($R^{13}$)($R^{14}$). Suitable CON($R^{13}$)($R^{14}$) groups include, but are not limited to, CONH$_2$. In certain embodiments, $R^{28}$ is SO$_2$C$_1$-C$_6$alkyl. Suitable SO$_2$C$_1$-C$_6$alkyl groups include, but are not limited to, SO$_2$CH$_3$. In certain embodiments, $R^2$ is SO$_2$N($R^{13}$)($R^{14}$). Suitable SO$_2$N($R^{13}$)($R^{14}$) groups include, but are not limited to, SO$_2$NH$_2$. In certain embodiments, $R^{28}$ is C$_1$-C$_6$alkylaryl. In certain embodiments, $R^{28}$ is C$_1$-C$_6$alkylhaloaryl. In certain embodiments, $R^{28}$ is C(NH)N($R^{13}$)($R^{14}$).

Also described herein are compounds of Formula VI:

[Structure VI]

or a pharmaceutically acceptable salt thereof, wherein:

Y is a straight or branched (C$_2$-C$_5$)alkylene, wherein one or more —CH$_2$— groups in Y are optionally and independently replaced with a moiety selected from the group consisting of O, S and NH;

$R^1$ is hydrogen or C$_1$-C$_6$alkyl or, taken with $R^2$ forms a C$_3$-C$_8$cycloalkyl, wherein the C$_3$-C$_8$cycloalkyl is unsubstituted or substituted with one to four substituents selected from the group consisting of halogen, C$_1$-C$_6$alkyl or OH;

$R^2$ is hydrogen or C$_1$-C$_6$alkyl or, taken with $R^1$ forms a C$_3$-C$_8$cycloalkyl, wherein the C$_3$-C$_8$cycloalkyl is unsubstituted or substituted with one to four substituents selected from the group consisting of halogen, C$_1$-C$_6$alkyl or OH;

$R^3$ is hydrogen, halogen, C$_3$-C$_6$cycloalkyl, C$_1$-C$_6$alkyl, haloC$_1$-C$_6$alkyl, OH, C$_1$-C$_6$alkylOH, COOH, N($R^{13}$)($R^{14}$), C$_1$-C$_6$alkylN($R^{13}$)($R^{14}$), C$_1$-C$_6$alkoxy or COOC$_1$-C$_6$alkyl;

$R^4$ is hydrogen, halogen, C$_3$-C$_6$cycloalkyl, C$_1$-C$_6$alkyl, haloC$_1$-C$_6$alkyl, OH, C$_1$-C$_6$alkylOH, COOH, N($R^{13}$)($R^{14}$), C$_1$-C$_6$alkylN($R^{13}$)($R^{14}$), C$_1$-C$_6$alkoxy or COOC$_1$-C$_6$alkyl;

Z is a bond or CR$^{11}$R$^{12}$;
U is a bond, O, NR$^{15}$ or CR$^7$R$^8$;
J is a bond O, NR$^{29}$ or CR$^{30}$R$^{31}$;
L is O, NR$^{32}$ or CR$^{33}$R$^{34}$;
G is a bond, O, NR$^{35}$ or CR$^{36}$R$^{37}$; wherein J and L cannot be simultaneously O, or O and NR$^{32}$, respectively, or NR$^{29}$ and O, respectively, or NR$^{29}$ and NR$^{32}$, respectively;

$R^1$ is a hydrogen, C$_3$-C$_6$cycloalkyl or —C$_1$-C$_6$alkyl or, taken with $R^2$ forms a C$_3$-C$_8$cycloalkyl, wherein the C$_3$-C$_8$cycloalkyl is unsubstituted or substituted with one to four substituents selected from the group consisting of halogen, C$_1$-C$_6$alkyl or OH;

$R^2$ is a hydrogen, C$_3$-C$_6$cycloalkyl or C$_1$-C$_6$alkyl or, taken with $R^1$ forms a C$_3$-C$_8$cycloalkyl, wherein the C$_3$-C$_8$cycloalkyl is unsubstituted or substituted with one to four substituents selected from the group consisting of halogen, C$_1$-C$_6$alkyl or OH;

$R^3$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N($R^{13}$)($R^{14}$), C$_1$-C$_6$alkyN($R^{13}$)($R^{14}$), C$_1$-C$_6$alkoxy or COOC$_1$-C$_6$alkyl;

$R^4$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N($R^{13}$)($R^{14}$), C$_1$-C$_6$alkyN($R^{13}$)($R^{14}$), C$_1$-C$_6$alkoxy or COOC$_1$-C$_6$alkyl;

$R^7$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N($R^{13}$)($R^{14}$), C$_1$-C$_6$alkyN($R^{13}$)($R^{14}$), C$_1$-C$_6$alkoxy, COOC$_1$-C$_6$alkyl;

$R^8$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N($R^{13}$)($R^{14}$), C$_1$-C$_6$alkyN($R^{13}$)($R^{14}$), C$_1$-C$_6$alkoxy, COOC$_1$-C$_6$alkyl;

$R^{11}$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N($R^{13}$)($R^{14}$), C$_1$-C$_6$alkyN($R^{13}$)($R^{14}$), C$_1$-C$_6$alkoxy, COOC$_1$-C$_6$alkyl;

$R^{12}$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N($R^{13}$)($R^{14}$), C$_1$-C$_6$alkyN($R^{13}$)($R^{14}$), C$_1$-C$_6$alkoxy, COOC$_1$-C$_6$alkyl;

$R^{13}$ is hydrogen, C$_3$-C$_6$cycloalkyl, C$_1$-C$_6$alkyl, COC$_1$-C$_6$alkylNH$_2$, COC$_1$-C$_6$alkylNH(C$_1$-C$_6$alkyl), COC$_1$-C$_6$alkylN(C$_1$-C$_6$alkyl)$_2$, C$_1$-C$_6$haloalkyl, C$_1$-C$_6$alkylOH or COC$_1$-C$_6$alkyl;

$R^{14}$ is hydrogen, C$_3$-C$_6$cycloalkyl, C$_1$-C$_6$alkyl, COC$_1$-C$_6$alkylNH$_2$, COC$_1$-C$_6$alkylNH(C$_1$-C$_6$alkyl), COC$_1$-C$_6$alkylN(C$_1$-C$_6$alkyl)$_2$, C$_1$-C$_6$haloalkyl, C$_1$-C$_6$alkylOH or COC$_1$-C$_6$alkyl;

$R^{15}$ is hydrogen, C$_3$-C$_6$cycloalkyl, C$_1$-C$_6$alkyl, COC$_1$-C$_6$alkyN($R^{13}$)($R^{14}$) or COC$_1$-C$_6$alkyl;

$R^{29}$ is hydrogen, C$_3$-C$_6$cycloalkyl, C$_1$-C$_6$alkyl, COC$_1$-C$_6$alkyN($R^{13}$)($R^{14}$) or COC$_1$-C$_6$alkyl;

$R^{30}$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N($R^{13}$)($R^{14}$), C$_1$-C$_6$alkyN($R^{13}$)($R^{14}$), C$_1$-C$_6$alkoxy, COOC$_1$-C$_6$alkyl, COC$_1$-C$_6$alkyl, COC$_1$-C$_6$alkyN($R^{13}$)($R^{14}$), COC$_1$-C$_6$alkyl(OH)N($R^{13}$)($R^{14}$), C$_1$-C$_6$alkylCON($R^{13}$)($R^{14}$), CON($R^{13}$)($R^{14}$), SO$_2$C$_1$-C$_6$alkyl, SO$_2$N($R^{13}$)($R^{14}$), C$_1$-C$_6$alkylaryl, C$_1$-C$_6$alkylhaloaryl, C(NH)N($R^{13}$)($R^{14}$) or heteroaryl or when combined with $R^{31}$, $R^{30}$ and $R^{31}$ form an oxo group;

$R^{31}$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N($R^{13}$)($R^{14}$), C$_1$-C$_6$alkyN($R^{13}$)($R^{14}$), C$_1$-C$_6$alkoxy, COOC$_1$-C$_6$alkyl, COC$_1$-C$_6$alkyl, COC$_1$-C$_6$alkyN($R^{13}$)($R^{14}$), COC$_1$-C$_6$alkyl(OH)N($R^{13}$)($R^{14}$), C$_1$-C$_6$alkylCON($R^{13}$)($R^{14}$), CON($R^{13}$)($R^{14}$), SO$_2$C$_1$-C$_6$alkyl, SO$_2$N($R^{13}$)($R^{14}$), C$_1$-C$_6$alkylaryl, C$_1$-C$_6$alkylhaloaryl, C(NH)N($R^{13}$)($R^{14}$) or heteroaryl or when combined with $R^{30}$, $R^{31}$ and $R^{3'}$ form an oxo group;

$R^{32}$ is hydrogen, C$_3$-C$_6$cycloalkyl, C$_1$-C$_6$alkyl, COC$_1$-C$_6$alkyN($R^{13}$)($R^{14}$) or COC$_1$-C$_6$alkyl;

$R^{33}$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N($R^{13}$)($R^{14}$), C$_1$-C$_6$alkyN($R^{13}$)($R^{14}$), C$_1$-C$_6$alkoxy, COOC$_1$-C$_6$alkyl, COC$_1$-C$_6$alkyl, COC$_1$-C$_6$alkyN($R^{13}$)($R^{14}$), COC$_1$-C$_6$alkyl(OH)N($R^{13}$)($R^{14}$), C$_1$-C$_6$alkylCON($R^{13}$)($R^{14}$), CON($R^{13}$)($R^{14}$), SO$_2$C$_1$-C$_6$alkyl, SO$_2$N($R^{13}$)($R^{14}$), C$_1$-C$_6$alkylaryl, C$_1$-C$_6$alkylhaloaryl, C(NH)N($R^{13}$)($R^{14}$) or heteroaryl;

$R^{34}$ is hydrogen, halogen, $C_3$-$C_6$cycloalkyl, $C_1$-$C_6$alkyl, haloC$_1$-C$_6$alkyl, OH, C$_1$-C$_6$alkylOH, C$_1$-C$_6$alkylOC$_1$-C$_6$alkyl, COOH, N(R$^{13}$)(R$^{14}$), C$_1$-C$_6$alkyN(R$^{13}$)(R$^{14}$), C$_1$-C$_6$alkoxy, COOC$_1$-C$_6$alkyl, COC$_1$-C$_6$alkyl, COC$_1$-C$_6$alkyN(R$^{13}$)(R$^{14}$), COC$_1$-C$_6$alkyl(OH)N(R$^{13}$)(R$^{14}$), C$_1$-C$_6$alkylCON(R$^{13}$)(R$^{14}$), CON(R$^{13}$)(R$^{14}$), SO$_2$C$_1$-C$_6$alkyl, SO$_2$N(R$^{13}$)(R$^{14}$), C$_1$-C$_6$alkylaryl, C$_1$-C$_6$alkylhaloaryl, C(NH)N(R$^{13}$)(R$^{14}$) or heteroaryl;

$R^{35}$ is hydrogen, C$_3$-C$_6$cycloalkyl, C$_1$-C$_6$alkyl, COC$_1$-C$_6$alkyN(R$^{13}$)(R$^{14}$) or COC$_1$-C$_6$alkyl;

$R^{36}$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N(R$^{13}$)(R$^{14}$), C$_1$-C$_6$alkyN(R$^{13}$)(R$^{14}$), C$_1$-C$_6$alkoxy, COOC$_1$-C$_6$alkyl, COC$_1$-C$_6$alkyl, COC$_1$-C$_6$alkyN(R$^{13}$)(R$^{14}$), COC$_1$-C$_6$alkyl(OH)N(R$^{13}$)(R$^{14}$), C$_1$-C$_6$alkylCON(R$^{13}$)(R$^{14}$), CON(R$^{13}$)(R$^{14}$), SO$_2$C$_1$-C$_6$alkyl, SO$_2$N(R$^{13}$)(R$^{14}$), C$_1$-C$_6$alkylaryl, C$_1$-C$_6$alkylhaloaryl, C(NH)N(R$^{13}$)(R$^{14}$) or heteroaryl; and $R^{37}$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N(R$^{13}$)(R$^{14}$), C$_1$-C$_6$alkyN(R$^{13}$)(R$^{14}$), C$_1$-C$_6$alkoxy, COOC$_1$-C$_6$alkyl, COC$_1$-C$_6$alkyl, COC$_1$-C$_6$alkyN(R$^{13}$)(R$^{14}$), COC$_1$-C$_6$alkyl(OH)N(R$^{13}$)(R$^{14}$), C$_1$-C$_6$alkylCON(R$^{13}$)(R$^{14}$), CON(R$^{13}$)(R$^{14}$), SO$_2$C$_1$-C$_6$alkyl, SO$_2$N(R$^{13}$)(R$^{14}$), C$_1$-C$_6$alkylaryl, C$_1$-C$_6$alkylhaloaryl, C(NH)N(R$^{13}$)(R$^{14}$) or heteroaryl.

With regard to the compounds of Formula VI, Y, U, Z, $R^1$, $R^2$, $R^3$, $R^4$, $R^7$, $R^8$, $R^{11}$, $R^{12}$, $R^{13}$, $R^{14}$ and $R^{15}$ are discussed in detail above.

With regard to the compounds described herein, J is a bond O, NR$^{29}$ or CR$^{30}$R$^{31}$. In certain embodiments, J is a bond. In certain embodiments, J is O. In certain embodiments, J is NR$^{29}$. In certain embodiments, J is CR$^{30}$R$^{31}$.

With regard to the compounds described herein, L is O, NR$^{32}$ or CR$^{33}$R$^{34}$. In certain embodiments, L is O. In certain embodiments, J is NR$^{32}$. In certain embodiments, L is CR$^{33}$R$^{34}$.

With regard to the compounds described herein, G is a bond, O, NR$^{35}$ or CR$^{36}$R$^{37}$. In certain embodiments, G is a bond. In certain embodiments, G is O. In certain embodiments, G is NR$^{35}$. In certain embodiments, J is CR$^{36}$R$^{37}$. In certain embodiments, J and L cannot be simultaneously O, O and NR$^{32}$ or NR$^{29}$ and O or NR$^{29}$ and NR$^{32}$.

With regard to the compounds described herein, $R^{29}$ is hydrogen, C$_3$-C$_6$cycloalkyl, C$_1$-C$_6$alkyl, COC$_1$-C$_6$alkylNH$_2$, COC$_1$-C$_6$alkylNH(C$_1$-C$_6$alkyl), COC$_1$-C$_6$alkylN(C$_1$-C$_6$alkyl)$_2$, or COC$_1$-C$_6$alkyl. In certain embodiments, R$^{29}$ is hydrogen. In certain embodiments, R$^{29}$ is C$_3$-C$_6$cycloalkyl. Suitable cycloalkyl groups include, but are not limited to, cyclopropyl, cyclobutyl, cyclopentyl, cyclohexyl. In certain embodiments described herein, R$^{29}$ is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, R$^{29}$ is COC$_1$-C$_6$alkylNH$_2$. In certain embodiments, R$^{29}$ is COC$_1$-C$_6$alkylNH(C$_1$-C$_6$alkyl). In certain embodiments, R$^{29}$ is COC$_1$-C$_6$alkyN(C$_1$-C$_6$alkyl)$_2$.

With regard to the compounds described herein, $R^3$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N(R$^{13}$)(R$^{14}$), C$_1$-C$_6$alkylN(R$^{13}$)(R$^{14}$), C$_1$-C$_6$alkoxy, COOC$_1$-C$_6$alkyl, COC$_1$-C$_6$alkyl, COC$_1$-C$_6$alkyN(R$^{13}$)(R$^{14}$), COC$_1$-C$_6$alkyl(OH)N(R$^{13}$)(R$^{14}$), C$_1$-C$_6$alkyCON(R$^{13}$)(R$^{14}$), CON(R$^{13}$)(R$^{14}$), SO$_2$C$_1$-C$_6$alkyl, SO$_2$N(R$^{13}$)(R$^{14}$), C$_1$-C$_6$alkylaryl, C$_1$-C$_6$alkylhaloaryl, C(NH)N(R$^{13}$)(R$^{14}$) or heteroaryl.

In certain embodiments, $R^{30}$ is hydrogen. In certain embodiments described herein, R$^{30}$ is halogen. Examples of suitable halogens include, but are not limited to, chlorine, bromine, fluorine and iodine. In certain embodiments, R$^{30}$ is C$_3$-C$_6$cycloalkyl. Suitable cycloalkyl groups include, but are not limited to, cyclopropyl, cyclobutyl, cyclopentyl, cyclohexyl. In certain embodiments described herein, R$^{30}$ is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{30}$ is haloC$_1$-C$_6$alkyl. Suitable haloC$_1$-C$_6$alkyls include but are not limited to, fluoromethyl, difluoromethyl, trifluoromethyl, 2-fluoroethyl, 1,2-difluoroethyl and 2,2-difluoroethyl. In certain embodiments, R$^{30}$ is OH. In certain embodiments, R$^{30}$ is C$_1$-C$_6$alkylOH. Examples of suitable alcohols, include, but are not limited to, methanol, ethanol, propanol, butanol and iso-butanol. In certain embodiments, R$^{30}$ is C$_1$-C$_6$alkylOC$_1$-C$_6$alkyl. Suitable C$_1$-C$_6$alkylOC$_1$-C$_6$alkyls include but are not limited to, dimethyl ether, ethyl methyl ether, diethyl ether, dipropyl ether, dibutyl ether and diisopropyl ether. In certain embodiments, R$^{30}$ is COOH.

In certain embodiments, $R^{30}$ is N(R$^{13}$)(R$^{14}$). Examples of suitable N(R$^{13}$)(R$^{14}$) groups include, but are not limited to, NH$_2$, NH(CH$_3$), N(CH$_3$)$_2$ and N(CH$_3$)$_2$. In certain embodiments, R$^{30}$ is C$_1$-C$_6$alkylN(R$^{13}$)(R$^{14}$). Examples of suitable C$_1$-C$_6$alkylN(R$^{13}$)(R$^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^{30}$ is C$_1$-C$_6$alkoxy. Examples of suitable alkoxys, include but are not limited to, methoxy, ethoxy, butoxy and propoxy. In certain embodiments, R$^{30}$ is COOC$_1$-C$_6$alkyl. Examples of suitable COOC$_1$-C$_6$alkyl groups include, but are not limited to, methoxycarbonyl, ethoxycarbonyl and butoxycarbonyl.

In certain embodiments, $R^{30}$ is COC$_1$-C$_6$alkyl. Suitable COC$_1$-C$_6$alkyl groups include COCH$_3$ and COCH$_2$CH$_3$. In certain embodiments, R$^{30}$ is COC$_1$-C$_6$alkyN(R$^{13}$)(R$^{14}$). Suitable examples of COC$_1$-C$_6$alkylN(R$^{13}$)(R$^{14}$) groups include, but are not limited to,

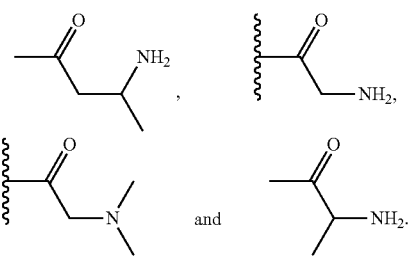

In certain embodiments, $R^{30}$ is COC$_1$-C$_6$alkyl(OH)N(R$^{13}$)(R$^{14}$). Suitable examples COC$_1$-C$_6$alkyl(OH)N(R$^{13}$)(R$^{14}$) groups include, but are not limited to,

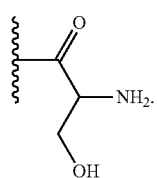 [SMILES: *C(=O)C(N)CO]

In certain embodiments, $R^{30}$ is $C_1$-$C_6$alkylCON($R^{13}$)($R^{14}$). Suitable groups include but are not to,

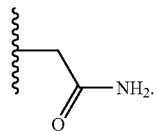 [SMILES: *CC(N)=O]

In certain embodiments, $R^{30}$ is CON($R^{13}$)($R^{14}$). Suitable CON($R^{13}$)($R^{14}$) groups include, but are not limited to, CONH$_2$. In certain embodiments, $R^{30}$ is SO$_2$C$_1$-C$_6$alkyl. Suitable SO$_2$C$_1$-C$_6$alkyl groups include, but are not limited to, SO$_2$CH$_3$. In certain embodiments, $R^{30}$ is SO$_2$N($R^{13}$)($R^{14}$). Suitable SO$_2$N($R^{13}$)($R^{14}$) groups include, but are not limited to, SO$_2$NH$_2$. In certain embodiments, $R^{30}$ is $C_1$-$C_6$alkylaryl. In certain embodiments, $R^{30}$ is $C_1$-$C_6$alkylhaloaryl. In certain embodiments, $R^{30}$ is C(NH)N($R^{13}$)($R^{14}$). In certain embodiments, $R^{30}$ is heteroaryl.

In certain embodiments, $R^{30}$ is selected from the group consisting of methyl, ethyl, isopropyl, NH$_2$,

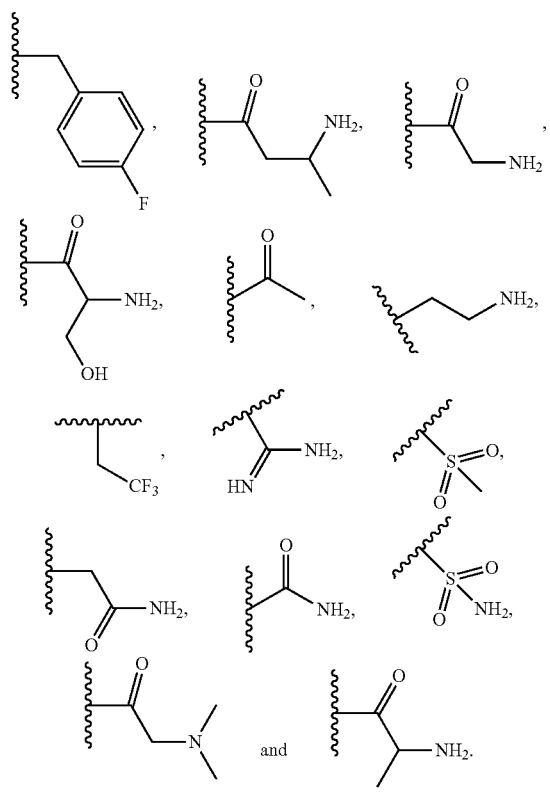

With regard to the compounds described herein, $R^{31}$ is hydrogen, halogen, $C_3$-$C_6$cycloalkyl, $C_1$-$C_6$alkyl, haloC$_1$-C$_6$alkyl, OH, $C_1$-$C_6$alkylOH, $C_1$-$C_6$alkylOC$_1$-$C_6$alkyl, COOH, N($R^{13}$)($R^{14}$), $C_1$-$C_6$alkylN($R^{13}$)($R^{14}$), $C_1$-$C_6$alkoxy, COOC$_1$-$C_6$alkyl, COC$_1$-$C_6$alkyl, COC$_1$-$C_6$alkyN($R^{13}$)($R^{14}$), COC$_1$-$C_6$alkyl(OH)N($R^{13}$)($R^{14}$), $C_1$-$C_6$alkyCON($R^{13}$)($R^{14}$), CON($R^{13}$)($R^{14}$), SO$_2$C$_1$-$C_6$alkyl, SO$_2$N($R^{13}$)($R^{14}$), $C_1$-$C_6$alkylaryl, $C_1$-$C_6$alkylhaloaryl, C(NH)N($R^{13}$)($R^{14}$) or heteroaryl.

In certain embodiments, $R^{31}$ is hydrogen. In certain embodiments described herein, $R^{31}$ is halogen. Examples of suitable halogens include, but are not limited to, chlorine, bromine, fluorine and iodine. In certain embodiments, $R^{31}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{31}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{31}$ is haloC$_1$-$C_6$alkyl. Suitable haloC$_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{31}$ is OH. In certain embodiments, $R^{31}$ is $C_1$-$C_6$alkylOH. Examples of suitable alcohols, include, but are not limited to, methanol, ethanol, propanol, butanol and iso-butanol. In certain embodiments, $R^{31}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether. In certain embodiments, $R^{31}$ is COOH.

In certain embodiments, $R^{31}$ is N($R^{13}$)($R^{14}$). Examples of suitable N($R^{13}$)($R^{14}$) groups include, but are not limited to, NH$_2$, NH(CH$_3$), N(CH$_3$)$_2$ and N(CH$_3$)$_2$. In certain embodiments, $R^{31}$ is $C_1$-$C_6$alkylN($R^{13}$)($R^{14}$). Examples of suitable $C_1$-$C_6$alkylN($R^{13}$)($R^{14}$) groups include, but are not limited to, CH$_2$NH$_2$, CH$_2$NH(CH$_3$), CH$_2$N(CH$_3$)$_2$ and CH$_2$CH$_2$N(CH$_3$)$_2$.

In certain embodiments, $R^{31}$ is $C_1$-$C_6$alkoxy. Examples of suitable alkoxys, include but are not limited to, methoxy, ethoxy, butoxy and propoxy. In certain embodiments, $R^{31}$ is COOC$_1$-$C_6$alkyl. Examples of suitable COOC$_1$-$C_6$alkyl groups include, but are not limited to, methoxycarbonyl, ethoxycarbonyl and butoxycarbonyl.

In certain embodiments, $R^{31}$ is COC$_1$-$C_6$alkyl. Suitable COC$_1$-$C_6$alkyl groups include COCH$_3$ and COCH$_2$CH$_3$. In certain embodiments, $R^{31}$ is COC$_1$-$C_6$alkyN($R^{13}$)($R^{14}$). Suitable examples of COC$_1$-$C_6$alkylN($R^{13}$)($R^{14}$) groups include, but are not limited to,

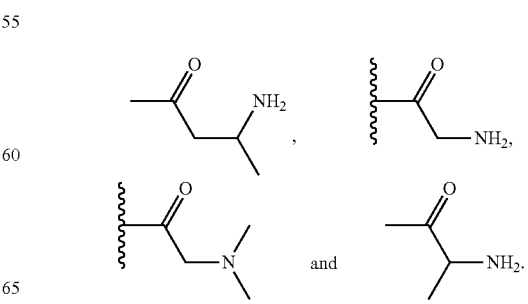

In certain embodiments, $R^{31}$ is $COC_1$-$C_6$alkyl(OH)N$(R^{13})(R^{14})$. Suitable examples $COC_1$-$C_6$alkyl(OH)N$(R^{13})(R^{14})$ groups include, but are not limited to,

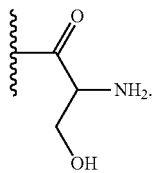 [SMILES: *C(=O)C(N)CO]

In certain embodiments, $R^{31}$ is $C_1$-$C_6$alkylCON$(R^{13})(R^{14})$. Suitable groups include but are not to,

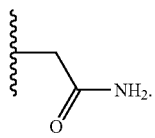 [SMILES: *CC(N)=O]

In certain embodiments, $R^{31}$ is CON$(R^{13})(R^{14})$. Suitable CON$(R^{13})(R^{14})$ groups include, but are not limited to, CONH$_2$. In certain embodiments, $R^{31}$ is SO$_2$C$_1$-C$_6$alkyl. Suitable SO$_2$C$_1$-C$_6$alkyl groups include, but are not limited to, SO$_2$CH$_3$. In certain embodiments, $R^{31}$ is SO$_2$N$(R^{13})(R^{14})$. Suitable SO$_2$N$(R^{13})(R^{14})$ groups include, but are not limited to, SO$_2$NH$_2$. In certain embodiments, $R^{31}$ is C$_1$-C$_6$alkylaryl. In certain embodiments, $R^{31}$ is C$_1$-C$_6$alkylhaloaryl. In certain embodiments, $R^{31}$ is C(NH)N$(R^{13})(R^{14})$. In certain embodiments, $R^{31}$ is heteroaryl.

In certain embodiments, $R^{31}$ is selected from the group consisting of methyl, ethyl, isopropyl, NH$_2$,

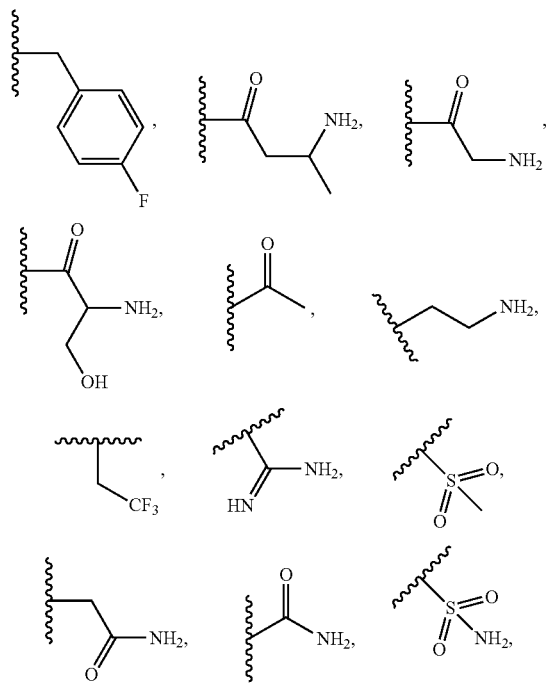

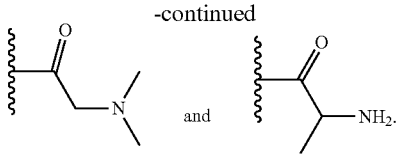

In certain embodiments, $R^{30}$, $R^{31}$ and $R^{30}$ combine to form an oxo group.

With regard to the compounds described herein, $R^{32}$ is hydrogen, C$_3$-C$_6$cycloalkyl, C$_1$-C$_6$alkyl, COC$_1$-C$_6$alkylNH$_2$, COC$_1$-C$_6$alkylNH(C$_1$-C$_6$alkyl), COC$_1$-C$_6$alkylN(C$_1$-C$_6$alkyl)$_2$, or COC$_1$-C$_6$alkyl. In certain embodiments, $R^{32}$ is hydrogen. In certain embodiments, $R^{32}$ is C$_3$-C$_6$cycloalkyl. Suitable cycloalkyl groups include, but are not limited to, cyclopropyl, cyclobutyl, cyclopentyl, cyclohexyl. In certain embodiments described herein, $R^{32}$ is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{32}$ is COC$_1$-C$_6$alkylNH$_2$. In certain embodiments, $R^{32}$ is COC$_1$-C$_6$alkylNH(C$_1$-C$_6$alkyl). In certain embodiments, $R^{32}$ is COC$_1$-C$_6$alkyN(C$_1$-C$_6$alkyl)$_2$.

With regard to the compounds described herein, $R^{33}$ is hydrogen, halogen, C$_3$-C$_6$cycloalkyl, C$_1$-C$_6$alkyl, haloC$_1$-C$_6$alkyl, OH, C$_1$-C$_6$alkylOH, C$_1$-C$_6$alkylOC$_1$-C$_6$alkyl, COOH, N$(R^{13})(R^{14})$, C$_1$-C$_6$alkylN$(R^{13})(R^{14})$, C$_1$-C$_6$alkoxy, COOC$_1$-C$_6$alkyl, COC$_1$-C$_6$alkyl, COC$_1$-C$_6$alkyN$(R^{13})(R^{14})$, COC$_1$-C$_6$alkyl(OH)N$(R^{13})(R^{14})$, C$_1$-C$_6$alkyCON$(R^{13})(R^{14})$, CON$(R^{13})(R^{14})$, SO$_2$C$_1$-C$_6$alkyl, SO$_2$N$(R^{13})(R^{14})$, C$_1$-C$_6$alkylaryl, C$_1$-C$_6$alkylhaloaryl, C(NH)N$(R^{13})(R^{14})$ or heteroaryl.

In certain embodiments, $R^{33}$ is hydrogen. In certain embodiments described herein, $R^{33}$ is halogen. Examples of suitable halogens include, but are not limited to, chlorine, bromine, fluorine and iodine. In certain embodiments, $R^{33}$ is C$_3$-C$_6$cycloalkyl. Suitable cycloalkyl groups include, but are not limited to, cyclopropyl, cyclobutyl, cyclopentyl, cyclohexyl. In certain embodiments described herein, $R^{33}$ is C$_1$-C$_6$alkyl. Examples of suitable C$_1$-C$_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{33}$ is haloC$_1$-C$_6$alkyl. Suitable haloC$_1$-C$_6$alkyls include but are not limited to, fluoromethyl, difluoromethyl, trifluoromethyl, 2-fluoroethyl, 1,2-difluoroethyl and 2,2-difluoroethyl. In certain embodiments, $R^{33}$ is OH. In certain embodiments, $R^{33}$ is —C$_1$-C$_6$alkylOH. Examples of suitable alcohols, include, but are not limited to, methanol, ethanol, propanol, butanol and iso-butanol. In certain embodiments, $R^{33}$ is C$_1$-C$_6$alkylOC$_1$-C$_6$alkyl. Suitable C$_1$-C$_6$alkylOC$_1$-C$_6$alkyls include but are not limited to, dimethyl ether, ethyl methyl ether, diethyl ether, dipropyl ether, dibutyl ether and diisopropyl ether. In certain embodiments, $R^{33}$ is COOH.

In certain embodiments, $R^{33}$ is $N(R^{13})(R^{14})$. Examples of suitable $N(R^{13})(R^{14})$ groups include, but are not limited to, $NH_2$, $NH(CH_3)$, $—N(CH_3)_2$ and $N(CH_3)_2$. In certain embodiments, $R^{33}$ is $C_1$-$C_6$alkylN$(R^{13})(R^{14})$. Examples of suitable $C_1$-$C_6$alkylN$(R^{13})(R^{14})$ groups include, but are not limited to, $CH_2NH_2$, $CH_2NH(CH_3)$, $CH_2N(CH_3)_2$ and $CH_2CH_2N(CH_3)_2$.

In certain embodiments, $R^{33}$ is $C_1$-$C_6$alkoxy. Examples of suitable alkoxys, include but are not limited to, methoxy, ethoxy, butoxy and propoxy. In certain embodiments, $R^{33}$ is $COOC_1$-$C_6$alkyl. Examples of suitable $COOC_1$-$C_6$alkyl groups include, but are not limited to, methoxycarbonyl, ethoxycarbonyl and butoxycarbonyl.

In certain embodiments, $R^{33}$ is $COC_1$-$C_6$alkyl. Suitable $COC_1$-$C_6$alkyl groups include $COCH_3$ and $COCH_2CH_3$. In certain embodiments, $R^{33}$ is $COC_1$-$C_6$alkyN$(R^{13})(R^{14})$. Suitable examples of $COC_1$-$C_6$alkyN$(R^{13})(R^{14})$ groups include, but are not limited to,

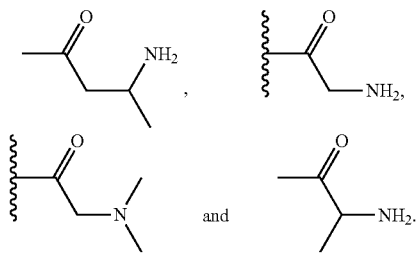

In certain embodiments, $R^{33}$ is $COC_1$-$C_6$alkyl(OH)N$(R^{13})(R^{14})$. Suitable examples $COC_1$-$C_6$alkyl(OH)N$(R^{13})(R^{14})$ groups include, but are not limited to

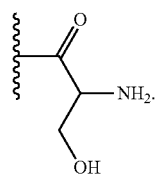 [SMILES: *C(=O)C(N)CO]

In certain embodiments, $R^{33}$ is $C_1$-$C_6$alkylCON$(R^{13})(R^{14})$. Suitable groups include but are not to,

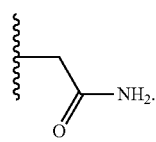 [SMILES: *CC(N)=O]

In certain embodiments, $R^{33}$ is $CON(R^{13})(R^{14})$. Suitable $CON(R^{13})(R^{14})$ groups include, but are not limited to, $CONH_2$. In certain embodiments, $R^{33}$ is $SO_2C_1$-$C_6$alkyl. Suitable $SO_2C_1$-$C_6$alkyl groups include, but are not limited to, $SO_2CH_3$. In certain embodiments, $R^{33}$ is $SO_2N(R^{13})(R^{14})$. Suitable $SO_2N(R^{13})(R^{14})$ groups include, but are not limited to, $SO_2NH_2$. In certain embodiments, $R^{33}$ is $C_1$-$C_6$alkylaryl. In certain embodiments, $R^{33}$ is $C_1$-$C_6$alkylhaloaryl. In certain embodiments, $R^{33}$ is $C(NH)N(R^{13})(R^{14})$. In certain embodiments, $R^{33}$ is heteroaryl.

In certain embodiments, $R^{33}$ is selected from the group consisting of methyl, ethyl, isopropyl, $NH_2$,

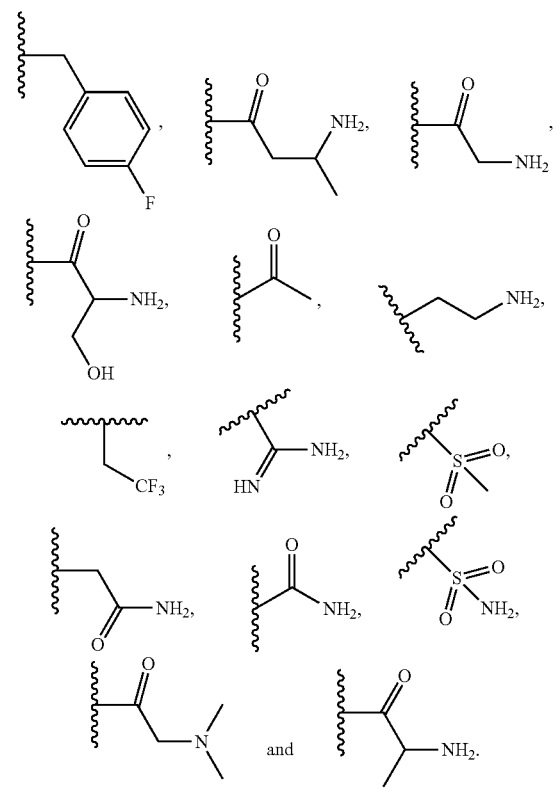

With regard to the compounds described herein, $R^{34}$ is hydrogen, halogen, $C_3$-$C_6$cycloalkyl, $C_1$-$C_6$alkyl, haloC$_1$-$C_6$alkyl, OH, $C_1$-$C_6$alkylOH, $C_1$-$C_6$alkylOC$_1$-$C_6$alkyl, COOH, $N(R^{13})(R^{14})$, $C_1$-$C_6$alkylN$(R^{13})(R^{14})$, $C_1$-$C_6$alkoxy, $COOC_1$-$C_6$alkyl, $COC_1$-$C_6$alkyl, $COC_1$-$C_6$alkyN$(R^{13})(R^{14})$, $COC_1$-$C_6$alkyl(OH)N$(R^{13})(R^{14})$, $C_1$-$C_6$alkyCON$(R^{13})(R^{14})$, $CON(R^{13})(R^{14})$, $SO_2C_1$-$C_6$alkyl, $SO_2N(R^{13})(R^{14})$, $C_1$-$C_6$alkylaryl, $C_1$-$C_6$alkylhaloaryl, $C(NH)N(R^{13})(R^{14})$ or heteroaryl.

In certain embodiments, $R^{34}$ is hydrogen. In certain embodiments described herein, $R^{34}$ is halogen. Examples of suitable halogens include, but are not limited to, chlorine, bromine, fluorine and iodine. In certain embodiments, $R^{34}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{34}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{34}$ is haloC$_1$-$C_6$alkyl. Suitable haloC$_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{34}$ is OH. In certain embodiments, $R^{34}$ is $C_1$-$C_6$alkylOH. Examples of suitable alcohols, include, but are not limited to, methanol, ethanol, propanol, butanol and iso-butanol. In certain embodiments, $R^{34}$ is $C_1$-$C_6$alkylOC$_1$-$C_6$alkyl. Suitable $C_1$-$C_6$alkylOC$_1$-$C_6$alkyls include but are not limited to, dimethyl ether, ethyl methyl ether, diethyl ether, dipropyl ether, dibutyl ether and diisopropyl ether. In certain embodiments, $R^{34}$ is COOH.

In certain embodiments, $R^{34}$ is $N(R^{13})(R^{14})$. Examples of suitable $N(R^{13})(R^{14})$ groups include, but are not limited to, $NH_2$, $NH(CH_3)$, $N(CH_3)_2$ and $N(CH_3)_2$. In certain embodiments, $R^{34}$ is $C_1$-$C_6$alkylN$(R^{13})(R^{14})$. Examples of suitable $C_1$-$C_6$alkylN$(R^{13})(R^{14})$ groups include, but are not limited to, $CH_2NH_2$, $CH_2NH(CH_3)$, $CH_2N(CH_3)_2$ and $CH_2CH_2N(CH_3)_2$.

In certain embodiments, $R^{34}$ is $C_1$-$C_6$alkoxy. Examples of suitable alkoxys, include but are not limited to, methoxy, ethoxy, butoxy and propoxy. In certain embodiments, $R^{34}$ is $COOC_1$-$C_6$alkyl. Examples of suitable $COOC_1$-$C_6$alkyl groups include, but are not limited to, methoxycarbonyl, ethoxycarbonyl and butoxycarbonyl.

In certain embodiments, $R^{34}$ is $COC_1$-$C_6$alkyl. Suitable $COC_1$-$C_6$alkyl groups include $COCH_3$ and $COCH_2CH_3$. In certain embodiments, $R^{34}$ is $COC_1$-$C_6$alkyN$(R^{13})(R^{14})$. Suitable examples of $COC_1$-$C_6$alkyN$(R^{13})(R^{14})$ groups include, but are not limited to,

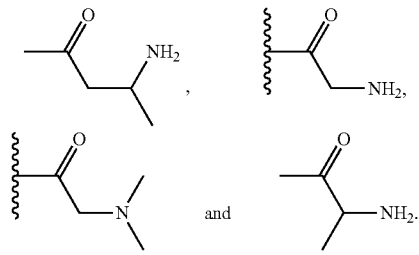

In certain embodiments, $R^{34}$ is $COC_1$-$C_6$alkyl(OH)N$(R^{13})(R^{14})$. Suitable examples $COC_1$-$C_6$alkyl(OH)N$(R^{13})(R^{14})$ groups include, but are not limited to,

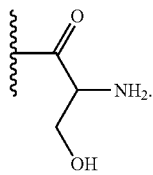 [SMILES: *C(=O)C(N)CO]

In certain embodiments, $R^{34}$ is $C_1$-$C_6$alkylCON$(R^{13})(R^{14})$. Suitable groups include but are not to,

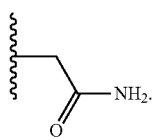 [SMILES: *CC(N)=O]

In certain embodiments, $R^{34}$ is CON$(R^{13})(R^{14})$. Suitable CON$(R^{13})(R^{14})$ groups include, but are not limited to, $CONH_2$. In certain embodiments, $R^{34}$ is $SO_2C_1$-$C_6$alkyl. Suitable $SO_2C_1$-$C_6$alkyl groups include but are not limited to, $SO_2CH_3$. In certain embodiments, $R^{34}$ is $SO_2N(R^{13})(R^{14})$. Suitable $SO_2N(R^{13})(R^{14})$ groups include, but are not limited to, $SO_2NH_2$. In certain embodiments, $R^{34}$ is $C_1$-$C_6$alkylaryl. In certain embodiments, $R^{34}$ is $C_1$-$C_6$alkylhaloaryl. In certain embodiments, $R^{34}$ is C(NH)N$(R^{13})(R^{14})$. In certain embodiments, $R^{34}$ is heteroaryl.

In certain embodiments, $R^{34}$ is selected from the group consisting of methyl, ethyl, isopropyl, $NH_2$,

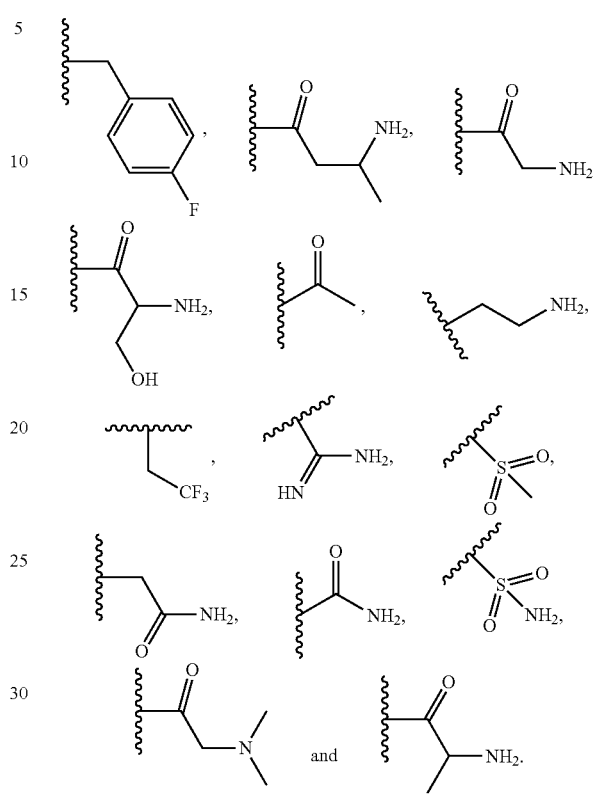

With regard to the compounds described herein, $R^{35}$ is hydrogen, $C_3$-$C_6$cycloalkyl, $C_1$-$C_6$alkyl, $COC_1$-$C_6$alkylNH$_2$, $COC_1$-$C_6$alkylNH($C_1$-$C_6$alkyl), $COC_1$-$C_6$alkylN($C_1$-$C_6$alkyl)$_2$, or $COC_1$-$C_6$alkyl. In certain embodiments, $R^{35}$ is hydrogen. In certain embodiments, $R^{35}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{35}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{35}$ is $COC_1$-$C_6$alkylNH$_2$. In certain embodiments, $R^{35}$ is $COC_1$-$C_6$alkylNH($C_1$-$C_6$alkyl). In certain embodiments, $R^{35}$ is $COC_1$-$C_6$alkyN($C_1$-$C_6$alkyl)$_2$.

With regard to the compounds described herein, $R^{36}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC$_1$-$C_6$alkyl, COOH, N$(R^{13})(R^{14})$, $C_1$-$C_6$alkylN$(R^{13})(R^{14})$, $C_1$-$C_6$alkoxy, COOC$_1$-$C_6$alkyl, COC$_1$-$C_6$alkyl, COC$_1$-$C_6$alkyN$(R^{13})(R^{14})$, COC$_1$-$C_6$alkyl(OH)N$(R^{13})(R^{14})$, $C_1$-$C_6$alkyCON$(R^{13})(R^{14})$, CON$(R^{13})(R^{14})$, SO$_2$C$_1$-$C_6$alkyl, SO$_2$N$(R^{13})(R^{14})$, $C_1$-$C_6$alkylaryl, $C_1$-$C_6$alkylhaloaryl, C(NH)N$(R^{13})(R^{14})$ or heteroaryl.

In certain embodiments, $R^{36}$ is hydrogen. In certain embodiments described herein, $R^{36}$ is halogen. Examples of suitable halogens include, but are not limited to, chlorine, bromine, fluorine and iodine. In certain embodiments, $R^{36}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{36}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{36}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{36}$ is OH. In certain embodiments, $R^{36}$ is —$C_1$-$C_6$alkylOH. Examples of suitable alcohols, include, but are not limited to, methanol, ethanol, propanol, butanol and iso-butanol. In certain embodiments, $R^{36}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^{36}$ is COOH.

In certain embodiments, $R^{36}$ is $N(R^{13})(R^{14})$. Examples of suitable $N(R^{13})(R^{14})$ groups include, but are not limited to, $NH_2$, $NH(CH_3)$, $N(CH_3)_2$ and $N(CH_3)_2$. In certain embodiments, $R^{36}$ is $C_1$-$C_6$alkylN$(R^{13})(R^{14})$. Examples of suitable $C_1$-$C_6$alkylN$(R^{13})(R^{14})$ groups include, but are not limited to, $CH_2NH_2$, $CH_2NH(CH_3)$, $CH_2N(CH_3)_2$ and $CH_2CH_2N(CH_3)_2$.

In certain embodiments, $R^{36}$ is $C_1$-$C_6$alkoxy. Examples of suitable alkoxys, include but are not limited to, methoxy, ethoxy, butoxy and propoxy. In certain embodiments, $R^{36}$ is COO$C_1$-$C_6$alkyl. Examples of suitable COO$C_1$-$C_6$alkyl groups include, but are not limited to, methoxycarbonyl, ethoxycarbonyl and butoxycarbonyl.

In certain embodiments, $R^{36}$ is CO$C_1$-$C_6$alkyl. Suitable CO$C_1$-$C_6$alkyl groups include $COCH_3$ and $COCH_2CH_3$. In certain embodiments, $R^{36}$ is CO$C_1$-$C_6$alkyN$(R^{13})(R^{14})$. Suitable examples of CO$C_1$-$C_6$alkylN$(R^{13})(R^{14}$ groups include, but are not limited to

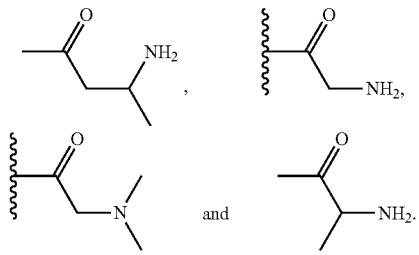

In certain embodiments, $R^{36}$ is CO$C_1$-$C_6$alkyl(OH)N$(R^{13})(R^{14})$. Suitable examples CO$C_1$-$C_6$alkyl(OH)N$(R^{13})(R^{14})$ groups include, but are not limited to,

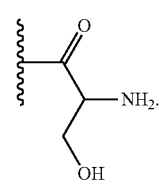 [SMILES: *C(=O)C(N)CO]

In certain embodiments, $R^{36}$ is $C_1$-$C_6$alkylCON$(R^{13})(R^{14})$. Suitable groups include but are not to,

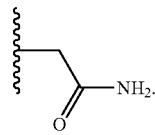

In certain embodiments, $R^{36}$ is CON$(R^{13})(R^{14})$. Suitable CON$(R^{13})(R^{14})$ groups include, but are not limited to, $CONH_2$. In certain embodiments, $R^{36}$ is $SO_2C_1$-$C_6$alkyl. Suitable $SO_2C_1$-$C_6$alkyl groups include, but are not limited to, $SO_2CH_3$. In certain embodiments, $R^{36}$ is $SO_2N(R^{13})(R^{14})$. Suitable $SO_2N(R^{13})(R^{14})$ groups include, but are not limited to, $SO_2NH_2$. In certain embodiments, $R^{36}$ is $C_1$-$C_6$alkylaryl. In certain embodiments, $R^{36}$ is $C_1$-$C_6$alkylhaloaryl. In certain embodiments, $R^{36}$ is C(NH)N$(R^{13})(R^{14})$. In certain embodiments, $R^{36}$ is heteroaryl.

In certain embodiments, $R^{36}$ is selected from the group consisting of methyl, ethyl, isopropyl, $NH_2$,

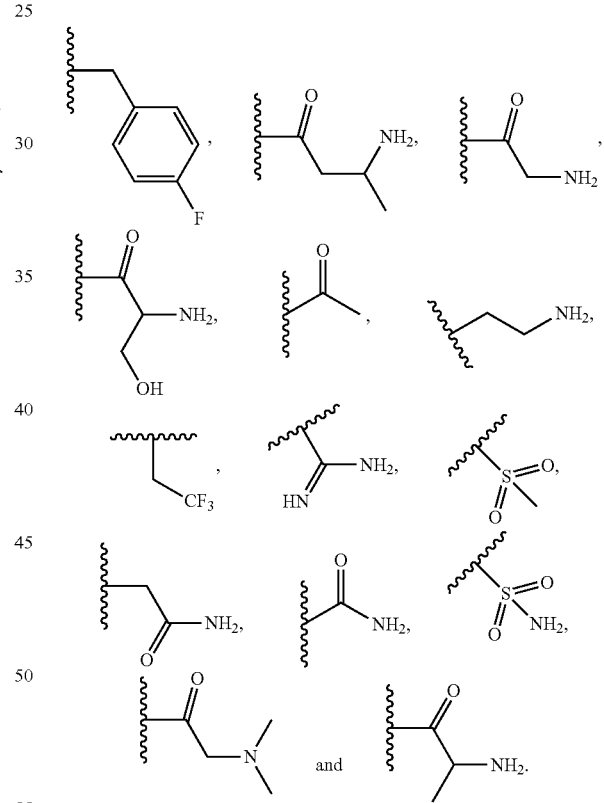

With regard to the compounds described herein, $R^3$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, $N(R^{13})(R^{14})$, $C_1$-$C_6$alkylN$(R^{13})(R^{14})$, $C_1$-$C_6$alkoxy, COO$C_1$-$C_6$alkyl, CO$C_1$-$C_6$alkyl, CO$C_1$-$C_6$alkyN$(R^{13})(R^{14})$, CO$C_1$-$C_6$alkyl(OH)N$(R^{13})(R^{14})$, $C_1$-$C_6$alkyCON$(R^{13})(R^{14})$, CON$(R^{13})(R^{14})$, $SO_2C_1$-$C_6$alkyl, $SO_2N(R^{13})(R^{14})$, $C_1$-$C_6$alkylaryl, $C_1$-$C_6$alkylhaloaryl, C(NH)N$(R^{13})(R^{14})$ or heteroaryl.

In embodiments, $R^{37}$ is hydrogen. In certain embodiments described herein, $R^{37}$ is halogen. Examples of suitable halogens include, but are not limited to, chlorine, bromine, fluorine and iodine. In certain embodiments, $R^{37}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{37}$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^{37}$ is halo$C_1$-$C_6$alkyl. Suitable halo$C_1$-$C_6$alkyls include but are not limited to, fluoromethyl, difluoromethyl, trifluoromethyl, 2-fluoroethyl, 1,2-difluoroethyl and 2,2-difluoroethyl. In certain embodiments, $R^{37}$ is OH. In certain embodiments, $R^{37}$ is —$C_1$-$C_6$alkylOH. Examples of suitable alcohols, include, but are not limited to, methanol, ethanol, propanol, butanol and iso-butanol. In certain embodiments, $R^{37}$ is $C_1$-$C_6$alkylO$C_1$-$C_6$alkyl. Suitable $C_1$-$C_6$alkylO$C_1$-$C_6$alkyls include but are not limited to, dimethyl ether, ethyl methyl ether, diethyl ether, dipropyl ether, dibutyl ether and diisopropyl ether. In certain embodiments, $R^{37}$ is COOH.

In certain embodiments, $R^{37}$ is $N(R^{13})(R^{14})$. Examples of suitable $N(R^{13})(R^{14})$ groups include, but are not limited to, $NH_2$, $NH(CH_3)$, $N(CH_3)_2$ and $N(CH_3)_2$. In certain embodiments, $R^{37}$ is $C_1$-$C_6$alkyl$N(R^{13})(R^{14})$. Examples of suitable $C_1$-$C_6$alkyl$N(R^{13})(R^{14})$ groups include, but are not limited to, $CH_2NH_2$, $CH_2NH(CH_3)$, $CH_2N(CH_3)_2$ and $CH_2CH_2N(CH_3)_2$.

In certain embodiments, $R^{37}$ is $C_1$-$C_6$alkoxy. Examples of suitable alkoxys, include but are not limited to, methoxy, ethoxy, butoxy and propoxy. In certain embodiments, $R^{37}$ is COO$C_1$-$C_6$alkyl. Examples of suitable COO$C_1$-$C_6$alkyl groups include, but are not limited to, methoxycarbonyl, ethoxycarbonyl and butoxycarbonyl.

In certain embodiments, $R^{37}$ is CO$C_1$-$C_6$alkyl. Suitable CO$C_1$-$C_6$alkyl groups include COCH$_3$ and COCH$_2$CH$_3$. In certain embodiments, $R^{37}$ is CO$C_1$-$C_6$alky$N(R^{13})(R^{14})$. Suitable examples of CO$C_1$-$C_6$alkyN$(R^{13})(R^{14})$ groups include, but are not limited to,

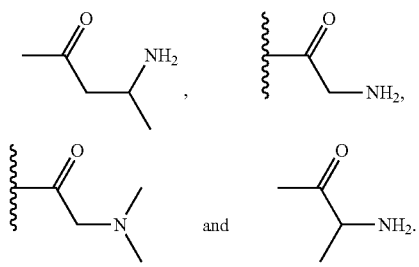

In certain embodiments, $R^{37}$ is CO$C_1$-$C_6$alkyl(OH)$N(R^{13})(R^{14})$. Suitable examples CO$C_1$-$C_6$alky(OH)$N(R^{13})(R^{14})$ groups include, but are not limited to,

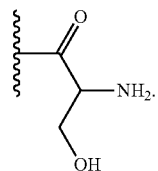 [SMILES: *C(=O)C(N)CO]

In certain embodiments, $R^{37}$ is $C_1$-$C_6$alkylCON$(R^{13})(R^{14})$ Suitable groups include but are not to,

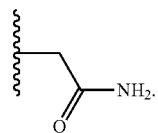

In certain embodiments, $R^{37}$ is $CON(R^{13})(R^{14})$. Suitable $CON(R^{13})(R^{14})$ groups include, but are not limited to, $CONH_2$. In certain embodiments, $R^{37}$ is $SO_2C_1$-$C_6$alkyl. Suitable $SO_2C_1$-$C_6$alkyl groups include, but are not limited to, $SO_2CH_3$. In certain embodiments, $R^{37}$ is $SO_2N(R^{13})(R^{14})$. Suitable $SO_2N(R^{13})(R^{14})$ groups include, but are not limited to, $SO_2NH_2$. In certain embodiments, $R^{37}$ is $C_1$-$C_6$alkylaryl. In certain embodiments, $R^{37}$ is $C_1$-$C_6$alkylhaloaryl. In certain embodiments, $R^{37}$ is $C(NH)N(R^{13})(R^{14})$. In certain embodiments, $R^{37}$ is heteroaryl.

In certain embodiments, $R^{37}$ is selected from the group consisting of methyl, ethyl, isopropyl, $NH_2$,

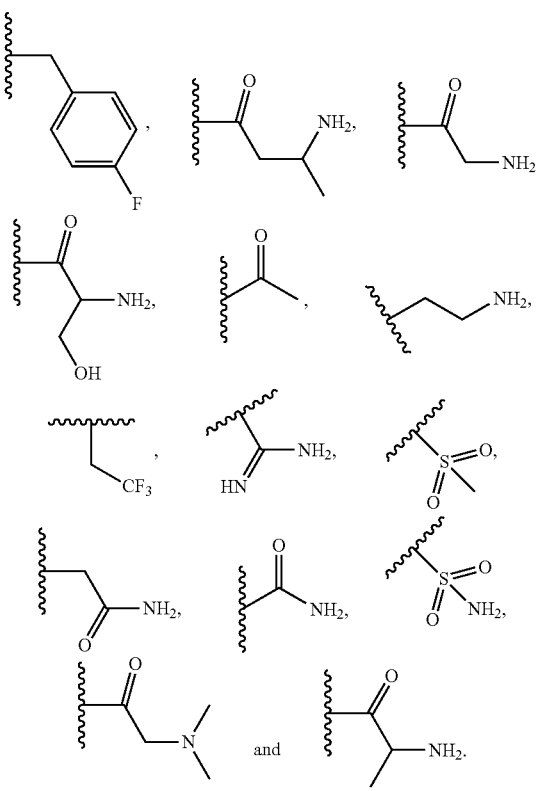

Also described herein are compounds having Formula VII:

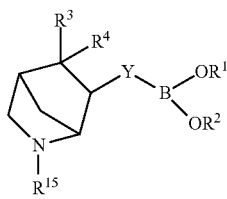

VII or a pharmaceutically acceptable salt thereof, wherein:

Y is selected from the group consisting of straight or branched $(C_2-C_5)$alkylene, wherein one or more —$CH_2$— groups in Y are optionally and independently replaced with a moiety selected from the group consisting of O, S or NH;

$R^1$ is hydrogen or —$C_1$-$C_6$alkyl or, taken with $R^2$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^2$ is hydrogen or $C_1$-$C_6$alkyl or, taken with $R^1$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^3$ is hydrogen, halogen, $C_3$-$C_6$cycloalkyl, $C_1$-$C_6$alkyl, halo$C_1$-$C_6$alkyl, OH, $C_1$-$C_6$alkylOH, COOH, $N(R^{13})(R^{14})$, $C_1$-$C_6$alkyl$N(R^{13})(R^{14})$, $C_1$-$C_6$alkoxy or COO$C_1$-$C_6$alkyl;

$R^4$ is hydrogen, halogen, $C_3$-$C_6$cycloalkyl, $C_1$-$C_6$alkyl, halo$C_1$-$C_6$alkyl, OH, $C_1$-$C_6$alkylOH, COOH, $N(R^{13})(R^{14})$, $C_1$-$C_6$alkyl$N(R^{13})(R^{14})$, $C_1$-$C_6$alkoxy or COO$C_1$-$C_6$alkyl;

$R^5$ is selected from the group consisting of hydrogen, OH, $C_1$-$C_6$alkyl, —$C_1$-$C_6$alkylOH or —$C_1$-$C_6$alkyN($R^{13}$)($R^{14}$);

$R^{13}$ is hydrogen, $C_3$-$C_6$cycloalkyl, $C_1$-$C_6$alkyl, CO$C_1$-$C_6$alkyl$NH_2$, CO$C_1$-$C_6$alkylNH($C_1$-$C_6$alkyl), CO$C_1$-$C_6$alkylN($C_1$-$C_6$alkyl)$_2$, $C_1$-$C_6$haloalkyl, $C_1$-$C_6$alkylOH or CO$C_1$-$C_6$alkyl;

$R^{14}$ is hydrogen, $C_3$-$C_6$cycloalkyl, $C_1$-$C_6$alkyl, CO$C_1$-$C_6$alkyl$NH_2$, CO$C_1$-$C_6$alkylNH($C_1$-$C_6$alkyl), CO$C_1$-$C_6$alkylN($C_1$-$C_6$alkyl)$_2$, $C_1$-$C_6$haloalkyl, $C_1$-$C_6$alkylOH or CO$C_1$-$C_6$alkyl; and $R^{15}$ is hydrogen, $C_3$-$C_6$cycloalkyl, $C_1$-$C_6$alkyl, CO$C_1$-$C_6$alkyN($R^{13}$)($R^{14}$) or CO$C_1$-$C_6$alkyl.

With regard to the compounds of Formula VII, Y, $R^1$, $R^2$, $R^3$, $R^4$, $R^5$, $R^{13}$, $R^{14}$ and $R^{15}$ are discussed in detail above.

Certain embodiments of the compounds described herein, provide for the following compounds:

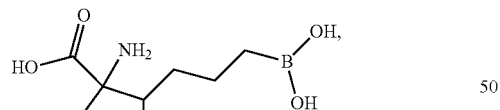

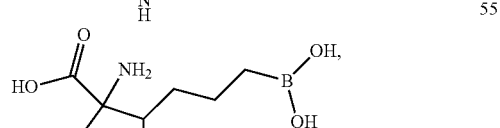

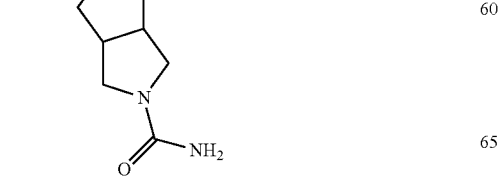

-continued

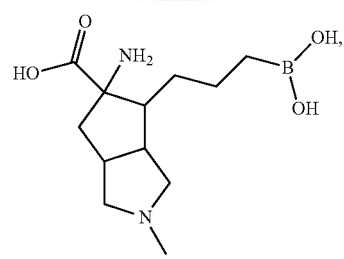

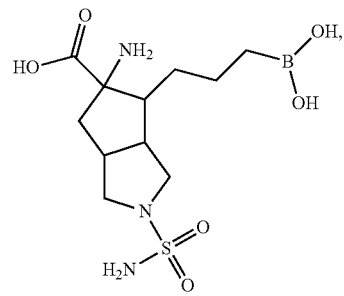

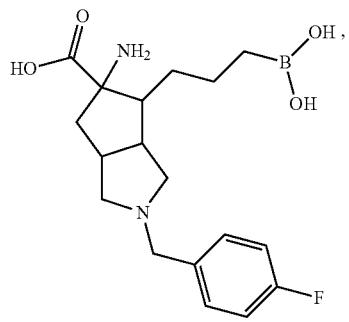

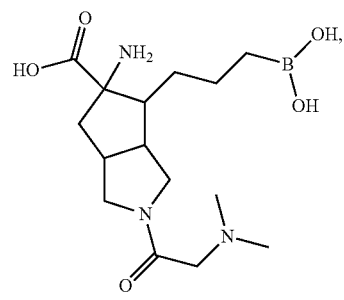

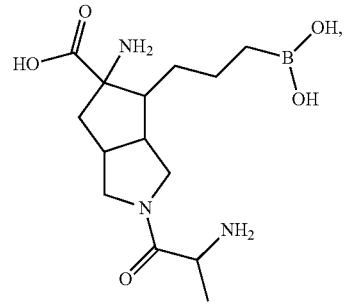

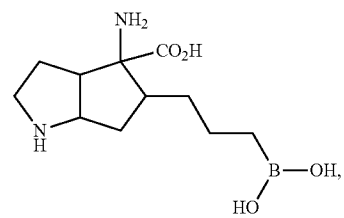

-continued
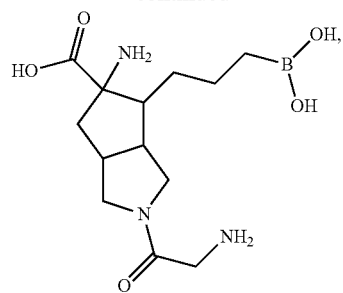
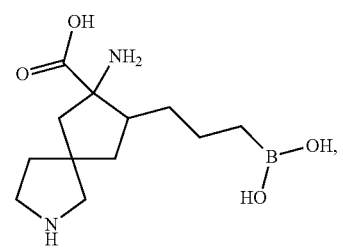
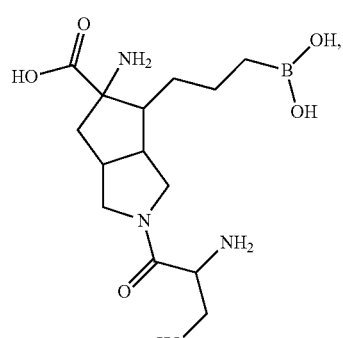
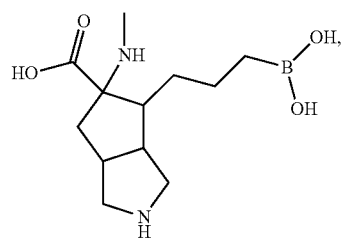
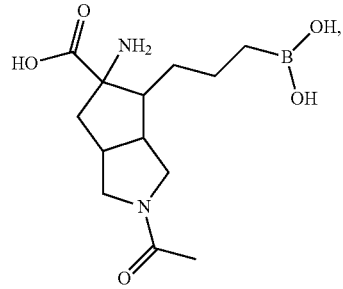
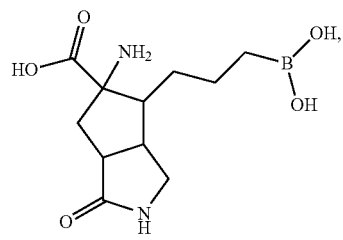
-continued
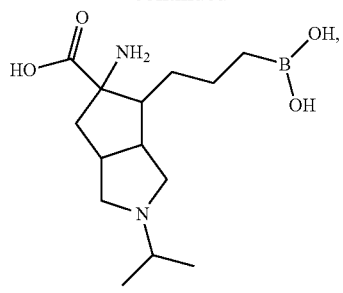
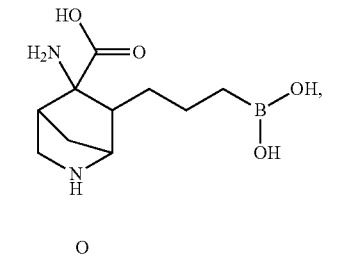
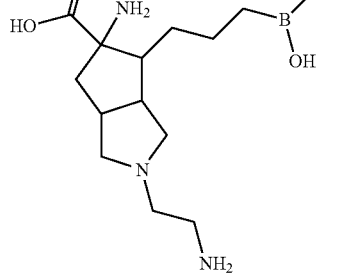
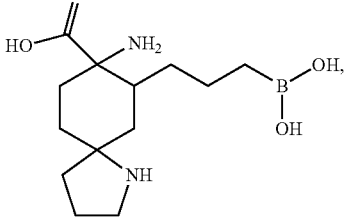
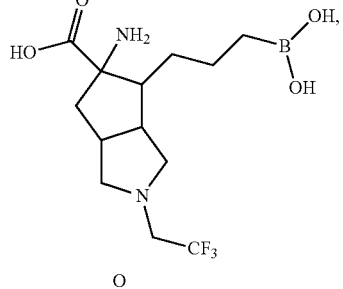
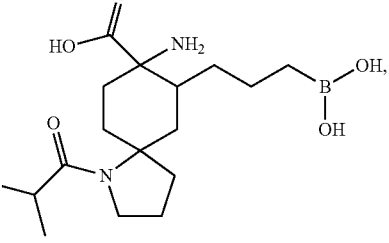

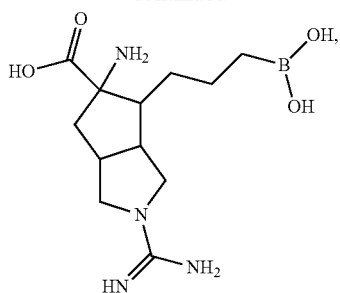
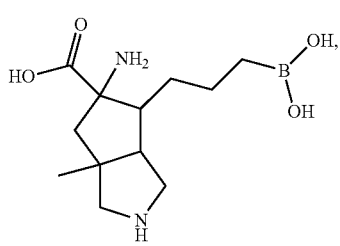
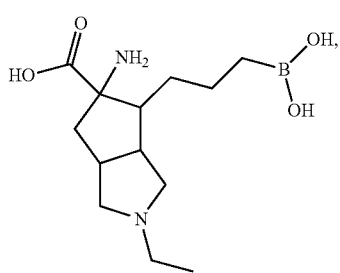
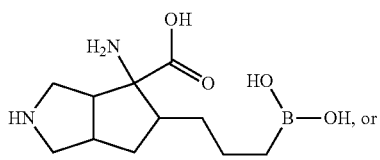
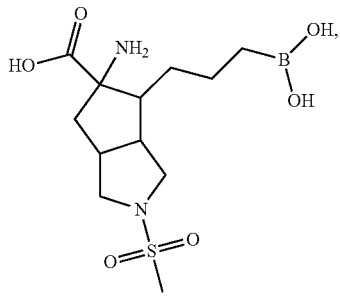
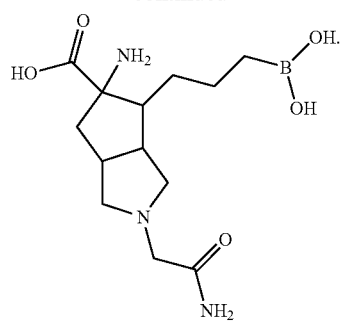
or a pharmaceutically acceptable salt thereof.
In other embodiments, the formulas described herein provide for the following compounds
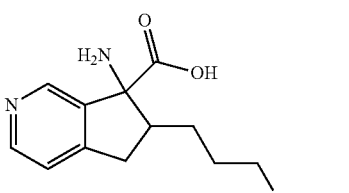
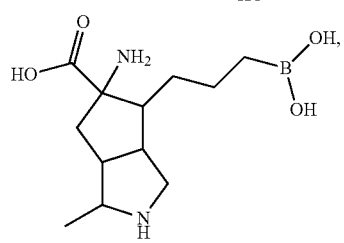
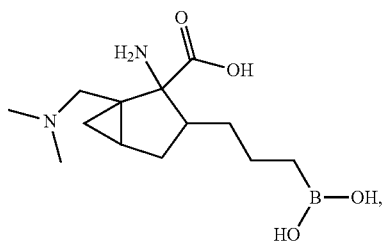
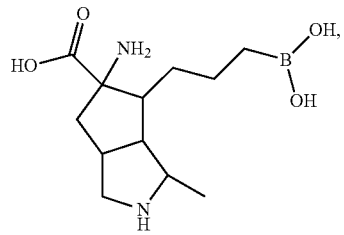
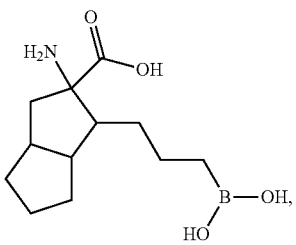

-continued
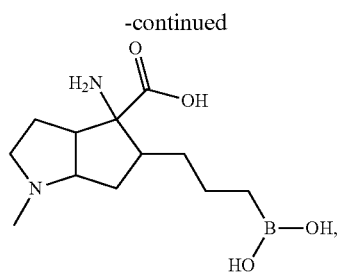
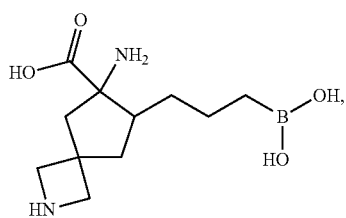
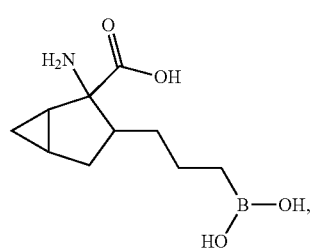
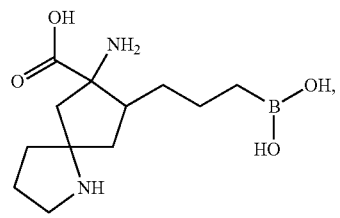
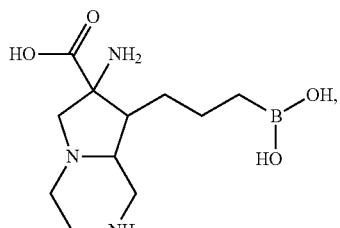
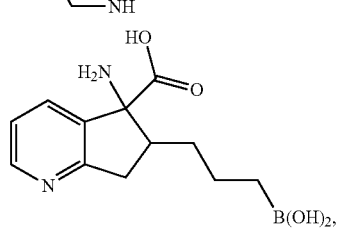
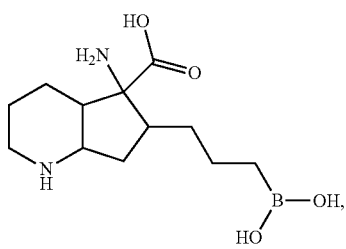
-continued
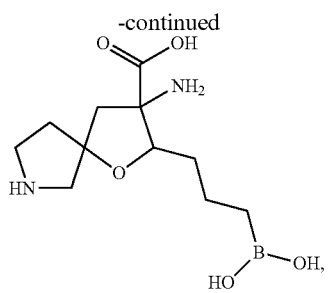
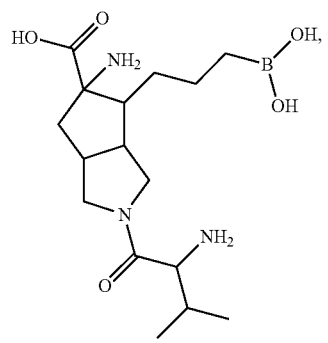
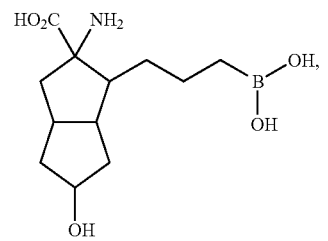
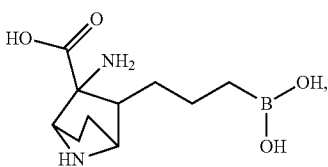
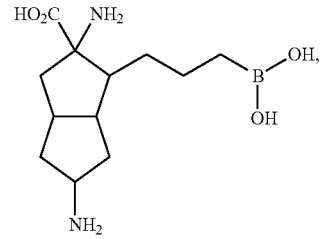
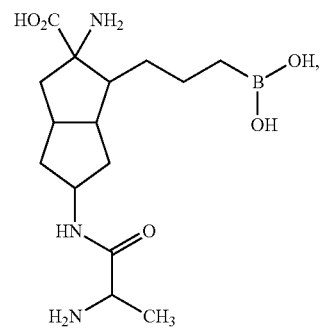

-continued

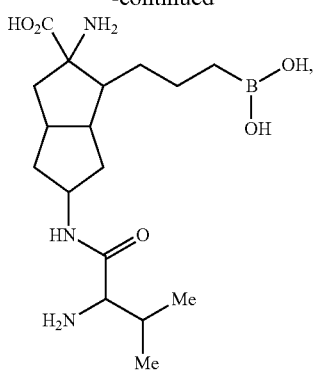

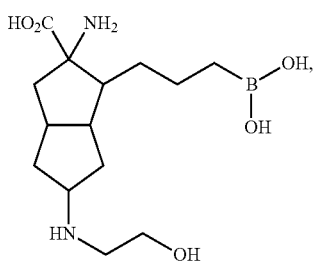

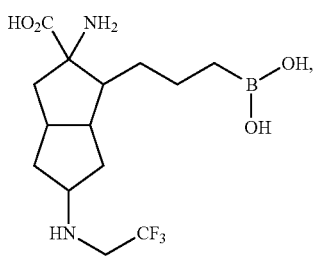

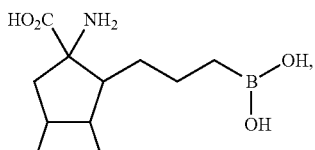

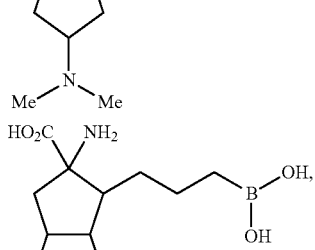

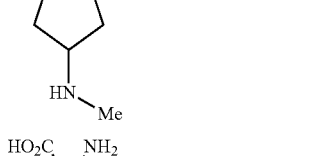

-continued

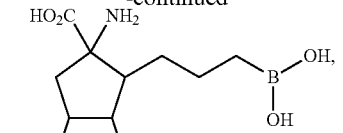

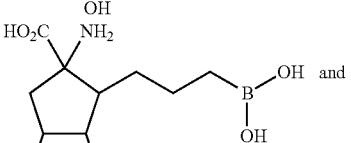

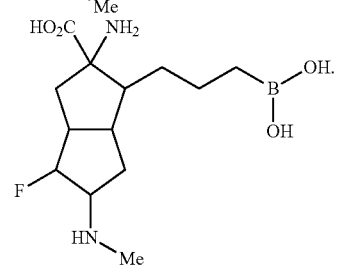

or pharmaceutically acceptable salts thereof.

Definitions

The term "alkylene," or "alkylenyl" by itself or as part of another substituent means a divalent straight, branched or cyclic chain hydrocarbon radical having the stated number of carbon atoms. For example, —($C_1$-$C_5$) alkylene, would include, e.g., —$CH_2$—, —$CH_2CH_2$—, —$CH_2CH_2CH_2$—, —$CH_2CH_2CH_2CH_2$—, —$CH_2CH(CH_3)CH_2$— or —$CH_2CH_2CH_2CH_2CH_2$—.

The term "halogen" includes a fluorine, a chlorine, a bromine or an iodine radical.

The term "$C_1$-$C_6$alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "$C_1$-$C_6$haloalkyl" means an $C_1$-$C_6$alkyl as defined above wherein one or more hydrogen atoms on the alkyl is replaced by a halo group defined above.

The term "$C_1$-$C_6$alkoxy" refers to an alkyl group having 1 to 6 carbons linked to oxygen. Examples include methoxy, ethoxy, butoxy, isopropoxy and propoxy.

The term "COO$C_1$-$C_6$alkyl" refers to a —COOH group wherein the —OH is replaced with an alkoxy group as defined above. Examples include methoxycarbonyl, ethoxycarbonyl, isopropylcarbonyl and butoxycarbonyl.

The term "CO$C_1$-$C_6$alkyl($N^{13}$)($N^{14}$)" refers to a CO attached to a linear or branched alkyl group any hydrogen on the alkyl group is replaced with a N(R$^{13}$)(R$^{14}$) group. Examples include, but are not limited to:

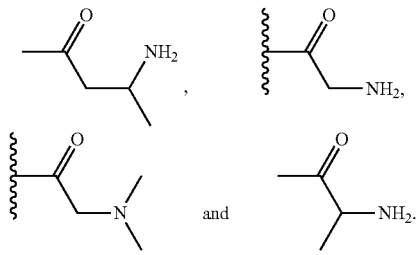

The term "COC$_1$-C$_6$alkyl(OH)(N$^{13}$)(N$^{14}$)" refers to a CO attached to a linear or branched alkyl group any two hydrogens on the alkyl group are replaced with an alcohol and a N(R$^{13}$)(R$^{14}$) group. Examples include, but are not limited to:

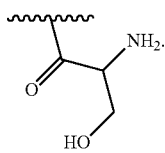 [SMILES: *C(=O)C(N)CO]

The term "C$_3$-C$_8$cycloalkyl" encompasses bridged, saturated or unsaturated cycloalkyl groups having 3 to 8 carbons. "Cycloalkyl" also includes non-aromatic rings as well as monocyclic, non-aromatic rings fused to a saturated cycloalkyl group. Examples of cycloalkyl include cyclopropyl, cyclobutyl, cyclopentyl, cyclohexyl, cycloheptyl, tetrahydronaphthyl, decahydronaphthyl, indanyl and the like.

The term "heteroaryl" means an aromatic heterocycle that contains at least one ring heteroatom selected from O, S and N. Examples of heteroaryl groups include pyridyl (pyridinyl), oxazolyl, imidazolyl, triazolyl, furyl, triazinyl, thienyl, pyrimidyl, pyridazinyl, indolizinyl, cinnolinyl, phthalazinyl, quinazolinyl, naphthyridinyl, quinoxalinyl, purinyl, benzimidazolyl, quinolyl, isoquinolyl, and the like.

The term "heterocycle" means mono- or bicyclic or bridged partially unsaturated and saturated rings containing at least one heteroatom selected from N, S and O, each of said ring having from 3 to 10 atoms in which the point of attachment may be carbon or nitrogen. Examples include tetrahydropyranyl, tetrahydrofuranyl, pyrrolidinyl, piperidinyl, piperazinyl, dioxanyl, imidazolidinyl, 2,3-dihydrofuro (2,3-b)pyridyl, benzoxazinyl, benzoxazolinyl, 2-H-phthalazinyl, isoindolinyl, benzoxazepinyl, 5,6-dihydroimidazo [2,1-b]thiazolyl, tetrahydroquinolinyl, morpholinyl, tetrahydroisoquinolinyl, dihydroindolyl, tetrahydropyran, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). The term also includes bridged rings such as 5-azabicyclo[2.2.1] heptyl, 2,5-diazabicyclo[2.2.1]heptyl, 2-azabicyclo[2.2.1] heptyl, 7-azabicyclo[2.2.1]heptyl, 2,5-diazabicyclo[2.2.2] octyl, 2-azabicyclo[2.2.2]octyl, and 3-azabicyclo[3.2.2] nonyl, and azabicyclo[2.2.1]heptanyl.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide,
isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidinyl, glucamine, glucosamine, histidine, hydrabamine, isopropylamine, lysine, methylglucamine, morpholine, piperazine, piperidinyl, polyamine resins, procaine, purines, theobromine, triethylamine, trimethylamine, tripropylamine, tromethamine, and the like.

The term "patient" refers to a mammalian patient, preferably a human patient, receiving or about to receive medical treatment.

The term "rac" or "rel" means a mixture.

The compounds of the present invention may contain one or more asymmetric centers and can thus occur as racemates, racemic mixtures, single enantiomers, diastereomeric mixtures, and individual diastereomers. The present invention is meant to comprehend all such isomeric forms of these compounds.

Some of the compounds described herein contain olefinic double bonds, and unless specified otherwise, are meant to include both E and Z geometric isomers.

Some of the compounds described herein contain substituted cycloalkanes having cis- and trans-isomers, and unless specified otherwise, are meant to include both cis- and trans-geometric isomers.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In certain embodiments, wherein $R^3$ is COOH, the compounds herein can have the following stereochemistry.

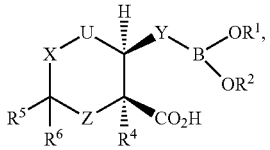

Ia

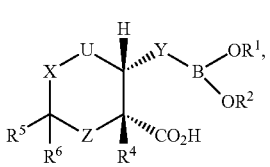

Ib

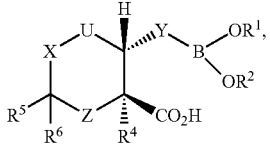

Ic

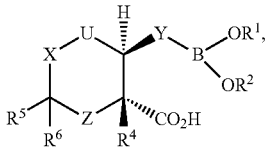

Id

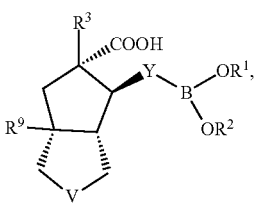

IVa

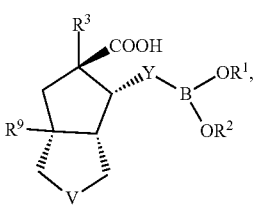

IVb

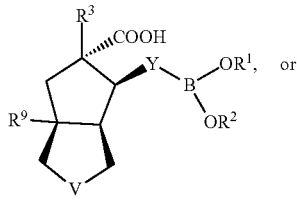

IVc

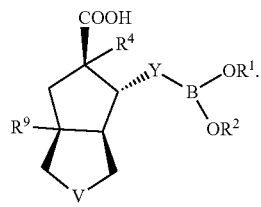

IVd

It will be understood that the present invention is meant to include the pharmaceutically acceptable salts, and also salts that are not pharmaceutically acceptable, of the compounds described herein, when they are used as precursors to the free compounds or their pharmaceutically acceptable salts or in other synthetic manipulations.

Solvates, and in particular, the hydrates of the compounds of the structural formulas described herein are included in the present invention as well.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

The compounds of the present invention may also exist in open-chain or cyclized forms. In some cases one or more of the cyclized forms may result in loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the invention.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the Schemes and Examples herein using appropriate isotopically-enriched reagents and/or Intermediates.

Methods of Treatment

Also encompassed by the present invention are methods of treating arginase-related diseases. The compounds described herein can be effective in preventing or treating various arginase-related diseases, such as gastrointestinal diseases, pulmonary inflammatory diseases, sexual arousal disorders, cardiovascular disorders, diseases caused by pathogenic microorganisms, immunological disorders, cancer, pre-term labor, Reynaud's disease, psoriasis, rheumatoid arthritis, and Peyronie's Disease, among others.

An increase in arginase activity has been associated with the pathophysiology of a number of conditions including impairment in non-adrenergic and non-cholinergic (NANC) nerve-mediated relaxation of gastrointestinal smooth muscle. An arginase inhibitor can be used to alleviate such impairment by administering the inhibitor to a mammal experiencing such impairment or a mammal which is anticipated to experience such impairment (e.g., a human afflicted with a gastrointestinal motility disorder).

Accordingly, the compounds of the invention may be useful in the treatment or prevention of gastrointestinal motility disorders, which is based on the observation that arginase is present in opossum internal anal sphincter muscle and the known arginase inhibitor, (S)-2-amino-6-boronohexanoic acid (ABH), has been shown to relax this muscle. See, e.g., Baggio et al., J. Pharm. Exp. Ther. 290, 1409-16 (1999).

The compounds of the invention may also be useful in the treatment or prevention of inflammatory bowel disease (IBD, e.g., Crohn's disease and ulcerative colitis). In fact, IBD has been shown to be characterized by increased arginase activity and endothelial dysfunction. See, e.g., Horowitz et al., Am. J. Physiol. Gastrointest. Liver Physiol. 292, G1323-36 (2007).

Likewise, the compounds of the invention may be useful in the treatment or prevention of gastric ulcers, because the bacterium that causes stomach ulcers, *Helicobacter pylori*, exhibits increased arginase activity upon colonization in order to evade the human immune response. See, e.g., Gobert et al., Proc. Natl. Acad. Sci. (USA) 98, 13844-49 (2001).

The compounds of the invention may be useful in the treatment or prevention of asthma based on the observation that arginase is upregulated in the asthmatic airway. See, e.g., Zimmermann and Rothenberg, Eur. J. Pharmacol. 533, 253-62 (2006). Furthermore, nebulizer treatment of guinea pigs with ABH in an allergic asthma model prevents airway hyperresponsiveness. See, e.g., Maarsingh, "Arginase: A Novel Key Enzyme in the Pathophysiology of Allergic Asthma," Ph. D. dissertation, Chapter 9, University of Groningen, Netherlands (2006); Maarsingh et al., Am. J. Respir. Crit. Care Med. 178, 565-73 (2008). The asthma phenotype is characterized by airway constriction, airway smooth muscle hyperplasia, and the chronic accumulation of fibrotic tissue; an arginase inhibitor can relax airway smooth muscle and attenuate cellular hyperplasia and fibrosis.

Additionally, the compounds of the invention may be useful in the treatment or prevention of chemically-induced lung fibrosis because arginase I and II are induced in bleomycin-induced lung fibrosis in order to provide more L-ornithine for collagen biosynthesis. See, e.g., Endo et al., Am. J. Physiol. Lung Cell Mol. Physiol. 285, L313-21 (2003).

The compounds of the invention may also be useful in the treatment or prevention of idiopathic pulmonary fibrosis, based on the observation that virus-induced upregulation of arginase I is observed in an animal model. See, e.g., Mora et al., Am. J. Respir. Cell Mol. Biol. 35, 466-73 (2006).

Furthermore, the compounds of the invention may be useful in the treatment or prevention of cystic fibrosis. Increased sputum arginase activity contributes to nitric oxide deficiency in cystic fibrosis lung disease; arginase activity also contributes to fibrosis. See, e.g., Graseman et al., Am. J. Respir. Crit. Care Med. 172, 1523-28 (2005).

Erectile dysfunction afflicts one-half of the male population over the age of forty. This malady often results from defects in the complex cascade of enzyme-catalyzed reactions governing blood flow into and out of the corpus cavernosum, a chamber of muscular, spongy tissue that becomes engorged with blood in the erect penis. Defects that compromise cavernosal blood flow often occur as secondary complications related to other health conditions, such as heart disease, hypertension, diabetes, use of certain medications, and the like.

In an important embodiment, the invention relates to use of an arginase inhibitor described herein for enhancing penile erectile function in a mammal (preferably a male human) or for alleviating erectile dysfunction in a mammal. Nitric oxide is an important regulator of erectile function and mediates NANC neurotransmission in penile corpus cavernosum smooth muscle, leading to rapid relaxation, which in turn leads to erection. Nitric oxide synthase, which catalyzes oxidation of L-arginine to form L-citrulline and nitric oxide, is for this reason a key enzyme in penile smooth muscle physiology. Arginase catalyzes hydrolysis of L-arginine to form L-ornithine and urea. Arginase regulates nitric oxide synthase activity by affecting the amount of L-arginine available for oxidation catalyzed by nitric oxide synthase activity. Thus, inhibition of arginase activity can enhance nitric oxide synthase activity, thereby enhancing nitric oxide-dependent smooth muscle relaxation in the corpus cavernosum and enhancing penile erection.

Arginase is present in rabbit and human penile corpus cavernosum and ABH enhances the nitric oxide-dependent relaxation of this tissue. See, e.g., Cox et al., Nature Struct. Biol. 6, 1043-47 (1999). The arginase inhibitor, ABH, enhances the erectile response in live male rabbits. See, e.g., Cama et al., Biochemistry 42, 8445-51 (2003). Arginase II is upregulated in the corpus cavernosum of the diabetic man, resulting in reduced nitric oxide biosynthesis which, in turn, leads to erectile dysfunction; administration of ABH in ex vivo experiments restores nitric oxide biosynthesis. See, e.g., Bivalacqua et al., Biochem. Biophys. Res. Commun. 283, 923-27 (2001). Arginase I is upregulated in the penis of aged mice and impairs erectile function. See, e.g., Bivalacqua et al., Am. J. Physiol. Heart Circ. Physiol. 292, H1340-51 (2007).

The compounds of the invention may also be useful in the treatment or prevention of female sexual arousal disorder. The arginase inhibitor, ABH, enhances the engorgement response in the genitalia of live female rabbits. See, e.g., Cama et al., Biochemistry 42, 8445-51 (2003).

The compounds of the invention may be useful in the treatment or prevention of endothelial vascular dysfunction in atherosclerosis, hypertension, hypercholesterolemia, and diabetes. Arginase modulates NOS activity by regulation of L-arginine availability, and the deleterious effects of arginase can be blocked by an arginase inhibitor. See, e.g., Berkowitz et al., Circulation 108, 2000-06 (2003); Yang and Ming, Clin. Med. Res. 4, 53-65 (2006). Increased arginase activity in diabetes contributes to vascular endothelial dysfunction by decreasing L-arginine availability to nitric oxide synthase. See, e.g., Romero et al., Circ. Res. 102, 95-102 (2008). Arginase inhibition attenuates hypertension in spontaneously hypertensive rats. See, e.g., Demougeot et al., J.

Hypertens. 23, 971-78 (2005). Other relevant conditions include ischemia-reperfusion injury, peripheral vascular disease (PVD), peripheral arterial disease (PAD), and subarachnoid hemorrhage. Arginase has been identified as a new drug target for the treatment of atherosclerosis. See, e.g., Yang and Ming, Curr. Hypertension Rep. 8, 54-59 (2006).

The compounds of the invention may be useful in the treatment or prevention of pulmonary arterial hypertension. Elevated arginase activity contributes to vascular endothelial dysfunction by compromising L-arginine availability to nitric oxide synthase. See, e.g., Morris et al., Adv. Pulmonary Hypertension 5, 31-36 (2007).

The compounds of the invention may be useful in the treatment or prevention of African sleeping sickness, Chagas' disease, leishmaniasis, malaria, and other diseases caused by pathogenic microorganisms. Polyamine biosynthetic enzymes are essential for growth and survival of protozoa. See, e.g., Heby et al., Biochem. Soc. Trans. 31, 415-19 (2003). Arginase is essential for viability. See, e.g., Roberts et al., J. Biol. Chem. 279, 23668-78 (2004). Therefore, inhibitors of protozoan arginases can kill the protozoa.

The compounds of the invention may be useful in the treatment or prevention of multiple sclerosis, and possibly other autoimmune diseases, based upon the observation that arginase I is upregulated in an animal model of multiple sclerosis (experimental autoimmune encephalomyelitis) and administration of the arginase inhibitor ABH improves the disease score of animals. See, e.g., Xu et al., Immunology 110, 141-48 (2003).

Tumor-induced tolerance impairs the therapeutic efficacy of immunotherapy; one mechanism leading to T-cell tolerance is the generation of myeloid-derived suppressor cells (MDSCs), which produce arginase, thereby depleting the tumor microenvironment of L-arginine, which impairs T-cell signal transduction and function. Notably, arginase activity is a mechanism of immune system evasion that is also shared by certain bacteria, e.g., *Helicobacter pylori*. MDSCs are regarded as "cancer's bulwark against immune attack." See, e.g., Marx, Science 319, 154-56 (2008).

Accordingly, arginase is upregulated in the following types of cancers, which may be treated with an arginase inhibitor described herein: Renal cell carcinoma (see, e.g., Zea et al., Cancer Res. 65, 3044-48 (2005); Ochoa et al., Clin. Cancer Res. 13, 721s-26s (2007)); prostate cancer (see, e.g., Bronte et al., J. Exp. Med. 201, 1257-68 (2005) (arginase inhibition with N-hydroxy-L-arginine facilitates tumor immunotherapy); colorectal cancer (see, e.g., Leu and Wang, Cancer 70, 733-36 (1992); Bronte and Zanovello, Nature Rev. Immunol. 5, 641-54 (2005)); breast cancer (see, e.g., Singh et al., Cancer Res. 60, 3305-12 (2000); Bronte and Zanovello, Nature Rev. Immunol. 5, 641-54 (2005) (the arginase inhibitor, N-hydroxy-L-arginine, inhibits cell proliferation and induces apoptosis)); skin cancer (squamous cell and basal cell cancers) (see, e.g., Gokmen et al., J. Lab. Clin. Med. 137, 340-44 (2001); Bronte and Zanovello, Nature Rev. Immunol. 5, 641-54 (2005)); lung cancer (see, e.g., Rodriguez et al., J. Exp. Med. 202, 931-39 (2005); Bronte and Zanovello, Nature Rev. Immunol. 5, 641-54 (2005)); ovarian cancer (see, e.g., Melichar et al., J. Translational Med. 1, 1-5 (2003) (doi: 10.11861479-5876-1-5)); and gastric cancer (see, e.g., Wu et al., Life Sci. 51, 1355-61 (1992)); among others.

Enhancement of uterine smooth muscle relaxation with an arginase inhibitor may be useful in the management of pre-term labor.

Reynaud's disease is a disease of the microvasculature. Because subcutaneous administration of the arginase inhibitor (S)-(2-Boronoethyl)-L-cysteine (BEC, which is an analogue of ABH) in humans is vasodilatory and enhances circulation, an arginase inhibitor may be useful in treating Reynaud's disease. See, e.g., Holowatz et al., J. Physiol. 574, 573-81 (2006).

Arginase I is highly overexpressed in the hyperproliferative psoriatic epidermis in human skin, and therefore arginase inhibitors may be useful in the treatment of psoriasis. See, e.g., Bruch-Gerharz et al., Am. J. Pathology 162, 203-11 (2003).

Arginase II is upregulated in synovial fluid from human patients, and therefore arginase inhibitors may be useful in the treatment of arthritis. See, e.g., Huang et al., Kaohsiung J. Med. Sci. 17, 358-63 (2001); Corraliza and Moncada, J. Rheumatol. 29, 2261-65 (2002).

The compounds of the invention may be useful in the treatment or prevention of Peyronie's disease. Arginase II is upregulated in the rat penis in an animal model for this disease. See, e.g., Bivalacqua et al., J. Andrology 22, 497-506 (2001). While this disorder can contribute to erectile dysfunction, it is principally an inflammatory condition in which fibrotic tissue builds up in the penis.

The composition of the invention can be used to treat a disorder in a mammal, wherein the disorder is associated with expression of an abnormally high level of arginase activity in a tissue of the mammal. Because nitric oxide synthase activity is regulated in a reciprocal fashion with respect to arginase activity in mammals, more particularly humans, the compounds and compositions of the invention can be used to treat a disorder in a mammal, wherein the disorder is associated with expression of an abnormally low level of nitric oxide synthase activity in a tissue of the mammal. Since the reciprocal interaction of arginase and nitric oxide synthase has implications for the function of smooth muscle, the use of the compounds described herein for the regulation of smooth muscle activity in an animal is also contemplated in the invention. Of course, a compound of the invention or a composition comprising the compound of the invention which comprises an arginase inhibitor described herein can also be used to inhibit arginase in a mammal having normal levels of arginase and nitric oxide synthase activity, particularly where the physiology which is desired to be effected is one which is affected by arginase or nitric oxide synthase activity, or where a disorder which is not caused by aberrant arginase or nitric oxide synthase activity levels can nonetheless be alleviated or inhibited by inhibiting arginase activity (e.g., certain forms of erectile dysfunction).

The invention also includes a method of enhancing smooth muscle relaxation comprising contacting the smooth muscle with an arginase inhibitor. The smooth muscle is preferably within the body of an animal. The type of smooth muscle to be relaxed includes, but is not limited to, gastrointestinal smooth muscle, anal sphincter smooth muscle, esophageal sphincter muscle, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle. When the smooth muscle is gastrointestinal smooth muscle, the type of gastrointestinal smooth muscle includes, but is not limited to, the internal anal sphincter muscle.

When the smooth muscle is within the body of the animal, the invention includes a method of alleviating (e.g., reducing the incidence or severity) or inhibiting (e.g., reducing the likelihood of developing, or preventing) an arginase-related disorder in an animal. In a preferred embodiment, the animal is a human.

To alleviate an arginase-related disorder in a mammal, an arginase inhibitor described herein is administered to a mammal afflicted with the disorder. The inhibitor is preferably administered in combination with one or more pharmaceutically acceptable carriers, as described in further detail herein. The inhibitor (preferably in combination with a carrier) can also be administered to a mammal afflicted with a disorder characterized by aberrant nitric oxide synthase activity, or to one which exhibits normal (i.e. non-diseased) levels of arginase and nitric oxide synthase activities, but in which inhibition of arginase activity is desired. The invention also contemplates use of an arginase inhibitor in an in vitro arginase inhibition/smooth muscle relaxation functional assay, for the purpose of identifying compounds which affect smooth muscle function.

Accordingly, in certain embodiments, the invention is directed to methods of inhibiting arginase in a mammal, comprising the step of administering to said mammal an effective amount of a compound of the formulas described herein or a pharmaceutically acceptable salt thereof.

Accordingly, in certain embodiments, the invention is directed to methods of treating an arginase-related disorder in a mammal, comprising the step of administering to said mammal an effective amount of a compound of any of the formulas described herein or a pharmaceutically acceptable salt thereof. In certain preferred embodiments, the arginase-related disorder is a disorder associated with an abnormally low level of nitric oxide synthase activity in a tissue of the human, a disorder associated with an abnormally high level of arginase activity in a tissue of the human, or combinations thereof, including heart disease, systemic hypertension, pulmonary hypertension, erectile dysfunction, autoimmune encephalomyelitis, chronic renal failure, gastrointestinal motility disorders, gastric cancers, reduced hepatic blood flow, insufficient hepatic blood flow, cerebral vasospasm, or a combination thereof.

In still other certain embodiments, the invention is directed to methods of relaxing smooth muscle in a mammal, comprising the step of administering to said mammal an effective amount of a compound of the formulas described herein or a pharmaceutically acceptable salt thereof. In certain preferred embodiments, the smooth muscle which is relaxed according to this method is at least one selected from the group consisting of a gastrointestinal smooth muscle, anal sphincter smooth muscle, esophageal sphincter muscle, corpus cavernosum, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle.

In certain embodiments, the invention is directed to methods of treating a disease or condition associated with upregulation of arginase in a mammal, comprising the step of administering to said mammal an effective amount of a compound of the formulas described herein or a pharmaceutically acceptable salt thereof; wherein said disease or condition is a gastrointestinal disease, a pulmonary inflammatory disease, a sexual arousal disorder, a cardiovascular disorder, a hemolytic disorder, an autoimmune disease, wound healing, a cancer, pre-term labor, psoriasis, or a combination thereof.

In certain embodiments, the invention is directed to methods of treating a disease or condition caused by parasitic protozoa, a disease caused by bacteria, or a combination thereof.

Inhibiting arginase impacts cancer in two ways. The first way is relief from immune-suppression that leads to tolerance of the tumor, and the second way is by restricting the production of ornithine and subsequent polyamines, which have a role in proliferation.

In certain preferred embodiments, the gastrointestinal disease is a gastrointestinal motility disorder, inflammatory bowel disease, Crohn's disease, ulcerative colitis, gastric ulcer, adenotonsilar disease or a combination thereof.

In certain preferred embodiments, the pulmonary inflammatory disease is asthma, chemically-induced lung fibrosis, idiopathic pulmonary fibrosis, cystic fibrosis, chronic obstructive pulmonary disease (COPD) or a combination thereof.

In certain preferred embodiments, the sexual arousal disorder is male erectile dysfunction, Peyronie's Disease, or a female sexual arousal disorder.

In certain preferred embodiments, the cardiovascular disorder is endothelial vascular dysfunction in atherosclerosis, hypertension, ischemia reperfusion injury, peripheral vascular disease, peripheral arterial disease, subarachnoid hemorrhage, hypercholesterolemia, diabetes, or a combination thereof, diabetic cardiovascular disease, pulmonary arterial hypertension, Reynaud's disease, or a combination thereof.

In certain preferred embodiments, the hemolytic disorder is paroxysmal nocturnal hemoglobinuria (PNH), sickle-cell disease, thalassemias, hereditary spherocytosis and stomatocytosis, microangiopathic hemolytic anemias, pyruvate kinase deficiency, ABO mismatch transfusion reaction, paroxysmal cold hemoglobinuria, severe idiopathic autoimmune hemolytic anemia, infection-induced anemia, malaria, cardiopulmonary bypass, mechanical heart valve-induced anemia, chemical induced anemia, or a combination thereof.

In certain preferred embodiments, the autoimmune disease is encephalomyelitis, multiple sclerosis, anti-phospholipid syndrome 1, autoimmune hemolytic anaemia, chronic inflammatory demyelinating polyradiculoneuropathy, dermatitis herpetiformis ("Celiac Disease"), dermatomyositis, myasthenia gravis, pemphigus, rheumatoid arthritis, stiff-person syndrome, type 1 diabetes, ankylosing spondylitis, or a combination thereof.

In certain preferred embodiments, the condition is wound healing.

In certain preferred embodiments, the disease caused by parasitic protozoa is African sleeping sickness, Chagas' disease, leishmaniasis, malaria, or a combination thereof.

In certain preferred embodiments, the cancer is renal cell carcinoma, prostate cancer, colorectal cancer, breast cancer, skin cancer, lung cancer, ovarian cancer, gastric cancer, or a combination thereof. In certain embodiments, the skin cancer is a squamous cell cancer, basal cell cancer, or a combination thereof.

In certain preferred embodiments, the condition is pre-term labor.

In certain preferred embodiments, the condition is Reynaud's disease.

In certain embodiments, the invention is directed to methods of providing relief from immune suppression in a mammal, comprising the step of administering to said mammal an effective amount of a compound of the formulas described herein or a pharmaceutically acceptable salt thereof, wherein said mammal is suffering from a disease or condition selected from the group consisting of a chronic infectious disease, a bacterial infection, a parasitic infection, trauma, leprosy, tuberculosis, liver transplantation, a cancer, and combinations thereof.

In certain embodiments, the invention is directed to methods of inhibiting the production of ornithine or other related metabolites (e.g. agmatine, putrescine, spermine, spermidine, citruline, proline, glutamate, etc.) in a mammal suffering from at least one tumor, comprising the step of administering to said mammal an effective amount of a compound of the formulas described herein or a pharmaceutically acceptable salt thereof.

Pharmaceutical Compositions

Compounds described herein may be administered orally or parenterally. As formulated into a dosage form suitable for administration, the compounds described herein can be used as a pharmaceutical composition for the prevention, treatment, or remedy of the above diseases.

In clinical use of the compounds described herein, usually, the compound is formulated into various preparations together with pharmaceutically acceptable additives according to the dosage form, and may then be administered. By "pharmaceutically acceptable" it is meant the additive, carrier, diluent or excipient must be compatible with the other ingredients of the formulation and not deleterious to the recipient thereof. As such, various additives ordinarily used in the field of pharmaceutical preparations are usable. Specific examples thereof include gelatin, lactose, sucrose, titanium oxide, starch, crystalline cellulose, hydroxypropyl methylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, hydroxypropyl cyclodextrin, and the like.

Preparations to be formed with those additives include, for example, solid preparations such as tablets, capsules, granules, powders, suppositories; and liquid preparations such as syrups, elixirs, injections. These may be formulated according to conventional methods known in the field of pharmaceutical preparations. The liquid preparations may also be in such a form that may be dissolved or suspended in water or in any other suitable medium in their use. Especially for injections, if desired, the preparations may be dissolved or suspended in physiological saline or glucose liquid, and a buffer or a preservative may be optionally added thereto.

The pharmaceutical compositions may contain the compound of the invention in an amount of from 1 to 99.9% by weight, preferably from 1 to 60% by weight of the composition. The compositions may further contain any other therapeutically-effective compounds.

In case where the compounds of the invention are used for prevention or treatment for the above-mentioned diseases, the dose and the dosing frequency may be varied, depending on the sex, the age, the body weight and the disease condition of the patient and on the type and the range of the intended remedial effect. In general, when orally administered, the dose may be from 0.001 to 50 mg/kg of body weight/day, and it may be administered at a time or in several times. In specific embodiments, the dose is from about 0.01 to about 25 mg/kg/day, in particular embodiments, from about 0.05 to about 10 mg/kg/day. For oral administration, the compositions are preferably provided in the form of tablets or capsules containing from 0.01 mg to 1,000 mg. In specific embodiments, the dose is 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of a compound described herein. This dosage regimen may be adjusted to provide the optimal therapeutic response.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds described herein or the other drugs may have utility, where the combination of the drugs together are safer or more effective than either drug alone. Such other drug(s) may be administered in an amount commonly used therefore, contemporaneously or sequentially with a compound described herein or a pharmaceutically acceptable salt thereof. When a compound described herein is used contemporaneously with one or more other drugs, the pharmaceutical composition may in specific embodiments contain such other drugs and the compound described herein or its pharmaceutically acceptable salt in unit dosage form. However, the combination therapy may also include therapies in which the compound described herein or its pharmaceutically acceptable salt and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound described herein or a pharmaceutically acceptable salt thereof.

Examples of other active ingredients that may be administered in combination with a compound of any of the Formulas described herein or a pharmaceutically acceptable salt thereof and either administered separately or in the same pharmaceutical composition, include, but are not limited to pain relieving agents, anti-angiogenic agents, anti-neoplastic agents, anti-diabetic agents, anti-infective agents, or gastrointestinal agents, or combinations thereof.

Suitable compounds that may be used in combination with a compound according to the present invention include without limitation sildenafil, vardenafil, tadalafil and alprostadil, epoprostenol, iloprost, bosentan, amlodipine, diltiazem, nifedipine, ambrisentan and warfarin, fluticasone, budesonide, mometasone, flunisolide, beclomethasone, montelukast, zafirlukast, zileuton, salmeterol, formoterol, theophylline, albuterol, levalbuterol, pirbuterol, ipratropium, prednisone, methylprednisolone, omalizumab, corticosteroid and cromolyn, atorvastatin, lovastatin, simvastatin, pravastatin, fluvastatin, rosuvastatin, gemfibrozil, fenofibrate, nicotinic acid and clopidogrel.

Additionally, a compound of any of the Formulas disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—(R)-1-(4-(4-Fluoro-2-methyl-1H-indol-5-yloxy)-5-methylpyrrolo[2,1-f][1,2,4]triazin-6-yloxy)propan-2-yl)$_2$-aminopropanoate, also known as BMS-582664), motesanib (N-(2,3-dihydro-3,3-dimethyl-1H-indoi-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUB EX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP 005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MED4736 and MSB0010718C of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and *Erwinia* L-asparaginase, sold under the tradenames ELSPAR and KIDROLASE)

When a compound of the present invention is used contemporaneously with one or more other drugs a specific embodiment hereof pertains to, a pharmaceutical composition containing such other drugs in addition to the compound of the present invention. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, in particular embodiments from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

EXAMPLES

The meanings of the abbreviations in Examples are shown below.

ACN=MeCN=CH$_3$CN=acetonitrile
AcOH=acetic acid
Ar=argon
Boc$_2$O=di-tert-butyl dicarbonate
Cbz=carboxybenzyl
CCl$_4$=carbontetrachloride
CELITE=diatomaceous earth
Conc.=concentrated
Cs$_2$CO$_3$=Cesium carbonate
DCE=dichloroethane
DCM=dichloromethane
DIBALH=diisobutylaluminum hydride
DIEA=N, N-Diisopropylethylamine, or Hünig's base
DMA=dimethylacetamide
DMAP=4-dimethylaminopyridine
DMF=N,N-Dimethylformamide
DMP=Dess-Martin periodinane
DPPE=1,2-Bis(diphenylphosphino)ethane
DPPF=1,1'-Bis(diphenylphosphino)ferrocene
EDCI=1-ethyl-3-(3-dimethylaminopropyl)carbodiimide
Et$_2$O=diethyl ether
EtOAc=ethyl acetate
EtOH=ethanol
h=hours
H$_2$=hydrogen
HATU=1-[Bis(dimethylamino)methylene]-1H-1,2,3-triazolo[4,5-b]pyridinium 3-oxid hexafluorophosphate
HCl=hydrochloric acid
HFBA=Heptafluorobutyric acid
HOAc=acetic acid
I$_2$=iodine
IPA=isopropyl alcohol
[Ir(cod)Cl]$_2$=cyclooctadiene iridium chloride dimer
K$_2$CO$_3$=potassium carbonate
K$_3$PO$_4$=Tripotassium phosphate
LCMS=Liquid chromatography-mass spectrometry
LHMDS=LiHMDS=lithium bis(trimethylsilyl)amide
LiAlH$_4$=lithium aluminum hydride
LiOH=lithium hydroxide
min=minutes
Me=methyl
MeOH=methanol
MsCl=methanesulfonyl chloride
N$_2$=nitrogen
NaBH$_4$=sodium borohydrate
NaH=sodium hydride
NaIO$_4$=sodium periodate
NaOH=sodium hydroxide
Na$_2$CO$_3$=sodium carbonate
Na$_2$SO$_3$=sodium sulfite
Na$_2$SO$_4$=sodium sulfate
NH$_4$Cl=Ammonium chloride
NH$_4$OH=Ammonium hydroxide
NH$_4$OAc=Ammonium acetate
NaHMDS=sodium bis(trimethylsilyl)amide
Pd—C=palladium over carbon
[Pd(C$_3$H$_5$)C$_2$]=Allylpalladium(II) chloride dimer
PdCl$_2$(dppf)-CH$_2$Cl$_2$=[1,1'-Bis(diphenylphosphino)ferrocene]dichloropalladium(II)
RuO$_2$.H$_2$O=ruthenium(IV)oxide hydrate
RP-HPLC=reverse phase high performance liquid chromatography
SFC=Supercritical Fluid Chromatography
TEA=triethylamine
TFA=trifluoroacetic acid
THF=tetrahydrofuran
TMS=Trimethylsilyl CDCl₃=heavy chloroform
CD₃OD=heavy methanol
1 Standard atmosphere [atm]=101325 pascal [Pa]= 14.6959488 psi The meanings of the abbreviations in the nuclear magnetic resonance spectra are shown below:
s=singlet, d=doublet, dd=double doublet, dt=double triplet, ddd=double double doublet, Sept=septet, t=triplet, m=multiplet, br=broad, brs=broad singlet, q=quartet
J=coupling constant and Hz=hertz.

Compounds of this invention can be prepared using the intermediates and processes outlined below. The various starting materials used are commercially available or are readily made by persons skilled in the art. An asterisk (*) may be used in a chemical structure drawing that indicates the location of a chiral center.

Intermediate I-1: rac-tert-butyl (3aR,6aS)-5-oxo-hexahydrocyclopenta[c]pyrrole-2(1H)-carboxylate

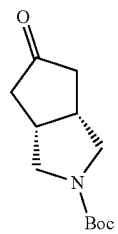 [SMILES: CC(C)(C)OC(=O)N1C[C@H]2CC(=O)C[C@H]2C1]

Intermediate I-1 was purchased from commercial sources or prepared by the following procedure.

Scheme A

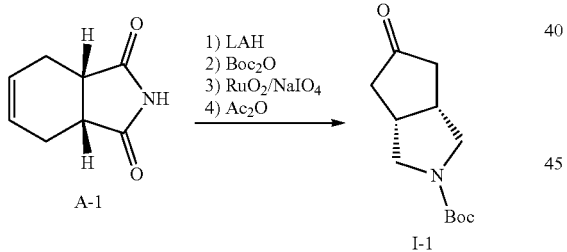

cis-1,2,3,6-Tetrahydrophthalimide (1000 g, 6.6 mol) was added in batches to a solution of lithium aluminum hydride (LAH, 653 g, 17 mol) in THF (10000 mL) at 0° C. The mixture was stirred at room temperature for 1 h and then followed by heating at 67° C. for 1 h. The reaction was cooled back to room temperature and then further cooled to 0° C. Then it was carefully quenched by slow addition of water (1000 mL), 15% aqueous NaOH solution (1000 mL) and followed by addition of anhydrous sodium sulfate (1500 g). The mixture was filtered and the filtrate was used directly in the next step.

Boc₂O (1731 g, 7.9 mol) was added to the filtrate from the previous step at 0° C. under N₂. The reaction mixture was warmed to room temperature and stirred for 3 h. The reaction mixture was diluted with ethyl acetate (5000 mL) followed by addition of water (5000 mL). The organic layer was separated, dried over anhydrous sodium sulfate and evaporated under reduced pressure. The residue was used in next step without further purification.

NaIO₄ (3903 g, 18 mol) was added to a solution of the residue prepared from the previous step in ACN (5500 mL), CCl₄ (3300 mL) and water (5500 mL), followed by addition of RuO₂·H₂O (23 g, 0.15 mol). The mixture was stirred at room temperature for 2 hours with mechanical stirring and then filtered through Celite. The filter cake was washed with DCM (2000 mL×2). The organic layer was separated, dried over anhydrous sodium sulfate, filtered and evaporated under reduced pressure. The residue was used in next step without further purification.

Sodium acetate (143 g, 1.7 mol) was added to a solution of the residue prepared from previous step in acetic anhydride (2000 mL) under inert atmosphere and resulting suspension was stirred at 120° C. for 1 h. The reaction mixture was cooled to room temperature, filtered and washed with ethyl acetate (2000 mL). The combined filtrate was evaporated under reduced pressure to get crude product. The crude product was purified by re-crystallization from methyl tert-butyl ether. The solids were collected by filtration to provide the title compound. LCMS ($C_{12}H_{19}NNaO_3^+$) (ES, m/z): 248 [M+Na]⁺.

Intermediate I-2: rac-tert-butyl (3aR,6aR)-4-allyl-5-oxohexahydrocyclopenta[c]pyrrole-2(1H)-carboxylate

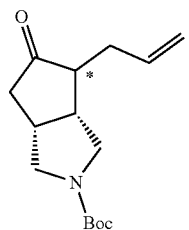 [SMILES: C=CCC1C(=O)C[C@H]2CN(C(=O)OC(C)(C)C)C[C@@H]12]

Scheme B

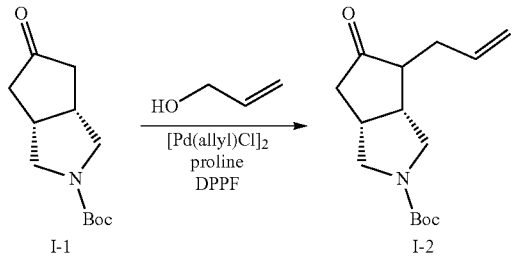

(Pd(allyl)Cl)₂ (57 g, 0.16 mol) was added to a mixture of 1,1'-ferrocenediyl-bis(diphenylphosphine) (DPPF, 173 g, 0.31 mol) in MeOH (1050 mL) under argon. The mixture was stirred at room temperature for 30 min, and then added to a mixture of rac-tert-butyl (3aR,6aS)-5-oxohexahydrocyclopenta[c]pyrrole-2(1H)-carboxylate (350 g, 1.6 mol), 4A MS (350 g), proline (54 g, 0.47 mol), and prop-2-en-1-ol (271 g, 4.7 mol) in MeOH (2450 mL). The resulting solution was stirred at room temperature for 36 h. The mixture was filtered and the filtrate was concentrated under reduced pressure. The residue was purified by silica gel column chromatography (EtOAc in hexanes) to provide rac-tertbutyl (3aR,6aR)-4-allyl-5-oxohexahydrocyclopenta[c]pyrrole-2(1H)-carboxylate. LCMS ($C_{15}H_{23}NO_3Na^+$) (ES, m/z): 288 [M+Na]$^+$.

Intermediate I-3: tert-butyl (3aR,4S,6aR)-4-allyl-5-oxohexahydrocyclopenta[c]pyrrole-2(1H)-carboxylate

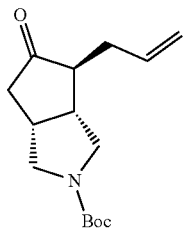

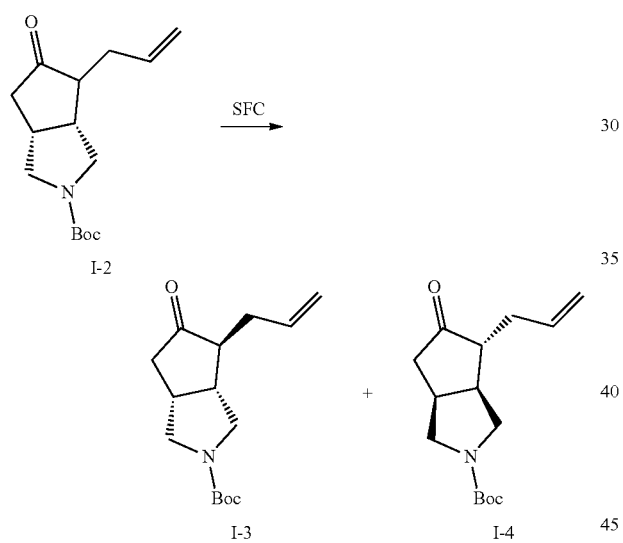

Rac-tert-butyl (3aR,6aR)-4-allyl-5-oxohexahydrocyclopenta[c]pyrrole-2(1H)-carboxylate (9.0 g, 34 mmol) was resolved by Chiral-SFC [Column: AD (250 mm*50 mm, 10 um), Mobile phase: A: $CO_2$, B: MeOH (neutral), Gradient: 15% of B in 3.5 min, and hold 15% of B for 1 min, Flow Rate (mL/min) 180, Column temperature: 40° C.] to give (3aR,6aR)-tert-butyl 4-allyl-5-oxohexahydrocyclopenta[c]pyrrole-2(1H)-carboxylate (I-3, $t_r$=2.051 min) as the first eluting peak, and (3aR,6aR)-tert-butyl 4-allyl-5-oxohexahydrocyclopenta[c]pyrrole-2(1H)-carboxylate (I-4, $t_r$=2.504 min) as the second eluting peak. I-3 LCMS ($C_{13}H_{19}N_2O_3^+$) (ES, m/z): 251 [M+H-t-Bu+$CH_3CN$]$^+$. $^1$H NMR (400 MHz, Chloroform-d) δ 5.82-5.67 (m, 1H), 5.09-5.00 (m, 2H), 3.75-3.68 (m, 2H), 3.60-3.55 (m, 1H), 3.12-3.02 (m, 1H), 2.98 (br s, 1H), 2.61-2.58 (m, 1H), 2.45-2.40 (m, 2H), 2.45-2.40 (m, 2H), 2.29-2.11 (m, 1H), 1.45 (s, 9H). I-4 LCMS ($C_{13}H_{19}N_2O_3^+$) (ES, m/z): 251 [M+H-t-Bu+$CH_3CN$]$^+$. $^1$H NMR (400 MHz, Chloroform-d) δ 5.76-5.67 (m, 1H), 5.10-5.00 (m, 2H), 3.73-3.69 (m, 2H), 3.60-3.55 (m, 1H), 3.12-3.02 (m, 1H), 2.98 (br s, 1H), 2.61-2.58 (m, 1H), 2.45-2.40 (m, 2H), 2.45-2.40 (m, 2H), 2.29-2.12 (m, 1H), 1.45 (s, 9H).

Intermediate I-5: rac-tert-butyl (3aR,6aR)-5-acetamido-4-allyl-5-(tert-butylcarbamoyl)hexahydrocyclopenta[c]pyrrole-2(1H)-carboxylate

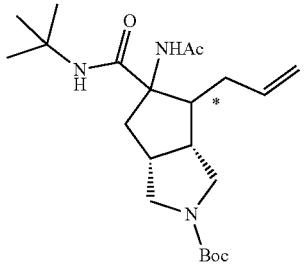 [SMILES: C=CCC1[C@@H]2CN(C(=O)OC(C)(C)C)C[C@@H]2CC1(NC(C)=O)C(=O)NC(C)(C)C]

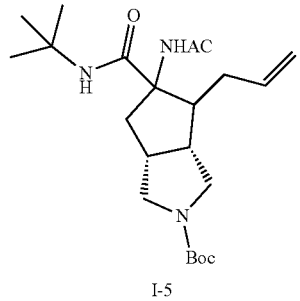

Tert-butyl isocyanide (1.9 g, 23 mmol) and ammonium acetate (2.7 g, 35 mmol) were added to a solution of rac-tert-butyl 4-allyl-5-oxohexahydrocyclopenta[c]pyrrole-2(1H)-carboxylate (2.0 g, 7.7 mmol) in 2,2,2-Trifluoroethyl alcohol (15 mL). The mixture was allowed to stir at 35° C. for 16 h under $N_2$. Water and EtOAc were added to the mixture. The aqueous layer was extracted with EtOAc. The combined organic layers were washed with brine, dried over anhydrous $Na_2SO_4$, then filtered and concentrated in vacuum. The residue was purified by silica gel column chromatography (EtOAc in hexanes) to give rac-tert-butyl 5-acetamido-4-allyl-5-(tert-butylcarbamoyl)hexahydrocyclopenta[c]pyrrole-2(1H)-carboxylate (mixture of diastereoisomers). LCMS ($C_{22}H_{38}N_3O_4^+$) (ES, m/z): 408 [M+H]$^+$.

Intermediate I-6: tert-butyl (3aR,4S,5S,6aR)-5-acetamido-4-allyl-5-(tert-butylcarbamoyl)hexahydrocyclopenta[c]pyrrole-2(1H)-carboxylate

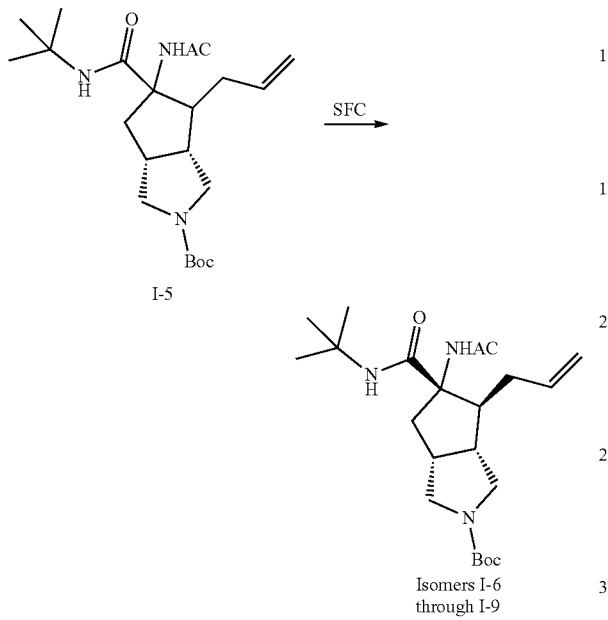

Scheme E

Isomers I-6 through I-9

Rac-tert-butyl 5-acetamido-4-allyl-5-(tert-butylcarbamoyl)hexahydrocyclopenta[c]pyrrole-2(1H)-carboxylate (I-5, 1.7 g, 4.2 mmol) was resolved by SFC [Column: ChiralPak IC-3 (250 mm*50 mm, 10 um), Mobile phase: A: $CO_2$, B: IPA (0.1% $NH_3 \cdot H_2O$), Gradient: 20% of B in 3.5 min, and hold 20% of B for 1 min, Flow Rate (mL/min) 50, Column temperature: 40° C.] to give tert-butyl 5-acetamido-4-allyl-5-(tert-butylcarbamoyl)hexahydrocyclopenta[c]pyrrole-2(1H)-carboxylate (I-6, $t_r$=1.623 min) as the first eluting peak, and tert-butyl 5-acetamido-4-allyl-5-(tert-butylcarbamoyl)hexahydrocyclopenta[c]pyrrole-2(1H)-carboxylate (I-8, $t_r$=2.378 min) as the third eluting peak and a mixture of I-7 and I-9. I-7/I-9 was further resolved by [Column: Chiral Cel OD-H (250 mm*50 mm, 10 um), Mobile phase: A: $CO_2$, B: EtOH (0.1% $NH_3 \cdot H_2O$), Gradient: 15% of B in 3.5 min, and hold 15% of B for 1 min, Flow Rate (mL/min) 50, Column temperature: 40° C.] to give tert-butyl 5-acetamido-4-allyl-5-(tert-butylcarbamoyl)hexahydrocyclopenta[c]pyrrole-2(1H)-carboxylate (I-7, $t_r$=2.160 min) as the second eluting peak, which was further confirmed by SFC [Column: ChiralPak IC-3 (250 mm*50 mm, 10 um), Mobile phase: A: $CO_2$, B: IPA (0.1% $NH_3 \cdot H_2O$), Gradient: 20% of B in 3.5 min, and hold 20% of B for 1 min, Flow Rate (mL/min) 50, Column temperature: 40° C.], and tert-butyl 5-acetamido-4-allyl-5-(tert-butylcarbamoyl)hexahydrocyclopenta[c]pyrrole-2(1H)-carboxylate (I-9, $t_r$=2.647 min) as the fourth eluting peak, which was further confirmed by SFC [Column: ChiralPak IC-3 (250 mm*50 mm, 10 um), Mobile phase: A: $CO_2$, B: IPA (0.1% $NH_3 \cdot H_2O$), Gradient: 20% of B in 3.5 min, and hold 20% of B for 1 min, Flow Rate (mL/min) 50, Column temperature: 40° C.]. I-6 LCMS ($C_{22}H_{38}N_3O_4^+$) (ES, m/z): 408 [M+H]$^+$. $^1$H NMR (400 MHz, Chloroform-d) δ 6.07 (br s, 2H), 5.81 (tdd, J=7.2, 10.0, 17.2 Hz, 1H), 5.19-5.06 (m, 2H), 3.44 (br s, 1H), 3.32 (br d, J=6.6 Hz, 2H), 3.23 (dd, J=4.4, 11.4 Hz, 1H), 3.04 (dd, J=9.0, 13.8 Hz, 1H), 2.92 (br s, 1H), 2.55 (br s, 1H), 2.30 (td, J=7.2, 14.1 Hz, 1H), 2.14 (td, J=7.2, 14.1 Hz, 1H), 2.05-1.99 (m, 1H), 1.98 (s, 3H), 1.71-1.59 (m, 1H), 1.44 (s, 9H), 1.33 (s, 9H). I-7 LCMS ($C_{22}H_{38}N_3O_4^+$) (ES, m/z): 408 [M+H]$^+$. $^1$H NMR (400 MHz, Chloroform-d) δ 6.25-6.00 (m, 2H), 5.89-5.75 (m, 1H), 5.20-5.08 (m, 2H), 3.45 (br s, 1H), 3.33 (br d, J=6.4 Hz, 2H), 3.24 (br dd, J=4.6, 11.2 Hz, 1H), 3.04 (dd, J=8.9, 13.6 Hz, 1H), 2.92 (br s, 1H), 2.56 (br s, 1H), 2.31 (td, J=7.2, 14.3 Hz, 1H), 2.14 (td, J=6.9, 13.9 Hz, 1H), 2.02 (br s, 1H), 1.98 (s, 3H), 1.66 (br dd, J=6.4, 14.1 Hz, 1H), 1.45 (s, 9H), 1.34 (s, 9H). I-8 LCMS ($C_{22}H_{38}N_3O_4^+$) (ES, m/z): 408 [M+H]$^+$. $^1$H NMR (400 MHz, Chloroform-d) δ 6.86-6.50 (m, 1H), 5.92-5.75 (m, 2H), 5.17-5.00 (m, 2H), 3.41-3.14 (m, 4H), 2.97 (br s, 1H), 2.74-2.61 (m, 1H), 2.54-2.29 (m, 3H), 2.12-2.04 (m, 1H), 2.03 (s, 3H), 1.86 (br d, J=7.9 Hz, 1H), 1.44 (s, 9H), 1.31 (s, 9H). I-9 LCMS ($C_{22}H_{38}N_3O_4^+$) (ES, m/z): 408 [M+H]$^+$. $^1$H NMR (400 MHz, chloroform-d) δ 6.86-6.53 (m, 1H), 5.89-5.77 (m, 2H), 5.16-5.02 (m, 2H), 3.43-3.19 (m, 4H), 3.06-2.87 (m, 1H), 2.74-2.62 (m, 1H), 2.52-2.33 (m, 3H), 2.13-2.04 (m, 1H), 2.03 (s, 3H), 1.86 (br d, J=8.8 Hz, 1H), 1.44 (s, 9H), 1.31 (s, 9H).

Intermediate I-10: tert-butyl (3aR,4S,5S,6aR)-5-acetamido-5-(tert-butylcarbamoyl)-4-(3-(4,4,5,5-tetramethyl-1,3,2-dioxaborolan-2-yl)propyl)hexahydrocyclopenta[c]pyrrole-2(1H)-carboxylate

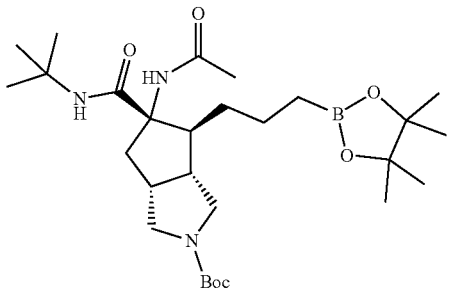

Scheme F

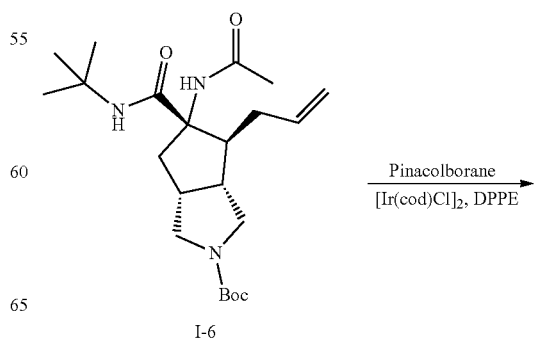

Pinacolborane
[Ir(cod)Cl]$_2$, DPPE

I-6

111
-continued

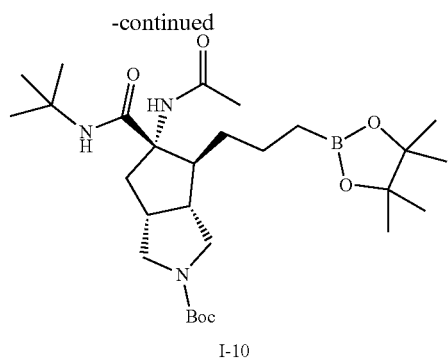

I-10

DPPE (5.9 g, 0.010 mol) and [Ir(cod)Cl]$_2$ (7.1 g, 0.010 mol) was added to a mixture of 4 Å MS (86 g) in DCM (430 mL) under N$_2$. The mixture was cooled to 0° C. 4,4,5,5-Tetramethyl-1,3,2-dioxaborolane (128 g, 0.84 mol) was added at 0° C. Tert-butyl (3aR,4S,6aR)-5-acetamido-4-allyl-5-(tert-butylcarbamoyl)hexahydrocyclopenta[c]pyrrole-2 (1H)-carboxylate (86 g, 0.21 mol) in DCM (430 mL) was then added under N$_2$. The mixture was stirred at room temperature for 1 h. Upon completion, the mixture was filtered and the filter cake was washed with DCM (160 mL) and DCM:MeOH (1:1, 160 mL). The filtrate was concentrated in vacuum. The residue was purified by silica gel column chromatography (MeOH in DCM) to give the product. Then the crude product was recrystallized with 10V ACN and further slurried in 10V methyl tert-butyl ether. Then the mixture was filtered and the filter cake was dried to afford (3aR,5S,6S,6aR)-tert-butyl 5-acetamido-5-(tert-butylcarbamoyl)-6-(3-(4,4,5,5-tetramethyl-1,3,2-dioxaborolan-2-yl)propyl) hexahydrocyclopenta[c]pyrrole-2(1H)-carboxylate. LCMS (C$_{28}$H$_{50}$BN$_3$O$_6$Na$^+$) (ES, m/z): 558 [M+Na]$^+$.

Intermediate I-11: (3aR,4S,5S,6aR)-5-acetamido-N-(tert-butyl)-4-(3-(4,4,5,5-tetramethyl-1,3,2-dioxaborolan-2-yl)propyl)octahydrocyclopenta[c]pyrrole-5-carboxamide

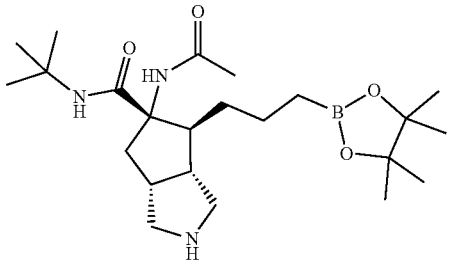

Scheme G

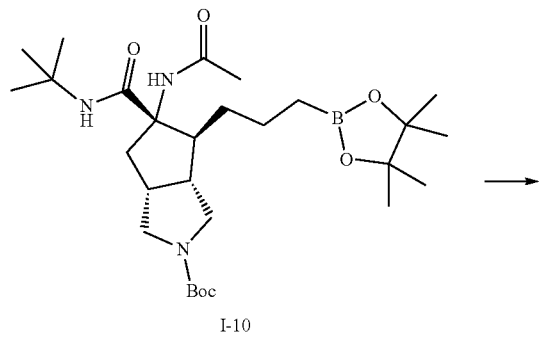

I-10

112
-continued

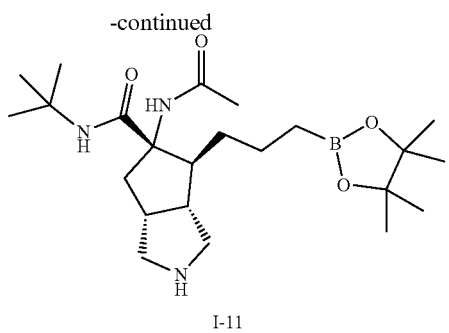

I-11

A mixture of tert-butyl (3aR,4S,5S,6aR)-5-acetamido-5-(tert-butylcarbamoyl)-4-(3-(4,4,5,5-tetramethyl-1,3,2-dioxaborolan-2-yl)propyl)hexahydrocyclopenta[c]pyrrole-2(1H)-carboxylate (1.0 g, 1.9 mmol) and 4.0 M HCl in dioxane (8.0 mL) was stirred at 20° C. for 20 min. The mixture was concentrated under reduced pressure to give (3aR,4S,5S,6aR)-5-acetamido-N-(tert-butyl)-4-(3-(4,4,5,5-tetramethyl-1,3,2-dioxaborolan-2-yl)propyl)octahydrocyclopenta[c]pyrrole-5-carboxamide as HCl salt, which was used in next step without purification. LCMS (C$_{23}$H$_{43}$BN$_3$O$_4$$^+$) (ES, m/z): 436 [M+H]$^+$.

Intermediate I-12: benzyl (3aR,4S,5S,6aR)-5-azido-4-(3-(4,4,5,5-tetramethyl-1,3,2-dioxaborolan-2-yl)propyl)octahydrocyclopenta[c]pyrrole-5-carboxylate

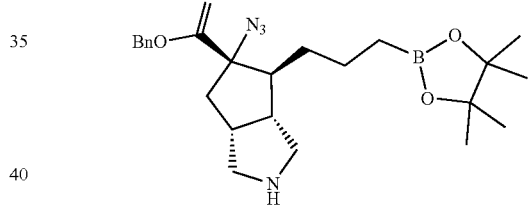

Scheme H

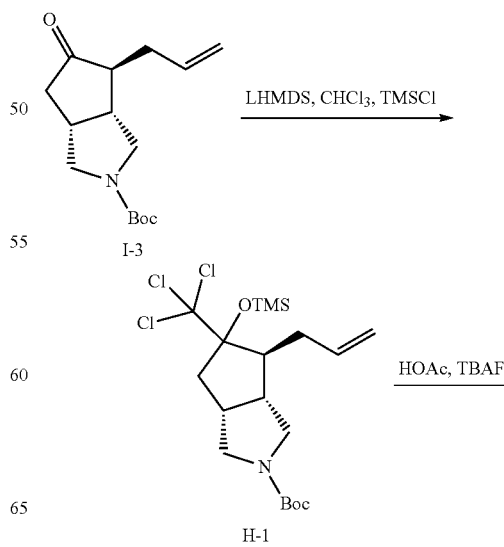

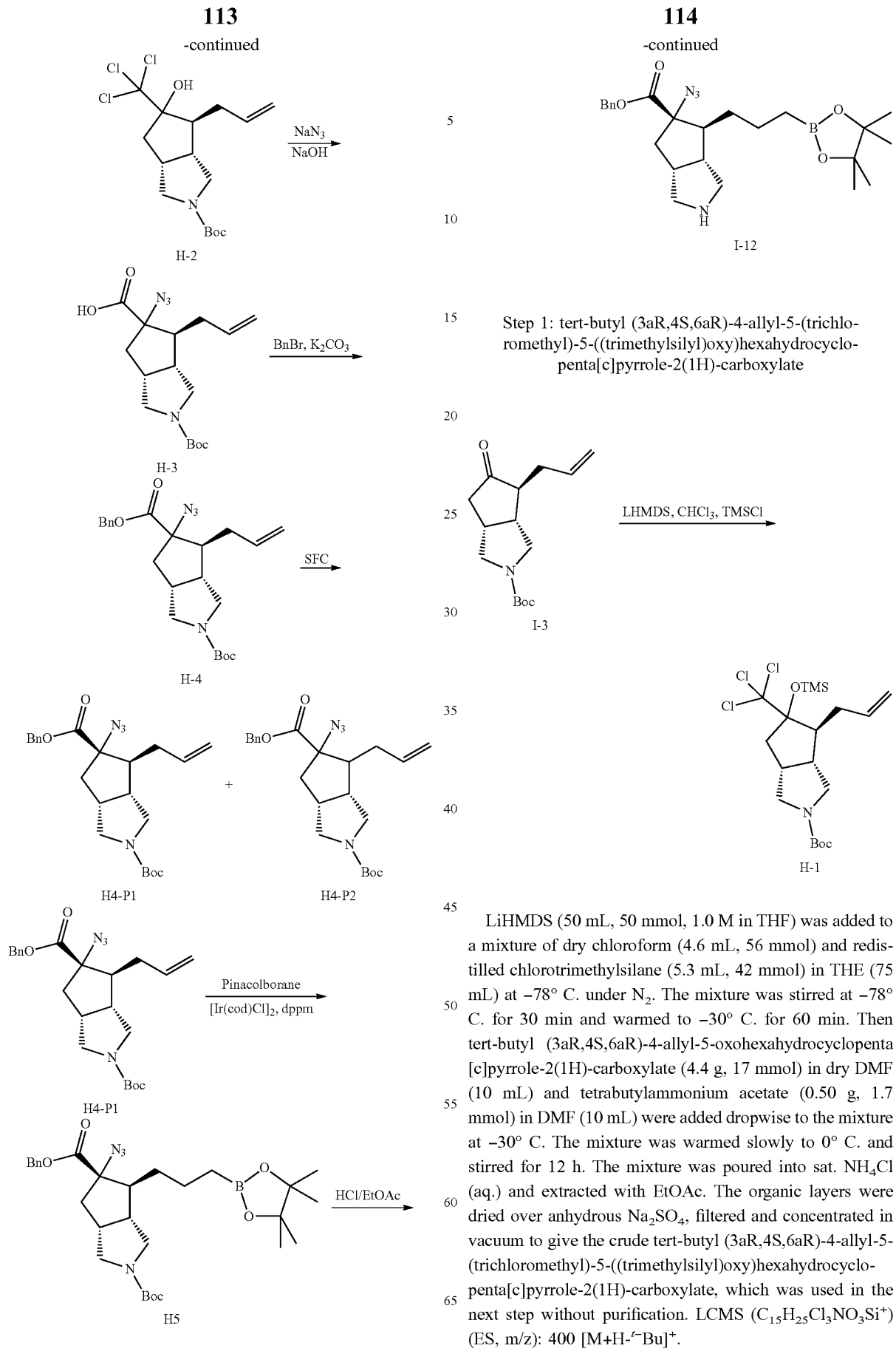

Step 1: tert-butyl (3aR,4S,6aR)-4-allyl-5-(trichloromethyl)-5-((trimethylsilyl)oxy)hexahydrocyclopenta[c]pyrrole-2(1H)-carboxylate LiHMDS (50 mL, 50 mmol, 1.0 M in THF) was added to a mixture of dry chloroform (4.6 mL, 56 mmol) and redistilled chlorotrimethylsilane (5.3 mL, 42 mmol) in THF (75 mL) at −78° C. under $N_2$. The mixture was stirred at −78° C. for 30 min and warmed to −30° C. for 60 min. Then tert-butyl (3aR,4S,6aR)-4-allyl-5-oxohexahydrocyclopenta[c]pyrrole-2(1H)-carboxylate (4.4 g, 17 mmol) in dry DMF (10 mL) and tetrabutylammonium acetate (0.50 g, 1.7 mmol) in DMF (10 mL) were added dropwise to the mixture at −30° C. The mixture was warmed slowly to 0° C. and stirred for 12 h. The mixture was poured into sat. $NH_4Cl$ (aq.) and extracted with EtOAc. The organic layers were dried over anhydrous $Na_2SO_4$, filtered and concentrated in vacuum to give the crude tert-butyl (3aR,4S,6aR)-4-allyl-5-(trichloromethyl)-5-((trimethylsilyl)oxy)hexahydrocyclopenta[c]pyrrole-2(1H)-carboxylate, which was used in the next step without purification. LCMS ($C_{15}H_{25}Cl_3NO_3Si^+$) (ES, m/z): 400 [M+H-$^t$Bu]$^+$.

115

Step 2: tert-butyl (3aR,4S,6aR)-4-allyl-5-hydroxy-5-(trichloromethyl)hexahydrocyclopenta[c]pyrrole-2(1H)-carboxylate

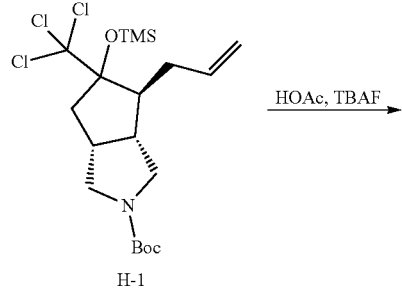
H-1

HOAc, TBAF →

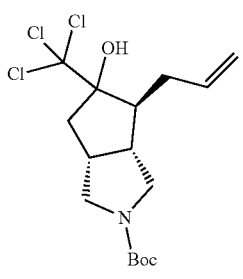
H-2

Tetrabutylammonium fluoride (TBAF) Acetic acid (6.0 mL, 105 mmol) and TBAF (63 mL, 63 mmol, 1.0 M in THF) were dropwise added to a mixture of tert-butyl (3aR,4S,6aR)-4-allyl-5-(trichloromethyl)-5-((trimethylsilyl)oxy)hexahydrocyclopenta[c]pyrrole-2(1H)-carboxylate (24 g, 53 mmol) in THE (150 mL) at 0° C. The mixture was stirred at 0° C. for 30 min and 20° C. for 5 h. The mixture was poured into sat. NaHCO₃ (aq.) and extracted with EtOAc. The organic layers were dried over anhydrous Na₂SO₄, filtered and concentrated in vacuum to give the crude tert-butyl (3aR,4S,6aR)-4-allyl-5-hydroxy-5-(trichloromethyl)hexahydrocyclopenta[c]pyrrole-2(1H)-carboxylate, which was used in the next step without further purification. LCMS ($C_{16}H_{25}Cl_3NO_3^+$) (ES, m/z): 384 [M+H]⁺.

Step 3: (3aR,4S,6aR)-4-allyl-5-azido-2-(tert-butoxycarbonyl)octahydrocyclopenta[c]pyrrole-5-carboxylic acid

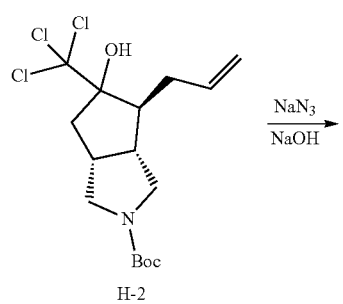
H-2

NaN₃ / NaOH →

116

-continued

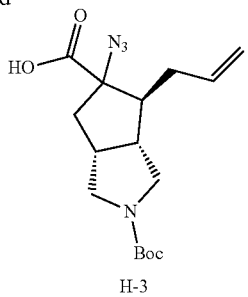
H-3

A solution of NaN₃ (8.6 g, 133 mmol) and NaOH (6.6 g, 164 mmol) in water (90 mL) was added to a solution of tert-butyl (3aR,4S,6aR)-4-allyl-5-hydroxy-5-(trichloromethyl)hexahydrocyclopenta[c]pyrrole-2(1H)-carboxylate (18 g, 47 mmol) in 1,4-dioxane (90 mL) at 0° C. The mixture was stirred at 25° C. for 20 h. The mixture was acidified to pH 6 by addition of HOAc, then poured into sat. NaCl (aq.) and extracted with EtOAc. The organic layer was dried over anhydrous Na₂SO₄, filtered and concentrated in vacuum to give the crude (3aR,4S,6aR)-4-allyl-5-azido-2-(tert-butoxycarbonyl)octahydrocyclopenta[c]pyrrole-5-carboxylic acid, which was used in the next step without further purification. LCMS ($C_{16}H_{25}N_4O_4^+$) (ES, m/z): 337 [M+H]⁺.

Step 4: 5-benzyl 2-(tert-butyl) (3aR,4S,6aR)-4-allyl-5-azidohexahydrocyclopenta[c]pyrrole-2,5(1H)-dicarboxylate

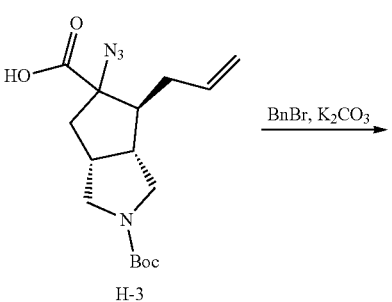
H-3

BnBr, K₂CO₃ →

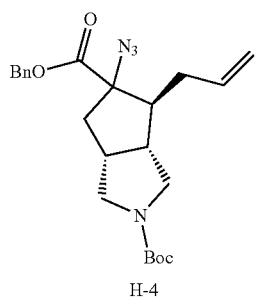
H-4

α-Bromotoluene (BnBr, 6.6 mL, 56 mmol) was added to a mixture of (3aR,4S,6aR)-4-allyl-5-azido-2-(tert-butoxycarbonyl)octahydrocyclopenta[c]pyrrole-5-carboxylic acid (17 g, 51 mmol) and potassium carbonate (10 g, 76 mmol) in DMF (100 mL) at 25° C. The mixture was stirred at 25° C. for 2.5 h. The mixture was poured into 1N NaCl (aq.) and extracted with EtOAc. The separated organic layers were dried over anhydrous Na₂SO₄, filtered and concentrated in vacuo. The residue was purified by silica gel column chromatography (EtOAc in hexanes) to give 5-benzyl 2-(tert-butyl) (3aR,4S,6aR)-4-allyl-5-azidohexahydrocyclopenta[c]pyrrole-2,5(1H)-dicarboxylate. LCMS ($C_{23}H_{31}N_4O_4^+$) (ES, m/z): 427 [M+H]$^+$.

Step 5: 5-benzyl 2-(tert-butyl) (3aR,4S,5S,6aR)-4-allyl-5-azidohexahydrocyclopenta[c]pyrrole-2,5(1H)-dicarboxylate

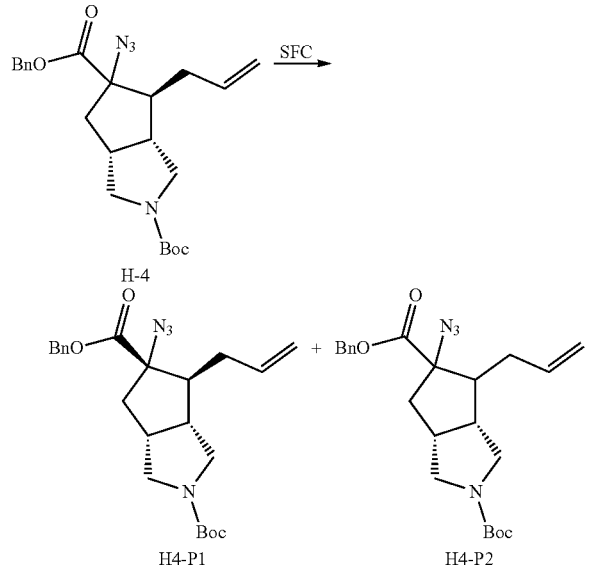

5-benzyl 2-(tert-butyl) (3aR,4S,6aR)-4-allyl-5-azidohexahydrocyclopenta[c]pyrrole-2,5(1H)-dicarboxylate (4.5 g, 11 mmol) was resolved by Chiral-SFC [Column: DAICEL CHIRALPAK IC (250 mm*30 mm, 5 um), Mobile phase: A: $CO_2$, B: EtOH (0.1% $NH_3.H_2O$), Gradient: 15% of B in 3.5 min, and hold 15% of B for 1 min, Flow Rate (mL/min) 180, Column temperature: 40° C.] to give 5-benzyl 2-(tert-butyl) (3aR,4S,5S,6aR)-4-allyl-5-azidohexahydrocyclopenta[c]pyrrole-2,5(1H)-dicarboxylate (H4-P1, $t_r$=1.86 min) as the first eluting peak, and 5-benzyl 2-tert-butyl 4-allyl-5-azidohexahydrocyclopenta[c]pyrrole-2,5(1H)-dicarboxylate (H4-P2, $t_r$=2.35 min) as the second eluting peak. H4-P1 LCMS ($C_{23}H_{31}N_4O_4^+$) (ES, m/z): 427 [M+H]$^+$. H4-P2 LCMS ($C_{23}H_{31}N_4O_4^+$) (ES, m/z): 427 [M+H]$^+$.

Step 6: 5-benzyl 2-(tert-butyl) (3aR,4S,5S,6aR)-5-azido-4-(3-(4,4,5,5-tetramethyl-1,3,2-dioxaborolan-2-yl)propyl)hexahydrocyclopenta[c]pyrrole-2,5(1H)-dicarboxylate

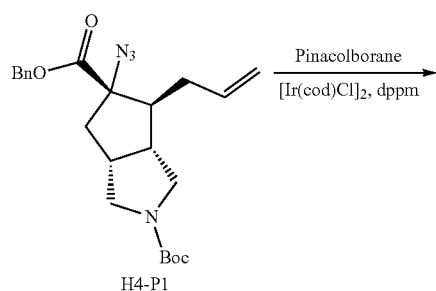

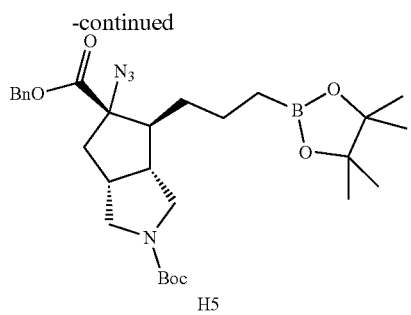

A solution of bis(diphenylphosphino)methane (0.10 g, 0.26 mmol), [Ir(cod)Cl]$_2$ (0.13 g, 0.19 mmol) and 4,4,5,5-tetramethyl-1,3,2-dioxaborolane (2.7 mL, 19 mmol) in anhydrous DCM (30 mL) was stirred at 25° C. for 20 min under N$_2$ and then 5-benzyl 2-(tert-butyl) (3aR,4S,5S,6aR)-4-allyl-5-azidohexahydrocyclopenta[c]pyrrole-2,5(1H)-dicarboxylate (1.6 g, 3.8 mmol) in anhydrous DCM (10 mL) was added into the mixture. The resulting mixture was stirred at 25° C. for 12 h under N$_2$. The reaction was concentrated in vacuo. The residue was purified by silica gel column chromatography (EtOAc in hexanes) to give 5-benzyl 2-(tert-butyl) (3aR,4S,5S,6aR)-5-azido-4-(3-(4,4,5,5-tetramethyl-1,3,2-dioxaborolan-2-yl)propyl)hexahydrocyclopenta[c]pyrrole-2,5(1H)-dicarboxylate. LCMS ($C_{29}H_{44}BN_4O_6^+$) (ES, m/z): 555 [M+H]$^+$.

Step 7: benzyl (3aR,4S,5S,6aR)-5-azido-4-(3-(4,4,5,5-tetramethyl-1,3,2-dioxaborolan-2-yl)propyl)octahydrocyclopenta[c]pyrrole-5-carboxylate

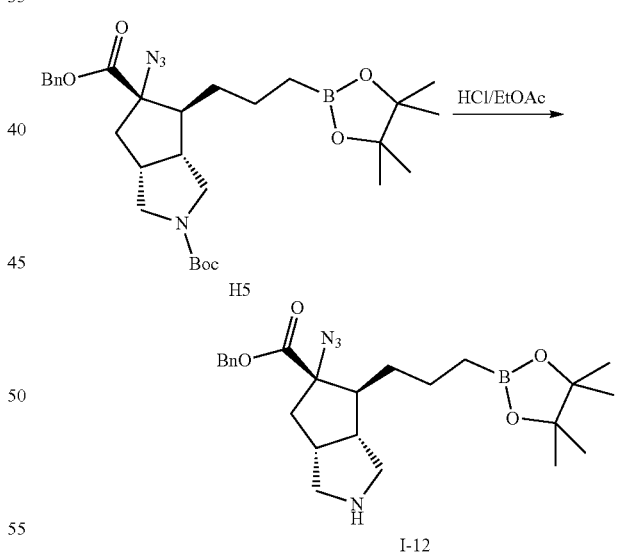

4N HCl in EtOAc (3.0 mL, 12 mmol) was added to a solution of 5-benzyl 2-(tert-butyl) (3aR,4S,5S,6aR)-5-azido-4-(3-(4,4,5,5-tetramethyl-1,3,2-dioxaborolan-2-yl)propyl)hexahydrocyclopenta[c]pyrrole-2,5(1H)-dicarboxylate (2.0 g, 3.6 mmol) in DCM (21 mL) at 25° C. The mixture was stirred at 25° C. for 12 h. The solution was concentrated in vacuo (at 25° C.) to give the benzyl (3aR,4S,5S,6aR)-5-azido-4-(3-(4,4,5,5-tetramethyl-1,3,2-dioxaborolan-2-yl)propyl)octahydrocyclopenta[c]pyrrole-5-carboxylate as a HCl salt. LCMS ($C_{24}H_{36}BN_4O_4^+$) (ES, m/z): 455 [M+H]$^+$.

Intermediate I-13: benzyl 5-azido-4-(3-(4,4,5,5-tetramethyl-1,3,2-dioxaborolan-2-yl)propyl)octahydrocyclopenta[c]pyrrole-5-carboxylate hydrochloride

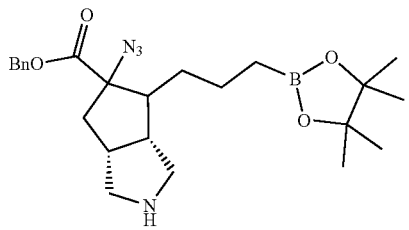

I-13

Intermediate I-13 was prepared by using the general procedure outlined above for I-12 by using intermediate I-2 as starting material. LCMS ($C_{24}H_{36}BN_4O_4^+$) (ES, m/z): 455 [M+H]$^+$.

Intermediate I-14: rac-(3aR,6aR)-5-acetamido-N-(tert-butyl)-4-(3-(4,4,5,5-tetramethyl-1,3,2-dioxaborolan-2-yl)propyl)octahydrocyclopenta[c]pyrrole-5-carboxamide

I-14

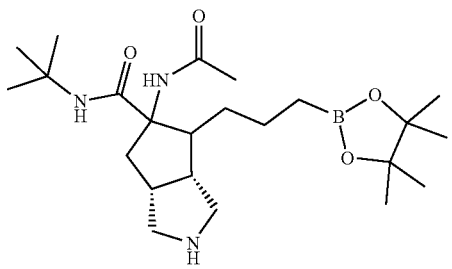

Intermediate I-14 was prepared by using the general procedure outlined above for I-11 by using intermediate I-2 as starting material. LCMS ($C_{23}H_{43}BN_3O_4^+$) (ES, m/z): 436 [M+H]$^+$.

Intermediate I-15: (1S,2S,3aS,6aR)-2-acetamido-1-allyl-N-(tert-butyl)-5-oxooctahydropentalene-2-carboxamide

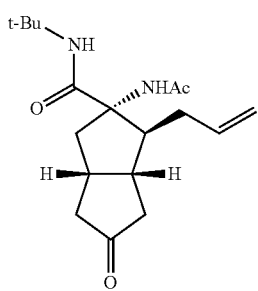 [SMILES: C=CC[C@H]1[C@@H]2CC(=O)C[C@@H]2C[C@@]1(NC(C)=O)C(=O)NC(C)(C)C]

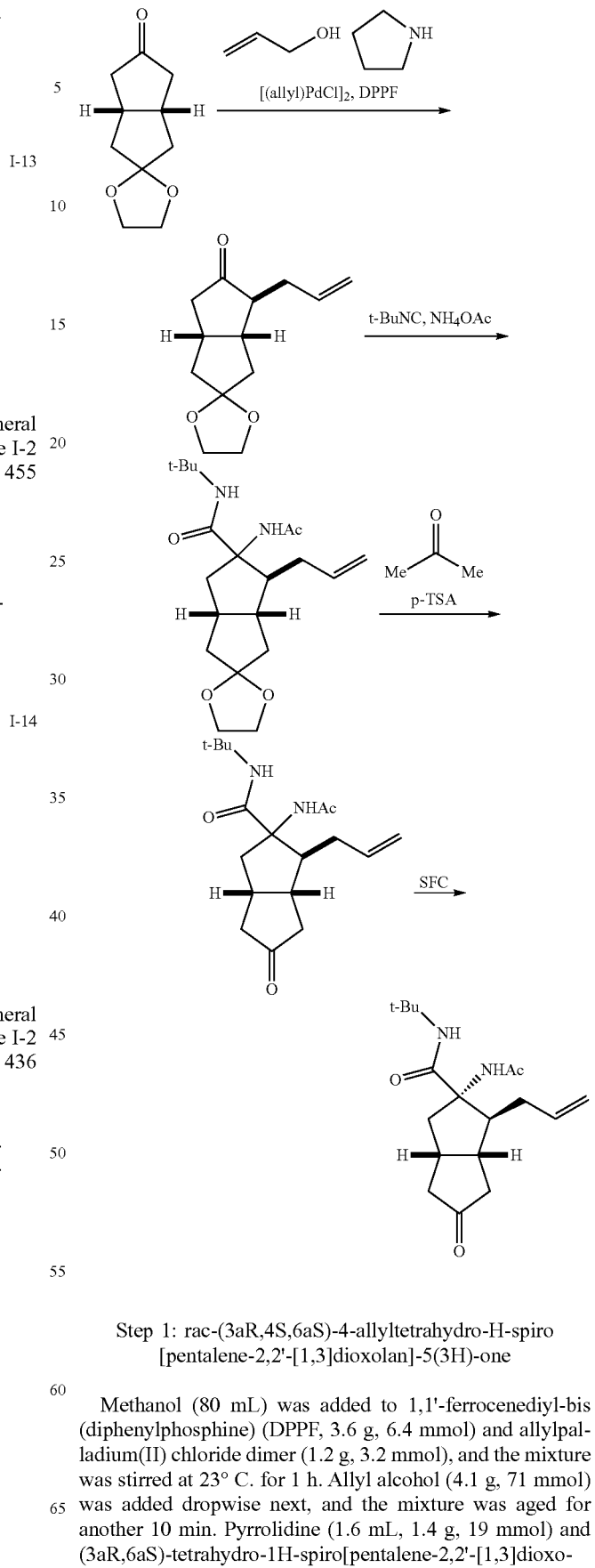

Step 1: rac-(3aR,4S,6aS)-4-allyltetrahydro-H-spiro[pentalene-2,2'-[1,3]dioxolan]-5(3H)-one Methanol (80 mL) was added to 1,1'-ferrocenediyl-bis(diphenylphosphine) (DPPF, 3.6 g, 6.4 mmol) and allylpalladium(II) chloride dimer (1.2 g, 3.2 mmol), and the mixture was stirred at 23° C. for 1 h. Allyl alcohol (4.1 g, 71 mmol) was added dropwise next, and the mixture was aged for another 10 min. Pyrrolidine (1.6 mL, 1.4 g, 19 mmol) and (3aR,6aS)-tetrahydro-1H-spiro[pentalene-2,2'-[1,3]dioxolan]-5(3H)-one (12 g, 64 mmol) were then added sequentially, and the reaction mixture was stirred at 23° C. for 17 h. The mixture was then diluted with saturated aqueous NH$_4$Cl solution (150 mL) and EtOAc (100 mL). The diluted mixture was stirred at 23° C. for 10 min before the layers were separated. The aqueous layer was extracted with EtOAc. The combined organic extracts were washed with saturated aqueous NaCl solution, dried over Na$_2$SO$_4$, filtered, and concentrated under reduced pressure. The residue was purified by silica gel column chromatography (EtOAc/hexanes) to give (3aR,4S,6aS)-4-allyltetrahydro-1H-spiro[pentalene-2,2'-[1,3]dioxolan]-5(3H)-one. LCMS (C$_{13}$H$_{19}$O$_3^+$) (ES, m/z): 223 [M+H]$^+$.

Step 2: rac-(3aR,4S,6aS)-5-acetamido-4-allyl-N-(tert-butyl)hexahydro-1H-spiro[pentalene-2,2'-[1,3]dioxolane]-5-carboxamide Ammonium acetate (8.5 g, 110 mmol) and tert-butyl isocyanide (13 mL, 9.2 g, 110 mmol) were added sequentially to a solution of (3aR,4S,6aS)-4-allyltetrahydro-1H-spiro[pentalene-2,2'-[1,3]dioxolan]-5(3H)-one (8.2 g, 37 mmol) in 2,2,2-trifluoroethanol (120 mL) at 23° C. The mixture was stirred at this temperature for 22 h before it was diluted with EtOAc (250 mL) and water (250 mL). The resulting mixture was shaken, and the layers were separated. The aqueous phase was extracted with EtOAc, the combined organic extracts were washed with saturated aqueous NaCl solution, and the washed organic solution was dried, filtered, and concentrated under reduced pressure to provide (3aR,4S,6aS)-5-acetamido-4-allyl-N-(tert-butyl)hexahydro-1H-spiro[pentalene-2,2'-[1,3]dioxolane]-5-carboxamide, which was used without further purification. LCMS (C$_{20}$H$_{33}$N$_2$O$_4^+$) (ES, m/z): 365 [M+H]$^+$.

Step 3: (1S,2S,3aS,6aR)-2-acetamido-1-allyl-N-(tert-butyl)-5-oxooctahydropentalene-2-carboxamide p-Toluenesulfonic acid monohydrate (700 mg, 3.7 mmol) was added to a suspension of (3aR,4S,6aS)-5-acetamido-4-allyl-N-(tert-butyl)hexahydro-1H-spiro[pentalene-2,2'-[1,3]dioxolane]-5-carboxamide in acetone (92 mL). The mixture was heated to reflux for 30 min before it was diluted with toluene (50 mL). The diluted mixture was concentrated to dryness under reduced pressure and the dried residue was re-suspended in fresh acetone (92 mL). The mixture was again brought to reflux for 30 min, diluted with toluene (50 mL), and concentrated under reduced pressure. The residue was purified by silica gel column chromatography (EtOAc/hexanes) to provide a racemic mixture of epimers. This mixture was resolved by SFC (column: IC, 21×250 mm; modifier: 0.1% v/v NH$_4$OH/MeOH; mobile phase: 15% modifier in CO$_2$; flow rate: 70 mL/min) to provide (1S,2S,3aS,6aR)-2-acetamido-1-allyl-N-(tert-butyl)-5-oxooctahydropentalene-2-carboxamide (t$_R$=3.1 min) as the first-eluting peak. LCMS (C$_{18}$H$_{29}$N$_2$O$_3^+$) (ES, m/z): 321 [M+H]$^+$.

Intermediate I-16: (1S,2S,3aS,5R,6aR)-2-acetamido-1-allyl-N-(tert-butyl)-5-hydroxyoctahydropentalene-2-carboxamide

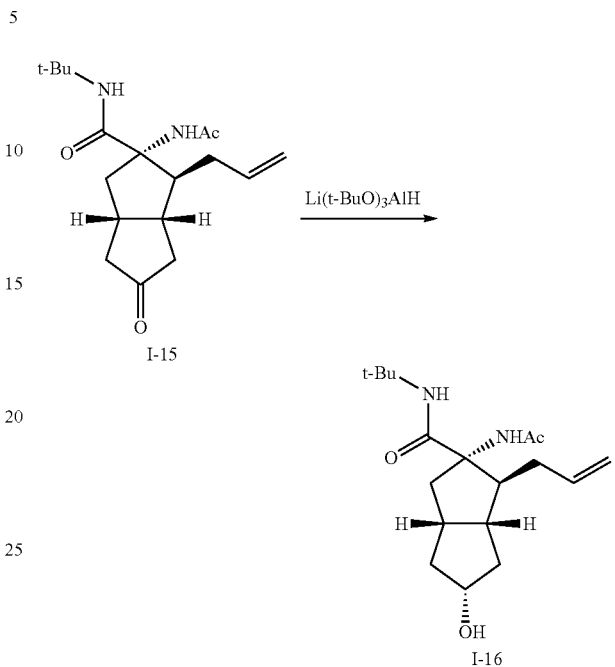

Lithium tri-tert-butoxyaluminum hydride solution (1.0 M in THF, 2.6 mL, 2.6 mmol) was added dropwise to a solution of (1S,2S,3aS,6aR)-2-acetamido-1-allyl-N-(tert-butyl)-5-oxooctahydropentalene-2-carboxamide (410 mg, 1.3 mmol) in THF (6.4 mL) at −40° C., and the reaction mixture was stirred for 2.5 h. The reaction mixture was then diluted with EtOAc (40 mL), and excess reductant was quenched with dropwise addition of 0.1 M aqueous NaOH solution (30 mL). The resulting mixture was stirred for 5 min; then the layers were separated. The aqueous layer was extracted with 5% v/v MeOH/EtOAc. The combined organic extracts were dried over Na$_2$SO$_4$, filtered, and concentrated under reduced pressure to give (1S,2S,3aS,5R,6aR)-2-acetamido-1-allyl-N-(tert-butyl)-5-hydroxyoctahydropentalene-2-carboxamide, which was used without further purification. LCMS (C$_{18}$H$_{31}$N$_2$O$_3^+$) (ES, m/z): 323 [M+H]$^+$.

Intermediate I-17: (2R,3aR,4S,5S,6aS)-5-acetamido-4-allyl-5-(tert-butylcarbamoyl)octahydropentalen-2-yl methanesulfonate

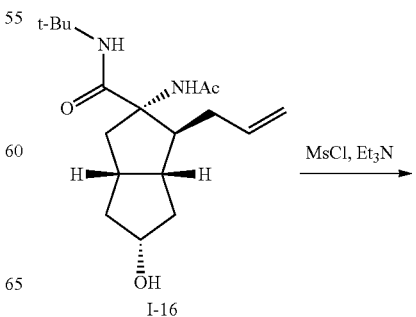

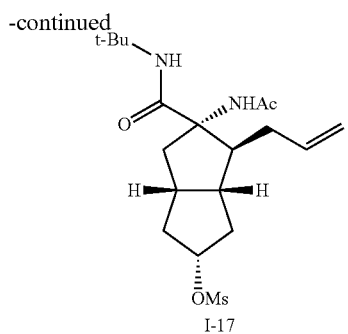

I-17

Methanesulfonyl chloride (150 µL, 210 mg, 1.9 mmol) was added dropwise to a suspension of (1S,2S,3aS,5R,6aR)-2-acetamido-1-allyl-N-(tert-butyl)-5-hydroxyoctahydropentalene-2-carboxamide (400 mg, 1.3 mmol) and triethylamine (520 µL, 380 mg, 3.7 mmol) in dichloromethane (13 mL) at 0° C. After 5 min at 0° C., excess methanesulfonyl chloride was quenched with the addition of saturated aqueous NaHCO$_3$ solution (25 mL). The resulting biphasic mixture was allowed to warm to 23° C. with stirring, and once warmed, the layers were separated. The aqueous phase was extracted with dichloromethane, and the combined organic layers were dried over Na$_2$SO$_4$. The dried organic solution was filtered and concentrated under reduced pressure to give (2R,3aR,4S,5S,6aS)-5-acetamido-4-allyl-5-(tert-butylcarbamoyl)octahydropentalen-2-yl methanesulfonate, which was used without further purification. LCMS ($C_{19}H_{33}N_2O_5S^+$) (ES, m/z): 401 [M+H]$^+$.

Intermediate I-18: (1S,2S,3aS,6aR)-2-acetamido-N-(tert-butyl)-5-oxo-1-(3-(4,4,5,5-tetramethyl-1,3,2-dioxaborolan-2-yl)propyl)octahydropentalene-2-carboxamide

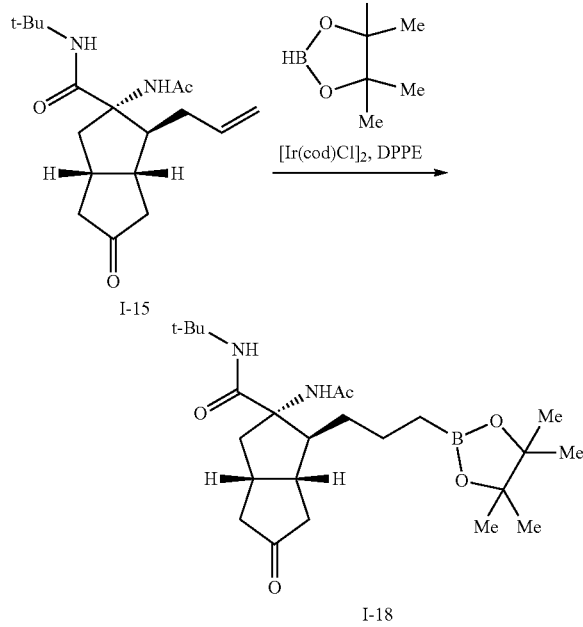

A solution of (1S,2S,3aS,6aR)-2-acetamido-1-allyl-N-(tert-butyl)-5-oxooctahydropentalene-2-carboxamide (100 mg, 0.310 mmol) in DCM (3.1 mL) was added to a solution of pinacolborane (230 µL, 200 mg, 1.6 mmol), chloro(1,5-cyclooctadiene)iridium(I) dimer (11 mg, 16 µmol), and bis(diphenylphosphino)ethane (12 mg, 31 µmol) in DCM (3.1 mL) at 23° C. The reaction mixture was stirred at 23° C. for 1.5 h under nitrogen gas. Excess reductant was quenched with the addition of methanol (1.0 mL), and the mixture was stirred for 10 min. Water (20 mL) was added, the layers were shaken, and the phases were separated. The aqueous phase was extracted with DCM. The combined organic extracts were dried over Na$_2$SO$_4$, filtered, and concentrated under reduced pressure to provide (1S,2S,3aS,6aR)-2-acetamido-N-(tert-butyl)-5-oxo-1-(3-(4,4,5,5-tetramethyl-1,3,2-dioxaborolan-2-yl)propyl)octahydropentalene-2-carboxamide. The residue was directly used in the next step without further purification. LCMS ($C_{24}H_{42}BN_2O_5^+$) (ES, m/z): 449 [M+H]$^+$.

Intermediate I-19: (1S,2S,3aS,6aR)-2-acetamido-N-(tert-butyl)-5-oxo-1-(3-((3aS,4S,6S,7aR)-3a,5,5-trimethylhexahydro-4,6-methanobenzo[d][1,3,2]dioxaborol-2-yl)propyl)octahydropentalene-2-carboxamide

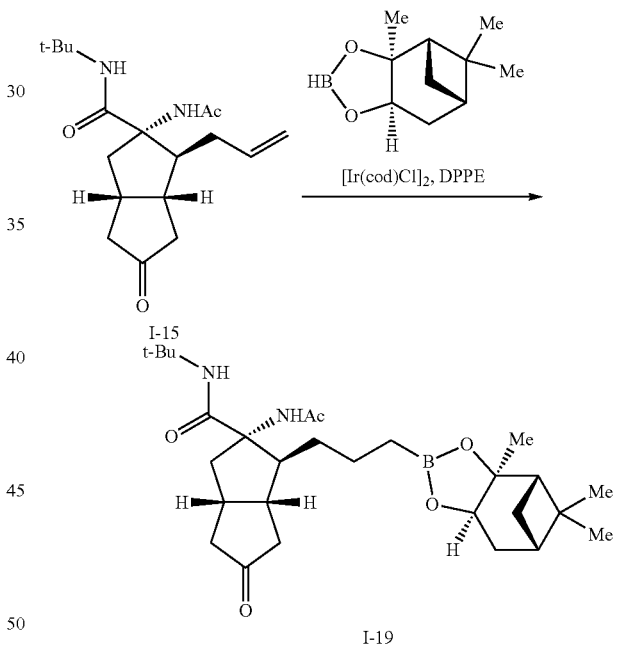

I-19

A solution of (1S,2S,3aS,6aR)-2-acetamido-1-allyl-N-(tert-butyl)-5-oxooctahydropentalene-2-carboxamide (200 mg, 0.62 mmol) in DCM (4.5 mL) was added to a solution of (3aS,4S,6S,7aR)-3a,5,5-trimethylhexahydro-4,6-methanobenzo[d][1,3,2]dioxaborole (230 mg, 1.30 mmol), chloro(1,5-cyclooctadiene)iridium(I) dimer (21 mg, 31 µmol), and bis(diphenylphosphino)ethane (25 mg, 63 µmol) in DCM (8.0 mL) at 23° C. The reaction mixture was stirred at 23° C. for 18 h under nitrogen gas. Excess reductant was quenched with the addition of methanol (1.0 mL), and the mixture was stirred for 10 min. Water (20 mL) was added, the layers were shaken, and the phases were separated. The aqueous layer was extracted with DCM. The combined organic extracts were dried over Na$_2$SO$_4$, filtered, and concentrated under reduced pressure to provide (1S,2S,3aS, 6aR)-2-acetamido-N-(tert-butyl)-5-oxo-1-(3-((3aS,4S,6S,7aR)-3a,5,5-trimethylhexahydro-4,6-methanobenzo[d][1,3,2]dioxaborol-2-yl)propyl)octahydropentalene-2-carboxamide. The residue was directly used in the next step without further purification. LCMS ($C_{28}H_{46}BN_2O_5^+$) (ES, m/z): 501 [M+H]$^+$.

Intermediates I-20 and I-21: (1S,2S,3aS,6R,6aR)-2-acetamido-N-(tert-butyl)-6-fluoro-5-oxo-1-(3-((3aS,4S,6S,7aR)-3a,5,5-trimethylhexahydro-4,6-methanobenzo[d][1,3,2]dioxaborol-2-yl)propyl)octahydropentalene-2-carboxamide and (1S,2S,3aR,4S,6aS)-2-acetamido-N-(tert-butyl)-4-fluoro-5-oxo-1-(3-((3aS,4S,6S,7aR)-3a,5,5-trimethylhexahydro-4,6-methanobenzo[d][1,3,2]dioxaborol-2-yl)propyl)octahydropentalene-2-carboxamide

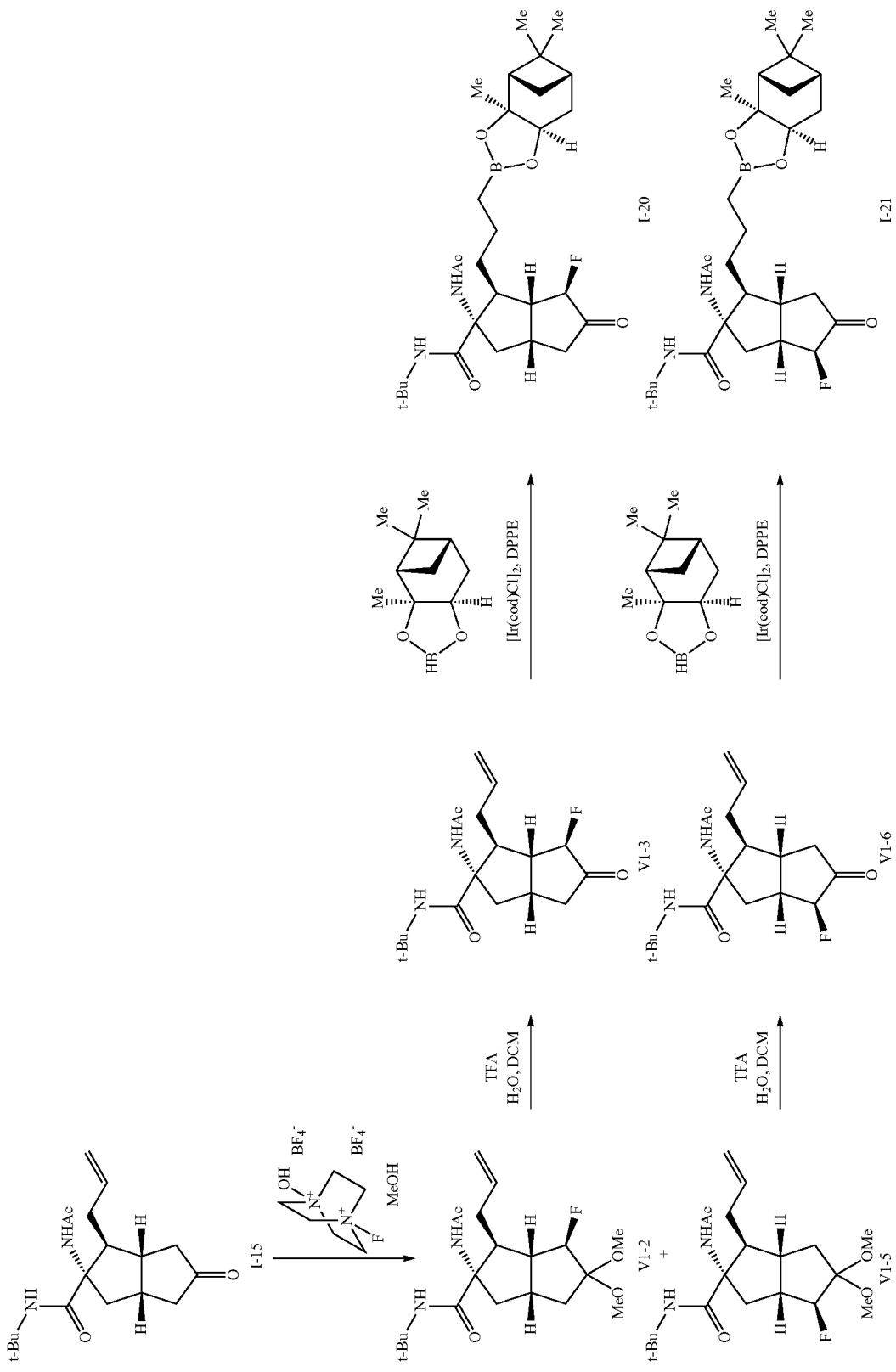

Step 1: (1S,2S,3aS,6R,6aR)-2-acetamido-1-allyl-N-(tert-butyl)-6-fluoro-5,5-dimethoxyoctahydropentalene-2-carboxamide and (1S,2S,3aR,4S,6aS)-2-acetamido-1-allyl-N-(tert-butyl)-4-fluoro-5,5-dimethoxyoctahydropentalene-2-carboxamide (1S,2S,3aS,6aR)-2-acetamido-1-allyl-N-(tert-butyl)-5-oxooctahydropentalene-2-carboxamide (400 mg, 1.3 mmol), 1-fluoro-4-hydroxy-1,4-diazoniabicyclo[2,2,2]octane bis(tetrafluoroborate) (~50% w/w on aluminum oxide, 1.2 g, ~1.9 mmol), and MeOH (25 mL) were combined, and the mixture was heated to 65° C. for 40 min. The mixture was then cooled to room temperature before it was diluted with DCM (50 mL). The diluted mixture was filtered through a pad of CELITE, and the filter cake was rinsed with DCM (25 mL). The filtrate was transferred to a separatory funnel, where it was washed with water. The washed organic solution was then dried over $Na_2SO_4$, filtered, and concentrated under reduced pressure. The residue was purified by SFC (column: Lux-4, 21×250 mm; modifier: 0.1% v/v $NH_4OH$/MeOH; mobile phase: 10% modifier in $CO_2$; flow rate: 70 mL/min) to provide (1S,2S,3aS,6R,6aR)-2-acetamido-1-allyl-N-(tert-butyl)-6-fluoro-5,5-dimethoxyoctahydropentalene-2-carboxamide (V1-3, $t_r$=4.1 min) as the first-eluting peak, and (1S,2S,3aR,4S,6aS)-2-acetamido-1-allyl-N-(tert-butyl)-4-fluoro-5,5-dimethoxyoctahydropentalene-2-carboxamide (V1-6, $t_r$=5.4 min) as the second-eluting peak. LCMS ($C_{19}H_{30}FN_2O_3^+$) (ES, m/z): 353 [M+H-$CH_3OH$]$^+$.

Step 2a: (1S,2S,3aS,6R,6aR)-2-acetamido-1-allyl-N-(tert-butyl)-6-fluoro-5-oxooctahydropentalene-2-carboxamide Water (2.3 mL) and TFA (4.6 mL) were added sequentially to a solution of (1S,2S,3aS,6R,6aR)-2-acetamido-1-allyl-N-(tert-butyl)-6-fluoro-5,5-dimethoxyoctahydropentalene-2-carboxamide (0.18 g, 0.46 mmol) in DCM (2.3 mL) at 23° C. The mixture was stirred for 1 h before it was poured into saturated aqueous $NaHCO_3$ solution (100 mL). The resulting mixture was stirred at 23° C. for 10 min. This mixture was then extracted with DCM, and the combined extracts were dried over $Na_2SO_4$, filtered, and concentrated under reduced pressure to provide (1S,2S,3aS,6R,6aR)-2-acetamido-1-allyl-N-(tert-butyl)-6-fluoro-5-oxooctahydropentalene-2-carboxamide, which was used without further purification. LCMS ($C_{18}H_{28}FN_2O_3^+$) (ES, m/z): 339 [M+H]$^+$.

Step 3a: (1S,2S,3aS,6R,6aR)-2-acetamido-N-(tert-butyl)-6-fluoro-5-oxo-1-(3-((3aS,4S,6S,7aR)-3a,5,5-trimethylhexahydro-4,6-methanobenzo[d][1,3,2]dioxaborol-2-yl)propyl)octahydropentalene-2-carboxamide A solution of (1S,2S,3aS,6R,6aR)-2-acetamido-1-allyl-N-(tert-butyl)-6-fluoro-5-oxooctahydropentalene-2-carboxamide (160 mg, 0.47 mmol) in DCM (3.3 mL) was added to a solution of (3aS,4S,6S,7aR)-3a,5,5-trimethylhexahydro-4,6-methanobenzo[d][1,3,2]dioxaborole (420 mg, 2.3 mmol), chloro(1,5-cyclooctadiene)iridium(I) dimer (16 mg, 23 µmol), and bis(diphenylphosphino)ethane (19 mg, 47 µmol) in DCM (6.0 mL) at 23° C. The reaction mixture was stirred at this temperature for 20 min under nitrogen gas. Excess reductant was quenched with the addition of methanol (1.0 mL), and the mixture was stirred for 10 min. Water (10 mL) was added, the layers were shaken, and the phases were separated. The aqueous layer was extracted with DCM. The combined organic extracts were dried over $Na_2SO_4$, filtered, and concentrated under reduced pressure. The crude residue, containing (1S,2S,3aS,6R,6aR)-2-acetamido-N-(tert-butyl)-6-fluoro-5-oxo-1-(3-((3aS,4S,6S,7aR)-3a,5,5-trimethylhexahydro-4,6-methanobenzo[d][1,3,2]dioxaborol-2-yl)propyl)octahydropentalene-2-carboxamide, was suitable for use in subsequent reductive-amination transformations without further purification. LCMS ($C_{28}H_{45}BFN_2O_5^+$) (ES, m/z): 519 [M+H]$^+$.

Step 2b: (1S,2S,3aR,4S,6aS)-2-acetamido-1-allyl-N-(tert-butyl)-4-fluoro-5-oxooctahydropentalene-2-carboxamide Water (2.0 mL) and TFA (3.9 mL) were added sequentially to a solution of (1S,2S,3aR,4S,6aS)-2-acetamido-1-allyl-N-(tert-butyl)-4-fluoro-5,5-dimethoxyoctahydropentalene-2-carboxamide (150 mg, 0.39 mmol) in DCM (2.0 mL) at 23° C. The mixture was stirred for 30 min before it was poured into saturated aqueous $NaHCO_3$ solution (100 mL). The resulting mixture was stirred at 23° C. for 10 min. This mixture was then extracted with DCM, and the combined extracts were dried over $Na_2SO_4$, filtered, and concentrated under reduced pressure to provide (1S,2S,3aR,4S,6aS)-2-acetamido-1-allyl-N-(tert-butyl)-4-fluoro-5-oxooctahydropentalene-2-carboxamide, which was used without further purification. LCMS ($C_{18}H_{28}FN_2O_3^+$) (ES, m/z): 339 [M+H]$^+$.

Step 3b: (1S,2S,3aR,4S,6aS)-2-acetamido-N-(tert-butyl)-4-fluoro-5-oxo-1-(3-((3aS,4S,6S,7aR)-3a,5,5-trimethylhexahydro-4,6-methanobenzo[d][1,3,2]dioxaborol-2-yl)propyl)octahydropentalene-2-carboxamide A solution of (1S,2S,3aR,4S,6aS)-2-acetamido-1-allyl-N-(tert-butyl)-4-fluoro-5-oxooctahydropentalene-2-carboxamide (130 mg, 0.38 mmol) in DCM (3.5 mL) was added to a solution of (3aS,4S,6S,7aR)-3a,5,5-trimethylhexahydro-4,6-methanobenzo[d][1,3,2]dioxaborole (340 mg, 1.9 mmol), chloro(1,5-cyclooctadiene)iridium(I) dimer (13 mg, 19 µmol), and bis(diphenylphosphino)ethane (15 mg, 38 µmol) in DCM (4.0 mL) at 23° C. The reaction mixture was stirred at this temperature for 25 min under nitrogen gas. Excess reductant was quenched with the addition of methanol (1.0 mL), and the mixture was stirred for 10 min. Water (10 mL) was added, the layers were shaken, and the phases were separated. The aqueous layer was extracted with DCM. The combined organic extracts were dried over $Na_2SO_4$, filtered, and concentrated under reduced pressure. The crude residue, containing (1S,2S,3aR,4S,6aS)-2-acetamido-N-(tert-butyl)-4-fluoro-5-oxo-1-(3-((3aS,4S,6S,7aR)-3a,5,5-trimethylhexahydro-4,6-methanobenzo[d][1,3,2]dioxaborol-2-yl)propyl)octahydropentalene-2-carboxamide, was used directly in the next step without further purification. LCMS ($C_{28}H_{45}BFN_2O_5^+$) (ES, m/z): 519 [M+H]$^+$.

131

Example 1

(3aR,6aR-rel-)-5-amino-4-(3-boronopropyl)octahydrocyclopenta[c]pyrrole-5-carboxylic acid

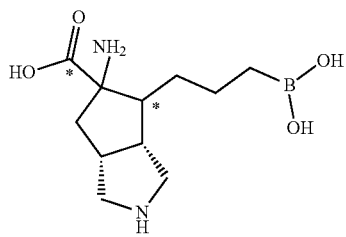

Scheme I

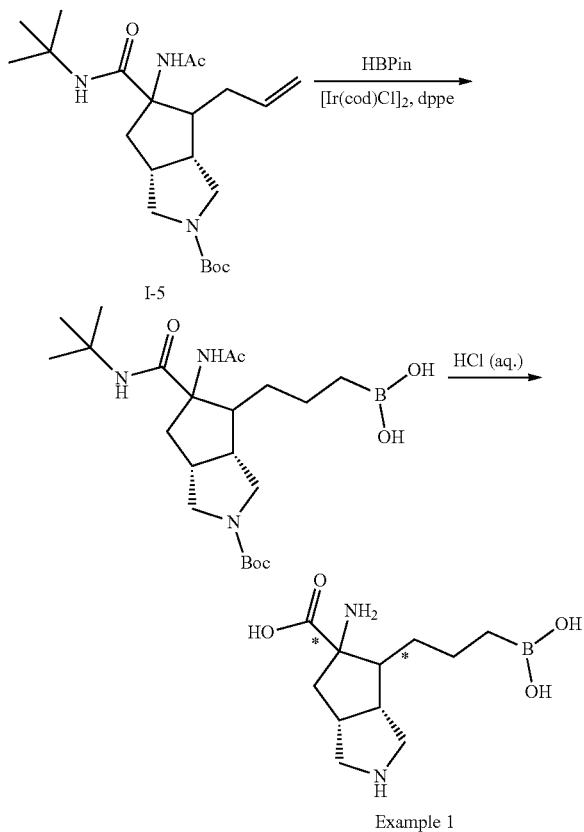

132

Step 1: (3-((3aR,6aR-rel-)-5-acetamido-2-(tert-butoxycarbonyl)-5-(tert-butylcarbamoyl)octahydrocyclopenta[c]pyrrol-4-yl)propyl)boronic acid A mixture of tert-butyl 5-acetamido-4-allyl-5-(tert-butylcarbamoyl)hexahydrocyclopenta[c]pyrrole-2(1H)-carboxylate (30 mg, 0.074 mmol), bis(diphenylphosphino)methane (28 mg, 0.074 mmol), 4,4,5,5-tetramethyl-1,3,2-dioxaborolane (19 mg, 0.15 mmol) and [Ir(cod)Cl]$_2$ (2.5 mg, 3.7 µmol) in DCM (3.0 mL) was degassed and backfilled with N$_2$ (three times). The mixture was stirred at 15° C. for 16 h. The reaction was concentrated and the residue was purified by RP-HPLC [C18 column, water (0.1% TFA)-CH$_3$CN] to give (3-(5-acetamido-2-(tert-butoxycarbonyl)-5-(tert-butylcarbamoyl)octahydrocyclopenta[c]pyrrol-4-yl)propyl)boronic acid. The boronic ester was hydrolyzed to the boronic acid under purification by RP-HPLC. LCMS (C$_{22}$H$_{41}$BN$_3$O$_6^+$) (ES, m/z): 454 [M+H]$^+$.

Step 2: (3aR,6aR-rel-)-5-amino-4-(3-boronopropyl)octahydrocyclopenta[c]pyrrole-5-carboxylic acid (3-((3aR,6aR-rel-)-5-acetamido-2-(tert-butoxycarbonyl)-5-(tert-butylcarbamoyl)octahydrocyclopenta[c]pyrrol-4-yl)propyl)boronic acid (40 mg, 0.088 mmol) in 12N HCl in water (2.0 mL) was stirred at 100° C. for 16 h. The mixture was concentrated under reduced pressure. The residue was purified by RP-HPLC [C18 column, water (0.1% TFA)-CH$_3$CN] to give (3aR,6aR-rel-)-5-amino-4-(3-boronopropyl)octahydrocyclopenta[c]pyrrole-5-carboxylic acid, Example 1, as a TFA salt. LCMS (C$_{11}$H$_{20}$BN$_2$O$_3^+$) (ES, m/z): 239 [M+H-H$_2$O]$^+$. $^1$H NMR (400 MHz, CD$_3$OD) δ 3.54-3.45 (m, 1H), 3.36 (br d, J=13.9 Hz, 2H), 3.25-3.13 (m, 1H), 2.98-2.78 (m, 1H), 2.64-2.51 (m, 1H), 2.45-2.28 (m, 1H), 2.10-1.99 (m, 1H), 1.98-1.77 (m, 1H), 1.69 (br t, J=11.0 Hz, 1H), 1.55-1.37 (m, 2H), 1.30 (br d, J=9.5 Hz, 1H), 0.93-0.67 (m, 2H).

Examples 1a through 1d were made from I-6, I-7, I-8 and I-9 using a similar procedure as Example 1.

| Ex. | Structure | MS and $^1$HNMR |
|---|---|---|
| 1a | 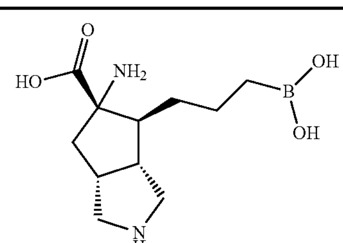 | LCMS (C$_{11}$H$_{20}$BN$_2$O$_3^+$) (ES, m/z): [M + H − H$_2$O]$^+$, 239. $^1$H NMR (400 MHz, Deuterium Oxide) δ 3.50 (dd, J = 8.6, 12.1 Hz, 1H), 3.45-3.37 (m, 1H), 3.33-3.24 (m, 1H), 3.21-3.08 (m, 2H), 2.98-2.84 (m, 1H), 2.73-2.55 (m, 1H), 2.04 (dt, J = 3.5, 9.9 Hz, 1H), 1.81-1.70 (m, 1H), 1.63-1.47 (m, 1H), 1.45-1.33 (m, 1H), 1.31-1.18 (m, 2H), 0.78-0.66 (m, 2H). |

1b LCMS ($C_{11}H_{20}BN_2O_3^+$) (ES, m/z): [M+H-$H_2O$]$^+$, 239. $^1$H NMR (400 MHz, Deuterium Oxide) δ 3.51 (dd, J=8.6, 12.1 Hz, 1H), 3.45-3.38 (m, 1H), 3.38-3.24 (m, 1H), 3.19 (dd, J=4.9, 12.1 Hz, 1H), 3.13 (dd, J=5.5, 11.9 Hz, 1H), 2.89 (dq, J=5.2, 9.4 Hz, 1H), 2.70-2.58 (m, 1H), 2.13-2.02 (m, 1H), 1.78 (dd, J=9.2, 13.8 Hz, 1H), 1.61-1.49 (m, 1H), 1.47-1.35 (m, 1H), 1.34-1.19 (m, 2H), 0.78-0.66 (m, 2H). 1c LCMS ($C_{11}H_{20}BN_2O_3^+$) (ES, m/z): [M+H-$H_2O$]$^+$, 239. $^1$H NMR (400 MHz, Deuterium Oxide) δ 3.46-3.37 (m, 1H), 3.36-3.25 (m, 3H), 3.13 (br d, J=8.3 Hz, 1H), 2.78-2.64 (m, 1H), 2.44 (br d, J=18.4 Hz, 1H), 2.40-2.31 (m, 1H), 2.28-2.05 (m, 1H), 1.50-1.18 (m, 4H), 0.85-0.60 (m, 2H). 1d LCMS ($C_{11}H_{20}BN_2O_3^+$) (ES, m/z): [M+H-$H_2O$]$^+$, 239. $^1$H NMR (400 MHz, Deuterium Oxide) δ 3.43-3.35 (m, 1H), 3.35-3.22 (m, 3H), 3.15-2.99 (m, 1H), 2.79-2.61 (m, 1H), 2.36-2.28 (m, 2H), 2.20-2.07 (m, 1H), 1.75-1.60 (m, 1H), 1.46-1.13 (m, 3H), 0.82-0.59 (m, 2H).

Example 1e: (3aR,4S,5S,6aR)-5-amino-4-(3-boronopropyl)octahydrocyclopenta[c]pyrrole-5-carboxylic acid, Free Base

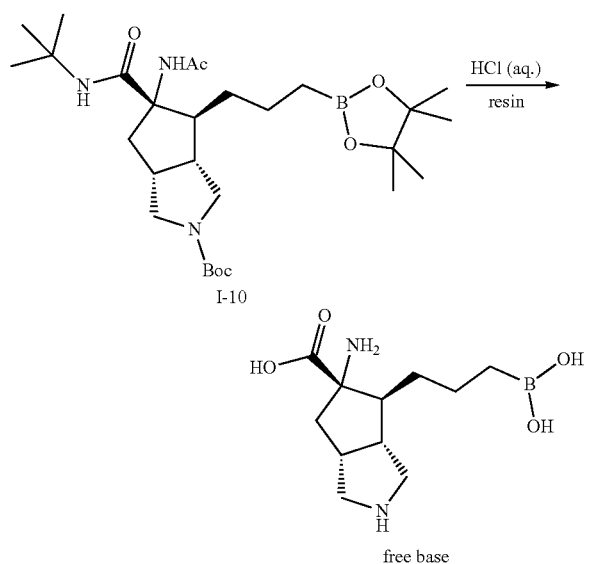

A solution of tert-butyl (3aR,4S,5S,6aR)-5-acetamido-5-(tert-butylcarbamoyl)-4-(3-(4,4,5,5-tetramethyl-1,3,2-dioxaborolan-2-yl)propyl)hexahydrocyclopenta[c]pyrrole-2 (1H)-carboxylate (1.1 g, 2.1 mmol) in 12N HCl in water (20 mL) was stirred at 100° C. for 15 h. The mixture was concentrated under reduced pressure. The residue was dissolved in water. The mixture was neutralized with $Na_2CO_3$ solid to pH=8. The aqueous phase was washed with DCM and then concentrated under reduced pressure to give the crude product. Dowex50WX8 resin (45 g) was activated (stirred once and then washed once) with water and MeOH successively. The resin was briefly suction dried. The above resin was added to the solution of the crude product in water at 25° C. The mixture was stirred for 40 min and aged for 20 min. The mixture was filtered and the filter cake was washed with MeOH and then water. The filter cake was then washed with 2N aqueous ammonium hydroxide solution. The aqueous ammonium hydroxide solution was lyophilized to give (3aR,4S,5S,6aR)-5-amino-4-(3-boronopropyl)octahydrocyclopenta[c]pyrrole-5-carboxylic acid as free base. LCMS ($C_{11}H_{20}BN_2O_3^+$) (ES, m/z): 239 [M+H-$H_2O$]$^+$. $^1$H NMR (500 MHz, Deuterium Oxide) δ 3.14-2.97 (m, 5H), 2.68-2.61 (m, 1H), 2.36-2.31 (m, 1H), 1.58-1.52 (m, 1H), 1.41-1.13 (m, 4H), 1.06-0.98 (m, 1H), 0.60-0.47 (m, 2H).

Example 1f: (3aR,4S,5S,6aR)-5-amino-4-(3-boronopropyl)octahydrocyclopenta[c]pyrrole-5-carboxylic acid, HCl Salt

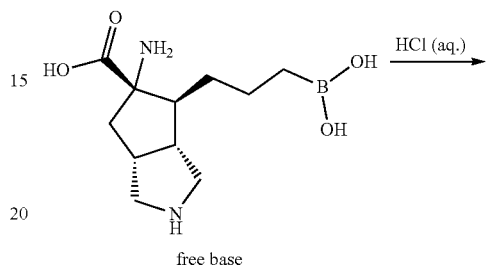

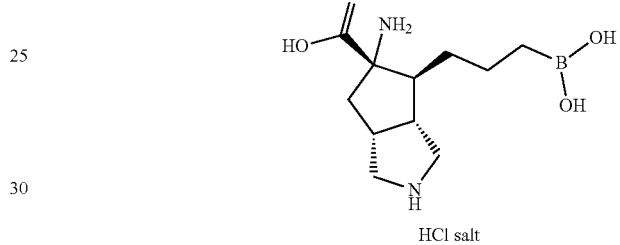

(3aR,4S,5S,6aR)-5-amino-4-(3-boronopropyl)octahydrocyclopenta[c]pyrrole-5-carboxylic acid was dissolved in water and 1N HCl in water (pH<1). The solution was lyophilized to give (3aR,4S,5S,6aR)-5-amino-4-(3-boronopropyl)octahydrocyclopenta[c]pyrrole-5-carboxylic acid as a HCl salt. LCMS ($C_{11}H_{20}BN_2O_3^+$) (ES, m/z): 239 [M+H-$H_2O$]$^+$. $^1$H NMR (499 MHz, Deuterium Oxide) δ 3.51 (dd, J=12.2, 8.5 Hz, 1H), 3.43 (dd, J=11.9, 8.4 Hz, 1H), 3.32-3.25 (m, 1H), 3.22-3.11 (m, 2H), 2.89 (ddt, J=14.8, 9.7, 5.0 Hz, 1H), 2.63 (dd, J=13.7, 8.7 Hz, 1H), 2.07 (td, J=10.0, 3.7 Hz, 1H), 1.78 (dd, J=13.8, 9.2 Hz, 1H), 1.57-1.52 (m, 1H), 1.44-1.35 (m, 1H), 1.32-1.18 (m, 2H), 0.77-0.67 (m, 2H).

Example 2: (3aR,4S,5S,6aR)-5-amino-4-(3-boronopropyl)-2-methyloctahydrocyclopenta[c]pyrrole-5-carboxylic acid

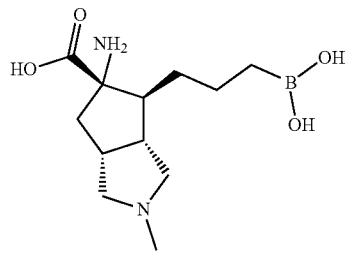

Scheme J

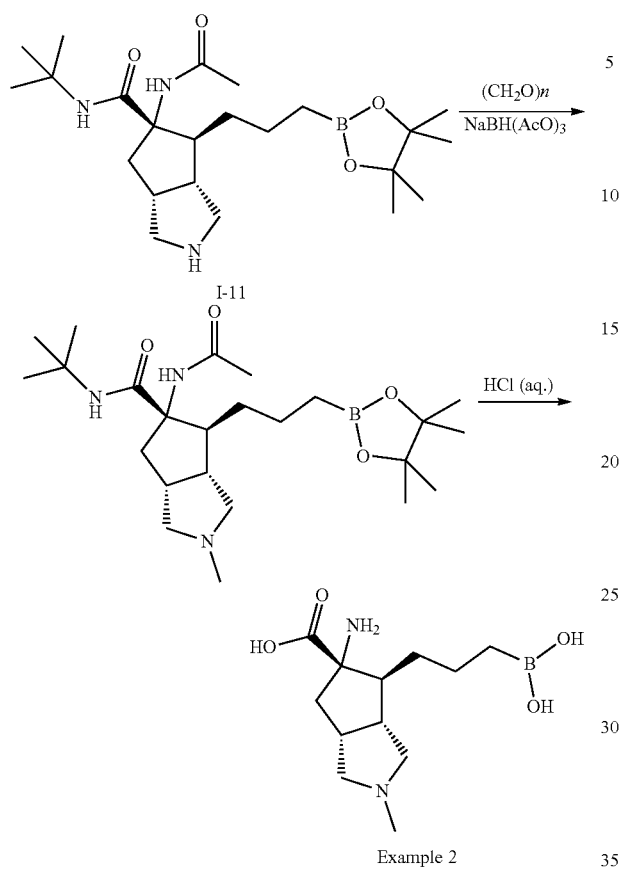

Example 2

Step 1: (3aR,4S,5S,6aR)-5-acetamido-N-(tert-butyl)-2-methyl-4-(3-(4,4,5,5-tetramethyl-1,3,2-dioxaborolan-2-yl)propyl)octahydrocyclopenta[c]pyrrole-5-carboxamide Sodium triacetoxyborohydride (608 mg, 2.9 mmol) was added to a mixture of (3aR,4S,5S,6aR)-5-acetamido-N-(tert-butyl)-4-(3-(4,4,5,5-tetramethyl-1,3,2-dioxaborolan-2-yl)propyl)octahydrocyclopenta[c]pyrrole-5-carboxamide (500 mg, 1.1 mmol) and paraformaldehyde (500 mg, 5.6 mmol) in DCE (10 mL) at 20° C. The reaction was stirred at 70° C. for 12 h. MeOH (10 mL) was added to the reaction mixture and then the mixture was concentrated under reduced pressure. The residue was purified by RP-HPLC [C18 column, water (0.1% TFA)-CH$_3$CN] to give (3aR,4S,5S,6aR)-5-acetamido-N-(tert-butyl)-2-methyl-4-(3-(4,4,5,5-tetramethyl-1,3,2-dioxaborolan-2-yl)propyl)octahydrocyclopenta[c]pyrrole-5-carboxamide, which contained some boronic acid. LCMS (C$_{24}$H$_{45}$BN$_3$O$_4{}^+$) (ES, m/z): 450 [M+H]$^+$.

Step 2: (3aR,4S,5S,6aR)-5-amino-4-(3-boronopropyl)-2-methyloctahydrocyclopenta[c]pyrrole-5-carboxylic acid A mixture of 5-acetamido-N-(tert-butyl)-2-methyl-4-(3-(4,4,5,5-tetramethyl-1,3,2-dioxaborolan-2-yl)propyl)octahydrocyclopenta[c]pyrrole-5-carboxamide (140 mg, 0.31 mmol) in 12N HCl in water (3 mL) was stirred at 100° C. for 12 h. The mixture was concentrated under reduced pressure. The residue was purified by RP-HPLC [C18 column, water (0.1% TFA)-CH$_3$CN] to give (3aR,4S,5S,6aR)-5-amino-4-(3-boronopropyl)-2-methyloctahydrocyclopenta[c]pyrrole-5-carboxylic acid as a TFA salt. LCMS (C$_{12}$H$_{22}$BN$_2$O$_3{}^+$) (ES, m/z): 253 [M+H-H$_2$O]. $^1$HNMR (400 MHz, Deuterium Oxide) δ 3.96-3.75 (m, 1H), 3.55-3.37 (m, 2H), 3.32-3.12 (m, 2H), 3.03-2.92 (m, 1H), 2.85 (br d, J=4.6 Hz, 3H), 2.68-2.50 (m, 1H), 2.25-1.96 (m, 1H), 1.91-1.69 (m, 1H), 1.53 (br d, J=10.8 Hz, 1H), 1.41-1.13 (m, 3H), 0.69 (br d, J=6.2 Hz, 2H).

Example 3: (3aR,4S,5S,6aR)-5-amino-4-(3-boronopropyl)-2-(4-fluorobenzyl)octahydrocyclopenta[c]pyrrole-5-carboxylic acid

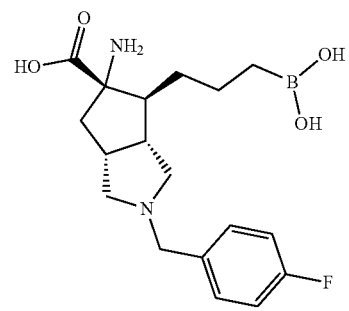 [SMILES: N[C@@]1(C(=O)O)C[C@H]2CN(Cc3ccc(F)cc3)C[C@H]2[C@@H]1CCCB(O)O]

Example 3 was prepared as a HCl salt by using the general procedure used for Example 2. LCMS (C$_{18}$H$_{25}$BFN$_2$O$_3{}^+$) (ES, m/z): 347 [M+H-H$_2$O]$^+$. $^1$HNMR (400 MHz, Deuterium Oxide) δ 7.54-7.39 (m, 2H), 7.23-7.07 (m, 2H), 4.43-4.26 (m, 2H), 3.91-3.65 (m, 1H), 3.49-3.26 (m, 2H), 3.24-2.93 (m, 2H), 2.87-2.73 (m, 1H), 2.60 (br dd, J=8.6, 13.5 Hz, 1H), 2.31-2.06 (m, 1H), 1.98-1.72 (m, 1H), 1.64-1.45 (m, 1H), 1.40-1.10 (m, 3H), 0.69 (br d, J=5.3 Hz, 2H).

Example 4: (3aR,4S,5S,6aR)-2-(L-alanyl)-5-amino-4-(3-boronopropyl)octahydrocyclopenta[c]pyrrole-5-carboxylic acid

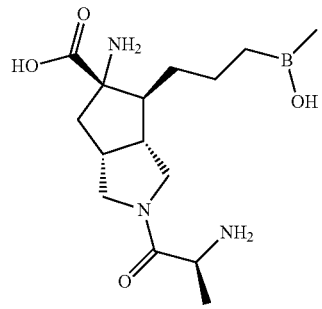 [SMILES: CB(O)CCC[C@H]1[C@@H]2CN(C(=O)[C@H](C)N)C[C@@H]2C[C@@]1(N)C(=O)O]

Scheme K

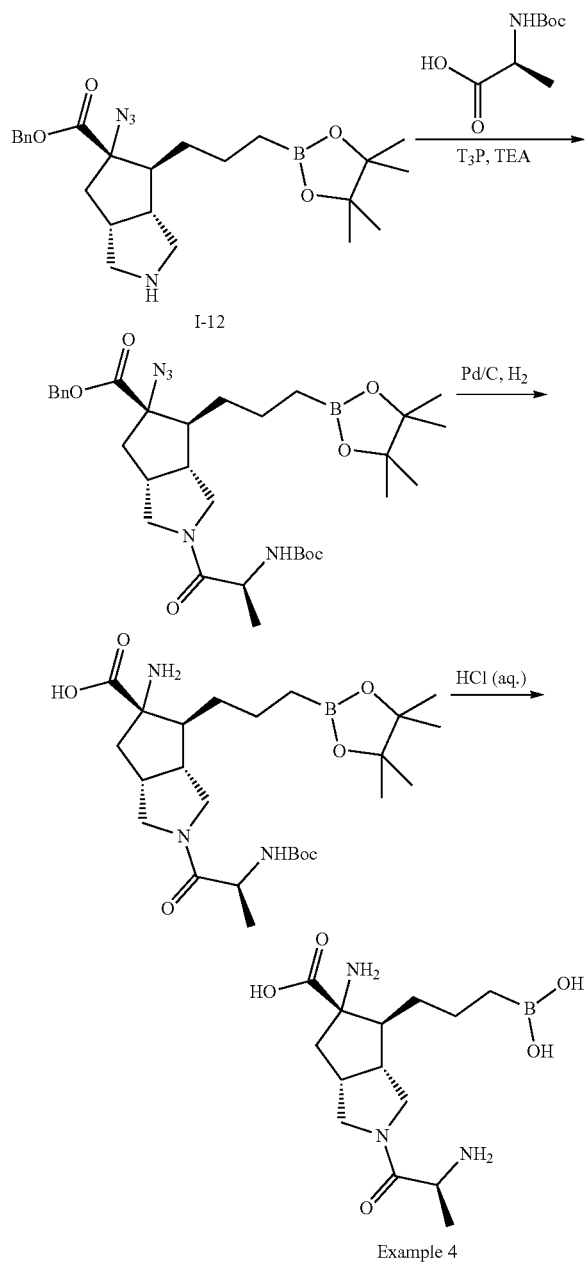

Example 4

Step 1: benzyl (3aR,4S,5S,6aR)-5-azido-2-((tert-butoxycarbonyl)-L-alanyl)-4-(3-(4,4,5,5-tetramethyl-1,3,2-dioxaborolan-2-yl)propyl)octahydrocyclopenta[c]pyrrole-5-carboxylate TEA (0.26 mL, 1.8 mmol) was added to a solution of benzyl (3aR,4S,5S,6aR)-5-azido-4-(3-(4,4,5,5-tetramethyl-1,3,2-dioxaborolan-2-yl)propyl)octahydrocyclopenta[c]pyrrole-5-carboxylate (180 mg, 0.37 mmol) and (S)-2-((tert-butoxycarbonyl)amino)propanoic acid (139 mg, 0.73 mmol) in anhydrous DMF (3.0 mL) at 25° C. The mixture was stirred at 25° C. for 2 min, and then 1.6 M Propylphosphonic anhydride ($T_3P$) in DMF (0.46 mL, 0.73 mmol) was added into the mixture. The mixture was stirred at 25° C. for 12 h. The reaction was poured into 1N NaCl in water and extracted with EtOAc. The separated organic layers were dried over anhydrous $Na_2SO_4$, filtered and concentrated in vacuo. The residue was purified by RP-HPLC [C18 column, water (0.1% TFA)-$CH_3CN$] to give benzyl (3aR,4S,5S,6aR)-5-azido-2-((tert-butoxycarbonyl)-L-alanyl)-4-(3-(4,4,5,5-tetramethyl-1,3,2-dioxaborolan-2-yl)propyl)octahydrocyclopenta[c]pyrrole-5-carboxylate. LCMS ($C_{32}H_{49}BN_5O_7^+$) (ES, m/z): 626 [M+H]$^+$. The product contained the corresponding boronic acid, (3-((3aR,4S,5S,6aR)-5-azido-5-((benzyloxy)carbonyl)-2-((tert-butoxycarbonyl)-L-alanyl)octahydrocyclopenta[c]pyrrol-4-yl)propyl)boronic acid. LCMS ($C_{26}H_{39}BN_5O_7^+$) (ES, m/z): 544 [M+H]$^+$. The resulting mixture was directly used in the next step.

Step 2: (3aR,4S,5S,6aR)-5-amino-2-((tert-butoxycarbonyl)-L-alanyl)-4-(3-(4,4,5,5-tetramethyl-1,3,2-dioxaborolan-2-yl)propyl)octahydrocyclopenta[c]pyrrole-5-carboxylic acid 10% Pd/C (30 mg, 0.030 mmol) was added to a solution of the product from Step 1 (174 mg) in MeOH (6.0 mL) under $N_2$ atmosphere. The mixture was degassed and backfilled with $H_2$ (three times). The resulting mixture was stirred under $H_2$ (15 psi) at 25° C. for 1 h. The mixture was filtered, and the filtrate was concentrated under reduced pressure to give (3aR,4S,5S,6aR)-5-amino-2-((tert-butoxycarbonyl)-L-alanyl)-4-(3-(4,4,5,5-tetramethyl-1,3,2-dioxaborolan-2-yl)propyl)octahydrocyclopenta[c]pyrrole-5-carboxylic acid LCMS ($C_{20}H_{37}BN_3O_5^+$) (ES, m/z): 410 [M+H-Boc]$^+$. The product contained the corresponding boronic acid. The resulting mixture was directly used in the next step.

Step 3: (3aR,4S,5S,6aR)-2-(L-alanyl)-5-amino-4-(3-boronopropyl)octahydrocyclopenta[c]pyrrole-5-carboxylic acid A mixture of the product from Step 2 (135 mg) in 6N HCl in water (4.0 mL, 24 mmol) was stirred at 20° C. for 13 h. The reaction was concentrated in vacuo and the residue was purified by RP-HPLC [C18 column, water (0.1% TFA)-$CH_3CN$] to give (3aR,4S,5S,6aR)-2-(L-alanyl)-5-amino-4-(3-boronopropyl)octahydrocyclopenta[c]pyrrole-5-carboxylic acid as a TFA salt. LCMS ($C_{14}H_{25}BN_3O_4^+$) (ES, m/z): 310 [M+H-$H_2O$]$^+$. $^1$H NMR (400 MHz, Deuterium Oxide) δ 4.34-4.18 (m, 1H), 3.80-3.58 (m, 2H), 3.53-3.30 (m, 2H), 3.24-3.04 (m, 1H), 2.87-2.66 (m, 1H), 2.61 (ddd, J=4.2, 8.7, 13.5 Hz, 1H), 2.05-1.88 (m, 1H), 1.70 (br dd, J=8.6, 12.1 Hz, 1H), 1.49 (br dd, J=4.0, 11.0 Hz, 1H), 1.43-1.37 (m, 4H), 1.36-1.22 (m, 2H), 0.79-0.63 (m, 2H).

Example 5: (3aR,4S,5S,6aR)-5-amino-4-(3-borono-propyl)-2-glycyloctahydrocyclopenta[c]pyrrole-5-carboxylic acid

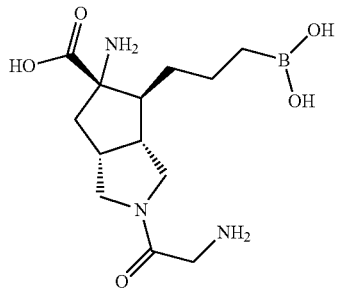 [SMILES: NCC(=O)N1C[C@@H]2C[C@@](N)(C(=O)O)[C@@H](CCCB(O)O)[C@@H]2C1]

Example 5 was prepared by using the general procedure used for Example 4 as a HCl salt. LCMS ($C_{13}H_{23}BN_3O_4^+$) (ES, m/z): 296 [M+H-H$_2$O]$^+$. $^1$H NMR (400 MHz, Deuterium Oxide) δ 4.00-3.81 (m, 2H), 3.76-3.57 (m, 1H), 3.76-3.56 (m, 2H), 3.50-3.33 (m, 1H), 3.29-3.09 (m, 1H), 2.90-2.73 (m, 1H), 2.67 (dd, J=8.3, 13.6 Hz, 1H), 2.14-1.97 (m, 1H), 1.78 (td, J=9.0, 13.6 Hz, 1H), 1.61-1.26 (m, 4H), 0.82-0.68 (m, 2H).

Example 6: 5-amino-2-((S)-2-amino-3-hydroxypropanoyl)-4-(3-boronopropyl)octahydrocyclopenta[c]pyrrole-5-carboxylic acid Scheme L

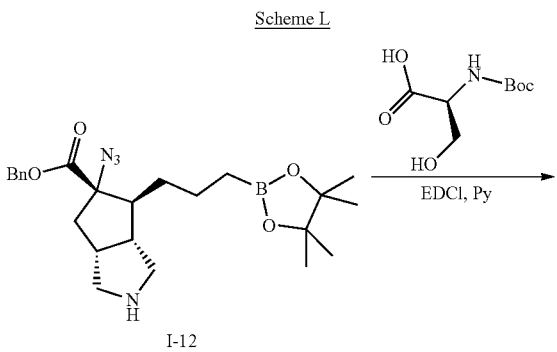

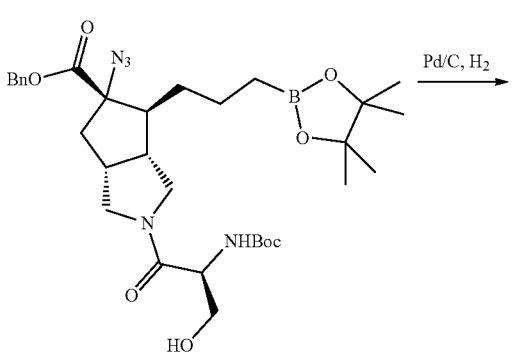

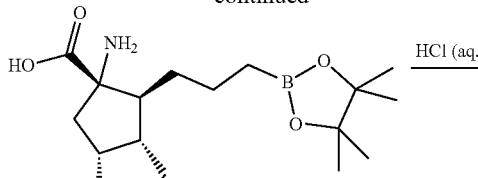

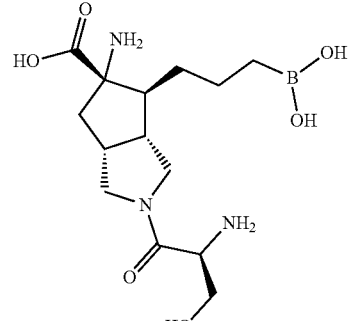

Example 6

Step 1: benzyl (3aR,4S,5S,6aR)-5-azido-2-((tert-butoxycarbonyl)-L-seryl)-4-(3-(4,4,5,5-tetramethyl-1,3,2-dioxaborolan-2-yl)propyl)octahydrocyclopenta[c]pyrrole-5-carboxylate EDCI (190 mg, 0.98 mmol) was added to a solution of benzyl (3aR,4S,5S,6aR)-5-azido-4-(3-(4,4,5,5-tetramethyl-1,3,2-dioxaborolan-2-yl)propyl)octahydrocyclopenta[c]pyrrole-5-carboxylate hydrochloride (120 mg, 0.24 mmol) and (S)-2-((tert-butoxycarbonyl)amino)-3-hydroxypropanoic acid (150 mg, 0.73 mmol) in pyridine (2 mL) at 0° C. The resulting mixture was stirred at 20° C. for 1 h. The reaction was concentrated under reduced pressure and the resulting residue was purified by RP-HPLC [C18 column, water (0.1% TFA)-CH$_3$CN] to give benzyl (3aR,4S,5S,6aR)-5-azido-2-((tert-butoxycarbonyl)-L-seryl)-4-(3-(4,4,5,5-tetramethyl-1,3,2-dioxaborolan-2-yl)propyl)octahydrocyclopenta[c]pyrrole-5-carboxylate. LCMS ($C_{32}H_{49}BN_5O_8^+$) (ES, m/z): 642 [M+H]$^+$. The product contained the corresponding boronic acid. The resulting mixture was directly used in the next step.

Step 2: (3aR,4S,5S,6aR)-5-amino-2-((tert-butoxycarbonyl)-L-seryl)-4-(3-(4,4,5,5-tetramethyl-1,3,2-dioxaborolan-2-yl)propyl)octahydrocyclopenta[c]pyrrole-5-carboxylic acid 10% Pd/C (14 mg, 0.014 mmol) was added to a solution of the product from Step 1 (85 mg) in MeOH (2 mL) under N$_2$ atmosphere. The mixture was degassed and backfilled with H$_2$ (three times). The resulting mixture was stirred under H$_2$ (15 psi) at 20° C. for 1 h. The catalyst was filtered off and the filtrate was concentrated under reduced pressure to give (3aR,4S,5S,6aR)-5-amino-2-((tert-butoxycarbonyl)-L-seryl)-4-(3-(4,4,5,5-tetramethyl-1,3,2-dioxaborolan-2-yl)propyl)octahydrocyclopenta[c]pyrrole-5-carboxylic acid.

LCMS ($C_{25}H_{45}BN_3O_8^+$) (ES, m/z): 526 [M+H]$^+$. The product contained the corresponding boronic acid. The resulting mixture was directly used in the next step.

Step 3: (3aR,4S,5S,6aR)-2-(L-seryl)-5-amino-4-(3-boronopropyl)octahydrocyclopenta[c]pyrrole-5-carboxylic acid A mixture of the product from Step 2 (85 mg) in 12N HCl in water (2 mL, 24 mmol) was stirred at 20° C. for 1 h. The mixture was concentrated under reduced pressure and the resulting residue was purified by RP-HPLC [C18 column, water (0.05% HCl)—CH$_3$CN] to give (3aR,4S,5S,6aR)-2-(L-seryl)-5-amino-4-(3-boronopropyl)octahydrocyclopenta[c]pyrrole-5-carboxylic acid as the HCl salt. LCMS ($C_{14}H_{25}BN_3O_5^+$) (ES, m/z): 326 [M+H-H$_2$O]$^+$. $^1$H NMR (400 MHz, Deuterium Oxide) δ 4.47-4.32 (m, 1H), 3.98-3.73 (m, 3H), 3.72-3.65 (m, 1H), 3.59-3.37 (m, 2H), 3.29-3.07 (m, 1H), 2.90-2.69 (m, 1H), 2.69-2.59 (m, 1H), 2.09-1.92 (m, 1H), 1.75 (br dd, J=13.2, 8.8 Hz, 1H), 1.57-1.42 (m, 2H), 1.33 (br s, 2H), 0.82-0.68 (m, 2H).

Example 7: (3aR,4S,5S,6aR)-2-acetyl-5-amino-4-(3-boronopropyl)octahydrocyclopenta[c]pyrrole-5-carboxylic acid

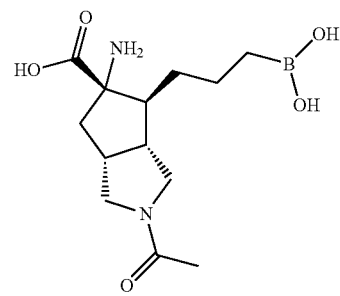 [SMILES: CC(=O)N1C[C@@H]2C[C@@](N)(C(=O)O)[C@@H](CCCB(O)O)[C@@H]2C1]

Scheme M

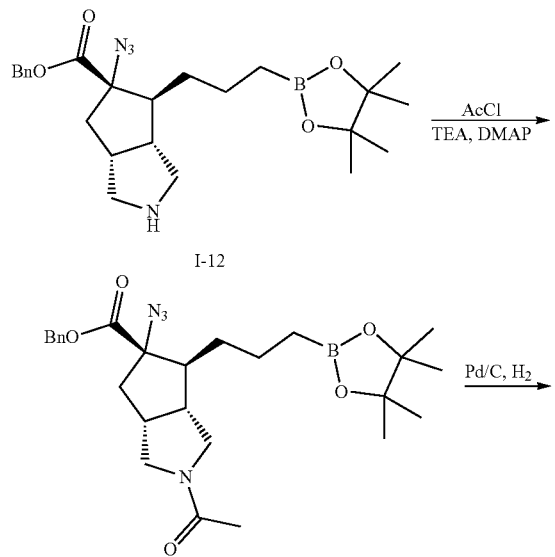

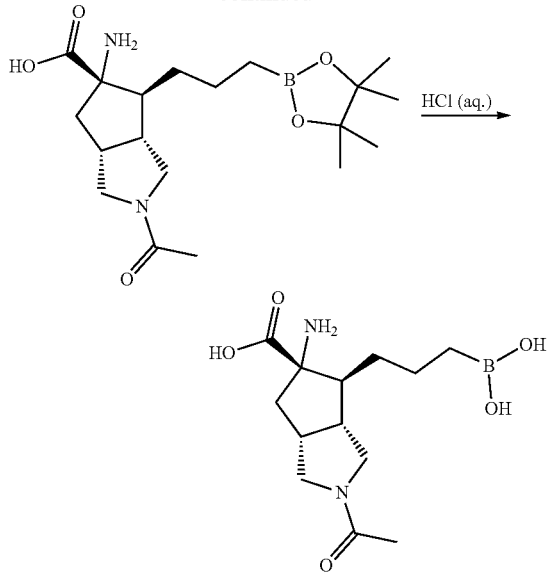

Example 7

Step 1: benzyl (3aR,4S,5S,6aR)-2-acetyl-5-azido-4-(3-(4,4,5,5-tetramethyl-1,3,2-dioxaborolan-2-yl)propyl)octahydrocyclopenta[c]pyrrole-5-carboxylate Acetyl chloride (0.056 mL, 0.79 mmol) was added to the mixture of benzyl (3aR,4S,5S,6aR)-5-azido-4-(3-(4,4,5,5-tetramethyl-1,3,2-dioxaborolan-2-yl)propyl)octahydrocyclopenta[c]pyrrole-5-carboxylate hydrochloride (130 mg, 0.26 mmol), TEA (0.1 mL, 0.79 mmol) and DMAP (3 mg, 0.026 mmol) in DCM (2 mL) at 0° C. The mixture was allowed to reach to 20° C. and stirred for 1 h. The mixture was concentrated under reduced pressure to give crude benzyl (3aR,4S,5S,6aR)-2-acetyl-5-azido-4-(3-(4,4,5,5-tetramethyl-1,3,2-dioxaborolan-2-yl)propyl)octahydrocyclopenta[c]pyrrole-5-carboxylate, which was used in the next step directly. LCMS ($C_{26}H_{38}BN_4O_5^+$) (ES, m/z): 497 [M+H]$^+$.

Step 2: (3aR,4S,5S,6aR)-2-acetyl-5-amino-4-(3-(4,4,5,5-tetramethyl-1,3,2-dioxaborolan-2-yl)propyl)octahydrocyclopenta[c]pyrrole-5-carboxylic acid 10% Pd/C (27 mg, 0.024 mmol) was added to a solution of benzyl (3aR,4S,5S,6aR)-2-acetyl-5-azido-4-(3-(4,4,5,5-tetramethyl-1,3,2-dioxaborolan-2-yl)propyl)octahydrocyclopenta[c]pyrrole-5-carboxylate (120 mg, 0.24 mmol) in MeOH (2 mL) under N$_2$ atmosphere. The mixture was degassed and backfilled with H$_2$ (three times). The resulting mixture was stirred under H$_2$ (15 psi) at 20° C. for 1 h. The catalyst was filtered off and the filtrate was concentrated under reduced pressure. The resulting residue was purified by RP-IPLC [C18 column, water (0.1% TFA)-CH$_3$CN] to give (3aR,4S,5S,6aR)-2-acetyl-5-amino-4-(3-(4,4,5,5-tetramethyl-1,3,2-dioxaborolan-2-yl)propyl)octahydrocyclopenta[c]pyrrole-5-carboxylic acid. LCMS ($C_{19}H_{34}BN_2O_5^+$) (ES, m/z): 381 [M+H]$^+$.

Step 3: (3aR,4S,5S,6aR)-2-acetyl-5-amino-4-(3-boronopropyl)octahydrocyclopenta[c]pyrrole-5-carboxylic acid A mixture of (3aR,4S,5S,6aR)-2-acetyl-5-amino-4-(3-(4,4,5,5-tetramethyl-1,3,2-dioxaborolan-2-yl)propyl)octahydrocyclopenta[c]pyrrole-5-carboxylic acid (25 mg, 0.066 mmol) in 12N HCl in water (2 mL, 24 mmol) was stirred at 20° C. for 1 h. The mixture was concentrated under reduced pressure and the resulting residue was purified by RP-HPLC [C18 column, water (0.05% HCl)—CH$_3$CN] to give (3aR, 4S,5S,6aR)-2-acetyl-5-amino-4-(3-boronopropyl)octahydrocyclopenta[c]pyrrole-5-carboxylic acid as the HCl salt. LCMS (C$_{13}$H$_{22}$BN$_2$O$_4^+$) (ES, m/z): 281 [M+H-H$_2$O]$^+$. $^1$HNMR (400 MHz, Deuterium Oxide) δ 3.73-3.54 (m, 1H), 3.51-3.29 (m, 3H), 3.16-2.92 (m, 1H), 2.75-2.49 (m, 2H), 2.03-1.92 (m, 4H), 1.71-1.57 (m, 1H), 1.50-1.34 (m, 2H), 1.33-1.20 (m, 2H), 0.68 (br t, J=6.4 Hz, 2H).

Example 8: (3aR,4S,5S,6aR)-5-amino-4-(3-boronopropyl)-2-isopropyloctahydrocyclopenta[c]pyrrole-5-carboxylic acid

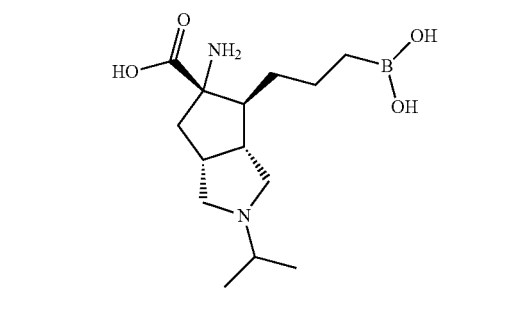 [SMILES: CC(C)N1C[C@@H]2C[C@@](N)(C(=O)O)[C@@H](CCCB(O)O)[C@@H]2C1]

Scheme N

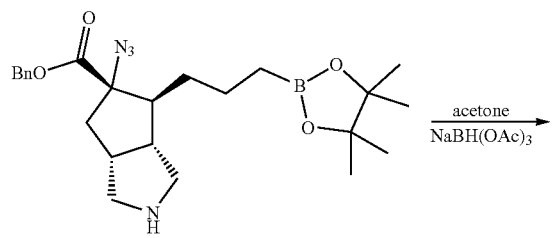

I-12

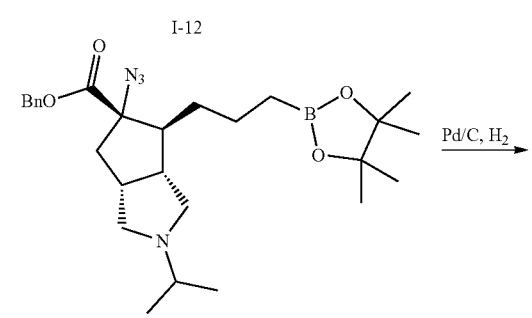

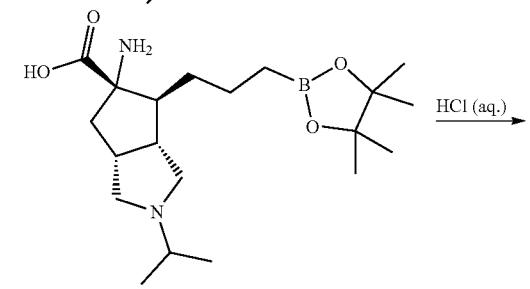

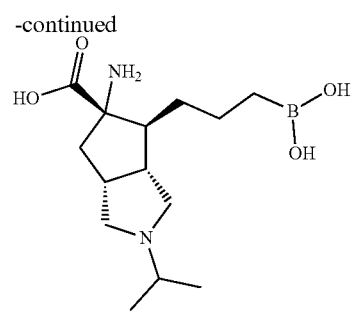

Example 8

Step 1: benzyl (3aR,4S,5S,6aR)-5-azido-2-isopropyl-4-(3-(4,4,5,5-tetramethyl-1,3,2-dioxaborolan-2-yl)propyl)octahydrocyclopenta[c]pyrrole-5-carboxylate Sodium triacetoxyborohydride (NaBH(OAc)$_3$, 100 mg, 0.49 mmol) was added to a solution of benzyl (3aR,4S,5S, 6aR)-5-azido-4-(3-(4,4,5,5-tetramethyl-1,3,2-dioxaborolan-2-yl)propyl)octahydrocyclopenta[c]pyrrole-5-carboxylate hydrochloride (120 mg, 0.24 mmol) and acetone (43 mg, 0.73 mmol) in DCE (2 mL) at 25° C. The mixture was stirred at 25° C. for 12 h under N$_2$. The reaction mixture was poured into water and extracted with DCM. The combined organic layers were washed with brine, dried over anhydrous Na$_2$SO$_4$, filtered and concentrated. The resulting residue was purified by RP-HPLC [C18 column, water (0.1% TFA)-CH$_3$CN] to give benzyl (3aR,4S,5S,6aR)-5-azido-2-isopropyl-4-(3-(4,4,5,5-tetramethyl-1,3,2-dioxaborolan-2-yl)propyl)octahydrocyclopenta[c]pyrrole-5-carboxylate. LCMS (C$_{27}$H$_{42}$BN$_4$O$_4^+$) (ES, m/z): 497 [M+H]$^+$.

Step 2: (3aR,4S,5S,6aR)-5-amino-2-isopropyl-4-(3-(4,4,5,5-tetramethyl-1,3,2-dioxaborolan-2-yl)propyl)octahydrocyclopenta[c]pyrrole-5-carboxylic acid 10% Pd/C (25 mg, 0.023 mmol) was added to a solution of benzyl (3aR,4S,5S,6aR)-5-azido-2-isopropyl-4-(3-(4,4,5,5-tetramethyl-1,3,2-dioxaborolan-2-yl)propyl)octahydrocyclopenta[c]pyrrole-5-carboxylate (90 mg, 0.18 mmol) in MeOH (6 mL) under N$_2$ atmosphere. The mixture was degassed and backfilled with H$_2$ (three times). The resulting mixture was stirred under H$_2$ (15 psi) at 25° C. for 1 h. The catalyst was filtered off and the filtrate was concentrated to give crude (3aR,4S,5S,6aR)-5-amino-2-isopropyl-4-(3-(4,4, 5,5-tetramethyl-1,3,2-dioxaborolan-2-yl)propyl)octahydrocyclopenta[c]pyrrole-5-carboxylic acid, which was used in next step directly. LCMS (C$_{20}$H$_{38}$BN$_2$O$_4^+$) (ES, m/z): 381 [M+H]$^+$.

Step 3: (3aR,4S,5S,6aR)-5-amino-4-(3-boronopropyl)-2-isopropyloctahydrocyclopenta[c]pyrrole-5-carboxylic acid A mixture of (3aR,4S,5S,6aR)-5-amino-2-isopropyl-4-(3-(4,4,5,5-tetramethyl-1,3,2-dioxaborolan-2-yl)propyl)octahydrocyclopenta[c]pyrrole-5-carboxylic acid (60 mg, 0.088 mmol) in 6N HCl in water (4 mL, 24 mmol) was stirred at 20° C. for 13 h. The reaction was concentrated under reduced pressure. The resulting residue was purified by RP-HPLC [C18 column, water (0.1% TFA)-CH$_3$CN] to afford (3aR,4S,5S,6aR)-5-amino-4-(3-boronopropyl)-2-isopropyloctahydrocyclopenta[c]pyrrole-5-carboxylic acid as the TFA salt. LCMS ($C_{14}H_{26}BN_2O_3^+$) (ES, m/z): 281 [M+H-H$_2$O]$^+$. $^1$H NMR (400 MHz, Deuterium Oxide) δ 3.91-3.72 (m, 1H), 3.52-3.36 (m, 1H), 3.36-3.27 (m, 1H), 3.27-3.18 (m, 1H), 3.16-3.05 (m, 1H), 2.92-2.66 (m, 2H), 2.51 (dt, J=8.8, 13.2 Hz, 1H), 2.13-1.85 (m, 1H), 1.85-1.59 (m, 2H), 1.51-1.39 (m, 1H), 1.25-1.16 (m, 8H), 0.70-0.57 (m, 2H).

Example 9: (3aR,4S,5S,6aR)-5-amino-2-(2-aminoethyl)-4-(3-boronopropyl)octahydrocyclopenta[c]pyrrole-5-carboxylic acid

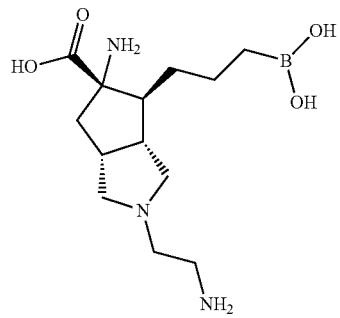 [SMILES: NCCN1C[C@@H]2C[C@@](N)(C(=O)O)[C@@H](CCCB(O)O)[C@@H]2C1]

Example 9 was prepared by using the general procedure outlined above for Example 8 by using tert-butyl (2-oxoethyl)carbamate as the starting material and isolated as the TFA salt. LCMS ($C_{13}H_{25}BN_3O_3^+$) (ES, m/z): 282 [M+H-H$_2$O]$^+$. $^1$H NMR (400 MHz, Deuterium Oxide) δ 3.63-3.52 (m, 3H), 3.48-3.26 (m, 5H), 3.06-2.89 (m, 1H), 2.70-2.55 (m, 1H), 2.14 (br s, 1H), 1.85 (br dd, J=9.5, 13.2 Hz, 1H), 1.63-1.50 (m, 1H), 1.38 (br d, J=7.3 Hz, 1H), 1.35-1.17 (m, 3H), 0.83-0.69 (m, 2H).

Example 10: (3aR,4S,5S,6aR)-5-amino-4-(3-boronopropyl)-2-(2,2,2-trifluoroethyl)octahydrocyclopenta[c]pyrrole-5-carboxylic acid

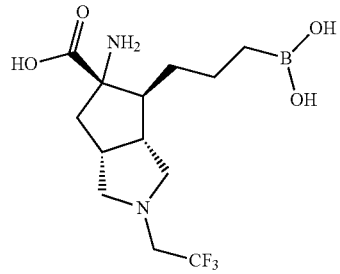 [SMILES: N[C@@]1(C(=O)O)C[C@H]2CN(CC(F)(F)F)C[C@H]2[C@@H]1CCCB(O)O]

Scheme O

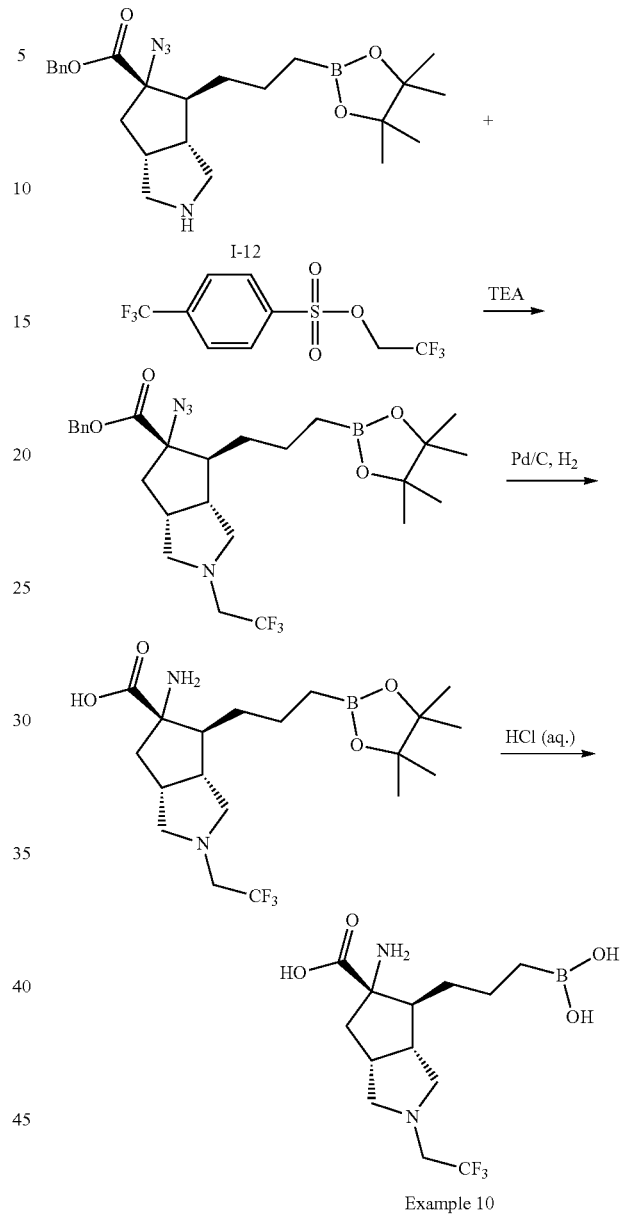

Example 10

Step 1: benzyl (3aR,4S,5S,6aR)-5-azido-4-(3-(4,4,5,5-tetramethyl-1,3,2-dioxaborolan-2-yl)propyl)-2-(2,2,2-trifluoroethyl)octahydrocyclopenta[c]pyrrole-5-carboxylate 2,2,2-trifluoroethyl 4-(trifluoromethyl)benzenesulfonate (280 mg, 0.92 mmol) was added to a solution of benzyl (3aR,4S,5S,6aR)-5-azido-4-(3-(4,4,5,5-tetramethyl-1,3,2-dioxaborolan-2-yl)propyl)octahydrocyclopenta[c]pyrrole-5-carboxylate hydrochloride (150 mg, 0.31 mmol) and TEA (0.21 mL, 1.5 mmol) in DMA (2 mL) at 15° C. The mixture was stirred at 115° C. for 12 h under N$_2$. The reaction was concentrated under reduced pressure affording crude product. The material was purified by RP-HPLC [C18 column, water (0.1% TFA)-CH$_3$CN] to give benzyl (3aR,4S,5S,6aR)-5-azido-4-(3-(4,4,5,5-tetramethyl-1,3,2-dioxaborolan- 2-yl)propyl)-2-(2,2,2-trifluoroethyl)octahydrocyclopenta[c]pyrrole-5-carboxylate. LCMS ($C_{26}H_{37}BF_3N_4O_4^+$) (ES, m/z): 537 [M+H]$^+$.

Step 2: (3aR,4S,5S,6aR)-5-amino-4-(3-(4,4,5,5-tetramethyl-1,3,2-dioxaborolan-2-yl)propyl)-2-(2,2,2-trifluoroethyl)octahydrocyclopenta[c]pyrrole-5-carboxylic acid 10% Pd/C (15 mg, 0.014 mmol) was added to a solution of benzyl (3aR,4S,5S,6aR)-5-azido-4-(3-(4,4,5,5-tetramethyl-1,3,2-dioxaborolan-2-yl)propyl)-2-(2,2,2-trifluoroethyl)octahydrocyclopenta[c]pyrrole-5-carboxylate (90 mg, 0.17 mmol) in MeOH (6 mL) under $N_2$ atmosphere. The mixture was degassed and backfilled with $H_2$ (three times). The resulting mixture was stirred under $H_2$ (15 psi) at 25° C. for 0.5 h. The catalyst was filtered off and filtrate was concentrated under reduced pressure to give crude (3aR,4S,5S,6aR)-5-amino-4-(3-(4,4,5,5-tetramethyl-1,3,2-dioxaborolan-2-yl)propyl)-2-(2,2,2-trifluoroethyl)octahydrocyclopenta[c]pyrrole-5-carboxylic acid, which was used in the next step directly. LCMS ($C_{19}H_{33}BF_3N_2O_4^+$) (ES, m/z): 421 [M+H]$^+$.

Step 3: (3aR,4S,5S,6aR)-5-amino-4-(3-boronopropyl)-2-(2,2,2-trifluoroethyl)octahydrocyclopenta[c]pyrrole-5-carboxylic acid A mixture of (3aR,4S,5S,6aR)-5-amino-4-(3-(4,4,5,5-tetramethyl-1,3,2-dioxaborolan-2-yl)propyl)-2-(2,2,2-trifluoroethyl)octahydrocyclopenta[c]pyrrole-5-carboxylic acid (60 mg, 0.14 mmol) and 6N HCl in water (4 mL, 24 mmol) was stirred at 20° C. for 13 h. The reaction was concentrated under reduced pressure. The resulting crude product was purified by RP-HPLC [C18 column, water (0.1% TFA)-$CH_3CN$] to give (3aR,4S,5S,6aR)-5-amino-4-(3-boronopropyl)-2-(2,2,2-trifluoroethyl)octahydrocyclopenta[c]pyrrole-5-carboxylic acid as the TFA salt. LCMS ($C_{13}H_{21}BF_3N_2O_3^+$) (ES, m/z): 321 [M+H-$H_2O$]$^+$. $^1$H NMR (400 MHz, Deuterium Oxide) δ 4.16 (q, J=8.5 Hz, 2H), 4.02-3.92 (m, 1H), 3.91-3.80 (m, 1H), 3.41-3.24 (m, 3H), 3.02-2.89 (m, 1H), 2.67-2.57 (m, 1H), 2.23-2.12 (m, 1H), 1.92-1.80 (m, 1H), 1.60-1.49 (m, 1H), 1.44-1.32 (m, 1H), 1.31-1.18 (m, 2H), 0.80-0.67 (m, 2H).

Examples 11a and 11b: (3aR,4S,5S,6aR)-5-amino-4-(3-boronopropyl)-2-carbamimidoyloctahydrocyclopenta[c]pyrrole-5-carboxylic acid

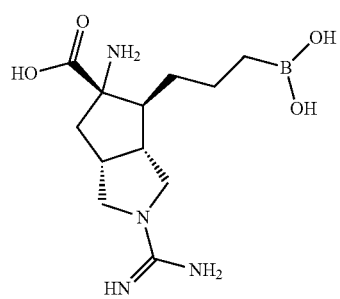

Examples 11a and 11b

Scheme P

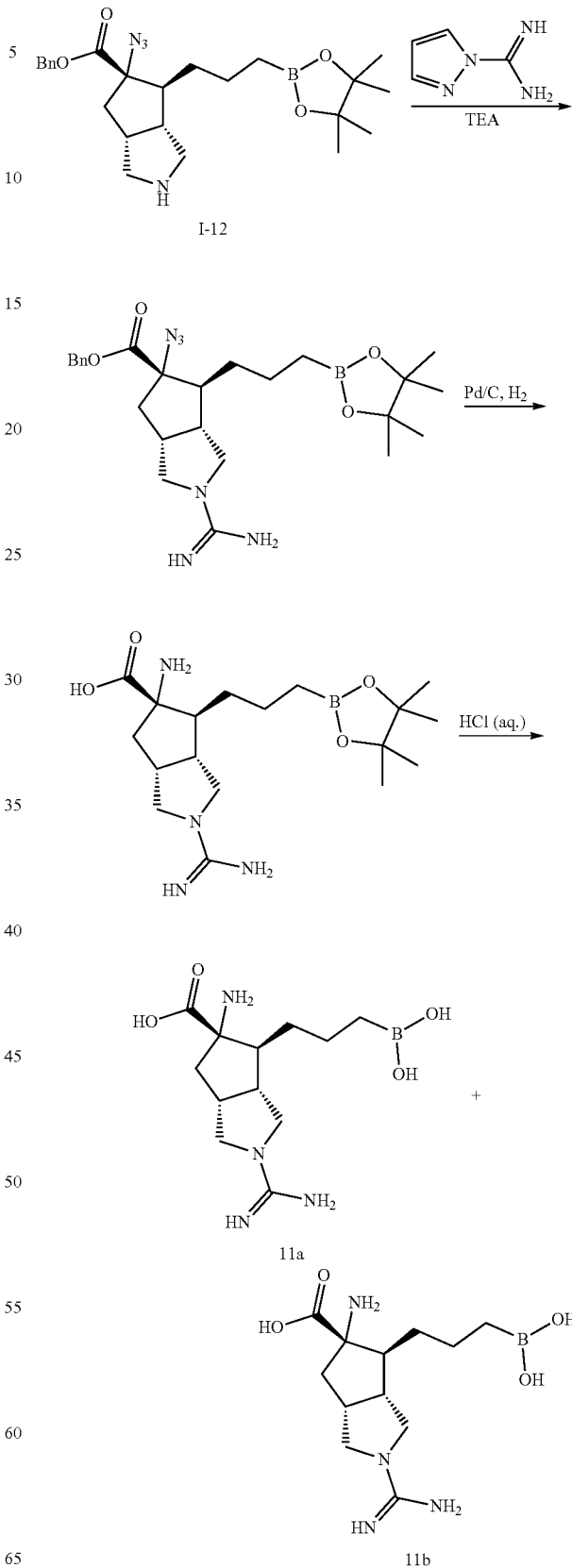

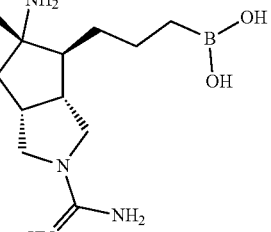

11b

Example 11: 5-amino-4-(3-boronopropyl)-2-carbamimidoyloctahydrocyclopenta[c]pyrrole-5-carboxylic acid

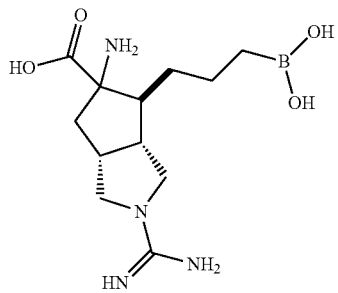 [SMILES: N=C(N)N1C[C@@H]2CC(N)(C(=O)O)[C@@H](CCCB(O)O)[C@@H]2C1]

Step 1: benzyl (3aR,4S,5S,6aR)-5-azido-2-carbamimidoyl-4-(3-(4,4,5,5-tetramethyl-1,3,2-dioxaborolan-2-yl)propyl)octahydrocyclopenta[c]pyrrole-5-carboxylate 1H-pyrazole-1-carboximidamide hydrochloride (54 mg, 0.37 mmol) was added to a mixture of TEA (0.13 mL, 0.92 mmol) and benzyl (3aR,4S,5S,6aR)-5-azido-4-(3-(4,4,5,5-tetramethyl-1,3,2-dioxaborolan-2-yl)propyl)octahydrocyclopenta[c]pyrrole-5-carboxylate hydrochloride (150 mg, 0.31 mmol) in acetonitrile (2 mL) at 25° C. The resulting mixture was stirred at 60° C. for 13 h. The reaction was purified by RP-HPLC [C18 column, water (0.1% TFA)-CH$_3$CN] to give benzyl (3aR,4S,5S,6aR)-5-azido-2-carbamimidoyl-4-(3-(4,4,5,5-tetramethyl-1,3,2-dioxaborolan-2-yl)propyl)octahydrocyclopenta[c]pyrrole-5-carboxylate. LCMS (C$_{25}$H$_{38}$BN$_6$O$_4^+$) (ES, m/z): 497 [M+H]$^+$.

Step 2: (3aR,4S,5S,6aR)-5-amino-2-carbamimidoyl-4-(3-(4,4,5,5-tetramethyl-1,3,2-dioxaborolan-2-yl)propyl)octahydrocyclopenta[c]pyrrole-5-carboxylic acid 10% Pd/C (30 mg, 0.028 mmol) was added to a solution of benzyl 5-azido-2-carbamimidoyl-4-(3-(4,4,5,5-tetramethyl-1,3,2-dioxaborolan-2-yl)propyl)octahydrocyclopenta[c]pyrrole-5-carboxylate (90 mg, 0.18 mmol) in MeOH (3 mL) and THF (3 mL) under N$_2$ atmosphere. The mixture was degassed and backfilled with H$_2$ (three times). The resulting mixture was stirred under H$_2$ (15 psi) at 25° C. for 1 h. The catalyst was filtered off and filtrate was concentrated under reduced pressure to give crude (3aR,4S,5S,6aR)-5-amino-2-carbamimidoyl-4-(3-(4,4,5,5-tetramethyl-1,3,2-dioxaborolan-2-yl)propyl)octahydrocyclopenta[c]pyrrole-5-carboxylic acid. LCMS (C$_{18}$H$_{34}$BN$_4$O$_4^+$) (ES, m/z): 381 [M+H]$^+$. The product contained the corresponding boronic acid, (3aR,4S,5S,6aR)-5-amino-4-(3-boronopropyl)-2-carbamimidoyloctahydrocyclopenta[c]pyrrole-5-carboxylic acid, LCMS (C$_{12}$H$_{24}$BN$_4$O$_4^+$) (ES, m/z): 299 [M+H]$^+$). The resulting mixture was directly used in the next step.

Step 3: (3aR,4S,5S,6aR)-5-amino-4-(3-boronopropyl)-2-carbamimidoyloctahydrocyclopenta[c]pyrrole-5-carboxylic acid A mixture of the product from Step 2 (60 mg) and 6N HCl in water (4 mL, 24 mmol) was stirred at 25° C. for 13 h. The reaction was concentrated under reduced pressure to give crude product. The resulting material was purified by RP-HPLC [C18 column, water (0.1% TFA)-CH$_3$CN] to give (3aR,4S,5S,6aR)-5-amino-4-(3-boronopropyl)-2-carbamimidoyloctahydrocyclopenta[c]pyrrole-5-carboxylic acid (11a, TFA salt) as the first eluting peak, and (3aR,4S,5S,6aR)-5-amino-4-(3-boronopropyl)-2-carbamimidoyloctahydrocyclopenta[c]pyrrole-5-carboxylic acid (11b, TFA salt) as the second eluting peak. Example 11a was dissolved in water and then the DOWEX 50WX8 resin (pretreated with water and MeOH) was added. The mixture was stirred for 40 min, and aged for 20 min. The mixture was filtered with a 10 mL PE frit and briefly section dried; then washed with water and MeOH. The resin was washed with 2N NH$_3$ (aqueous, twice) and the filtrate was concentrated under reduced pressure to give 5-amino-4-(3-boronopropyl)-2-carbamimidoyloctahydrocyclopenta[c]pyrrole-5-carboxylic acid as 11a (free base). 11a (free base) LCMS (C$_{12}$H$_{22}$BN$_4$O$_3^+$) (ES, m/z): 281 [M+H-H$_2$O]$^+$. $^1$H NMR (400 MHz, Deuterium Oxide) δ 3.65-3.49 (m, 2H), 3.41-3.33 (m, 1H), 3.24 (dd, J=6.1, 10.5 Hz, 1H), 3.11-2.98 (m, 1H), 2.77-2.64 (m, 1H), 2.44 (dd, J=8.3, 13.6 Hz, 1H), 1.84-1.72 (m, 1H), 1.56 (dd, J=6.6, 14.0 Hz, 1H), 1.48-1.15 (m, 4H), 0.63-0.46 (m, 2H). 11b (free base) was prepared from 11b (TFA salt) by using the general procedure outlined above for 11a (free base). LCMS (C$_{12}$H$_{22}$BN$_4$O$_3^+$) (ES, m/z): 281 [M+H-H$_2$O]$^+$. $^1$H NMR (400 MHz, Deuterium Oxide) δ 3.64-3.52 (m, 2H), 3.51-3.40 (m, 3H), 2.97-2.89 (m, 1H), 2.78-2.67 (m, 1H), 2.56-2.42 (m, 1H), 2.29 (br d, J=5.8 Hz, 1H), 2.07 (br s, 1H), 1.52-1.34 (m, 1H), 1.34-1.19 (m, 2H), 0.66-0.53 (m, 2H).

Example 12: (3aR,4S,5S,6aR)-5-amino-4-(3-boronopropyl)-2-ethyloctahydrocyclopenta[c]pyrrole-5-carboxylic acid

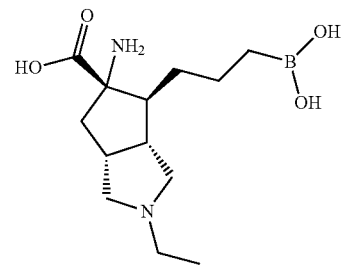 [SMILES: CCN1C[C@@H]2C[C@@](N)(C(=O)O)[C@@H](CCCB(O)O)[C@@H]2C1]

Scheme Q

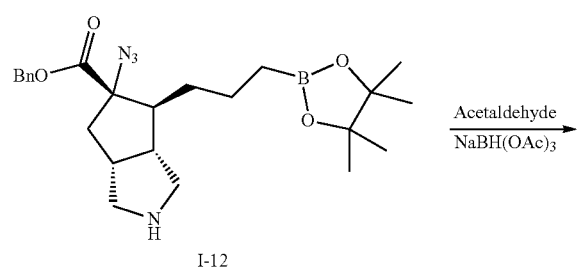

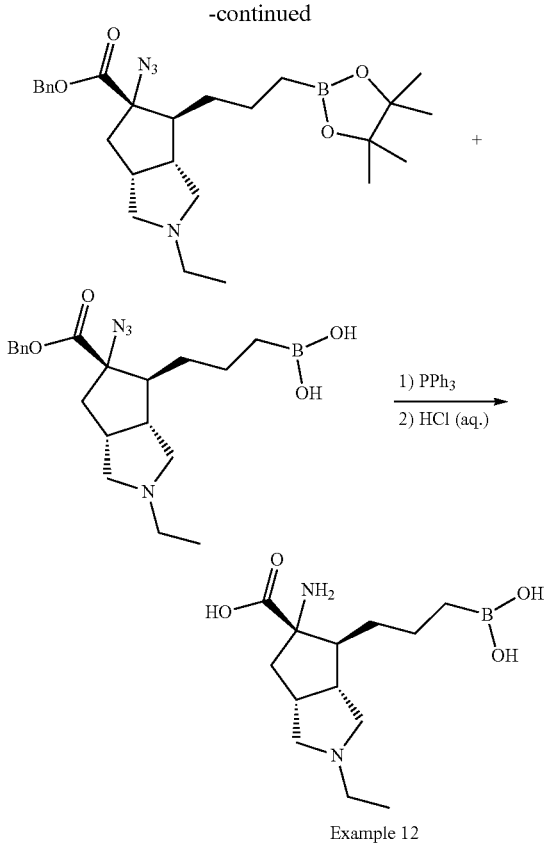

Example 12

Step 1: benzyl (3aR,4S,5S,6aR)-5-azido-2-ethyl-4-(3-(4,4,5,5-tetramethyl-1,3,2-dioxaborolan-2-yl)propyl)octahydrocyclopenta[c]pyrrole-5-carboxylate and (3-((3aR,4S,5S,6aR)-5-azido-5-((benzyloxy)carbonyl)-2-ethyloctahydrocyclopenta[c]pyrrol-4-yl)propyl)boronic acid Benzyl (3aR,4S,5S,6aR)-5-azido-4-(3-(4,4,5,5-tetramethyl-1,3,2-dioxaborolan-2-yl)propyl)octahydrocyclopenta[c]pyrrole-5-carboxylate (100 mg, 0.22 mmol) was added to a solution of acetaldehyde (190 mg, 4.4 mmol) in DCE (3 mL) followed by addition of NaBH(OAc)$_3$ (230 mg, 1.1 mmol). The reaction was stirred at 20° C. for 3 h under N$_2$. The reaction mixture was quenched with water and extracted with DCM. The combined organic phases were washed with brine, dried over anhydrous Na$_2$SO$_4$, filtered and concentrated under reduced pressure. The resulting residue was purified by flash silica gel column chromatography (EtOAc in hexanes) to give benzyl (3aR,4S,5S,6aR)-5-azido-2-ethyl-4-(3-(4,4,5,5-tetramethyl-1,3,2-dioxaborolan-2-yl)propyl)octahydrocyclopenta[c]pyrrole-5-carboxylate (Q1) as the first eluting peak and (3-((3aR,4S,5S,6aR)-5-azido-5-((benzyloxy)carbonyl)-2-ethyloctahydrocyclopenta[c]pyrrol-4-yl)propyl)boronic acid (Q2) as the second eluting peak. Q1, LCMS (C$_{26}$H$_{40}$BN$_4$O$_4^+$) (ES, m/z): 483 [M+H]$^+$. Q2, LCMS (C$_{20}$H$_{30}$BN$_4$O$_4^+$) (ES, m/z): 401 [M+H]$^+$.

Step 2: (3aR,4S,5S,6aR)-5-amino-4-(3-boronopropyl)-2-ethyloctahydrocyclopenta[c]pyrrole-5-carboxylic acid Benzyl (3aR,4S,5S,6aR)-5-azido-2-ethyl-4-(3-(4,4,5,5-tetramethyl-1,3,2-dioxaborolan-2-yl)propyl)octahydrocyclopenta[c]pyrrole-5-carboxylate (20 mg, 0.087 mmol) and (3-((3aR,4S,5S,6aR)-5-azido-5-((benzyloxy)carbonyl)-2-ethyloctahydrocyclopenta[c]pyrrol-4-yl)propyl)boronic acid (15 mg, 0.037 mmol) were dissolved in toluene (5 mL). Triphenylphosphine (230 mg, 0.87 mmol) was added to this solution. The reaction mixture was stirred at 90° C. for 15 h under N$_2$. The reaction mixture was concentrated under reduced pressure. The resulting residue was dissolved in DCM and 12N HCl in water (10 mL, 120 mmol). The water layer was separated and the aqueous was stirred at 90° C. for 3 h. The reaction mixture was cooled to 20° C. and washed with DCM. The water layer was concentrated under reduced pressure. The resulting residue was purified by RP-HPLC [C18 column, water (0.1% TFA)-CH$_3$CN] to give (3aR,4S,5S,6aR)-5-amino-4-(3-boronopropyl)-2-ethyloctahydrocyclopenta[c]pyrrole-5-carboxylic acid as the TFA salt. LCMS (C$_{13}$H$_{24}$BN$_2$O$_3^+$) (ES, m/z): 267 [M–H$_2$O+H]$^+$. $^1$H NMR (400 MHz, Deuterium Oxide) δ 3.96-3.69 (m, 1H), 3.57-2.96 (m, 5H), 2.92-2.66 (m, 2H), 2.60-2.42 (m, 1H), 2.15-1.85 (m, 1H), 1.82-1.57 (m, 1H), 1.51-1.01 (m, 7H), 0.70-0.28 (m, 2H).

Example 13a and 13b: rac-(3aR,6aR)-2-acetyl-5-amino-4-(3-boronopropyl)octahydrocyclopenta[c]pyrrole-5-carboxylic acid and rac-(3aR,6aR)-2-acetyl-5-amino-4-(3-boronopropyl)octahydrocyclopenta[c]pyrrole-5-carboxylic acid Examples 13a and 13b were prepared as HCl salts by using the general procedure outlined above for Example 7 by using I-13 as starting material.

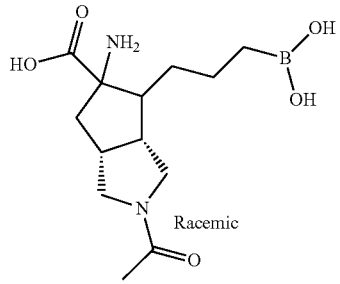

Example 13a and 13b

RP-HPLC [C18 column, water (0.1% HCl)—CH$_3$CN] of the crude mixture of 13a and 13b gave (3aR,6aR)-2-acetyl-5-amino-4-(3-boronopropyl)octahydrocyclopenta[c]pyrrole-5-carboxylic acid (13a) as the first eluting peak, and (3aR,6aR)-2-acetyl-5-amino-4-(3-boronopropyl)octahydrocyclopenta[c]pyrrole-5-carboxylic acid (13b) as the second eluting peak. 13a: LCMS (C$_{13}$H$_{22}$BN$_2$O$_4^+$) (ES, m/z): 281 [M+H-H$_2$O]$^+$. $^1$H NMR (400 MHz, Deuterium Oxide) δ 3.72-3.33 (m, 4H), 3.15-2.86 (m, 2H), 2.45 (br s, 1H), 2.38-2.12 (m, 2H), 1.98 (s, 3H), 1.54-1.21 (m, 4H), 0.85-0.57 (m, 2H). 13b: LCMS (C$_{13}$H$_{22}$BN$_2$O$_4^+$) (ES, m/z): 281 [M+H-H$_2$O]. $^1$H NMR (400 MHz, Deuterium Oxide) δ 3.73-3.35 (m, 4H), 3.18-3.01 (m, 1H), 2.80-2.54 (m, 2H), 2.07-1.89 (m, 4H), 1.79-1.62 (m, 1H), 1.52-1.20 (m, 4H), 0.80-0.60 (m, 2H).

Examples 14a and 14b 5-amino-4-(3-boronopropyl)-2-(methylsulfonyl)octahydrocyclopenta[c]pyrrole-5-carboxylic acid

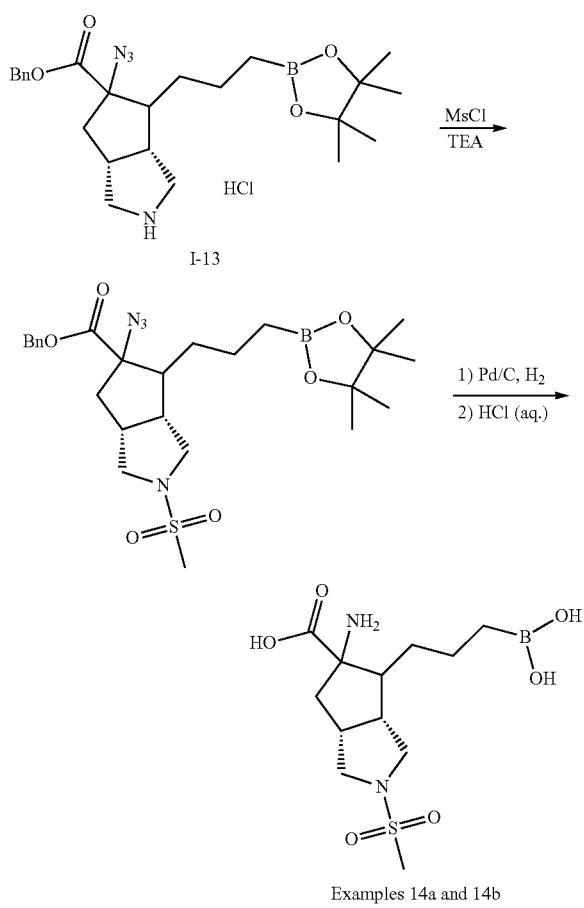

Examples 14a and 14b

Step 1 benzyl 5-azido-2-(methylsulfonyl)-4-(3-(4,4,5,5-tetramethyl-1,3,2-dioxaborolan-2-yl)propyl)octahydrocyclopenta[c]pyrrole-5-carboxylate Ms-Cl (1.3 mL, 17 mmol) was added to a mixture of benzyl 5-azido-4-(3-(4,4,5,5-tetramethyl-1,3,2-dioxaborolan-2-yl)propyl)octahydrocyclopenta[c]pyrrole-5-carboxylate (100 mg, 0.220 mmol) and TEA (3.1 mL, 22 mmol) in DCM (100 mL) at 0° C. The resulting mixture was stirred at 0° C. for 1 h then warmed to 25° C. and stirred for 12 h. The reaction mixture was quenched with water and adjusted with 2 N HCl in water to pH=7. The DCM layer was separated. The water layer was extracted with DCM. The combined organic phases were washed with brine, dried over anhydrous $Na_2SO_4$, filtered and concentrated under reduced pressure. The resulting residue was purified by RP-HPLC [C18 column, water (0.1% TFA)-$CH_3CN$] to give benzyl 5-azido-2-(methylsulfonyl)-4-(3-(4,4,5,5-tetramethyl-1,3,2-dioxaborolan-2-yl)propyl)octahydrocyclopenta[c]pyrrole-5-carboxylate. LCMS ($C_{25}H_{37}BN_4O_6SNa^+$) (ES, m/z): 555 [M+Na]+.

Step 2: 5-amino-4-(3-boronopropyl)-2-(methylsulfonyl)octahydrocyclopenta[c]pyrrole-5-carboxylic acid 10% Pd/C (24 mg, 0.23 mmol) was added to a solution of benzyl 5-azido-2-(methylsulfonyl)-4-(3-(4,4,5,5-tetramethyl-1,3,2-dioxaborolan-2-yl)propyl)octahydrocyclopenta[c]pyrrole-5-carboxylate (60 mg, 0.11 mmol) in $CH_3OH$ (2 mL) under $N_2$ atmosphere. The mixture was degassed and backfilled with $H_2$ (three times). The resulting mixture was stirred under $H_2$ (15 psi) at 25° C. for 3 h. The catalyst was filtered off and filtrate was concentrated under reduced pressure to give crude product. The crude product was suspended in water (2 mL) and then 12N HCl in water (2 mL, 24 mmol) was added. The resulting mixture was stirred at 25° C. for 15 h. Solvent was evaporated in $N_2$ stream. The resulting residue was purified by RP-HPLC [C18 column, water (0.1% TFA)-$CH_3CN$] to give 14a as the first eluting peak, and 14b as the second eluting peak. 14a was treated with 6N HCl in water (0.2 mL, 1.2 mmol) then dried to give 5-amino-4-(3-boronopropyl)-2-(methylsulfonyl)octahydrocyclopenta[c]pyrrole-5-carboxylic acid as the HCl salt (14a). 14b was treated with 6 M HCl (0.2 mL, 1.2 mmol) then dried to give 5-amino-4-(3-boronopropyl)-2-(methylsulfonyl)octahydrocyclopenta[c]pyrrole-5-carboxylic acid as the HCl salt (14b). 14a: LCMS ($C_{12}H_{22}BN_2O_5S^+$) (ES, m/z): 317 [M+H-$H_2O$]+. $^1$H NMR (400 MHz, $D_2O$) δ 3.46-3.18 (m, 4H), 3.16-2.89 (m, 2H), 2.87 (s, 3H), 2.41-2.24 (m, 2H), 2.21-2.17 (m, 1H), 1.44-1.14 (m, 4H), 0.72-0.51 (m, 2H). 14b: LCMS ($C_{12}H_{22}BN_2O_5S^+$) (ES, m/z): 317 [M+H-$H_2O$]. $^1$HNMR (400 MHz, Deuterium Oxide) δ 3.16-2.98 (m, 5H), 2.93-2.80 (m, 3H), 2.68-2.43 (m, 2H), 1.99-1.88 (m, 1H), 1.65 (br dd, J=8.7, 13.6 Hz, 1H), 1.49-1.07 (m, 4H), 0.78-0.49 (m, 2H).

Example 15: 5-amino-2-(2-amino-2-oxoethyl)-4-(3-boronopropyl)octahydrocyclopenta[c]pyrrole-5-carboxylic acid

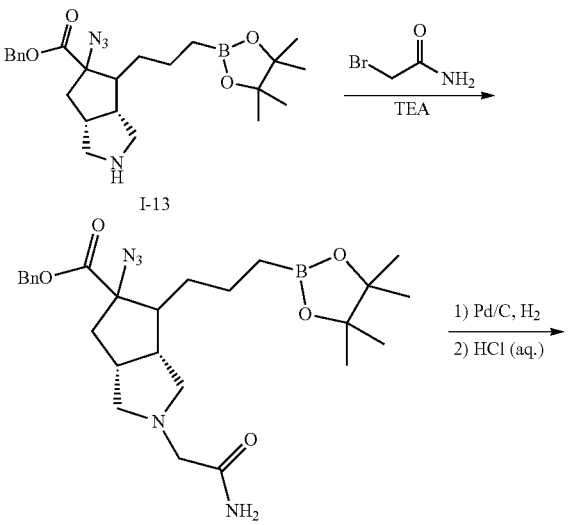

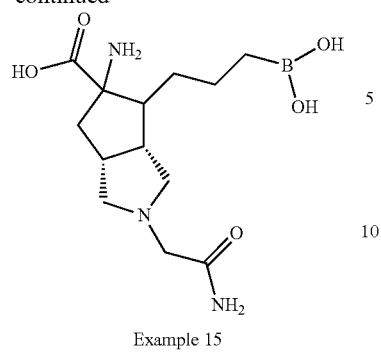

Example 15

Step 1: benzyl 2-(2-amino-2-oxoethyl)-5-azido-4-(3-(4,4,5,5-tetramethyl-1,3,2-dioxaborolan-2-yl)propyl)octahydrocyclopenta[c]pyrrole-5-carboxylate 2-bromoacetamide (36 mg, 0.26 mmol) was added to a solution of benzyl 5-azido-4-(3-(4,4,5,5-tetramethyl-1,3,2-dioxaborolan-2-yl)propyl)octahydrocyclopenta[c]pyrrole-5-carboxylate hydrochloride (100 mg, 0.22 mmol) and TEA (0.09 mL, 0.66 mmol) in DCM (5 mL) at 0° C. The mixture was stirred at 30° C. for 16 h. The resulting mixture was filtered and concentrated under reduced pressure. The resulting residue was purified by RP-HPLC [C18 column, water (0.1% HCl)—CH$_3$CN] to give benzyl 2-(2-amino-2-oxoethyl)-5-azido-4-(3-(4,4,5,5-tetramethyl-1,3,2-dioxaborolan-2-yl)propyl)octahydrocyclopenta[c]pyrrole-5-carboxylate. LCMS (C$_{26}$H$_{39}$BN$_5$O$_5$$^+$) (ES, m/z): 512 [M+H]$^+$.

Step 2: 5-amino-2-(2-amino-2-oxoethyl)-4-(3-boronopropyl)octahydrocyclopenta[c]pyrrole-5-carboxylic acid 10% Pd/C (10 mg) was added to a solution of benzyl 2-(2-amino-2-oxoethyl)-5-azido-4-(3-(4,4,5,5-tetramethyl-1,3,2-dioxaborolan-2-yl)propyl)octahydrocyclopenta[c]pyrrole-5-carboxylate (60 mg, 0.12 mmol) in MeOH (5 mL) under N$_2$ atmosphere. The mixture was degassed and back-filled with H$_2$ (three times). The resulting mixture was stirred under H$_2$ (15 psi) at 25° C. for 2 h. The catalyst was filtered off and filtrate was concentrated under reduced pressure. 12N HCl in water (3 mL, 36 mmol) was added to the residue and stirred at 25° C. for 1 h. The solvent was removed and the residue was purified by RP-HPLC [C18 column, water (0.1% HCl)—CH$_3$CN] to give 5-amino-2-(2-amino-2-oxoethyl)-4-(3-boronopropyl)octahydrocyclopenta[c]pyrrole-5-carboxylic acid as the HCl salt. LCMS (C$_{13}$H$_{25}$BN$_3$O$_5$$^+$) (ES, m/z): 314 [M+H]$^+$. $^1$HNMR (400 MHz, D$_2$O) δ 4.81-4.01 (m, 3H), 3.75-3.68 (m, 1H), 3.37-3.27 (m, 2H), 3.10-3.00 (m, 1H), 2.65-2.50 (m, 2H), 2.39-1.88 (m, 2H), 1.58 (br, 1H), 1.33-1.31 (m, 3H), 0.74-0.71 (m, 2H).

Example 16: 5-amino-2-(2-aminoacetyl)-4-(3-boronopropyl)octahydrocyclopenta[c]pyrrole-5-carboxylic acid

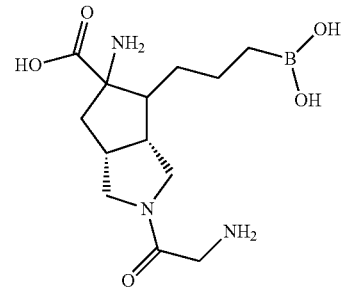 [SMILES: NCC(=O)N1C[C@@H]2CC(N)(C(=O)O)C(CCCB(O)O)[C@@H]2C1]

Example 16 was prepared as the HCl salt by using the general procedure outlined above for Example 4 by using I-13 as starting material. LCMS (C$_{13}$H$_{23}$BN$_3$O$_4$$^+$) (ES, m/z): 296 [M+H-H$_2$O]$^+$. $^1$H NMR (400 MHz, Deuterium Oxide) δ 3.87-3.71 (m, 2H), 3.61-3.22 (m, 4H), 3.15-2.61 (m, 2H), 2.59-2.47 (m, 1H), 2.43-2.09 (m, 1H), 2.00-1.65 (m, 1H), 1.51-1.12 (m, 4H), 0.64 (br t, J=7.6 Hz, 2H).

Example 17a: 5-amino-4-(3-boronopropyl)-2-carbamoyloctahydrocyclopenta[c]pyrrole-5-carboxylic acid Scheme T

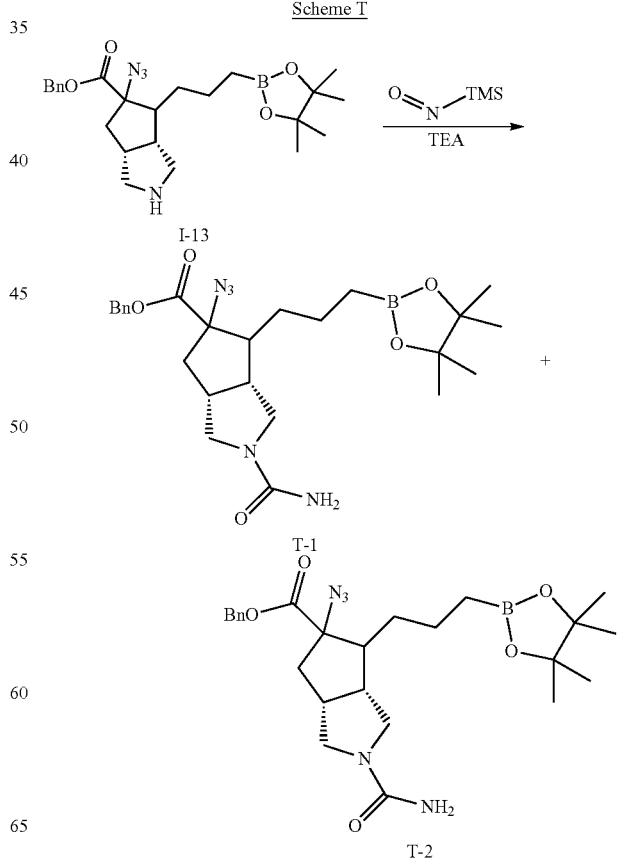

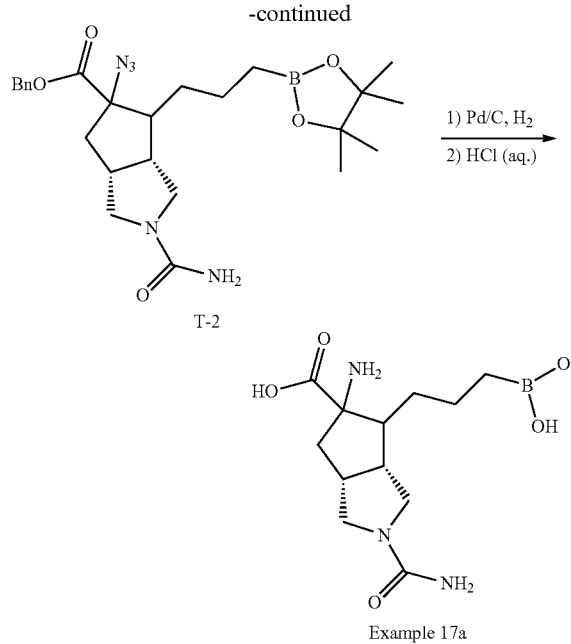

Step 1: benzyl 5-azido-2-carbamoyl-4-(3-(4,4,5,5-tetramethyl-1,3,2-dioxaborolan-2-yl)propyl)octahydrocyclopenta[c]pyrrole-5-carboxylate Isocyanatotrimethylsilane (50 mg, 0.44 mmol) was added to a solution of benzyl 5-azido-4-(3-(4,4,5,5-tetramethyl-1,3,2-dioxaborolan-2-yl)propyl)octahydrocyclopenta[c]pyrrole-5-carboxylate hydrochloride (100 mg, 0.22 mmol) and TEA (0.12 mL, 0.88 mmol) in DCM (5 mL) at 0° C. The mixture was stirred at 30° C. for 16 h. The resulting mixture was filtered and concentrated under reduced pressure. The resulting residue was purified by RP-HPLC [C18 column, water (0.05% HCl)—CH$_3$CN] to give benzyl 5-azido-2-carbamoyl-4-(3-(4,4,5,5-tetramethyl-1,3,2-dioxaborolan-2-yl)propyl)octahydrocyclopenta[c]pyrrole-5-carboxylate as the first eluting peak T-1, and benzyl 5-azido-2-carbamoyl-4-(3-(4,4,5,5-tetramethyl-1,3,2-dioxaborolan-2-yl)propyl)octahydrocyclopenta[c]pyrrole-5-carboxylate as the second eluting peak T-2. Both products contained the corresponding boronic acids. The resulting mixtures were directly used in the next step. T-1: LCMS (C$_{25}$H$_{37}$BN$_5$O$_5^+$) (ES, m/z): 498 [M+H]$^+$. $^1$HNMR (400 MHz, METHANOL-d$_4$) δ 7.51-7.27 (m, 5H), 5.25 (s, 2H), 3.55-3.34 (m, 4H), 3.02-2.99 (m, 1H), 2.63-2.57 (m, 2H), 1.99-1.75 (m, 2H), 1.41-1.32 (m, 3H), 1.24-1.19 (m, 12H), 1.18-1.12 (m, 1H), 0.68-0.57 (m, 2H). T-2: LCMS (C$_{25}$H$_{37}$BN$_5$O$_5^+$) (ES, m/z): 498 [M+H]$^+$. $^1$HNMR (400 MHz, METHANOL-d$_4$) δ 7.54-7.26 (m, 5H), 5.33-5.15 (m, 2H), 3.58-3.35 (m, 4H), 3.07-2.82 (m, 2H), 2.54-2.42 (m, 1H), 2.31-2.03 (m, 2H), 1.46-1.24 (m, 4H), 1.24-1.17 (m, 7H), 0.70-0.53 (m, 2H).

Step 2: 5-amino-4-(3-boronopropyl)-2-carbamoyloctahydrocyclopenta[c]pyrrole-5-carboxylic acid 10% Pd/C (0.03 g) was added to a solution of T-1 (0.041 g) prepared from Step 1 in MeOH (5 mL) under N$_2$ atmosphere. The mixture was degassed and backfilled with H$_2$ (three times). The resulting mixture was stirred under H$_2$ (15 psi) at 30° C. for 2 h. The catalyst was filtered off, and the filtrate was concentrated under reduced pressure to give a crude residue. 12N HCl in water (5 mL, 60 mmol) was added to the residue and the resulting mixture was stirred at 30° C. for 2 h. The residue was concentrated under reduced pressure to give the 5-amino-4-(3-boronopropyl)-2-carbamoyloctahydrocyclopenta[c]pyrrole-5-carboxylic acid as the HCl salt. LCMS (C$_{12}$H$_{21}$BN$_3$O$_4^+$) (ES, m/z): 282 [M+H-H$_2$O]$^+$. $^1$HNMR (400 MHz, METHANOL-d$_4$) δ 3.67-3.44 (m, 4H), 3.28-3.15 (m, 1H), 2.82-2.79 (m, 1H), 2.64 (dd, J=8.3, 13.6 Hz, 1H), 2.14-1.99 (m, 1H), 1.81 (dd, J=8.8, 13.6 Hz, 1H), 1.72-1.58 (m, 1H), 1.55-1.29 (m, 3H), 0.94-0.71 (m, 2H).

Example 17b was made from T-2 using the same procedure. 17b LCMS (C$_{12}$H$_2$BN$_3$O$_4^+$) (ES, m/z): 282 [M+H-H$_2$O]$^+$. $^1$H NMR (400 MHz, METHANOL-d$_4$) δ 3.74-3.50 (m, 4H), 3.24-3.01 (m, 2H), 2.54-2.38 (m, 2H), 2.35-2.20 (m, 1H), 1.64 (m, 1H), 1.56-1.38 (m, 3H), 0.94-0.71 (m, 2H).

Example 18: 5-amino-4-(3-boronopropyl)-2-sulfamoyloctahydrocyclopenta[c]pyrrole-5-carboxylic acid Scheme U

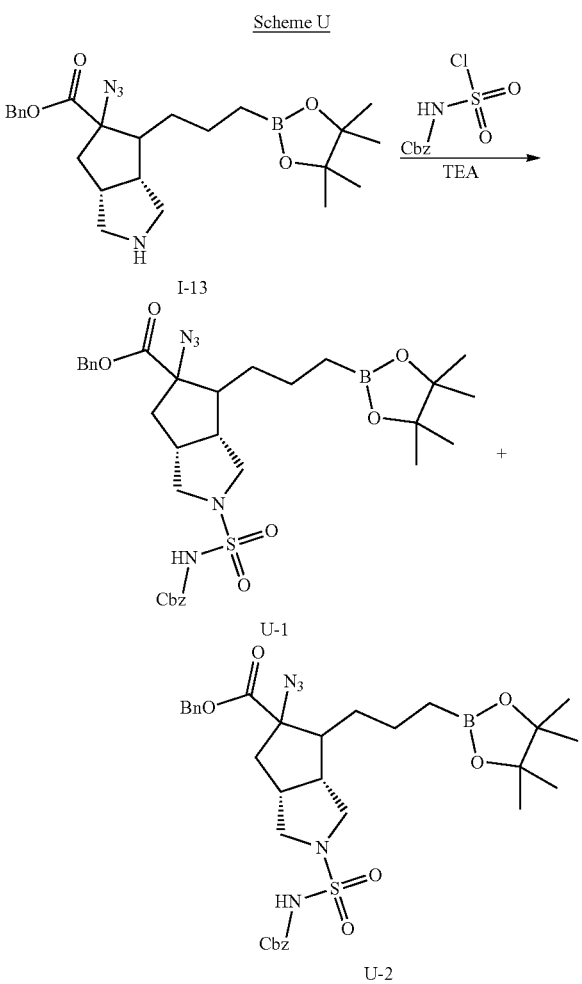

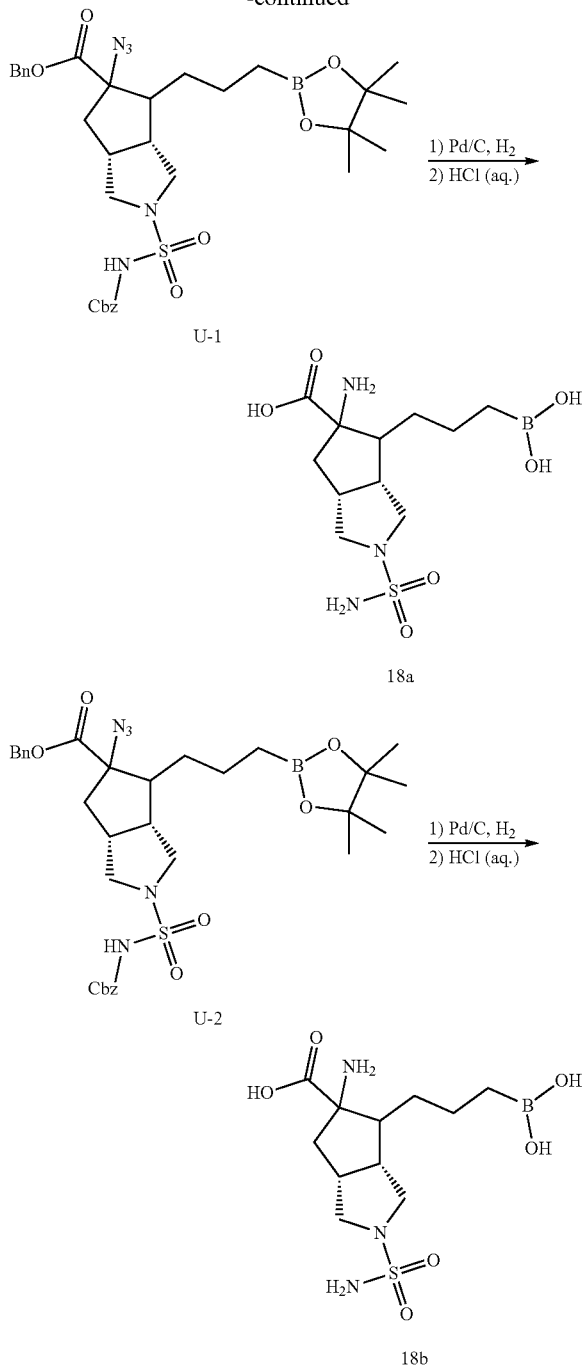

reduced pressure. The residue was purified by RP-HPLC [C18 column, water (0.1% TFA)-CH$_3$CN] to give benzyl 5-azido-2-(N-((benzyloxy)carbonyl)sulfamoyl)-4-(3-(4,4,5,5-tetramethyl-1,3,2-dioxaborolan-2-yl)propyl)octahydrocyclopenta[c]pyrrole-5-carboxylate (U-1) as the first eluting peak, and benzyl 5-azido-2-(N-((benzyloxy)carbonyl)sulfamoyl)-4-(3-(4,4,5,5-tetramethyl-1,3,2-dioxaborolan-2-yl)propyl)octahydrocyclopenta[c]pyrrole-5-carboxylate (U-2) as the second eluting peak. Both products contained the corresponding boronic acids. The resulting mixtures were directly used in the next step. U-1: LCMS (C$_{32}$H$_{42}$BN$_5$O$_8$SNa$^+$) (ES, m/z): 690 [M+Na]$^+$. U-2: LCMS (C$_{32}$H$_{42}$BN$_5$O$_8$SNa$^+$) (ES, m/z): 690 [M+Na]$^+$.

Step 2: 5-amino-4-(3-boronopropyl)-2-sulfamoyloctahydrocyclopenta[c]pyrrole-5-carboxylic acid 10% Pd/C (0.02 g) was added to a solution of U-1 (0.04 g) prepared from Step 1 in MeOH (5 mL) under N$_2$ atmosphere. The mixture was degassed and backfilled with H$_2$ (three times). The resulting mixture was stirred under H$_2$ (15 psi) at 30° C. for 2 h. LCMS showed that the starting material was consumed and the catalyst was filtered off, and the filtrate was concentrated under reduced pressure to give the residue. 12N HCl in water (5 mL, 60 mmol) was added to the residue. The resulting mixture was stirred at 30° C. for 2 h. LCMS showed the reaction was complete. The reaction was concentrated in vacuo. The residue was purified by RP-HPLC [C18 column, water (0.05% HCl)—CH$_3$CN] to give the 5-amino-4-(3-boronopropyl)-2-sulfamoyloctahydrocyclopenta[c]pyrrole-5-carboxylic acid as the HCl salt. LCMS (C$_{11}$H$_{21}$BN$_3$O$_5$S$^+$) (ES, m/z): 318 [M+H-H$_2$O]$^+$. $^1$HNMR (400 MHz, METHANOL-d$_4$) δ 3.19-3.15 (m, 1H), 3.12-3.09 (m, 2H), 3.07-3.01 (m, 1H), 2.99-2.92 (m, 1H), 2.70-2.56 (m, 2H), 2.06-2.01 (m, 1H), 1.79 (dd, J=9.6, 13.2 Hz, 1H), 1.49-1.48 (m, 2H), 1.44-1.28 (m, 2H), 0.90-0.75 (m, 2H).

Example 18b was made from U-2 using the same procedure. 18b LCMS (C$_{11}$H$_{2}$BN$_3$O$_5$S$^+$) (ES, m/z): 318 [M+H-H$_2$O]$^+$. $^1$H NMR (400 MHz, METHANOL-d$_4$) δ 3.52-3.42 (m, 2H), 3.39-3.27 (m, 2H), 3.10-2.94 (m, 2H), 2.61-2.57 (m, 1H), 2.36-2.34 (m, 1H), 2.23-2.11 (m, 1H), 1.62-1.32 (m, 4H), 0.94-0.70 (m, 2H).

Example 19: 5-amino-4-(3-boronopropyl)-2-(2-(dimethylamino)acetyl)octahydrocyclopenta[c]pyrrole-5-carboxylic acid

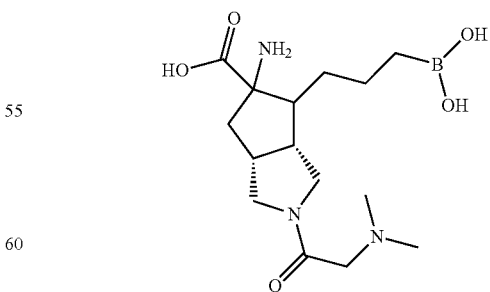

Example 19 was prepared as a HCl salt by using the general procedure outlined above for Example 4 by using I-13 as starting material. LCMS (C$_{15}$H$_{27}$BN$_3$O$_4$$^+$) (ES, m/z): 324 [M+H-H$_2$O]$^+$. $^1$HNMR (400 MHz, Deuterium Oxide) δ

Step 1: benzyl 5-azido-2-(N-((benzyloxy)carbonyl)sulfamoyl)-4-(3-(4,4,5,5-tetramethyl-1,3,2-dioxaborolan-2-yl)propyl)octahydrocyclopenta[c]pyrrole-5-carboxylate Benzyl (chlorosulfonyl)carbamate (101 mg, 0.40 mmol) was added to a solution of benzyl 5-azido-4-(3-(4,4,5,5-tetramethyl-1,3,2-dioxaborolan-2-yl)propyl)octahydrocyclopenta[c]pyrrole-5-carboxylate hydrochloride (100 mg, 0.20 mmol) and TEA (0.11 mL, 0.82 mmol) in DCM (10 mL) at 0° C. The mixture was stirred at 30° C. for 16 h. The resulting mixture was filtered and concentrated under 4.22-4.02 (m, 2H), 3.71-3.29 (m, 4H), 2.95-2.88 (m, 6H), 2.86-2.71 (m, 1H), 2.70-2.60 (m, 1H), 2.58-2.21 (m, 2H), 2.15-1.69 (m, 1H), 1.61-1.25 (m, 4H), 0.83-0.65 (m, 2H).

Example 20b: (3aR,4R,5R,6aR)-4-amino-5-(3-boronopropyl)octahydrocyclopenta[b]pyrrole-4-carboxylic acid

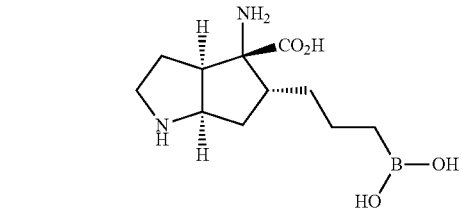 [SMILES: N[C@]1(C(=O)O)[C@H](CCCB(O)O)C[C@H]2NCC[C@H]21]

Scheme V

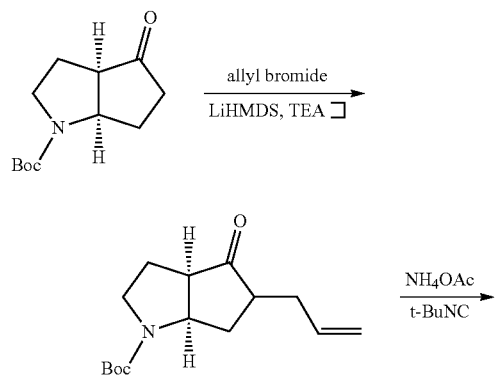

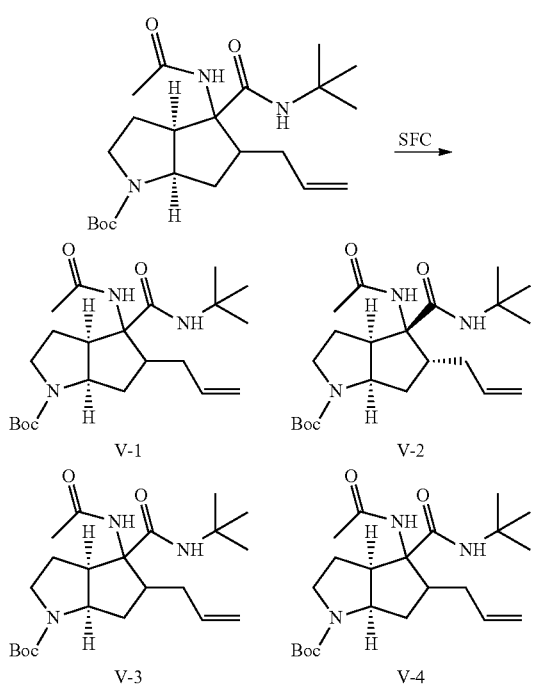

-continued

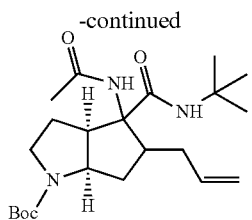
V-5

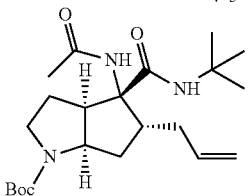
V-6 pinacolborane
[Ir(cod)Cl]$_2$, dppe

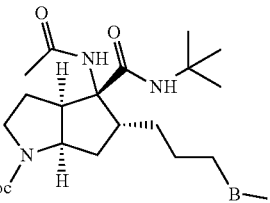

HCl (aq.)

Example 20b

Step 1: rac-tert-butyl (3aR,6aR)-5-allyl-4-oxohexahydrocyclopenta[b]pyrrole-1(2H)-carboxylate LiHMDS (13 mL, 13 mmol, 1M in THF) was added to a solution of rac-(3aR,6aR)-tert-butyl 4-oxohexahydrocyclopenta[b]pyrrole-1(2H)-carboxylate (2 g, 8.9 mmol) and dry TEA (2.5 mL, 18 mmol) in THF (12 mL) at −30° C. After stirring for 30 min at −30° C. under N$_2$, 3-bromoprop-1-ene (0.77 mL, 8.9 mmol) was added to the reaction mixture slowly. The mixture was allowed to stir at 0° C. for 1.5 h under N$_2$. The reaction mixture was quenched with water and extracted with EtOAc. The organic phase was dried over anhydrous Na$_2$SO$_4$, filtered and concentrated under reduced pressure. The residue was purified by silica gel chromatography (ethyl acetate in hexanes) to give rac-(3aR,6aR)-tert-butyl 5-allyl-4-oxohexahydrocyclopenta[b]pyrrole-1(2H)-carboxylate. LCMS (C$_{13}$H$_{19}$N$_2$O$_3^+$) (ES, m/z): 251 [M+H−C$_4$H$_8$+CH$_3$CN]$^+$.

Step 2: rac-tert-butyl (3aR,6aR)-4-acetamido-5-allyl-4-(tert-butylcarbamoyl)hexahydrocyclopenta[b]pyrrole-1(2H)-carboxylate NH$_4$OAc (3.3 g, 42 mmol) and 2-isocyano-2-methylpropane (2.4 mL, 21 mmol) were added to a solution of (3aR,6aR)-tert-butyl 5-allyl-4-oxohexahydrocyclopenta[b]

pyrrole-1(2H)-carboxylate (1.4 g, 5.3 mmol) in 2,2,2-trifluoroethyl alcohol (2 mL). The reaction was stirred at 35° C. for 12 h under $N_2$. The reaction mixture was quenched with water and extracted with EtOAc. The combined organic phases were washed with brine, dried over anhydrous $Na_2SO_4$, filtered and concentrated under reduced pressure. The residue was purified by silica gel chromatography (MeOH in DCM). The residue was re-purified by RP-HPLC (Column: C18, water (0.1% TFA)-ACN) to give rac-(3aR,6aR)-tert-butyl 4-acetamido-5-allyl-4-(tert-butylcarbamoyl)hexahydrocyclopenta[b]pyrrole-1(2H)-carboxylate. LCMS ($C_{22}H_{38}N_3O_4^+$) (ES, m/z): 408 [M+H]$^+$.

Step 3: tert-butyl (3aR,6aR)-4-acetamido-5-allyl-4-(tert-butylcarbamoyl)hexahydrocyclopenta[b]pyrrole-1(2H)-carboxylate Rac-(3aR,6aR)-tert-butyl 4-acetamido-5-allyl-4-(tert-butylcarbamoyl)hexahydrocyclopenta[b]pyrrole-1(2H)-carboxylate (1.05 g, 2.58 mmol) was resolved by Chiral-SFC [Column: Phenomenex-Cellulose-2 (250 mm*50 mm, 10 um), Mobile phase: A: $CO_2$, B: EtOH (0.1% $NH_3.H_2O$), Gradient: 15% of B in 10 min and hold 15% for 1 min, Flow Rate (mL/min) 180 mL/min, Column temperature: 40° C.] to give (3aR,6aR)-tert-butyl 4-acetamido-5-allyl-4-(tert-butylcarbamoyl)hexahydrocyclopenta[b]pyrrole-1(2H)-carboxylate (V-1, $t_r$=2.08 min) as the first eluting peak and (3aR,6aR)-tert-butyl 4-acetamido-5-allyl-4-(tert-butylcarbamoyl)hexahydrocyclopenta[b]pyrrole-1(2H)-carboxylate (V-2, $t_r$=2.50 min) as the second eluting peak and (3aR,6aR)-tert-butyl 4-acetamido-5-allyl-4-(tert-butylcarbamoyl)hexahydrocyclopenta[b]pyrrole-1(2H)-carboxylate (V-3, $t_r$=3.69 min) as the third eluting peak and (3aR,6aR)-tert-butyl 4-acetamido-5-allyl-4-(tert-butylcarbamoyl)hexahydrocyclopenta[b]pyrrole-1(2H)-carboxylate (V-4, $t_r$=4.88 min) as the fourth eluting peak and (3aR,6aR)-tert-butyl 4-acetamido-5-allyl-4-(tert-butylcarbamoyl)hexahydrocyclopenta[b]pyrrole-1(2H)-carboxylate (V-5, $t_r$=5.7 min) as the fifth eluting peak. V-1: LCMS ($C_{22}H_{38}N_3O_4^+$) (ES, m/z): 408 [M+H]$^+$. $^1$H NMR (400 MHz, chloroform-d) δ 8.02 (br s, 1H), 5.97-5.78 (m, 1H), 5.74 (br s, 1H), 5.15-4.97 (m, 2H), 4.08 (br s, 1H), 3.86-3.62 (m, 1H), 3.57-3.40 (m, 1H), 3.22 (br s, 1H), 2.87 (dtd, J=4.2, 8.6, 12.6 Hz, 1H), 2.58-2.43 (m, 1H), 2.05 (s, 3H), 1.99-1.83 (m, 2H), 1.80-1.56 (m, 3H), 1.46 (s, 9H), 1.33 (s, 9H). V-2: LCMS ($C_{22}H_{38}N_3O_4^+$) (ES, m/z): 408 [M+H]$^+$. $^1$H NMR (400 MHz, chloroform-d) δ 8.02 (br s, 1H), 5.87 (qd, J=8.2, 16.1 Hz, 1H), 5.73 (br s, 1H), 5.23-4.92 (m, 2H), 4.08 (br s, 1H), 3.82-3.63 (m, 1H), 3.53-3.44 (m, 1H), 3.22 (br s, 1H), 2.93-2.80 (m, 1H), 2.53-2.50 (m, 1H), 2.05 (s, 3H), 1.96-1.81 (m, 2H), 1.78-1.58 (m, 3H), 1.46 (s, 9H), 1.34 (s, 9H). V-3: LCMS ($C_{22}H_{38}N_3O_4^+$) (ES, m/z): 408 [M+H]$^+$. $^1$H NMR (400 MHz, chloroform-d) δ 6.28-6.16 (m, 1H), 6.08-5.68 (m, 2H), 5.42-4.93 (m, 2H), 4.38-3.97 (m, 1H), 3.73-3.16 (m, 3H), 2.68-2.20 (m, 3H), 2.04 (br s, 2H), 2.10-1.99 (m, 1H), 1.84-1.57 (m, 4H), 1.45 (br s, 9H), 1.38-1.24 (m, 9H). V-4: LCMS ($C_{22}H_{38}N_3O_4^+$) (ES, m/z): 408 [M+H]$^+$. $^1$H NMR (400 MHz, chloroform-d) δ 5.96-5.64 (m, 3H), 5.25-5.02 (m, 2H), 4.41-3.99 (m, 1H), 3.75-3.41 (m, 3H), 3.38-3.04 (m, 1H), 2.83-2.33 (m, 1H), 2.18 (br d, J=6.4 Hz, 1H), 2.05-2.00 (m, 3H), 1.86 (br s, 1H), 1.75-1.73 (m, 3H), 1.44 (s, 9H), 1.33 (s, 9H). V-5: LCMS ($C_{22}H_{38}N_3O_4^+$) (ES, m/z): 408 [M+H]$^+$. $^1$H NMR (400 MHz, chloroform-d) δ 6.18 (br s, 1H), 5.98 (br s, 1H), 5.87-5.68 (m, 2H), 5.24-4.97 (m, 2H), 4.11-4.17 (m, 1H), 3.85-3.76 (m, 1H), 3.65-3.56 (m, 1H), 3.54-3.50 (m, 1H), 3.34 (br d, J=7.3 Hz, 1H), 3.41-3.29 (m, 1H), 2.85-2.72 (m, 1H), 2.16-2.07 (m, 1H), 2.07-2.01 (m, 3H), 1.90-1.72 (m, 3H), 1.46-1.42 (m, 9H), 1.36-1.30 (m, 9H).

Step 4: tert-butyl (3aR,6aR)-4-acetamido-4-(tert-butylcarbamoyl)-5-(3-(4,4,5,5-tetramethyl-1,3,2-dioxaborolan-2-yl)propyl)hexahydrocyclopenta[b]pyrrole-1(2H)-carboxylate (3aR,6aR)-tert-butyl 4-acetamido-5-allyl-4-(tert-butylcarbamoyl)hexahydrocyclopenta[b]pyrrole-1(2H)-carboxylate (140 mg, 0.344 mmol, V-2), 4,4,5,5-tetramethyl-1,3,2-dioxaborolane (66 mg, 0.52 mmol) and 1,2-bis(diphenylphosphino)ethane (14 mg, 0.034 mmol) in anhydrous DCM (3 mL) was bubbled with a stream of $N_2$ for 3 min. The mixture was stirred at 25° C. for 10 min and then treated with chloro(1,5-cyclooctadiene)iridium(I) dimer (12 mg, 0.017 mmol). The resulting mixture was stirred at 25° C. for 10 h under $N_2$. The reaction was filtered and concentrated under reduced pressure. The residue was purified by RP-HPLC [C18 column, water (0.1% TFA)-$CH_3CN$] to give (3aR,6aR)-tert-butyl 4-acetamido-4-(tert-butylcarbamoyl)-5-(3-(4,4,5,5-tetramethyl-1,3,2-dioxaborolan-2-yl)propyl)hexahydrocyclopenta[b]pyrrole-1(2H)-carboxylate. LCMS ($C_{28}H_{51}BN_3O_6^+$) (ES, m/z): 536 [M+H]$^+$. The product contained the corresponding boronic acid. The resulting mixture was directly used in the next step.

Step 5: (3aR,6aR)-4-amino-5-(3-boronopropyl)octahydrocyclopenta[b]pyrrole-4-carboxylic acid hydrochloride A mixture of the product prepared from Step 4 (85 mg) in 12N HCl in water (3 mL, 36 mmol) was stirred at 100° C. for 12 h. The mixture was concentrated under reduced pressure. sat.$NaHCO_3$ (aq.) was added to the residue till pH~8. The aqueous layer was washed with DCM. The aqueous layer was concentrated under reduced pressure. 2N HCl in water was added to the residue till pH~6 and the mixture was concentrated under reduced pressure. The residue was purified by RP-HPLC [C18 column, water (0.05% HCl)—$CH_3CN$] to give (3aR,6aR)-4-amino-5-(3-boronopropyl)octahydrocyclopenta[b]pyrrole-4-carboxylic acid as a HCl salt. LCMS ($C_{11}H_{20}BN_2O_3^+$) (ES, m/z): 239 [M+H-$H_2O$]. $^1$H NMR (400 MHz, Deuterium Oxide) δ 4.33 (br t, J=8.2 Hz, 1H), 3.48-3.33 (m, 1H), 3.23-3.06 (m, 2H), 2.91-2.73 (m, 1H), 2.36 (br dd, J=7.1, 15.4 Hz, 1H), 2.26-2.15 (m, 1H), 2.11-1.89 (m, 2H), 1.41 (br d, J=3.7 Hz, 2H), 1.31-1.22 (m, 2H), 0.83-0.63 (m, 2H).

Example 20a was made from V-1, Example 20c was made from V-3, Examples 20d and 20e were made from V-4 and Example 20f was made from rac-(3aR,6aR)-tert-butyl 4-oxohexahydrocyclopenta[b]pyrrole-1(2H)-carboxylate, all using the same procedure. 20a LCMS ($C_{11}H_{20}BN_2O_3^+$) (ES, m/z): 239 [M+H-$H_2O$]. $^1$H NMR (400 MHz, deuterium oxide) δ 4.33-4.31 (m, 1H), 3.49-3.35 (m, 1H), 3.28-3.05 (m, 2H), 2.83 (br s, 1H), 2.39-2.36 (m, 1H), 2.26-2.15 (m, 1H), 2.12-1.87 (m, 2H), 1.53-1.16 (m, 4H), 0.88-0.62 (m, 2H). 20c LCMS ($C_{11}H_{20}BN_2O_3^+$) (ES, m/z): 239 [M+H-$H_2O$]$^+$. $^1$H NMR (400 MHz, deuterium oxide) δ 4.45-4.25 (m, 1H), 3.61-3.38 (m, 1H), 3.33-3.07 (m, 2H), 2.42-2.20 (m, 2H), 2.19-2.02 (m, 1H), 1.98-1.94 (m, 1H), 1.91-1.74 (m, 2H), 1.58-1.38 (m, 1H), 1.34-1.21 (m, 1H), 1.16-0.91 (m, 1H), 0.86-0.49 (m, 2H). 20d LCMS ($C_{11}H_{20}BN_2O_3^+$) (ES, m/z): 239 [M+H-$H_2O$]$^+$. $^1$H NMR (400 MHz, deuterium oxide) δ 4.39 (br t, J=8.6 Hz, 1H), 3.53-3.42 (m, 1H), 3.38-3.28 (m, 1H), 3.25-3.13 (m, 1H), 2.56-2.39 (m, 1H), 2.35-2.03 (m, 3H), 1.94-1.79 (m, 1H), 1.57-1.16 (m, 3H), 1.14-0.96 (m, 1H), 0.81-0.52 (m, 2H). 20e LCMS ($C_{11}H_{20}BN_2O_3^+$) (ES, m/z): 239 [M+H-$H_2O$]$^+$. $^1$H NMR (400 MHz, deuterium oxide) δ 4.39 (br t, J=8.3 Hz, 1H), 3.49-3.46 (m, 1H), 3.35-3.30 (m, 1H), 3.21-3.16 (m, 1H), 2.53-2.40 (m, 1H), 2.29-2.04 (m, 3H), 1.93-1.79 (m, 1H), 1.54-1.24 (m, 3H), 1.14-1.00 (m, 1H), 0.76-0.64 (m, 2H). 20f LCMS ($C_{11}H_{20}BN_2O_3^+$) (ES, m/z): 239 [M+H-$H_2O$]$^+$. $^1$H NMR (400 MHz, deuterium oxide) δ 4.21-4.04 (m, 1H), 3.59-3.39 (m, 1H), 3.27-3.00 (m, 2H), 2.51-2.08 (m, 3H), 1.88-1.68 (m, 2H), 1.45-1.25 (m, 2H), 1.23-1.07 (m, 2H), 0.73-0.47 (m, 2H).
Example 21: 7-amino-8-(3-boronopropyl)-2-azaspiro[4.4]nonane-7-carboxylic acid
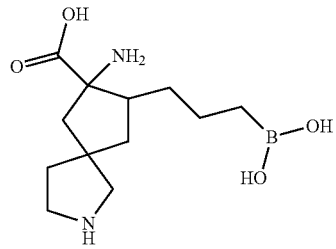 [SMILES: NC1(C(=O)O)CC2(CCNC2)CC1CCCB(O)O]
Scheme W
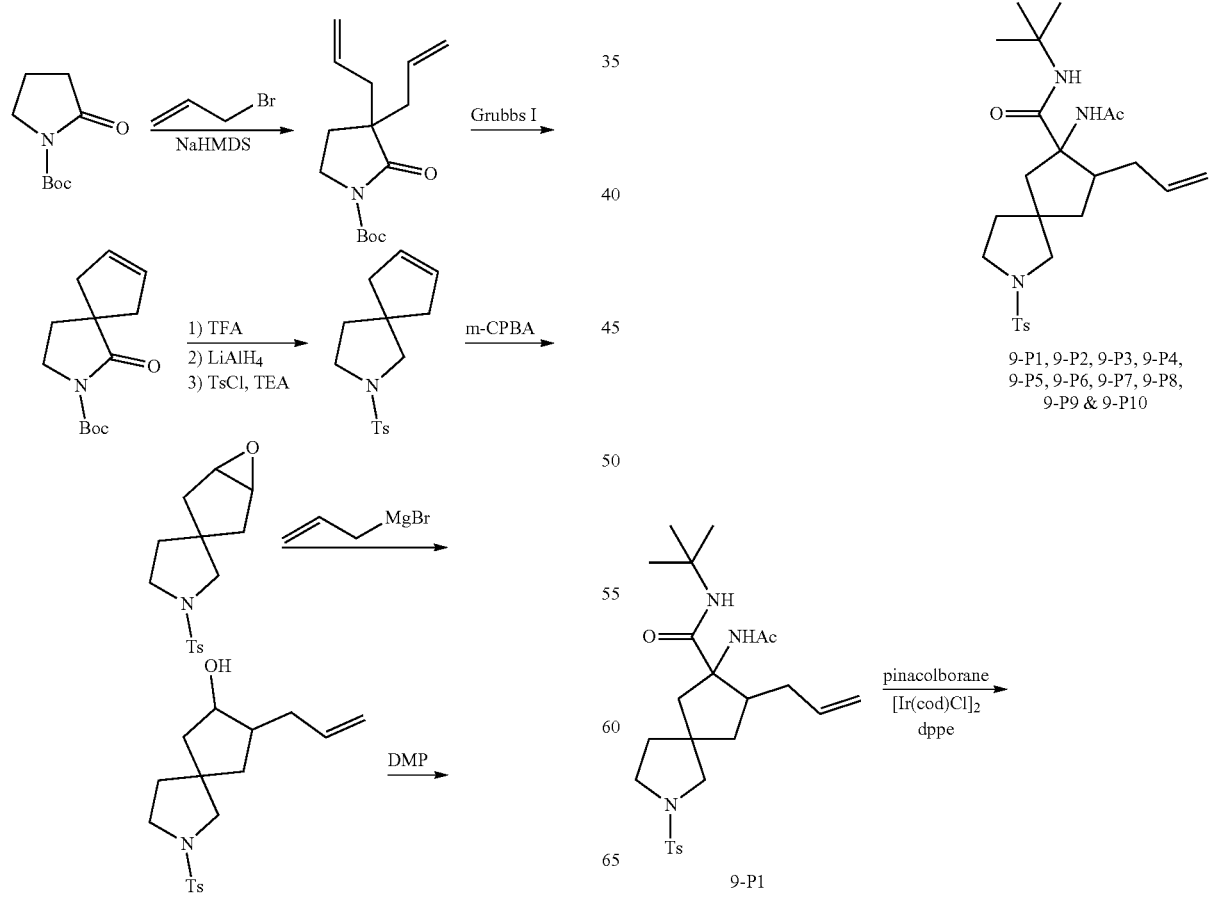
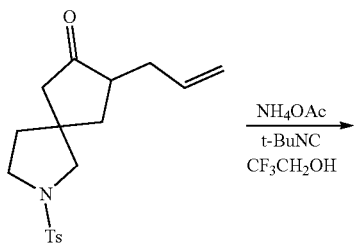
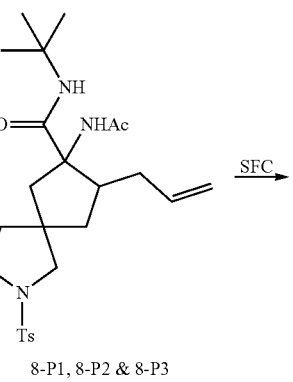
8-P1, 8-P2 & 8-P3
9-P1, 9-P2, 9-P3, 9-P4, 9-P5, 9-P6, 9-P7, 9-P8, 9-P9 & 9-P10
9-P1

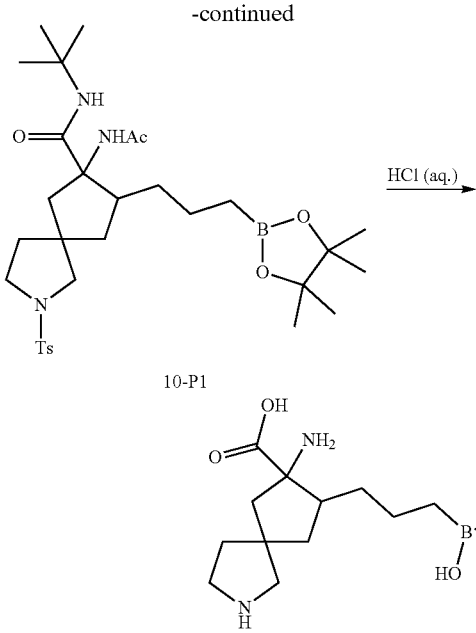

Example 21a

Step 1: tert-butyl 3,3-diallyl-2-oxopyrrolidine-1-carboxylate

NaHMDS (324 mL, 324 mmol, 1 M in THF) was added dropwise to a solution of tert-butyl 2-oxopyrrolidine-1-carboxylate (30 g, 162 mmol) and 3-bromoprop-1-ene (49 g, 405 mmol) in THF (300 mL) at −78° C. under $N_2$ over 30 min. The reaction was stirred at −78° C. for 2 h. The reaction mixture was quenched with saturated $NH_4Cl$ (aq.), then extracted with EtOAc. The combined organic phases were washed with brine, dried over anhydrous $Na_2SO_4$, filtered and concentrated under reduced pressure. The residue was purified by silica gel column chromatography (EtOAc in hexanes) to give tert-butyl 3,3-diallyl-2-oxopyrrolidine-1-carboxylate. LCMS ($C_{11}H_{16}NO_3^+$) (ES, m/z): 210[M+H-tBu]$^+$.

Step 2: tert-butyl 1-oxo-2-azaspiro[4.4]non-7-ene-2-carboxylate

A mixture of tert-butyl 3,3-diallyl-2-oxopyrrolidine-1-carboxylate (17 g, 64 mmol) and Grubbs I (2.7 g, 3.2 mmol) in DCM (250 mL) was degassed and backfilled with $N_2$ (three times). The mixture was stirred at 25° C. for 192 h. The reaction mixture was quenched with water and extracted with DCM. The combined organic phases were washed with brine, dried over anhydrous $Na_2SO_4$, filtered and concentrated under reduced pressure. The residue was purified by silica gel column chromatography (EtOAc in hexanes) to give tert-butyl 1-oxo-2-azaspiro[4.4]non-7-ene-2-carboxylate. LCMS ($C_{13}H_{19}NO_3Na^+$) (ES, m/z): 260 [M+Na]$^+$.

Step 3: 2-tosyl-2-azaspiro[4.4]non-7-ene

Tert-butyl 1-oxo-2-azaspiro[4.4]non-7-ene-2-carboxylate (8 g, 34 mmol) was added to TFA (2.6 mL, 33 mmol) portionwise at 0° C. The resulting mixture was stirred at 25° C. for 2 h. TFA was evaporated in vacuo and the residue was diluted with saturated $Na_2CO_3$ (aq.) and extracted with EtOAc. The combined organic layer was dried over anhydrous $Na_2SO_4$, filtered and concentrated reduced pressure. The residue was dissolved in THF (50 mL). $LiAlH_4$ (1.54 g, 41 mmol) in THF (30 mL) was added at 0° C. The reaction was stirred at 60° C. for 2 h. The reaction was cooled to 25° C. and quenched with 30% KOH in water and extracted with EtOAc. The combined organic phases were washed with brine, dried over anhydrous $Na_2SO_4$, filtered and concentrated reduced pressure. The residue was dissolved in DCM (100 mL). 4-methylbenzene-1-sulfonyl chloride (13 g, 67 mmol) and TEA (14 mL, 101 mmol) were added. The suspension was stirred at 25° C. for 16 h. The reaction was quenched with water and extracted with DCM. The combined organic phases were dried over anhydrous $Na_2SO_4$, filtered and concentrated under reduced pressure. The residue was purified by silica gel column chromatography (EtOAc in hexanes) to give 2-tosyl-2-azaspiro[4.4]non-7-ene. LCMS ($C_{15}H_{20}NO_2S^+$) (ES, m/z): 278 [M+H]$^+$.

Step 4: 1'-tosyl-6-oxaspiro[bicyclo[3.1.0]hexane-3,3'-pyrrolidine]

meta-chloroperoxybenzoic acid (7.8 g, 36 mmol, 80% purity) was added to a solution of 2-tosyl-2-azaspiro[4.4]non-7-ene (8 g, 30.3 mmol) in DCM (100 mL) at 0° C. The reaction mixture was stirred at 25° C. for 5 h. The reaction was quenched with 4 N NaOH in water and extracted with DCM. The combined organic phases were washed with brine, dried over anhydrous $Na_2SO_4$, filtered and concentrated under reduced pressure. The residue was purified by silica gel column chromatography (EtOAc in hexanes) to give 1'-tosyl-6-oxaspiro[bicyclo[3.1.0]hexane-3,3'-pyrrolidine]. LCMS ($C_{15}H_{20}NO_3S^+$) (ES, m/z): 294 [M+H]$^+$.

Step 5: 8-allyl-2-tosyl-2-azaspiro[4.4]nonan-7-ol

Allylmagnesium bromide (33 mL, 33 mmol, 1 M in diethyl ether) was added to a solution of 1'-tosyl-6-oxaspiro[bicyclo[3.1.0]hexane-3,3'-pyrrolidine] (4.8 g, 16 mmol) in THF (20 mL) over 5 min at 25° C. The reaction was stirred at 25° C. for 2 h under $N_2$. The reaction was quenched with saturated $NH_4Cl$ (aq.) and extracted with EtOAc. The combined organic phases were washed with brine, dried over anhydrous $Na_2SO_4$, filtered and concentrated under reduced pressure. The crude product was used in the next step directly. LCMS ($C_{18}H_{26}NO_3S^+$) (ES, m/z): 336 [M+H]$^+$.

Step 6: 8-allyl-2-tosyl-2-azaspiro[4.4]nonan-7-one

DMP (10 g, 24.6 mmol) was added to a solution of 8-allyl-2-tosyl-2-azaspiro[4.4]nonan-7-ol (5.5 g, 16 mmol) in DCM (100 mL) at 0° C. The reaction suspension was stirred at 25° C. for 15 h.

The reaction was quenched with water and extracted with DCM. The combined organic phases were filtered. The filtrate washed with brine (30 mL), dried over anhydrous $Na_2SO_4$, filtered and concentrated under reduced pressure. The residue was purified by silica gel column chromatography (EtOAc in hexanes) to give 8-allyl-2-tosyl-2-azaspiro[4.4]nonan-7-one. LCMS ($C_{18}H_{24}NO_3S^+$) (ES, m/z): 334 [M+H]$^+$.

Step 7: 7-acetamido-8-allyl-N-(tert-butyl)-2-tosyl-2-azaspiro[4.4]nonane-7-carboxamide $NH_4OAc$ (8.4 g, 108 mmol) and 2-isocyano-2-methylpropane (4.5 g, 54 mmol) was added to a solution of 8-allyl-2-tosyl-2-azaspiro[4.4]nonan-7-one (4.3 g, 10 mmol) in 2,2,2-trifluoroethyl alcohol (20 mL). The reaction mixture was stirred at 35° C. for 15 h under $N_2$. The reaction mixture was quenched with water and extracted with EtOAc. The combined organic phases were washed with brine, dried over anhydrous $Na_2SO_4$, filtered and concentrated under reduced pressure. The residue was purified by silica gel column chromatography (EtOAc in hexanes) to give three isomers of 7-acetamido-8-allyl-N-(tert-butyl)-2-tosyl-2-azaspiro[4.4]nonane-7-carboxamide (8-P1, 8-P2 and 8-P3). 8-P1: LCMS ($C_{25}H_{38}N_3O_4S^+$) (ES, m/z): 476 [M+H]$^+$. $^1$H NMR (400 MHz, chloroform-d) δ 7.67 (d, J=8.3 Hz, 2H), 7.31 (br d, J=7.9 Hz, 2H), 6.64 (br s, 1H), 6.01 (br s, 1H), 5.78-5.59 (m, 1H), 5.09-4.92 (m, 2H), 3.37-3.14 (m, 3H), 2.95 (d, J=9.2 Hz, 1H), 2.61-2.48 (m, 1H), 2.42 (s, 3H), 2.36-2.19 (m, 3H), 2.02 (s, 3H), 1.99-1.86 (m, 1H), 1.84-1.60 (m, 3H), 1.53-1.39 (m, 1H), 1.27 (s, 9H). 8-P2: (LCMS ($C_{25}H_{38}N_3O_4S^+$) (ES, m/z): 476 [M+H]$^+$. $^1$H NMR (400 MHz, chloroform-d) δ 7.69 (br d, J=7.9 Hz, 2H), 7.31 (br d, J=7.5 Hz, 2H), 6.69 (br s, 0.3H), 6.13-5.92 (m, 1.4H), 5.81 (br s, 0.3H), 5.67-5.55 (m, 1H), 5.11-4.95 (m, 2H), 3.34-3.13 (m, 3H), 3.05-3.00 (m, 1H), 2.79-2.68 (m, 0.5H), 2.60-2.49 (m, 0.5H), 2.43 (s, 3H), 2.33-2.06 (m, 2H), 1.99 (br s, 3H), 1.95-1.76 (m, 3H), 1.71-1.65 (m, 1H), 1.58-1.41 (m, 1.5H), 1.32-1.28 (m, 9.5H). 8-P3: LCMS ($C_{25}H_{38}N_3O_4S^+$) (ES, m/z): 476 [M+H]$^+$. $^1$H NMR (400 MHz, chloroform-d) δ 7.69 (d, J=8.3 Hz, 2H), 7.30 (br d, J=7.9 Hz, 2H), 6.68 (br s, 0.3H), 6.05 (br s, 0.7H), 5.97 (br s, 0.7H), 5.83 (br s, 0.3H), 5.73-5.55 (m, 1H), 5.08-4.95 (m, 2H), 3.36-3.23 (m, 3H), 3.21-3.15 (m, 1H), 2.99 (d, J=9.6 Hz, 0.3H), 2.62 (d, J=14.5 Hz, 0.7H), 2.56-2.48 (m, 0.3H), 2.42 (s, 3H), 2.40-2.33 (m, 0.3H), 2.32-2.13 (m, 2H), 2.08-2.01 (m, 0.4H), 2.00-1.94 (m, 3H), 1.92-1.81 (m, 1H), 1.79-1.59 (m, 2H), 1.58-1.40 (m, 1.5H), 1.36-1.22 (m, 9.5H).

Step 8: 7-acetamido-8-allyl-N-(tert-butyl)-2-tosyl-2-azaspiro[4.4]nonane-7-carboxamide 9-P1, 9-P2, 9-P3, 9-P4, 9-P5, 9-P6, 9-P7, 9-P8, 9-P9 and 9-P10

7-acetamido-8-allyl-N-(tert-butyl)-2-tosyl-2-azaspiro[4.4]nonane-7-carboxamide (8-P1) (1 g, 2.102 mmol) was resolved by Chiral-SFC [Column: DAICEL CHIRALPAK AD (250 mm*50 mm, 10 um), Mobile phase: A: $CO_2$, B: Condition, EtOH (0.1% $NH_3H_2O$), Gradient: 20% of B in 3.5 min, and hold 20% for 1 min, Flow Rate (mL/min) 180 mL/min, Column temperature: 40° C.] to give 7-acetamido-8-allyl-N-(tert-butyl)-2-tosyl-2-azaspiro[4.4]nonane-7-carboxamide (9-P1, $t_r$=2.81 min) as the first eluting peak, and 7-acetamido-8-allyl-N-(tert-butyl)-2-tosyl-2-azaspiro[4.4]nonane-7-carboxamide (9-P2, $t_r$=3.07 min) as the second eluting peak. 9-P1: LCMS ($C_{25}H_{38}N_3O_4S^+$) (ES, m/z): 476 [M+H]$^+$. $^1$H NMR (400 MHz, chloroform-d) δ 7.68 (d, J=8.3 Hz, 2H), 7.32 (d, J=7.9 Hz, 2H), 6.69 (s, 1H), 5.92 (s, 1H), 5.79-5.62 (m, 1H), 5.13-4.97 (m, 2H), 3.35-3.26 (m, 1H), 3.25-3.16 (m, 2H), 2.95 (d, J=9.2 Hz, 1H), 2.63-2.50 (m, 1H), 2.43 (s, 3H), 2.38-2.32 (m, 1H), 2.32-2.27 (m, 1H), 2.26 (s, 1H), 2.03 (s, 3H), 1.97-1.85 (m, 1H), 1.80-1.59 (m, 3H), 1.49-1.38 (m, 1H), 1.28 (s, 9H). 9-P2: LCMS ($C_{25}H_{38}N_3O_4S^+$) (ES, m/z): 476 [M+H]$^+$. $^1$H NMR (400 MHz, chloroform-d) δ 7.68 (d, J=8.3 Hz, 2H), 7.32 (d, J=7.9 Hz, 2H), 6.71 (s, 1H), 5.89 (s, 1H), 5.77-5.62 (m, 1H), 5.12-4.98 (m, 2H), 3.34-3.24 (m, 1H), 3.20 (d, J=9.6 Hz, 2H), 2.95 (d, J=9.2 Hz, 1H), 2.64-2.51 (m, 1H), 2.43 (s, 3H), 2.39-2.33 (m, 1H), 2.28 (br s, 1H), 2.26-2.21 (m, 1H), 2.04 (s, 3H), 1.98-1.85 (m, 1H), 1.79-1.59 (m, 3H), 1.50-1.40 (m, 1H), 1.28 (s, 9H).

7-acetamido-8-allyl-N-(tert-butyl)-2-tosyl-2-azaspiro[4.4]nonane-7-carboxamide (8-P2) (1.40 g, 2.102 mmol) was resolved by Chiral-SFC [Column: DAICEL CHIRAL-PAK AD (250 mm*50 mm, 10 um), Mobile phase: A: $CO_2$, B: Condition, EtOH (0.1% $NH_3H_2O$), Gradient: 20% of B in 6.1 min, and hold 20% for 1 min, Flow Rate (mL/min) 180 mL/min, Column temperature: 40° C.] to give 7-acetamido-8-allyl-N-(tert-butyl)-2-tosyl-2-azaspiro[4.4]nonane-7-carboxamide (9-P3, $t_r$=2.73 min) as the first eluting peak, and (7R,8S)-7-acetamido-8-allyl-N-(tert-butyl)-2-tosyl-2-azaspiro[4.4]nonane-7-carboxamide (9-P4, $t_r$=3.00 min) as the second eluting peak, and 7-acetamido-8-allyl-N-(tert-butyl)-2-tosyl-2-azaspiro[4.4]nonane-7-carboxamide (9-P5, $t_r$=3.19 min) as the third eluting peak, and 7-acetamido-8-allyl-N-(tert-butyl)-2-tosyl-2-azaspiro[4.4]nonane-7-carboxamide (9-P6, $t_r$=3.75 min) as the fourth eluting peak. 9-P3: LCMS ($C_{25}H_{38}N_3O_4S^+$) (ES, m/z): 476 [M+H]$^+$. $^1$H NMR (400 MHz, chloroform-d) δ 7.69 (d, J=7.9 Hz, 2H), 7.31 (d, J=7.9 Hz, 2H), 6.12 (br s, 1H), 6.02 (s, 1H), 5.71-5.57 (m, 1H), 5.05-4.97 (m, 2H), 3.33-3.17 (m, 3H), 3.01 (d, J=9.2 Hz, 1H), 2.76 (d, J=14.9 Hz, 1H), 2.43 (s, 3H), 2.33-2.21 (m, 1H), 2.19-2.09 (m, 1H), 1.98 (s, 3H), 1.95-1.87 (m, 1H), 1.86-1.77 (m, 2H), 1.71 (d, J=14.9 Hz, 1H), 1.58-1.53 (m, 1H), 1.51-1.44 (m, 1H), 1.30 (s, 9H). 9-P4: LCMS ($C_{25}H_{38}N_3O_4S^+$) (ES, m/z): 476 [M+H]$^+$. $^1$H NMR (400 MHz, chloroform-d) δ 7.69 (d, J=8.3 Hz, 2H), 7.30 (d, J=7.9 Hz, 2H), 6.69 (s, 1H), 5.80 (s, 1H), 5.74-5.61 (m, 1H), 5.07-4.97 (m, 2H), 3.36-3.23 (m, 2H), 3.19 (d, J=9.6 Hz, 1H), 2.99 (d, J=9.6 Hz, 1H), 2.60-2.48 (m, 1H), 2.42-2.39 (m, 4H), 2.33-2.25 (m, 1H), 2.18-2.14 (m, 1H), 1.99 (s, 3H), 1.93-1.82 (m, 1H), 1.71-1.62 (m, 4H), 1.30 (s, 9H). 9-P5: LCMS ($C_{25}H_{37}N_3O_4SNa^+$) (ES, m/z): 498 [M+Na]$^+$. $^1$H NMR (400 MHz, chloroform-d) δ 7.69 (d, J=8.3 Hz, 2H), 7.30 (d, J=7.9 Hz, 2H), 6.69 (s, 1H), 5.80 (s, 1H), 5.74-5.57 (m, 1H), 5.07-4.98 (m, 2H), 3.35-3.23 (m, 2H), 3.19 (d, J=9.6 Hz, 1H), 2.99 (d, J=9.6 Hz, 1H), 2.63-2.47 (m, 1H), 2.42-2.39 (m, 4H), 2.34-2.23 (m, 1H), 2.18-2.14 (m, 1H), 1.99 (s, 3H), 1.94-1.80 (m, 1H), 1.71-1.61 (m, 4H), 1.30 (s, 9H). 9-P6: LCMS ($C_{25}H_{38}N_3O_4S^+$) (ES, m/z): 476 [M+H]$^+$. $^1$H NMR (400 MHz, chloroform-d) δ 7.69 (d, J=8.3 Hz, 2H), 7.31 (d, J=7.9 Hz, 2H), 6.05 (s, 1H), 6.01 (s, 1H), 5.72-5.51 (m, 1H), 5.06-4.98 (m, 2H), 3.34-3.18 (m, 3H), 3.01 (d, J=9.2 Hz, 1H), 2.75 (d, J=14.9 Hz, 1H), 2.43 (s, 3H), 2.32-2.20 (m, 1H), 2.19-2.09 (m, 1H), 1.99 (s, 3H), 1.95-1.87 (m, 1H), 1.87-1.77 (m, 2H), 1.72 (br d, J=14.5 Hz, 1H), 1.61-1.53 (m, 1H), 1.52-1.46 (m, 1H), 1.30 (s, 9H).

7-acetamido-8-allyl-N-(tert-butyl)-2-tosyl-2-azaspiro[4.4]nonane-7-carboxamide (0.95 g, 1.997 mmol, 8-P3) was resolved by Chiral-SFC [Column: DAICEL CHIRALPAK AD (250 mm*50 mm, 10 um), Mobile phase: A: $CO_2$, B: Condition, EtOH (0.1% $NH_3H_2O$), Gradient: 20% of B in 5 min, and hold 20% for 1 min, Flow Rate (mL/min) 180 mL/min, Column temperature: 40° C.] to give 7-acetamido-8-allyl-N-(tert-butyl)-2-tosyl-2-azaspiro[4.4]nonane-7-carboxamide (9-P7, $t_r$=2.77 min) as the first eluting peak, and 7-acetamido-8-allyl-N-(tert-butyl)-2-tosyl-2-azaspiro[4.4]nonane-7-carboxamide (9-P8, $t_r$=3.03 min) as the second eluting peak, and 7-acetamido-8-allyl-N-(tert-butyl)-2-tosyl-2-azaspiro[4.4]nonane-7-carboxamide (9-P9, $t_r$=3.19 min) as the third eluting peak, and 7-acetamido-8-allyl-N-(tert-butyl)-2-tosyl-2-azaspiro[4.4]nonane-7-carboxamide (9-P10, $t_r$=4.15 min) as the fourth eluting peak. 9-P7: LCMS ($C_{25}H_{38}N_3O_4S^+$) (ES, m/z): 476 [M+H]$^+$. $^1$H NMR (400 MHz, chloroform-d) δ 7.69 (d, J=7.9 Hz, 2H), 7.30 (d, J=7.9 Hz, 2H), 6.05 (br s, 1H), 5.97 (s, 1H), 5.70-5.55 (m, 1H), 5.04-4.97 (m, 2H), 3.34-3.27 (m, 3H), 3.18 (d, J=10.1 Hz, 1H), 2.60 (d, J=14.9 Hz, 1H), 2.42 (s, 3H), 2.28-2.17 (m, 2H), 1.96 (s, 3H), 1.86 (br d, J=4.8 Hz, 1H), 1.77 (br d, J=14.9 Hz, 1H), 1.70 (t, J=6.8 Hz, 2H), 1.54 (br d, J=6.1 Hz, 1H), 1.48 (br d, J=10.5 Hz, 1H), 1.32 (s, 9H). 9-P8: LCMS ($C_{25}H_{37}N_3O_4SNa^+$) (ES, m/z): 498 [M+Na]$^+$. $^1$H NMR (400 MHz, chloroform-d) δ 7.69 (d, J=7.9 Hz, 2H), 7.31 (d, J=7.9 Hz, 2H), 6.70 (s, 1H), 5.79 (s, 1H), 5.73-5.61 (m, 1H), 5.08-4.99 (m, 2H), 3.35-3.23 (m, 2H), 3.20 (d, J=9.6 Hz, 1H), 2.99 (d, J=9.6 Hz, 1H), 2.62-2.49 (m, 1H), 2.42 (s, 3H), 2.40-2.37 (m, 1H), 2.35-2.25 (m, 1H), 2.15 (d, J=14.5 Hz, 1H), 1.99 (s, 3H), 1.93-1.81 (m, 1H), 1.74-1.58 (m, 4H), 1.30 (s, 9H). 9-P9: LCMS ($C_{25}H_{38}N_3O_4S^+$) (ES, m/z): 476 [M+H]$^+$. $^1$H NMR (400 MHz, chloroform-d) δ 7.69 (d, J=7.9 Hz, 2H), 7.31 (d, J=7.9 Hz, 2H), 6.70 (s, 1H), 5.78 (s, 1H), 5.73-5.61 (m, 1H), 5.08-4.99 (m, 2H), 3.38-3.23 (m, 2H), 3.20 (d, J=9.6 Hz, 1H), 2.99 (d, J=9.6 Hz, 1H), 2.63-2.48 (m, 1H), 2.42 (s, 3H), 2.41-2.39 (m, 1H), 2.34-2.24 (m, 1H), 2.15 (d, J=14.5 Hz, 1H), 1.99 (s, 3H), 1.93-1.81 (m, 1H), 1.71-1.62 (m, 4H), 1.30 (s, 9H). 9-P10: LCMS ($C_{25}H_{37}N_3O_4SNa^+$) (ES, m/z): 498 [M+Na]$^+$. $^1$H NMR (400 MHz, chloroform-d) δ 7.70 (d, J=7.9 Hz, 2H), 7.30 (d, J=7.9 Hz, 2H), 5.99 (s, 1H), 5.95 (s, 1H), 5.74-5.57 (m, 1H), 5.06-4.97 (m, 2H), 3.35-3.27 (m, 3H), 3.18 (d, J=9.6 Hz, 1H), 2.59 (d, J=14.5 Hz, 1H), 2.42 (s, 3H), 2.29-2.19 (m, 2H), 1.96 (s, 3H), 1.93-1.84 (m, 1H), 1.78 (d, J=14.9 Hz, 1H), 1.71 (t, J=7.0 Hz, 2H), 1.59-1.53 (m, 1H), 1.51-1.42 (m, 1H), 1.32 (s, 9H).

Step 9: 7-acetamido-N-(tert-butyl)-8-(3-(4,4,5,5-tetramethyl-1,3,2-dioxaborolan-2-yl)propyl)-2-tosyl-2-azaspiro[4.4]nonane-7-carboxamide Chloro(1,5-cyclooctadiene)iridium(I) dimer (9.9 mg, 0.015 mmol) and 1,2-bis(diphenylphosphino)ethane (17 mg, 0.042 mmol) were added to a mixture of 7-acetamido-8-allyl-N-(tert-butyl)-2-tosyl-2-azaspiro[4.4]nonane-7-carboxamide (9-P1) (100 mg, 0.21 mmol), 4,4,5,5-tetramethyl-1,3,2-dioxaborolane (269 mg, 2.1 mmol), cyclohexene (86 mg, 1.1 mmol) in DCM (10 mL) at 20° C. The reaction mixture was degassed and backfilled with N$_2$ (three times). The reaction mixture was stirred at 20° C. for 15 h under N$_2$. The reaction mixture was quenched with water and extracted with DCM. The combined organic phases were washed with brine, dried over anhydrous Na$_2$SO$_4$, filtered and concentrated under reduced pressure. The residue was purified by RP-HPLC [C18 column, water (0.1% TFA)-CH$_3$CN] to give 7-acetamido-N-(tert-butyl)-8-(3-(4,4,5,5-tetramethyl-1,3,2-dioxaborolan-2-yl)propyl)-2-tosyl-2-azaspiro[4.4]nonane-7-carboxamide (10-P1). LCMS ($C_{31}H_{51}BN_3O_6S^+$) (ES, m/z): 604 [M+H]$^+$.

Step 10: 7-amino-8-(3-boronopropyl)-2-azaspiro[4.4]nonane-7-carboxylic acid

A solution of 7-acetamido-N-(tert-butyl)-8-(3-(4,4,5,5-tetramethyl-1,3,2-dioxaborolan-2-yl)propyl)-2-tosyl-2-azaspiro[4.4]nonane-7-carboxamide (100 mg, 0.17 mmol) in 12 N HCl in water (5 mL, 60 mmol) was stirred at 120° C. for 15 h. The reaction mixture was concentrated under reduced pressure. The residue was dissolved in 4 N NaOH in water. The mixture was concentrated under reduced pressure. The residue was purified by RP-HPLC [C18 column, water (0.05% HCl)—CH$_3$CN] to give 7-amino-8-(3-boronopropyl)-2-azaspiro[4.4]nonane-7-carboxylic acid as a HCl salt (21a). LCMS ($C_{12}H_{22}BN_2O_3^+$) (ES, m/z): 253 [M+H-H$_2$O]$^+$. $^1$H NMR (400 MHz, Deuterium Oxide) δ 3.35-3.23 (m, 2H), 3.22-3.06 (m, 2H), 2.64-2.56 (m, 1H), 2.55-2.40 (m, 1H), 2.04-1.77 (m, 4H), 1.65-1.45 (m, 1H), 1.41-1.06 (m, 4H), 0.69-0.44 (m, 2H).

Example 21b, 21c, 21d, 21e, 21f, 21g, 21h, 21i and 21j were made from 9-P2, 9-P3, 9-P4, 9-P5, 9-P6, 9-P7, 9-P8, 9-P9 and 9-P10, respectively, using the same procedure as above. 21b LCMS ($C_{12}H_{22}BN_2O_3^+$) (ES, m/z): 253 [M+H-H$_2$O]$^+$. $^1$H NMR (400 MHz, Deuterium Oxide) δ 3.43-3.30 (m, 2H), 3.29-3.09 (m, 2H), 2.84-2.63 (m, 1H), 2.62-2.49 (m, 1H), 2.17-1.87 (m, 4H), 1.73-1.55 (m, 1H), 1.48-1.12 (m, 4H), 0.77-0.52 (m, 2H). 20c LCMS ($C_{12}H_{22}BN_2O_3^+$) (ES, m/z): 253 [M+H-H$_2$O]$^+$. $^1$H NMR (400 MHz, Deuterium Oxide) δ 3.45-3.23 (m, 3H), 3.19-3.16 (m, 1H), 2.68-2.65 (m, 1H), 2.37-2.23 (m, 1H), 2.18-2.02 (m, 4H), 1.87-1.73 (m, 1H), 1.61-1.50 (m, 1H), 1.50-1.38 (m, 1H), 1.37-1.23 (m, 1H), 1.23-1.07 (m, 1H), 0.82-0.64 (m, 2H). 20d LCMS ($C_{12}H_{22}BN_2O_3^+$) (ES, m/z): 253 [M+H-H$_2$O]$^+$. $^1$H NMR (400 MHz, Deuterium Oxide) δ 3.46-3.17 (m, 4H), 2.61-2.56 (m, 2H), 2.18-1.88 (m, 4H), 1.77-1.56 (m, 2H), 1.45-1.18 (m, 3H), 0.98-0.57 (m, 2H). 20e LCMS ($C_{12}H_{22}BN_2O_3^+$) (ES, m/z): 253 [M+H-H$_2$O]$^+$.

$^1$H NMR (400 MHz, Deuterium Oxide) δ 3.54-3.18 (m, 4H), 2.70-2.56 (m, 2H), 2.21-1.88 (m, 4H), 1.82-1.56 (m, 2H), 1.50-1.14 (m, 3H), 0.96-0.58 (m, 2H). 20f LCMS ($C_{12}H_{22}BN_2O_3^+$) (ES, m/z): 253 [M+H-H$_2$O]$^+$. $^1$H NMR (400 MHz, Deuterium Oxide) δ 3.48-3.11 (m, 4H), 2.75-2.61 (m, 1H), 2.42-2.26 (m, 1H), 2.18-1.98 (m, 4H), 1.89-1.72 (m, 1H), 1.65-1.50 (m, 1H), 1.49-1.38 (m, 1H), 1.36-1.24 (m, 1H), 1.22-1.08 (m, 1H), 0.84-0.64 (m, 2H). 20 g LCMS ($C_{12}H_{22}BN_2O_3^+$) (ES, m/z): 253 [M+H-H$_2$O]$^+$. $^1$H NMR (400 MHz, Deuterium Oxide) δ 3.49-3.30 (m, 4H), 2.72-2.52 (m, 1H), 2.45-2.29 (m, 1H), 2.19-1.94 (m, 4H), 1.84-1.72 (m, 1H), 1.64-1.50 (m, 1H), 1.49-1.40 (m, 1H), 1.39-1.25 (m, 1H), 1.21-1.09 (m, 1H), 0.82-0.67 (m, 2H). 20h LCMS ($C_{12}H_{22}BN_2O_3^+$) (ES, m/z): 253 [M+H-H$_2$O]$^+$. $^1$H NMR (400 MHz, Deuterium Oxide) δ 3.47-3.19 (m, 4H), 2.78-2.54 (m, 2H), 2.41-1.89 (m, 5H), 1.70-1.63 (m, 1H), 1.51-1.17 (m, 3H), 1.00-0.59 (m, 2H). 20i LCMS ($C_{12}H_{22}BN_2O_3^+$) (ES, m/z): 253 [M+H-H$_2$O]$^+$. $^1$H NMR (400 MHz, Deuterium Oxide) δ 3.44-3.16 (m, 4H), 2.67-2.27 (m, 2H), 2.15-1.91 (m, 5H), 1.78-1.55 (m, 2H), 1.46-1.17 (m, 2H), 1.01-0.59 (m, 2H). 20j LCMS ($C_{12}H_{22}BN_2O_3^+$) (ES, m/z): 253 [M+H-H$_2$O]$^+$. $^1$H NMR (400 MHz, Deuterium Oxide) δ 3.43-3.30 (m, 4H), 2.66-2.62 (m, 1H), 2.14-1.94 (m, 4H), 1.85-1.74 (m, 1H), 1.66-1.43 (m, 2H), 1.43-1.24 (m, 1H), 1.23-1.11 (m, 1H), 0.83-0.64 (m, 2H).

Example 22: (3aR,4S,5S,6aR)-4-(3-boronopropyl)-5-(methylamino)octahydrocyclopenta[c]pyrrole-5-carboxylic acid

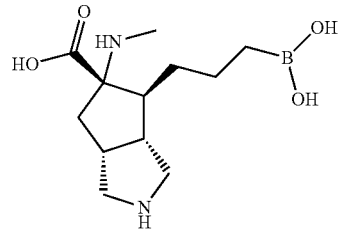 [SMILES: CN[C@@]1(C(=O)O)C[C@H]2CNC[C@H]2[C@@H]1CCCB(O)O]

Scheme X

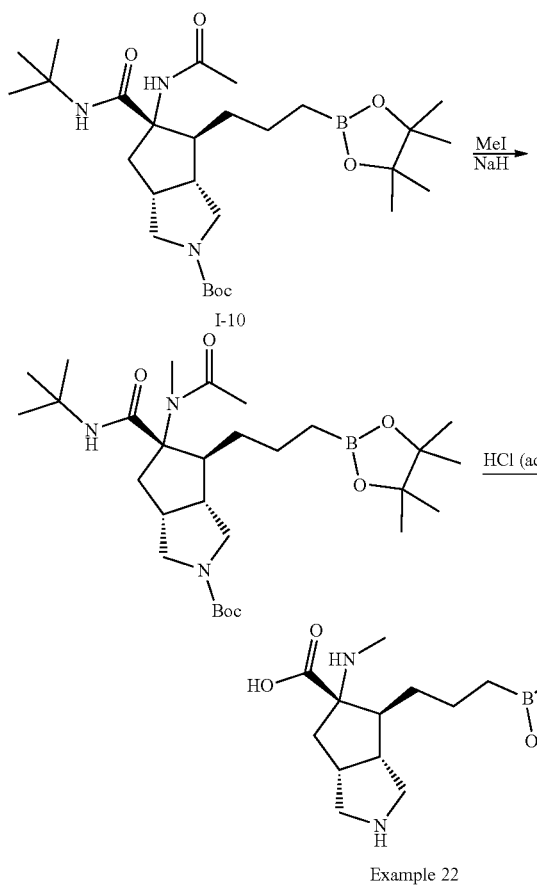

Step 1: tert-butyl (3aR,4S,5S,6aR)-5-(tert-butylcarbamoyl)-5-(N-methylacetamido)-4-(3-(4,4,5,5-tetramethyl-1,3,2-dioxaborolan-2-yl)propyl)hexahydrocyclopenta[c]pyrrole-2(1H)-carboxylate NaH (67 mg, 1.7 mmol, 60% in oil) was added to a mixture of tert-butyl (3aR,4S,5S,6aR)-5-acetamido-5-(tert-butylcarbamoyl)-4-(3-(4,4,5,5-tetramethyl-1,3,2-dioxaborolan-2-yl)propyl)hexahydrocyclopenta[c]pyrrole-2(1H)-carboxylate (300 mg, 0.56 mmol) in dry THF (3 mL) at 0° C. The reaction mixture was stirred for 10 min. Then, iodomethane (1.3 mL, 20 mmol) was added to the mixture. The reaction was warmed to 20° C. slowly and stirred for 12 h. The reaction was quenched with sat. NH$_4$Cl(aq.) and extracted with EtOAc. The organic layer was separated and the aqueous layer was re-extracted with EtOAc. The combined organics were dried over anhydrous Na$_2$SO$_4$, filtered and concentrated under reduced pressure. The residue was purified by RP-HPLC [C18 column, water (0.1% TFA)-CH$_3$CN] to give tert-butyl (3aR,4S,5S,6aR)-5-(tert-butylcarbamoyl)-5-(N-methylacetamido)-4-(3-(4,4,5,5-tetramethyl-1,3,2-dioxaborolan-2-yl)propyl)hexahydrocyclopenta[c]pyrrole-2(1H)-carboxylate. LCMS (C$_{24}$H$_{45}$BN$_3$O$_4$$^+$) (ES, m/z): 450 [M+H-Boc]$^+$.

Step 2: (3aR,4S,5S,6aR)-4-(3-boronopropyl)-5-(methylamino)octahydrocyclopenta[c]pyrrole-5-carboxylic acid A mixture of tert-butyl (3aR,4S,5S,6aR)-5-(tert-butylcarbamoyl)-5-(N-methylacetamido)-4-(3-(4,4,5,5-tetramethyl-1,3,2-dioxaborolan-2-yl)propyl)hexahydrocyclopenta[c]pyrrole-2(1H)-carboxylate (120 mg, 0.22 mmol) in 12N HCl in water (3 mL, 36 mmol) was stirred at 100° C. for 12 h. The mixture was concentrated under reduced pressure. The residue was treated with sat. NaHCO$_3$ (aq.) till pH~8, and the mixture was washed with DCM. The aqueous was concentrated under reduced pressure. The residue was acidified with 1N HCl in water till pH~6. The mixture was filtered and concentrated under reduced pressure to afford (3aR,4S,5S,6aR)-4-(3-boronopropyl)-5-(methylamino)octahydrocyclopenta[c]pyrrole-5-carboxylic acid as the HCl salt. LCMS (C$_{12}$H$_{22}$BN$_2$O$_3$$^+$) (ES, m/z): 253 [M+H-H$_2$O]. $^1$H NMR (400 MHz, Deuterium Oxide) δ 3.50-3.34 (m, 2H), 3.31-3.20 (m, 1H), 3.20-3.06 (m, 2H), 2.86-2.71 (m, 1H), 2.61 (s, 3H), 2.57 (br s, 1H), 2.09 (dt, J=3.4, 10.1 Hz, 1H), 1.76 (dd, J=9.0, 13.5 Hz, 1H), 1.52-1.41 (m, 1H), 1.38-1.18 (m, 2H), 1.17-1.05 (m, 1H), 0.74-0.54 (m, 2H).

Example 23a: (3aS,4S,5S,6aR)-5-amino-4-(3-boronopropyl)-1-oxooctahydrocyclopenta[c]pyrrole-5-carboxylic acid

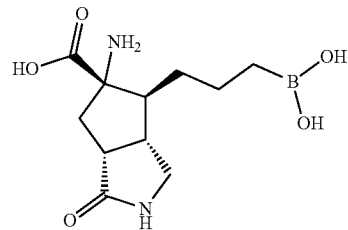

Example 23b: (3aR,5S,6S,6aR)-5-amino-6-(3-boronopropyl)-1-oxooctahydrocyclopenta[c]pyrrole-5-carboxylic acid

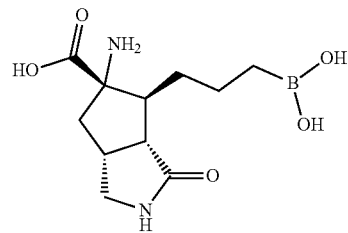

Scheme Y

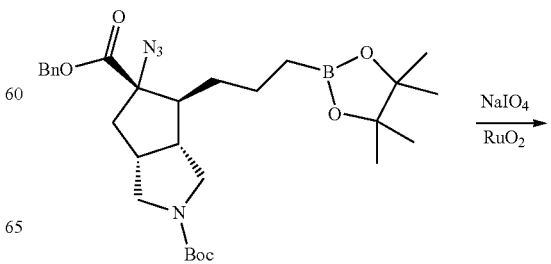

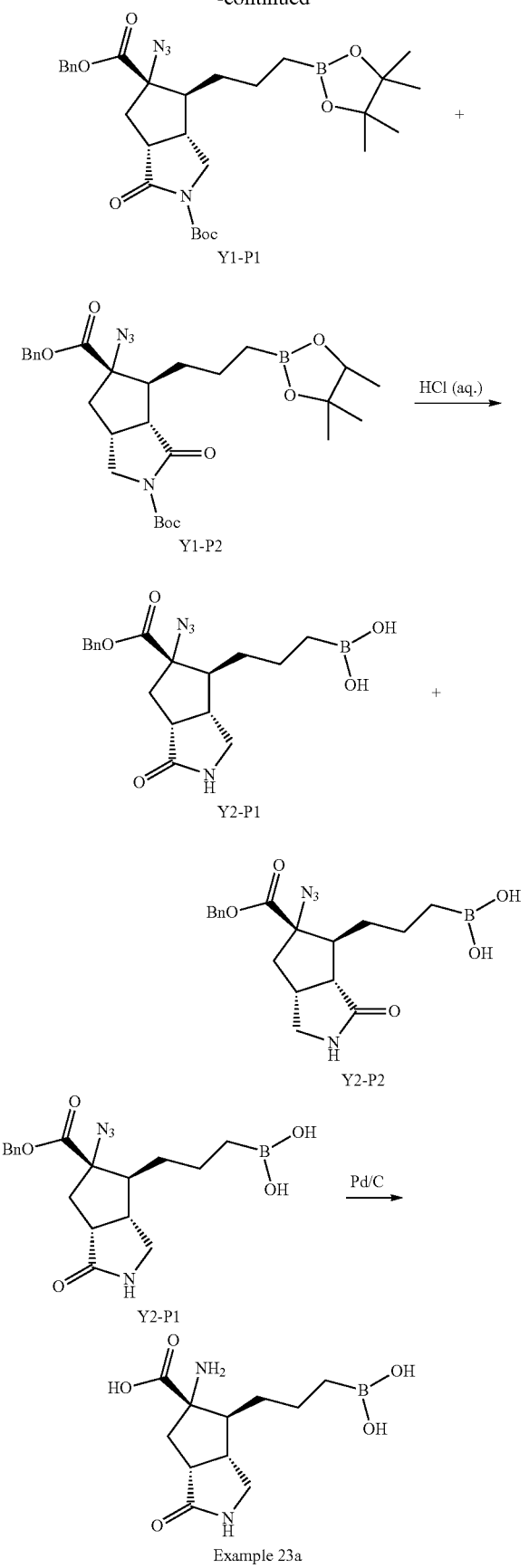

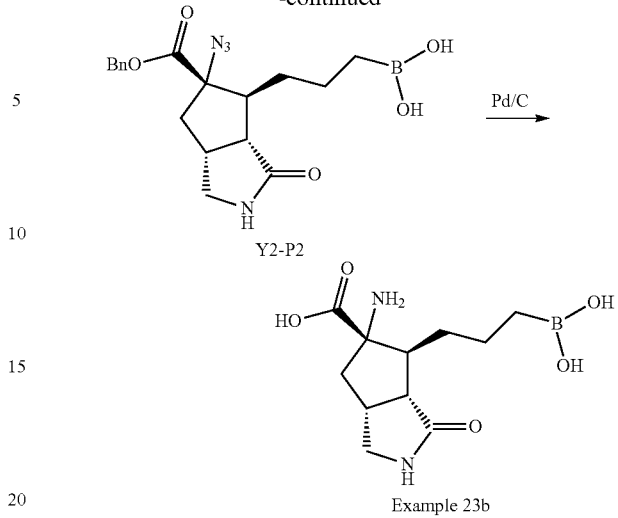

Example 23b

Step 1: 5-benzyl 2-(tert-butyl) (3aS,4S,5S,6aR)-5-azido-1-oxo-4-(3-(4,4,5,5-tetramethyl-1,3,2-dioxaborolan-2-yl)propyl)hexahydrocyclopenta[c]pyrrole-2,5(1H)-dicarboxylate and 5-benzyl 2-(tert-butyl) (3aR,5S,6S,6aR)-5-azido-1-oxo-6-(3-(4,4,5,5-tetramethyl-1,3,2-dioxaborolan-2-yl)propyl)hexahydrocyclopenta[c]pyrrole-2,5(1H)-dicarboxylate A mixture of ruthenium(IV) oxide (14 mg, 0.11 mmol) and sodium periodate (386 mg, 1.8 mmol) in water (3 mL) was stirred at 20° C. for 10 min. Then 5-benzyl 2-(tert-butyl) (3aR,4S,5S,6aR)-5-azido-4-(3-(4,4,5,5-tetramethyl-1,3,2-dioxaborolan-2-yl)propyl)hexahydrocyclopenta[c]pyrrole-2,5(1H)-dicarboxylate (200 mg, 0.36 mmol) in DCM (3 mL) was added to the mixture. The reaction mixture was stirred at 20° C. for another 15 h. The mixture was filtered and the organic layer was separated. The aqueous layer was extracted with DCM. The combined organics were dried over anhydrous Na$_2$SO$_4$, filtered and concentrated under reduced pressure. The residue was purified by RP-HPLC [C18 column, water (0.1% TFA)-CH$_3$CN] to give the mixture of 5-benzyl 2-(tert-butyl) (3aS,4S,5S,6aR)-5-azido-1-oxo-4-(3-(4,4,5,5-tetramethyl-1,3,2-dioxaborolan-2-yl)propyl)hexahydrocyclopenta[c]pyrrole-2,5(1H)-dicarboxylate and 5-benzyl 2-(tert-butyl) (3aR,5S,6S,6aR)-5-azido-1-oxo-6-(3-(4,4,5,5-tetramethyl-1,3,2-dioxaborolan-2-yl)propyl)hexahydrocyclopenta[c]pyrrole-2,5(1H)-dicarboxylate (1:1). LCMS (C$_{25}$H$_{34}$BN$_4$O$_7{}^+$) (ES, m/z) 513 [M+H-t-Bu]$^+$.

Step 2: (3-((3aS,4S,5S,6aR)-5-azido-5-((benzyloxy)carbonyl)-1-oxooctahydrocyclopenta[c]pyrrol-4-yl)propyl)boronic acid and (3-((3aR,4S,5S,6aR)-5-azido-5-((benzyloxy)carbonyl)-3-oxooctahydrocyclopenta[c]pyrrol-4-yl)propyl)boronic acid 12 N HCl in water (5 mL, 60 mmol) was added to the mixture of 5-benzyl 2-(tert-butyl) (3aS,4S,5S,6aR)-5-azido-1-oxo-4-(3-(4,4,5,5-tetramethyl-1,3,2-dioxaborolan-2-yl)propyl)hexahydrocyclopenta[c]pyrrole-2,5(1H)-dicarboxylate and 5-benzyl 2-(tert-butyl) (3aR,5S,6S,6aR)-5-azido-1-oxo-6-(3-(4,4,5,5-tetramethyl-1,3,2-dioxaborolan-2-yl)propyl)hexahydrocyclopenta[c]pyrrole-2,5(1H)-dicarboxylate (140 mg, 0.12 mmol) and the mixture was stirred at 15° C. for 80 h. The mixture was concentrated under reduced pressure. The residue was purified by RP-HPLC [C18 column, water (0.1% TFA)-CH₃CN] to give (3-((3aS,4S,5S,6aR)-5-azido-5-((benzyloxy)carbonyl)-1-oxooctahydrocyclopenta[c]pyrrol-4-yl)propyl)boronic acid (Y2-P1, t$_r$=0.761 min) as first eluting peak and (3-((3aR,4S,5S,6aR)-5-azido-5-((benzyloxy)carbonyl)-3-oxooctahydrocyclopenta[c]pyrrol-4-yl)propyl)boronic acid (Y2-P2, t$_r$=0.782 min) as second eluting peak. Y2-P1: LCMS (C$_{18}$H$_{24}$BN$_4$O$_5^+$) (ES, m/z) 387 [M+H]$^+$. $^1$H NMR (400 MHz, chloroform-d) δ 7.38 (br s, 5H), 7.10 (br s, 1H), 5.24 (s, 2H), 3.65 (dd, J=8.6, 10.3 Hz, 1H), 3.21 (br d, J=10.5 Hz, 1H), 3.15-3.07 (m, 1H), 2.80-2.57 (m, 2H), 2.19 (dd, J=5.3, 14.0 Hz, 1H), 2.03-1.99 (m, 1H), 1.48-1.22 (m, 3H), 1.21-1.08 (m, 1H), 0.68 (br t, J=7.5 Hz, 2H). Y2-P2: LCMS (C$_{18}$H$_{24}$BN$_4$O$_5^+$) (ES, m/z) 387 [M+H]$^+$. $^1$H NMR (400 MHz, CDCl$_3$) δ 7.37 (br s, 5H), 6.75 (br s, 1H), 5.23 (s, 2H), 3.63 (br s, 1H), 3.30-3.02 (m, 2H), 2.83 (br s, 1H), 2.67-2.37 (m, 2H), 2.05-1.98 (m, 1H), 1.75 (br d, J=10.5 Hz, 1H), 1.63-1.31 (m, 2H), 1.16 (br s, 1H), 0.85-0.52 (m, 2H).

Step 3: (3aS,4S,5S,6aR)-5-amino-4-(3-boronopropyl)-1-oxooctahydrocyclopenta[c]pyrrole-5-carboxylic acid 10% Pd/C (8 mg, 7.8 μmol) was added to a solution of (3-((3aS,4S,5S,6aR)-5-azido-5-((benzyloxy)carbonyl)-1-oxooctahydrocyclopenta[c]pyrrol-4-yl)propyl)boronic acid (30 mg, 0.078 mmol) in MeOH (2 mL) and 1 drop of 30% NH$_3$—H$_2$O under N$_2$ atmosphere. The mixture was degassed and backfilled with H$_2$ (three times). The resulting mixture was stirred under H$_2$ (15 psi) at 15° C. for 1 h. The catalyst was filtered off and the filtrate was concentrated under reduced pressure. The residue was purified by RP-HPLC [C18 column, water (0.1% HCl)—CH₃CN] to give (3aS,4S,5S,6aR)-5-amino-4-(3-boronopropyl)-1-oxooctahydrocyclopenta[c]pyrrole-5-carboxylic acid as the HCl salt. LCMS (C$_{11}$H$_{18}$BN$_2$O$_4$) (ES, m/z) 253 [M+H-H$_2$O]$^+$. $^1$H NMR (400 MHz, D$_2$O) δ 3.57-3.50 (m, 1H), 3.22-3.05 (m, 2H), 2.85-2.75 (m, 1H), 2.60 (dd, J=10.5, 14.0 Hz, 1H), 2.03 (br t, J=9.9 Hz, 1H), 1.86 (br dd, J=7.2, 14.3 Hz, 1H), 1.51-1.40 (m, 1H), 1.34-1.16 (m, 3H), 0.63 (br t, J=7.7 Hz, 2H).

Example 23b was made from Y2-P2 using the same procedure. 23b LCMS (C$_{11}$H$_{18}$BN$_2$O$_4$) (ES, m/z) 253 [M+H-H$_2$O]$^+$. $^1$H NMR (500 MHz, Deuterium Oxide) δ 3.74-3.55 (m, 1H), 3.47-3.35 (m, 1H), 3.26-3.15 (m, 1H), 2.88-2.85 (m, 1H), 2.73-2.57 (m, 1H), 2.33-2.19 (m, 1H), 1.97-1.77 (m, 1H), 1.61-1.57 (m, 1H), 1.52-1.39 (m, 2H), 1.19-1.16 (m, 1H), 0.94-0.52 (m, 2H).

Example 24: 5-amino-6-(3-boronopropyl)-2-azabicyclo[2.2.1]heptane-5-carboxylic acid

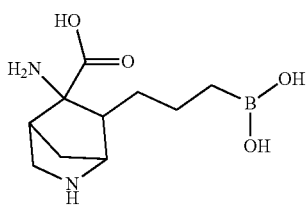

Scheme Z

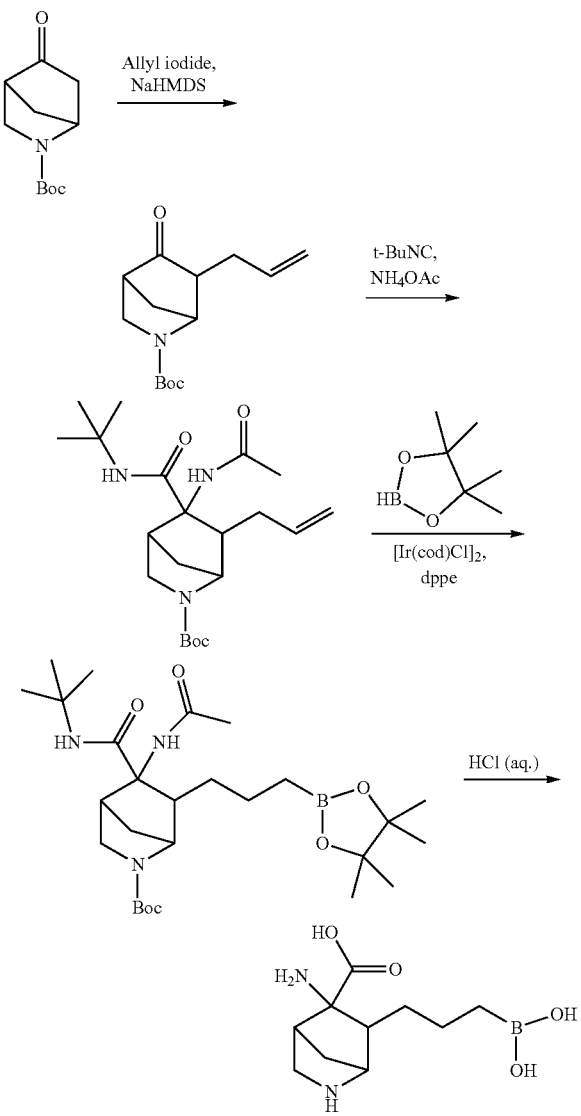

Step 1: tert-butyl 6-allyl-5-oxo-2-azabicyclo[2.2.1]heptane-2-carboxylate

Sodium bis(trimethylsilyl)amide (3.41 mL, 3.41 mmol, 1 M in THF) was added to a solution of tert-butyl 5-oxo-2-azabicyclo[2.2.1]heptane-2-carboxylate (600 mg, 2.8 mmol) and 3-iodoprop-1-ene (2.6 mL, 28 mmol) in THF (10 mL) at −40° C. under N$_2$ atmosphere. The mixture was stirred at −40° C. for 0.5 h then 20° C. for 0.5 h. Water and EtOAc were added to the mixture. The aqueous layer was extracted with EtOAc. The combined organic layers were washed with brine, dried over anhydrous Na$_2$SO$_4$, then filtered and concentrated under reduced pressure. The residue was purified by flash silica gel chromatography (EtOAc in hexanes) to give tert-butyl 6-allyl-5-oxo-2-azabicyclo[2.2.1]heptane-2-carboxylate. LCMS (C$_{10}$H$_{14}$NO$_3^+$) (ES, m/z): 196 [M+H-C$_4$H$_8$]$^+$.

Step 2: tert-butyl 5-acetamido-6-allyl-5-(tert-butyl-carbamoyl)-2-azabicyclo[2.2.1]heptane-2-carboxylate 2-Isocyano-2-methylpropane (164 mg, 2.0 mmol) and NH$_4$OAc (228 mg, 30 mmol) were added to a solution of tert-butyl 6-allyl-5-oxo-2-azabicyclo[2.2.1]heptane-2-carboxylate (165 mg, 0.66 mmol) in 2,2,2-trifluoroethyl alcohol (2 mL). The mixture was allowed to stir at 35° C. for 48 h. The reaction mixture was concentrated under reduced pressure. EtOAc was added to the residue, and the mixture was stirred at 35° C. for 10 min, then filtered off and filtrate was concentrated under reduced pressure. The residue was purified by flash silica gel chromatography (EtOAc in hexanes) to give tert-butyl 5-acetamido-6-allyl-5-(tert-butylcarbamoyl)-2-azabicyclo[2.2.1]heptane-2-carboxylate. LCMS (C$_{21}$H$_{36}$N$_3$O$_4^+$) (ES, m/z): 394 [M+H]$^+$.

Step 3: (tert-butyl 5-acetamido-5-(tert-butylcarbamoyl)-6-(3-(4,4,5,5-tetramethyl-1,3,2-dioxaborolan-2-yl)propyl)-2-azabicyclo[2.2.1]heptane-2-carboxylate A solution of 4,4,5,5-tetramethyl-1,3,2-dioxaborolane (0.11 mL, 0.76 mmol), chloro(1,5-cyclooctadiene)iridium (I) dimer (12 mg, 0.018 mmol) and 1,2-bis(diphenylphosphaneyl)ethane (10 mg, 0.025 mmol) in anhydrous DCM (10 mL) was bubbled with a stream of N$_2$ for 3 min. The mixture was stirred at 20° C. for 20 min and then treated with tert-butyl 5-acetamido-6-allyl-5-(tert-butylcarbamoyl)-2-azabicyclo[2.2.1]heptane-2-carboxylate (100 mg, 0.25 mmol). The resulting mixture was stirred at 20° C. for 16 h under N$_2$. The solution was directly purified by silica gel column chromatography (EtOAc in hexanes) to give (tert-butyl 5-acetamido-5-(tert-butylcarbamoyl)-6-(3-(4,4,5,5-tetramethyl-1,3,2-dioxaborolan-2-yl)propyl)-2-azabicyclo[2.2.1]heptane-2-carboxylate. LCMS (C$_{27}$H$_{49}$BN$_3$O$_6^+$) (ES, m/z): 522 [M+H]$^+$.

Step 4: 5-amino-6-(3-boronopropyl)-2-azabicyclo[2.2.1]heptane-5-carboxylic acid

A mixture of tert-butyl 5-acetamido-5-(tert-butylcarbamoyl)-6-(3-(4,4,5,5-tetramethyl-1,3,2-dioxaborolan-2-yl)propyl)-2-azabicyclo[2.2.1]heptane-2-carboxylate (90 mg, 0.17 mmol) in 12 N HCl in water (2.5 mL, 30 mmol) was stirred at 100° C. for 13 h. The reaction mixture was concentrated under reduced pressure. The residue was purified by RP-HPLC [C18 column, water (0.1% TFA)-CH$_3$CN] to give 5-amino-6-(3-boronopropyl)-2-azabicyclo[2.2.1]heptane-5-carboxylic acid as TFA salt. LCMS (C$_{10}$H$_{18}$BN$_2$O$_3^+$) (ES, m/z): 225 [M+H-H$_2$O]$^+$. $^1$H NMR (400 MHz, Deuterium Oxide) δ 4.38-3.80 (m, 2H), 3.40-2.66 (m, 3H), 2.17-1.70 (m, 3H), 1.47-1.01 (m, 3H), 0.87-0.18 (m, 2H).

Example 25: 8-amino-7-(3-boronopropyl)-1-azaspiro[4.5]decane-8-carboxylic acid

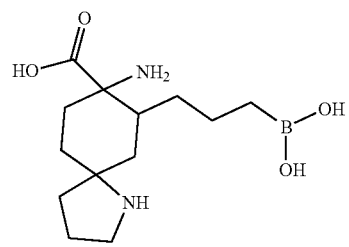

Scheme A1

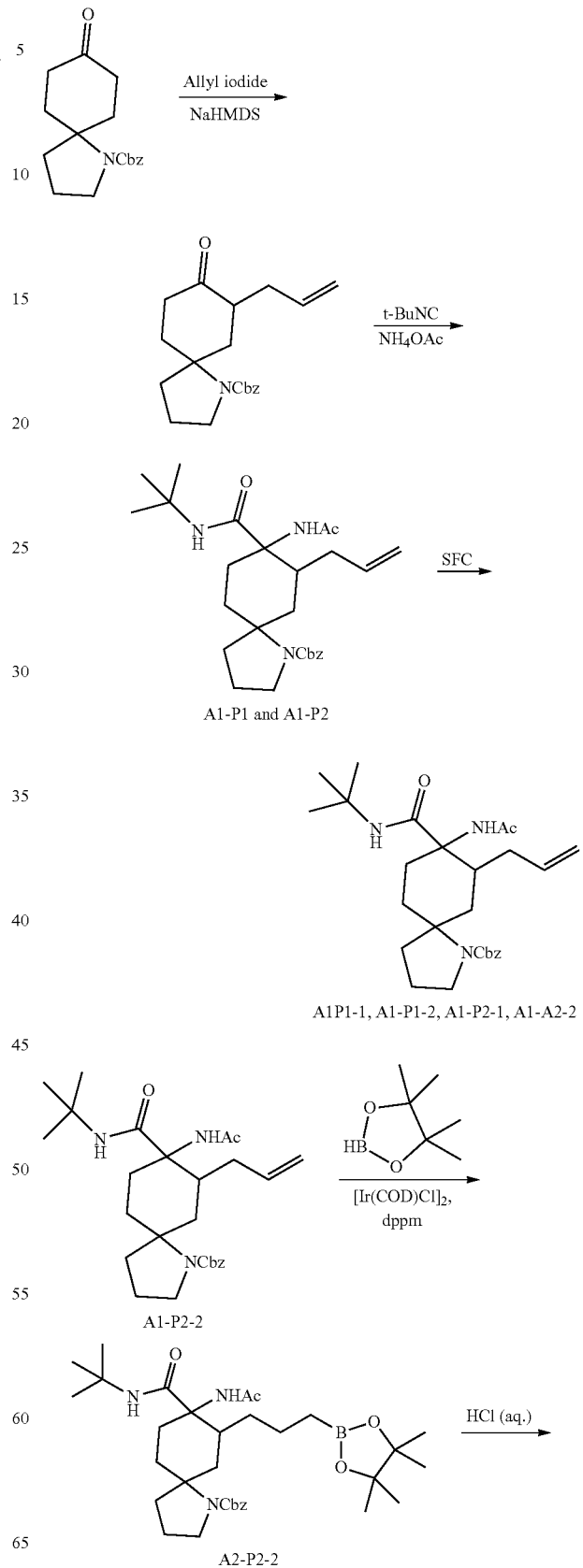

-continued

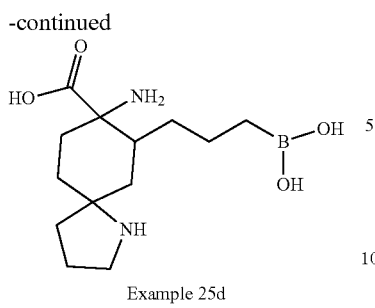

Example 25d

Step 1: benzyl 7-allyl-8-oxo-1-azaspiro[4.5]decane-1-carboxylate

Sodium bis(trimethylsilyl)amide (4.2 mL, 4.2 mmol, 1M in THF) was added to a solution of benzyl 8-oxo-1-azaspiro[4.5]decane-1-carboxylate (1 g, 3.5 mmol) and 3-iodoprop-1-ene (1.6 mL, 17 mmol) in THE (20 mL) at −40° C. under $N_2$ atmosphere. The mixture was stirred at −40° C. for 1 h then warmed to 20° C. for 2 h. The mixture was quenched with water. The aqueous layer was extracted with EtOAc. The combined organic layers were washed with brine, dried over anhydrous $Na_2SO_4$, then filtered and concentrated under reduced pressure. The residue was purified by silica gel chromatography (EtOAc in hexanes) to give benzyl 7-allyl-8-oxo-1-azaspiro[4.5]decane-1-carboxylate. LCMS ($C_{20}H_{26}NO_3^+$) (ES, m/z): 328 $[M+H]^+$.

Step 2: benzyl 8-acetamido-7-allyl-8-(tert-butylcarbamoyl)-1-azaspiro[4.5]decane-1-carboxylate and benzyl 8-acetamido-7-allyl-8-(tert-butylcarbamoyl)-1-azaspiro[4.5]decane-1-carboxylate Tert-butyl isocyanide (0.76 g, 9.2 mmol) and $NH_4OAc$ (1.1 g, 14 mmol) were added to a solution of benzyl 7-allyl-8-oxo-1-azaspiro[4.5]decane-1-carboxylate (1 g, 3.1 mmol) in 2,2,2-trifluoroethyl alcohol (10 mL). The mixture was allowed to stir at 35° C. for 12 h. The reaction was quenched with water. The mixture was extracted with EtOAc. The combined organic layers were washed with brine, dried over anhydrous $Na_2SO_4$, then filtered and concentrated under reduced pressure. The residue was purified by silica gel chromatography (EtOAc in hexanes) to give two isomers of benzyl 8-acetamido-7-allyl-8-(tert-butylcarbamoyl)-1-azaspiro[4.5]decane-1-carboxylate (A1-P1, top spot on TLC and A1-P2, lower spot on TLC). Y-P: LCMS ($C_{27}H_{40}N_3O_4^+$) (ES, m/z): 470 $[M+H]^+$. $^1H$ NMR (400 MHz, chloroform-d) δ 7.53 (br s, 1H), 7.37-7.28 (m, 5H), 6.64 (br s, 1H), 5.72-5.56 (m, 1H), 4.96 (br d, J=13.0 Hz, 2H), 3.55-3.40 (m, 3H), 3.11-2.95 (m, 2H), 2.71 (dt, J=5.0, 14.50 Hz, 1H), 2.42 (br t, J=14.0 Hz, 1H), 2.32-2.17 (m, 2H), 2.09-2.00 (m, 1H), 1.98 (s, 3H), 1.79-1.76 (m, 2H), 1.68-1.58 (m, 3H), 1.57-1.49 (m, 2H), 1.46 (s, 9H). Y1-2: LCMS ($C_{27}H_{40}N_3O_4^+$) (ES, m/z): 470 $[M+H]^+$. $^1H$ NMR (400 MHz, chloroform-d) δ 7.40-7.27 (m, 5H), 6.90 (br s, 1H), 5.79-5.62 (m, 1H), 5.54 (br s, 1H), 5.04-4.99 (m, 2H), 3.51-3.44 (m, 3H), 2.76 (td, J=3.5, 14.1 Hz, 1H), 2.41-2.25 (m, 3H), 2.20 (s, 3H), 2.00-1.91 (m, 2H), 1.88-1.80 (m, 1H), 1.80-1.66 (m, 4H), 1.53-1.48 (m, 1H), 1.46 (br s, 1H), 1.45-1.40 (m, 1H), 1.33-1.29 (m, 9H).

Step 3: benzyl 8-acetamido-7-allyl-8-(tert-butylcarbamoyl)-1-azaspiro[4.5]decane-1-carboxylate (A1-P1-1) and benzyl 8-acetamido-7-allyl-8-(tert-butylcarbamoyl)-1-azaspiro[4.5]decane-1-carboxylate (A1-P1-2)

Benzyl 8-acetamido-7-allyl-8-(tert-butylcarbamoyl)-1-azaspiro[4.5]decane-1-carboxylate (A1-P1) was resolved by [Column: (R,R)-WHELK-01 (250 mm*50 mm, 10 um), Mobile phase: A: $CO_2$, B: MeOH (0.1% $NH_3.H_2O$), Gradient: 25% of B in 4 min, and hold 25% of B for 1 min, Flow Rate (mL/min) 50, Column temperature: 40° C.] to give benzyl 8-acetamido-7-allyl-8-(tert-butylcarbamoyl)-1-azaspiro[4.5]decane-1-carboxylate (A1-P1-1, $t_r$=3.349 min) as the first eluting peak, and benzyl 8-acetamido-7-allyl-8-(tert-butylcarbamoyl)-1-azaspiro[4.5]decane-1-carboxylate (A1-P1-2, $t_r$=3.015 min) as the second eluting peak. A1-P1-1: LCMS ($C_{27}H_{40}N_3O_4^+$) (ES, m/z): 470 $[M+H]^+$. A1-P1-2: LCMS ($C_{27}H_{40}N_3O_4^+$) (ES, m/z): 470 $[M+H]^+$.

Step 4: benzyl 8-acetamido-7-allyl-8-(tert-butylcarbamoyl)-1-azaspiro[4.5]decane-1-carboxylate (A1-P2-1) and benzyl 8-acetamido-7-allyl-8-(tert-butylcarbamoyl)-1-azaspiro[4.5]decane-1-carboxylate (A1-P2-2)

Benzyl 8-acetamido-7-allyl-8-(tert-butylcarbamoyl)-1-azaspiro[4.5]decane-1-carboxylate (A1-P2) was resolved by [Column: Lux Cellulose-2 (250 mm*50 mm, 10 um), Mobile phase: A: $CO_2$, B: MeOH (0.1% $NH_3.H_2O$), Gradient: 25% of B in 4 min, and hold 25% of B for 1 min, Flow Rate (mL/min) 200, Column temperature: 40° C.] to give two isomers of benzyl 8-acetamido-7-allyl-8-(tert-butylcarbamoyl)-1-azaspiro[4.5]decane-1-carboxylate (A1-P2-1, $t_r$=3.362 min and A1-P2-2, $t_r$=3.821 min). A1-P2-1: LCMS ($C_{27}H_{40}N_3O_4^+$) (ES, m/z): 470 $[M+H]^+$. Y1-P2-2: LCMS ($C_{27}H_{40}N_3O_4^+$) (ES, m/z): 470 $[M+H]^+$.

Step 5: benzyl 8-acetamido-8-(tert-butylcarbamoyl)-7-(3-(4,4,5,5-tetramethyl-1,3,2-dioxaborolan-2-yl)propyl)-1-azaspiro[4.5]decane-1-carboxylate (A1-P2-3)

A solution of 4,4,5,5-tetramethyl-1,3,2-dioxaborolane (0.23 mL, 1.6 mmol), chloro(1,5-cyclooctadiene)iridium (I) dimer (21 mg, 0.032 mmol) and bis(diphenylphosphino)methane (20 mg, 0.053 mmol) in anhydrous DCM (15 mL) was bubbled with a stream of $N_2$ for 3 min. The mixture was stirred at 25° C. for 20 min and then benzyl 8-acetamido-7-allyl-8-(tert-butylcarbamoyl)-1-azaspiro[4.5]decane-1-carboxylate (250 mg, 0.53 mmol) in DCM (5 mL) was added to the mixture. The resulting mixture was stirred at 25° C. for 5 h under $N_2$. The mixture was directly purified by silica gel chromatography (EtOAc in hexanes) to give benzyl 8-acetamido-8-(tert-butylcarbamoyl)-7-(3-(4,4,5,5-tetramethyl-1,3,2-dioxaborolan-2-yl)propyl)-1-azaspiro[4.5]decane-1-carboxylate. LCMS ($C_{33}H_{53}BN_3O_6^+$) (ES, m/z): 598 $[M+H]^+$.

Step 6: 8-amino-7-(3-boronopropyl)-1-azaspiro[4.5]decane-8-carboxylic acid (A2-P2-3)

A mixture of benzyl 8-acetamido-8-(tert-butylcarbamoyl)-7-(3-(4,4,5,5-tetramethyl-1,3,2-dioxaborolan-2-yl)propyl)-1-azaspiro[4.5]decane-1-carboxylate (A2-P2-2 from scheme A1, 150 mg, 0.25 mmol) in 12 N HCl in water (3 mL, 36 mmol) was stirred at 100° C. for 13 h. The reaction mixture was concentrated under reduced pressure. The residue was treated with sat. Na$_2$CO$_3$ (aq.) till pH around 9. The resulting aqueous solution was washed with DCM. The aqueous solution was then concentrated under reduced pressure. The residue was purified by RP-HPLC [C18 column, water (0.1% TFA)-CH$_3$CN] to give 8-amino-7-(3-boronopropyl)-1-azaspiro[4.5]decane-8-carboxylic acid as TFA salt. LCMS (C$_{13}$H$_{24}$BN$_2$O$_3$$^+$) (ES, m/z): 267 [M+H-H$_2$O]$^+$. $^1$H NMR (400 MHz, Deuterium Oxide) δ 3.36-3.29 (m, 2H), 2.18-1.92 (m, 9H), 1.79-1.67 (m, 1H), 1.60-1.41 (m, 2H), 1.39-1.07 (m, 3H), 0.80-0.46 (m, 2H).

Examples 25a, 25b and 25c were made from A1-P1-1, A1-P1-2 and A1-P2-1, respectively, using the same procedure. 25a LCMS (C$_{13}$H$_{24}$BN$_2$O$_3$$^+$) (ES, m/z): 267 [M+H-H$_2$O]$^+$. $^1$H NMR (400 MHz, Deuterium Oxide) δ 3.37-3.23 (m, 2H), 2.50-2.19 (m, 2H), 2.13-1.93 (m, 5H), 1.93-1.60 (m, 4H), 1.56-1.44 (m, 2H), 1.40-1.20 (m, 1H), 1.18-1.00 (m, 1H), 0.78-0.62 (m, 1H), 0.59-0.38 (m, 1H). 25b LCMS (C$_{13}$H$_{24}$BN$_2$O$_3$$^+$) (ES, m/z): 267 [M+H-H$_2$O]$^+$. $^1$H NMR (400 MHz, Deuterium Oxide) δ 3.37-3.24 (m, 2H), 2.52-2.18 (m, 2H), 2.15-1.92 (m, 5H), 1.91-1.61 (m, 4H), 1.55-1.50 (m, 2H), 1.44-1.19 (m, 1H), 1.18-1.00 (m, 1H), 0.81-0.63 (m, 1H), 0.61-0.39 (m, 1H). 25c LCMS (C$_{13}$H$_{24}$BN$_2$O$_3$$^+$) (ES, m/z): 267 [M+H-H$_2$O]$^+$. $^1$H NMR (400 MHz, Deuterium Oxide) δ 3.34-3.31 (m, 2H), 2.19-1.90 (m, 9H), 1.80-1.66 (m, 1H), 1.59-1.40 (m, 2H), 1.38-1.06 (m, 3H), 0.79-0.42 (m, 2H).

Example 26: 8-amino-1-((S)-2-aminopropanoyl)-7-(3-boronopropyl)-1-azaspiro[4.5]decane-8-carboxylic acid hydrochloride

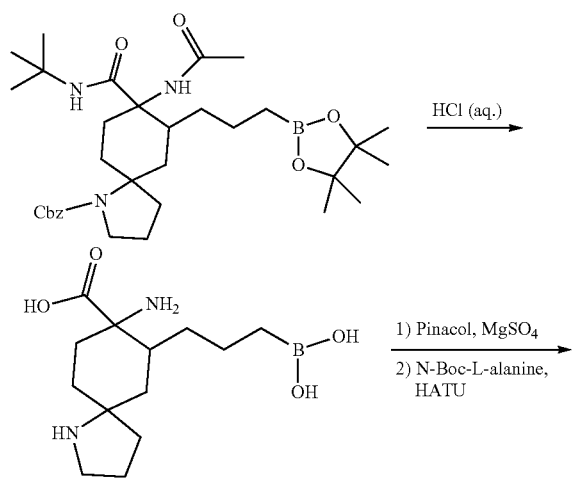

Scheme B1

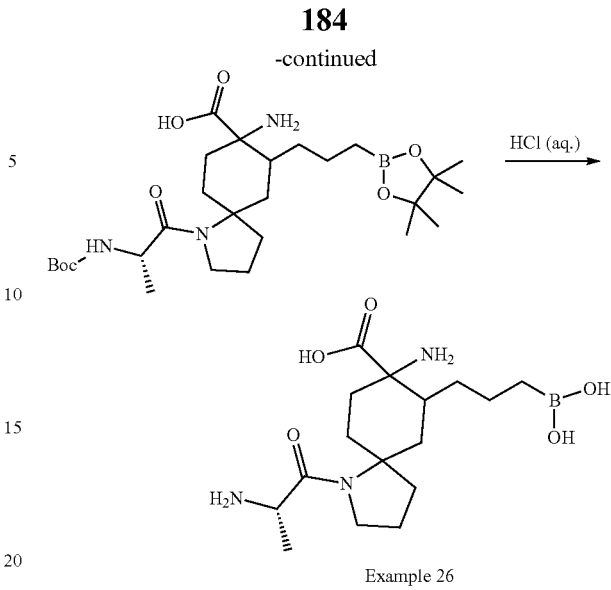

Step 1: 8-amino-7-(3-boronopropyl)-1-azaspiro[4.5]decane-8-carboxylic acid

A mixture of benzyl 8-acetamido-8-(tert-butylcarbamoyl)-7-(3-(4,4,5,5-tetramethyl-1,3,2-dioxaborolan-2-yl)propyl)-1-azaspiro[4.5]decane-1-carboxylate (150 mg, 0.25 mmol) in 12 N HCl in water (2.5 mL, 30 mmol) was stirred at 100° C. for 13 h. The reaction mixture was concentrated under reduced pressure. The residue was treated with sat. Na$_2$CO$_3$ (aq.) till pH 9. The resulting aqueous solution was washed with DCM. The aqueous solution was then concentrated under reduced pressure to afford the crude 8-amino-7-(3-boronopropyl)-1-azaspiro[4.5]decane-8-carboxylic acid. LCMS (C$_{13}$H$_{24}$BN$_2$O$_3$$^+$) (ES, m/z): 267 [M+H-H$_2$O]. The resulting product was directly used in the next step.

Step 2: 8-amino-1-((S)-2-((tert-butoxycarbonyl)amino)propanoyl)-7-(3-(4,4,5,5-tetramethyl-1,3,2-dioxaborolan-2-yl)propyl)-1-azaspiro[4.5]decane-8-carboxylic acid A mixture of 8-amino-7-(3-boronopropyl)-1-azaspiro[4.5]decane-8-carboxylic acid (300 mg, 1.1 mmol), 2,3-dimethylbutane-2,3-diol (250 mg, 2.1 mmol) and MgSO$_4$ (254 mg, 2.1 mmol) in dry THF (5 mL) was stirred at 25° C. for 24 h. The crude boronate ester solution was used in the next step directly. In a separate flask, TEA (0.21 mL, 1.5 mmol) was added to a solution of (S)-2-((tert-butoxycarbonyl)amino)propanoic acid (95 mg, 0.50 mmol) and HATU (210 mg, 0.55 mmol) in anhydrous DCM (7 mL) at 25° C. The mixture was stirred at 25° C. for 10 min, then the boronate ester solution prepared above was added to the mixture. The mixture was stirred at 25° C. for 13 h. The mixture was filtered off and the filtrate was concentrated under reduced pressure. The residue was purified by RP-HPLC [C18 column, water (0.1% TFA)-CH$_3$CN] to give 8-amino-1-((S)-2-((tert-butoxycarbonyl)amino)propanoyl)-7-(3-(4,4,5,5-tetramethyl-1,3,2-dioxaborolan-2-yl)propyl)-1-azaspiro[4.5]decane-8-carboxylic acid. LCMS (C$_{27}$H$_{49}$BN$_3$O$_7$$^+$) (ES, m/z): 538 [M+H]$^+$. The product contained the corresponding boronic acid. The resulting mixture was directly used in the next step.

Step 3: 8-amino-1-((S)-2-aminopropanoyl)-7-(3-boronopropyl)-1-azaspiro[4.5]decane-8-carboxylic acid hydrochloride A solution of the product prepared in Step 2 (80 mg) in 12 N HCl in water (5 mL, 60 mmol) was stirred at 25° C. for 10 h. The mixture was concentrated under reduced pressure. The residue was purified by RP-HPLC [C18 column, water (0.1% TFA)-CH$_3$CN] to give 8-amino-1-((S)-2-aminopropanoyl)-7-(3-boronopropyl)-1-azaspiro[4.5]decane-8-carboxylic acid. The product was dissolved in water and treated with DOWEX 50WX8 resin (the resin was washed with MeOH and water before using) and the mixture was stirred for 40 min, and aged for 20 min. The mixture was filtered and the filter cake was washed with MeOH and then water. The filter cake was then washed with 2N aqueous ammonium hydroxide solution. The aqueous ammonium hydroxide solution was concentrated under reduced pressure. The residue was dissolved in water, and acidified with 1N HCl in water to pH=1. The solution was lyophilized to give 8-amino-1-((S)-2-aminopropanoyl)-7-(3-boronopropyl)-1-azaspiro[4.5]decane-8-carboxylic acid as the HCl salt. LCMS (C$_{16}$H$_{29}$BN$_3$O$_4^+$) (ES, m/z): 338 [M+H-H$_2$O]$^+$. $^1$H NMR (400 MHz, Deuterium Oxide) δ 4.19 (q, J=6.7 Hz, 1H), 3.65-3.57 (m, 1H), 3.56-3.47 (m, 1H), 2.47 (dt, J=4.2, 14.1 Hz, 1H), 2.21-2.04 (m, 4H), 2.03-1.94 (m, 2H), 1.90 (br d, J=6.1 Hz, 2H), 1.74-1.64 (m, 1H), 1.57 (br d, J=12.7 Hz, 1H), 1.41 (d, J=7.0 Hz, 4H), 1.30-1.19 (m, 1H), 1.15 (br t, J=6.8 Hz, 2H), 0.77-0.58 (m, 2H).

Example 27a: Rac-(3aR,6aS)-5-amino-6-(3-boronopropyl)-3a-methyloctahydrocyclopenta[c]pyrrole-5-carboxylic acid

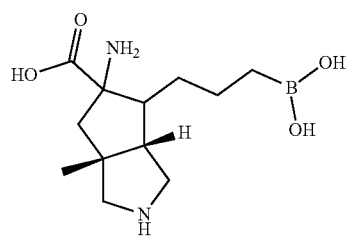

Step 1: 4-methyl-N-(prop-2-yn-1-yl)benzenesulfonamide

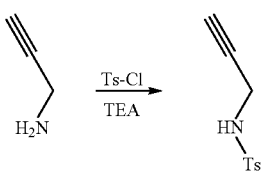

Prop-2-yn-1-amine (14 g, 254 mmol), Ts-Cl (53 g, 280 mmol) and TEA (53 mL, 381 mmol) was added to DCM (500 mL) successively and stirred at 20° C. for 2 h. The reaction mixture was diluted with H$_2$O. The organic phase was washed with brine, dried over anhydrous Na$_2$SO$_4$, filtered and concentrated under reduced pressure. The residue was purified by silica gel column chromatography (EtOAc in hexanes) to afford 4-methyl-N-(prop-2-yn-1-yl)benzenesulfonamide. LCMS (C$_{10}$H$_{12}$NO$_2$S$^+$) (ES, m/z) 210 [M+H]$^+$.

Step 2: 4-methyl-N-(2-methylallyl)-N-(prop-2-yn-1-yl)benzene sulfonamide

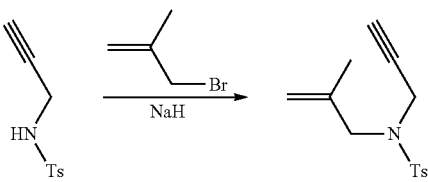

Sodium hydride (4.0 g, 99 mmol, 60% in oil) was added to a solution of 4-methyl-N-(prop-2-yn-1-yl)benzene sulfonamide (16 g, 76 mmol) and 3-bromo-2-methylprop-1-ene (11 g, 84 mmol) in THF (150 mL) and DMF (150 mL) at 0° C. After stirring at 0° C. for 0.5 h, the resulting mixture was stirred at 20° C. for another 12 h. The reaction mixture was quenched with water and extracted with EtOAc. The combined organic phases were washed with brine, dried over anhydrous Na$_2$SO$_4$, filtered and concentrated under reduced pressure. The residue was purified by silica gel column chromatography (EtOAc in hexanes) to afford 4-methyl-N-(2-methylallyl)-N-(prop-2-yn-1-yl)benzene sulfonamide. LCMS (C$_{14}$H$_{18}$NO$_2$S$^+$) (ES, m/z) 264 [M+H]$^+$.

Step 3: 3a-methyl-2-tosyl-2,3,3a,4-tetrahydrocyclopenta[c]pyrrol-5(1H)-one

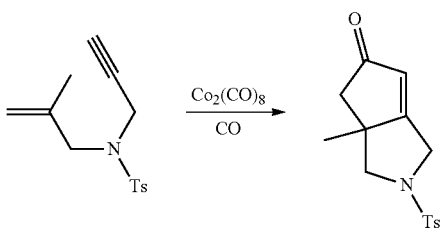 [SMILES: C#CCN(CC(=C)C)S(=O)(=O)c1ccc(C)cc1 ; "Co2(CO)8" ; "CO" ; Cc1ccc(S(=O)(=O)N2CC3=CC(=O)CC3(C)C2)cc1]

4-methyl-N-(2-methylallyl)-N-(prop-2-yn-1-yl)benzene sulfonamide (10 g, 38 mmol) was added to toluene (150 mL) and then Co$_2$(CO)$_8$ (1.3 g, 3.8 mmol) was added to the mixture under N$_2$. The mixture was degassed and backfilled with CO (three times). The resulting mixture was stirred under CO (50 psi) at 70° C. for 16 h. The mixture was filtered and the filtrate was concentrated under reduced pressure. The residue was purified by silica gel column chromatography (EtOAc in hexanes) to afford 3a-methyl-2-tosyl-2,3,3a,4-tetrahydrocyclopenta[c]pyrrol-5(1H)-one. LCMS (C$_{15}$H$_{18}$NO$_3$S$^+$) (ES, m/z) 292 [M+H]$^+$.

Step 4: 3a-methyl-2-tosylhexahydrocyclopenta[c]pyrrol-5(1H)-one

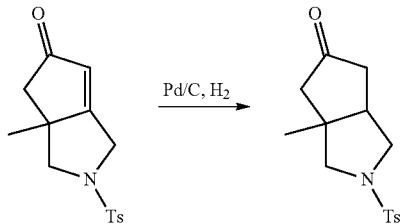 [SMILES: Cc1ccc(S(=O)(=O)N2CC3=CC(=O)CC3(C)C2)cc1 ; "Pd/C, H2" ; Cc1ccc(S(=O)(=O)N2CC3CC(=O)CC3(C)C2)cc1]

3a-methyl-2-tosyl-2,3,3a,4-tetrahydrocyclopenta[c]pyrrol-5(1H)-one (6.9 g, 23 mmol) was added to MeOH (100 mL) and then 10% Pd/C (2.5 g, 2.4 mmol) was added to the mixture under $N_2$ atmosphere. The mixture was degassed and backfilled with $H_2$ (three times). The resulting mixture was stirred under $H_2$ (15 psi) at 20° C. for 1 h. The catalyst was filtered off and the filtrate was concentrated under reduced pressure to give crude 3a-methyl-2-tosylhexahydrocyclopenta[c]pyrrol-5(1H)-one, which was used in next step directly. LCMS ($C_{15}H_{20}NO_3S^+$) (ES, m/z) 294 $[M+H]^+$.

Step 5: rac-(3aR,6aS)-6-allyl-3a-methyl-2-tosylhexahydrocyclopenta[c]pyrrol-5(1H)-one

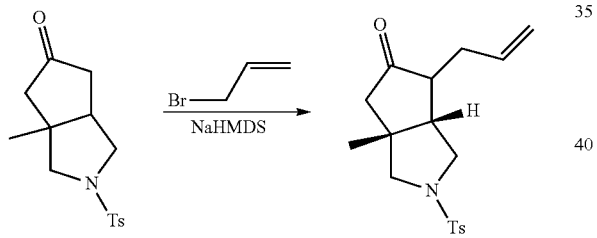

NaHMDS (7.5 mL, 7.5 mmol, 1M in THF) was added dropwise to a solution of 3a-methyl-2-tosylhexahydrocyclopenta[c]pyrrol-5(1H)-one (2 g, 6.8 mmol) in (15 mL) at −78° C. under $N_2$. After stirring at −78° C. for 0.5 h, 3-bromoprop-1-ene (0.53 mL, 6.1 mmol) was added to the mixture at −78° C. under $N_2$. The resulting mixture was stirred for another 1 h at −78° C. under $N_2$. Then the mixture was stirred at 20° C. for 12 h under $N_2$. The reaction mixture was quenched with water and extracted with EtOAc. The combined organic phases were washed with brine, dried over anhydrous $Na_2SO_4$, filtered and concentrated under reduced pressure. The residue was purified by silica gel column chromatography (EtOAc in hexanes) to afford the product. The product was re-purified by RP-HPLC [C18 column, water (0.1% TFA)-$CH_3CN$] to give rac-(3aR,6aS)-6-allyl-3a-methyl-2-tosylhexahydrocyclopenta[c]pyrrol-5(1H)-one. LCMS ($C_{18}H_{24}NO_3S^+$) (ES, m/z) 334 $[M+H]^+$.

Step 6: rac-(3aR,6aS)-5-acetamido-6-allyl-N-(tert-butyl)-3a-methyl-2-tosyloctahydrocyclopenta[c]pyrrole-5-carboxamide

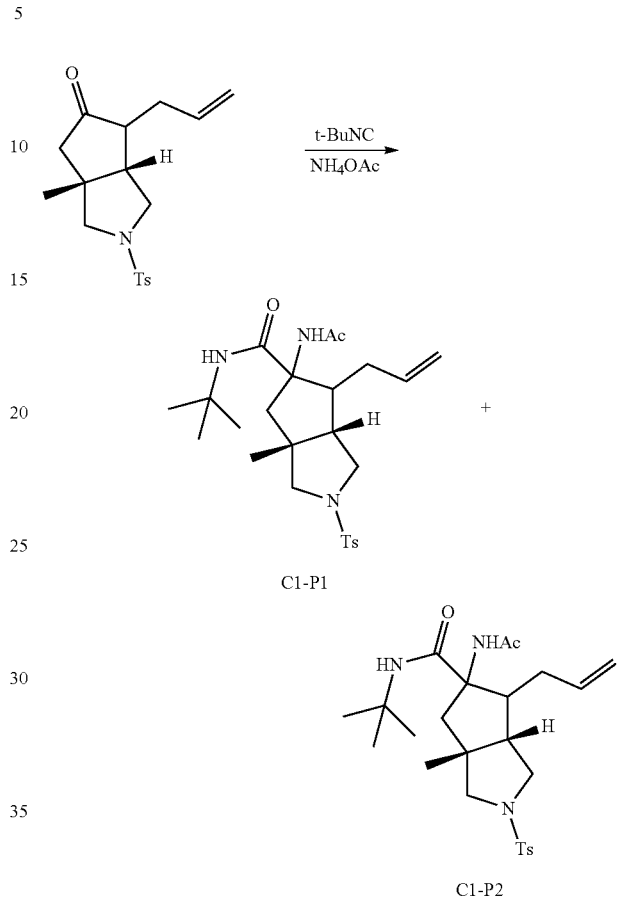

Rac-(3aR,6aS)-6-allyl-3a-methyl-2-tosylhexahydrocyclopenta[c]pyrrol-5(1H)-one (650 mg, 2.0 mmol) was added to 2,2,2-trifluoroethyl alcohol (5 mL) and then $NH_4OAc$ (1503 mg, 20 mmol) and 2-isocyano-2-methylpropane (1.1 mL, 9.8 mmol) was added to the mixture. The reaction mixture was stirred at 35° C. for 20 h. The reaction mixture was quenched with water and extracted with EtOAc. The combined organic phases were washed with brine, dried over anhydrous $Na_2SO_4$, filtered and concentrated under reduced pressure. The resulting crude was purified by RP-HPLC [C18 column, water (0.1% TFA)-$CH_3CN$] to give rac-(3aR,6aS)-5-acetamido-6-allyl-N-(tert-butyl)-3a-methyl-2-tosyloctahydrocyclopenta[c]pyrrole-5-carboxamide (C1-P1, $t_r$=0.913 min) as the first eluting peak and rac-(3aR,6aS)-5-acetamido-6-allyl-N-(tert-butyl)-3a-methyl-2-tosyloctahydrocyclopenta[c]pyrrole-5-carboxamide (C1-P2, $t_r$=0.939 min) as the second eluting peak. C1-P1. LCMS ($C_{25}H_{38}N_3O_4S^+$) (ES, m/z) 476 $[M+H]^+$. $^1$H NMR (400 MHz, $CDCl_3$) δ 7.67 (d, J=8.3 Hz, 2H), 7.34 (d, J=7.9 Hz, 2H), 6.73 (br s, 1H), 6.00 (br s, 1H), 5.82-5.69 (m, 1H), 5.14-5.03 (m, 2H), 3.12-3.01 (m, 3H), 2.74 (d, J=14.0 Hz, 1H), 2.65 (d, J=9.6 Hz, 1H), 2.46 (s, 3H), 2.43-2.33 (m, 2H), 2.08-1.98 (m, 6H), 1.32 (s, 9H), 1.09 (s, 3H). C1-P2: LCMS ($C_{25}H_{38}N_3O_4S^+$) (ES, m/z) 476 $[M+H]^+$. $^1$H NMR (400 MHz, $CDCl_3$) δ 7.68 (d, J=7.9 Hz, 2H), 7.41-7.34 (m, 2H), 6.62 (br s, 1H), 6.44 (br s, 1H), 5.79-5.67 (m, 1H), 5.14-5.06

(m, 2H), 3.32 (br d, J=9.6 Hz, 2H), 2.84-2.72 (m, 2H), 2.53-2.33 (m, 6H), 2.15-2.01 (m, 6H), 1.33 (s, 9H), 1.11-1.02 (m, 3H).

Step 7: rac-(3aR,6aS)-5-acetamido-N-(tert-butyl)-3a-methyl-6-(3-(4,4,5,5-tetramethyl-1,3,2-dioxaborolan-2-yl)propyl)-2-tosyloctahydrocyclopenta[c]pyrrole-5-carboxamide

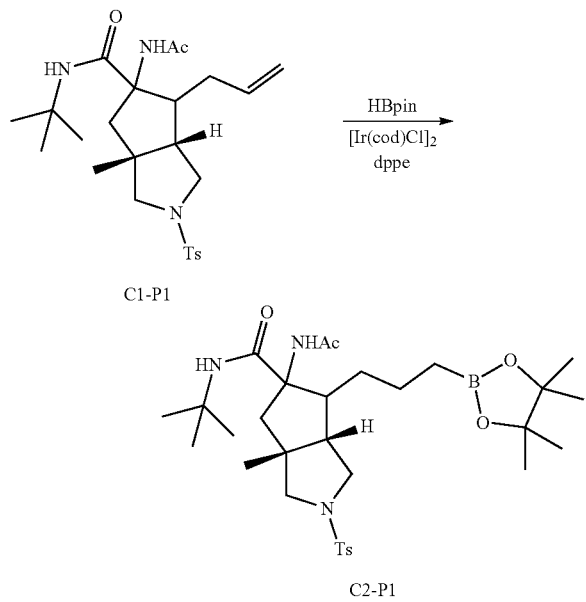

4,4,5,5-tetramethyl-1,3,2-dioxaborolane (0.076 mL, 0.53 mmol) was added to a solution of DPPE (3.4 mg, 8.4 μmol) and [Ir(cod)Cl]₂ (3.5 mg, 5.3 μmol) in DCM (5 mL) under N₂. The mixture was degassed and backfilled with N₂ (three times). After stirring for 10 min at 20° C., rac-(3aR,6aS)-5-acetamido-6-allyl-N-(tert-butyl)-3a-methyl-2-tosyloctahydrocyclopenta[c]pyrrole-5-carboxamide (50 mg, 0.11 mmol) was added to the mixture. The resulting mixture was stirred at 20° C. for 16 h. The reaction was concentrated under reduced pressure. The residue was purified by silica gel column chromatography (MeOH in DCM) to afford rac-(3aR,6aS)-5-acetamido-N-(tert-butyl)-3a-methyl-6-(3-(4,4,5,5-tetramethyl-1,3,2-dioxaborolan-2-yl)propyl)-2-tosyloctahydrocyclopenta[c]pyrrole-5-carboxamide. LCMS ($C_{31}H_{51}BN_3O_6S^+$) (ES, m/z) 604 [M+H]⁺.

Step 8: rac-(3aR,6aS)-5-amino-6-(3-boronopropyl)-3a-methyloctahydrocyclopenta[c]pyrrole-5-carboxylic acid

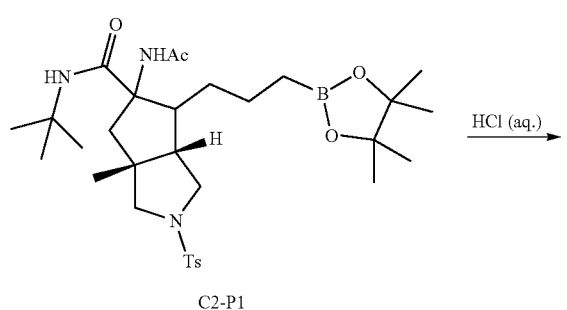

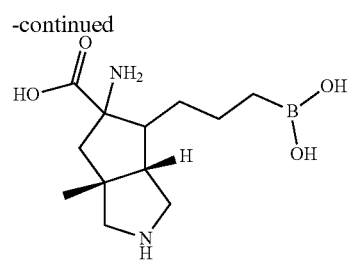

Example 27a rac-(3aR,6aS)-5-acetamido-N-(tert-butyl)-3a-methyl-6-(3-(4,4,5,5-tetramethyl-1,3,2-dioxaborolan-2-yl)propyl)-2-tosyloctahydrocyclopenta[c]pyrrole-5-carboxamide (15 mg, 0.025 mmol) was added to 12N HCl in water (5 mL, 60 mmol) and stirred at 100° C. for 96 h. Then the mixture was stirred at 120° C. for 48 h. The reaction was concentrated under reduced pressure. The residue was purified by RP-HPLC [C18 column, water (20 mM HFBA and 0.1% TFA)-CH₃CN] to give rac-(3aR,6aS)-5-amino-6-(3-boronopropyl)-3a-methyloctahydrocyclopenta[c]pyrrole-5-carboxylic acid as the HFBA salt. LCMS ($C_{12}H_{22}BN_2O_3^+$) (ES, m/z) 253 [M+H-H₂O]⁺. ¹H NMR (400 MHz, D₂O) δ 3.56-3.27 (m, 3H), 3.16-3.03 (m, 1H), 2.67-2.63 (m, 1H), 2.58-2.39 (m, 1H), 2.33-2.25 (m, 1H), 2.17-2.04 (m, 1H), 2.02-1.90 (m, 1H), 1.71 (br s, 1H), 1.45-1.28 (m, 2H), 1.24 (d, J=6.6 Hz, 3H), 0.94-0.33 (m, 2H).

Example 27b was made from C1-P2 using the same procedure. LCMS ($C_{12}H_{22}BN_2O_3^+$) (ES, m/z) 253 [M+H-H₂O]⁺. ¹H NMR (400 MHz, Deuterium Oxide) δ 3.65-3.60 (m, 1H), 3.37-3.10 (m, 3H), 2.72-2.58 (m, 1H), 2.46-2.42 (m, 1H), 2.30-2.08 (m, 2H), 1.57-1.44 (m, 1H), 1.41-1.31 (m, 3H), 1.30-1.23 (m, 4H), 0.72 (br t, J=7.0 Hz, 2H).

Example 28: rac-(3aS,6aR)-4-amino-5-(3-boronopropyl)octahydrocyclopenta[c]pyrrole-4-carboxylic acid

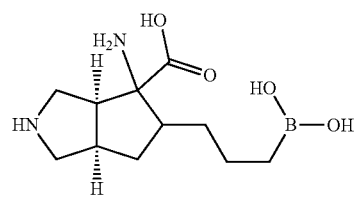 [SMILES: NC1(C(=O)O)C(CCCB(O)O)C[C@H]2CNC[C@H]21]

Step 1: rac-benzyl (3aS,6aR)-5-allyl-4-oxohexahydrocyclopenta[c]pyrrole-2(1H)-carboxylate

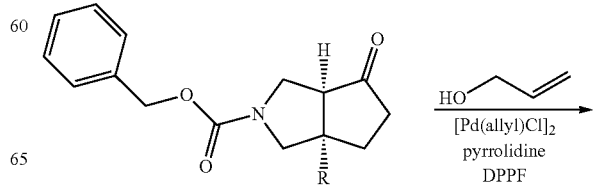

-continued

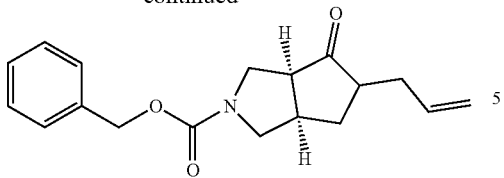

Allylpalladium(II) chloride dimer (90 mg, 0.247 mmol) and prop-2-en-1-ol (0.37 ml, 5.4 mmol) were added to a mixture of rac-(3aS,6aR)-benzyl 4-oxohexahydrocyclopenta[c]pyrrole-2(1H)-carboxylate (1280 mg, 4.9 mmol), pyrrolidine (105 mg, 1.5 mmol) and DPPF (274 mg, 0.49 mmol) in MeOH (10 ml) under N$_2$ at 20° C. The resulting mixture was stirred at 20° C. for 48 h. The solvent was removed under reduced pressure. The residue was suspended in EtOAc and stirred at room temperature for 10 min, then filtered through CELITE. The filtrate was washed with water, brine, dried over anhydrous Na$_2$SO$_4$, filtered and concentrated under reduced pressure. The residue was purified by silica gel column chromatography (EtOAc in hexanes) to afford rac-benzyl (3aS,6aR)-5-allyl-4-oxohexahydrocyclopenta[c]pyrrole-2(1H)-carboxylate. LCMS (C$_{18}$H$_{22}$NO$_3^+$) (ES, m/z): 300 [M+H]$^+$.

Step 2: rac-benzyl (3aS,6aR)-4-oxo-5-(3-(4,4,5,5-tetramethyl-1,3,2-dioxaborolan-2-yl)propyl)hexahydrocyclopenta[c]pyrrole-2(1H)-carboxylate

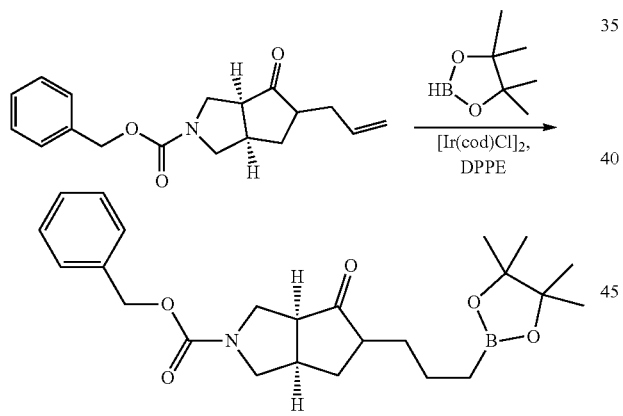

4,4,5,5-Tetramethyl-1,3,2-dioxaborolane (1.3 mL, 8.2 mmol) was added to a mixture of chloro(1,5-cyclooctadiene)iridium(I) dimer (84 mg, 0.16 mmol) and DPPE (130 mg, 0.33 mmol) in DCM (16 mL) under N$_2$. The mixture was degassed and backfilled with N$_2$ (three times). After stirring at 25° C. for 20 min, rac-(3aS,6aR)-benzyl 5-allyl-4-oxohexahydrocyclopenta[c]pyrrole-2(1H)-carboxylate (977 mg, 3.3 mmol) in DCM (16 mL) was added to the mixture under N$_2$. The resulting mixture was stirred at 25° C. for 15 h. The reaction was quenched with MeOH and water. The mixture was concentrated under reduced pressure. The residue was purified by silica gel column chromatography (EtOAc in hexanes) to afford rac-benzyl (3aS,6aR)-4-oxo-5-(3-(4,4,5,5-tetramethyl-1,3,2-dioxaborolan-2-yl)propyl)hexahydrocyclopenta[c]pyrrole-2(1H)-carboxylate. LCMS (C$_{24}$H$_{35}$BNO$_5^+$) (ES, m/z): 428 [M+H]$^+$.

Step 3: rac-(3-((3aS,6aR)-4-acetamido-2-((benzyloxy)carbonyl)-4-(tert-butylcarbamoyl)octahydrocyclopenta[c]pyrrol-5-yl)propyl)boronic acid

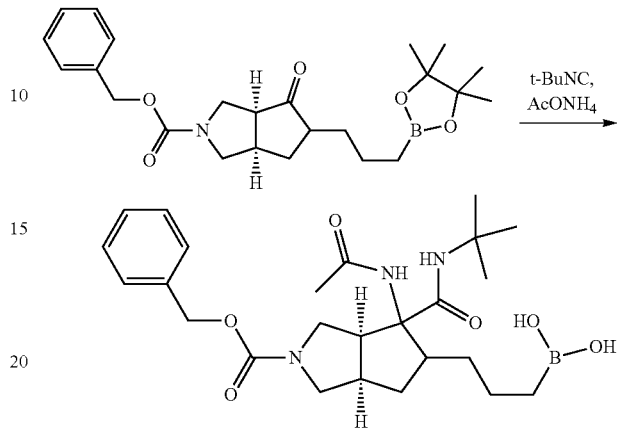

Tert-butyl isocyanide (729 mg, 8.8 mmol) and ammonium acetate (676 mg, 8.8 mmol) was added to a mixture of rac-benzyl (3aS,6aR)-4-oxo-5-(3-(4,4,5,5-tetramethyl-1,3,2-dioxaborolan-2-yl)propyl)hexahydrocyclopenta[c]pyrrole-2(1H)-carboxylate (750 mg, 1.8 mmol) in 2,2,2-trifluoroethyl alcohol (10 ml). The mixture was stirred at 40° C. for 18 h. The reaction was diluted with water and DCM. The organic layer was separated and the aqueous layer was re-extracted with DCM. The combined organic layers were washed with brine, dried over anhydrous Na$_2$SO$_4$, filtered and concentrated under reduced pressure. The residue was purified by silica gel column chromatography (EtOAc in DCM) and mass-directed RP-HPLC (MeCN/water gradient with 0.1% TFA modifier) to give rac-(3-((3aS,6aR)-4-acetamido-2-((benzyloxy)carbonyl)-4-(tert-butylcarbamoyl)octahydrocyclopenta[c]pyrrol-5-yl)propyl)boronic acid. LCMS (C$_{25}$H$_{37}$BN$_3$O$_5^+$): 470 [M–H$_2$O+H]$^+$.

Step 4: rac-(3aS,6aR)-4-amino-5-(3-boronopropyl)octahydrocyclopenta[c]pyrrole-4-carboxylic acid

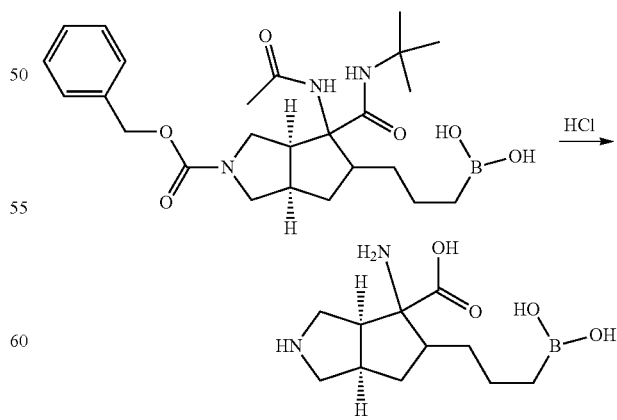

HCl in water (36%, 1.0 mL) was added to a solution of rac-(3-((3aS,6aR)-4-acetamido-2-((benzyloxy)carbonyl)-4-(tert-butylcarbamoyl)octahydrocyclopenta[c]pyrrol-5-yl)

propyl)boronic acid (70 mg, 0.14 mmol) and Dioxane (1.0 mL). The reaction mixture was heated in a microwave at 120° C. for 1 h. The reaction mixture was then concentrated under reduced pressure. Water was added to the residue. The mixture was washed with DCM. The aqueous layer was concentrated under reduced pressure. The residue was dissolved in water and lyophilized to give rac-(3aS,6aR)-4-amino-5-(3-boronopropyl)octahydrocyclopenta[c]pyrrole-4-carboxylic acid hydrochloride. LCMS ($C_{11}H_{20}BN_2O_3^+$): 239 [M−H$_2$O+H]$^+$. $^1$H NMR (499 MHz, Deuterium Oxide) 3.87-3.76 (m, 1H), 3.71 (td, J=12.5, 11.8, 6.6 Hz, 2H), 3.64 (td, J=11.1, 9.2, 4.5 Hz, 2H), 3.58-3.39 (m, 2H), 3.12 (ddt, J=24.8, 16.9, 8.4 Hz, 2H), 2.85-2.73 (m, 1H), 2.08 (dd, J=14.2, 7.6 Hz, 1H), 1.81 (td, J=13.9, 13.5, 9.0 Hz, 1H), 1.57-1.36 (m, 2H), 0.77 (tt, J=15.4, 8.4 Hz, 2H).

Example 29

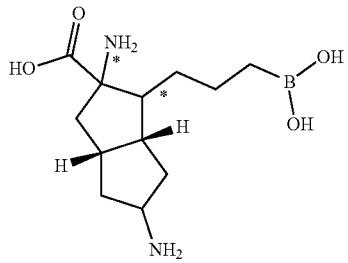

Example 29a through 29d

Step 1: rac-(3aR,6aS)—N,N-dibenzylhexahydro-H-spiro[pentalene-2,2'-[1,3]dioxolan]-5-amine

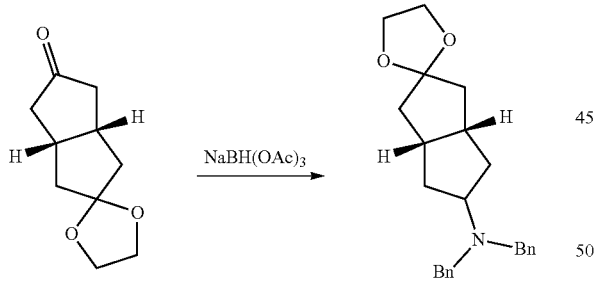

Dibenzylamine (14 mL, 72 mmol) and acetic acid (12 mL) was added to a solution of rac-(3aR,6aS)-tetrahydro-1H-spiro[pentalene-2,2'-[1,3]dioxolan]-5(3H)-one (11 g, 60 mmol) in THF (180 ml) at room temperature. The mixture was stirred at room temperature for 30 min, and sodium triacetoxyborohydride (19 g, 91 mmol) was added. The mixture was stirred at room temperature for 24h, and concentrated under reduced pressure. The residue was diluted with DCM, washed with saturated aqueous NaHCO$_3$ and brine, dried over Na$_2$SO$_4$, and concentrated under reduced pressure. The residue was purified by silica gel column chromatography (EtOAc in Hexanes) to give rac-(3aR, 6aS)—N,N-dibenzylhexahydro-1H-spiro[pentalene-2,2'-[1, 3]dioxolan]-5-amine. LCMS ($C_{24}H_{30}NO_2^+$): 364 [M+H]$^+$.

Step 2: rac-(3aR,6aS)-5-(dibenzylamino)hexahydro-pentalen-2(1H)-one

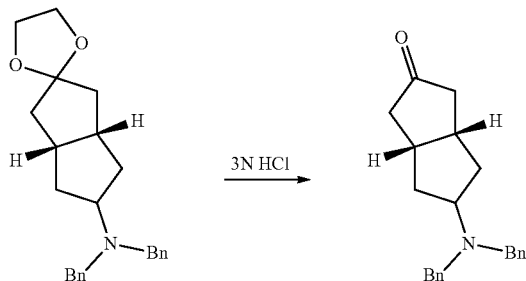

3N HCl in water (15 ml, 45 mmol) was added to a solution of rac-(3aR,6aS)—N,N-dibenzylhexahydro-1H-spiro[pentalene-2,2'-[1,3]dioxolan]-5-amine (1624 mg, 4.6 mmol) in THF (20 ml). The resulting solution was stirred at 75° C. for 2h and then cooled to room temperature. The pH of the solution was adjusted to 8. The mixture was extracted with ethyl acetate. The combined organic layers was washed with brine, dried over sodium sulfate, filtered and the solvent was evaporated under reduced pressure. The residue was purified by silica gel column chromatography (EtOAc in Hexanes) to give rac-(3aR,6aS)-5-(dibenzylamino)hexahydropentalen-2 (1H)-one. LCMS ($C_{22}H_{26}NO^+$): 320 [M+H]$^+$.

Step 3: rac-(3aR,6aR)-1-allyl-5-(dibenzylamino)hexahydropentalen-2(1H)-one

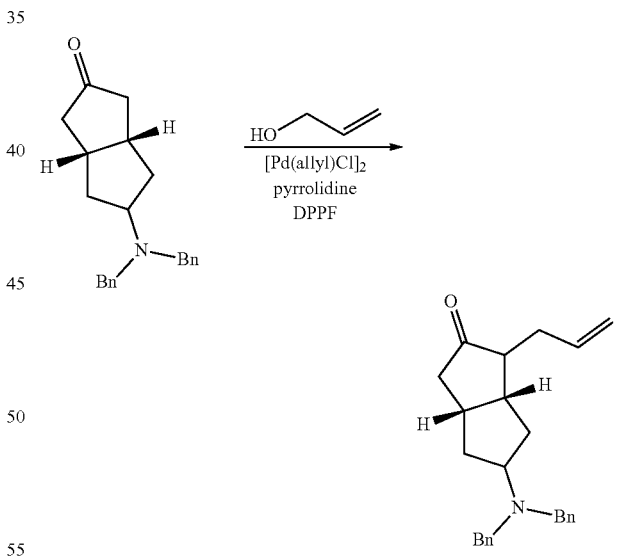

Allylpalladium(II) chloride dimer (66 mg, 0.18 mmol) and prop-2-en-1-ol (0.27 ml, 4.0 mmol) was added to a mixture of rac-(3aR,6aS)-5-(dibenzylamino)hexahydropentalen-2(1H)-one (1155 mg, 3.6 mmol), pyrrolidine (77 mg, 1.1 mmol) and DPPF (200 mg, 0.36 mmol) in MeOH (10 mL) under N$_2$ at 20° C. The resulting mixture was stirred at 20° C. for 14 h. The solvent was removed under reduced pressure. The residue was suspended in EtOAc and stirred at room temperature for 10 min, then filtered through Celite. The filtrate was washed with water, brine, dried over anhydrous Na$_2$SO$_4$, filtered and concentrated under reduced pressure. The residue was purified by silica gel column chromatography (EtOAc in hexanes) to afford rac-(3aR,6aR)-1-allyl-5-(dibenzylamino)hexahydropentalen-2(1H)-one. LCMS ($C_{25}H_{30}NO^+$): 360 [M+H]$^+$.

Step 4: rac-(3aR,6aR)-2-acetamido-1-allyl-N-(tert-butyl)-5-(dibenzylamino)octahydropentalene-2-carboxamide

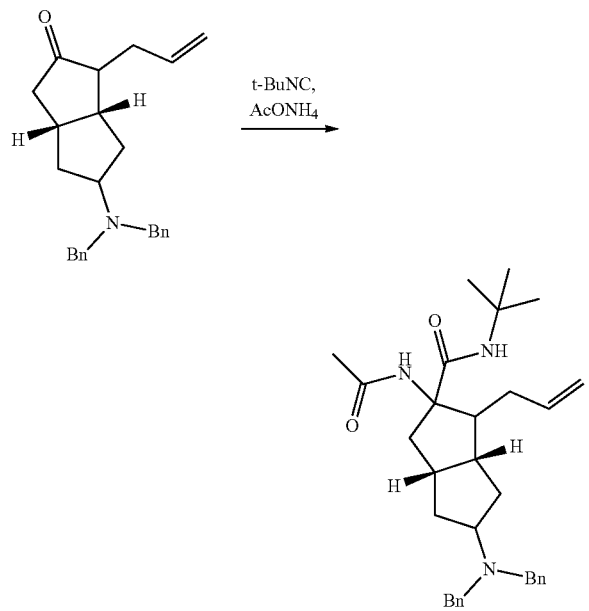

Tert-butyl isocyanide (3.5 g mg, 42 mmol) and ammonium acetate (3.2 g, 42 mmol) was added to a mixture of rac-(3aR,6aR)-1-allyl-5-(dibenzylamino)hexahydropentalen-2(1H)-one (5.0 g, 14 mmol) in 2,2,2-trifluoroethyl alcohol (20 mL) at room temperature. The reaction mixture was stirred at 40° C. for 18 h. The reaction was diluted with water and DCM. The organic layer was separated and the aqueous layer was re-extracted with DCM. The combined organic layers were washed with brine, dried over anhydrous Na$_2$SO$_4$, filtered and concentrated. The residue was purified by silica gel column chromatography (EtOAc in DCM) to afford rac-(3aR,6aR)-2-acetamido-1-allyl-N-(tert-butyl)-5-(dibenzylamino)octahydropentalene-2-carboxamide. LCMS ($C_{32}H_{44}N_3O_2$). 502 [M+H]$^+$.

Step 5: rac-(3aR,6aR)-2-acetamido-N-(tert-butyl)-5-(dibenzylamino)-1-(3-(4,4,5,5-tetramethyl-1,3,2-dioxaborolan-2-yl)propy)octahydropentalene-2-carboxamide\

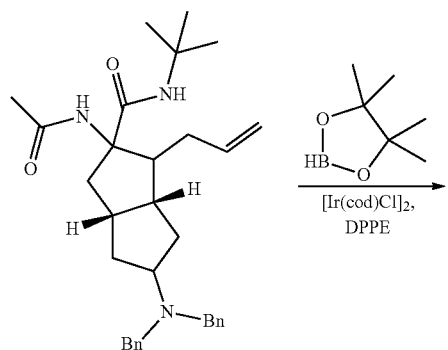

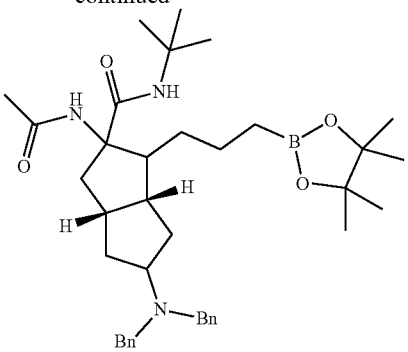

4,4,5,5-Tetramethyl-1,3,2-dioxaborolane (1.2 mL, 7.4 mmol) was added to a mixture of chloro(1,5-cyclooctadiene)iridium(I) dimer (76 mg, 0.15 mmol), and DPPE (118 mg, 0.30 mmol) in DCM (15 mL) under N$_2$. The mixture was degassed and backfilled with N$_2$ (three times). After stirring at 25° C. for 20 min, rac-(3aR,6aR)-2-acetamido-1-allyl-N-(tert-butyl)-5-(dibenzylamino)octahydropentalene-2-carboxamide (1.5 g, 3.0 mmol) in DCM (15 mL) was added under N$_2$. The resulting mixture was stirred at 25° C. for 15 h. The reaction was quenched with MeOH and water. The mixture was concentrated under reduced pressure. The residue was purified by silica gel column chromatography (EtOAc in DCM). The resulting product was then purified by RP-HPLC [C18 column, water (0.05% HCl)—CH$_3$CN] to give to give rac-(3aR,6aR)-2-acetamido-N-(tert-butyl)-5-(dibenzylamino)-1-(3-(4,4,5,5-tetramethyl-1,3,2-dioxaborolan-2-yl)propyl)octahydropentalene-2-carboxamide. LCMS ($C_{38}H_{57}BN_3O_4^+$): 630[M+H]$^+$.

Step 6: rel-((3aR,6aR)-2-acetamido-N-(tert-butyl)-5-(dibenzylamino)-1-(3-(4,4,5,5-tetramethyl-1,3,2-dioxaborolan-2-yl)propyl)octahydropentalene-2-carboxamide, P1, P2-1, P2-2 and P3

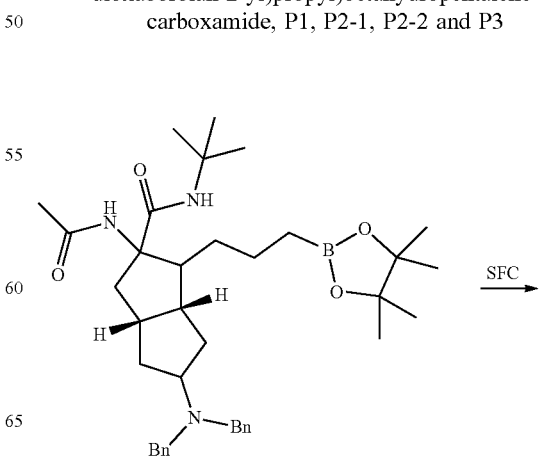

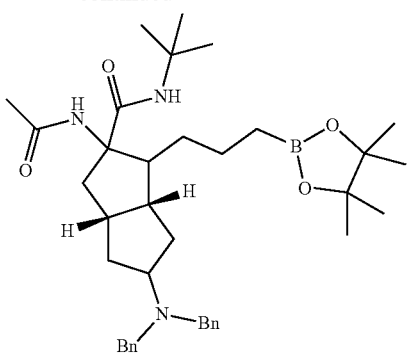

P1

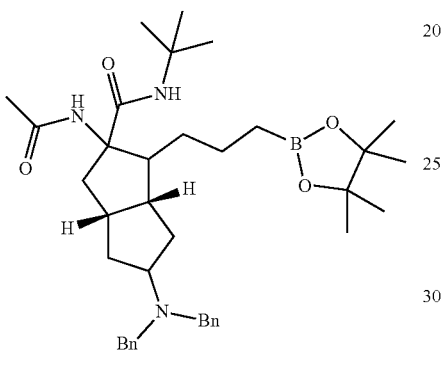

P2

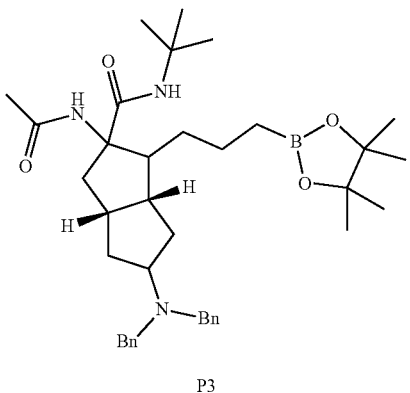

P3

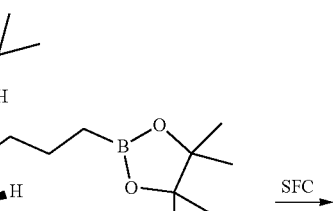 SFC →

P2

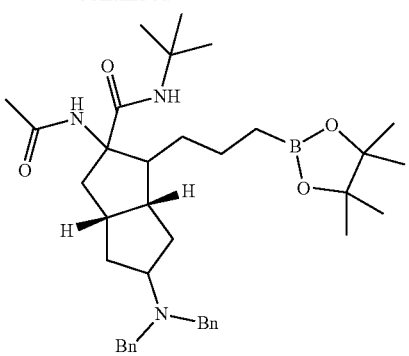

P2-1

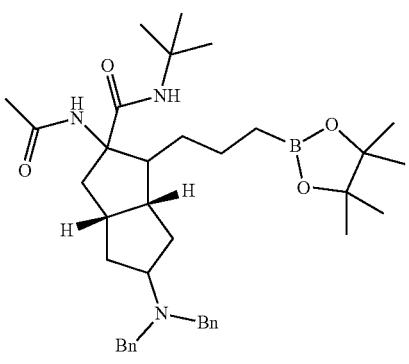

P2-2

Rac-(3aR,6aR)-2-acetamido-N-(tert-butyl)-5-(dibenzylamino)-1-(3-(4,4,5,5-tetramethyl-1,3,2-dioxaborolan-2-yl)propyl)octahydropentalene-2-carboxamide was resolved by Chiral-SFC [Column: IC, 21×250, Outlet Pressure (bar): 100, UV wavelength (nm): 212, Flow rate (ml/min): 70, Modifier: Isopropanol w/ 0.1% NH$_4$OH, % modifier in CO$_2$: 25] to give P1 (t$_r$=3.1 min), P2 (t$_r$=4.1 min), and P3 (t$_r$=5.0 min).

P2 has two peaks and was subject to additional SFC purification [Column: R,R Whelk-01, 21×250, Outlet Pressure (bar): 100, UV wavelength (nm): 220, Flow rate (ml/min): 70, Modifier: IPA w/ 0.1% NH$_4$OH, % modifier in CO$_2$: 30] to afford P2-1 (t$_r$=3.7 min) and P2-2 (t$_r$=5.0 min). P1 LCMS (C$_{38}$H$_{57}$BN$_3$O$_4{}^+$): 630[M+H]$^+$. P2-1 LCMS (C$_{38}$H$_{57}$BN$_3$O$_4{}^+$): 630[M+H]$^+$. P2-2 LCMS (C$_{38}$H$_{57}$BN$_3$O$_4{}^+$): 630[M+H]$^+$. P3 LCMS (C$_{38}$H$_{57}$BN$_3$O$_4{}^+$): 630[M+H]$^+$.

Step 7: rel-(3aR,6aR)-2-acetamido-5-amino-N-(tert-butyl)-1-(3-(4,4,5,5-tetramethyl-1,3,2-dioxaborolan-2-yl)propyl)octahydropentalene-2-carboxamide P'1

Step 8: Rel-(3aR,6aR)-2,5-diamino-1-(3-boronopropyl)octahydropentalene-2-carboxylic acid hydrochloride

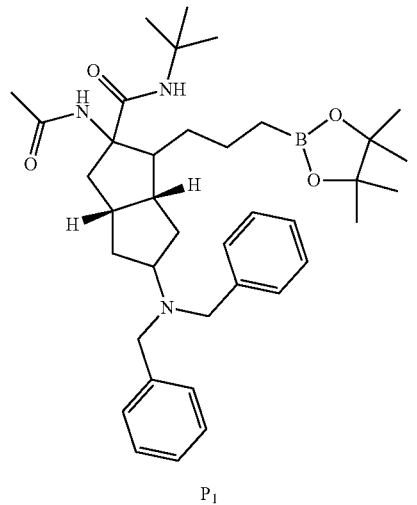

P1

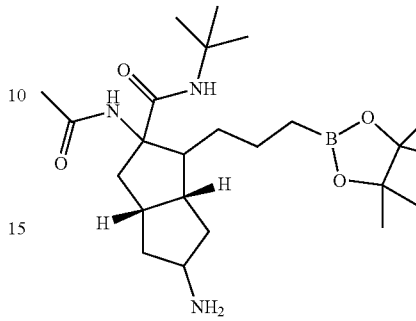

P'1

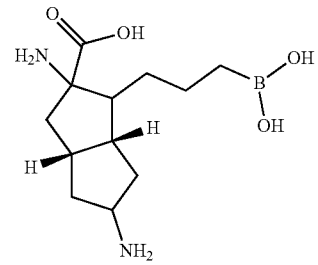

Example 29a

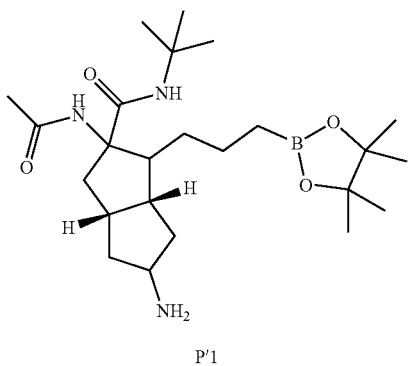

P'1

Rel-(3aR,6aR)-2-acetamido-N-(tert-butyl)-5-(dibenzylamino)-1-(3-(4,4,5,5-tetramethyl-1,3,2-dioxaborolan-2-yl)propyl)octahydropentalene-2-carboxamide (P1, 330 mg, 0.52 mmol), Pd/C (112 mg, 0.11 mmol) and TFA (4.0 µl, 0.052 mmol) in MeOH (10 mL) was placed under a parr shaker. The mixture was degassed and backfilled with $H_2$ (three times). The mixture was hydrogenated at room temperature under hydrogen pressure of 50 psi for 96 hours. After completion, the reaction mixture was filtered through a celite bed then washed with methanol. The filtrate was concentrated under reduced pressure to obtain rel-(3aR,6aR)-2-acetamido-5-amino-N-(tert-butyl)-1-(3-(4,4,5,5-tetramethyl-1,3,2-dioxaborolan-2-yl)propyl)octahydropentalene-2-carboxamide (P'1). The crude product was used in next step without further purification. LCMS $(C_{24}H_{45}BN_3O_4^+)$: 450 [M+H]$^+$.

(3aR,6aR)-2-acetamido-5-amino-N-(tert-butyl)-1-(3-(4,4,5,5-tetramethyl-1,3,2-dioxaborolan-2-yl)propyl)octahydropentalene-2-carboxamide P'1 (100 mg, 0.22 mmol) was dissolved in 2:1:1 concentrated HCl (aq.):glacial acetic acid:water (2 mL). The mixture was stirred in a microwave at 130° C. for 30 min, and then cooled to room temperature. The solution was diluted with water, washed with dichloromethane and concentrated under reduced pressure. The residue was purified by RP-HPLC [C18 column, water (20 mM HFBA and 0.1% TFA)-CH$_3$CN]. The fractions were lyophilized. The product was dissolved in 2 mL of 1N HCl in water and lyophilized to give (3aR,6aR)-2,5-diamino-1-(3-boronopropyl)octahydropentalene-2-carboxylic acid as the HCl salt. (I) LCMS $(C_{12}H_{22}BN_2O_3^+)$ (ES, m/z): 253 [M–H$_2$O+H]$^+$. $^1$H NMR (499 MHz, Deuterium Oxide) d 3.63 (tt, J=12.6, 6.3 Hz, 2H), 3.21 (q, J=7.3 Hz, 3H), 3.09 (dq, J=14.3, 7.2 Hz, 2H), 2.82-2.68 (m, 1H), 2.62-2.50 (m, 1H), 2.52-2.27 (m, 2H), 2.22 (d, J=9.4 Hz, 1H), 1.69-1.43 (m, 2H), 0.78 (dt, J=16.2, 7.9 Hz, 2H).

Example 29b was prepared from P2-1, Example 29c was prepared from P2-2 and Example 29d was prepared from P3 using a similar method. 29b LCMS $(C_{12}H_{22}BN_2O_3^+)$ (ES, m/z): 253 [M–H$_2$O+H]$^+$. $^1$H NMR (499 MHz, Deuterium Oxide) d 3.52 (tt, J=12.2, 6.3 Hz, 1H), 2.83 (h, J=8.8 Hz, 1H), 2.65-2.51 (m, 1H), 2.42 (ddt, J=19.1, 13.5, 8.0 Hz, 2H), 2.31 (dt, J=12.5, 6.8 Hz, 1H), 2.12-1.94 (m, 1H), 1.73 (dd, J=13.7, 8.8 Hz, 1H), 1.44 (ddd, J=23.0, 9.8, 3.7 Hz, 3H), 1.39-1.28 (m, 1H), 1.15 (ddt, J=13.1, 9.0, 4.2 Hz, 2H), 0.67 (ddd, J=15.4, 12.1, 7.7 Hz, 2H). 29c LCMS $(C_{12}H_{22}BN_2O_3^+)$ (ES, m/z): 253 [M–H$_2$O+H]$^+$. $^1$HNMR (499 MHz, Deuterium Oxide) d 3.61-3.41 (m, 2H), 2.75-2.53 (m, 2H), 2.47-2.38 (m, 2H), 2.31 (ddd, J=22.9, 12.5, 6.4 Hz, 3H), 2.18 (dd, J=14.7, 9.6 Hz, 1H), 1.57-1.30 (m, 4H), 0.68 (q, J=7.5 Hz, 2H). 29d LCMS ($C_{12}H_{22}BN_2O_3^+$) (ES, m/z): 253 [M–$H_2$O+H]$^+$. $^1$H NMR (499 MHz, Deuterium Oxide) d 3.58 (tt, J=12.2, 6.3 Hz, 1H), 2.89 (h, J=9.1 Hz, 1H), 2.74-2.56 (m, 1H), 2.48 (ddd, J=19.5, 16.5, 8.3 Hz, 2H), 2.38 (dt, J=12.8, 6.9 Hz, 1H), 2.14-2.01 (m, 1H), 1.79 (dd, J=13.6, 8.8 Hz, 1H), 1.59-1.35 (m, 4H), 1.21 (td, J=11.8, 3.6 Hz, 2H), 0.82-0.59 (m, 2H).

Scheme C1

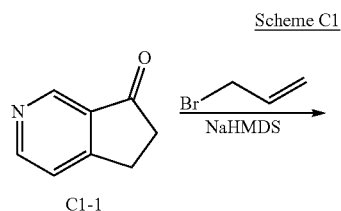

C1-1

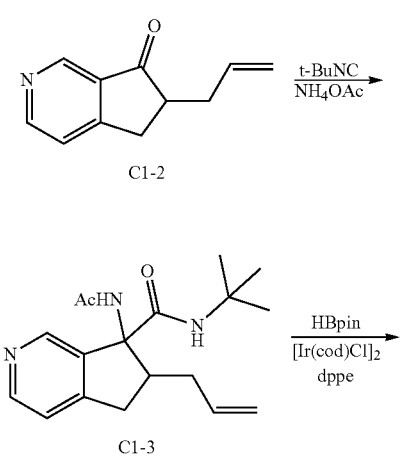

C1-2

C1-3

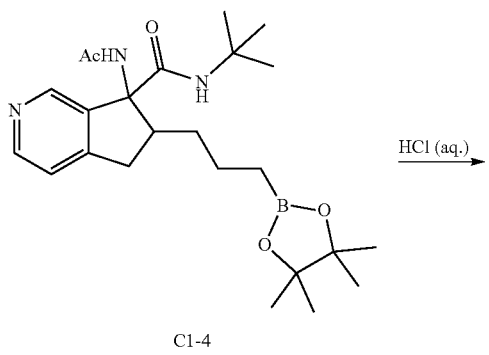

C1-4

Example 30: 7-amino-6-(3-boronopropyl)-6,7-dihydro-5H-cyclopenta[c]pyridine-7-carboxylic acid

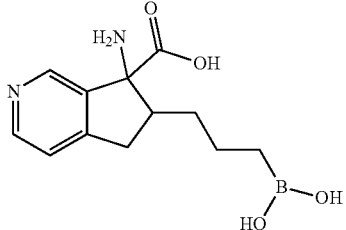 [SMILES: NC1(C(=O)O)c2cnccc2CC1CCCB(O)O]

Step 1: 6-allyl-5,6-dihydro-7H-cyclopenta[c]pyridin-7-one

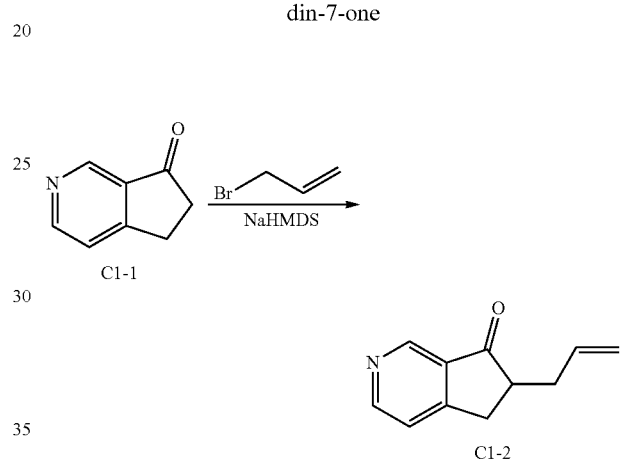

C1-1

C1-2

NaHMDS (2.6 mL, 5.2 mmol, 2M in THF) was added to a solution of 5,6-dihydro-7H-cyclopenta[c]pyridin-7-one hydrochloride (350 mg, 2.1 mmol) and 3-bromoprop-1-ene (300 mg, 2.5 mmol) in DMF (10 mL) at −40° C. under $N_2$. The reaction was stirred at −40° C. for 20 min. The reaction mixture was quenched with brine and extracted with EtOAc. The combined organic phases were washed with brine, dried over anhydrous $Na_2SO_4$, filtered and concentrated under reduced pressure. The residue was purified by silica gel column chromatography (EtOAc in hexanes) to give 6-allyl-5,6-dihydro-7H-cyclopenta[c]pyridin-7-one. LCMS ($C_{11}H_{12}NO^+$) (ES, m/z): 174 [M+H]$^+$.

Step 2: 7-acetamido-6-allyl-N-(tert-butyl)-6,7-dihydro-5H-cyclopenta[c]pyridine-7-carboxamide

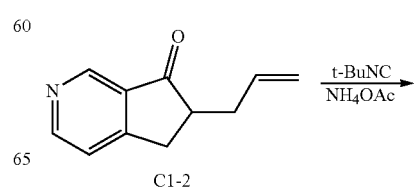

C1-2

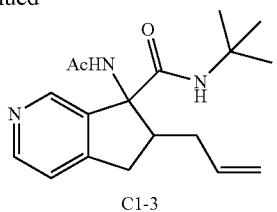

C1-3

NH₄OAc (289 mg, 3.8 mmol) and 2-isocyano-2-methylpropane (156 mg, 1.9 mmol) were added to a solution of 6-allyl-5,6-dihydro-7H-cyclopenta[c]pyridin-7-one (65 mg, 0.38 mmol) in 2,2,2-trifluoroethyl alcohol (1 mL) under N₂. The reaction was stirred at 35° C. for 60 h under N₂. The reaction mixture was quenched with water and extracted with EtOAc. The combined organic phases were washed with brine, dried over anhydrous Na₂SO₄, filtered and concentrated under reduced pressure. The resulting residue was purified by RP-HPLC [C18 column, water (0.1% TFA)-CH₃CN] to give 7-acetamido-6-allyl-N-(tert-butyl)-6,7-dihydro-5H-cyclopenta[c]pyridine-7-carboxamide. LCMS $(C_{18}H_{26}N_3O_2^+)$ (ES, m/z): 316 [M+H]⁺.

Step 3: 7-acetamido-N-(tert-butyl)-6-(3-(4,4,5,5-tetramethyl-1,3,2-dioxaborolan-2-yl)propyl)-6,7-dihydro-5H-cyclopenta[c]pyridine-7-carboxamide

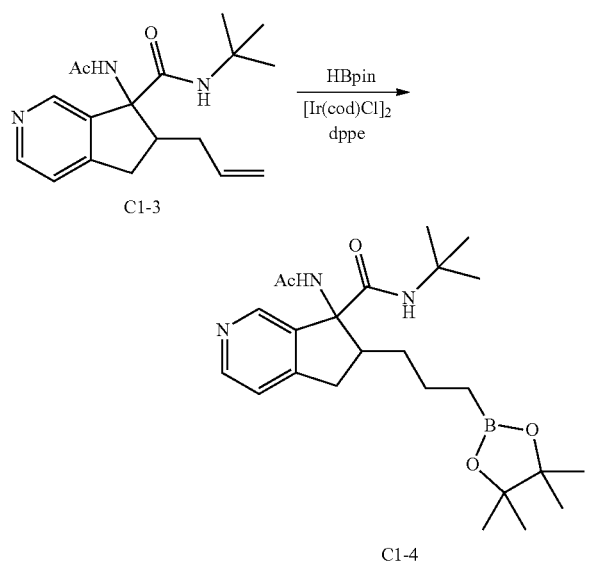

C1-4

[Ir(cod)Cl]₂ (4.1 mg, 6 μmol) was added to a solution of 7-acetamido-6-allyl-N-(tert-butyl)-6,7-dihydro-5H-cyclopenta[c]pyridine-7-carboxamide (38 mg, 0.12 mmol), 1,2-bis(diphenylphosphino)ethane (3.4 mg, 8.4 μmol) and 4,4,5,5-tetramethyl-1,3,2-dioxaborolane (308 mg, 2.4 mmol) in DCM (2 mL). The reaction mixture was degassed and backfilled with N₂ (three times). The reaction mixture was stirred at 15° C. for 15 h under N₂. The reaction mixture was quenched with water and extracted with DCM. The combined organic phases were washed with brine, dried over anhydrous Na₂SO₄, filtered and concentrated under reduced pressure. The resulting residue was purified by RP-HPLC [C18 column, water (0.1% TFA)-CH₃CN] to give 7-acetamido-N-(tert-butyl)-6-(3-(4,4,5,5-tetramethyl-1,3,2-dioxaborolan-2-yl)propyl)-6,7-dihydro-5H-cyclopenta[c]pyridine-7-carboxamide, which contained the corresponding boronic acid. LCMS $(C_{24}H_{39}BN_3O_4^+)$ (ES, m/z): 444 [M+H]⁺. LCMS of boronic acid $(C_{18}H_{29}BN_3O_4^+)$ ES, m/z): 362 [M+H]³⁰

Step 4: 7-amino-6-(3-boronopropyl)-6,7-dihydro-5H-cyclopenta[c]pyridine-7-carboxylic acid

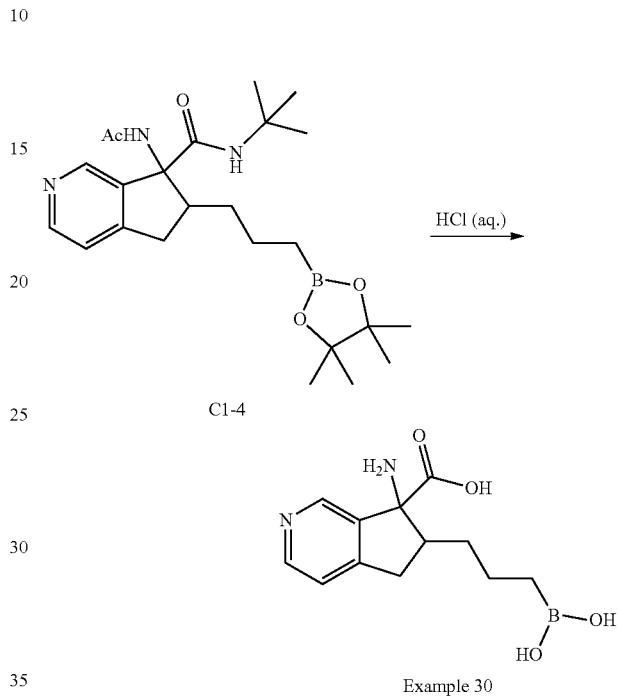

Example 30

7-acetamido-N-(tert-butyl)-6-(3-(4,4,5,5-tetramethyl-1,3,2-dioxaborolan-2-yl)propyl)-6,7-dihydro-5H-cyclopenta[c]pyridine-7-carboxamide (20 mg, 0.045 mmol) was added to 12 N HCl in water (10 mL, 120 mmol). The resulting mixture was stirred at 120° C. for 10 h. Solvent was evaporated in vacuum. The residue was dissolved in 4M NaOH in water. Solvent was evaporated in vacuum. The resulting residue was purified by RP-HPLC [C18 column, water (0.1% TFA)-CH₃CN] to give 7-amino-6-(3-boronopropyl)-6,7-dihydro-5H-cyclopenta[c]pyridine-7-carboxylic acid. LCMS $(C_{12}H_{16}BN_2O_3^+)$ (ES, m/z): 247 [M+H-H₂O]⁺. ¹H NMR (400 MHz, deuterium oxide) δ 8.70-8.62 (m, 1H), 8.62-8.57 (m, 1H), 7.99-7.85 (m, 1H), 3.50-3.46 (m, 1H), 2.99-2.95 (m, 1H), 2.75-2.62 (m, 1H), 1.65-1.63 (m, 1H), 1.49-1.20 (m, 3H), 0.78-0.58 (m, 2H).

Scheme D1

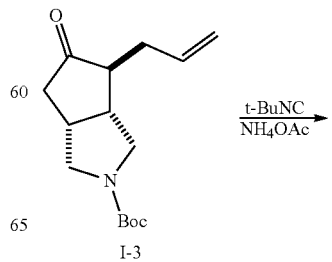

I-3

-continued
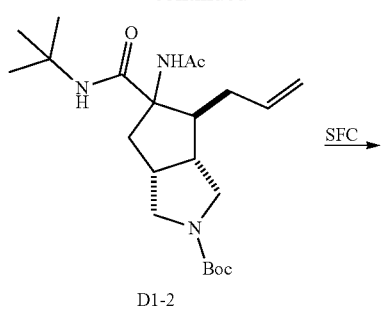
D1-2
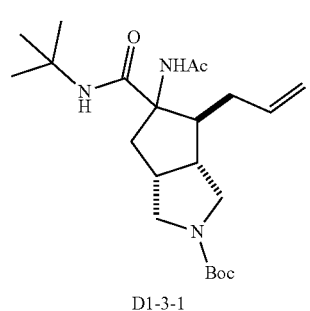
D1-3-1
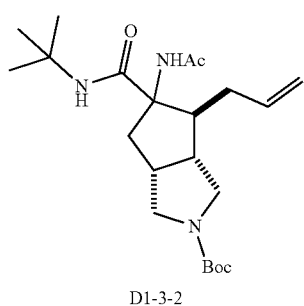
D1-3-2
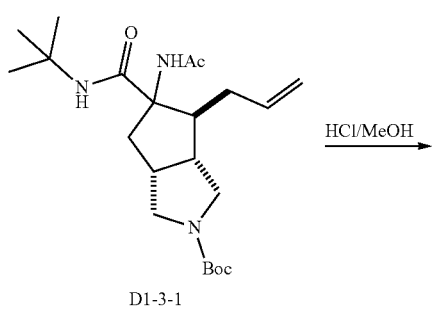
D1-3-1
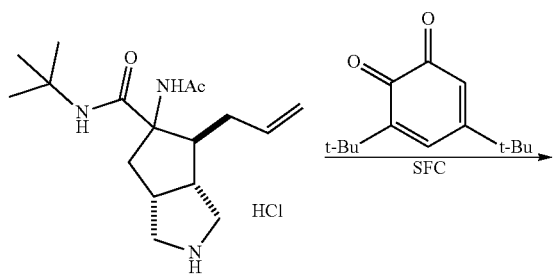
D1-4
-continued
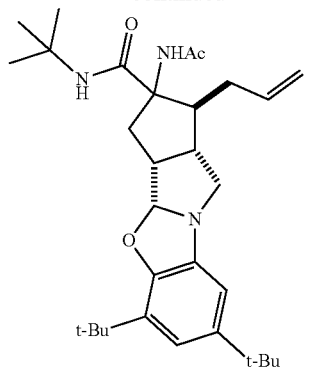
D1-5A
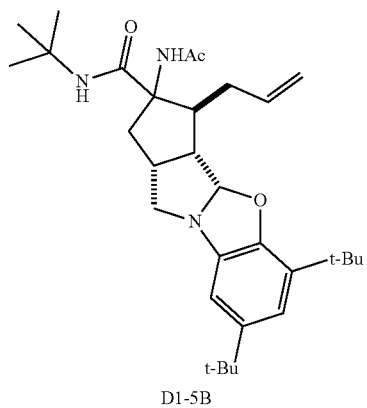
D1-5B
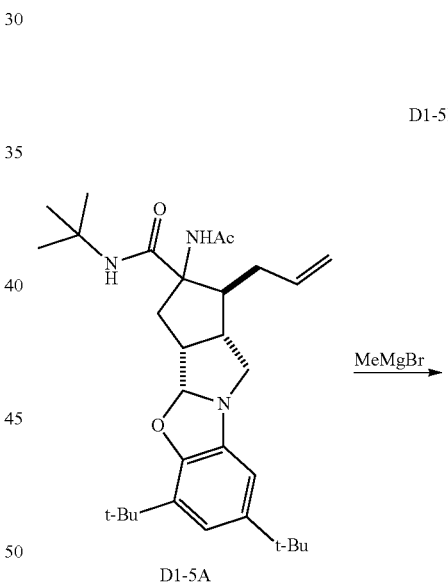
D1-5A
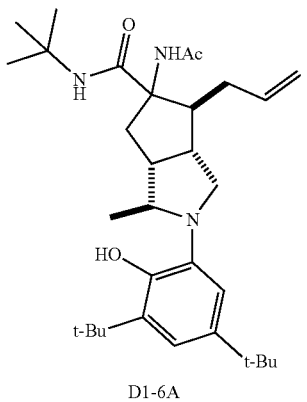
D1-6A 207
-continued

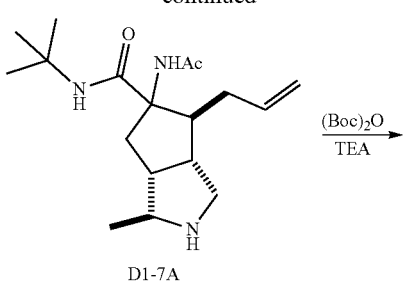

D1-7A

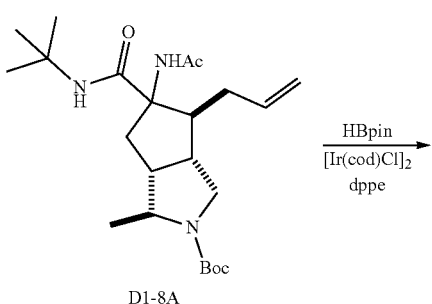

D1-8A

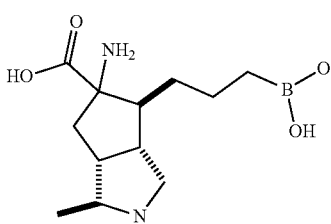

D1-9A

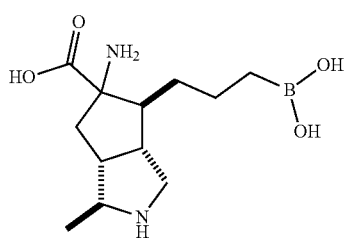

Example 31A

Example 31A: (3aR,4S,6aR)-5-amino-4-(3-borono-propyl)-1-methyloctahydrocyclopenta[c]pyrrole-5-carboxylic acid

208

Step 1: tert-butyl (3aR,4S,6aR)-5-acetamido-4-allyl-5-(tert-butylcarbamoyl)hexahydrocyclopenta[c]pyrrole-2(1H)-carboxylate Tert-butyl isocyanide (8.5 mL, 75 mmol) and ammonium acetate (7.3 g, 94 mmol) were added to a solution of tert-butyl (3aR,4S,6aR)-4-allyl-5-oxohexahydrocyclopenta[c]pyrrole-2(1H)-carboxylate (5 g, 19 mmol) in 2,2,2-trifluoroethyl alcohol (25 mL). The mixture was allowed to stir at 40° C. for 12 h under $N_2$. The reaction was quenched with water. The mixture was diluted with EtOAc and organic layers were washed with brine, dried over anhydrous $Na_2SO_4$, then filtered and concentrated in vacuum. The residual was purified by flash silica gel chromatography (EtOAc in hexanes) to give the title compound. LCMS ($C_{22}H_{38}N_3O_4^+$) (ES, m/z): 408 [M+H]$^+$.

Step 2: (3aR,4S,6aR)-5-acetamido-4-allyl-5-(tert-butylcarbamoyl)hexahydrocyclopenta[c]pyrrole-2(1H)-carboxylate (D1-3-1) and (3aR,4S,6aR)-5-acetamido-4-allyl-5-(tert-butylcarbamoyl)hexahydrocyclopenta[c]pyrrole-2(1H)-carboxylate (D1-3-2)

(3aR,4S,6aR)-5-acetamido-4-allyl-5-(tert-butylcarbamoyl)hexahydrocyclopenta[c]pyrrole-2(1H)-carboxylate (5.7 g, 14 mmol) was resolved by [Column: DAICEL CHIRALPAK IC (250 mm*50 mm, 10 um), Mobile phase: A: $CO_2$, B: EtOH (0.1% $NH_3.H_2O$), Gradient: 25% of B in 4 min, and hold 25% of B for 1 min, Flow Rate (mL/min) 200, Column temperature: 40° C.] to give (3aR,4S,6aR)-5-acetamido-4-allyl-5-(tert-butylcarbamoyl)hexahydrocyclopenta[c]pyrrole-2(1H)-carboxylate (D1-1, $t_r$=1.6 min) as the first eluting peak, and (3aR,4S,6aR)-5-acetamido-4-allyl-5-(tert-butylcarbamoyl)hexahydrocyclopenta[c]pyrrole-2(1H)-carboxylate (D1-2, $t_r$=2.3 min) as the 15 second eluting peak. D1-1: LCMS ($C_{22}H_{38}N_3O_4^+$) (ES, m/z): 408 [M+H]$^+$. D1-2: LCMS ($C_{22}H_{38}N_3O_4^+$) (ES, m/z): 408 [M+H]$^+$.

Step 3: (3aR,4S,6aR)-5-acetamido-4-allyl-N-(tert-butyl)octahydrocyclopenta[c]pyrrole-5-carboxamide hydrochloride A mixture of (3aR,4S,6aR)-5-acetamido-4-allyl-5-(tert-butylcarbamoyl)hexahydrocyclopenta[c]pyrrole-2(1H)-carboxylate (1 g, 2.5 mmol) and 4M HCl in MeOH (10 mL, 40 mmol) was stirred at 15° C. for 12 h. The solution was concentrated in vacuum to give the crude product, which was used in the next step without further purification. LCMS ($C_{17}H_{3}N_3O_2^+$) (ES, m/z): 308 [M+H]$^+$.

Step 4: (1S,3aR,3bR,10aS)-2-acetamido-1-allyl-N,5,7-tri-tert-butyl-2,3,3a,3b,10,10a-hexahydro-H-benzo[d]cyclopenta[3,4]pyrrolo[2,1-b]oxazole-2-carboxamide (D1-5A) and (3S,3aR,3bS,10aR)-2-acetamido-3-allyl-N,5,7-tri-tert-butyl-2,3,3a,3b,10,10a-hexahydro-H-benzo[d]cyclopenta[3,4]pyrrolo[2,1-b]oxazole-2-carboxamide (D1-5B)

$K_2CO_3$ (512 mg, 3.7 mmol) and 3,5-di-tert-butylcyclohexa-3,5-diene-1,2-dione (545 mg, 2.5 mmol) were added to a mixture of (3aR,4S,6aR)-5-acetamido-4-allyl-N-(tert-butyl)octahydrocyclopenta[c]pyrrole-5-carboxamide hydrochloride (850 mg, 2.5 mmol) in trifluoroethanol (15 mL) at 20° C. under $N_2$. The mixture was stirred at 20° C. for 3 h. The reaction was concentrated in vacuum. The residual was purified by flash silica gel chromatography (EtOAc in hexanes) to give a mixture of (1S,3aR,3bR,10aS)-2-acetamido-1-allyl-N,5,7-tri-tert-butyl-2,3,3a,3b,10,10a-hexahydro-1H-benzo[d]cyclopenta[3,4]pyrrolo[2,1-b]oxazole-2-carboxamide (D1-5A) and (3S,3aR,3bS,10aR)-2-acetamido-3-allyl-N,5,7-tri-tert-butyl-2,3,3a,3b,10,10a-hexahydro-1H-benzo[d]cyclopenta[3,4]pyrrolo[2,1-b]oxazole-2-carboxamide (D1-5B) which was resolved by [Column: Phenomenex-Cellulose-2 (250 mm*30 mm, 5 um); Mobile phase: A: $CO_2$, B: MeOH (0.1% $NH_3.H_2O$), Gradient: 20% of B in 4.2 min and hold 20% for 1 min, Flow Rate (mL/min) 60, Column temperature: 40° C.] to give (1S,3aR,3bR,10aS)-2-acetamido-1-allyl-N,5,7-tri-tert-butyl-2,3,3a,3b,10,10a-hexahydro-1H-benzo[d]cyclopenta[3,4]pyrrolo[2,1-b]oxazole-2-carboxamide (D1-5A, $t_r$=2.6 min) as the first eluting peak and (3S,3aR,3bS,10aR)-2-acetamido-3-allyl-N,5,7-tri-tert-butyl-2,3,3a,3b,10,10a-hexahydro-1H-benzo[d]cyclopenta[3,4]pyrrolo[2,1-b]oxazole-2-carboxamide (D1-5B, $t_r$=2.8 min) as the second eluting peak. D1-5A: LCMS ($C_{31}H_{48}N_3O_3^+$) (ES, m/z): 510 $[M+H]^+$. D1-5B: LCMS ($C_{31}H_{48}N_3O_3^+$) (ES, m/z): 510 $[M+H]^+$.

Step 5: (3aR,4S,6aR)-5-acetamido-4-allyl-N-(tert-butyl)-2-(3,5-di-tert-butyl-2-hydroxyphenyl)-1-methyloctahydrocyclopenta[c]pyrrole-5-carboxamide Methylmagnesium bromide (1.1 mL, 3.3 mmol, 3M in diethyl ether) was added to a mixture of (1S,3aR,3bR,10aS)-2-acetamido-1-allyl-N,5,7-tri-tert-butyl-2,3,3a,3b,10,10a-hexahydro-1H-benzo[d]cyclopenta[3,4]pyrrolo[2,1-b]oxazole-2-carboxamide (330 mg, 0.65 mmol) in DCE (5 mL) at 0° C. under $N_2$. The mixture was stirred at 0° C. for 4 h. The reaction was quenched with saturated aqueous $NH_4Cl$. The mixture was extracted with DCM. The combined organic layers were washed with brine, dried over anhydrous $Na_2SO_4$, filtered and the filtrate was concentrated under reduced pressure. The residue was purified by flash silica gel chromatography (EtOAc in hexanes) to give the title compound. LCMS ($C_{32}H_{52}N_3O_3^+$) (ES, m/z): 526 $[M+H]^+$.

Step 6: (3aR,4S,6aR)-5-acetamido-4-allyl-N-(tert-butyl)-1-methyloctahydrocyclopenta[c]pyrrole-5-carboxamide $I_2$ (157 mg, 0.62 mmol) was added to a solution of (3aR,4S,6aR)-5-acetamido-4-allyl-N-(tert-butyl)-2-(3,5-di-tert-butyl-2-hydroxyphenyl)-1-methyloctahydrocyclopenta[c]pyrrole-5-carboxamide (310 mg, 0.59 mmol) in a mixture of 1N NaOH in water (15 mL, 15 mmol) and acetonitrile (30 mL) at 0° C. under argon protection. The resulting mixture was stirred at 0° C. for 1 h. The reaction mixture was extracted with DCM. The combined organic phases were extracted with 2N HCl in water twice. The combined acidic aqueous phases were washed with petroleum ether and the acidic aqueous phase was concentrated under reduced pressure to give the crude product as a HCl salt, which was used in the next step directly. LCMS ($C_{18}H_{32}N_3O_2^+$) (ES, m/z): 322 $[M+H]^+$.

Step 7: tert-butyl (3aR,4S,6aR)-5-acetamido-4-allyl-5-(tert-butylcarbamoyl)-1-methylhexahydrocyclopenta[c]pyrrole-2(1H)-carboxylate Di-tert-butyl dicarbonate (224 mg, 1.0 mmol) and N,N-dimethylpyridin-4-amine (11.4 mg, 0.093 mmol) were added to a stirred mixture of (3aR,4S,6aR)-5-acetamido-4-allyl-N-(tert-butyl)-1-methyloctahydrocyclopenta[c]pyrrole-5-carboxamide (HCl salt from previous step, 300 mg, 0.84 mmol) and triethylamine (0.52 mL, 3.7 mmol) in THF (10 mL) at 0° C. under $N_2$. The reaction mixture was slowly warmed to 15° C. and stirred at 15° C. for 40 min. The mixture was quenched with saturated aqueous $NH_4Cl$. The mixture was extracted with DCM. The combined organic layers were washed with brine, dried over anhydrous $Na_2SO_4$, filtered and concentrated. The residue was purified by flash silica gel chromatography (EtOAc in hexanes) to give the title compound. LCMS ($C_{23}H_{40}N_3O_4^+$) (ES, m/z): 422 $[M+H]^+$.

Step 8: tert-butyl (3aR,4S,6aR)-5-acetamido-5-(tert-butylcarbamoyl)-1-methyl-4-(3-(4,4,5,5-tetramethyl-1,3,2-dioxaborolan-2-yl)propyl)hexahydrocyclopenta[c]pyrrole-2(1H)-carboxylate A mixture of bis(diphenylphosphino)methane (7 mg, 0.018 mmol), $[Ir(cod)Cl]_2$ (8.8 mg, 0.013 mmol) and 4,4,5,5-tetramethyl-1,3,2-dioxaborolane (0.11 mL, 0.78 mmol) in anhydrous DCM (4 mL) was stirred at 15° C. for 20 minutes under $N_2$ and then tert-butyl (3aR,4S,6aR)-5-acetamido-4-allyl-5-(tert-butylcarbamoyl)-1-methylhexahydrocyclopenta[c]pyrrole-2(1H)-carboxylate (110 mg, 0.26 mmol) in anhydrous DCM (4 mL) was added to the mixture. The resulting mixture was stirred at 15° C. for 12 h under $N_2$. The reaction was concentrated and the residue was purified by flash silica gel chromatography (EtOAc in hexanes) to give the title compound. LCMS ($C_{29}H_{53}BN_3O_6^+$) (ES, m/z): 550 $[M+H]^+$.

Step 9: (3aR,4S,6aR)-5-amino-4-(3-boronopropyl)-1-methyloctahydrocyclopenta[c]pyrrole-5-carboxylic acid A mixture of tert-butyl (3aR,4S,6aR)-5-acetamido-5-(tert-butylcarbamoyl)-1-methyl-4-(3-(4,4,5,5-tetramethyl-1,3,2-dioxaborolan-2-yl)propyl)hexahydrocyclopenta[c]pyrrole-2(1H)-carboxylate (165 mg, 0.3 mmol) and 12 N HCl in water (4 mL, 48 mmol) was stirred at 100° C. for 13 h. The reaction mixture was concentrated in vacuum, the residue was basified with saturated aqueous $Na_2CO_3$ until pH=9-10. The aqueous layer was washed with DCM and concentrated in vacuum. The residue was purified by RP-HPLC [C18 column, water (20 mM HFBA and 0.1% TFA)-$CH_3CN$] to give (3aR,4S,6aR)-5-amino-4-(3-boronopropyl)-1-methyloctahydrocyclopenta[c]pyrrole-5-carboxylic acid as a HFBA salt. LCMS ($C_{12}H_{22}BN_2O_3^+$) (ES, m/z): 253 $[M+H-H_2O]^+$. $^1H$ NMR (400 MHz, deuterium oxide) δ 3.70-3.60 (m, 1H), 3.55-3.40 (m, 1H), 3.14-3.10 (m, 1H), 3.01-2.79 (m, 2H), 2.70-2.60 (m, 1H), 2.21-2.08 (m, 1H), 1.86-1.71 (m, 1H), 1.60-1.47 (m, 1H), 1.43-1.35 (m, 1H), 1.35-1.31 (m, 3H), 1.31-1.14 (m, 2H), 0.80-0.65 (m, 2H).

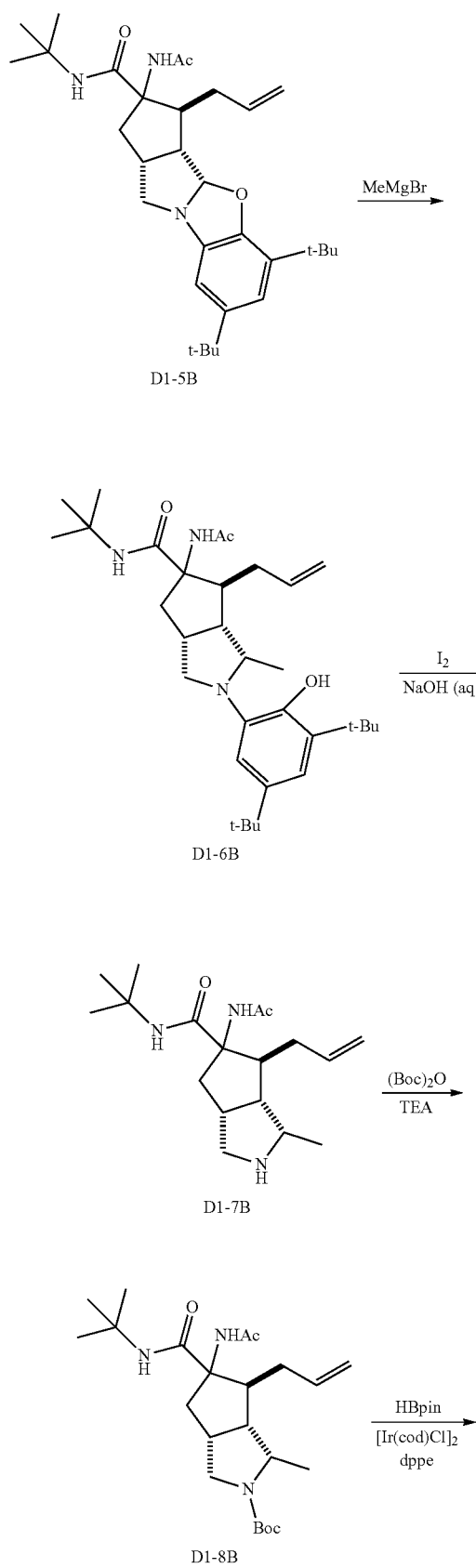
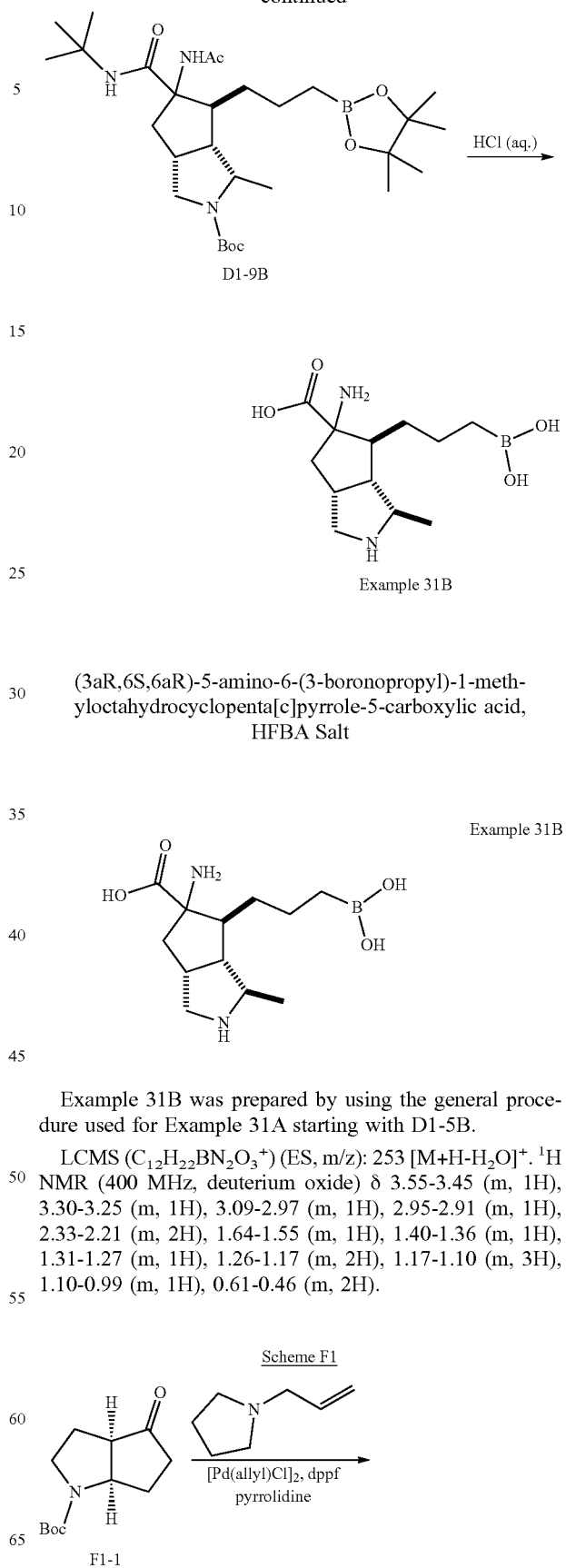
(3aR,6S,6aR)-5-amino-6-(3-boronopropyl)-1-methyloctahydrocyclopenta[c]pyrrole-5-carboxylic acid, HFBA Salt
Example 31B was prepared by using the general procedure used for Example 31A starting with D1-5B.
LCMS ($C_{12}H_{22}BN_2O_3^+$) (ES, m/z): 253 [M+H-H$_2$O]$^+$. $^1$H NMR (400 MHz, deuterium oxide) δ 3.55-3.45 (m, 1H), 3.30-3.25 (m, 1H), 3.09-2.97 (m, 1H), 2.95-2.91 (m, 1H), 2.33-2.21 (m, 2H), 1.64-1.55 (m, 1H), 1.40-1.36 (m, 1H), 1.31-1.27 (m, 1H), 1.26-1.17 (m, 2H), 1.17-1.10 (m, 3H), 1.10-0.99 (m, 1H), 0.61-0.46 (m, 2H).

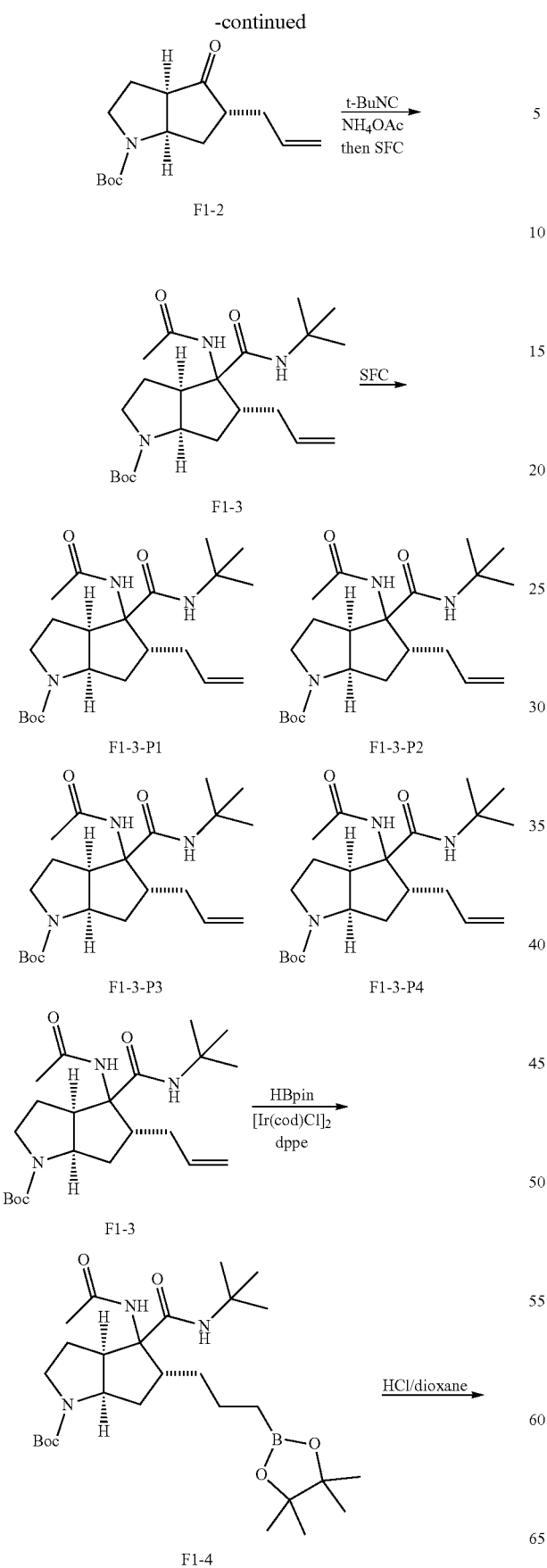
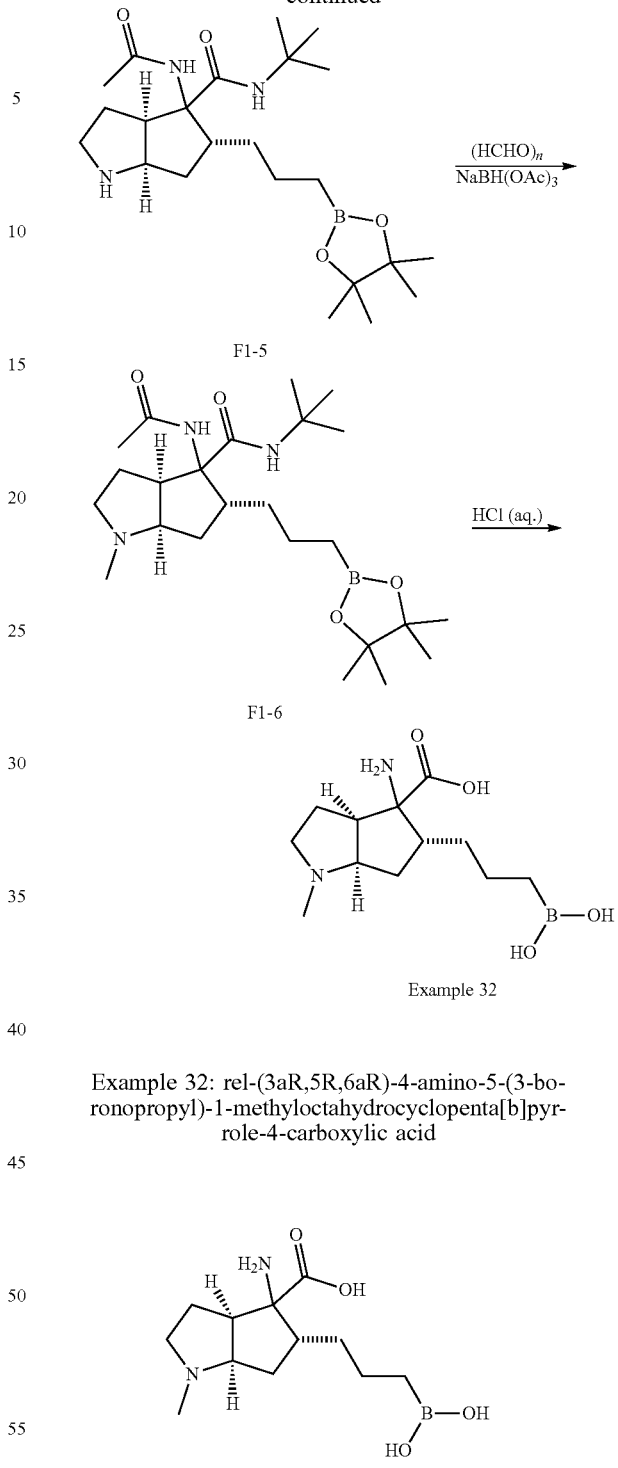

Example 32: rel-(3aR,5R,6aR)-4-amino-5-(3-boronopropyl)-1-methyloctahydrocyclopenta[b]pyrrole-4-carboxylic acid Step 1: Rac-cis-tert-butyl 5-allyl-4-oxohexahydrocyclopenta[b]pyrrole-1(2H)-carboxylate

[Pd(C$_3$H$_5$)Cl]$_2$ (0.41 g, 1.1 mmol) and dppf (1.23 g, 2.2 mmol) in dry MeOH (50 mL) was stirred at 15° C. under N$_2$ atmosphere for 1 hour. 1-allylpyrrolidine (2.22 g, 20 mmol) in MeOH (10 mL) was added and the mixture was stirred for another 10 minutes, followed by the addition of pyrrolidine (0.32 g, 4.4 mmol) in MeOH (10 mL) and rac-cis-tert-butyl 4-oxohexahydrocyclopenta[b]pyrrole-1(2H)-carboxylate (5 g, 22.2 mmol). The reaction was stirred at 15° C. under $N_2$ for 3 hours and then the solvent was evaporated under vacuum. The residue was dissolved in EtOAc and washed with water. The organic phase was washed with brine, dried over anhydrous $Na_2SO_4$, filtered and concentrated under reduced pressure. The residue was purified by silica gel column chromatography (EtOAc in hexanes) to give the title compound. LCMS ($C_{11}H_{16}NO_3^+$) (ES, m/z): 210 [M+H-$C_4H_8$]$^+$.

Step 2: rel-(3aR,5R,6aR)-tert-butyl 4-acetamido-5-allyl-4-(tert-butylcarbamoyl)hexahydrocyclopenta[b]pyrrole-1(2H)-carboxylate $NH_4OAc$ (1.16 g, 15.1 mmol) and 2-isocyano-2-methylpropane (0.85 mL, 7.5 mmol) were added to a solution of (3aR,5R,6aR)-tert-butyl 5-allyl-4-oxohexahydrocyclopenta[b]pyrrole-1(2H)-carboxylate (1 g, 3.8 mmol) in 2,2,2-trifluoroethanol (3 mL). The reaction was stirred at 35° C. for 12 hours. The reaction mixture was concentrated under reduced pressure. The residue was purified by RP-HPLC [C18 column, water (0.1% TFA)-$CH_3CN$] to give rel-(3aR, 5R,6aR)-tert-butyl 4-acetamido-5-allyl-4-(tert-butylcarbamoyl)hexahydrocyclopenta[b]pyrrole-1(2H)-carboxylate, which was resolved by Chiral-SFC [Column: Phenomenex-Cellulose-2 (250 mm*50 mm, 10 um), Mobile phase: A: $CO_2$ B: EtOH (0.1% $NH_3.H_2$), Gradient: from 10% to 15% of B in 4 min and hold 15% for 5 min, Flow rate: 180 mL/min, Column temperature: 40° C.] to give rel-(3aR,5R,6aR)-tert-butyl 4-acetamido-5-allyl-4-(tert-butylcarbamoyl)hexahydrocyclopenta[b]pyrrole-1(2H)-carboxylate ($t_r$=2.1 min, F1-3-P1) as the first eluting peak, rel-(3aR,5R,6aR)-tert-butyl 4-acetamido-5-allyl-4-(tert-butylcarbamoyl)hexahydrocyclopenta[b]pyrrole-1(2H)-carboxylate ($t_r$=2.5 min, F1-3-P2) as the second eluting peak, rel-3aR,5R,6aR)-tert-butyl 4-acetamido-5-allyl-4-(tert-butylcarbamoyl)hexahydrocyclopenta[b]pyrrole-1(2H)-carboxylate ($t_r$=3.9 min, F1-3-P3) as the third eluting peak, rel-3aR,5R,6aR)-tert-butyl 4-acetamido-5-allyl-4-(tert-butylcarbamoyl)hexahydrocyclopenta[b]pyrrole-1(2H)-carboxylate ($t_r$=4.8 min, F1-3-P4) as the fourth eluting peak. 3-P1, 3-P2, 3-P3, 3-P4 LCMS ($C_{22}H_{38}N_3O_4^+$) (ES, m/z): 408 [M+H]$^+$.

Step 4: rel-(3aR,5R,6aR)-tert-butyl 4-acetamido-4-(tert-butylcarbamoyl)-5-(3-(4,4,5,5-tetramethyl-1,3,2-dioxaborolan-2-yl)propyl)hexahydrocyclopenta[b]pyrrole-1(2H)-carboxylate rel-(3aR,5R,6aR)-tert-butyl 4-acetamido-5-allyl-4-(tert-butylcarbamoyl)hexahydrocyclopenta[b]pyrrole-1(2H)-carboxylate (270 mg, 0.66 mmol, F1-3-P2), 4,4,5,5-tetramethyl-1,3,2-dioxaborolane (127 mg, 0.99 mmol) and 1,2-bis(diphenylphosphino)ethane (26.4 mg, 0.066 mmol) in anhydrous DCM (5 mL) were bubbled with a stream of $N_2$ for 3 min. The reaction mixture was stirred at 25° C. for 10 min and then treated with [Ir(cod)Cl]$_2$ (22.3 mg, 0.033 mmol). The resulting mixture was stirred at 25° C. for 10 h under $N_2$. The reaction was filtered and concentrated in vacuum. The residue was purified by RP-HPLC [C18 column, water (0.10% TFA)-$CH_3CN$] to give rel-(3aR,5R, 6aR)-tert-butyl 4-acetamido-4-(tert-butylcarbamoyl)-5-(3-(4,4,5,5-tetramethyl-1,3,2-dioxaborolan-2-yl)propyl)hexahydrocyclopenta[b]pyrrole-1(2H)-carboxylate. LCMS ($C_{28}H_{51}BN_3O_6^+$) (ES, m/z): 536 [M+H]$^+$.

Step 5: rel-(3aR,5R,6aR)-4-acetamido-N-(tert-butyl)-5-(3-(4,4,5,5-tetramethyl-1,3,2-dioxaborolan-2-yl)propyl)octahydrocyclopenta[b]pyrrole-4-carboxamide hydrochloride A mixture of rel-(3aR,5R,6aR)-tert-butyl 4-acetamido-4-(tert-butylcarbamoyl)-5-(3-(4,4,5,5-tetramethyl-1,3,2-dioxaborolan-2-yl)propyl)hexahydrocyclopenta[b]pyrrole-1(2H)-carboxylate (210 mg, 0.39 mmol) and 4N HCl in dioxane (3 mL) was stirred at 20° C. for 1 hour. The mixture was concentrated under reduced pressure to give rel-(3aR, 5R,6aR)-4-acetamido-N-(tert-butyl)-5-(3-(4,4,5,5-tetramethyl-1,3,2-dioxaborolan-2-yl)propyl)octahydrocyclopenta[b]pyrrole-4-carboxamide hydrochloride, which was used directly in next step. LCMS ($C_{23}H_{43}BN_3O_4^+$) (ES, m/z): 436 [M+H]$^+$.

Step 6: rel-(3-((3aR,5R,6aR)-4-acetamido-4-(tert-butylcarbamoyl)-1-methyloctahydrocyclopenta[b]pyrrol-5-yl)propyl)boronic acid Sodium triacetoxyborohydride was added to rel-(3aR,5R, 6aR)-4-acetamido-N-(tert-butyl)-5-(3-(4,4,5,5-tetramethyl-1,3,2-dioxaborolan-2-yl)propyl)octahydrocyclopenta[b]pyrrole-4-carboxamide hydrochloride (175 mg, 0.37 mmol) and paraformaldehyde (175 mg, 0.37 mmol) in DCE (5 mL) (197 mg, 0.93 mmol) at 20° C. The reaction was heated to 70° C. and stirred for 12 hours. The reaction mixture was quenched with MeOH (10 mL) and concentrated under reduced pressure. The residue was purified by RP-HPLC [C18 column, water (0.1% TFA)-$CH_3CN$] to give rel-(3-((3aR,5R,6aR)-4-acetamido-4-(tert-butylcarbamoyl)-1-methyloctahydrocyclopenta[b]pyrrol-5-yl)propyl)boronic acid. LCMS ($C_{18}H_{35}BN_3O_4^+$) (ES, m/z): 368 [M+H]$^+$.

Step 7: rel-(3aR,5R,6aR)-4-amino-5-(3-boronopropyl)-1-methyloctahydrocyclopenta[b]pyrrole-4-carboxylic acid rel-(3aR,5R,6aR)-4-acetamido-N-(tert-butyl)-1-methyl-5-(3-(4,4,5,5-tetramethyl-1,3,2-dioxaborolan-2-yl)propyl)octahydrocyclopenta[b]pyrrole-4-carboxamide (140 mg, 0.31 mmol) was added to 12N HCl in water (3 mL) and stirred at 100° C. for 14 hours. The mixture was concentrated under reduced pressure and saturated $NaHCO_3$ was added to the residue until pH~8. The mixture was washed with DCM and the aqueous layer was concentrated under reduced pressure. The residue was acidized with 2N HCl in water till pH~6 and concentrated under reduced pressure. The residue was purified by RP-HPLC [C18 column, water (20 mM HFBA and 0.1% TFA)-$CH_3CN$] to give rel-(3aR, 5R,6aR)-4-amino-5-(3-boronopropyl)-1-methyloctahydrocyclopenta[b]pyrrole-4-carboxylic acid as a HFBA salt. LCMS ($C_{12}H_{24}BN_2O_4^+$) (ES, m/z): 271 [M+H]$^+$. $^1$H NMR (400 MHz, deuterium oxide) δ 4.03-3.98 (m, 1H), 3.75-3.50 (m, 1H), 3.30-3.19 (m, 1H), 3.07-3.05 (m, 1H), 2.89 (s, 3H), 2.83-2.80 (m, 1H), 2.38-2.35 (m, 1H), 2.30-2.19 (m, 1H), 2.06-2.04 (m, 1H), 1.99-1.88 (m, 1H), 1.51-1.35 (m, 2H), 1.34-1.18 (m, 2H), 0.87-0.57 (m, 2H).

Scheme G1

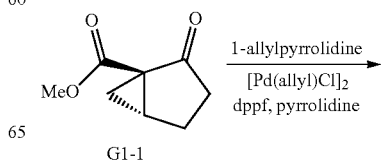

G1-1

-continued

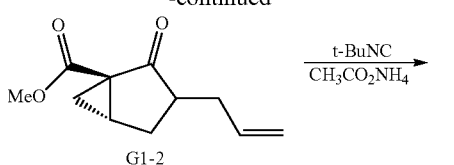
G1-2

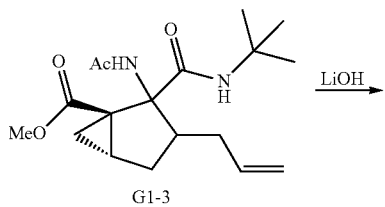
G1-3

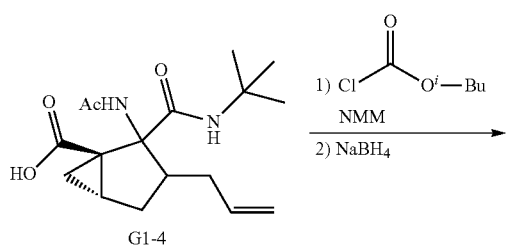
G1-4

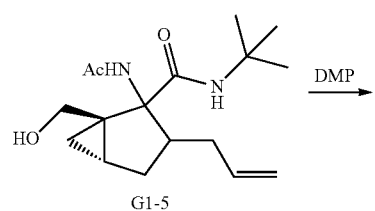
G1-5

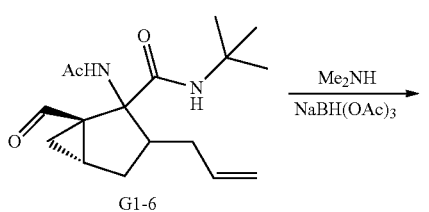
G1-6

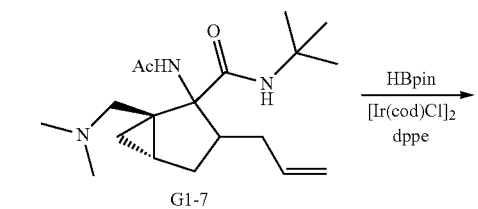
G1-7

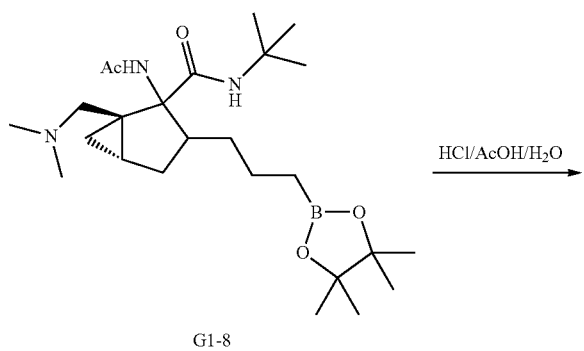
G1-8

-continued

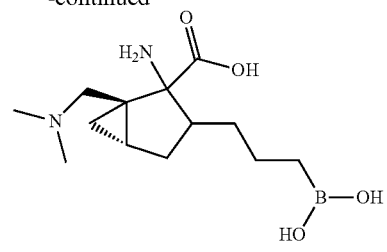
Example 33A

Example 33A: (1S,5R)-2-amino-3-(3-boronopropyl)-1-((dimethylamino)methyl)bicyclo[3.1.0]hexane-2-carboxylic acid

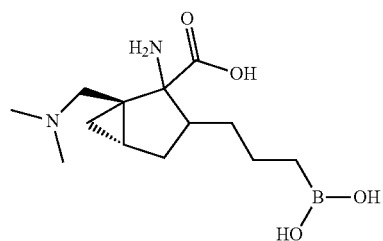 [SMILES: CN(C)C[C@]12C[C@H]1CC(CCCB(O)O)C2(N)C(=O)O]

Step 1: (1R,5R)-methyl 3-allyl-2-oxobicyclo[3.1.0]hexane-1-carboxylate

[Pd(C$_3$H$_5$)Cl]$_2$ (0.24 g, 0.65 mmol) and dppf (0.86 g, 1.6 mmol) in dry MeOH (24 mL) were stirred at 15° C. under N$_2$ atmosphere for 1 hour. 1-allylpyrrolidine (1.44 g, 13 mmol) in MeOH (4 mL) was added and the mixture was stirred for another 10 min, followed by the addition of pyrrolidine (0.185 g, 2.6 mmol) and (1R,5R)-methyl 2-oxobicyclo[3.1.0]hexane-1-carboxylate (2 g, 13 mmol) in MeOH (4 mL). The reaction was stirred at 15° C. under N$_2$ for 3 hours. Solvent was evaporated in vacuum. The residue was dissolved in EtOAc and washed with water. The organic phase was washed with brine, dried over anhydrous Na$_2$SO$_4$, filtered and concentrated under reduced pressure. The residue was purified by silica gel column chromatography (EtOAc in hexanes) to give (1R,5R)-methyl 3-allyl-2-oxobicyclo[3.1.0]hexane-1-carboxylate. LCMS (C$_{11}$H$_{15}$O$_3^+$) (ES, m/z): 195 [M+H]$^+$.

Step 2: (1R,5R)-methyl 2-acetamido-3-allyl-2-(tert-butylcarbamoyl)bicyclo[3.1.0]hexane-1-carboxylate NH$_4$OAc (1.11 g, 14.4 mmol) and 2-isocyano-2-methylpropane (0.82 mL, 7.2 mmol) were added to a solution of (1R,5R)-methyl 3-allyl-2-oxobicyclo[3.1.0]hexane-1-carboxylate (700 mg, 3.6 mmol) in 2,2,2-trifluoroethanol (5 mL). The reaction mixture was stirred at 50° C. for 14 h. The reaction mixture was concentrated under reduced pressure. The resulting residue was purified by RP-HPLC [C18 column, water (0.1% TFA)-acetonitrile] to give (1R,5R)-methyl 2-acetamido-3-allyl-2-(tert-butylcarbamoyl)bicyclo[3.1.0]hexane-1-carboxylate. LCMS (C$_{18}$H$_{29}$N$_2$O$_4^+$) (ES, m/z): 337 [M+H]$^+$.

Step 3: (1R,5R)-2-acetamido-3-allyl-2-(tert-butylcarbamoyl)bicyclo[3.1.0]hexane-1-carboxylic acid 4M LiOH in water (1.5 mL, 6 mmol) was added to a mixture of (1R,5R)-methyl 2-acetamido-3-allyl-2-(tert-butylcarbamoyl)bicyclo[3.1.0]hexane-1-carboxylate (200 mg, 0.59 mmol) and water (3 mL) at 20° C. The resulting mixture was stirred at 80° C. for 4 h. The reaction mixture was filtered and concentrated in vacuum to give (1R,5R)-2-acetamido-3-allyl-2-(tert-butylcarbamoyl)bicyclo[3.1.0]hexane-1-carboxylic acid without further purification. LCMS ($C_{17}H_{27}N_2O_4^+$) (ES, m/z): 323 [M+H]$^+$.

Step 4: (1R,5R)-2-acetamido-3-allyl-N-(tert-butyl)-1-(hydroxymethyl)bicyclo[3.1.0]hexane-2-carboxamide Isobutyl chloroformate (0.23 mL, 1.8 mmol) was added to a mixture of (1R,5R)-2-acetamido-3-allyl-2-(tert-butylcarbamoyl)bicyclo[3.1.0]hexane-1-carboxylic acid (190 mg, 0.59 mmol) and 4-methylmorpholine (119 mg, 1.2 mmol) in THF at 0° C. and the reaction mixture was stirred at 15° C. for 12 hours. Then NaBH$_4$ (33 mg, 0.88 mmol) was added to the mixture and stirred for another 4 hours at 15° C. The solvent was removed under reduced pressure. The residue was purified by RP-HPLC [C18 column, water (0.1% TFA)-CH$_3$CN] to give (1R,5R)-2-acetamido-3-allyl-N-(tert-butyl)-1-(hydroxymethyl)bicyclo[3.1.0]hexane-2-carboxamide. LCMS ($C_{17}H_{29}N_2O_3^+$) (ES, m/z): 309 [M+H]$^+$.

Step 5: (1R,5R)-2-acetamido-3-allyl-N-(tert-butyl)-1-formylbicyclo[3.1.0]hexane-2-carboxamide Dess-Martin periodinane (234 mg, 0.55 mmol) was added to a solution of (1R,5R)-2-acetamido-3-allyl-N-(tert-butyl)-1-(hydroxymethyl)bicyclo[3.1.0]hexane-2-carboxamide (85 mg, 0.28 mmol) in DCM (3 mL) at 20° C. The reaction was stirred at the same temperature for 2 hours. The reaction mixture was quenched with saturated aqueous Na$_2$SO$_3$ and stirred for another 10 minutes. The mixture was extracted with DCM. The combined organic phases were washed with brine, dried over anhydrous Na$_2$SO$_4$ and concentrated under reduce pressure to give (1R,5R)-2-acetamido-3-allyl-N-(tert-butyl)-1-formylbicyclo[3.1.0]hexane-2-carboxamide without further purification. LCMS ($C_{17}H_{27}N_2O_3^+$) (ES, m/z): 307 [M+H]$^+$.

Step 6: (1S,5R)-2-acetamido-3-allyl-N-(tert-butyl)-1-((dimethylamino)methyl)bicyclo[3.1.0]hexane-2-carboxamide Sodium triacetoxyborohydride (145 mg, 0.69 mmol) was added to a mixture of (1R,5R)-2-acetamido-3-allyl-N-(tert-butyl)-1-formylbicyclo[3.1.0]hexane-2-carboxamide (70 mg, 0.23 mmol) and 2M dimethylamine in THF (1.1 mL, 2.3 mmol) in DCE (5 mL) at 20° C. The resulting mixture was stirred at 20° C. for 16 hours. The reaction mixture was concentrated in vacuum and the resulting residue was purified by RP-HPLC [C18 column, water (0.1% TFA)-CH$_3$CN] to give (1S,5R)-2-acetamido-3-allyl-N-(tert-butyl)-1-((dimethylamino)methyl)bicyclo[3.1.0]hexane-2-carboxamide. LCMS ($C_{19}H_{34}N_3O_2^+$) (ES, m/z): 336 [M+H]$^+$.

Step 7: (1S,5R)-2-acetamido-N-(tert-butyl)-1-((dimethylamino)methyl)-3-(3-(4,4,5,5-tetramethyl-1,3,2-dioxaborolan-2-yl)propyl)bicyclo[3.1.0]hexane-2-carboxamide (1S,5R)-2-acetamido-3-allyl-N-(tert-butyl)-1-((dimethylamino)methyl)bicyclo[3.1.0]hexane-2-carboxamide (25 mg, 0.075 mmol), 4,4,5,5-tetramethyl-1,3,2-dioxaborolane (29 mg, 0.22 mmol) and 1,2-bis(diphenylphosphino)ethane (3 mg, 7.4 μmol) in anhydrous DCM (3 mL) was bubbled with a stream of N$_2$ for 3 min. The reaction mixture was stirred at 25° C. for 10 min. and then treated with [Ir(cod)Cl]$_2$ (2.5 mg, 3.7 μmol). The resulting mixture was stirred at 25° C. for 10 h under N$_2$. The reaction was filtered and concentrated in vacuum. The residue was purified by RP-HPLC [C18 column, water (0.1% TFA)-acetonitrile] to give (1S,5R)-2-acetamido-N-(tert-butyl)-1-((dimethylamino)methyl)-3-(3-(4,4,5,5-tetramethyl-1,3,2-dioxaborolan-2-yl)propyl)bicyclo[3.1.0]hexane-2-carboxamide. LCMS ($C_{19}H_{37}BN_3O_4^+$) (ES, m/z): 382 [M-C$_6$H$_{10}$+H]$^+$.

Step 8: (1S,5R)-2-amino-3-(3-boronopropyl)-1-((dimethylamino)methyl)bicyclo[3.1.0]hexane-2-carboxylic acid A mixture of (1S,5R)-2-acetamido-N-(tert-butyl)-1-((dimethylamino)methyl)-3-(3-(4,4,5,5-tetramethyl-1,3,2-dioxaborolan-2-yl)propyl)bicyclo[3.1.0]hexane-2-carboxamide (25 mg, 0.054 mmol), 12N HCl in water (1 mL), AcOH (0.5 mL) and water (0.5 mL) was stirred at 130° C. for 0.5 h in microwave reactor. The reaction mixture was concentrated under reduced pressure. The residue was dissolved in water and basified with saturated aqueous NaHCO$_3$ until pH~8, and the aqueous layer was washed with DCM. The aqueous layer was concentrated under reduced pressure. The residue was acidified with 2N HCl in water till pH~6 and concentrated under reduced pressure. The residue was purified by RP-HPLC [C18 column, water (20 mM HFBA and 0.1% TFA)-CH$_3$CN] to give (1S,5R)-2-amino-3-(3-boronopropyl)-1-((dimethylamino)methyl)bicyclo[3.1.0]hexane-2-carboxylic acid as a HFBA salt. LCMS ($C_{13}H_{26}BN_2O_4^+$) (ES, m/z): 285 [M+H]$^+$. $^1$H NMR (500 MHz, deuterium oxide) δ 3.88-3.85 (m, 1H), 2.86-2.80 (m, 7H), 2.52-2.31 (m, 1H), 2.15-1.99 (m, 1H), 1.67-1.49 (m, 2H), 1.45-1.40 (m, 1H), 1.40-1.28 (m, 2H), 1.27-1.20 (m, 1H), 1.19-1.11 (m, 1H), 1.05-1.03 (m, 1H), 0.82-0.57 (m, 2H).

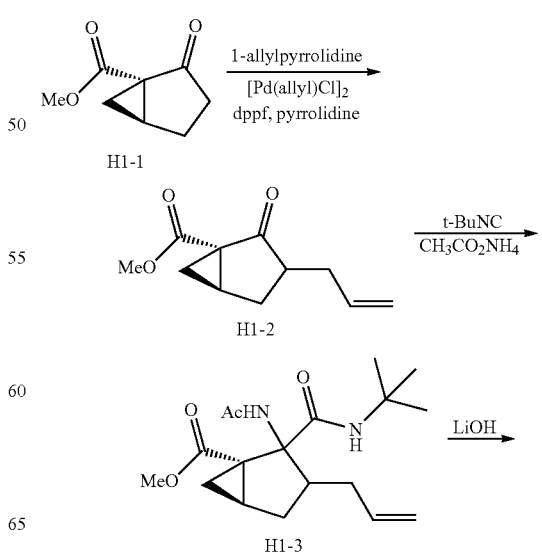

Scheme H1

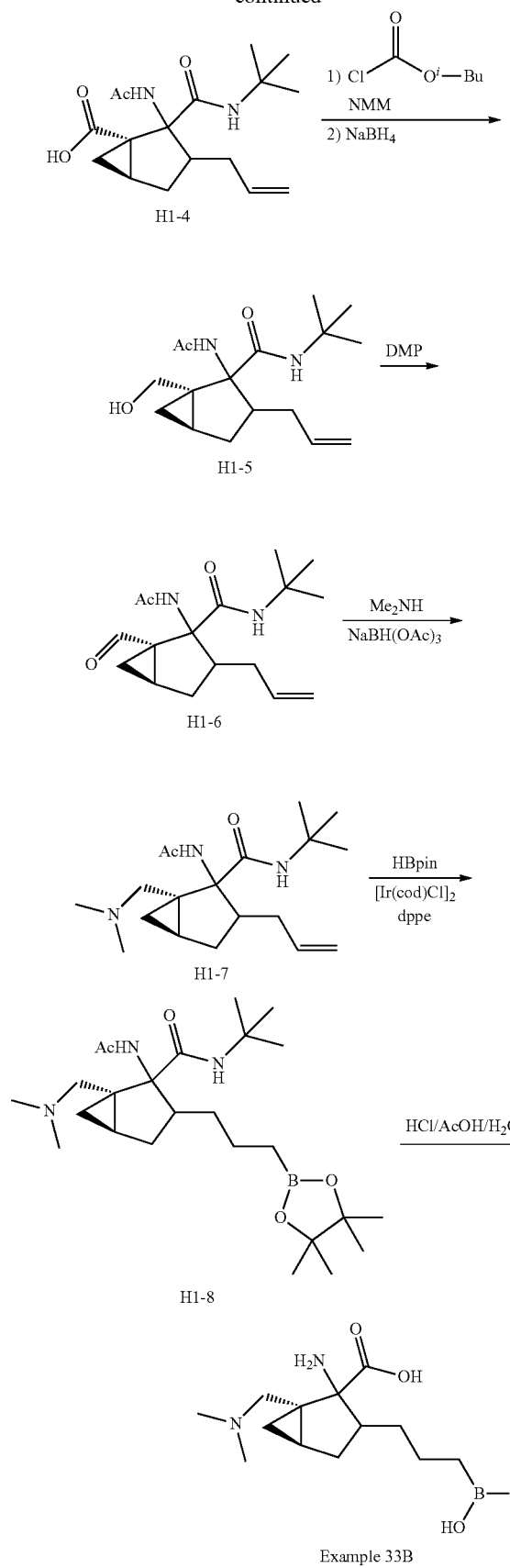
Example: 33B (1R,5S)-2-amino-3-(3-boronopropyl)-1-((dimethylamino)methyl)bicyclo[3.1.0]hexane-2-carboxylic acid
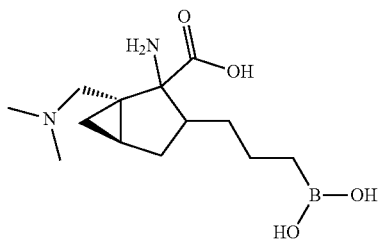 [SMILES: CN(C)C[C@@]12C[C@@H]1CC(CCCB(O)O)C2(N)C(=O)O]
Example 33B was prepared as a HFBA salt by using the general procedure used for Example 33A starting with methyl (1S,5S)-2-oxobicyclo[3.1.0]hexane-1-carboxylate. LCMS ($C_{13}H_{26}BN_2O_4^+$) (ES, m/z): 285 [M+H]$^+$. $^1$H NMR (500 MHz, deuterium oxide) δ 3.84-3.82 (m, 1H), 2.83-2.81 (m, 7H), 2.47-2.29 (m, 1H), 2.15-1.99 (m, 1H), 1.62-1.52 (m, 2H), 1.46-1.44 (m, 1H), 1.39-1.26 (m, 2H), 1.25-1.11 (m, 2H), 1.06 (m, 1H), 0.76-0.58 (m, 2H).
Scheme I1
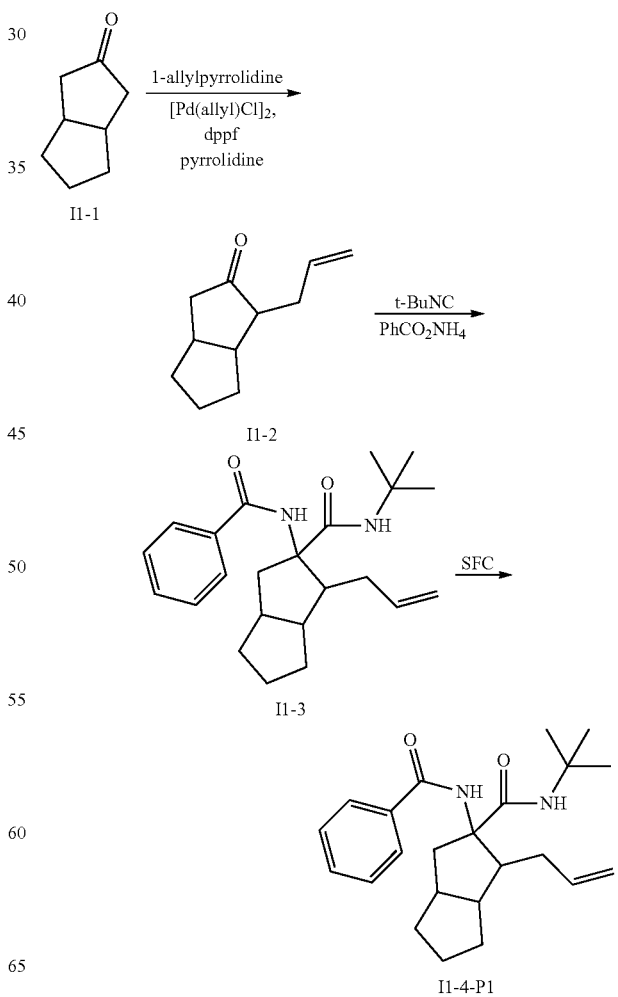

223

-continued

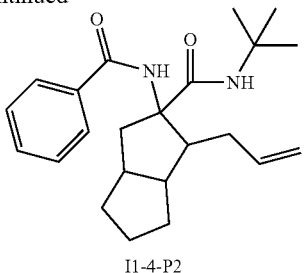

I1-4-P2

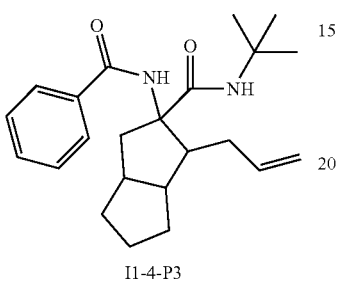

I1-4-P3

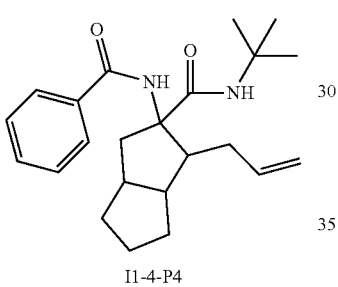

I1-4-P4

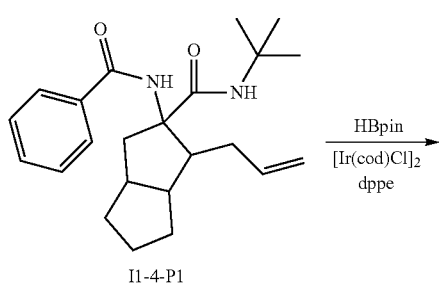

I1-4-P1

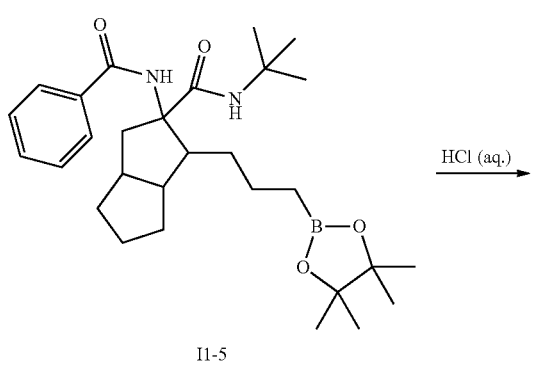

I1-5

224

-continued

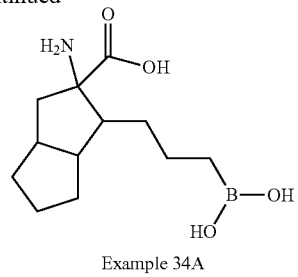

Example 34A

Example 34A: 2-amino-1-(3-boronopropyl)octahydropentalene-2-carboxylic acid

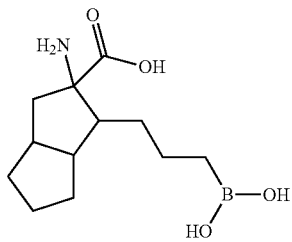 [SMILES: NC1(C(=O)O)CC2CCCC2C1CCCB(O)O]

Step 1: 1-allylhexahydropentalen-2(1H)-one

A mixture of [Pd(C$_3$H$_5$)Cl]$_2$ (0.31 g, 0.85 mmol) and dppf (0.94 g, 1.7 mmol) in dry MeOH (30 mL) was stirred at 20° C. under N$_2$ atmosphere for 1 hour. 1-allylpyrrolidine (1.9 g, 17 mmol) in MeOH (5 mL) was added and the mixture was stirred for another 10 min., followed by the addition of pyrrolidine (0.25 mL, 3.4 mmol) and hexahydropentalen-2(1H)-one (2.1 g, 17 mmol) in MeOH (10 mL). The reaction mixture was stirred at 20° C. under N$_2$ for 15 h. The reaction mixture was concentrated under reduced pressure, and the residue was dissolved in DCM and washed with water. The aqueous phase was re-extracted with DCM. The combined organic phases were washed with brine, dried over anhydrous Na$_2$SO$_4$, filtered and the filtrate was concentrated under reduced pressure to give crude product, which was directly used in the next step without further purification. LCMS (C$_{11}$H$_7$O$^+$) (ES, m/z): 165 [M+H]$^+$.

Step 2: 1-allyl-2-benzamido-N-(tert-butyl)octahydropentalene-2-carboxamide

Ammonium benzoate (5.3 g, 38 mmol) and 2-isocyano-2-methylpropane (4.3 mL, 38 mmol) were added to a solution of allylhexahydropentalen-2(1H)-one (2.1 g, 13 mmol) in 2,2,2-trifluoroethyl alcohol (10 mL). And the reaction mixture was stirred at 60° C. for 14 h. The solvent was removed under reduced pressure and the residue was dissolved in water and EtOAc. The organic layer was separated and the aqueous was re-extracted with EtOAc and the combined organic layers were washed with brine, dried over anhydrous Na$_2$SO$_4$, filtered and concentrated under reduced pressure. The residue was purified by RP-HPLC [C18 column, water (0.1% TFA)-acetonitrile] to give 1-allyl-2-benzamido-N-(tert-butyl)octahydropentalene-2-carboxamide. LCMS (C$_{23}$H$_{33}$N$_2$O$_2$$^+$) (ES, m/z): 369 [M+H]$^+$.

Step 3: 1-allyl-2-benzamido-N-(tert-butyl)octahydropentalene-2-carboxamide 1-allyl-2-benzamido-N-(tert-butyl)octahydropentalene-2-carboxamide (1.3 g, 3.5 mmol) was resolved by SFC [Column: REGIS (S,S) Whelk-01 (250 mm*50 mm, 10 um), Mobile phase: A: $CO_2$, B: IPA (0.1% $NH_3 \cdot H_2O$), Gradient: 25% of B in 15 min and hold 100% of B for 2 min, Flow Rate (mL/min) 180, Column temperature: 40° C.] to give 4 peaks; 1-allyl-2-benzamido-N-(tert-butyl)octahydropentalene-2-carboxamide (I1-4-P1, $t_r$=6.9 min) as the first eluting peak, 1-allyl-2-benzamido-N-(tert-butyl)octahydropentalene-2-carboxamide (I1-4-P2, $t_r$=7.8 min) as the second eluting peak, 1-allyl-2-benzamido-N-(tert-butyl)octahydropentalene-2-carboxamide (I1-4-P3, $t_r$=8.7 min) as the third eluting peak and 1-allyl-2-benzamido-N-(tert-butyl)octahydropentalene-2-carboxamide (I1-4-P4, $t_r$=11.2 min) as the fourth eluting peak. Stereochemistry not determined. The ee % values were checked by chiral-SFC using REGIS (R,R) Whelk-01 column. I1-4-P1: LCMS ($C_{23}H_{33}N_2O_2^+$) (ES, m/z): 369 [M+H]$^+$. I1-4-P2: LCMS ($C_{23}H_{33}N_2O_2^+$) (ES, m/z): 369 [M+H]$^+$. I1-4-P3: LCMS ($C_{23}H_{33}N_2O_2^+$) (ES, m/z): 369 [M+H]$^+$. I1-4-P4: LCMS ($C_{23}H_{33}N_2O_2^+$) (ES, m/z): 369 [M+H]$^+$.

Step 4: 2-benzamido-N-(tert-butyl)-1-(3-(4,4,5,5-tetramethyl-1,3,2-dioxaborolan-2-yl)propyl)octahydropentalene-2-carboxamide 1-llyl-2-benzamido-N-(tert-butyl)octahydropentalene-2-carboxamide (300 mg, 0.81 mmol, I1-4-P1), 4,4,5,5-tetramethyl-1,3,2-dioxaborolane (313 mg, 2.4 mmol) and 1,2-bis(diphenylphosphino)ethane (32 mg, 0.081 mmol) in anhydrous DCM (3 mL) was bubbled with a stream of $N_2$ for 3 min. The reaction mixture was stirred at 25° C. for 10 min. and then treated with [Ir(cod)Cl]$_2$ (27 mg, 0.041 mmol). The resulting mixture was stirred at 25° C. for 10 h. under $N_2$. The reaction was filtered and concentrated in vacuum. The residue was purified by RP-HPLC [C18 column, water (20 mM HFBA and 0.1% TFA)-acetonitrile] to give 2-benzamido-N-(tert-butyl)-1-(3-(4,4,5,5-tetramethyl-1,3,2-dioxaborolan-2-yl)propyl)octahydropentalene-2-carboxamide. LCMS ($C_{23}H_{36}BN_2O_4^+$) (ES, m/z): 415 [M+H-$C_6H_{10}$]$^+$.

Step 5: 2-amino-1-(3-boronopropyl)octahydropentalene-2-carboxylic acid

A mixture of 2-benzamido-N-(tert-butyl)-1-(3-(4,4,5,5-tetramethyl-1,3,2-dioxaborolan-2-yl)propyl)octahydropentalene-2-carboxamide (250 mg, 0.5 mmol), 12N HCl in water (1 mL), AcOH (0.5 mL) and water (0.5 mL) was stirred at 120° C. for 1 h. in a microwave reactor. The reaction mixture was washed with DCM and the aqueous layer was concentrated under reduced pressure. The residue was purified by RP-HPLC [C18 column, water (20 mM HFBA and 0.1% TFA)-acetonitrile] to give 2-amino-1-(3-boronopropyl)octahydropentalene-2-carboxylic acid as a HFBA salt. LCMS ($C_{12}H_{23}BNO_4^+$) (ES, m/z): 256 [M+H]$^+$. $^1$H NMR (400 MHz, deuterium oxide) δ 2.68-2.51 (m, 1H), 2.26-2.08 (m, 3H), 1.92-1.82 (m, 1H), 1.62-1.44 (m, 5H), 1.43-1.26 (m, 5H), 0.71-0.70 (m, 2H).

Example 34B, Example 34C and Example 34 D were made using the same procedure as Example 34A using the appropriate product of step 3.

Ex. MS and $^1$HNMR

34B LCMS ($C_{12}H_{23}BNO_4^+$) (ES, m/z): 256 [M+H]$^+$. $^1$H NMR (500 MHz, deuterium oxide) δ 2.65-2.41 (m, 1H), 2.18-2.00 (m, 3H), 1.86-1.73 (m, 1H), 1.55-1.35 (m, 5H), 1.35-1.16 (m, 5H), 0.78-0.45 (m, 2H).

34C LCMS ($C_{12}H_{23}BNO_4^+$) (ES, m/z): 256 [M+H]$^+$. $^1$H NMR (400 MHz, deuterium oxide) δ 2.92-2.66 (m, 1H), 2.55-2.26 (m, 2H), 1.76-1.72 (m, 1H), 1.66-1.39 (m, 8H), 1.34-1.32 (m, 2H), 1.28-1.11 (m, 1H), 0.87-0.54 (m, 2H).

34D LCMS ($C_{12}H_{23}BNO_4^+$) (ES, m/z): 256 [M+H]$^+$. $^1$H NMR (400 MHz, deuterium oxide) δ 2.87-2.73 (m, 1H), 2.47-2.44 (m, 1H), 2.38-2.28 (m, 1H), 1.76-1.73 (m, 1H), 1.62-1.40 (m, 8H), 1.38-1.28 (m, 2H), 1.27-1.16 (m, 1H), 0.80-0.62 (m, 2H).

Scheme J1

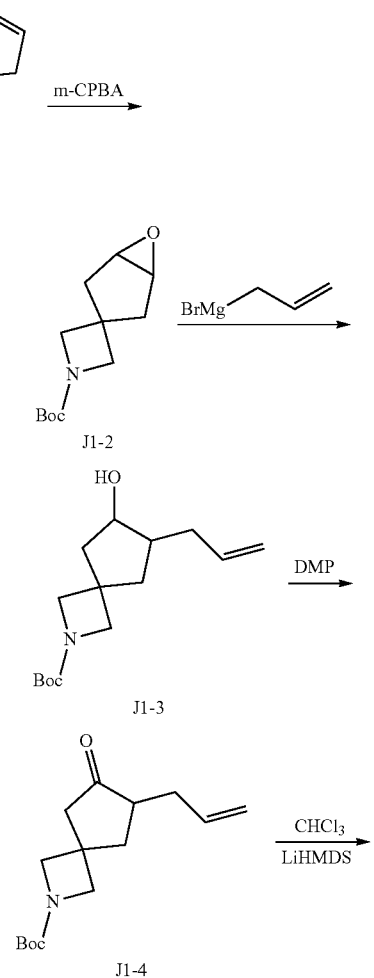

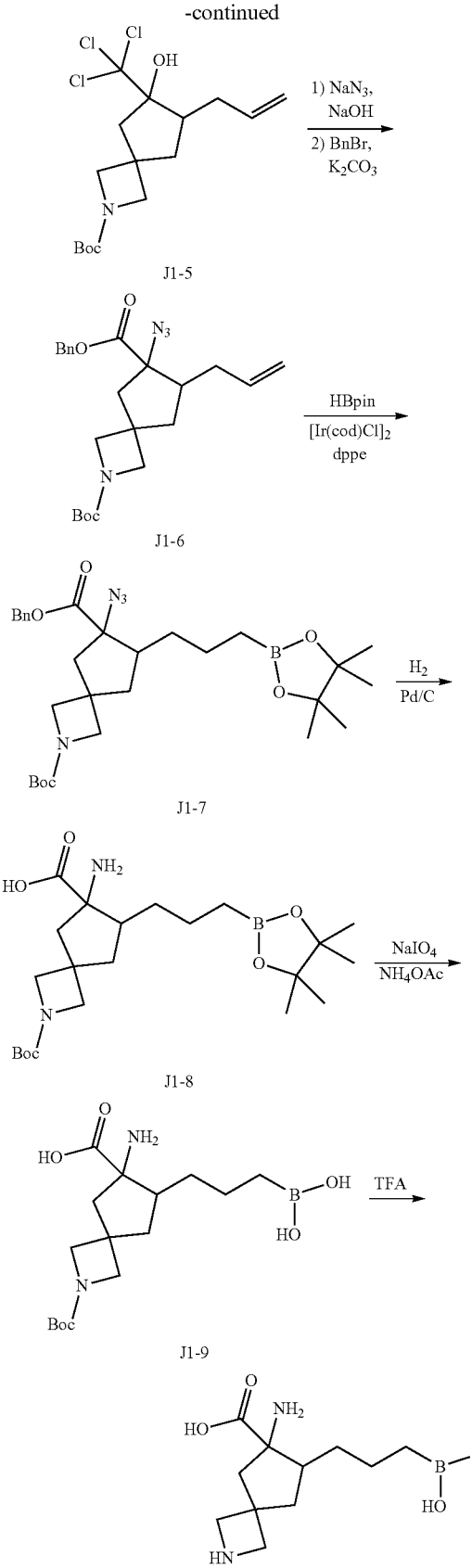

J1-5

J1-6

J1-7

J1-8

J1-9

Example 35A

Example 35A: 6-amino-7-(3-boronopropyl)-2-azaspiro[3.4]octane-6-carboxylic acid

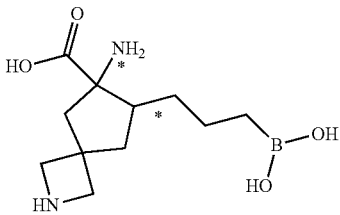 [SMILES: NC1(C(=O)O)CC2(CNC2)CC1CCCB(O)O]

Step 1: tert-butyl 6'-oxaspiro[azetidine-3,3'-bicyclo[3.1.0]hexane]-1-carboxylate 80% meta-chloroperoxybenzoic acid (3.7 g, 17 mmol) was added to a solution of tert-butyl 2-azaspiro[3.4]oct-6-ene-2-carboxylate (3 g, 14 mmol) in DCM (50 mL) at 0° C. The reaction was stirred at 25° C. for 2 h. The reaction was quenched with saturated Na$_2$CO$_3$ and extracted with DCM. The combined organic phases were washed with brine, dried over anhydrous Na$_2$SO$_4$, filtered and concentrated under reduced pressure to give tert-butyl 6'-oxaspiro[azetidine-3,3'-bicyclo[3.1.0]hexane]-1-carboxylate, which was used in the next step without further purification.

Step 2: tert-butyl 6-allyl-7-hydroxy-2-azaspiro[3.4]octane-2-carboxylate 1M allylmagnesium bromide in Et$_2$O (24 mL, 24 mmol) was added dropwise to a solution of tert-butyl 6'-oxaspiro[azetidine-3,3'-bicyclo[3.1.0]hexane]-1-carboxylate (2.7 g, 12 mmol)) in Et$_2$O (100 mL) at 0° C. under N$_2$. The reaction was stirred at 20° C. for 12 h. saturated aqueous NH$_4$Cl and EtOAc were added to the reaction mixture. The separated organic was dried over anhydrous Na$_2$SO$_4$, filtered and concentrated in vacuum. The residue was purified by silica gel column chromatography (EtOAc in hexanes) to give tert-butyl 6-allyl-7-hydroxy-2-azaspiro[3.4]octane-2-carboxylate. LCMS (C$_{11}$H$_{18}$NO$_3^+$) (ES, m/z): 212 [M+H-C$_4$H$_8$]$^+$.

Step 3: tert-butyl 6-allyl-7-oxo-2-azaspiro[3.4]octane-2-carboxylate

Dess-Martin Periodinane (3.2 g, 7.6 mmol) was added to a solution of tert-butyl 6-allyl-7-hydroxy-2-azaspiro[3.4]octane-2-carboxylate (1.7 g, 6.4 mmol) in DCM (30 mL) at 0° C. under N$_2$.

The reaction was stirred at 20° C. for 2 h. saturated aqueous NaHCO$_3$ and DCM were added to the reaction mixture. The separated organic layer was dried over anhydrous Na$_2$SO$_4$, filtered and concentrated in vacuum. The residue was purified by silica gel column chromatography (EtOAc in hexanes) to give the tert-butyl 6-allyl-7-oxo-2-azaspiro[3.4]octane-2-carboxylate. LCMS (C$_{10}$H$_{16}$NO$^+$) (ES, m/z): 166 [M+H-Boc]$^+$.

Step 4: tert-butyl 7-allyl-6-hydroxy-6-(trichloromethyl)-2-azaspiro[3.4]octane-2-carboxylate 1M Lithium bis(trimethylsilyl)amide in THF (5.7 mL, 5.7 mmol) was added dropwise to a mixture of tert-butyl 6-allyl-7-oxo-2-azaspiro[3.4]octane-2-carboxylate (0.5 g, 1.9 mmol) and redistilled chloroform (0.76 mL, 9.4 mmol) in THF (10 mL) at −78° C. under $N_2$. The mixture was stirred for 60 min. at −78° C. Then the mixture was warmed to 20° C. for 60 min. The mixture was poured into saturated aqueous $NH_4Cl$ and extracted with EtOAc. The separated organic layer was dried over anhydrous $Na_2SO_4$, filtered and concentrated in vacuum to give the crude tert-butyl 7-allyl-6-hydroxy-6-(trichloromethyl)-2-azaspiro[3.4]octane-2-carboxylate, which was used in the next step without further purification. LCMS ($C_{12}H_{17}C_3NO_3^+$) (ES, m/z): 328 [M+H-$C_4H_8$]$^+$.

Step 5: 6-benzyl 2-(tert-butyl) 7-allyl-6-azido-2-azaspiro[3.4]octane-2,6-dicarboxylate A solution of tert-butyl 7-allyl-6-hydroxy-6-(trichloromethyl)-2-azaspiro[3.4]octane-2-carboxylate (0.8 g, 2.1 mmol) in 1,4-dioxane (5 mL) was added to a solution of sodium azide (0.67 g, 10.3 mmol) and sodium hydroxide (0.25 g, 6.2 mmol) in water (5 mL) at 0° C. The mixture was stirred for 12 hours at 20° C. HOAc was added to acidify to pH ~6. The mixture was poured into water and extracted with EtOAc. The separated organic layer was dried over anhydrous $Na_2SO_4$, filtered and concentrated in vacuum to give the crude intermediate, which was dissolved in DMF (8 mL) and then treated with potassium carbonate (1.4 g, 10 mmol) and (bromomethyl)benzene (0.37 mL, 3.1 mmol) at 20° C. The resulting mixture was stirred for 2 h. The mixture was poured into brine and extracted with EtOAc. The separated organic layer was dried over anhydrous $Na_2SO_4$, filtered and concentrated in vacuum. The residue was purified by silica gel column chromatography (EtOAc in hexanes) to give 6-benzyl 2-tert-butyl 7-allyl-6-azido-2-azaspiro[3.4]octane-2,6-dicarboxylate. LCMS ($C_{23}H_3N_3O_4^+$) (ES, m/z): 412 [M-N]$^+$.

Step 6: 6-benzyl 2-(tert-butyl) 6-azido-7-(3-(4,4,5,5-tetramethyl-1,3,2-dioxaborolan-2-yl)propyl)-2-azaspiro[3.4]octane-2,6-dicarboxylate A solution of 1,2-bis(diphenylphosphino)ethane (7.5 mg, 0.019 mmol), [Ir(cod)Cl]$_2$ (7.9 mg, 0.012 mmol) and 4,4,5,5-tetramethyl-1,3,2-dioxaborolane (0.17 mL, 1.2 mmol) in anhydrous DCM (2 mL) was bubbled with a stream of $N_2$ for 3 min. The mixture was stirred at 20° C. for 20 min and then 6-benzyl 2-tert-butyl 7-allyl-6-azido-2-azaspiro[3.4]octane-2,6-dicarboxylate (100 mg, 0.23 mmol) in DCM (1 mL) was added into the mixture. The resulting mixture was stirred at 20° C. for 15 hours under $N_2$. The solution was concentrated in vacuum. The residue was purified by silica gel column chromatography (EtOAc in hexanes) to give the 6-benzyl 2-tert-butyl 6-azido-7-(3-(4,4,5,5-tetramethyl-1,3,2-dioxaborolan-2-yl)propyl)-2-azaspiro[3.4]octane-2,6-dicarboxylate. LCMS ($C_{25}H_{36}BN_2O_6^+$) (ES, m/z): 471 [M+H-$C_4H_8$-$N_2$]$^+$.

Step 7: 6-amino-2-(tert-butoxycarbonyl)-7-(3-(4,4,5,5-tetramethyl-1,3,2-dioxaborolan-2-yl)propyl)-2-azaspiro[3.4]octane-6-carboxylic acid 10% Pd—C (38 mg, 0.036 mmol) was added to a solution of 6-benzyl 2-tert-butyl 6-azido-7-(3-(4,4,5,5-tetramethyl-1,3,2-dioxaborolan-2-yl)propyl)-2-azaspiro[3.4]octane-2,6-dicarboxylate (40 mg, 0.072 mmol) in MeOH (4 mL) under $N_2$. The mixture was degassed and backfilled with $H_2$ (three times). The resulting mixture was stirred under $H_2$ (pressure: 15 psi) at 15° C. for 3 h. The catalyst was filtered off, and the filtrate was concentrated under reduced pressure to give 6-amino-2-(tert-butoxycarbonyl)-7-(3-(4,4,5,5-tetramethyl-1,3,2-dioxaborolan-2-yl)propyl)-2-azaspiro[3.4]octane-6-carboxylic acid, which was used in next step directly. LCMS ($C_{12}H_{20}BN_2O_5^+$) (ES, m/z): 283 [M+H-$C_4H$-$C_6H_2$-$H_2O$]$^+$.

Step 8: 6-amino-7-(3-boronopropyl)-2-(tert-butoxycarbonyl)-2-azaspiro[3.4]octane-6-carboxylic acid $NH_4OAc$ (165 mg, 2.1 mmol) and sodium periodate (229 mg, 1.1 mmol) were added to a mixture of 6-amino-2-(tert-butoxycarbonyl)-7-(3-(4,4,5,5-tetramethyl-1,3,2-dioxaborolan-2-yl)propyl)-2-azaspiro[3.4]octane-6-carboxylic acid (47 mg, 0.11 mmol), THF (2 mL) and water (1 mL) at 20° C. The milky suspension was stirred at 20° C. for 15 h. The mixture was filtered, and the filtrate was concentrated in vacuum to give the crude 6-amino-7-(3-boronopropyl)-2-(tert-butoxycarbonyl)-2-azaspiro[3.4]octane-6-carboxylic acid, which was used in the next step without further purification. LCMS ($C_{16}H_{30}BN_2O_6^+$) (ES, m/z): 357 [M+H]$^+$.

Step 9: 6-amino-7-(3-boronopropyl)-2-azaspiro[3.4]octane-6-carboxylic acid

A mixture of 6-amino-7-(3-boronopropyl)-2-(tert-butoxycarbonyl)-2-azaspiro[3.4]octane-6-carboxylic acid (43 mg, 0.12 mmol) and TFA (0.5 mL) in DCM (2.5 mL) was stirred at 0° C. for 1 h. The mixture was concentrated under $N_2$ stream. The residual was purified by RP-HPLC [C18 column, water (20 mM HFBA and 0.1% TFA)-acetonitrile] to give 6-amino-7-(3-boronopropyl)-2-azaspiro[3.4]octane-6-carboxylic acid as HFBA salt. LCMS ($C_{11}H_{20}BN_2O_3^+$) (ES, m/z): 239 [M+H-$H_2O$]$^+$. $^1$H NMR (500 MHz, deuterium oxide) δ 4.16-4.13 (m, 1H), 4.04-3.90 (m, 3H), 2.70 (d, J=14.8 Hz, 1H), 2.56-2.39 (m, 1H), 2.26-2.11 (m, 2H), 1.98-1.86 (m, 1H), 1.56-1.32 (m, 2H), 1.31-1.16 (m, 1H), 1.11-0.98 (m, 1H), 0.77-0.58 (m, 2H).

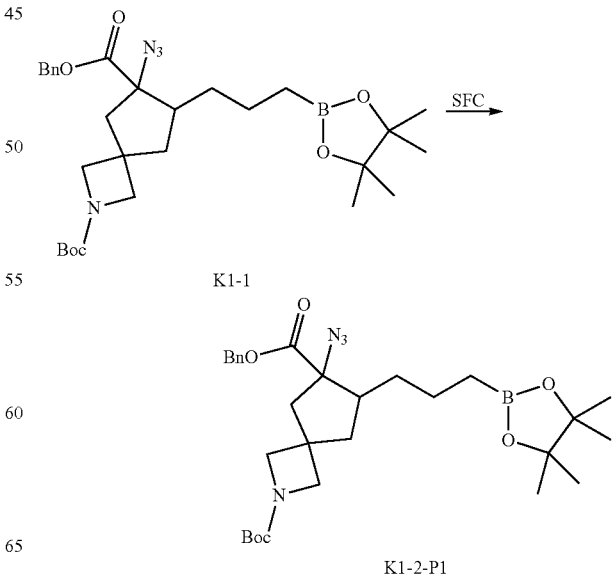

Scheme K1

-continued

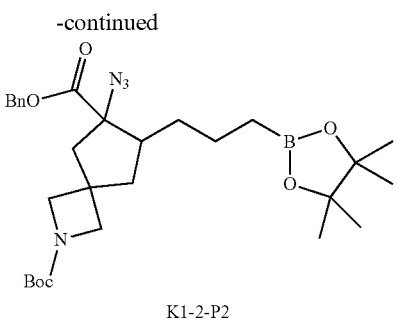

K1-2-P2

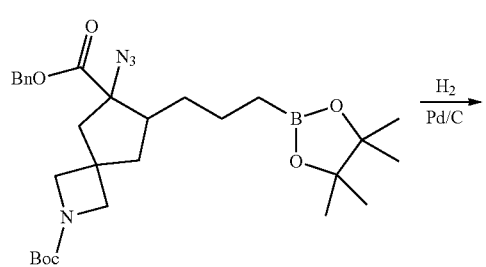

K1-2-P1

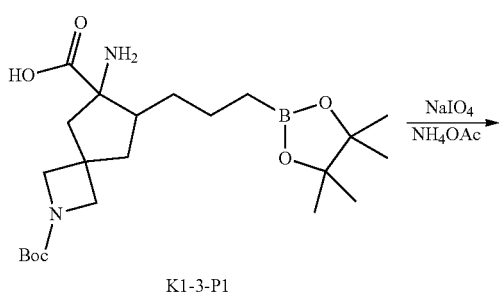

K1-3-P1

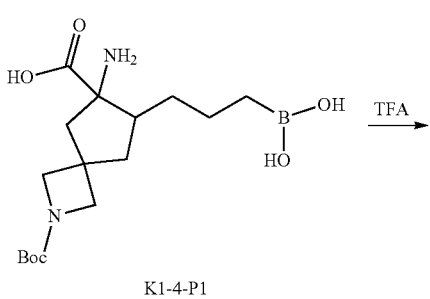

K1-4-P1

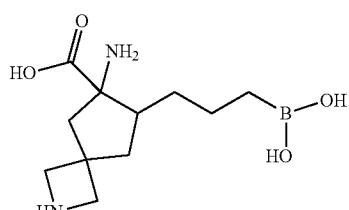

Example 35B

Example 35B: 6-amino-7-(3-boronopropyl)-2-azaspiro[3.4]octane-6-carboxylic acid

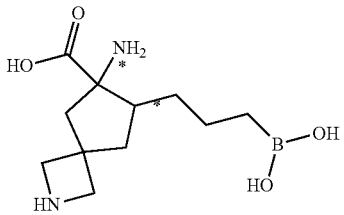 [SMILES: NC1(C(=O)O)CC2(CNC2)CC1CCCB(O)O]

Step 1: 6-benzyl 2-(tert-butyl) 6-azido-7-(3-(4,4,5,5-tetramethyl-1,3,2-dioxaborolan-2-yl)propyl)-2-azaspiro[3.4]octane-2,6-dicarboxylate 6-benzyl 2-tert-butyl 6-azido-7-(3-(4,4,5,5-tetramethyl-1,3,2-dioxaborolan-2-yl)propyl)-2-azaspiro[3.4]octane-2,6-dicarboxylate (300 mg, 0.54 mmol) was resolved by SFC [Column: Regis (S,S) WHELK-01 (250 mm*30 mm, 5 um), Mobile phase: A: $CO_2$, B: EtOH (0.1% $NH_3.H_2O$), Gradient: 25% of B in 4.5 min, and hold 25% of B for 1 min, Flow Rate (mL/min) 60, Column temperature: 40° C.] to give 6-benzyl 2-tert-butyl 6-azido-7-(3-(4,4,5,5-tetramethyl-1,3,2-dioxaborolan-2-yl)propyl)-2-azaspiro[3.4]octane-2,6-dicarboxylate (K1-2-P1, $t_r$=3.4 min) as the first eluting peak and 6-benzyl 2-tert-butyl 6-azido-7-(3-(4,4,5,5-tetramethyl-1,3,2-dioxaborolan-2-yl)propyl)-2-azaspiro[3.4]octane-2,6-dicarboxylate (K1-2-P2, $t_r$=3.6 min) as the second eluting peak. K1-2-P1: LCMS ($C_{25}H_{36}BN_2O_6^+$) (ES, m/z): 471 [M+H-$C_4H_8$-$N_2$]$^+$. K1-2-P2: LCMS ($C_{25}H_{36}BN_2O_6^+$) (ES, m/z): 471 [M+H-$C_4H_8$-$N_2$]$^+$.

Step 2: 6-amino-2-(tert-butoxycarbonyl)-7-(3-(4,4,5,5-tetramethyl-1,3,2-dioxaborolan-2-yl)propyl)-2-azaspiro[3.4]octane-6-carboxylic acid 10% Pd/C (38 mg, 0.036 mmol) was added to a solution of 6-benzyl 2-tert-butyl 6-azido-7-(3-(4,4,5,5-tetramethyl-1,3,2-dioxaborolan-2-yl)propyl)-2-azaspiro[3.4]octane-2,6-dicarboxylate (40 mg, 0.072 mmol, K1-2-P1) in MeOH (3 mL) under $N_2$. The mixture was degassed and backfilled with $H_2$ (three times). The resulting mixture was stirred under $H_2$ (pressure: 15 psi) at 24° C. for 1 h. The catalyst was filtered off, and the filtrate was concentrated under reduced pressure to give 6-amino-2-(tert-butoxycarbonyl)-7-(3-(4,4,5,5-tetramethyl-1,3,2-dioxaborolan-2-yl)propyl)-2-azaspiro[3.4]octane-6-carboxylic acid, which was used in next step directly. LCMS ($C_{22}H_{40}BN_2O_6^+$) (ES, m/z): 439 [M+H]$^+$.

Step 3: 6-amino-7-(3-boronopropyl)-2-(tert-butoxycarbonyl)-2-azaspiro[3.4]octane-6-carboxylic acid $NH_4OAc$ (88 mg, 1.1 mmol) and sodium periodate (122 mg, 0.57 mmol) were added to a mixture of 6-amino-2-(tert-butoxycarbonyl)-7-(3-(4,4,5,5-tetramethyl-1,3,2-dioxaborolan-2-yl)propyl)-2-azaspiro[3.4]octane-6-carboxylic acid (25 mg, 0.057 mmol), THF (2 mL) and water (1 mL) at 20° C. The suspension was stirred at 20° C. for 15 h. The mixture was filtered, and the filtrate was concentrated in vacuum to give 6-amino-7-(3-boronopropyl)-2-(tert-butoxycarbonyl)-2-azaspiro[3.4]octane-6-carboxylic acid, which was used in the next step without further purification. LCMS ($C_{16}H_{30}BN_2O_6^+$) (ES, m/z): 357 [M+H]$^+$.

Step 4: 6-amino-7-(3-boronopropyl)-2-azaspiro[3.4] octane-6-carboxylic acid

A mixture of 6-amino-7-(3-boronopropyl)-2-(tert-butoxycarbonyl)-2-azaspiro[3.4]octane-6-carboxylic acid (50 mg, 0.14 mmol) and TFA (0.3 mL) in DCM (2 mL) was stirred at 0° C. for 1 h. The mixture was concentrated under reduced pressure. The residue was purified by RP-HPLC [C18 column, water (20 mM HFBA and 0.1% TFA)-acetonitrile] to give 6-amino-7-(3-boronopropyl)-2-azaspiro[3.4]octane-6-carboxylic acid. LCMS ($C_{11}H_{20}BN_2O_3^+$) (ES, m/z): 239 [M+H-$H_2O$]$^+$. $^1$H NMR (500 MHz, deuterium oxide) δ 3.24 (s, 2H), 3.15 (s, 2H), 2.35-2.15 (m, 1H), 2.08 (d, J=11.4 Hz, 1H), 2.02-1.92 (m, 1H), 1.85 (d, J=11.6 Hz, 1H), 1.55-1.44 (m, 1H), 1.42-1.29 (m, 2H), 1.25-1.05 (m, 2H), 0.75-0.57 (m, 2H).

Example 35C was made from K1-4-P2 using the same procedure.

Ex. MS and $^1$HNMR

LCMS ($C_{11}H_{20}BN_2O_3^+$) (ES, m/z): 239 [M+H-$H_2O$]$^+$.

35C $^1$H NMR (500 MHz, deuterium oxide) δ 3.24 (s, 2H), 3.15 (s, 2H), 2.35-2.15 (m, 1H), 2.09 (d, J=11.4 Hz, 1H), 2.01-1.91 (m, 1H), 1.85 (d, J=11.6 Hz, 1H), 1.54-1.43 (m, 1H), 1.41-1.28 (m, 2H), 1.26-1.06 (m, 2H), 0.75-0.56 (m, 2H).

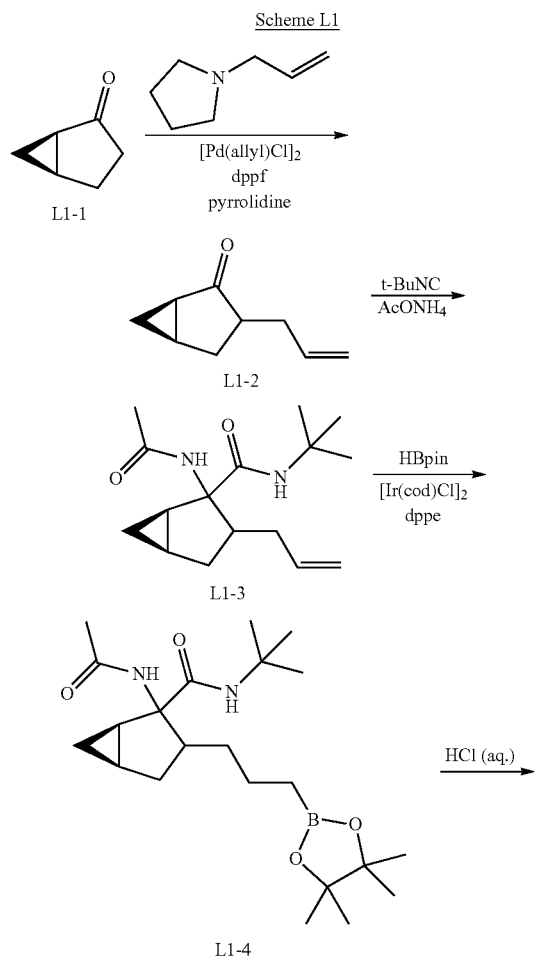

Scheme L1

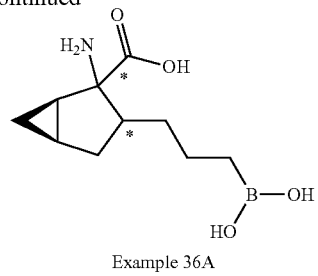

Example 36A

Example 36A: rel-(1R,5R)-2-amino-3-(3-boronopropyl)bicyclo[3.1.0]hexane-2-carboxylic acid

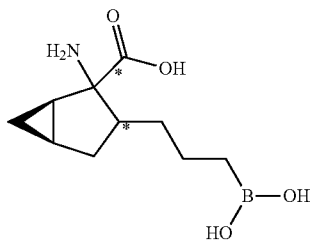 [SMILES: NC1(C(=O)O)C(CCCB(O)O)C[C@H]2C[C@H]21]

Step 1: (1R,5R)-3-allylbicyclo[3.1.0]hexan-2-one

[Pd($C_3H_5$)Cl]$_2$ (190 mg, 0.52 mmol) was added to a mixture of dppf (577 mg, 1.0 mmol) in dry MeOH (20 mL) under $N_2$. The reaction was stirred at 15° C. under $N_2$ for 1 hour. 1-allylpyrrolidine (1.1 g, 10.4 mmol) in MeOH (4 mL) was added to the mixture and the resulting mixture was stirred for another 10 min., followed by the addition of pyrrolidine (148 mg, 2.1 mmol) in MeOH (4 mL) and (1R,5S)-bicyclo[3.1.0]hexan-2-one (1 g, 10.4 mmol). The reaction was stirred at 15° C. under $N_2$ for 15 h. Solvent was distilled off at 90° C. at 1 atm. The residue was dissolved in DCM and washed with 2 N HCl in water. The DCM layer was separated and distilled at 1 atm at 60° C. The residue was suspended in hexane, filtered. The filtrate was distilled at 90° C. at 1 atm to give crude product, which was used in the next step without further purification. LCMS ($C_9H_{13}O^+$) (ES, m/z): 137 [M+H]$^+$.

Step 2: (1R,5R)-2-acetamido-3-allyl-N-(tert-butyl) bicyclo[3.1.0]hexane-2-carboxamide NH$_4$OAc (566 mg, 7.3 mmol) and 2-isocyano-2-methylpropane (305 mg, 3.7 mmol) were added to a mixture of (1R,5R)-3-allylbicyclo[3.1.0]hexan-2-one (100 mg, 0.73 mmol) in 2,2,2-trifluoroethanol (2 mL) under $N_2$. The mixture was stirred at 35° C. for 15 h. The reaction mixture was quenched with water and extracted with DCM. The combined organic phases were washed with brine, dried over anhydrous Na$_2$SO$_4$, filtered and concentrated under reduced pressure. The residue was purified by silica gel column chromatography (EtOAc in hexanes) to give (1R,5R)-2-acetamido-3-allyl-N-(tert-butyl)bicyclo[3.1.0]hexane-2-carboxamide. LCMS ($C_{16}H_{27}N_2O_2^+$) (ES, m/z): 279 [M+H]$^+$.

Step 3: (1R,5R)-2-acetamido-N-(tert-butyl)-3-(3-(4,4,5,5-tetramethyl-1,3,2-dioxaborolan-2-yl)propyl) bicyclo[3.1.0]hexane-2-carboxamide 1,2-bis(diphenylphosphino)ethane (8 mg, 0.02 mmol) was added to a mixture of [Ir(cod)Cl]$_2$ (9.7 mg, 0.014 mmol)

in dry DCM (2 mL) under N₂. The reaction mixture was stirred at 15° C. under N₂ for 5 min. To this mixture, 4,4,5,5-tetramethyl-1,3,2-dioxaborolane (184 mg, 1.4 mmol) and (1R,5R)-2-acetamido-3-allyl-N-(tert-butyl)bicyclo[3.1.0]hexane-2-carboxamide (80 mg, 0.29 mmol) were added. The reaction was stirred at 15° C. under N₂ for 15 h. The reaction mixture was quenched with water and extracted with DCM. The combined organic phases were washed with brine, dried over anhydrous Na₂SO₄, filtered and concentrated under reduced pressure. The residue was purified by silica gel column chromatography (EtOAc in hexanes) to give (1R,5R)-2-acetamido-N-(tert-butyl)-3-(3-(4,4,5,5-tetramethyl-1,3,2-dioxaborolan-2-yl)propyl)bicyclo[3.1.0]hexane-2-carboxamide. LCMS ($C_{22}H_{40}BN_2O_4^+$) (ES, m/z): 407 [M+H]⁺.

Step 4: (1R,5R)-2-amino-3-(3-boronopropyl)bicyclo[3.1.0]hexane-2-carboxylic acid (1R,5R)-2-acetamido-N-(tert-butyl)-3-(3-(4,4,5,5-tetramethyl-1,3,2-dioxaborolan-2-yl)propyl)bicyclo[3.1.0]hexane-2-carboxamide (40 mg, 0.098 mmol) was added to 6 N HCl in water (10 mL, 60 mmol). The reaction was stirred at 80° C. for 15 h. The reaction mixture was concentrated in vacuum. The resulting residue was purified by RP-HPLC [C18 column, water (20 mM HFBA and 0.1% TFA)-acetonitrile] to give (1R,5R)-2-amino-3-(3-boronopropyl)bicyclo[3.1.0]hexane-2-carboxylic acid. LCMS ($C_{10}H_{19}BNO_4^+$) (ES, m/z): 228 [M+H]⁺. ¹H NMR (400 MHz, deuterium oxide) δ 2.25-2.10 (m, 1H), 2.05-1.94 (m, 1H), 1.52-1.37 (m, 3H), 1.32-1.00 (m, 4H), 0.77-0.45 (m, 4H).

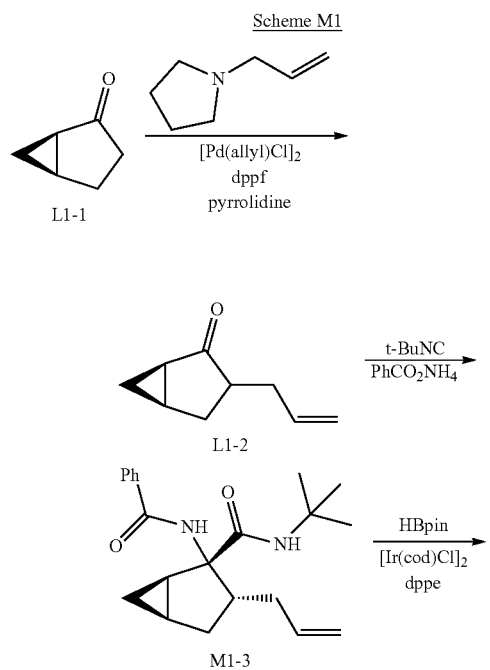

Scheme M1

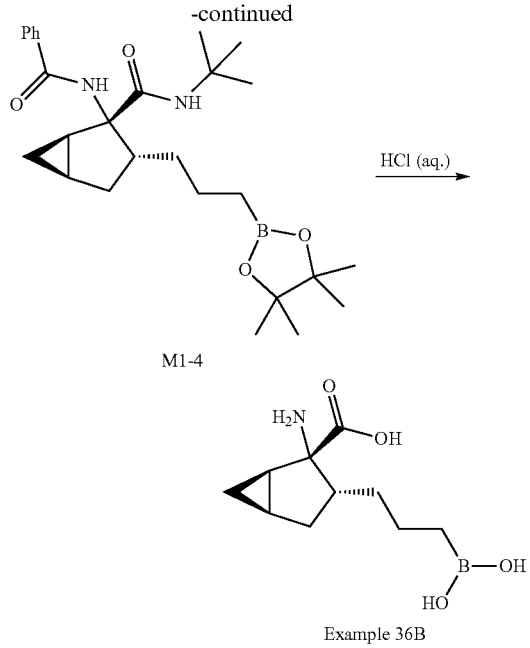

Example 36B: (1R,2R,3R,5R)-2-amino-3-(3-boronopropyl)bicyclo[3.1.0]hexane-2-carboxylic acid

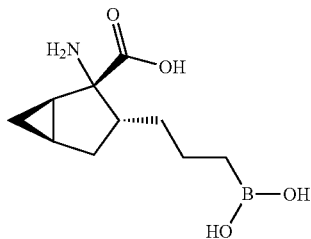 [SMILES: N[C@]1(C(=O)O)[C@H](CCCB(O)O)C[C@H]2C[C@H]21]

Step 1: (1R,5R)-3-allylbicyclo[3.1.0]hexan-2-one

[Pd(C₃H₅)Cl]₂ (666 mg, 1.8 mmol) was added to a mixture of dppf (2.0 g, 3.6 mmol) in dry MeOH (50 mL) under N₂. The reaction was stirred at 15° C. under N₂ atmosphere for 1 h. 1-allylpyrrolidine (4.1 g, 36 mmol) in MeOH (10 mL) was added, and the mixture was stirred for another 10 min, followed by the addition of pyrrolidine (518 mg, 7.3 mmol) in MeOH (10 mL) and (1R,5S)-bicyclo[3.1.0]hexan-2-one (3.5 g, 36 mmol). The reaction was stirred at 20° C. under N₂ for 15 h. The reaction mixture was quenched with 2 N HCl and DCM and extracted with pentane. The combined organic phases were washed with brine, dried over anhydrous Na₂SO₄ and filtered. Solvent was distilled off at 80° C. at 1 atm. The residue was dissolved in DCM and diluted with pentane. The precipitate was filtered off. The filtrate was distilled at 1 atm at 80° C. to give the crude product, which was used in the next step without further purification. LCMS ($C_9H_{13}O^+$) (ES, m/z): 137 [M+H]⁺.

Step 2: (1R,2R,3R,5R)-3-allyl-2-benzamido-N-(tert-butyl)bicyclo[3.1.0]hexane-2-carboxamide Ammonium benzoate (2.6 g, 18 mmol) and 2-isocyano-2-methylpropane (2.1 mL, 18 mmol) were added to a solution of (1R,5R)-3-allylbicyclo[3.1.0]hexan-2-one (0.5 g, 3.7 mmol) in 2,2,2-trifluoroethyl alcohol (5 mL). The reaction mixture was stirred at 80° C. for 15 h. The reaction mixture was quenched with water and extracted with EtOAc. The combined organic phases were washed with brine, dried over anhydrous $Na_2SO_4$, filtered and concentrated under reduced pressure. The resulting residue was purified by flash silica gel chromatography (EtOAc in hexanes) to give (1R,2R,3R,5R)-3-allyl-2-benzamido-N-(tert-butyl)bicyclo[3.1.0]hexane-2-carboxamide. The stereochemistry was assigned by 2D NMR. LCMS ($C_{21}H_{29}N_2O_2^+$) (ES, m/z): 341 [M+H]$^+$.

Step 3: (1R,2R,3R,5R)-2-benzamido-N-(tert-butyl)-3-(3-(4,4,5,5-tetramethyl-1,3,2-dioxaborolan-2-yl)propyl)bicyclo[3.1.0]hexane-2-carboxamide 1,2-bis(diphenylphosphino)ethane (9.4 mg, 0.023 mmol) was added to a solution of [Ir(cod)Cl]$_2$ (16 mg, 0.023 mmol) in DCM (3 mL) under $N_2$. The reaction was stirred at 20° C. under $N_2$ for 5 min. To this mixture (1R,2R,3R,5R)-3-allyl-2-benzamido-N-(tert-butyl)bicyclo[3.1.0]hexane-2-carboxamide (80 mg, 0.24 mmol) and 4,4,5,5-tetramethyl-1,3,2-dioxaborolane (150 mg, 1.2 mmol) were added. The reaction was stirred at 20° C. under $N_2$ for 15 h. The reaction mixture was quenched with water and extracted with DCM. The combined organic phases were washed with brine, dried over anhydrous $Na_2SO_4$, filtered and concentrated under reduced pressure. The resulting residue was purified by flash silica gel chromatography (EtOAc in hexanes) to give (1R,2R,3R,5R)-2-benzamido-N-(tert-butyl)-3-(3-(4,4,5,5-tetramethyl-1,3,2-dioxaborolan-2-yl)propyl)bicyclo[3.1.0]hexane-2-carboxamide. LCMS ($C_{27}H_{42}BN_2O_4^+$) (ES, m/z): 469 [M+H]$^+$.

Step 4: (1R,2R,3R,5R)-2-amino-3-(3-boronopropyl)bicyclo[3.1.0]hexane-2-carboxylic acid 12 N HCl in water (1 mL, 12 mmol) was diluted with water (0.5 mL). The resulting HCl aqueous solution was added to a solution (1R,2R,3R,5R)-2-benzamido-N-(tert-butyl)-3-(3-(4,4,5,5-tetramethyl-1,3,2-dioxaborolan-2-yl)propyl)bicyclo[3.1.0]hexane-2-carboxamide (80 mg, 0.17 mmol) in acetic acid (0.5 mL). The reaction mixture was stirred at 80° C. for 15 h, and concentrated under reduced pressure. The resulting residue was purified by RP-HPLC [C18 column, water (20 mM HFBA and 0.1% TFA)-acetonitrile] to give (1R,2R,3R,5R)-2-amino-3-(3-boronopropyl)bicyclo[3.1.0]hexane-2-carboxylic acid. LCMS ($C_{10}H_{19}BNO_4^+$) (ES, m/z): 288 [M+H]$^+$. $^1$H NMR (400 MHz, deuterium oxide) δ 2.25-2.10 (m, 1H), 2.04-1.92 (m, 1H), 1.52-1.39 (m, 3H), 1.30-0.96 (m, 4H), 0.74-0.43 (m, 4H).

Scheme N1

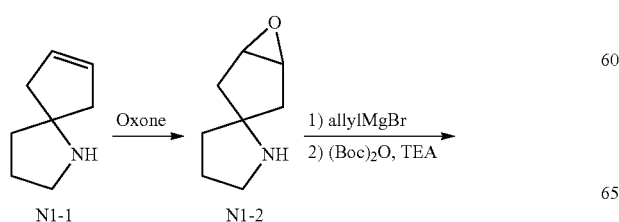

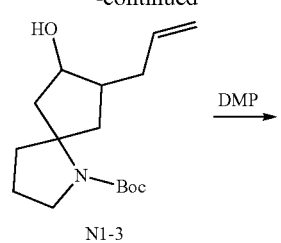

N1-3

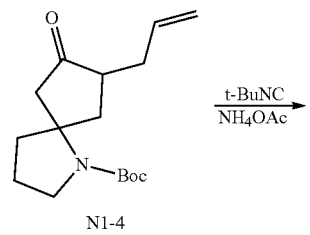

N1-4

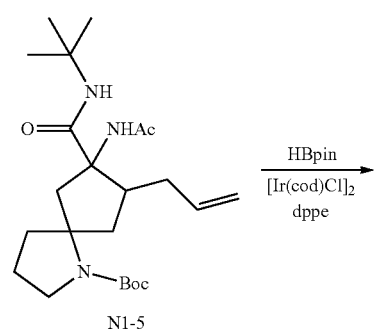

N1-5

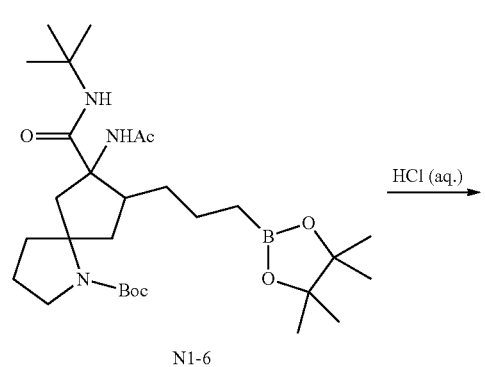

N1-6

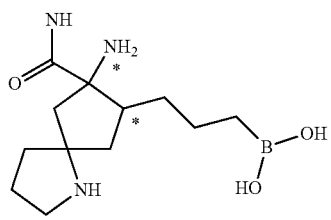

Example 37

Example 37A: rel-7-amino-8-(3-boronopropyl)-1-azaspiro[4.4]nonane-7-carboxylic acid

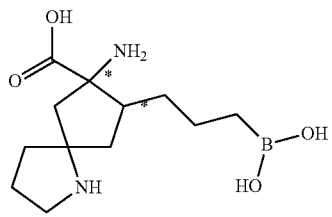

Step 1: 6-oxaspiro[bicyclo[3.1.0]hexane-3,2'-pyrrolidine] 2,2,2-trifluoroacetate A solution of oxone (1.3 g, 2 mmol) in water (5 mL) was added dropwise to a solution of 1-azaspiro[4.4]non-7-ene (500 mg, 4.1 mmol) in water (5 mL) at 0° C. over 5 min. The reaction solution was stirred at 20° C. for 1 h. Then the reaction solution was purified by RP-HPLC [C18 column, water (0.1% TFA)-acetonitrile] to give 6-oxaspiro[bicyclo[3.1.0]hexane-3,2'-pyrrolidine]. LCMS ($C_8H_{14}NO^+$) (ES, m/z): 140 [M+H]$^+$.

Step 2: tert-butyl 7-allyl-8-hydroxy-1-azaspiro[4.4]nonane-1-carboxylate

Allylmagnesium bromide (6.1 mL, 6.1 mmol, 1M in diethyl ether) was added to a solution of 6-oxaspiro[bicyclo[3.1.0]hexane-3,2'-pyrrolidine] TFA salt (500 mg, 1.2 mmol) in THF (10 mL) under $N_2$. The resulting suspension was stirred under $N_2$ at 20° C. for 5 h. The reaction mixture was quenched with water (5 mL). TEA (0.85 mL, 6.1 mmol) and BOC-Anhydride (0.85 mL, 3.7 mmol) were added. The resulting suspension was stirred 20° C. for 15 h. The reaction mixture was quenched with brine and extracted with EtOAc. The combined organic phases were washed with brine, dried over anhydrous $Na_2SO_4$, filtered and concentrated under reduced pressure. The residue was purified by silica gel column chromatography (EtOAc in hexanes) to give tert-butyl 7-allyl-8-hydroxy-1-azaspiro[4.4]nonane-1-carboxylate. LCMS ($C_{16}H_{28}NO_3^+$) (ES, m/z): 282 [M+H]$^+$.

Step 3: tert-butyl 7-allyl-8-oxo-1-azaspiro[4.4]nonane-1-carboxylate

DMP (624 mg, 1.5 mmol) was added to a solution of tert-butyl 7-allyl-8-hydroxy-1-azaspiro[4.4]nonane-1-carboxylate (230 mg, 0.82 mmol) in DCM (5 mL). The resulting suspension was stirred at 20° C. for 15 h. The mixture was filtered and the filtrate was concentrated under reduced pressure. The residue was purified by silica gel column chromatography (EtOAc in hexanes) to afford tert-butyl 7-allyl-8-oxo-1-azaspiro[4.4]nonane-1-carboxylate. LCMS ($C_{11}H_{18}NO^+$) (ES, m/z): 180 [M+H-Boc]$^+$.

Step 4: 7-acetamido-8-allyl-7-(tert-butylcarbamoyl)-1-azaspiro[4.4]nonane-1-carboxylate Ammonium acetate (207 mg, 2.7 mmol) and 2-isocyano-2-methylpropane (0.3 mL, 2.7 mmol) were added to a solution of tert-butyl 7-allyl-8-oxo-1-azaspiro[4.4]nonane-1-carboxylate (150 mg, 0.54 mmol) in 2,2,2-trifluoroethyl alcohol (1 mL). The reaction mixture was stirred at 35° C. for 15 h. The reaction mixture was quenched with water and extracted with EtOAc. The combined organic phases were washed with brine, dried over anhydrous $Na_2SO_4$, filtered and concentrated under reduced pressure. The residue was purified by silica gel column chromatography (EtOAc in hexanes) to afford 7-acetamido-8-allyl-7-(tert-butylcarbamoyl)-1-azaspiro[4.4]nonane-1-carboxylate. LCMS ($C_{23}H_{40}N_3O_4^+$) (ES, m/z): 422 [M+H]$^+$.

Step 5: tert-butyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate 1,2-bis(diphenylphosphino)ethane (13 mg, 0.033 mmol) was added to a solution of [Ir(cod)Cl]$_2$ (11 mg, 0.017 mmol) in DCM (5 mL) under $N_2$. The reaction was stirred at 20° C. under $N_2$ for 5 min. To this mixture, tert-butyl 7-acetamido-8-allyl-7-(tert-butylcarbamoyl)-1-azaspiro[4.4]nonane-1-carboxylate (70 mg, 0.17 mmol) and 4,4,5,5-tetramethyl-1,3,2-dioxaborolane (106 mg, 0.83 mmol) were added. The reaction was stirred at 20° C. under $N_2$ for 2 h. The reaction mixture was quenched with water and extracted with DCM. The combined organic phases were washed with brine, dried over anhydrous $Na_2SO_4$, filtered and concentrated under reduced pressure. The residue was purified by RP-HPLC [C18 column, water (0.05% HCl)-acetonitrile] to give tert-butyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate. LCMS ($C_{29}H_{53}BN_3O_6^+$) (ES, m/z): 550 [M+H]$^+$.

Step 6: 7-amino-8-(3-boronopropyl)-1-azaspiro[4.4]nonane-7-carboxylic acid

12 N HCl in water (4 mL, 48 mmol) was diluted with water (2 mL). The resulting HCl aqueous solution was added to a solution of tert-butyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate (15 mg, 0.027 mmol) in acetic acid (2 mL). The reaction mixture was stirred at 100° C. for 15 h., and then evaporated under reduced pressure. The resulting residue was purified by RP-HPLC [C18 column, water (0.1% TFA)-acetonitrile] to give 7-amino-8-(3-boronopropyl)-1-azaspiro[4.4]nonane-7-carboxylic acid. LCMS ($C_{12}H_{22}BN_2O_3^+$) (ES, m/z): 253 [M+H]$^+$. $^1$H NMR (400 MHz, deuterium oxide) δ 3.28-3.13 (m, 2H), 2.83-2.64 (m, 1H), 2.37-2.17 (m, 3H), 2.07-1.82 (m, 5H), 1.53-1.26 (m, 2H), 1.25-0.94 (m, 2H), 0.70-0.51 (m, 2H).

Scheme O1

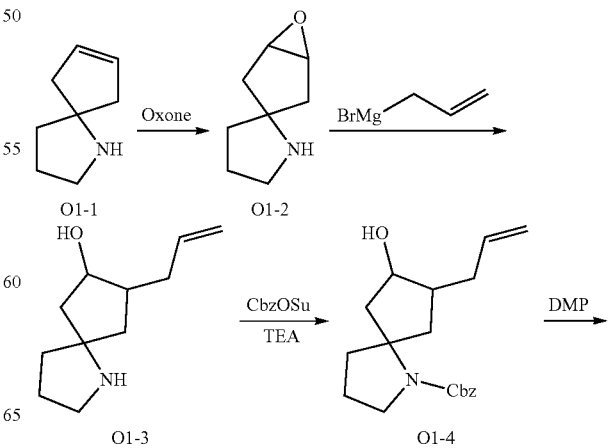

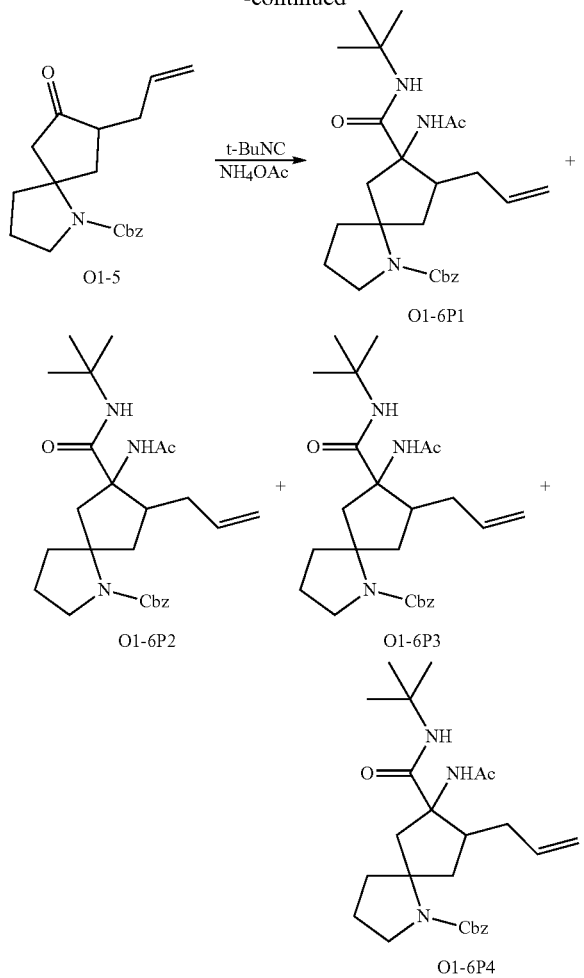

Step 1: 6-oxaspiro[bicyclo[3.1.0]hexane-3,2'-pyrrolidine]

A solution of oxone (10 g, 16 mmol) in water (50 mL) was added to a solution of 1-azaspiro[4.4]non-7-ene (4 g, 33 mmol) in water (50 mL) over 0.5 h at 0° C. The reaction solution was stirred at 25° C. for 0.5 h. NaHCO$_3$ (4.1 g, 49 mmol) was added to the reaction to adjust pH=6. The solvent was removed via lyophilization to give crude product, which was used in the next step directly without further purification. LCMS ($C_8H_{14}NO^+$) (ES, m/z): 140 [M+H]$^+$.

Step 2: 8-allyl-1-azaspiro[4.4]nonan-7-ol 6-oxaspiro[bicyclo[3.1.0]hexane-3,2'-pyrrolidine] (9 g, 16 mmol, 25% wt) was added to allylmagnesium bromide (52 mL, 52 mmol, 1M in diethyl ether) under N$_2$ at 0° C. The resulting mixture was stirred under N$_2$ at 25° C. for 15 h. The reaction mixture was quenched with water. Solvent was evaporated in vacuum. The residue was suspended in MeOH, filtered. The filtrate was evaporated in vacuum give crude product, which was used in the next step directly without further purification. LCMS ($C_{11}H_{20}NO^+$) (ES, m/z): 182 [M+H]$^+$.

Step 3: benzyl 7-allyl-8-hydroxy-1-azaspiro[4.4]nonane-1-carboxylate

TEA (14 mL, 102 mmol) and benzyl (2,5-dioxopyrrolidin-1-yl) carbonate (15 g, 61 mmol) was added to a solution of 8-allyl-1-azaspiro[4.4]nonan-7-ol (5.3 g, 21 mmol) in DCM (100 mL) under N$_2$. The resulting suspension was stirred under N$_2$ at 25° C. for 2 h. The reaction mixture was quenched with water and extracted with DCM. The combined organic phases were washed with brine, dried over anhydrous Na$_2$SO$_4$, filtered and concentrated under reduced pressure. The residue was purified by silica gel column chromatography (EtOAc in hexanes) to give benzyl 7-allyl-8-hydroxy-1-azaspiro[4.4]nonane-1-carboxylate. LCMS ($C_{19}H_{26}NO_3^+$) (ES, m/z): 316 [M+H]$^+$.

Step 4: benzyl 7-allyl-8-oxo-1-azaspiro[4.4]nonane-1-carboxylate

DMP (9.7 g, 23 mmol) was added to a solution of benzyl 7-allyl-8-hydroxy-1-azaspiro[4.4]nonane-1-carboxylate (3.6 g, 11 mmol) in DCM (100 mL). The resulting white suspension was stirred at 25° C. for 1 h. The reaction mixture was filtered. The filtrate was concentrated under reduced pressure to give the crude. The residue was purified by silica gel column chromatography (EtOAc in hexanes) to give benzyl 7-allyl-8-oxo-1-azaspiro[4.4]nonane-1-carboxylate. LCMS ($C_{19}H_{24}NO_3^+$) (ES, m/z): 314 [M+H]$^+$.

Step 5: benzyl 7-acetamido-8-allyl-7-(tert-butylcarbamoyl)-1-azaspiro[4.4]nonane-1-carboxylate Ammonium acetate (1.23 g, 16 mmol) and 2-isocyano-2-methylpropane (1.8 mL, 16 mmol) were added to a solution of benzyl 7-allyl-8-oxo-1-azaspiro[4.4]nonane-1-carboxylate (1 g, 3.2 mmol) in 2,2,2-trifluoroethyl alcohol (5 mL). The reaction mixture was stirred at 35° C. for 15 h. The reaction mixture was quenched with water (20 mL) and extracted with EtOAc. The combined organic phases were washed with brine, dried over anhydrous Na$_2$SO$_4$, filtered and concentrated under reduced pressure. The resulting residue was purified by RP-HPLC [C18 column, water (0.1% TFA)-acetonitrile] to give benzyl 7-acetamido-8-allyl-7-(tert-butylcarbamoyl)-1-azaspiro[4.4]nonane-1-carboxylate (O1-6P1) as the first eluting peak and benzyl 7-acetamido-8-allyl-7-(tert-butylcarbamoyl)-1-azaspiro[4.4]nonane-1-carboxylate (O1-6P2) as the second eluting peak and benzyl 7-acetamido-8-allyl-7-(tert-butylcarbamoyl)-1-azaspiro[4.4]nonane-1-carboxylate (O1-6P3) as the third eluting peak and benzyl 7-acetamido-8-allyl-7-(tert-butylcarbamoyl)-1-azaspiro[4.4]nonane-1-carboxylate (O1-6P4) as the fourth eluting peak. O1-6P1: LCMS ($C_{26}H_{38}N_3O_4^+$) (ES, m/z): 456 [M+H]$^+$. O1-6P2: LCMS ($C_{26}H_{38}N_3O_4^+$) (ES, m/z): 456 [M+H]$^+$. O1-6P3: LCMS ($C_{26}H_{37}N_3O_4Na^+$) (ES, m/z): 478 [M+Na]$^+$. O1-6P4: LCMS ($C_{26}H_{37}N_3O_4Na^+$) (ES, m/z): 478 [M+Na]$^+$.

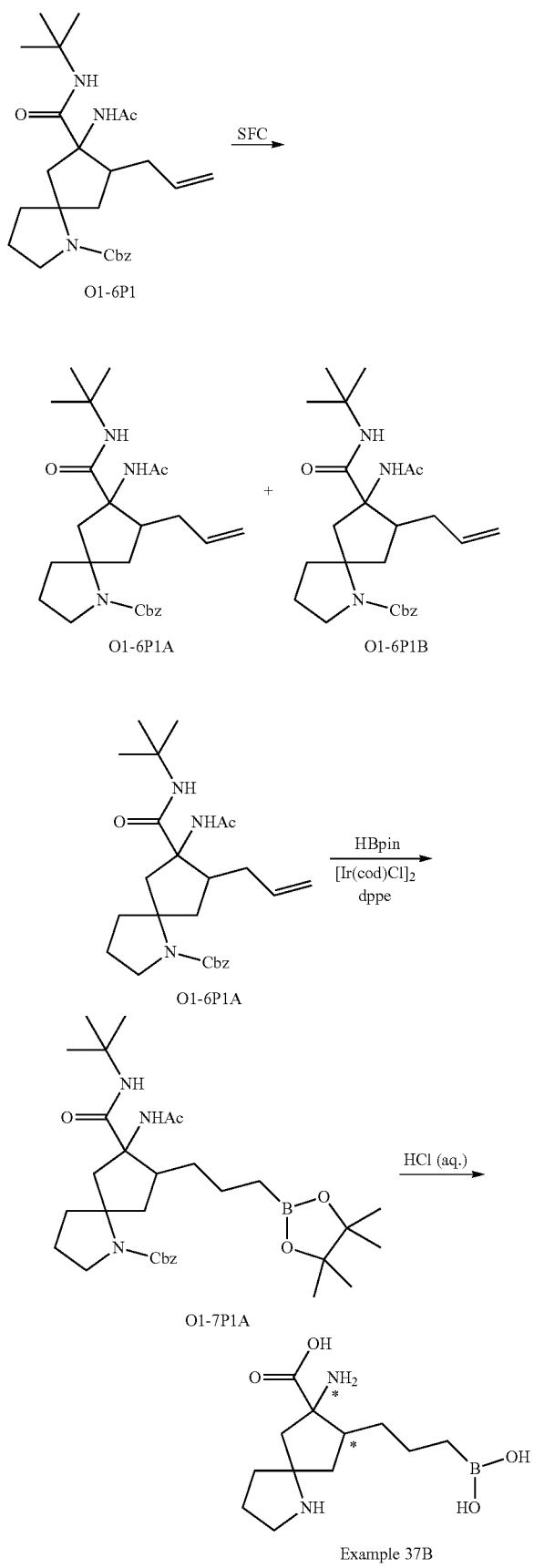

Example 37B: 7-amino-8-(3-boronopropyl)-1-azaspiro[4.4]nonane-7-carboxylic acid

Step 6: benzyl 7-acetamido-8-allyl-7-(tert-butylcarbamoyl)-1-azaspiro[4.4]nonane-1-carboxylate and benzyl 7-acetamido-8-allyl-7-(tert-butylcarbamoyl)-1-azaspiro[4.4]nonane-1-carboxylate The benzyl 7-acetamido-8-allyl-7-(tert-butylcarbamoyl)-1-azaspiro[4.4]nonane-1-carboxylate (580 mg, 1.27 mmol, O1-6P1) was resolved by Chiral-SFC (Column: AD-H (250 mm*30 mm, 5 um), Mobile phase: A: $CO_2$, B: EtOH (0.1% $NH_3.H_2O$), Gradient: 15% of B in 3.5 min, and hold 15% of B for 1 min, Flow Rate (mL/min) 50, 40° C.) to give benzyl 7-acetamido-8-allyl-7-(tert-butylcarbamoyl)-1-azaspiro[4.4]nonane-1-carboxylate (O1-6P1A) ($t_r$=1.9 min) as the first eluting peak and benzyl 7-acetamido-8-allyl-7-(tert-butylcarbamoyl)-1-azaspiro[4.4]nonane-1-carboxylate (O1-6P1B) ($t_r$=3.0 min) as the second eluting peak. 2D NMR showed that acetamide group and allyl group was at same face. O1-6P1A: LCMS ($C_{26}H_{38}N_3O_4^+$) (ES, m/z): 456 [M+H]$^+$. O1-6P1B: LCMS ($C_{26}H_{38}N_3O_4^+$) (ES, m/z): 456 [M+H]$^+$.

Step 7: benzyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate

[Ir(cod)Cl]$_2$ (29.5 mg, 0.044 mmol) was added to a solution of 1,2-bis(diphenylphosphino)ethane (35 mg, 0.088 mmol) in DCM (20 mL) under N$_2$. The reaction was stirred at 0° C. under N$_2$ for 5 min. To this mixture, 4,4,5,5-tetramethyl-1,3,2-dioxaborolane (0.4 mL, 2.2 mmol) was added. A solution of benzyl 7-acetamido-8-allyl-7-(tert-butylcarbamoyl)-1-azaspiro[4.4]nonane-1-carboxylate (200 mg, 0.44 mmol) in DCM (2 mL) was added. The reaction was stirred at 0° C. under N$_2$ for 2 h. The reaction was stirred at 25° C. under N$_2$ for an additional 15 h. The solvent was removed under reduced pressure and the residue was purified by RP-HPLC [C18 column, water (0.1% TFA)-acetonitrile] to give benzyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate. LCMS ($C_{32}H_5BN_3O_6^+$) (ES, m/z): 584 [M+H]$^+$.

Step 8: 7-amino-8-(3-boronopropyl)-1-azaspiro[4.4]nonane-7-carboxylic acid

A mixture of benzyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate (120 mg, 0.21 mmol) and 12 N HCl in water (15 mL, 180 mmol) was stirred at 100° C. for 15 h. The reaction mixture was concentrated under reduced pressure. The resulting residue was purified by RP-HPLC [C18 column, water (20 mM HFBA and 0.1% TFA)-acetonitrile] to give 7-amino-8-(3-boronopropyl)-1-azaspiro[4.4]nonane-7-carboxylic acid as a HFBA salt. LCMS ($C_{12}H_{24}BN_2O_4^+$) (ES, m/z): 271 [M+H]$^+$. $^1$H NMR (400 MHz, deuterium oxide) δ 3.30-3.23 (m, 2H), 2.86-2.74 (m, 1H), 2.72-2.55 (m, 1H), 2.41-2.26 (m, 1H), 2.21-2.11 (m, 1H), 2.02-1.85 (m, 5H), 1.80-1.72 (m, 1H), 1.44-1.20 (m, 3H), 0.74-0.47 (m, 2H).

Example 37C was made from O1-6P1B using the same procedure of Example 37B.

Ex. MS and $^1$HNMR

37C LCMS ($C_{12}H_{24}BN_2O_4^+$) (ES, m/z): 271 [M+H]$^+$. $^1$H NMR (400 MHz, deuterium oxide) δ 3.34-3.14 (m, 2H), 2.87-2.76 (m, 1H), 2.73-2.59 (m, 1H), 2.40-2.26 (m, 1H), 2.25-2.13 (m, 1H), 2.02-1.86 (m, 5H), 1.78-1.65 (m, 1H), 1.46-1.18 (m, 3H), 0.76-0.49 (m, 2H).

Examples 37D and 37E were made from O1-6P2 using the same procedure as Example 37B.

Example 37D: 7-amino-8-(3-boronopropyl)-1-azaspiro[4.4]nonane-7-carboxylic acid

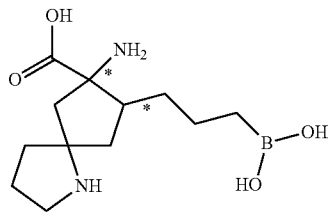 [SMILES: NC1(C(=O)O)CC2(CCCN2)CC1CCCB(O)O]

Step 9: benzyl 7-acetamido-8-allyl-7-(tert-butylcarbamoyl)-1-azaspiro[4.4]nonane-1-carboxylate Benzyl 7-acetamido-8-allyl-7-(tert-butylcarbamoyl)-1-azaspiro[4.4]nonane-1-carboxylate (530 mg, 1.2 mmol) was resolved by Chiral-SFC [Column: OD (250 mm*50 mm, 10 um), Mobile phase: A: $CO_2$, B: EtOH (0.1% $NH_3 \cdot H_2O$), Gradient: 15% of B in 4 min, and hold 15% of B for 1 min, Flow Rate (mL/min) 50, Column temperature: 40° C.] to give benzyl 7-acetamido-8-allyl-7-(tert-butylcarbamoyl)-1-azaspiro[4.4]nonane-1-carboxylate (O1-6P2A) ($t_r$=2.3 min) as the first eluting peak and benzyl 7-acetamido-8-allyl-7-(tert-butylcarbamoyl)-1-azaspiro[4.4]nonane-1-carboxylate (O1-6P2B) ($t_r$=3.1 min) as the second eluting peak. 2D NMR showed that acetamide group and allyl group was at different face. O1-6P2A: LCMS ($C_{26}H_{38}N_3O_4^+$) (ES, m/z): 456 [M+H]$^+$. O1-6P2B: LCMS ($C_{26}H_{38}N_3O_4^+$) (ES, m/z): 456 [M+H]$^+$.

Step 10: benzyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate A mixture of 1,2-bis(diphenylphosphino)ethane (26.2 mg, 0.066 mmol) and [Ir(cod)Cl]$_2$ (22.1 mg, 0.033 mmol) in DCM (50 mL) was stirred at 0° C. under $N_2$ for 5 min. Then benzyl 7-acetamido-8-allyl-7-(tert-butylcarbamoyl)-1-azaspiro[4.4]nonane-1-carboxylate (150 mg, 0.33 mmol) and 4,4,5,5-tetramethyl-1,3,2-dioxaborolane (0.3 mL, 1.6 mmol) were added to this mixture. The reaction was stirred at 25° C. under $N_2$ for 15 h. The mixture was concentrated under reduced pressure, and then the residue was purified by RP-HPLC [C18 Column, water (0.1% TFA)-acetonitrile] to give boronic ester. Then the eluent was concentrated under reduced pressure to give benzyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate. LCMS ($C_{32}H_{51}BN_3O_6^+$) (ES, m/z): 584 [M+H]$^+$.

Step 11: 7-amino-8-(3-boronopropyl)-1-azaspiro[4.4]nonane-7-carboxylic acid

A mixture of benzyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate (55 mg, 0.11 mmol) and 12 N HCl in water (15 mL, 180 mmol) was stirred at 110° C. for 12 h. The mixture was concentrated under reduced pressure. Then the residue was dissolved in 3 mL of water, and the pH was adjusted to pH=8 with solid $NaHCO_3$. The mixture was extracted with DCM, and the pH of the water phase was adjusted to pH=2 with 12 N HCl in water. The water phase was filtered and concentrated under reduced pressure. The residue was purified by RP-HPLC [C18 column, water (20 mM HFBA and 0.1% TFA)-acetonitrile] to give 7-amino-8-(3-boronopropyl)-1-azaspiro[4.4]nonane-7-carboxylic acid. LCMS ($C_{12}H_{22}BN_2O_3^+$) (ES, m/z): 253 [M+H-$H_2O$]$^+$. $^1$H NMR (400 MHz, $D_2O$) δ 3.32 (t, J=7.6 Hz, 2H), 2.84-2.80 (m, 1H), 2.51-2.30 (m, 3H), 2.18-2.05 (m, 2H), 2.03-1.89 (m, 3H), 1.63-1.49 (m, 1H), 1.45-1.32 (m, 1H), 1.32-1.18 (m, 1H), 1.18-1.06 (m, 1H), 0.78-0.60 (m, 2H).

Ex. MS and $^1$HNMR

37E LCMS ($C_{12}H_{22}BN_2O_3^+$) (ES, m/z): 253 [M+H-$H_2O$]$^+$. $^1$H NMR (400 MHz, $D_2O$) δ 3.34 (t, J=7.6 Hz, 2H), 2.86-2.82 (m, 1H), 2.51-2.30 (m, 3H), 2.20-2.07 (m, 2H), 2.07-1.90 (m, 3H), 1.67-1.50 (m, 1H), 1.49-1.34 (m, 1H), 1.32-1.22 (m, 1H), 1.20-1.08 (m, 1H), 0.80-0.61 (m, 2H).

Examples 37F and 37G were made from O1-6P3 using the same procedure as Example 37B.

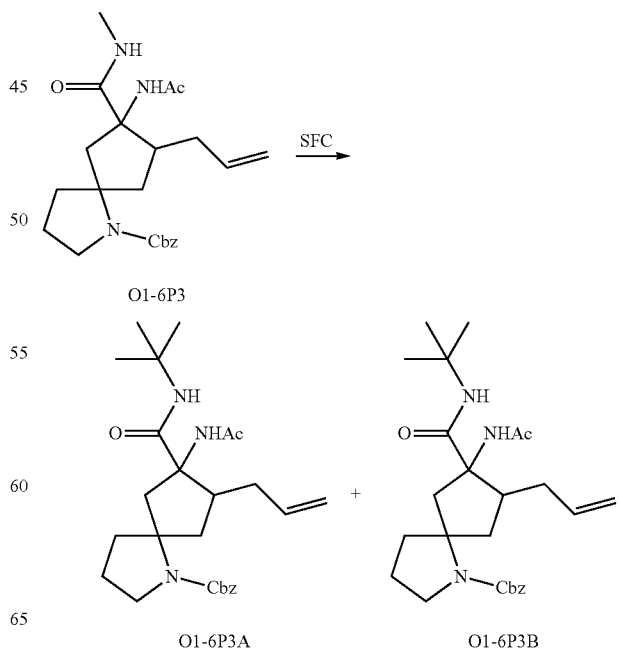

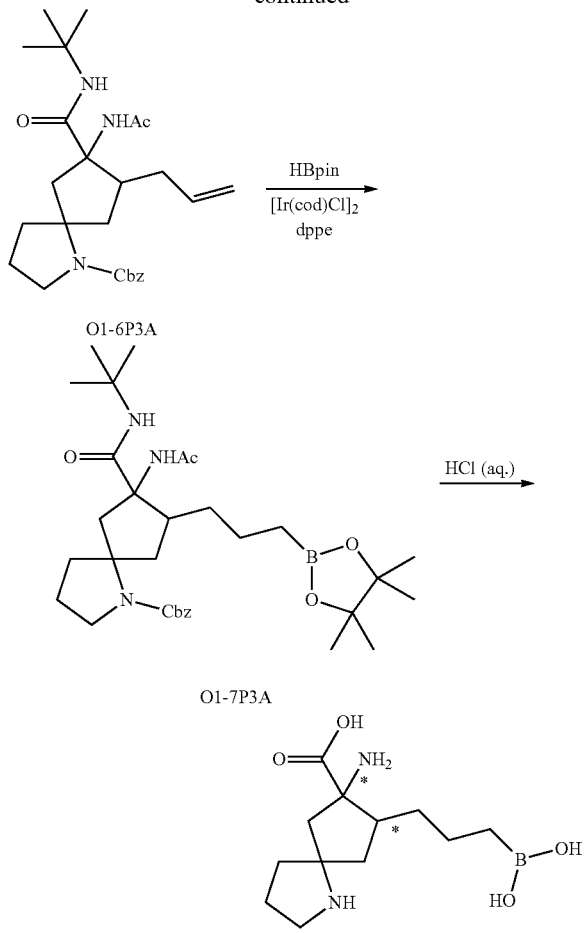

Example 37F: 7-amino-8-(3-boronopropyl)-1-azaspiro[4.4]nonane-7-carboxylic acid

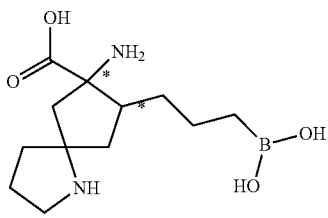 [SMILES: NC1(C(=O)O)CC2(CCCN2)CC1CCCB(O)O]

Step 12: benzyl 7-acetamido-8-allyl-7-(tert-butylcarbamoyl)-1-azaspiro[4.4]nonane-1-carboxylate Benzyl 7-acetamido-8-allyl-7-(tert-butylcarbamoyl)-1-azaspiro[4.4]nonane-1-carboxylate (150 mg, 0.33 mmol) was resolved by Chiral-SFC [Column: REGIS (S,S) Whelk-01 (100 mm×4.6 mm, 5 um), Mobile phase: A: $CO_2$, B: IPA (0.05% DEA), Gradient: 5% to 40% of B in 5.5 min, then 40% of B for 1.5 min, Flow Rate (mL/min) 25, Column temperature: 40° C.] to give benzyl 7-acetamido-8-allyl-7-(tert-butylcarbamoyl)-1-azaspiro[4.4]nonane-1-carboxylate (O1-6P3A) ($t_r$=3.6 min) as the first eluting peak and give benzyl 7-acetamido-8-allyl-7-(tert-butylcarbamoyl)-1-azaspiro[4.4]nonane-1-carboxylate (O1-6P3B) ($t_r$=3.9 min) as the second eluting peak. O1-6P3A: LCMS ($C_{26}H_{38}N_3O_4^+$) (ES, m/z): 456 [M+H]$^+$. O1-6P3B: LCMS ($C_{26}H_{38}N_3O_4^+$) (ES, m/z): 456 [M+H]$^+$.

Step 13: benzyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate A mixture of [Ir(cod)Cl]$_2$ (3 mg, 4.5 μmol) and 1,2-bis(diphenylphosphino)ethane (4 mg, 10 μmol) in DCM (2 mL) was degassed and backfilled with $N_2$ (three times). Then the mixture was stirred for 10 min at 26° C. Next 4,4,5,5-tetramethyl-1,3,2-dioxaborolane (0.064 mL, 0.44 mmol) and benzyl 7-acetamido-8-allyl-7-(tert-butylcarbamoyl)-1-azaspiro[4.4]nonane-1-carboxylate (40 mg, 0.088 mmol) in DCM (3 mL) were added to the mixture in sequence. The mixture was stirred at 26° C. for 14 h. The reaction was then open to air and quenched with methanol. The mixture was stirred until gas evolution ceased, then concentrated in vacuum and the crude product was purified by RP-HPLC [C18 column, water (0.1% TFA)-acetonitrile] to give benzyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate. LCMS ($C_{32}H_{51}BN_3O_6^+$) (ES, m/z): 584 [M+H]$^+$.

Step 14: 7-amino-8-(3-boronopropyl)-1-azaspiro[4.4]nonane-7-carboxylic acid

A mixture of 12 N HCl in water (2 mL, 24 mmol) and benzyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate (40 mg, 0.069 mmol) were stirred at 100° C. for 20 h. Then the solvent was removed in vacuum. Sat. $Na_2CO_3$ was added to the residue and washed with DCM. The aqueous layer was separated and purified by RP-HPLC [C18 column, water (20 mM HFBA and 0.1% TFA)-acetonitrile] to give 7-amino-8-(3-boronopropyl)-1-azaspiro[4.4]nonane-7-carboxylic acid. LCMS ($C_{12}H_{24}BN_2O_4^+$) (ES, m/z): 271 [M+H]$^+$. $^1$H NMR (400 MHz, deuterium oxide) δ 3.34-3.28 (m, 2H), 2.80-2.74 (m, 1H), 2.67-2.61 (m, 0.5H), 2.43-2.29 (m, 2H), 2.19-1.87 (m, 6H), 1.77-1.71 (m, 0.5H), 1.44-1.25 (m, 2.5H), 0.97-0.76 (m, 0.5H), 0.74-0.35 (m, 2H).

Example 37G was made from O1-6P3B using the same procedure Example 37F.

Ex. MS and $^1$HNMR

37G LCMS ($C_{12}H_{24}BN_2O_4^+$) (ES, m/z): 271 [M+H]$^+$. $^1$H NMR (400 MHz, deuterium oxide) δ 3.35-3.29 (m, 2H), 2.81-2.77 (m, 1H), 2.70-2.65 (m, 0.5H), 2.44-2.30 (m, 2H), 2.20-1.89 (m, 6H), 1.78-1.72 (m, 0.5H), 1.45-0.86 (m, 2.5H), 1.00-0.79 (m, 0.5H), 0.77-0.32 (m, 2H).

Examples 37H and 37I were made from O1-6P4 using the same procedure as Example 37B.

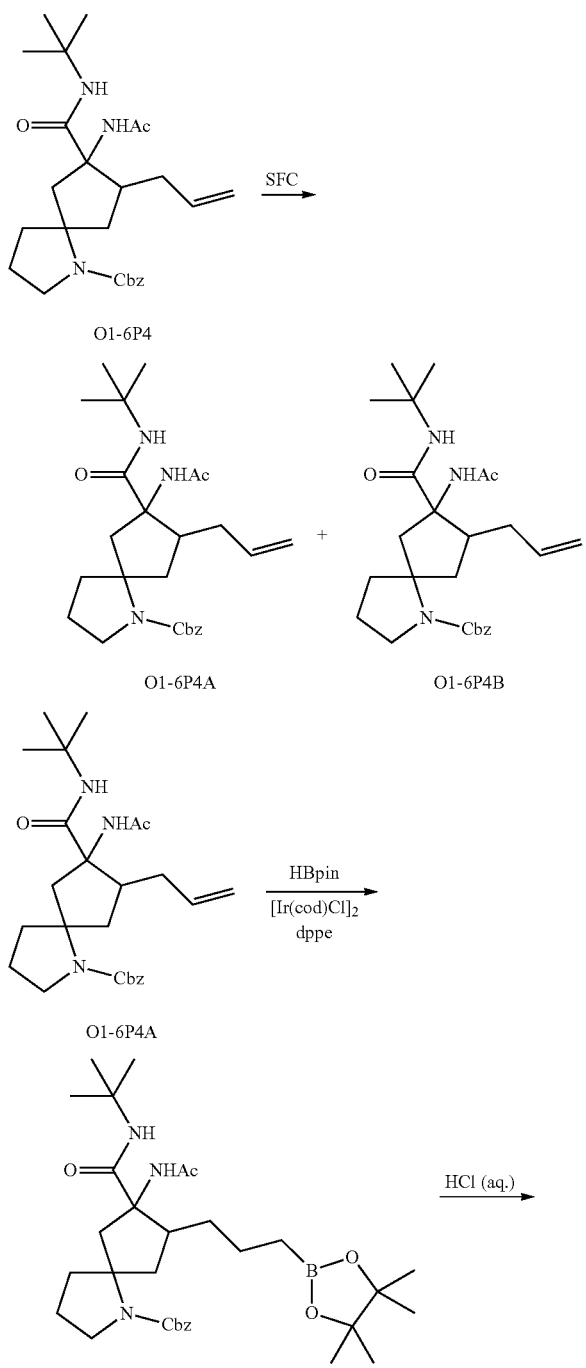

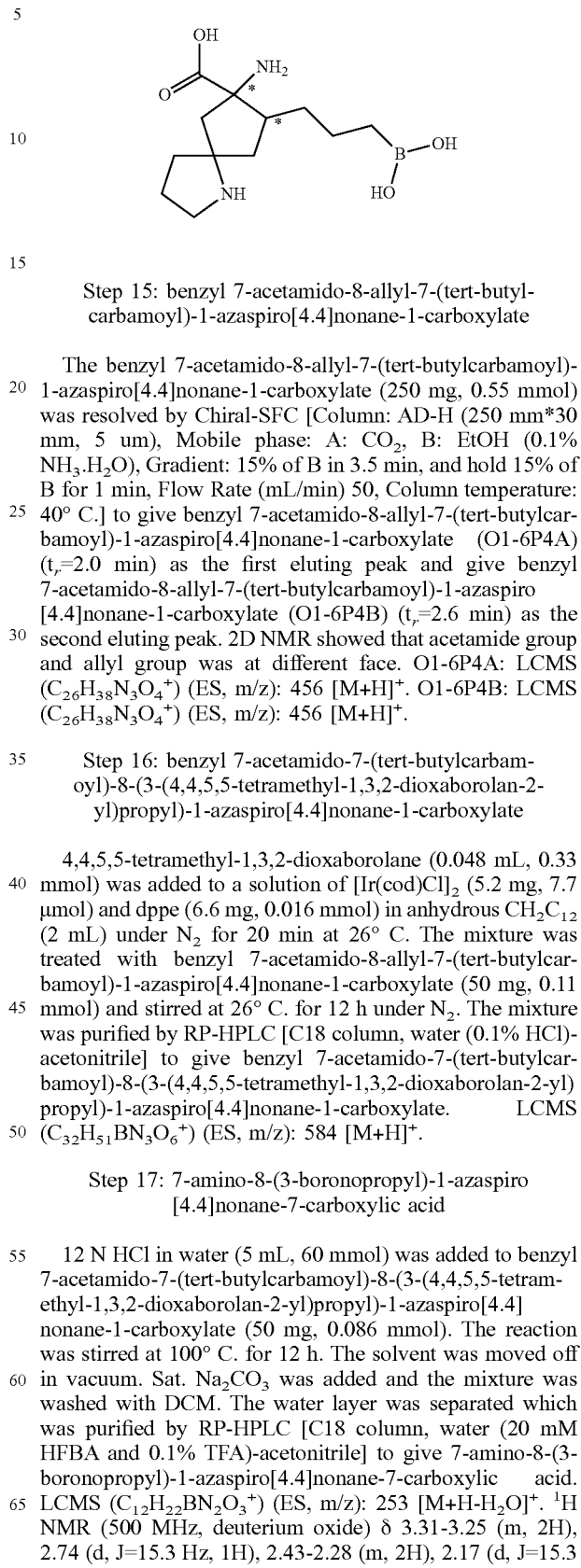

Example 37H: 7-amino-8-(3-boronopropyl)-1-azaspiro[4.4]nonane-7-carboxylic acid

Step 15: benzyl 7-acetamido-8-allyl-7-(tert-butyl-carbamoyl)-1-azaspiro[4.4]nonane-1-carboxylate The benzyl 7-acetamido-8-allyl-7-(tert-butylcarbamoyl)-1-azaspiro[4.4]nonane-1-carboxylate (250 mg, 0.55 mmol) was resolved by Chiral-SFC [Column: AD-H (250 mm*30 mm, 5 um), Mobile phase: A: $CO_2$, B: EtOH (0.1% $NH_3.H_2O$), Gradient: 15% of B in 3.5 min, and hold 15% of B for 1 min, Flow Rate (mL/min) 50, Column temperature: 40° C.] to give benzyl 7-acetamido-8-allyl-7-(tert-butylcarbamoyl)-1-azaspiro[4.4]nonane-1-carboxylate (O1-6P4A) ($t_r$=2.0 min) as the first eluting peak and give benzyl 7-acetamido-8-allyl-7-(tert-butylcarbamoyl)-1-azaspiro[4.4]nonane-1-carboxylate (O1-6P4B) ($t_r$=2.6 min) as the second eluting peak. 2D NMR showed that acetamide group and allyl group was at different face. O1-6P4A: LCMS ($C_{26}H_{38}N_3O_4^+$) (ES, m/z): 456 [M+H]$^+$. O1-6P4B: LCMS ($C_{26}H_{38}N_3O_4^+$) (ES, m/z): 456 [M+H]$^+$.

Step 16: benzyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate 4,4,5,5-tetramethyl-1,3,2-dioxaborolane (0.048 mL, 0.33 mmol) was added to a solution of [Ir(cod)Cl]$_2$ (5.2 mg, 7.7 μmol) and dppe (6.6 mg, 0.016 mmol) in anhydrous $CH_2Cl_2$ (2 mL) under $N_2$ for 20 min at 26° C. The mixture was treated with benzyl 7-acetamido-8-allyl-7-(tert-butylcarbamoyl)-1-azaspiro[4.4]nonane-1-carboxylate (50 mg, 0.11 mmol) and stirred at 26° C. for 12 h under $N_2$. The mixture was purified by RP-HPLC [C18 column, water (0.1% HCl)-acetonitrile] to give benzyl 7-acetamido-7-(tert-butylcarbamoyl)-8-(3-(4,4,5,5-tetramethyl-1,3,2-dioxaborolan-2-yl)propyl)-1-azaspiro[4.4]nonane-1-carboxylate. LCMS ($C_{32}H_{51}BN_3O_6^+$) (ES, m/z): 584 [M+H]$^+$.

Step 17: 7-amino-8-(3-boronopropyl)-1-azaspiro[4.4]nonane-7-carboxylic acid

12 N HCl in water (5 mL, 60 mmol) was added to benzyl 7-acetamido-7-(tert-butylcarbamoyl)-8-(3-(4,4,5,5-tetramethyl-1,3,2-dioxaborolan-2-yl)propyl)-1-azaspiro[4.4] nonane-1-carboxylate (50 mg, 0.086 mmol). The reaction was stirred at 100° C. for 12 h. The solvent was moved off in vacuum. Sat. $Na_2CO_3$ was added and the mixture was washed with DCM. The water layer was separated which was purified by RP-HPLC [C18 column, water (20 mM HFBA and 0.1% TFA)-acetonitrile] to give 7-amino-8-(3-boronopropyl)-1-azaspiro[4.4]nonane-7-carboxylic acid. LCMS ($C_{12}H_{22}BN_2O_3^+$) (ES, m/z): 253 [M+H-$H_2O$]$^+$. $^1$H NMR (500 MHz, deuterium oxide) δ 3.31-3.25 (m, 2H), 2.74 (d, J=15.3 Hz, 1H), 2.43-2.28 (m, 2H), 2.17 (d, J=15.3

Hz, 1H), 2.11-1.89 (m, 5H), 1.60-1.55 (m, 1H), 1.45-1.34 (m, 1H), 1.32-1.19 (m, 1H), 1.18-1.04 (m, 1H), 0.78-0.61 (m, 2H).
Example 37I was made from O1-6P4B using the same procedure as Example 37H.
Ex. MS and $^1$HNMR
37I LCMS ($C_{12}H_{22}BN_2O_3^+$) (ES, m/z): 253 [M+H-H$_2$O]$^+$. $^1$H NMR (400 MHz, DEUTERIUM-OXIDE) δ 3.27-3.20 (m, 2H), 2.72 (d, J=15.3 Hz, 1H), 2.36-2.24 (m, 2H), 2.15 (d, J=15.3 Hz, 1H), 2.05-1.84 (m, 5H), 1.57-1.45 (m, 1H), 1.41-1.27 (m, 1H), 1.26-1.15 (m, 1H), 1.13-1.00 (m, 1H), 0.73-0.54 (m, 2H).
Scheme P1
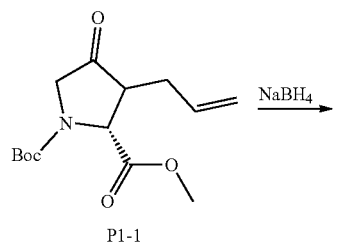
P1-1
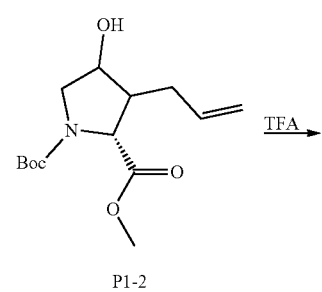
P1-2
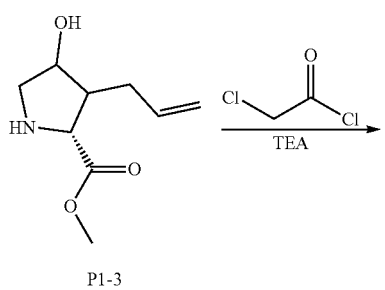
P1-3
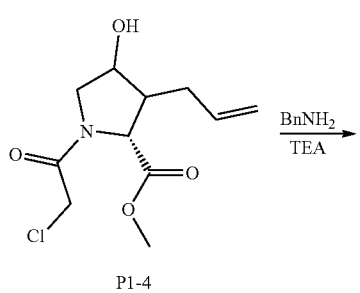
P1-4
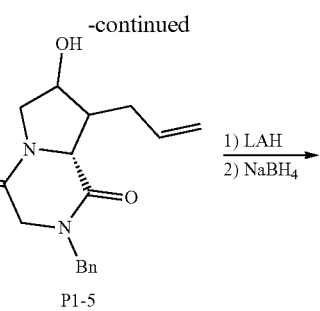
P1-5
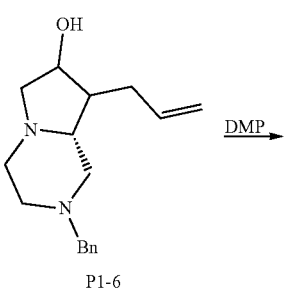
P1-6
P1-7
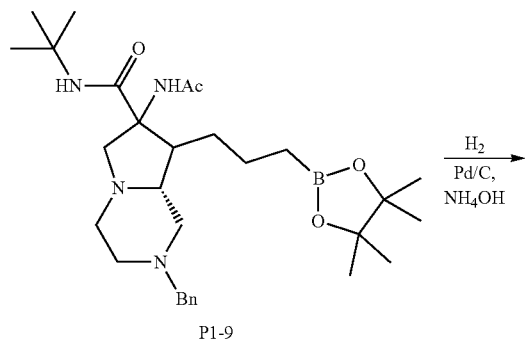
P1-8
P1-9

-continued

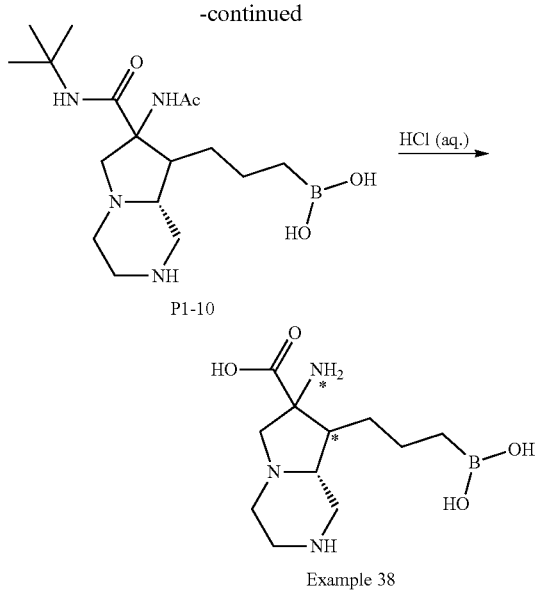

P1-10

Example 38

Example 38A: (8aR)-7-amino-8-(3-boronopropyl) octahydropyrrolo[1,2-a]pyrazine-7-carboxylic acid Step 1: 1-(tert-butyl) 2-methyl (2R)-3-allyl-4-hydroxypyrrolidine-1,2-dicarboxylate NaBH$_4$ (3.2 g, 85 mmol) was added to a solution of (2R)-1-tert-butyl 2-methyl 3-allyl-4-oxopyrrolidine-1,2-dicarboxylate (20 g, 70.6 mmol) in MeOH (200 mL) at 0° C. After stirring at 0° C. for 3 h, the reaction mixture was quenched with H$_2$O and extracted with EtOAc. The combined organic phases were washed with brine, dried over anhydrous Na$_2$SO$_4$, filtered and concentrated under reduced pressure to give crude product, which was used directly in the next step without further purification. LCMS (C$_9$H$_{12}$NO$_3^+$) (ES, m/z): 186 [M+H-Boc]$^+$.

Step 2: methyl (2R)-3-allyl-4-hydroxypyrrolidine-2-carboxylate

TFA (16 mL, 210 mmol) was added to a solution of (2R)-1-tert-butyl 2-methyl 3-allyl-4-hydroxypyrrolidine-1,2-dicarboxylate (20 g, 70 mmol) in DCM (100 mL) at 20° C. After stirring at 20° C. for 16 h, the solvent was removed under reduced pressure to give crude product which was used directly in the next step without further purification. LCMS (C$_9$H$_{16}$NO$_3^+$) (ES, m/z): 186 [M+H]$^+$.

Step 3: methyl (2R)-3-allyl-1-(2-chloroacetyl)-4-hydroxypyrrolidine-2-carboxylate TEA (39 mL, 280 mmol) and 2-chloroacetyl chloride (6.7 mL, 84 mmol) were added to a solution of (2R)-methyl 3-allyl-4-hydroxypyrrolidine-2-carboxylate (13 g, 70 mmol) in DCM (100 mL) at 0° C. After stirring at 0° C. for 2 h, the reaction was diluted with water. The mixture was extracted by DCM twice, and the organic layers were collected, washed with brine, dried over anhydrous Na$_2$SO$_4$. After filtration, the filtrate was concentrated to give crude product, which was used directly in the next step without further purification. LCMS (C$_{11}$H$_{17}$ClNO$_4^+$) (ES, m/z): 262 [M+H]$^+$.

Step 4: (8aR)-8-allyl-2-benzyl-7-hydroxyhexahydropyrrolo[1,2-a]pyrazine-1,4-dione Phenylmethanamine (15 mL, 138 mmol) was added to a solution of (2R)-methyl 3-allyl-1-(2-chloroacetyl)-4-hydroxypyrrolidine-2-carboxylate (18 g, 68.8 mmol) and TEA (19 mL, 138 mmol) in 2-ethoxyethanol (200 mL) at 10° C. The mixture was stirred at 130° C. for 16 h. The reaction mixture was cooled to 10° C. and quenched with H$_2$O and extracted with EtOAc. The combined organic phases were washed with brine, dried over anhydrous Na$_2$SO$_4$, filtered and concentrated under reduced pressure. The residue was purified by RP-HPLC [C18 column, water (0.1% TFA)-acetonitrile] to give (8aR)-8-allyl-2-benzyl-7-hydroxyhexahydropyrrolo[1,2-a]pyrazine-1,4-dione. LCMS (C$_{17}$H$_2$N$_2$O$_3^+$) (ES, m/z): 301 [M+H]$^+$.

Step 5: (8aR)-8-allyl-2-benzyloctahydropyrrolo[1,2-a]pyrazin-7-ol

LiAlH$_4$ in THF (40 mL, 40 mmol, 1M in THF) was added to a solution of (8aR)-8-allyl-2-benzyl-7-hydroxyhexahydropyrrolo[1,2-a]pyrazine-1,4-dione (4 g, 13 mmol) in THF (50 mL) at 0° C. The resulting mixture was stirred at 25° C. for 1 h and then NaBH$_4$ (0.5 g, 13 mmol) and MeOH (10 mL) were added to the mixture. The resulting mixture was stirred at 25° C. for another 1 h. The reaction mixture was quenched with H$_2$O, 15% NaOH in water and diluted with EtOAc. The reaction mixture was filtered. The solvent was removed under reduced pressure to give crude product, which was used in the next step without further purification. LCMS (C$_{17}$H$_{25}$N$_2$O$^+$) (ES, m/z): 273 [M+H]$^+$.

Step 6: (8aR)-8-allyl-2-benzylhexahydropyrrolo[1,2-a]pyrazin-7(6H)-one

DMP (14 g, 33 mmol) was added to a solution of (8aR)-8-allyl-2-benzyloctahydropyrrolo[1,2-a]pyrazin-7-ol (3 g, 11 mmol) in DCM (40 mL) at 25° C. The resulting mixture was stirred at 25° C. for 4 h. The reaction mixture was quenched with saturated NaHCO$_3$ and extracted with DCM. The combined organic phases were washed with brine, dried over anhydrous Na$_2$SO$_4$, filtered and concentrated under reduced pressure. The residue was purified by RP-HPLC [C18 column, water (0.1% TFA)-acetonitrile] to give (8aR)-8-allyl-2-benzylhexahydropyrrolo[1,2-a]pyrazin-7(6H)-one. LCMS (C$_{17}$H$_{23}$N$_2$O$^+$) (ES, m/z): 271 [M+H]$^+$.

Step 7: (8aR)-7-acetamido-8-allyl-2-benzyl-N-(tert-butyl)octahydropyrrolo[1,2-a]pyrazine-7-carboxamide Ammonium acetate (456 mg, 5.9 mmol) and tert-butyl isocyanide (0.33 mL, 3 mmol) were added a solution of (8aR)-8-allyl-2-benzylhexahydropyrrolo[1,2-a]pyrazin-7 (6H)-one (200 mg, 0.74 mmol) in 2,2,2-trifluoroethyl alcohol (2 mL) at 25° C. The reaction mixture was stirred at 50° C. for 12 h. The mixture was filtered and concentrated in vacuum. The residue was purified by RP-HPLC [C18 column, water (0.1% TFA)-acetonitrile] to give (8aR)-7-acetamido-8-allyl-2-benzyl-N-(tert-butyl)octahydropyrrolo[1,2-a]pyrazine-7-carboxamide. LCMS ($C_{24}H_{37}N_4O_2^+$) (ES, m/z): 413 $[M+H]^+$.

Step 8: (8aR)-7-acetamido-2-benzyl-N-(tert-butyl)-8-(3-(4,4,5,5-tetramethyl-1,3,2-dioxaborolan-2-yl)propyl)octahydropyrrolo[1,2-a]pyrazine-7-carboxamide A solution of 1,2-bis(diphenylphosphino)ethane (11.6 mg, 0.029 mmol), $[Ir(cod)Cl]_2$ (11 mg, 0.017 mmol) and 4,4,5,5-tetramethyl-1,3,2-dioxaborolane (0.18 mL, 1.2 mmol) in anhydrous DCM (2 mL) was bubbled with a stream of $N_2$ for 3 min. The mixture was stirred at 25° C. for 20 min and then (8aR)-7-acetamido-8-allyl-2-benzyl-N-(tert-butyl)octahydropyrrolo[1,2-a]pyrazine-7-carboxamide (100 mg, 0.24 mmol) in DCM (1 mL) was added into the mixture. The resulting mixture was stirred at 25° C. for 15 h under $N_2$. The solution was concentrated in vacuum. The residual was purified by RP-HPLC [C18 column, water (0.1% TFA)-acetonitrile] to give (8aR)-7-acetamido-2-benzyl-N-(tert-butyl)-8-(3-(4,4,5,5-tetramethyl-1,3,2-dioxaborolan-2-yl)propyl)octahydropyrrolo[1,2-a]pyrazine-7-carboxamide. LCMS ($C_{30}H_{50}BN_4O_4^+$) (ES, m/z): 541 $[M+H]^+$.

Step 9: (8aR)-7-acetamido-N-(tert-butyl)-8-(3-(4,4,5,5-tetramethyl-1,3,2-dioxaborolan-2-yl)propyl)octahydropyrrolo[1,2-a]pyrazine-7-carboxamide 10% Pd—C (12 mg, 0.011 mmol) and 30% $NH_3.H_2O$ (0.1 mL) were added to a solution of (8aR)-7-acetamido-2-benzyl-N-(tert-butyl)-8-(3-(4,4,5,5-tetramethyl-1,3,2-dioxaborolan-2-yl)propyl)octahydropyrrolo[1,2-a]pyrazine-7-carboxamide (30 mg, 0.055 mmol) in MeOH (3 mL) under $N_2$ atmosphere. The mixture was degassed and backfilled with $H_2$ (three times). The resulting mixture was stirred under $H_2$ (Pressure: 15 psi) at 30° C. for 12 h. The catalyst was filtered, and the filtrate was concentrated under reduced pressure to give the crude product, which was used in next step directly without further purification. LCMS ($C_{17}H_{34}BN_4O_4^+$) (ES, m/z): 369 $[M+H]^+$.

Step 10: (8aR)-7-amino-8-(3-boronopropyl)octahydropyrrolo[1,2-a]pyrazine-7-carboxylic acid 12 N HCl in water (2 mL) and water (1 mL) and AcOH (1 mL) was added to (8aR)-7-acetamido-N-(tert-butyl)-8-(3-(4,4,5,5-tetramethyl-1,3,2-dioxaborolan-2-yl)propyl)octahydropyrrolo[1,2-a]pyrazine-7-carboxamide (20 mg, 0.044 mmol) under $N_2$ atmosphere. The mixture was degassed and backfilled with $N_2$ (three times). The resulting mixture was stirred at 130° C. for 0.5 h under microwave. The solution was concentrated in vacuum. The residue was purified by RP-HPLC [C18 column, water (20 mM HFBA and 0.1% TFA)-acetonitrile] to give (8aR)-7-amino-8-(3-boronopropyl)octahydropyrrolo[1,2-a]pyrazine-7-carboxylic acid as a HFBA salt. LCMS ($C_{11}H_{21}BN_3O_3^+$) (ES, m/z): 254 $[M+H-H_2O]^+$. $^1H$ NMR (400 MHz, deuterium oxide) δ 3.96-3.82 (m, 1H), 3.74-3.61 (m, 1H), 3.57-3.40 (m, 2H), 3.24-3.01 (m, 2H), 2.94-2.86 (m, 1H), 2.83-2.68 (m, 2H), 2.38-2.18 (m, 1H), 1.92-1.80 (m, 1H), 1.58-1.33 (m, 2H), 1.07-0.86 (m, 1H), 0.75-0.65 (m, 1H), 0.51-0.31 (m, 1H).

Scheme Q1

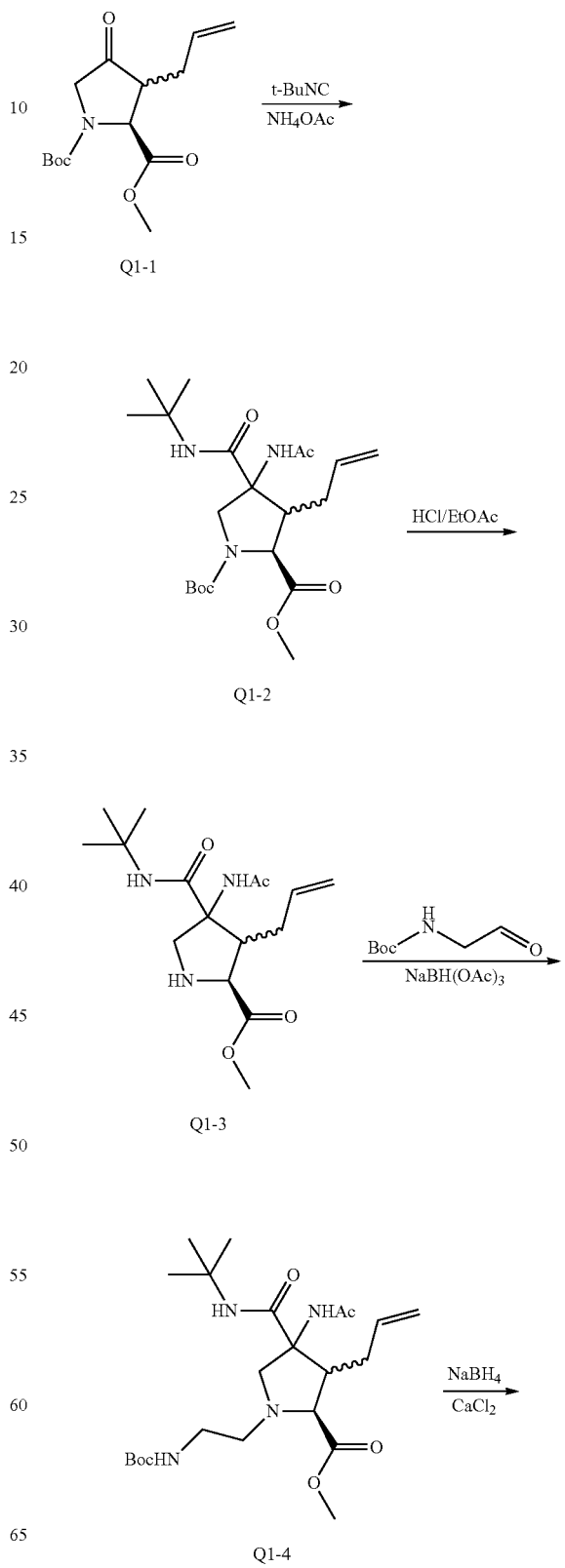

-continued

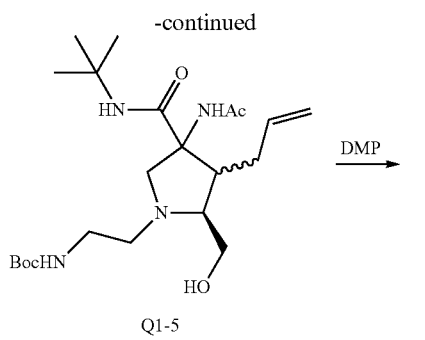

Q1-5

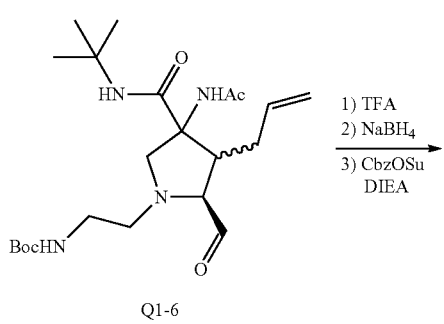

Q1-6

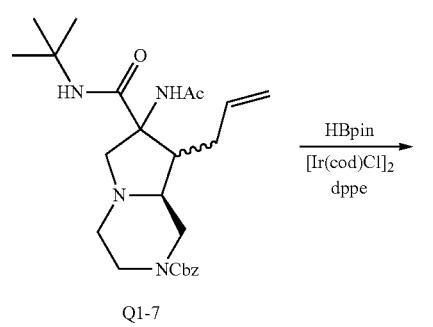

Q1-7

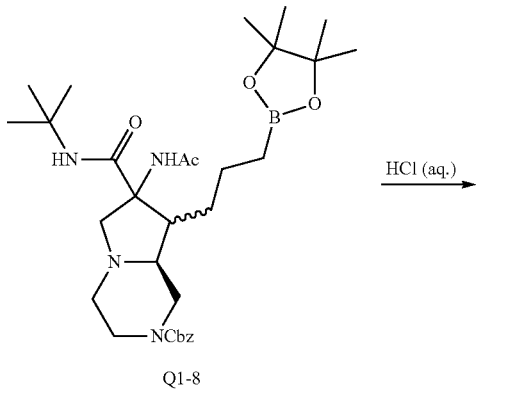

Q1-8

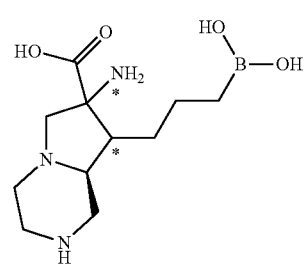

Example 38B

Example 38B: (8aS)-7-amino-8-(3-boronopropyl) octahydropyrrolo[1,2-a]pyrazine-7-carboxylic acid

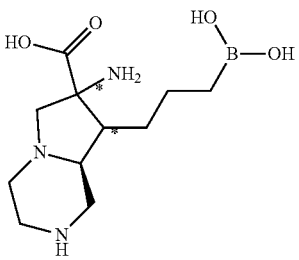 [SMILES: NC1(C(=O)O)CN2CCNC[C@@H]2C1CCCB(O)O]

Step 1: 1-(tert-butyl) 2-methyl (2S)-4-acetamido-3-allyl-4-(tert-butylcarbamoyl)pyrrolidine-1,2-dicarboxylate Tert-butyl isocyanide (7.2 mL, 64 mmol) was added to a mixture of (2S)-1-tert-butyl 2-methyl 3-allyl-4-oxopyrrolidine-1,2-dicarboxylate (3 g, 11 mmol) and ammonium acetate (5.7 g, 74 mmol) in 2,2,2-trifluoroethyl alcohol (30 mL) at 30° C. The mixture was allowed to stir at 30° C. for 12 h. The reaction was quenched with water. The mixture was extracted with EtOAc. The combined organic layers were washed with brine, dried over anhydrous $Na_2SO_4$, then filtered and concentrated in vacuum. The residue was purified by flash silica gel chromatography (EtOAc in DCM) to give the title compound. LCMS ($C_{16}H_{28}N_3O_4^+$) (ES, m/z): 326 [M+H-Boc]$^+$.

Step 2: methyl (2S)-4-acetamido-3-allyl-4-(tert-butylcarbamoyl)pyrrolidine-2-carboxylate A solution of (2S)-1-tert-butyl 2-methyl 4-acetamido-3-allyl-4-(tert-butylcarbamoyl)pyrrolidine-1,2-dicarboxylate (3.4 g, 8.0 mmol) in HCl/dioxane (4 M, 20 mL) was stirred at 30° C. for 1 h. The solution was concentrated in vacuum to give the crude product which was used in the next step without further purification. LCMS ($C_{16}H_{28}N_3O_4^+$) (ES, m/z): 326 [M+H]$^+$.

Step 3: methyl (2S)-4-acetamido-3-allyl-1-(2-((tert-butoxycarbonyl)amino)ethyl)-4-(tert-butylcarbamoyl)pyrrolidine-2-carboxylate A solution of the (2S)-methyl 4-acetamido-3-allyl-4-(tert-butylcarbamoyl)pyrrolidine-2-carboxylate hydrochloride (1.7 g, 4.7 mmol) and tert-butyl (2-oxoethyl)carbamate (1.1 g, 7.0 mmol) in DCE (30 mL) at 10° C. was treated with sodium triacetoxyhydroborate (3.0 g, 14 mmol) and stirred at 10° C. for 4 h. DCM and saturated aqueous $NaHCO_3$ were added to the reaction mixture. The separated organic phase was dried over anhydrous $Na_2SO_4$, filtered and concentrated in vacuum. The residual was purified by flash silica gel chromatography (EtOAc in DCM) to give (2S)-methyl 4-acetamido-3-allyl-1-(2-((tert-butoxycarbonyl)amino)ethyl)-4-(tert-butylcarbamoyl)pyrrolidine-2-carboxylate. LCMS ($C_{23}H_{41}N_4O_6^+$) (ES, m/z): 469 [M+H]$^+$.

Step 4: tert-butyl (2-((2S)-4-acetamido-3-allyl-4-(tert-butylcarbamoyl)-2-(hydroxymethyl)pyrrolidin-1-yl)ethyl)carbamate $NaBH_4$ (646 mg, 17 mmol) was added to a suspension of (2S)-methyl 4-acetamido-3-allyl-1-(2-((tert-butoxycarbonyl)amino)ethyl)-4-(tert-butylcarbamoyl)pyrrolidine-2-carboxylate (800 mg, 1.7 mmol) and calcium chloride (568 mg, 5.1 mmol) in MeOH (10 mL) at 10° C. under $N_2$. The mixture was stirred at 70° C. for 16 h. Acetone was added to the solution to quench the reaction and the mixture was filtered and concentrated under reduced pressure. The residue was purified by flash silica gel chromatography (MeOH in DCM) to give tert-butyl (2-((2S)-4-acetamido-3-allyl-4-(tert-butylcarbamoyl)-2-(hydroxymethyl)pyrrolidin-1-yl)ethyl)carbamate. LCMS ($C_{22}H_{41}N_4O_5^+$) (ES, m/z): 441 $[M+H]^+$.

Step 5: tert-butyl (2-((2S)-4-acetamido-3-allyl-4-(tert-butylcarbamoyl)-2-formylpyrrolidin-1-yl)ethyl) carbamate Dess-Martin Periodinane (1017 mg, 2.4 mmol) was added to a solution of the tert-butyl (2-((2S)-4-acetamido-3-allyl-4-(tert-butylcarbamoyl)-2-(hydroxymethyl)pyrrolidin-1-yl)ethyl)carbamate (880 mg, 0.80 mmol) in DCM (20 mL) at 0° C. The mixture was stirred at 20° C. for 4 h. DCM and saturated aqueous $NaHCO_3$ were added. The separated organic phase was dried over anhydrous $Na_2SO_4$, filtered and concentrated in vacuum. The residue was purified by flash silica gel chromatography (MeOH in DCM) to give crude tert-butyl (2-((2S)-4-acetamido-3-allyl-4-(tert-butylcarbamoyl)-2-formylpyrrolidin-1-yl)ethyl)carbamate. LCMS ($C_{22}H_{39}N_4O_5^+$) (ES, m/z): 439 $[M+H]^+$.

Step 6: benzyl (8aS)-7-acetamido-8-allyl-7-(tert-butylcarbamoyl)hexahydropyrrolo[1,2-a]pyrazine-2(1H)-carboxylate TFA (3 mL) was added to a solution of the tert-butyl (2-((2S)-4-acetamido-3-allyl-4-(tert-butylcarbamoyl)-2-formylpyrrolidin-1-yl)ethyl)carbamate (850 mg, 1.9 mmol) in DCM (12 mL) at 10° C. The mixture was stirred at 10° C. for 2 h. The solution was concentrated in vacuum $NaBH_4$ (147 mg, 3.88 mmol) was added to a solution of the residue in MeOH (10 mL) at 10° C. and the mixture was stirred at 10° C. for 2 h. Acetone was added to the solution to quench the reaction. The mixture was concentrated in vacuum. Benzyl 2,5-dioxopyrrolidine-1-carboxylate (904 mg, 3.98 mmol) was added to a solution of the residue in THF (10 mL) and then treated with DIEA (1.0 mL, 5.8 mmol) at 10° C. and stirred at 10° C. for 2 h. The mixture was filtered, and the filtrate was concentrated in vacuum. The residue was purified by RP-HPLC [C18 column, water (0.1% TFA)-acetonitrile] to give the (8aS)-benzyl 7-acetamido-8-allyl-7-(tert-butylcarbamoyl)hexahydropyrrolo[1,2-a]pyrazine-2(1H)-carboxylate LCMS ($C_{25}H_{37}N_4O_4^+$) (ES, m/z): 457 [M+H Step 7: benzyl (8aS)-7-acetamido-7-(tert-butylcarbamoyl)-8-(3-(4,4,5,5-tetramethyl-1,3,2-dioxaborolan-2-yl)propyl)hexahydropyrrolo[1,2-a]pyrazine-2(1H)-carboxylate A solution of 1,2-bis(diphenylphosphino)ethane (3.84 mg, 9.6 µmol), [Ir(cod)Cl]$_2$ (4.1 mg, 6.0 µmol) and 4,4,5,5-tetramethyl-1,3,2-dioxaborolane (0.087 mL, 0.60 mmol) in anhydrous DCM (2 mL) was bubbled with a stream of $N_2$ for 3 min. The mixture was stirred at 10° C. for 20 min and then (8aS)-benzyl 7-acetamido-8-allyl-7-(tert-butylcarbamoyl) hexahydropyrrolo[1,2-a]pyrazine-2(1H)-carboxylate (55 mg, 0.12 mmol) was added into the mixture. The resulting mixture was stirred at 10° C. for 15 h under $N_2$. The solution was concentrated in vacuum. The residue was purified by RP-HPLC [C18 column, water (0.1% TFA)-acetonitrile] to give the (8aS)-benzyl 7-acetamido-7-(tert-butylcarbamoyl)-8-(3-(4,4,5,5-tetramethyl-1,3,2-dioxaborolan-2-yl)propyl) hexahydropyrrolo[1,2-a]pyrazine-2(1H)-carboxylate. LCMS ($C_{31}H_{50}BN_4O_6^+$) (ES, m/z): 585 $[M+H]^+$.

Step 8: (8aS)-7-amino-8-(3-boronopropyl)octahydropyrrolo[1,2-a]pyrazine-7-carboxylic acid A solution of (8aS)-benzyl 7-acetamido-7-(tert-butylcarbamoyl)-8-(3-(4,4,5,5-tetramethyl-1,3,2-dioxaborolan-2-yl) propyl)hexahydropyrrolo[1,2-a]pyrazine-2(1H)-carboxylate (27 mg, 0.046 mmol) in 12N HCl in water (5 mL) was stirred at 100° C. for 12 h. The solution was concentrated in vacuum. The residual was dissolved in water, $Na_2CO_3$ solid was added to basified the solution pH=7. EtOAc were added to extract the byproduct. The water phase was purified by RP-HPLC [C18 column, water (20 mM HFBA and 0.1% TFA)-acetonitrile] to give (8aS)-7-amino-8-(3-boronopropyl)octahydropyrrolo[1,2-a]pyrazine-7-carboxylic acid as a HFBA salt. LCMS ($C_{11}H_{21}BN_3O_3^+$) (ES, m/z): 254 [M+H-$H_2O]^+$. $^1H$ NMR (500 MHz, deuterium oxide) δ 4.13-3.60 (m, 2H), 3.43-3.37 (m, 3H), 3.02-2.97 (m, 1H), 2.86-2.72 (m, 2H), 2.24-2.22 (m, 1H), 1.83-1.78 (m, 1H), 1.48-1.28 (m, 3H), 0.94-0.92 (m, 0.5H), 0.70-0.63 (m, 2H), 0.39-0.37 (m, 0.5H).

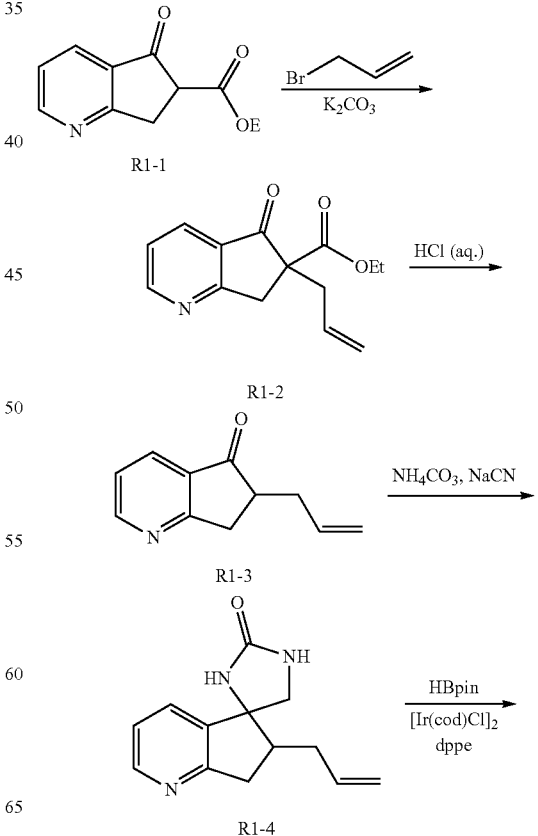

Scheme R1

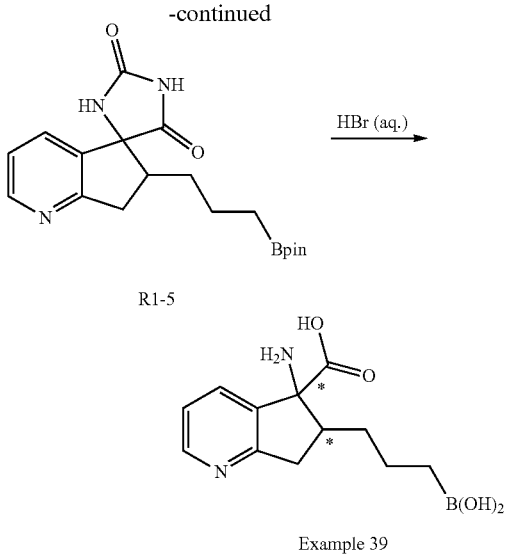

R1-5

Example 39: 5-amino-6-(3-boronopropyl)-6,7-dihydro-5H-cyclopenta[b]pyridine-5-carboxylic acid

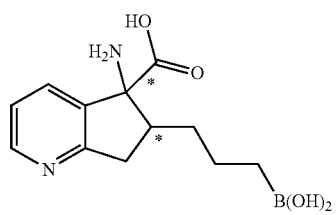 [SMILES: NC1(C(=O)O)c2cccnc2CC1CCCB(O)O]

Step 1: ethyl 6-allyl-5-oxo-6,7-dihydro-5H-cyclopenta[b]pyridine-6-carboxylate $K_2CO_3$ (0.8 g, 5.9 mmol) and 3-bromoprop-1-ene (0.5 mL, 5.9 mmol) were added to a mixture of ethyl 5-oxo-6,7-dihydro-5H-cyclopenta[b]pyridine-6-carboxylate (1 g, 4.9 mmol) and acetone (20 mL). The mixture was degassed and backfilled with $N_2$ (three times). Then the mixture was stirred at 55° C. for 3 h. Water and brine were added to the mixture and the aqueous layer was extracted with EtOAc. The combined organic layers were dried over anhydrous $Na_2SO_4$, filtered and concentrated under reduced pressure. The residue was purified by silica gel column chromatography (EtOAc in hexanes) to afford ethyl 6-allyl-5-oxo-6,7-dihydro-5H-cyclopenta[b]pyridine-6-carboxylate. LCMS ($C_{14}H_{16}NO_3^+$) (ES, m/z): 246 [M+H]$^+$.

Step 2: 6-allyl-6,7-dihydro-5H-cyclopenta[b]pyridin-5-one

A mixture of ethyl 6-allyl-5-oxo-6,7-dihydro-5H-cyclopenta[b]pyridine-6-carboxylate (300 mg, 1.2 mmol) and 6 N HCl in water (1.6 mL, 9.6 mmol) in MeOH (20 mL) was stirred at 110° C. for 15 h. The mixture was dissolved in water and basified with saturated aqueous $NaHCO_3$ until pH~7, then extracted with DCM. The combined organic phases were washed with brine, dried over anhydrous $Na_2SO_4$, filtered and concentrated under reduced pressure to give crude product, which was used in the next step without further purification. LCMS ($C_{11}H_{12}NO^+$) (ES, m/z): 174 [M+H]$^+$.

Step 3: 6-allyl-6,7-dihydrospiro[cyclopenta[b]pyridine-5,4'-imidazolidine]-2',5'-dione Ammonium carbonate (899 mg, 9.4 mmol) and cyanosodium (102 mg, 2.1 mmol) were added to a solution of 6-allyl-6,7-dihydro-5H-cyclopenta[b]pyridin-5-one (180 mg, 1.0 mmol) in EtOH (5 mL) and water (5 mL). The mixture was stirred at 100° C. for 18 h. Then water was added to the mixture, and the mixture was neutralized with AcOH until pH~7, then extracted with DCM. The combined organic phases were dried over anhydrous $Na_2SO_4$, filtered and concentrated under reduced pressure. The residue was purified by RP-HPLC [C18 column, water (0.1% TFA)-acetonitrile] to give 6-allyl-6,7-dihydrospiro[cyclopenta[b]pyridine-5,4'-imidazolidine]-2',5'-dione. LCMS ($C_{13}H_{14}N_3O_2^+$) (ES, m/z): 244 [M+H]$^+$.

Step 4: 6-(3-(4,4,5,5-tetramethyl-1,3,2-dioxaborolan-2-yl)propyl)-6,7-dihydrospiro[cyclopenta[b]pyridine-5,4'-imidazolidine]-2',5'-dione A mixture of 6-allyl-6,7-dihydrospiro[cyclopenta[b]pyridine-5,4'-imidazolidine]-2',5'-dione (100 mg, 0.41 mmol) and 4,4,5,5-tetramethyl-1,3,2-dioxaborolane (0.3 mL, 2.1 mmol) in DCM (10 mL) was stirred at 20° C., the mixture was degassed and backfilled with $N_2$ (three times), then dppe (33 mg, 0.082 mmol) and [Ir(cod)Cl]$_2$ (33 mg, 0.049 mmol) were added to the mixture under $N_2$. The mixture was degassed and backfilled with $N_2$ (three times). The resulting mixture was stirred at 20° C. for 15 h. The solvent was removed under reduced pressure. The residue was purified by RP-HPLC [C18 column, water (0.1% TFA)-acetonitrile] to give 6-(3-(4,4,5,5-tetramethyl-1,3,2-dioxaborolan-2-yl)propyl)-6,7-dihydrospiro[cyclopenta[b]pyridine-5,4'-imidazolidine]-2',5'-dione. LCMS ($C_{19}H_{27}BN_3O_4^+$) (ES, m/z): 372 [M+H]$^+$.

Step 5: 5-amino-6-(3-boronopropyl)-6,7-dihydro-5H-cyclopenta[b]pyridine-5-carboxylic acid A mixture of 6-(3-(4,4,5,5-tetramethyl-1,3,2-dioxaborolan-2-yl)propyl)-6,7-dihydrospiro[cyclopenta[b]pyridine-5,4'-imidazolidine]-2',5'-dione (50 mg, 0.14 mmol) and 48% HBr in water (1 mL) was stirred at 110° C. for 24 h. The resulting residue was purified by RP-HPLC [C18 column, water (20 mM HFBA and 0.1% TFA)-acetonitrile] to give 5-amino-6-(3-boronopropyl)-6,7-dihydro-5H-cyclopenta[b]pyridine-5-carboxylic acid as a HFBA salt. LCMS ($C_{12}H_{16}BN_2O_3^+$) (ES, m/z): 247 [M+H-H$_2$O]$^+$. $^1$H NMR (400 MHz, deuterium oxide) δ 8.68-8.63 (m, 1H), 8.51-8.45 (m, 1H), 7.93-7.85 (m, 1H), 3.70-3.57 (m, 1H), 3.24-3.05 (m, 1H), 2.87-2.72 (m, 1H), 1.86-1.73 (m, 1H), 1.64-1.32 (m, 3H), 0.87-0.70 (m, 2H).

Scheme S1

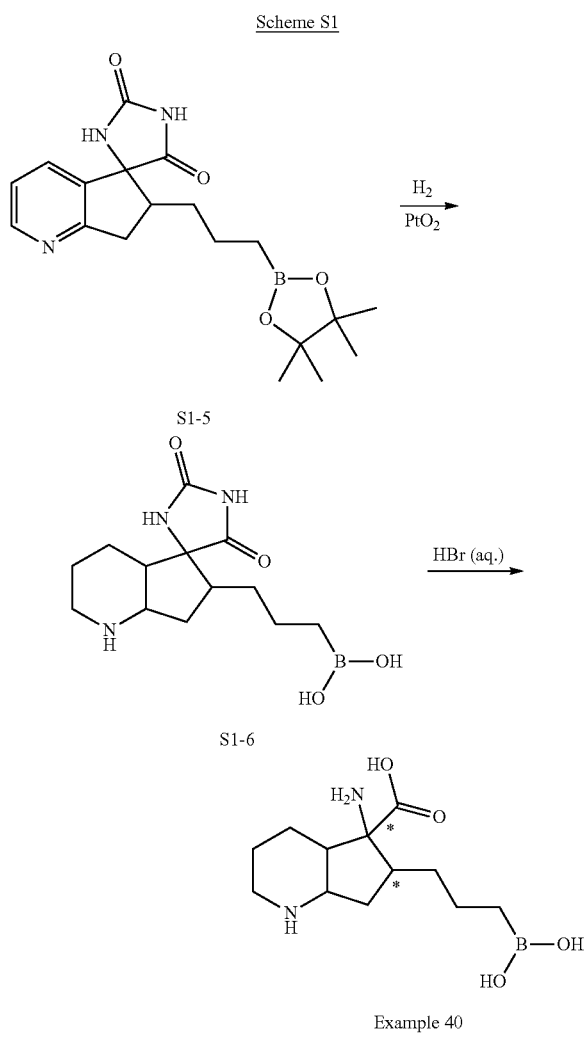

was degassed and backfilled with H₂ (three times). The resulting mixture was stirred under H₂ (50 psi) at 50° C. for 15 h. The mixture was filtered and the filtrate was concentrated under reduced pressure to give the crude product, which was used in the next step without further purification. LCMS ($C_{13}H_{23}BN_3O_4^+$) (ES, m/z): 296 [M+H]⁺.

Step 2: 5-amino-6-(3-boronopropyl)octahydro-1H-cyclopenta[b]pyridine-5-carboxylic acid A mixture of 48% HBr in water (1.5 mL) and (3-(2',5'-dioxooctahydrospiro[cyclopenta[b]pyridine-5,4'-imidazolidin]-6-yl)propyl)boronic acid (50 mg, 0.17 mmol) was stirred at 120° C. for 34 h. Then the solvent was removed under reduced pressure, and the residue was purified by RP-HPLC [C18 column, water (20 mM HFBA and 0.1% TFA)-acetonitrile] to give 5-amino-6-(3-boronopropyl)octahydro-1H-cyclopenta[b]pyridine-5-carboxylic acid as a HFBA salt. LCMS ($C_{12}H_{22}BN_2O_3^+$) (ES, m/z): 253 [M+H-H₂O]⁺. ¹H NMR (400 MHz, deuterium oxide) δ 3.77-3.72 (m, 1H), 3.31-3.26 (m, 1H), 2.92-2.82 (m, 1H), 2.76-2.67 (m, 1H), 2.58-2.53 (m, 1H), 2.21-2.10 (m, 1H), 1.97-1.69 (m, 3H), 1.67-1.56 (m, 2H), 1.54-1.35 (m, 2H), 1.33-1.18 (m, 2H), 0.79-0.63 (m, 2H).

Example 40: 5-amino-6-(3-boronopropyl)octahydro-1H-cyclopenta[b]pyridine-5-carboxylic acid

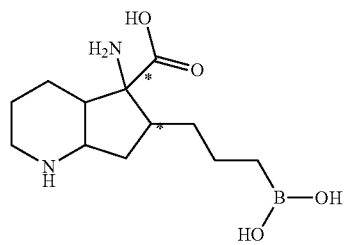 [SMILES: NC1(C(=O)O)C(CCCB(O)O)CC2NCCCC21]

Step 1: (3-(2',5'-dioxooctahydrospiro[cyclopenta[b]pyridine-5,4'-imidazolidin]-6-yl)propyl)boronic acid Platinum(IV) oxide (100 mg, 0.440 mmol) was added to a solution of 6-(3-(4,4,5,5-tetramethyl-1,3,2-dioxaborolan-2-yl)propyl)-6,7-dihydrospiro[cyclopenta[b]pyridine-5,4'-imidazolidine]-2',5'-dione (60 mg, 0.16 mmol) in 12 N HCl in water (2 mL) and MeOH (6 mL) under argon. The mixture Scheme T1

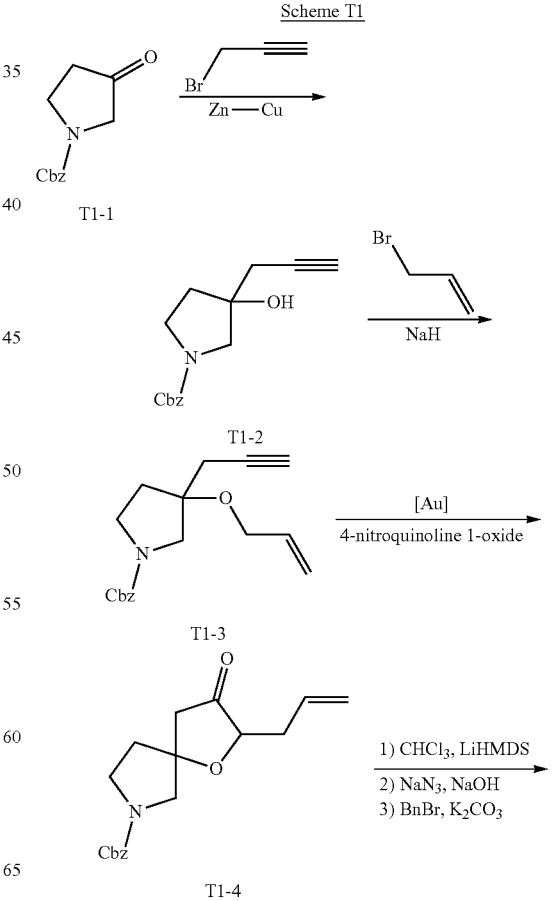

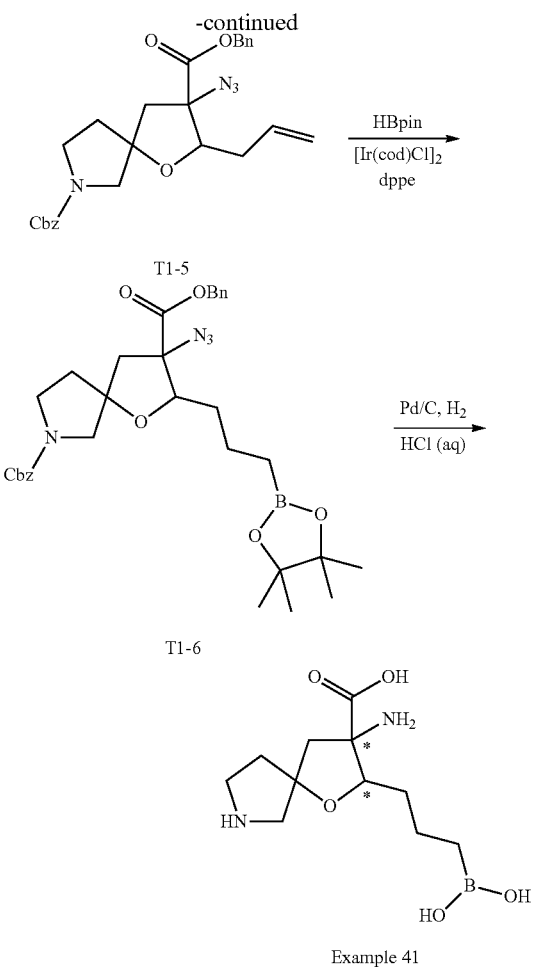

Example 41: 3-amino-2-(3-boronopropyl)-1-oxa-7-azaspiro[4.4]nonane-3-carboxylic acid

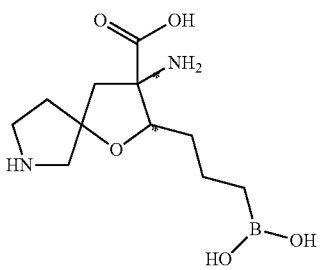 [SMILES: NC1(C(=O)O)CC2(CCNC2)OC1CCCB(O)O]

Step 1: benzyl 3-hydroxy-3-(prop-2-yn-1-yl)pyrrolidine-1-carboxylate

Zn—Cu couple (2.6 g, 20 mmol) was added to a mixture of benzyl 3-oxopyrrolidine-1-carboxylate (4 g, 18.1 mmol) and 3-bromoprop-1-yne (4.1 g, 27 mmol, 80% in toluene) in THF (50 mL) at 0° C. in portions. The mixture was sonicated (20° C.~40° C.) for 2 h. After the reaction was finished, the reaction mixture was quenched with saturated aqueous NH$_4$Cl and extracted with EtOAc. The combined organic phases were washed with brine, dried over anhydrous Na$_2$SO$_4$, filtered and concentrated under reduced pressure. The residue was purified by silica gel column chromatography (EtOAc in hexanes) to give benzyl 3-hydroxy-3-(prop-2-yn-1-yl)pyrrolidine-1-carboxylate. LCMS (C$_{15}$H$_{18}$NO$_3{}^+$) (ES, m/z): 260 [M+H]$^+$.

Step 2: benzyl 3-(allyloxy)-3-(prop-2-yn-1-yl)pyrrolidine-1-carboxylate

Benzyl 3-hydroxy-3-(prop-2-yn-1-yl)pyrrolidine-1-carboxylate (2.6 g, 10 mmol) was added to a suspension of NaH (0.6 g, 15 mmol, 60% in oil) in DMF (25 mL) at 0° C. under N$_2$. After stirring for 10 min at 0° C., 3-bromoprop-1-ene (2.4 g, 20 mmol) was added to the mixture, and the mixture was stirred at room temperature (20° C.) for another 4 h under N$_2$. The reaction mixture was quenched with saturated aqueous NH$_4$Cl and extracted with EtOAc. The combined organic phases were washed with water, brine, dried over anhydrous Na$_2$SO$_4$, filtered and concentrated under reduced pressure. The residue was purified by silica gel column chromatography (EtOAc in hexanes) to give benzyl 3-(allyloxy)-3-(prop-2-yn-1-yl)pyrrolidine-1-carboxylate. LCMS (C$_{18}$H$_{22}$NO$_3{}^+$) (ES, m/z): 300 [M+H]$^+$.

Step 3: benzyl 2-allyl-3-oxo-1-oxa-7-azaspiro[4.4]nonane-7-carboxylate (Acetonitrile)[(2-biphenyl)di-tert-butylphosphine]gold(I) hexafluoroantimonate (0.52 g, 0.67 mmol) was added to a mixture of benzyl 3-(allyloxy)-3-(prop-2-yn-1-yl)pyrrolidine-1-carboxylate (1 g, 3.3 mmol) and 4-nitroquinoline 1-oxide (1.8 g, 9.5 mmol) in DCE (60 mL) at room temperature (20° C.) under N$_2$. The resulting mixture was heated to 65° C. and stirred for 24 h under N$_2$. After being cooled to room temperature, the reaction mixture was quenched with water and extracted with DCM. The combined organic phases were washed with brine, dried over anhydrous Na$_2$SO$_4$, filtered and concentrated under reduced pressure. The residue was purified by silica gel column chromatography (EtOAc in hexanes) to give product, which was re-purified by RP-HPLC [C18 column, water (0.1% TFA)-acetonitrile] to give benzyl 2-allyl-3-oxo-1-oxa-7-azaspiro[4.4]nonane-7-carboxylate. LCMS (C$_{18}$H$_{22}$NO$_4{}^+$) (ES, m/z): 316 [M+H]$^+$.

Step 4: benzyl 2-allyl-3-hydroxy-3-(trichloromethyl)-1-oxa-7-azaspiro[4.4]nonane-7-carboxylate LiHMDS (0.48 mL, 0.48 mmol, 1M in THF) was added dropwise to a mixture of benzyl 2-allyl-3-oxo-1-oxa-7-azaspiro[4.4]nonane-7-carboxylate (50 mg, 0.16 mmol) and redistilled CHCl$_3$ (0.064 mL, 0.79 mmol) in THF (2.5 mL) at −78° C. under N$_2$. After stirring at −78° C. for 1 h, the mixture was stirred at room temperature (25° C.) for another 18 h. The reaction mixture was quenched with saturated NH$_4$Cl and extracted with EtOAc. The combined organic phases were washed with brine, dried over anhydrous Na$_2$SO$_4$, filtered and concentrated under reduced pressure to give the crude intermediate benzyl 2-allyl-3-hydroxy-3-(trichloromethyl)-1-oxa-7-azaspiro[4.4]nonane-7-carboxylate (LCMS (C$_{19}$H$_{23}$Cl$_3$NO$_4{}^+$) (ES, m/z): 434 [M+H]$^+$). NaN$_3$ (58 mg, 0.89 mmol) and NaOH (18 mg, 0.45 mmol) in water (2 mL) were added to a solution of benzyl 2-allyl-3-hydroxy-3-(trichloromethyl)-1-oxa-7-azaspiro[4.4]nonane-7-carboxylate (65 mg, 0.15 mmol) in dioxane (2 mL) at 0° C. After the addition was finished, the mixture was stirred at room temperature (25° C.) for 16 h. The mixture was acidified to pH ~6 with HOAc. The mixture was poured into water and extracted with EtOAc. The separated organic layer was dried over anhydrous $Na_2SO_4$, filtered and concentrated in vacuum to give the crude intermediate. $K_2CO_3$ (83 mg, 0.6 mmol) and (bromomethyl)benzene (0.026 mL, 0.22 mmol) were added to a mixture of the above crude intermediate in DMF (2 mL) at 25° C. The mixture was stirred for 3 h. The mixture was poured into water and extracted with EtOAc. The separated organic layer was dried over anhydrous $Na_2SO_4$, filtered and concentrated in vacuum. The residue was purified by RP-HPLC [C18 column, water (0.1% TFA)-acetonitrile] to give dibenzyl 2-allyl-3-azido-1-oxa-7-azaspiro[4.4]nonane-3,7-dicarboxylate. LCMS ($C_{26}H_{29}N_4O_5^+$) (ES, m/z): 477 [M+H]$^+$.

Step 5: dibenzyl 3-azido-2-(3-(4,4,5,5-tetramethyl-1,3,2-dioxaborolan-2-yl)propyl)-1-oxa-7-azaspiro[4.4]nonane-3,7-dicarboxylate 4,4,5,5-tetramethyl-1,3,2-dioxaborolane (27 mg, 0.21 mmol) was added to a mixture of $[Ir(cod)Cl]_2$ (2 mg, 3 μmol) and dppe (2 mg, 5 μmol) in DCM (1 mL) at room temperature (25° C.) under $N_2$. After stirred for 10 min, a solution of dibenzyl 2-allyl-3-azido-1-oxa-7-azaspiro[4.4]nonane-3,7-dicarboxylate (20 mg, 0.042 mmol) in DCM (0.5 mL) was added to the mixture. The mixture was stirred for 6 h at 25° C. under $N_2$. The reaction mixture was diluted with water and extracted with EtOAc. The combined organic phases were washed with brine, dried over anhydrous $Na_2SO_4$, filtered and concentrated under reduced pressure. The residue was purified by RP-HPLC [C18 column, water (0.1% TFA)-acetonitrile] to give dibenzyl 3-azido-2-(3-(4,4,5,5-tetramethyl-1,3,2-dioxaborolan-2-yl)propyl)-1-oxa-7-azaspiro[4.4]nonane-3,7-dicarboxylate. LCMS ($C_{32}H_{42}BN_4O_7^+$) (ES, m/z): 605 [M+H]$^+$.

Step 6: 3-amino-2-(3-(4,4,5,5-tetramethyl-1,3,2-dioxaborolan-2-yl)propyl)-1-oxa-7-azaspiro[4.4]nonane-3-carboxylic acid 10% Pd/C (40 mg, 0.038 mmol) was added to a solution of dibenzyl 3-azido-2-(3-(4,4,5,5-tetramethyl-1,3,2-dioxaborolan-2-yl)propyl)-1-oxa-7-azaspiro[4.4]nonane-3,7-dicarboxylate (50 mg, 0.083 mmol) in MeOH (15 mL) under Ar atmosphere. The mixture was degassed and backfilled with $H_2$ (three times). The resulting mixture was stirred under $H_2$ (15 psi) at room temperature (25° C.) for 2 h. The catalyst was filtered, and the filtrate was concentrated under reduced pressure to give the crude product, which was dissolved in 3N HCl in water (0.3 mL) and THF (1.5 mL). The resulting mixture was stirred for 15 h at room temperature (25° C.). The reaction mixture was concentrated under reduced pressure. The residue was purified by RP-HPLC [C18 column, water (20 mM HFBA and 0.1% TFA)-acetonitrile] to give 3-amino-2-(3-boronopropyl)-1-oxa-7-azaspiro[4.4]nonane-3-carboxylic acid as a HFBA salt. LCMS ($C_{11}H_{22}BN_2O_5^+$) (ES, m/z): 273.0 [M+H]$^+$. $^1$H NMR (400 MHz, deuterium oxide) δ 4.10-4.03 (m, 1H), 3.66-3.57 (m, 1H), 3.56-3.51 (m, 1H), 3.45-3.38 (m, 1.5H), 3.24-3.21 (m, 0.5H), 3.01-2.97 (m, 1H), 2.48-2.37 (m, 2H), 2.31-2.02 (m, 1H), 1.76-1.39 (m, 4H), 0.85-0.70 (m, 2H).

Example 42: (3aR,4S,5S,6aR)-2-(L-valyl)-5-amino-4-(3-boronopropyl)octahydrocyclopenta[c]pyrrole-5-carboxylic acid

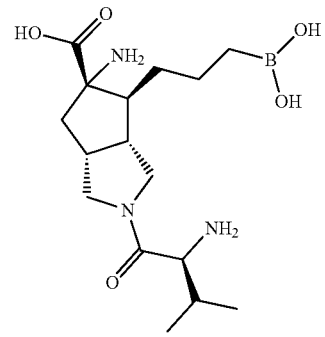 [SMILES: CC(C)[C@H](N)C(=O)N1C[C@@H]2C[C@@](N)(C(=O)O)[C@@H](CCCB(O)O)[C@@H]2C1]

Example 42 was prepared by using the general procedure used for Example 4.

TFA salt. LCMS ($C_{16}H_{29}BN_3O_4^+$) (ES, m/z): 338 [M+H-$H_2O$]. $^1$H NMR (500 MHz, deuterium oxide) δ 4.27-3.98 (m, 1H), 3.95-3.61 (m, 2H), 3.59-3.28 (m, 2H), 3.27-3.04 (m, 1H), 2.95-2.50 (m, 2H), 2.30-2.12 (m, 1H), 2.10-1.89 (m, 1H), 1.85-1.66 (m, 1H), 1.64-1.19 (m, 4H), 1.11-0.83 (m, 6H), 0.80-0.63 (m, 2H).

Scheme U1

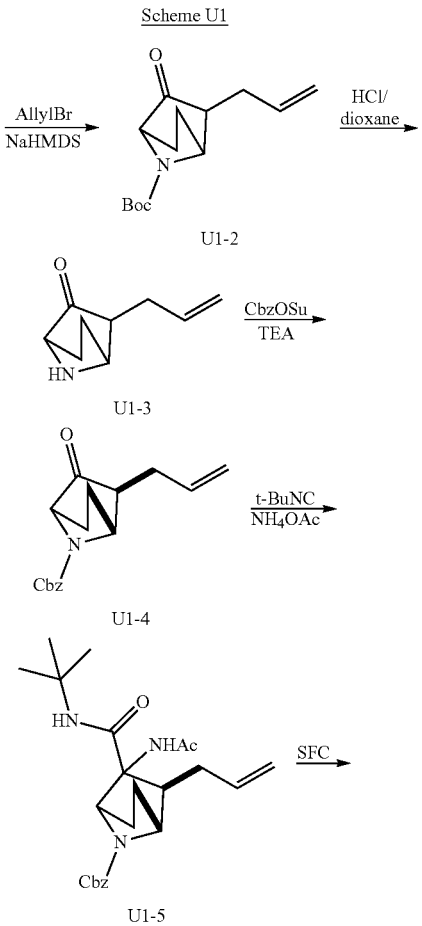

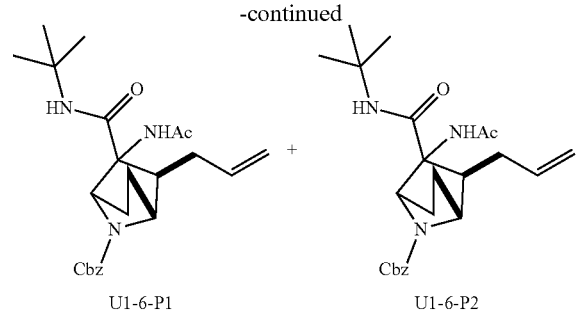

U1-6-P1   U1-6-P2

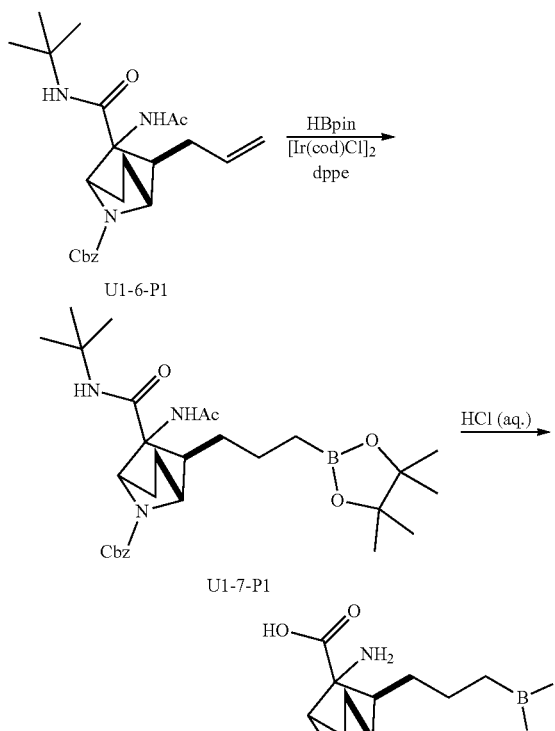

Example 43A: rel-(3S,4R)-2-amino-3-(3-boronopropyl)-7-azabicyclo[2.2.1]heptane-2-carboxylic acid

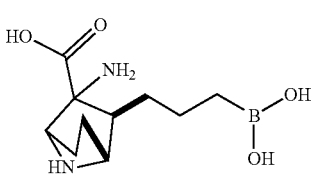 [SMILES: NC1(C(=O)O)C2CC[C@@H](N2)[C@@H]1CCCB(O)O]

Step 1: tert-butyl 2-allyl-3-oxo-7-azabicyclo[2.2.1]heptane-7-carboxylate

NaHMDS (10 mL, 10 mmol, 1M in THF) was added to a mixture of tert-butyl 2-oxo-7-azabicyclo[2.2.1]heptane-7-carboxylate (2 g, 9.5 mmol) in THF (30 mL) at −40° C. under $N_2$ atmosphere. The mixture was stirred at −40° C. for 0.5 hours. Then pyrrolidine (0.34 g, 4.7 mmol) in THF (1 mL) was added dropwise to the mixture at −40° C. One minute later, 3-bromoprop-1-ene (0.86 mL, 9.9 mmol) in THF (1 mL) was dropwise added to the mixture at −40° C. under $N_2$ and stirred at −40° C. for 0.5 h then stirred at 25° C. for 14 h. The mixture was quenched with water. The mixture was extracted with EtOAc, and the combined organic layers were washed with brine, dried over anhydrous $Na_2SO_4$, then filtered and concentrated in vacuum to give crude product, which was used into next step directly without further purification. LCMS ($C_{10}H_{14}NO_3^+$) (ES, m/z): 196 [M+H−$C_4H_8$]$^+$.

Step 2: 3-allyl-7-azabicyclo[2.2.1]heptan-2-one

4N HCl in dioxane (20 mL, 80 mmol) was added to a mixture of tert-butyl 2-allyl-3-oxo-7-azabicyclo[2.2.1]heptane-7-carboxylate (6.3 g, 8.36 mmol) in DCM (4 mL) at 25° C. The mixture was stirred at 25° C. for 2 h The mixture was concentrated in vacuum to give crude product, which was used in the next step without further purification. LCMS ($C_9H_{14}NO^+$) (ES, m/z): 152 [M+H]$^+$.

Step 3: rel-(1R,2S)-benzyl 2-allyl-3-oxo-7-azabicyclo[2.2.1]heptane-7-carboxylate Benzyl (2,5-dioxopyrrolidin-1-yl) carbonate (7 g, 28 mmol) was added to a mixture of 3-allyl-7-azabicyclo[2.2.1]heptan-2-one (6.3 g, 13.89 mmol) and triethylamine (10 mL, 72 mmol) in DCM (80 mL) at 25° C. The mixture was stirred at 25° C. for 3 h. The reaction was quenched with saturated aqueous $NaHCO_3$. The mixture was extracted with DCM. The combined organic layers were washed with brine, dried over anhydrous $Na_2SO_4$, filtered and concentrated. The residue was purified by silica gel column chromatography (EtOAc in hexanes) to give the product. The product was further purified by RP-HPLC [C18 column, water (0.1% TFA)-acetonitrile] to give rel-(1R,2S)-benzyl 2-allyl-3-oxo-7-azabicyclo[2.2.1]heptane-7-carboxylate. LCMS ($C_{17}H_{2}NO_3^+$) (ES, m/z): 286 [M+H]$^+$. $^1$H NMR (400 MHz, METHANOL-$d_4$) δ 7.41-7.27 (m, 5H), 5.88-5.75 (m, 1H), 5.14 (s, 2H), 5.11-5.01 (m, 2H), 4.55-4.50 (m, 1H), 4.32-4.27 (m, 1H), 2.62-2.53 (m, 1H), 2.52-2.42 (m, 1H), 2.09-2.02 (m, 1H), 1.99-1.90 (m, 1H), 1.89-1.71 (m, 2H), 1.57-1.47 (m, 1H).

Step 4: rel-(3S,4R)-benzyl 2-acetamido-3-allyl-2-(tert-butylcarbamoyl)-7-azabicyclo[2.2.1]heptane-7-carboxylate Tert-butyl isocyanide (0.60 mL, 5.3 mmol) was added to a mixture of (1R,2S)-benzyl 2-allyl-3-oxo-7-azabicyclo[2.2.1]heptane-7-carboxylate (500 mg, 1.8 mmol) and ammonium acetate (540 mg, 7.0 mmol) in 2,2,2-trifluoroethyl alcohol (5 mL) under $N_2$. The mixture was allowed to stir at 40° C. for 13 h. The reaction was quenched with water. The mixture was extracted with EtOAc. The combined organic layers were washed with brine, dried over anhydrous $Na_2SO_4$, then filtered and concentrated in vacuum. The residue was purified by silica gel column chromatography (EtOAc in hexanes) to give (3S,4R)-benzyl 2-acetamido-3-allyl-2-(tert-butylcarbamoyl)-7-azabicyclo[2.2.1]heptane-7-carboxylate. LCMS ($C_{24}H_{34}N_3O_4^+$) (ES, m/z): 428 [M+H]$^+$.

Step 5: rel-(benzyl (3S,4R)-2-acetamido-3-allyl-2-(tert-butylcarbamoyl)-7-azabicyclo[2.2.1]heptane-7-carboxylate The rel-(3S,4R)-benzyl 2-acetamido-3-allyl-2-(tert-butylcarbamoyl)-7-azabicyclo[2.2.1]heptane-7-carboxylate (660 mg, 1.5 mmol) was resolved by SFC [Column: DAICEL CHIRALPAK IC (250 mm*30 mm, 5 um), Mobile phase: A: CO$_2$, B: IPA (0.1% NH$_3$.H$_2$O), Gradient: 35% of B in 5.5 min, and hold 35% of B for 1 min, Flow Rate (mL/min) 60, Column temperature: 40° C.] to give rel-(benzyl (3S,4R)-2-acetamido-3-allyl-2-(tert-butylcarbamoyl)-7-azabicyclo[2.2.1]heptane-7-carboxylate (U1-6-P1, t$_r$=4.50 min) as the first eluting peak, and rel-(benzyl (3S,4R)-2-acetamido-3-allyl-2-(tert-butylcarbamoyl)-7-azabicyclo[2.2.1]heptane-7-carboxylate (U1-6-P2, t$_r$=4.96 min) as the second eluting peak LCMS (C$_{24}$H$_{34}$N$_3$O$_4$$^+$) (ES, m/z): 428 [M+H]$^+$. U1-6-P: $^1$H NMR (400 MHz, CHLOROFORM-d) δ 7.39-7.27 (m, 5H), 6.81 (br s, 1H), 5.94 (s, 1H), 5.86-5.73 (m, 1H), 5.24-5.05 (m, 5H), 4.23 (t, J=3.9 Hz, 1H), 2.77-2.66 (m, 1H), 2.27-2.06 (m, 2H), 2.00 (s, 3H), 1.69-1.59 (m, 4H), 1.23 (s, 9H). U1-6-P2: $^1$H NMR (400 MHz, CHLOROFORM-d) δ 7.39-7.29 (m, 5H), 6.81 (br s, 1H), 5.93 (s, 1H), 5.86-5.71 (m, 1H), 5.24-5.07 (m, 5H), 4.23 (t, J=3.9 Hz, 1H), 2.79-2.67 (m, 1H), 2.29-2.09 (m, 2H), 2.00 (s, 3H), 1.69-1.61 (m, 4H), 1.23 (s, 9H).

Step 6: rel-benzyl (3S,4R)-2-acetamido-2-(tert-butylcarbamoyl)-3-(3-(4,4,5,5-tetramethyl-1,3,2-dioxaborolan-2-yl)propyl)-7-azabicyclo[2.2.1]heptane-7-carboxylate

[Ir(cod)Cl]$_2$ (19 mg, 0.028 mmol) and dppe (22 mg, 0.056 mmol) were added to a mixture of 4,4,5,5-tetramethyl-1,3,2-dioxaborolane (0.24 mL, 1.7 mmol) in anhydrous DCM (5 mL) and stirred at 25° C. under N$_2$ for 20 min. The mixture was treated with rel-(benzyl (3S,4R)-2-acetamido-3-allyl-2-(tert-butylcarbamoyl)-7-azabicyclo[2.2.1]heptane-7-carboxylate (240 mg, 0.56 mmol) and stirred at 25° C. for 12 h under N$_2$. The reaction mixture was concentrated in vacuum. The residue was purified by silica gel column chromatography (EtOAc in hexanes) to give the title compound. LCMS (C$_{30}$H$_{47}$BN$_3$O$_6$$^+$) (ES, m/z): 556 [M+H]$^+$.

Step 7: rel-(3S,4R)-2-amino-3-(3-boronopropyl)-7-azabicyclo[2.2.1]heptane-2-carboxylic acid A mixture of rel-benzyl (3S,4R)-2-acetamido-2-(tert-butylcarbamoyl)-3-(3-(4,4,5,5-tetramethyl-1,3,2-dioxaborolan-2-yl)propyl)-7-azabicyclo[2.2.1]heptane-7-carboxylate (290 mg, 0.52 mmol) and 12N HCl in water (5 mL, 60 mmol) was stirred at 105° C. for 13 h. The reaction mixture was extracted with DCM, the organic layer was separated. The aqueous layer was concentrated in vacuum. The residue was dissolved in saturated aqueous Na$_2$CO$_3$ and extracted with DCM. The organic layer was separated, and the aqueous layer was concentrated in vacuum. The residue was purified by RP-HPLC [C18 column, water (20 mM HFBA and 0.1% TFA)-acetonitrile] to the title compound as a HFBA salt. LCMS (C$_{10}$H$_{20}$BN$_2$O$_4$$^+$) (ES, m/z): 243 [M+H]$^+$. $^1$H NMR (400 MHz, deuterium oxide) δ 4.52-4.39 (m, 1H), 4.36-4.17 (m, 1H), 2.79-2.29 (m, 1H), 2.07-1.72 (m, 5H), 1.56-0.91 (m, 3H), 0.84-0.36 (m, 2H).

Example 43B was made from U1-6P2 using the same procedure as Example 43A.

Ex. MS and $^1$HNMR

43B LCMS (C$_{10}$H$_{18}$BN$_2$O$_3$$^+$) (ES, m/z): 225 [M+H-H$_2$O]$^+$. $^1$H NMR (400 MHz, deuterium oxide) δ 4.54-4.40 (m, 1H), 4.37-4.15 (m, 1H), 2.76-2.31 (m, 1H), 2.07-1.71 (m, 5H), 1.55-0.91 (m, 3H), 0.83-0.34 (m, 2H).

Example 44A: (1S,2S,3aS,5R,6aR)-2-amino-1-(3-boronopropyl)-5-hydroxyoctahydropentalene-2-carboxylic acid (HFBA Salt)

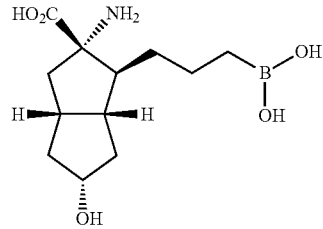

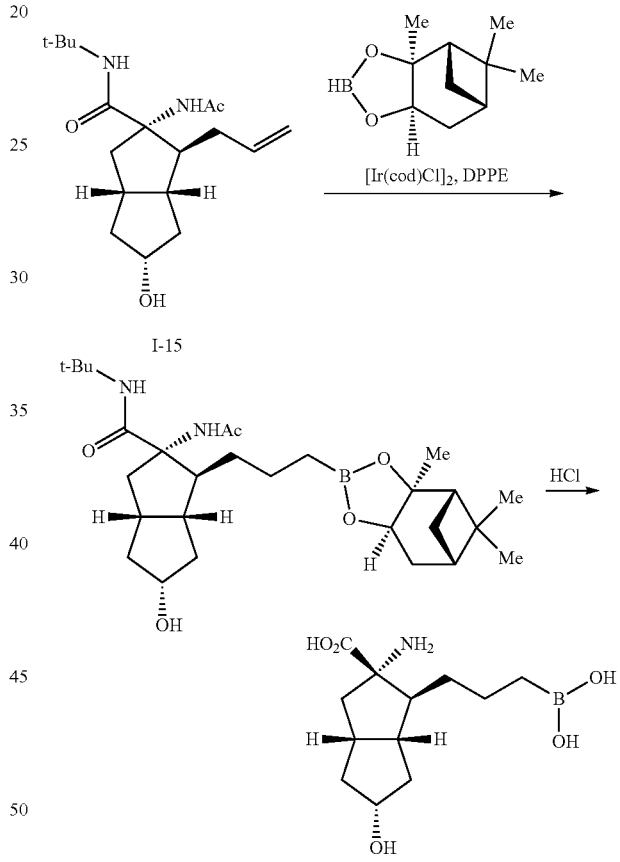

44

Step 1: (1S,2S,3aS,5R,6aR)-2-acetamido-N-(tert-butyl)-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide A solution of (1S,2S,3aS,5R,6aR)-2-acetamido-1-allyl-N-(tert-butyl)-5-hydroxyoctahydropentalene-2-carboxamide (380 mg, 1.2 mmol) in DCM (6.0 mL) was added to a solution of (3aS,4S,6S,7aR)-3a,5,5-trimethylhexahydro-4,6-methanobenzo[d][1,3,2]dioxaborole (1.1 g, 6.0 mmol), chloro(1,5-cyclooctadiene)iridium(I) dimer (40 mg, 0.060 mmol), and bis(diphenylphosphino)ethane (47 mg, 0.12 mmol) in DCM (6.0 mL) at 23° C. The reaction mixture was stirred at this temperature for 1.5 h under nitrogen gas. Excess reductant was quenched with the addition of methanol (2 mL), and the mixture was stirred for 10 min. Half-saturated aqueous NaCl solution (10 mL) was then added, the mixture was shaken, and the layers were separated. The aqueous phase was extracted with DCM. The combined organic extracts were dried over $Na_2SO_4$, filtered, and concentrated under reduced pressure. The residue was purified by silica gel column chromatography (EtOAc/DCM) to give (1S,2S,3aS,5R,6aR)-2-acetamido-N-(tert-butyl)-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide. LCMS ($C_{28}H_{48}BN_2O_5^+$) (ES, m/z): 503 [M+H]$^+$.

Step 2: (1S,2S,3aS,5R,6aR)-2-amino-1-(3-boronopropyl)-5-hydroxyoctahydropentalene-2-carboxylic acid (HFBA Salt)

(1S,2S,3aS,5R,6aR)-2-acetamido-N-(tert-butyl)-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (100 mg, 0.20 mmol) and 6N HCl solution (4.0 mL, 24 mmol) were combined, and the resulting mixture was heated at 125° C. for 1 h. The mixture was then cooled to room temperature and was diluted with water (20 mL). The diluted aqueous mixture was washed with DCM until both the aqueous solution and the organic washes were colorless. The aqueous solution was then diluted with acetonitrile (20 mL), and the resulting mixture was concentrated under reduced pressure. The residue was purified by RP-HPLC (Column: Waters Atlantis T3 19×250 mm, 5 μm, water [20 mM HFBA and 0.1% TFA]-acetonitrile). Fractions containing product were concentrated by lyophilization to provide (1S,2S,3aS,5R,6aR)-2-amino-1-(3-boronopropyl)-5-hydroxyoctahydropentalene-2-carboxylic acid as an HFBA salt. LCMS ($C_{12}H_{21}BNO_4^+$) (ES, m/z): 254 [M–$H_2O$+H]$^+$. $^1$H NMR (499 MHz, Deuterium Oxide) δ: 4.31 (app p, J=6.1 Hz, 1H), 2.88 (app h, J=8.8 Hz, 1H), 2.61 (dd, J=13.4, 8.8 Hz, 1H), 2.46 (app qd, J=9.4, 6.4 Hz, 1H), 2.29-2.18 (m, 2H), 2.11 (ddd, J=13.2, 8.4, 5.4 Hz, 1h), 1.91 (dd, J=13.4, 9.2 Hz, 1H), 1.60-1.51 (m, 3H), 1.46 (app dt, J=13.3, 6.9 Hz, 1H), 1.41-1.38 (m, 1H), 1.30-1.22 (m, 1H), 0.86-0.74 (m, 2H).

Example 44B: (1S,2S,3aS,5S,6aR)-2-amino-1-(3-boronopropyl)-5-hydroxyoctahydropentalene-2-carboxylic acid (HFBA Salt)

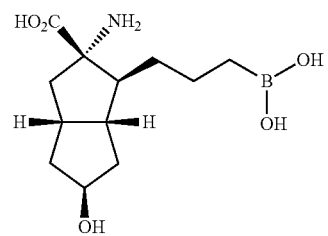

Step 1: (2S,3aR,4S,5S,6aS)-5-acetamido-4-allyl-5-(tert-butylcarbamoyl)octahydropentalen-2-yl acetate

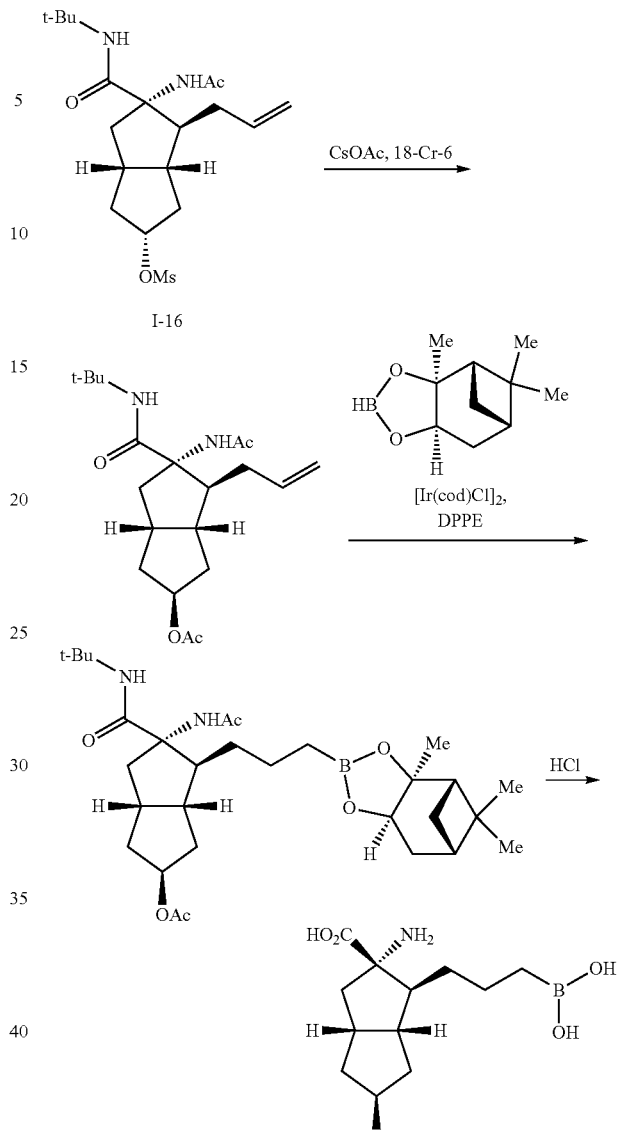

1,4,7,10,13,16-Hexaoxacyclooctadecane (18-Crown-6, 16.5 mg, 62.0 mmol) was added to a suspension of (2R,3aR,4S,5S,6aS)-5-acetamido-4-allyl-5-(tert-butylcarbamoyl)octahydropentalen-2-yl methanesulfonate (50 mg, 130 mmol) and cesium acetate (72 mg, 380 mmol) in toluene (1.3 mL) at 23° C. The mixture was heated to 80° C. for 3 days. The mixture was then cooled to 23° C., and the cooled mixture was diluted with saturated aqueous $NaHCO_3$ solution (10 mL) and EtOAc (10 mL). The layers were shaken and were separated. The aqueous layer was extracted with EtOAc. The combined organic extracts were dried over $Na_2SO_4$, filtered, and concentrated under reduced pressure to provide (2S,3aR,4S,5S,6aS)-5-acetamido-4-allyl-5-(tert-butylcarbamoyl)octahydropentalen-2-yl acetate, which was used without further purification. LCMS ($C_{20}H_{33}N_2O_4^+$) (ES, m/z): 365 (M+H)$^+$.

Step 2: (2S,3aR,4S,5S,6aS)-5-acetamido-5-(tert-butylcarbamoyl)-4-(3-((3aS,4S,6S,7aR)-3a,5,5-trimethylhexahydro-4,6-methanobenzo[d][1,3,2]dioxaborol-2-yl)propyl)octahydropentalen-2-yl acetate A solution of (2S,3aR,4S,5S,6aS)-5-acetamido-4-allyl-5-(tert-butylcarbamoyl)octahydropentalen-2-yl acetate (46 mg, 0.13 mmol) in DCM (750 µL) was added to a solution of (3aS,4S,6S,7aR)-3a,5,5-trimethylhexahydro-4,6-methanobenzo[d][1,3,2]dioxaborole (110 mg, 0.63 mmol), chloro(1,5-cyclooctadiene)iridium(I) dimer (4.2 mg, 6.3 µmol), and bis(diphenylphosphino)ethane (5.0 mg, 13 µmol) in DCM (750 L) at 23° C. The reaction mixture was stirred at 23° C. for 2.5 h under nitrogen gas. Excess reductant was quenched with the addition of methanol (500 µL), and the mixture was stirred for 10 min. Water (5 mL) and DCM (5 mL) were added, the mixture was shaken, and the layers were separated. The aqueous phase was extracted with DCM. The combined organic extracts were dried over $Na_2SO_4$, filtered, and concentrated under reduced pressure. The residue was purified by RP-HPLC (C18 column, water [0.1% TFA]-acetonitrile) to give (2S,3aR,4S,5S,6aS)-5-acetamido-5-(tert-butylcarbamoyl)-4-(3-((3aS,4S,6S,7aR)-3a,5,5-trimethylhexahydro-4,6-methanobenzo[d][1,3,2]dioxaborol-2-yl)propyl)octahydropentalen-2-yl acetate. LCMS ($C_{30}H_{50}BN_2O_6^+$) (ES, m/z): 545 $[M+H]^+$.

Step 3: (1S,2S,3aS,5S,6aR)-2-amino-1-(3-boronopropyl)-5-hydroxyoctahydropentalene-2-carboxylic acid (HFBA Salt)

(2S,3aR,4S,5S,6aS)-5-acetamido-5-(tert-butylcarbamoyl)-4-(3-((3aS,4S,6S,7aR)-3a,5,5-trimethylhexahydro-4,6-methanobenzo[d][1,3,2]dioxaborol-2-yl)propyl)octahydropentalen-2-yl acetate (32 mg, 58 µmol) and 6N aqueous HCl solution (1.2 mL, 7.2 mmol) were combined, and the resulting mixture was heated at 125° C. for 1 h. The mixture was then cooled to RT and was diluted with water (9.0 mL). The diluted solution was washed with DCM until both the aqueous layer and the organic washes were colorless. The washed aqueous layer was then diluted with acetonitrile (10 mL), and the diluted mixture was concentrated under reduced pressure. The residue was purified by RP-HPLC (Column: Waters Atlantis T3 19×250 mm, 5 µm, water [20 mM HFBA and 0.1% TFA]-acetonitrile). Fractions containing product were concentrated under pressure to provide (1S,2S,3aS,5S,6aR)-2-amino-1-(3-boronopropyl)-5-hydroxyoctahydropentalene-2-carboxylic acid as an HFBA salt. LCMS ($C_{12}H_{21}BNO_4^+$) (ES, m/z): 254 $[M-H_2O+H]^+$. $^1H$ NMR (499 MHz, Deuterium Oxide) δ: 4.43 (app p, J=5.0 Hz, 1H), 3.03 (app dq, J=18.0, 9.0 Hz, 1H), 2.64-2.56 (m, 2H), 1.98-1.86 (m, 2H), 1.85-1.74 (m, 2H), 1.70-1.64 (m, 3H), 1.57-1.54 (m, 1H), 1.43-1.35 (m, 1H), 1.33-1.24 (m, 1H), 0.85-0.74 (m, 2H).

Example 45: (1S,2S,3aR,5S,6aR)-2,5-diamino-1-(3-boronopropyl)octahydropentalene-2-carboxylic acid (Salt with t-Butylamine and HCl)

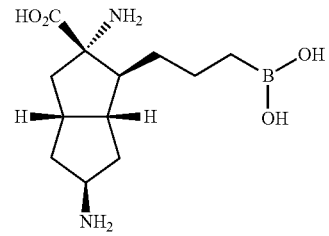

Scheme W1

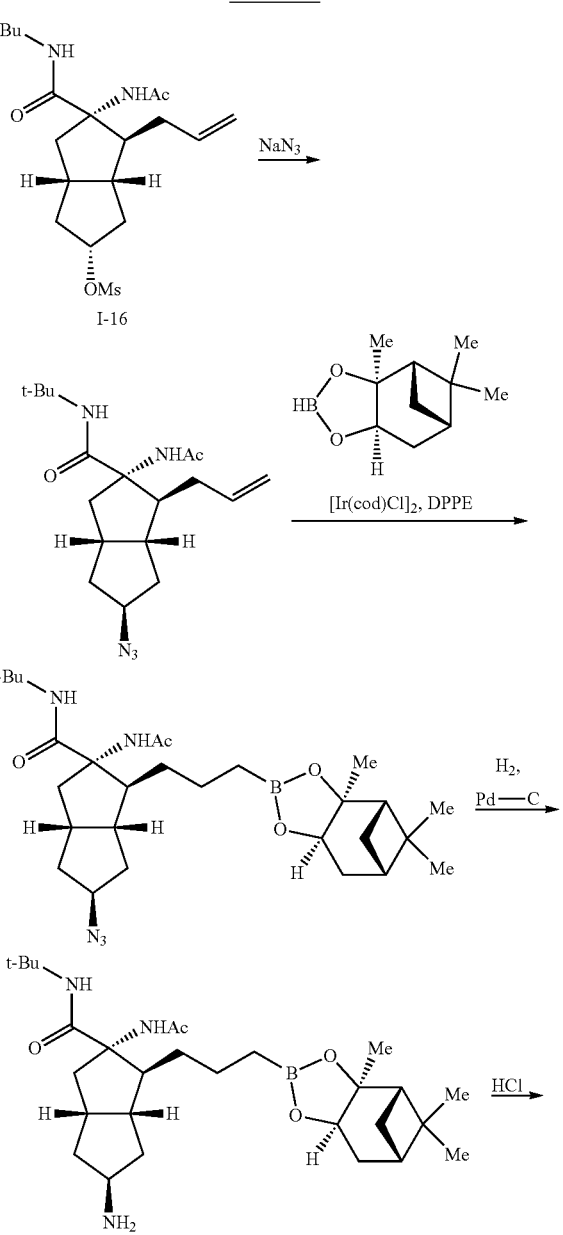

-continued

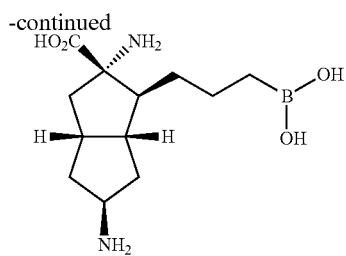

Step 1: (1S,2S,3aR,5S,6aR)-2-acetamido-1-allyl-5-azido-N-(tert-butyl)octahydropentalene-2-carboxamide DMF (11 mL) was added to a mixture of (2R,3aR,4S,5S,6aS)-5-acetamido-4-allyl-5-(tert-butylcarbamoyl)octahydropentalen-2-yl methanesulfonate (460 mg, 1.1 mmol) and sodium azide (110 mg, 1.7 mmol). The mixture was heated at 60° C. with magnetic stirring for 2.5 h, and was then allowed to cool to 23° C. Once cooled, the reaction mixture was diluted with EtOAc (30 mL), and the diluted solution was washed with saturated aqueous $NaHCO_3$ solution (20 mL). The aqueous phase was extracted with EtOAc. The combined organic extracts were washed with saturated aqueous NaCl solution (20 mL), dried over $Na_2SO_4$, filtered, and concentrated under reduced pressure to provide (1S,2S,3aR,5S,6aR)-2-acetamido-1-allyl-5-azido-N-(tert-butyl)octahydropentalene-2-carboxamide, which was used without further purification. LCMS ($C_{18}H_{30}N_5O_2^+$) (ES, m/z): 348 [M+H]$^+$.

Step 2: (1S,2S,3aR,5S,6aR)-2-acetamido-5-azido-N-(tert-butyl)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide A solution of (1S,2S,3aR,5S,6aR)-2-acetamido-1-allyl-5-azido-N-(tert-butyl)octahydropentalene-2-carboxamide (370 mg, 1.1 mmol) in DCM (3.00 mL) was added to a solution of (3aS,4S,6S,7aR)-3a,5,5-trimethylhexahydro-4,6-methanobenzo[d][1,3,2]dioxaborole (970 mg, 5.4 mmol), chloro(1,5-cyclooctadiene)iridium(I) dimer (36 mg, 54 µmol), and bis(diphenylphosphino)ethane (43 mg, 110 µmol) in DCM (21 mL) at 23° C. The reaction mixture was stirred at 23° C. for 3 h under nitrogen gas. Excess reductant was quenched with the addition of methanol (1.0 mL), and the mixture was stirred for 10 min. Water (30 mL) was added, the layers were shaken, and the phases were separated. The aqueous layer was extracted with DCM. The combined organic extracts were dried over $Na_2SO_4$, filtered, and concentrated under reduced pressure. The residue was purified by silica gel column chromatography (EtOAc in hexanes) to give (1S,2S,3aR,5S,6aR)-2-acetamido-5-azido-N-(tert-butyl)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide. LCMS ($C_{28}H_{47}BN_5O_4^+$) (ES, m/z): 528 [M+H]$^+$.

Step 3: (1S,2S,3aR,5S,6aR)-2-acetamido-5-amino-N-(tert-butyl)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide Palladium on carbon (10% w/w, 48 mg, 45 µmol) was added to a solution of (1S,2S,3aR,5S,6aR)-2-acetamido-5-azido-N-(tert-butyl)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (480 mg, 0.91 mmol) in 50% v/v EtOAc/MeOH (18 mL). The headspace within the reaction flask was replaced with hydrogen gas via three evacuation/backfill cycles, and the reaction mixture was stirred under an atmosphere of hydrogen gas at 23° C. for 6 h. The mixture was filtered through a pad of CELITE, the filtrate was concentrated under reduced pressure, and the residue was purified by SFC (column: Polar-RP, 21×250 mm; modifier: 0.1% v/v $NH_4OH$/MeOH; mobile phase: 15% modifier in $CO_2$; flow rate: 70 mL/min) to give (1S,2S,3aR,5S,6aR)-2-acetamido-5-amino-N-(tert-butyl)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide. LCMS ($C_{28}H_{49}BN_3O_4^+$) (ES, m/z): 502 [M+H]$^+$.

Step 4: (1S,2S,3aR,5S,6aR)-2,5-diamino-1-(3-boronopropyl)octahydropentalene-2-carboxylate (Salt with t-Butylamine and HCl)

(1S,2S,3aR,5S,6aR)-2-acetamido-5-amino-N-(tert-butyl)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (270 mg, 0.53 mmol) and 6N aqueous HCl solution (11 mL, 66 mmol) were combined, and the resulting mixture was heated at 125° C. for 1 h. The mixture was then cooled to RT and was diluted with water (50 mL). The diluted solution was washed with DCM until both the aqueous layer and the organic washes were colorless. The washed aqueous layer was then diluted with acetonitrile (50 mL) and the diluted mixture was concentrated under reduced pressure to provide (1S,2S,3aR,5S,6aR)-2,5-diamino-1-(3-boronopropyl)octahydropentalene-2-carboxylate as a 1:1:3 salt with t-butylamine and HCl. LCMS ($C_{12}H_{24}BN_2O_4^+$) (ES, m/z): 253 [M–$H_2O$+H]$^+$. $^1$H NMR (499 MHz, Deuterium Oxide) δ: 3.74 (ddd, J=15.4, 9.3, 6.3 Hz, 1H), 3.06 (app pd, J=9.5, 2.5 Hz, 1H), 2.64-2.57 (m, 2H), 1.98-1.94 (m, 2H), 1.92-1.88 (m, 2H), 1.86-1.77 (m, 1H), 1.66 (dd, J=13.6, 9.8 Hz, 1H), 1.57-1.48 (m, 2H), 1.38-1.35 (m, 1H), 1.28-1.19 (m, 1H), 0.81-0.70 (m, 2H).

Example 46: (1S,2S,3aR,5S,6aR)-2-amino-5-((S)-2-aminopropanamido)-1-(3-boronopropyl)octahydropentalene-2-carboxylic acid (HFBA Salt)

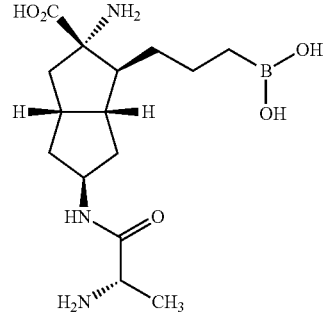

279

Scheme: X1

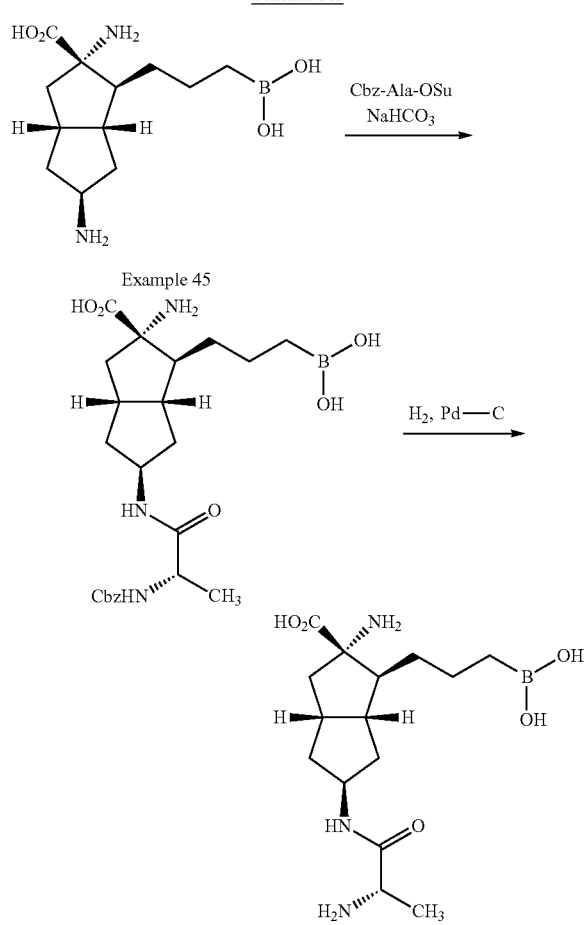

Example 45

Step 1: (1S,2S,3aR,5S,6aR)-2-amino-5-((S)-2-(((benzyloxy)carbonyl)amino)propanamido)-1-(3-boronopropyl)octahydropentalene-2-carboxylic acid (TFA Salt)

Saturated aqueous NaHCO₃ solution (200 µL) was added to a solution of (1S,2S,3aR,5S,6aR)-2,5-diamino-1-(3-boronopropyl)octahydropentalene-2-carboxylate (1:1:3 salt with t-butylamine and HCl, 61 mg, 0.14 mmol) in water (880 µL) and acetonitrile (1.0 mL) at 23° C., until pH=9 was achieved. A solution of 2,5-dioxopyrrolidin-1-yl ((benzyloxy)carbonyl)-L-alaninate (Cbz-Ala-OSu, 65 mg, 0.20 mmol) in acetonitrile (2.5 mL) was added next. Additional saturated aqueous NaHCO₃ solution was added as required in order to maintain pH=9. The mixture was stirred at 23° C. for 16 h before it was concentrated under reduced pressure. The crude residue was purified by RP-HPLC (C18 column, water [0.1% TFA]-acetonitrile) to give (1S,2S,3aR,5S,6aR)-2-amino-5-((S)-2-(((benzyloxy)carbonyl)amino)propanamido)-1-(3-boronopropyl)octahydropentalene-2-carboxylic acid as a TFA salt. LCMS ($C_{23}H_{33}BN_3O_6^+$) (ES, m/z): 458 [M−H₂O+H]⁺.

280

Step 2: (1S,2S,3aR,5S,6aR)-2-amino-5-((S)-2-aminopropanamido)-1-(3-boronopropyl)octahydropentalene-2-carboxylic acid (HFBA Salt)

Palladium on carbon (10% w/w, 3.0 mg, 2.8 µmol) was added to a solution of (1S,2S,3aR,5S,6aR)-2-amino-5-((S)-2-(((benzyloxy)carbonyl)amino)propanamido)-1-(3-boronopropyl)octahydropentalene-2-carboxylic acid (1:1 salt with TFA, 29 mg, 48 µmol) in water (1.9 mL) at 23° C. The headspace of the reaction vessel was replaced with hydrogen gas via three evacuation/backfill cycles, and the reaction mixture was stirred under an atmosphere of hydrogen gas at 23° C. for 45 min. The reaction mixture was then filtered through a 0.2 µm PTFE syringe filter in order to remove the heterogeneous catalyst, and the filtrate was purified by RP-HPLC (Column: Waters Atlantis T3 19×250 mm, 5 µm, water [20 mM HFBA and 0.1% TFA]-acetonitrile). Fractions containing product were concentrated under reduced pressure to provide (1S,2S,3aR,5S,6aR)-2-amino-5-((S)-2-aminopropanamido)-1-(3-boronopropyl)octahydropentalene-2-carboxylic acid as an HFBA salt. LCMS ($C_{15}H_{27}BN_3O_4^+$) (ES, m/z): 324 [M−H₂O+H]⁺. ¹H NMR (499 MHz, Deuterium Oxide) δ: 4.24 (ddd, J=15.5, 9.6, 6.2 Hz, 1H), 4.00 (q, J=7.1 Hz, 1H), 3.03 (app pd, J=9.6, 2.5 Hz, 1H), 2.60 (dd, J=13.6, 8.9 Hz, 1H), 2.60-2.52 (m, 1H), 1.95 (td, J=10.1, 3.0 Hz, 1H), 1.88 (dd, J=11.6, 5.7 Hz, 1H), 1.83-1.75 (m, 2H), 1.70-1.64 (m, 2H), 1.61-1.53 (m, 2H), 1.50 (d, J=7.1 Hz, 3H), 1.44-1.36 (m, 1H), 1.32-1.26 (m, 1H), 0.86-0.74 (m, 2H).

Example 47: (1S,2S,3aR,5S,6aR)-2-amino-5-((S)-2-amino-3-methylbutanamido)-1-(3-boronopropyl)octahydropentalene-2-carboxylic acid (HFBA Salt)

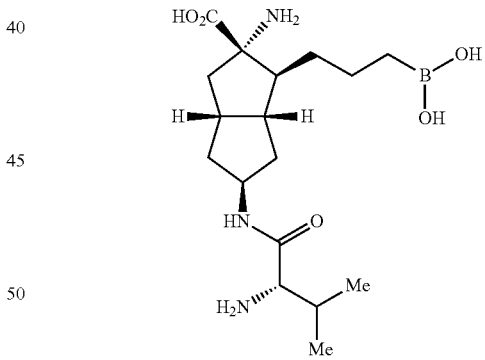

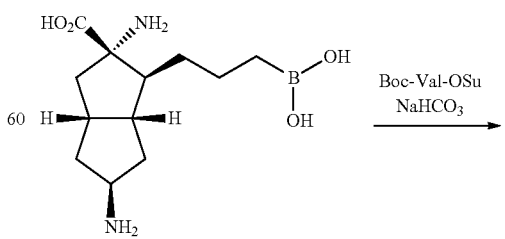

Example 45

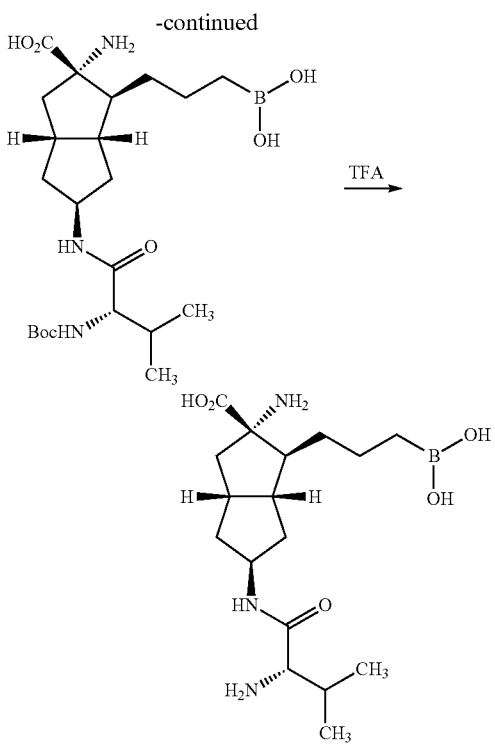

Example 47

Step 1: (1S,2S,3aR,5S,6aR)-2-amino-1-(3-borono-propyl)-5-((S)-2-((tert-butoxycarbonyl)amino)-3-methylbutanamido)octahydropentalene-2-carboxylic acid (TFA Salt)

Saturated aqueous NaHCO₃ solution (200 µL) was added to a solution of (1S,2S,3aR,5S,6aR)-2,5-diamino-1-(3-boronopropyl)octahydropentalene-2-carboxylate (Example 45, 1:1:3 salt with t-butylamine and HCl, 20.0 mg, 44 µmol) in water (880 µL) and acetonitrile (1.0 mL) at 23° C., until pH=9 was achieved. A solution of 2,5-dioxopyrrolidin-1-yl (tert-butoxycarbonyl)-L-valinate (Boc-Val-OSu, 21 mg, 66 µmol) in acetonitrile (2.5 mL) was added next. Additional saturated aqueous NaHCO₃ solution was added as required in order to maintain pH=9. The mixture was stirred at 23° C. for 4.5 h before it was concentrated under reduced pressure. The crude residue was purified by RP-HPLC (C18 column, water [0.1% TFA]-acetonitrile) to give (1S,2S,3aR,5S,6aR)-2-amino-1-(3-boronopropyl)-5-((S)-2-((tert-butoxycarbonyl)amino)-3-methylbutanamido)octahydropentalene-2-carboxylic acid as a TFA salt. LCMS ($C_{17}H_{31}BN_3O_4^+$) (ES, m/z): 352 [M-$C_5H_8O_2$-$H_2O$+H]⁺.

Step 2: (1S,2S,3aR,5S,6aR)-2-amino-5-((S)-2-amino-3-methylbutanamido)-1-(3-boronopropyl)octahydropentalene-2-carboxylic acid (HFBA Salt)

TFA (500 µL) was added to a mixture of (1S,2S,3aR,5S,6aR)-2-amino-1-(3-boronopropyl)-5-((S)-2-((tert-butoxycarbonyl)amino)-3-methylbutanamido)octahydropentalene-2-carboxylic acid (1:1 salt with TFA, 15 mg, 25 µmol) and DCM (500 L) at 23° C. The resulting solution was stirred at this temperature for 25 min before it was diluted with water (7.0 mL). The diluted aqueous solution was washed with DCM. The washed aqueous solution was then diluted with acetonitrile (7.0 mL), and the diluted solution was concentrated under reduced pressure. The residue was purified by RP-HPLC (Column: Waters Atlantis T3 19×250 mm, 5 µm, water [20 mM HFBA and 0.1% TFA]-acetonitrile). Fractions containing product were concentrated under reduced pressure to provide (1S,2S,3aR,5S,6aR)-2-amino-5-((S)-2-amino-3-methylbutanamido)-1-(3-boronopropyl)octahydropentalene-2-carboxylic acid as an HFBA salt. LCMS ($C_{17}H_{31}BN_3O_4^+$) (ES, m/z): 352 [M-$H_2O$+H]⁺. ¹H NMR (499 MHz, Deuterium Oxide) δ: 8.52 (d, J=7.3 Hz, 1H), 4.28 (app h, J=5.9 Hz, 1H), 3.69 (d, J=6.5 Hz, 1H), 3.04 (app pd, J=9.8, 3.0 Hz, 1H), 2.62-2.53 (m, 2H), 2.18 (oct, J=7.0 Hz, 1H), 1.96-1.87 (m, 2H), 1.83-1.77 (m, 2H), 1.74-1.65 (m, 2H), 1.59-1.53 (m, 2H), 1.42-1.36 (m, 1H), 1.32-1.25 (m, 1H), 1.03 (d, J=6.9 Hz, 3H), 1.01 (d, J=7.0 Hz, 3H), 0.86-0.74 (m, 2H).

Example 48: (1S,2S,3aR,5R,6aR)-2-amino-1-(3-boronopropyl)-5-((2-hydroxyethyl)amino)octahydropentalene-2-carboxylic acid (HFBA Salt)

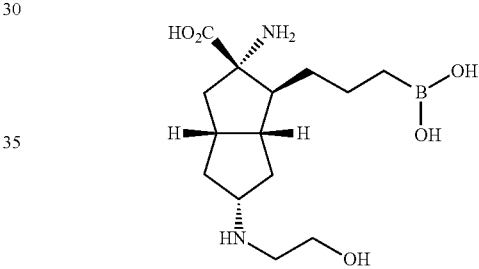

Scheme Y1

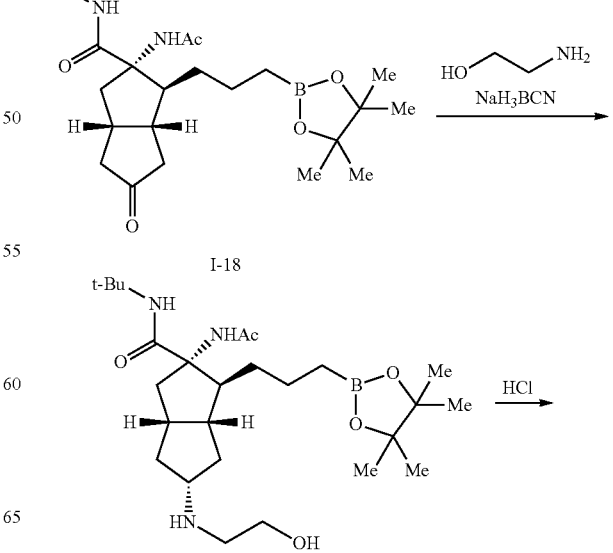

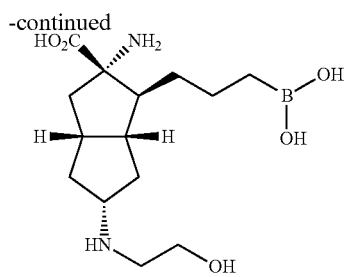

Step 1: (1S,2S,3aR,5R,6aR)-2-acetamido-N-(tert-butyl)-5-((2-hydroxyethyl)amino)-1-(3-(4,4,5,5-tetramethyl-1,3,2-dioxaborolan-2-yl)propyl)octahydropentalene-2-carboxamide Ethanolamine (31 µL, 32 mg, 0.52 mmol) was added to a solution of (1S,2S,3aS,6aR)-2-acetamido-N-(tert-butyl)-5-oxo-1-(3-(4,4,5,5-tetramethyl-1,3,2-dioxaborolan-2-yl)propyl)octahydropentalene-2-carboxamide (I-18, crude residue from hydroboration, 0.10 mmol theoretical) in absolute ethanol (2.1 mL) at 23° C. After 45 min, sodium cyanoborohydride (20 mg, 0.31 mmol) was added in one portion. The mixture was stirred at 23° C. for an additional 16 h before it was concentrated under reduced pressure to afford (1S,2S,3aR,5R,6aR)-2-acetamido-N-(tert-butyl)-5-((2-hydroxyethyl)amino)-1-(3-(4,4,5,5-tetramethyl-1,3,2-dioxaborolan-2-yl)propyl)octahydropentalene-2-carboxamide, which was used without further purification. LCMS ($C_{26}H_{49}BN_3O_5^+$) (ES, m/z): 494 [M+H]$^+$.

Step 2: (1S,2S,3aR,5R,6aR)-2-amino-1-(3-boronopropyl)-5-((2-hydroxyethyl)amino)octahydropentalene-2-carboxylic acid (HFBA Salt)

(1S,2S,3aR,5S,6aR)-2-acetamido-5-amino-N-(tert-butyl)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (crude residue from Step 1, 0.10 mmol theoretical) and 6N HCl in H$_2$O (2.1 mL, 12 mmol) were combined, and the resulting mixture was heated at 125° C. for 1 h. The mixture was then cooled to room temperature and was diluted with water (10 mL). The diluted solution was washed with DCM, and the aqueous layer was diluted with acetonitrile (10 mL) and then concentrated under reduced pressure. The residue was purified by RP-HPLC (Column: Waters Atlantis T3 19×250 mm, 5 µm, water [20 mM HFBA and 0.1% TFA]-acetonitrile) to provide (1S,2S,3aR,5R,6aR)-2-amino-1-(3-boronopropyl)-5-((2-hydroxyethyl)amino)octahydropentalene-2-carboxylic acid as an HFBA salt. LCMS ($C_{14}H_{26}BN_2O_4^+$) (ES, m/z): 297 [M−H$_2$O+H]$^+$. $^1$H NMR (499 MHz, Deuterium Oxide) δ: 3.84 (t, J=5.0 Hz, 2H), 3.68 (tt, J=11.6, 6.0 Hz, 1H), 3.21 (t, J=5.1 Hz, 2H), 2.95 (app h, J=9.1 Hz, 1H), 2.66 (dd, J=13.6, 8.6 Hz, 1H), 2.62-2.56 (m, 2H), 2.50 (dt, J=12.6, 6.9 Hz, 1H), 2.13 (app t, J=8.4 Hz, 1H), 1.83 (dd, J=13.6, 8.7 Hz, 1H), 1.61-1.45 (m, 4H), 1.40-1.32 (m, 1H), 1.30-1.23 (m, 1H), 0.85-0.74 (m, 2H).

Example 49: (1S,2S,3aR,5R,6aR)-2-amino-1-(3-boronopropyl)-5-((2,2,2-trifluoroethyl)amino)octahydropentalene-2-carboxylic acid (HFBA Salt)

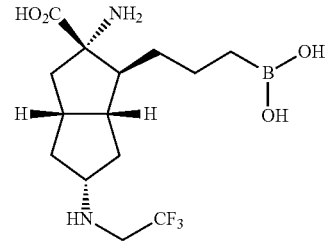

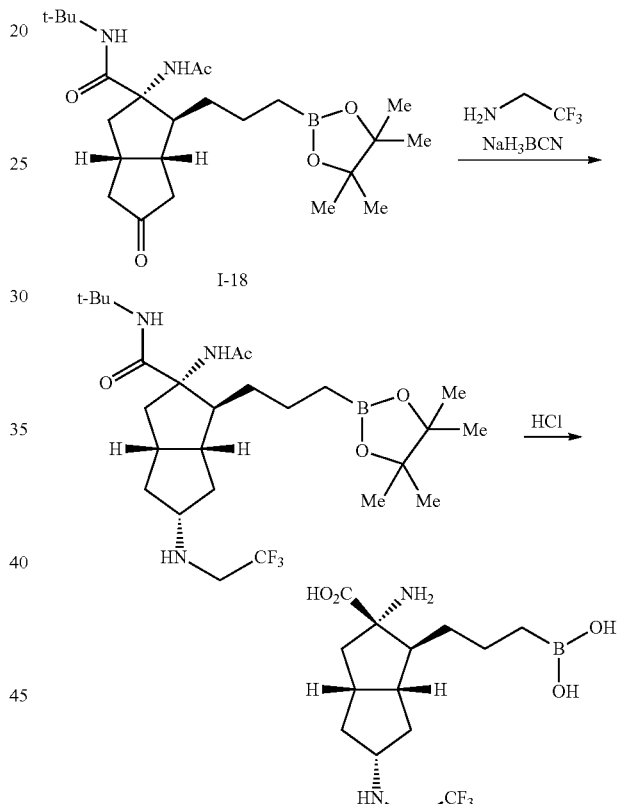

Step 1: (1S,2S,3aR,5R,6aR)-2-acetamido-N-(tert-butyl)-1-(3-(4,4,5,5-tetramethyl-1,3,2-dioxaborolan-2-yl)propyl)-5-((2,2,2-trifluoroethyl)amino)octahydropentalene-2-carboxamide 2,2,2-Trifluoroethylamine (41 µL, 52 mg, 0.52 mmol) was added to a solution of (1S,2S,3aS,6aR)-2-acetamido-N-(tert-butyl)-5-oxo-1-(3-(4,4,5,5-tetramethyl-1,3,2-dioxaborolan-2-yl)propyl)octahydropentalene-2-carboxamide (I-18, crude residue from hydroboration, 0.10 mmol theoretical) in absolute ethanol (2.1 mL) at 23° C. After 1.5 h, sodium cyanoborohydride (20 mg, 0.31 mmol) was added in one portion. The mixture was stirred at 23° C. for 16 h before another portion of 2,2,2-trifluoroethylamine (41 µL, 52 mg, 0.52 mmol), powdered 4-Å molecular sieves (100 mg), and additional sodium cyanoborohydride (20 mg, 0.31 mmol), and acetic acid (30 μL, 31 mg, 0.52 mmol) were added. After 20 min of additional stirring at 23° C., the mixture was filtered through a pad of Celite. The filter cake was rinsed with methanol. The filtrate was concentrated under reduced pressure to afford the crude product, (1S,2S,3aR,5R,6aR)-2-acetamido-N-(tert-butyl)-1-(3-(4,4,5,5-tetramethyl-1,3,2-dioxaborolan-2-yl)propyl)-5-((2,2,2-trifluoroethyl)amino) octahydropentalene-2-carboxamide, which was used directly in the next step without further purification. LCMS ($C_{26}H_{46}BF_3N_3O_4^+$) (ES, m/z): 532 [M+H]$^+$.

Step 2: (1S,2S,3aR,5R,6aR)-2-amino-1-(3-borono-propyl)-5-((2,2,2-trifluoroethyl)amino)octahydro-pentalene-2-carboxylic acid (HFBA Salt)

(1S,2S,3aR,5R,6aR)-2-acetamido-N-(tert-butyl)-1-(3-(4,4,5,5-tetramethyl-1,3,2-dioxaborolan-2-yl)propyl)-5-((2,2,2-trifluoroethyl)amino)octahydropentalene-2-carboxamide (crude residue from Step 1, 0.10 mmol theoretical) and 6N HCl in H$_2$O (2.1 mL, 12 mmol) were combined, and the resulting mixture was heated at 125° C. for 1 h. The mixture was then cooled to room temperature and was diluted with water (10 mL). The diluted solution was washed with DCM, and the aqueous layer was diluted with acetonitrile (10 mL) and then concentrated under reduced pressure. The residue was purified by RP-HPLC (Column: Waters Atlantis T3 19×250 mm, 5 μm, water [20 mM HFBA and 0.1% TFA]-acetonitrile) to provide (1S,2S,3aR,5R,6aR)-2-amino-1-(3-boronopropyl)-5-((2,2,2-trifluoroethyl)amino)octahydropentalene-2-carboxylic acid as an HFBA salt. LCMS ($C_{14}H_{23}BF_3N_2O_3^+$) (ES, m/z): 335 [M−H$_2$O+H]$^+$. $^1$H NMR (499 MHz, Deuterium Oxide) δ: 4.00 (q, J=8.7 Hz, 2H), 3.77 (tt, J=11.5, 5.6 Hz, 1H), 2.95 (app dq, J=18.9, 9.8 Hz, 1H), 2.67 (dd, J=13.7, 8.7 Hz, 1H), 2.62-2.57 (m, 2H), 2.55-2.48 (m, 1H), 2.14 (t, J=8.1 Hz, 1H), 1.84 (dd, J=13.7, 8.8 Hz, 1H), 1.62-1.48 (m, 4H), 1.38-1.31 (m, 1H), 1.29-1.22 (m, 1H), 0.84-0.72 (m, 2H).

Example 50: (1S,2S,3aR,5R,6aR)-2-amino-1-(3-boronopropyl)-5-(dimethylamino)octahydropental-ene-2-carboxylic acid (HFBA Salt)

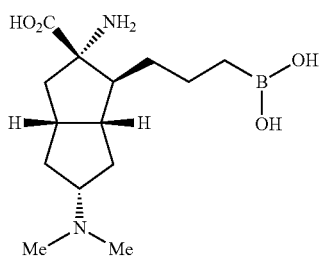

Scheme A2

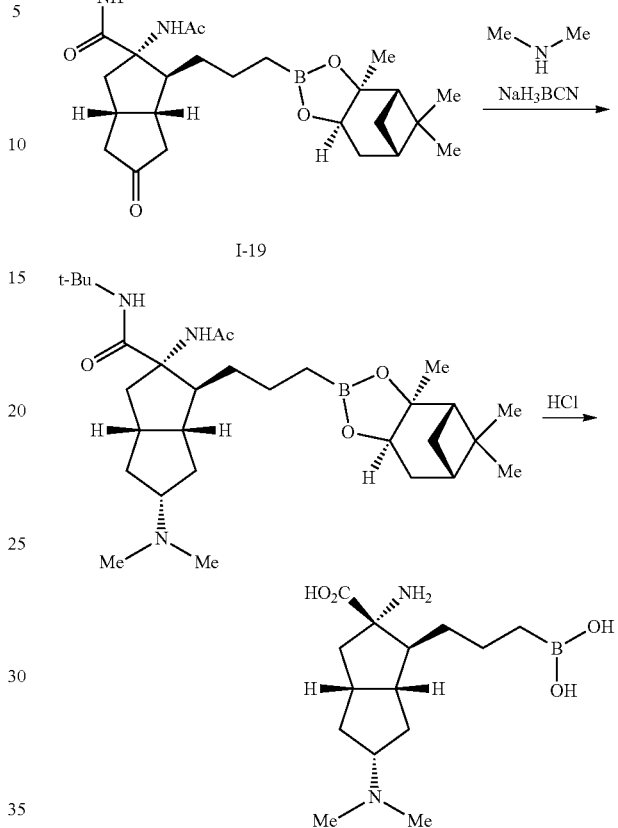

Step 1: (1S,2S,3aR,5R,6aR)-2-acetamido-N-(tert-butyl)-5-(dimethylamino)-1-(3-((3aS,4S,6S,7aR)-3a,5,5-trimethylhexahydro-4,6-methanobenzo[d][1,3,2] dioxaborol-2-yl)propyl)octahydropentalene-2-carboxamide 2,2,2-trifluoroacetate (TFA Salt)

Dimethylamine solution (2.0 M in THF, 310 μL, 0.63 mmol) was added to a solution of (1S,2S,3aS,6aR)-2-acetamido-N-(tert-butyl)-5-oxo-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (I-19, crude residue from hydroboration, 0.13 mmol theoretical) in absolute ethanol (2.5 mL) at 0° C. After 1 h, sodium cyanoborohydride (24 mg, 0.38 mmol) was added in one portion. Stirring was maintained at 0° C. for an additional 18 h, at which point the mixture was diluted with saturated aqueous NaHCO$_3$ solution (5 mL) and EtOAc (10 mL). The aqueous layer was separated and extracted with EtOAc. The combined extracts were dried over Na$_2$SO$_4$, filtered, and concentrated under reduced pressure. The residue was purified by RP-HPLC (C18 column, water [0.1% TFA]-acetonitrile) to give (1S,2S,3aR,5R,6aR)-2-acetamido-N-(tert-butyl)-5-(dimethylamino)-1-(3-((3aS,4S,6S,7aR)-3a,5,5-trimethylhexahydro-4,6-methanobenzo[d][1,3,2] dioxaborol-2-yl)propyl)octahydropentalene-2-carboxamide 2,2,2-trifluoroacetate as a TFA salt. LCMS ($C_{30}H_{53}BN_3O_4^+$) (ES, m/z): 530 [M+H]$^+$.

287

Step 2: (1S,2S,3aR,5R,6aR)-2-amino-1-(3-borono-propyl)-5-(dimethylamino)octahydropentalene-2-carboxylic acid (HFBA Salt)

(1S,2S,3aR,5R,6aR)-2-acetamido-N-(tert-butyl)-5-(dimethylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (TFA salt, 69 mg, 0.11 mmol) and 6N HCl in H$_2$O (2.2 mL, 13 mmol) were combined, and the resulting mixture was heated at 125° C. for 1 h. The mixture was then cooled to room temperature and was diluted with water (8.0 mL). The diluted solution was washed with DCM, and the aqueous layer was diluted with acetonitrile (10 mL) and then concentrated under reduced pressure. The residue was purified by RP-HPLC (Column: Waters Atlantis T3 19×250 mm, 5 μm, water [20 mM HFBA and 0.1% TFA]-acetonitrile) to provide (1S,2S,3aR,5R,6aR)-2-amino-1-(3-boronopropyl)-5-(dimethylamino)octahydropentalene-2-carboxylic acid as an HFBA salt. LCMS (C$_{14}$H$_{26}$BN$_2$O$_3{}^+$) (ES, m/z): 281 [M–H$_2$O+H]$^+$. $^1$H NMR (499 MHz, Deuterium Oxide) δ: 3.63 (tt, J=12.0, 5.9 Hz, 1H), 2.95 (app q, J=9.1 Hz, 1H), 2.89 (s, 6H), 2.67 (dd, J=13.7, 8.6 Hz, 1H), 2.63-2.56 (m, 2H), 2.51 (app dt, J=12.8, 7.2 Hz, 1H), 2.14 (t, J=8.5 Hz, 1H), 1.84 (dd, J=13.7, 8.7 Hz, 1H), 1.61-1.47 (m, 4H), 1.38-1.31 (m, 1H), 1.29-1.22 (m, 1H), 0.84-0.73 (m, 2H).

288

Examples 51a and 51b: (1S,2S,3aR,5R,6aR)-2-amino-1-(3-boronopropyl)-5-(methylamino)octahydropentalene-2-carboxylic acid (HFBA salt) and (1S,2S,3aR,5S,6aR)-2-amino-1-(3-boronopropyl)-5-(methylamino)octahydropentalene-2-carboxylate (Salt with t-Butylamine and HCl)

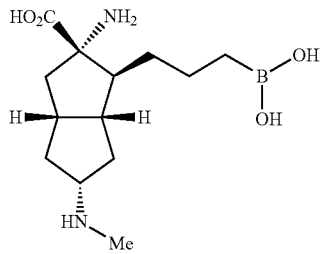

Example 51a

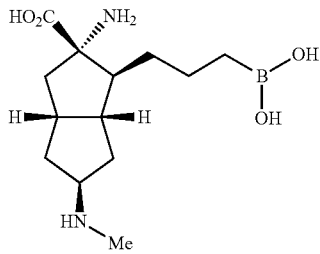

Example 51b

Scheme B2

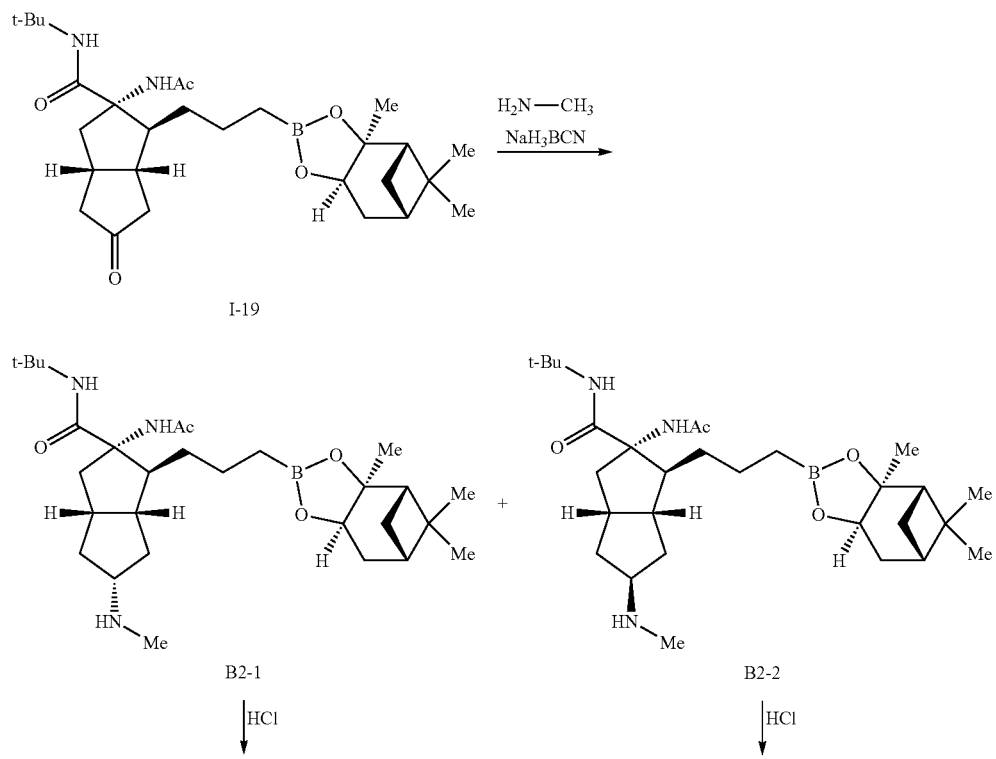

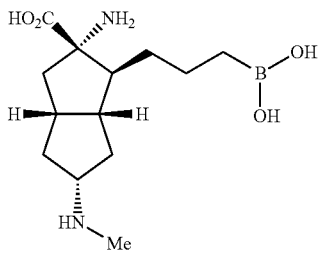

Example 51a

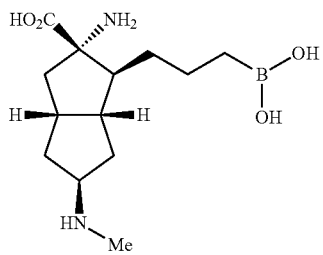

Example 51b

Step 1: (1S,2S,3aR,5R,6aR)-2-acetamido-N-(tert-butyl)-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (TFA Salt) and (1S,2S,3aR,5S,6aR)-2-acetamido-N-(tert-butyl)-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (TFA Salt)

Methylamine solution (2.0 M in THF, 630 µL, 1.3 mmol) was added to a solution of (1S,2S,3aS,6aR)-2-acetamido-N-(tert-butyl)-5-oxo-1-(3-((3aS,4S,6S,7aR)-5,5,7a-trimethyl-hexahydro-4,6-methanobenzo[d][1,3,2]dioxaborol-2-yl)propyl)octahydropentalene-2-carboxamide (I-19, crude residue from hydroboration, 0.25 mmol theoretical) in absolute ethanol (5.0 mL) at 0° C. After 30 min, sodium cyanoborohydride (47 mg, 0.75 mmol) was added in one portion. Stirring was maintained at 0° C. for 24 h. The reaction mixture was then diluted with saturated aqueous NaHCO$_3$ solution (10 mL), saturated aqueous NaCl solution (10 mL), and EtOAc (10 mL). The aqueous layer was separated and extracted with EtOAc. The combined extracts were dried over Na$_2$SO$_4$, filtered, and concentrated under reduced pressure. The residue was purified by RP-HPLC (C18 column, water [0.1% TFA]-acetonitrile) to give a mixture of epimeric products, (1S,2S,3aR,5R,6aR)-2-acetamido-N-(tert-butyl)-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (B2-1) and (1S,2S,3aR,5S,6aR)-2-acetamido-N-(tert-butyl)-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (B2-2), as their corresponding TFA salts. These stereoisomeric products were separated by SFC (column: Lux-2, 21×250 mm; modifier: 0.1% v/v NH$_4$OH/MeOH; mobile phase: 30% modifier in CO$_2$; flow rate: 70 mL/min) to provide B2-1 (Rt=3.1 min) as the first-eluting peak, LCMS (C$_{29}$H$_{51}$BN$_3$O$_4{}^+$) (ES, m/z): 516 [M+H]$^+$, and B2-2 (Rt=3.8 min) as the second-eluting peak. LCMS (C$_{29}$H$_{51}$BN$_3$O$_4{}^+$) (ES, m/z): 516 [M+H]$^+$.

Step 2a: (1S,2S,3aR,5R,6aR)-2-amino-1-(3-boronopropyl)-5-(methylamino)octahydropentalene-2-carboxylic acid (HFBA Salt)

(1S,2S,3aR,5R,6aR)-2-acetamido-N-(tert-butyl)-5-(methylamino)-1-(3-((3aS,4S,6S,7aR)-3a,5,5-trimethyl-hexahydro-4,6-methanobenzo[d][1,3,2]dioxaborol-2-yl)propyl)octahydropentalene-2-carboxamide (45 mg, 87 µmol) and 6N HCl in H$_2$O (1.7 mL, 10 mmol) were combined, and the resulting mixture was heated at 125° C. for 1 h. The mixture was then cooled to room temperature and was diluted with water (10 mL). The diluted solution was washed with DCM, and the aqueous layer was diluted with acetonitrile (10 mL) and then concentrated under reduced pressure. The residue was purified by RP-HPLC (Column: Waters Atlantis T3 19×250 mm, 5 µm, water [20 mM HFBA and 0.1% TFA]-acetonitrile) to provide (1S,2S,3aR,5R,6aR)-2-amino-1-(3-boronopropyl)-5-(methylamino)octahydropentalene-2-carboxylic acid as an HFBA salt. LCMS (C$_{13}$H$_{24}$BN$_2$O$_3{}^+$) (ES, m/z): 267 [M−H$_2$O+H]$^+$. $^1$H NMR (499 MHz, Deuterium Oxide) δ: 3.57 (tt, J=12.1, 5.9 Hz, 1H), 2.94 (app h, J=9.3 Hz, 1H), 2.71 (s, 3H), 2.66 (dd, J=13.6, 8.7 Hz, 1H), 2.59-2.54 (m, 2H), 2.48 (app dt, J=12.9, 7.1 Hz, 1H), 2.13 (app t, J=8.5 Hz, 1H), 1.83 (dd, J=13.6, 8.7 Hz, 1H), 1.61-1.50 (m, 3H), 1.44 (app q, J=11.7 Hz, 1H), 1.37-1.32 (m, 1H), 1.29-1.23 (m, 1H), 0.84-0.73 (m, 2H).

Step 2b: (1S,2S,3aR,5S,6aR)-2-amino-1-(3-boronopropyl)-5-(methylamino)octahydropentalene-2-carboxylate (Salt with t-Butylamine and HCl)

(1S,2S,3aR,5S,6aR)-2-acetamido-N-(tert-butyl)-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (27 mg, 52 µmol) and 6N HCl in H$_2$O (1.0 mL, 6.0 mmol) were combined, and the resulting mixture was heated at 125° C. for 1 h. The mixture was then cooled to room temperature and was diluted with water (10 mL). The diluted solution was washed with DCM, and the aqueous layer was diluted with acetonitrile (10 mL) and then concentrated under reduced pressure to provide (1S,2S,3aR,5S,6aR)-2-amino-1-(3-boronopropyl)-5-(methylamino)octahydropentalene-2-carboxylate as a salt with t-butylamine and HCl. LCMS (C$_{13}$H$_{24}$BN$_2$O$_3{}^+$) (ES, m/z): 267 [M−H$_2$O+H]$^+$. $^1$H NMR (499 MHz, Deuterium Oxide) δ: 3.68 (ddd, J=15.5, 9.7, 6.2 Hz, 1H), 3.12 (app p, J=9.0 Hz, 1H), 2.74 (s, 3H), 2.69-2.60 (m, 2H), 2.10-1.92 (m, 4H), 1.89-1.83 (m, 1H), 1.67 (dd, J=13.5, 9.8 Hz, 1H), 1.62-1.52 (m, 2H), 1.45-1.40 (m, 1H), 1.34-1.28 (m, 1H), 0.86-0.76 (m, 2H).

Examples 52a, 52b, 53a, and 53b: (1S,2S,3aS,5S,6R,6aR)-2-amino-1-(3-boronopropyl)-6-fluoro-5-hydroxyoctahydropentalene-2-carboxylate (Salt with t-Butylamine and HCl); (1S,2S,3aS,5R,6R,6aR)-2-amino-1-(3-boronopropyl)-6-fluoro-5-hydroxyoctahydropentalene-2-carboxylate (Salt with t-Butylamine and HCl); (1S,2S,3aR,5S,6R,6aR)-2-amino-1-(3-boronopropyl)-6-fluoro-5-(methylamino)octahydropentalene-2-carboxylate (Salt with t-Butylamine and HCl); and (1S,2S,3aR,5R,6R,6aR)-2-amino-1-(3-boronopropyl)-6-fluoro-5-(methylamino)octahydropentalene-2-carboxylate (Salt with t-Butylamine and HCl)

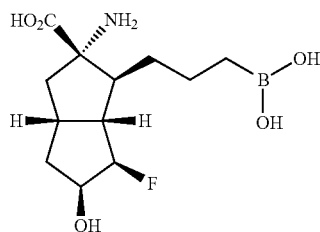

Example 52a

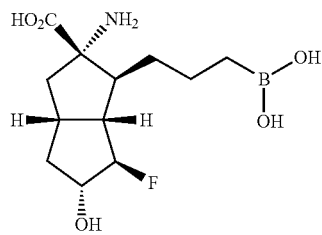

Example 52b

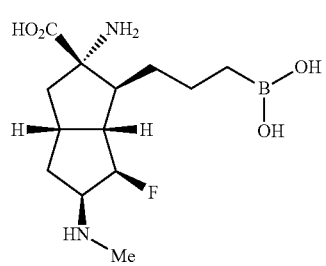

Example 53a

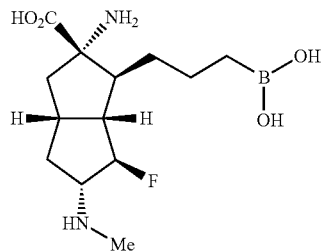

Example 53b

Scheme C2

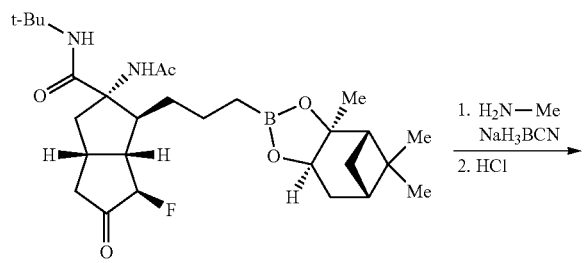

I-20

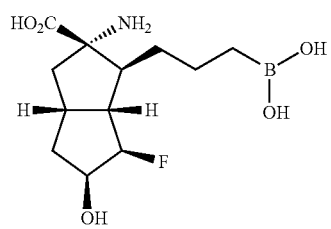

Example 52a

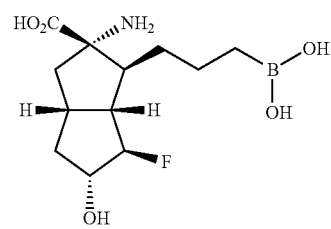

Example 52b

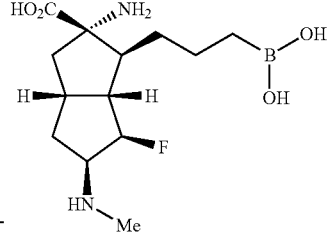

Example 53a

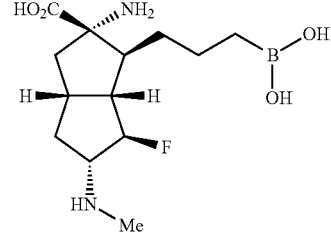

Example 53b

Step 1: (1S,2S,3aR,5R,6R,6aR)-2-acetamido-N-(tert-butyl)-6-fluoro-5-(methylamino)-1-(3-(3aS,4S,6S,7aR)-3a,5,5-trimethylhexahydro-4,6-methanobenzo[d][1,3,2]dioxaborol-2-yl)propyl)octahydropentalene-2-carboxamide; (1S,2S,3aS,5R,6R,6aR)-2-acetamido-N-(tert-butyl)-6-fluoro-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide; (1S,2S,3aR,5S,6R,6aR)-2-acetamido-N-(tert-butyl)-6-fluoro-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide; and (1S,2S,3aR,5R,6R,6aR)-2-acetamido-N-(tert-butyl)-6-fluoro-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide Methylamine solution (2.0 M in THF, 1.2 mL, 2.3 mmol) was added to a solution of (1S,2S,3aS,6R,6aR)-2-acetamido-N-(tert-butyl)-6-fluoro-5-oxo-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (I-20, crude residue from hydroboration, 0.47 mmol theoretical) in absolute ethanol (9.3 mL) at 0° C. After 30 min, sodium cyanoborohydride (88 mg, 1.4 mmol) was added in one portion. Stirring was maintained while the temperature was allowed to warm gradually to 23° C. over 18 h. The reaction mixture was then diluted with saturated aqueous NaHCO$_3$ solution (20 mL), saturated aqueous NaCl solution (20 mL), and EtOAc (20 mL). The aqueous layer was separated and extracted with EtOAc. The combined extracts were dried over Na$_2$SO$_4$, filtered, and concentrated under reduced pressure. The residue was purified by RP-HPLC (C18 column, water [0.1% TFA]-acetonitrile) to give a mixture of epimeric methylamino compounds C2-3 and C2-4 as a TFA salt as the first-eluting peak; (1S,2S,3aR,5R,6R,6aR)-2-acetamido-N-(tert-butyl)-6-fluoro-5-(methylamino)-1-(3-(3aS,4S,6S,7aR)-3a,5,5-trimethylhexahydro-4,6-methanobenzo[d][1,3,2]dioxaborol-2-yl)propyl)octahydropentalene-2-carboxamide (C2-1) as the second-eluting peak; and (1S,2S,3aS,5R,6R,6aR)-2-acetamido-N-(tert-butyl)-6-fluoro-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (C2-2) as the third-eluting peak. The mixture of C2-3 and C2-4 was then subjected to SFC purification (column: CCA, 21×250 mm; modifier: 0.1% v/v NH$_4$OH/MeOH; mobile phase: 8% modifier in CO$_2$; flow rate: 70 mL/min) to provide (1S,2S,3aR,5S,6R,6aR)-2-acetamido-N-(tert-butyl)-6-fluoro-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (C2-3) as the first-eluting peak, and (1S,2S,3aR,5R,6R,6aR)-2-acetamido-N-(tert-butyl)-6-fluoro-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (C2-4) as the second-eluting peak. C2-1 and C2-2 LCMS (C$_{28}$H$_{47}$BFN$_2$O$_5^+$) (ES, m/z): 521 [M+H]$^+$; C2-3 and C2-4 LCMS (C$_{29}$H$_{50}$BFN$_3$O$_4^+$) (ES, m/z): 534 [M+H]$^+$.

Step 2a: (1S,2S,3aS,5S,6R,6aR)-2-amino-1-(3-boronopropyl)-6-fluoro-5-hydroxyoctahydropentalene-2-carboxylate (Salt with t-Butylamine and HCl)

(1S,2S,3aS,5S,6R,6aR)-2-acetamido-N-(tert-butyl)-6-fluoro-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (36 mg, 57 mol) and 6N HCl in H$_2$O (1.4 mL, 8.4 mmol) were combined, and the resulting mixture was heated at 125° C. for 1 h. The mixture was then cooled to room temperature and was diluted with water (10 mL). The diluted solution was washed with DCM, and the washed aqueous layer was then diluted with acetonitrile (10 mL) and concentrated under reduced pressure to provide (1S,2S,3aS,5S,6R,6aR)-2-amino-1-(3-boronopropyl)-6-fluoro-5-hydroxyoctahydropentalene-2-carboxylate as a salt with t-butylamine and HCl. LCMS (C$_{12}$H$_{20}$BFN$_2$O$_4^+$) (ES, m/z): 272 [M–H$_2$O+H]$^+$. $^1$H NMR (499 MHz, Deuterium Oxide) δ: 4.78 (dt, J=52.4, 4.4 Hz, 1H), 4.38 (app dq, J=12.9, 6.0 Hz, 1H), 3.07 (app h, J=8.8 Hz, 1H), 2.61 (dd, J=13.4, 8.9 Hz, 1H), 2.56 (td, J=10.4, 3.8 Hz, 1H), 2.34 (td, J=10.2, 2.8 Hz, 1H), 2.27-2.21 (m, 1H), 1.86 (dd, J=13.5, 9.2 Hz, 1H), 1.67-1.53 (m, 3H), 1.49-1.42 (m, 1H), 1.39-1.33 (m, 1H), 0.87-0.75 (m, 2H).

Step 2b: (1S,2S,3aS,5R,6R,6aR)-2-amino-1-(3-boronopropyl)-6-fluoro-5-hydroxyoctahydropentalene-2-carboxylate (Salt with t-Butylamine and HCl)

(1S,2S,3aS,5R,6R,6aR)-2-acetamido-N-(tert-butyl)-6-fluoro-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (30 mg, 58 mol) and 6N HCl in H$_2$O (1.2 mL, 7.2 mmol) were combined, and the resulting mixture was heated at 125° C. for 1 h. The mixture was then cooled to room temperature and was diluted with water (10 mL). The diluted solution was washed with DCM and the aqueous layer was then diluted with acetonitrile (10 mL) and concentrated under reduced pressure to provide (1S,2S,3aS,5R,6R,6aR)-2-amino-1-(3-boronopropyl)-6-fluoro-5-hydroxyoctahydropentalene-2-carboxylate as a salt with t-butylamine and HCl. LCMS (C$_{12}$H$_{20}$BFN$_3$O$_4^+$) (ES, m/z): 272 [M–H$_2$O+H]$^+$. $^1$H NMR (499 MHz, Deuterium Oxide) δ: 4.79 (dd, J=53.1, 2.9 Hz, 1H), 4.37 (dddd, J=24.4, 10.0, 6.4, 3.2 Hz, 1H), 3.12 (app p, J=8.8 Hz, 1H), 2.69-2.58 (m, 2H), 1.97-1.91 (m, 2H), 1.79 (ddd, J=12.8, 6.4, 1.5 Hz, 1H), 1.67 (dd, J=13.6, 10.0 Hz, 1H), 1.64-1.58 (m, 2H), 1.47-1.36 (m, 2H), 0.86-0.77 (m, 2H).

Step 2c: (1S,2S,3aR,5S,6R,6aR)-2-amino-1-(3-boronopropyl)-6-fluoro-5-(methylamino)octahydropentalene-2-carboxylate (Salt with t-Butylamine and HCl)

(1S,2S,3aR,5S,6R,6aR)-2-acetamido-N-(tert-butyl)-6-fluoro-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (12 mg, 22 μmol) and 6N HCl in H$_2$O (450 μL, 2.7 mmol) were combined, and the resulting mixture was heated at 125° C. for 1 h. The mixture was then cooled to room temperature and was diluted with water (10 mL). The diluted solution was washed with DCM, and the aqueous layer was then diluted with acetonitrile (10 mL) and concentrated under reduced pressure to provide (1S,2S,3aR,5S,6R,6aR)-2-amino-1-(3-boronopropyl)-6-fluoro-5-(methylamino)octahydropentalene-2-carboxylate as a salt with t-butylamine and HCl. LCMS (C$_{13}$H$_{23}$BFN$_2$O$_3^+$) (ES, m/z): 285 [M–H$_2$O+H]$^+$. $^1$H NMR (499 MHz, Deuterium Oxide) δ: 5.14 (dd, J=52.5, 2.9 Hz, 1H), 3.85 (dtd, J=27.7, 10.6, 2.6 Hz, 1H), 3.34-3.26 (m, 1H), 2.88-2.78 (m, 1H), 2.84 (s, 3H), 2.63 (dd, J=13.6, 9.0 Hz, 1H), 2.11-2.08 (m, 2H), 1.91 (app t, J=9.7 Hz, 1H), 1.68-1.62 (m, 3H), 1.47-1.40 (m, 2H), 0.84-0.81 (m, 2H).

Step 2d: (1S,2S,3aR,5R,6R,6aR)-2-amino-1-(3-bo-ronopropyl)-6-fluoro-5-(methylamino)octahydropen-talene-2-carboxylate (Salt with t-Butylamine and HCl)

(1S,2S,3aR,6R,6aR)-2-acetamido-N-(tert-butyl)-6-fluoro-5-(methylamino)-1-(3-((3aS,4S,6S,7aR)-3a,5,5-trim-ethylhexahydro-4,6-methanobenzo[d][1,3,2]dioxaborol-2-yl)propyl)octahydropentalene-2-carboxamide (35 mg, 65 mol) and 6N HCl in H$_2$O (1.3 mL, 7.8 mmol) were combined, and the resulting mixture was heated at 125° C. for 1 h. The mixture was then cooled to room temperature and was diluted with water (10 mL). The diluted solution was washed with DCM and the aqueous layer was then diluted with acetonitrile (10 mL) and concentrated under reduced pressure to provide (1S,2S,3aR,5R,6R,6aR)-2-amino-1-(3-boronopropyl)-6-fluoro-5-(methylamino)octahydropentalene-2-carboxylate as a salt with t-butylamine and HCl. LCMS (C$_{13}$H$_{23}$BFN$_2$O$_3^+$) (ES, m/z): 285 [M–H$_2$O+H]$^+$. $^1$H NMR (499 MHz, Deuterium Oxide) δ: 5.09 (ddd, J=53.9, 8.0, 6.2 Hz, 1H), 3.93 (app ddt, J=15.5, 12.8, 7.5 Hz, 1H), 3.17 (app dq, J=19.4, 8.7 Hz, 1H), 2.79 (s, 3H), 2.78-2.70 (m, 1H), 2.66 (dd, J=13.7, 8.7 Hz, 1H), 2.57 (app dt, J=12.8, 6.4 Hz, 1H), 2.35 (app td, J=10.1, 2.5 Hz, 1H), 1.79 (dd, J=13.7, 8.6 Hz, 1H), 1.64-1.56 (m, 3H), 1.46-1.34 (m, 2H), 0.87-0.75 (m, 2H).

Examples 54a, 54b, 55a, 55b: 1S,2S,3aR,4S,5S,6aS)-2-amino-1-(3-boronopropyl)-4-fluoro-5-hydroxyoctahydropentalene-2-carboxylate (Salt with t-Butylamine and HCl); (1S,2S,3aR,4S,5R,6aS)-2-amino-1-(3-boronopropyl)-4-fluoro-5-hydroxyoctahydropentalene-2-carboxylate (Salt with t-Butylamine and HCl); (1S,2S,3aR,4S,5R,6aS)-2-amino-1-(3-boronopropyl)-4-fluoro-5-(methylamino)octahydropentalene-2-carboxylate (Salt with t-Butylamine and HCl); and (1S,2S,3aR,4S,5S,6aS)-2-amino-1-(3-boronopropyl)-4-fluoro-5-(methylamino)octahydropentalene-2-carboxylate (Salt with t-Butylamine and HCl)

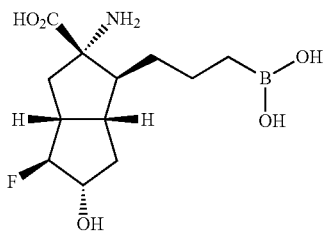

Example 54a

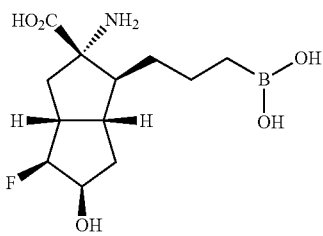

Example 54b

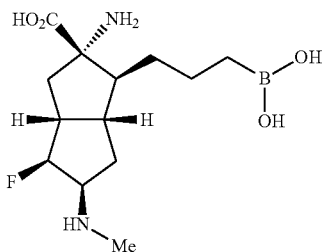

Example 55a

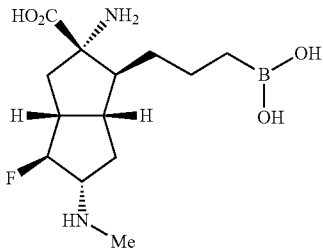

Example 55b

Scheme B2

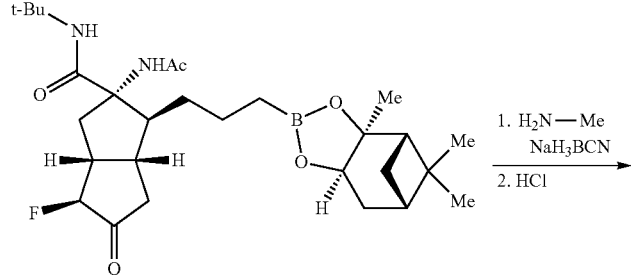

I-21

-continued

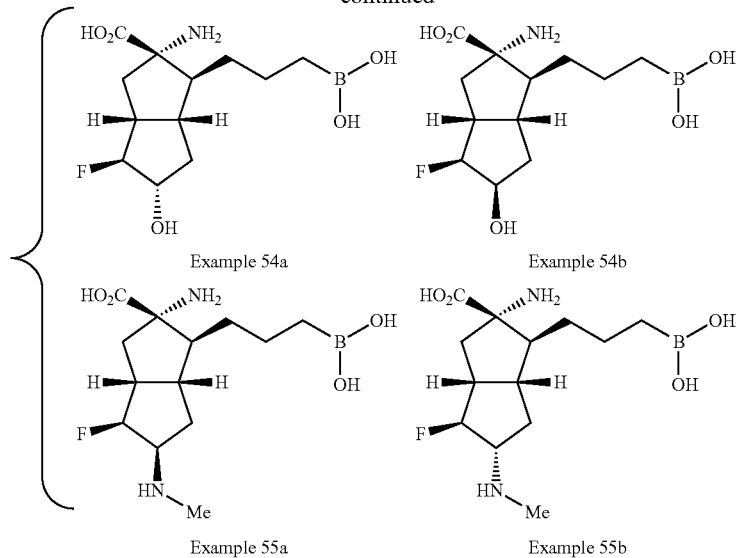

Example 54a
Example 54b
Example 55a
Example 55b

Step 1: (1S,2S,3aR,4S,5S,6aS)-2-acetamido-N-(tert-butyl)-4-fluoro-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide; (1S,2S,3aR,4S,5R,6aS)-2-acetamido-N-(tert-butyl)-4-fluoro-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide; (1S,2S,3aR,4S,5R,6aS)-2-acetamido-N-(tert-butyl)-4-fluoro-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (TFA salt); and (1S,2S,3aR,4S,5S,6aS)-2-acetamido-N-(tert-butyl)-4-fluoro-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (TFA Salt)

Methylamine solution (2.0 M in THF, 950 µL, 1.9 mmol) was added to a solution of (1S,2S,3aR,4S,6aS)-2-acetamido-N-(tert-butyl)-4-fluoro-5-oxo-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (I-20, crude residue from hydroboration, 0.38 mmol theoretical) in absolute ethanol (7.6 mL) at 0° C. After 30 min, sodium cyanoborohydride (88 mg, 1.4 mmol) was added in one portion. Stirring was maintained while the temperature was allowed to warm gradually to 23° C. over 2 h. The reaction mixture was then diluted with saturated aqueous NaHCO₃ solution (20 mL), saturated aqueous NaCl solution (20 mL), and EtOAc (20 mL). The aqueous layer was separated and extracted with EtOAc. The combined extracts were dried over Na₂SO₄, filtered, and concentrated under reduced pressure. The residue was purified by RP-HPLC (C18 column, water [0.1% TFA]-acetonitrile) to give a mixture of epimeric methylamino compounds D2-3 and D2-4 as a TFA salt as the first-eluting peak; (1S,2S,3aR,4S,5S,6aS)-2-acetamido-N-(tert-butyl)-4-fluoro-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (D2-1) as the second-eluting peak; and (1S,2S,3aR,4S,5R,6aS)-2-acetamido-N-(tert-butyl)-4-fluoro-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (D2-2) as the third-eluting peak. The mixture of D2-3 and D2-4 was then subjected to SFC purification (column: [R,R] Whelk-O, 21×250 mm; modifier: 0.1% v/v NH₄OH/MeOH; mobile phase: 20% modifier in CO₂; flow rate: 70 mL/min) to provide the minor epimer D2-3 as the first-eluting peak ($t_R$=4.6 min), and the major epimer D2-4 as the second-eluting peak ($t_R$=5.3 min). The purity of these samples was further boosted by re-subjecting them separately to RP-HPLC (C18 column, water [0.1% TFA]-acetonitrile) to provide (1S,2S,3aR,4S,5R,6aS)-2-acetamido-N-(tert-butyl)-4-fluoro-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (D2-3) as a TFA salt, and (1S,2S,3aR,4S,5S,6aS)-2-acetamido-N-(tert-butyl)-4-fluoro-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (D2-4) as a TFA salt. D2-1 and D2-2 LCMS ($C_{28}H_{47}BFN_2O_5^+$) (ES, m/z): 521 [M+H]⁺; D2-3 and D2-4 LCMS ($C_{29}H_{50}BFN_3O_4^+$) (ES, m/z): 534 [M+H]⁺.

Step 2a: (1S,2S,3aR,4S,5S,6aS)-2-amino-1-(3-boronopropyl)-4-fluoro-5-hydroxyoctahydropentalene-2-carboxylate (Salt with t-Butylamine and HCl)

(1S,2S,3aR,4S,5S,6aS)-2-acetamido-N-(tert-butyl)-4-fluoro-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (34 mg, 65 mol) and 6N HCl in H₂O (1.3 mL, 7.8 mmol) were combined, and the resulting mixture was heated at 125° C. for 1 h. The mixture was then cooled to room temperature and was diluted with water (10 mL). The diluted solution was washed with DCM and the aqueous layer was then diluted with acetonitrile (10 mL) and concentrated under reduced pressure to provide (1S,2S,3aR,4S,5S,6aS)-2-amino-1-(3-boronopropyl)-4-fluoro-5-hydroxyoctahydropentalene-2-carboxylate as a salt with t-butylamine and HCl. LCMS ($C_{12}H_{20}BFNO_4^+$) (ES, m/z): 272 [M–$H_2$O]$^+$. $^1$H NMR (499 MHz, Deuterium Oxide) δ: 4.38 (dddd, J=23.7, 9.7, 6.3, 3.0 Hz, 1H), 3.09 (app dq, J=28.2, 10.0 Hz, 1H), 2.69-2.59 (m, 2H), 2.04 (app q, J=11.2 Hz, 1H), 1.96 (app td, J=9.4, 2.7 Hz, 1H), 1.86 (ddd, J=13.3, 6.7, 1.1 Hz, 1H), 1.66 (dd, J=13.4, 10.7 Hz, 1H), 1.61-1.53 (m, 2H), 1.46-1.40 (m, 1H), 1.30-1.24 (m, 1H), 0.86-0.74 (m, 2H). The α-fluoro methine signal at δ~4.72 was partially obscured by the residual solvent signal, HDO.

Step 2b: (1S,2S,3aR,4S,5R,6aS)-2-amino-1-(3-boronopropyl)-4-fluoro-5-hydroxyoctahydropentalene-2-carboxylate (Salt with t-Butylamine and HCl)

(1S,2S,3aR,4S,5R,6aS)-2-acetamido-N-(tert-butyl)-4-fluoro-5-hydroxy-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (28 mg, 55 mol) and 6N HCl in $H_2O$ (1.0 mL, 6.0 mmol) were combined, and the resulting mixture was heated at 125° C. for 1 h. The mixture was then cooled to room temperature and was diluted with water (10 mL). The diluted solution was washed with DCM and the aqueous layer was then diluted with acetonitrile (10 mL) and concentrated under reduced pressure to provide (1S,2S,3aR,4S,5R,6aS)-2-amino-1-(3-boronopropyl)-4-fluoro-5-hydroxyoctahydropentalene-2-carboxylate as a salt with t-butylamine and HCl. LCMS ($C_{12}H_{20}BFNO_4^+$) (ES, m/z): 272 [M–$H_2$O]$^+$. $^1$H NMR (499 MHz, Deuterium Oxide) δ: 4.37 (app dq, J=12.9, 6.4 Hz, 1H), 3.01 (app dqd 25.1, 9.6, 4.8 Hz, 1H), 2.70 (dd, J=13.5, 9.3 Hz, 1H), 2.66-2.60 (m, 1H), 2.36-2.30 (m, 1H), 2.18 (app td, J=10.0, 2.6 Hz, 1H), 2.04 (dd, J=13.5, 9.5 Hz, 1H), 1.65-1.54 (m, 3H), 1.42-1.37 (m, 1H), 1.24 (app q, J=10.6 Hz, 1H), 0.86-0.74 (m, 2H). The α-fluoro methine signal at δ~4.74 was partially obscured by the residual solvent signal, HDO.

Step 2c: (1S,2S,3aR,4S,5R,6aS)-2-amino-1-(3-boronopropyl)-4-fluoro-5-(methylamino)octahydropentalene-2-carboxylate (Salt with t-Butylamine and HCl)

(1S,2S,3aR,4S,5R,6aS)-2-acetamido-N-(tert-butyl)-4-fluoro-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (TFA salt, 10 mg, 16 mol) and 6N HCl in $H_2O$ (320 µL, 1.9 mmol) were combined, and the resulting mixture was heated at 125° C. for 1 h. The mixture was then cooled to room temperature and was diluted with water (10 mL). The diluted solution was washed with DCM and the aqueous layer was then diluted with acetonitrile (10 mL) and concentrated under reduced pressure to provide (1S,2S,3aR,4S,5R,6aS)-2-amino-1-(3-boronopropyl)-4-fluoro-5-(methylamino)octahydropentalene-2-carboxylate as a salt with t-butylamine and HCl. LCMS ($C_{13}H_{23}BFN_2O_3^+$) (ES, m/z): 285 [M–$H_2$O+H]$^+$. $^1$H NMR (499 MHz, Deuterium Oxide) δ: 5.13 (dd, J=52.7, 3.0 Hz, 1H), 3.86 (dddd, J=27.5, 11.2, 7.0, 2.7 Hz, 1H), 3.29 (app dq, J=29.1, 9.8 Hz, 1H), 2.86-2.77 (m, 1H), 2.83 (s, 3H), 2.66 (dd, J=13.7, 9.6 Hz, 1H), 2.24-2.12 (m, 2H), 1.95 (app td, J=9.8, 3.3 Hz, 1H), 1.65-1.55 (m, 3H), 1.47-1.40 (m, 1H), 1.35-1.29 (m, 1H), 0.85-0.79 (m, 2H).

Step 2d: (1S,2S,3aR,4S,5S,6aS)-2-amino-1-(3-boronopropyl)-4-fluoro-5-(methylamino)octahydropentalene-2-carboxylate (Salt with t-Butylamine and HCl)

(1S,2S,3aR,4S,5S,6aS)-2-acetamido-N-(tert-butyl)-4-fluoro-5-(methylamino)-1-(3-((3aS,4S,6S,7aR)-3a,5,5-trimethylhexahydro-4,6-methanobenzo[d][1,3,2]dioxaborol-2-yl)propyl)octahydropentalene-2-carboxamide (TFA salt, 34 mg, 52 mol) and 6N HCl in $H_2O$ (1.0 mL, 6.0 mmol) were combined, and the resulting mixture was heated at 125° C. for 1 h. The mixture was then cooled to room temperature and was diluted with water (10 mL). The diluted solution was washed with DCM, and the aqueous layer was then diluted with acetonitrile (10 mL) and concentrated under reduced pressure to provide (1S,2S,3aR,4S,5S,6aS)-2-amino-1-(3-boronopropyl)-4-fluoro-5-(methylamino)octahydropentalene-2-carboxylate as a salt with t-butylamine and HCl. LCMS ($C_{13}H_{23}BFN_2O_3^+$) (ES, m/z): 285 [M–$H_2$O+H]$^+$. $^1$H NMR (499 MHz, Deuterium Oxide) δ: 5.07 (app dt, J=54.7, 8.0 Hz, 1H), 3.92 (app tt, J=15.5, 8.1 Hz, 1H), 3.13 (app ddt, J=24.3, 20.3, 8.6 Hz, 1H), 2.82-2.73 (m, 2H), 2.77 (s, 3H), 2.67-2.61 (m, 1H), 2.14 (app td, J=10.7, 3.2 Hz, 1H), 2.10 (dd, J=13.8, 8.8 Hz, 1H), 1.70-1.60 (m, 1H), 1.60-1.48 (m, 2H), 1.39-1.32 (m, 1H), 1.24 (app qd, J=11.3, 4.0 Hz, 1H), 0.84-0.74 (m, 2H).

Assay

Arginase Thioornithine Generating Assay (TOGA)

Compounds were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 555 acoustic liquid handler (Labcyte).

Arginase protein was recombinantly expressed in *Escherichia coli*. Purified protein was then diluted in assay buffer (50 mM Tris pH 7.5, 50 mM NaCl, 1 mM manganese chloride, 0.05% bovine serum albumin to obtain a final Arginase concentration of 1.88 nM. Arginase solution (20 µL) or buffer alone (20 µL) were dispensed to wells of the assay plate using a BioRAPTR liquid dispenser (Beckman Coulter). Assay plates containing compound and arginase enzyme were incubated at room temperature for 30 minutes. Afterwards, 5 µL of 2.5 mM thioarginine (Cayman Chemicals) in assay buffer were added to each well of the assay plate using a BioRAPTR liquid dispenser. Plates were incubated at room temperature for 60 minutes and reactions were quenched by addition of 15 µL of 200 uM 7-Diethylamine-3-(4-maleimidophenyl)-4-methylcoumarin (Sigma Chemical) in 70% ethanol. Plates were briefly shaken to mix and the fluorescence was measured in an Spectramax plate reader (Molecular Devices) with a 410 nm excitation wavelength and an 490 nm emission wavelength.

The fluorescence intensity of each well was corrected for the background observed in wells that did not receive arginase and was expressed as a fraction of the intensity observed in wells that received arginase enzyme and DMSO only. Potencies were calculated by linear least squares fit to the four parameter logistic IC50 equation.

| Example | TOGA IC50(nM) | Percent Inhibition at Top Dose | Top Dose (nM) |
|---|---|---|---|
| 1 | 34.82 | 99.43 | 100000 |
| 1a | 15.26 | 103.6 | 100000 |
| 1b | 8942 | 94.87 | 100000 |
| 1c | 12970 | 93.17 | 100000 |
| 1d | 1258 | 101 | 100000 |
| 1e | 36.04 | 98.88 | 10000 |
| 1f | 18.54 | 87.81 | 16000 |
| 2 | 82.7 | 82.61 | 16000 |
| 3 | 307.6 | 99.82 | 10000 |
| 4 | 107.9 | 97.38 | 10000 |
| 5 | 160.1 | 95.12 | 10000 |
| 6 | 178.9 | 94.22 | 10000 |

| Example | TOGA IC50(nM) | Percent Inhibition at Top Dose | Top Dose (nM) |
|---|---|---|---|
| 7 | 1391 | 72.76 | 10000 |
| 8 | 1468 | 74.84 | 10000 |
| 9 | 197 | 98 | 10000 |
| 10 | 5273 | 55.853 | 10000 |
| 11a | 1858 | 67.24 | 10000 |
| 11b | 2433 | 51.52 | 10000 |
| 12 | 800 | 85.34 | 10000 |
| 13a | 658.9 | 99.01 | 10000 |
| 13b | 503 | 98.41 | 10000 |
| 14a | 640.6 | 97.44 | 10000 |
| 14b | 4327 | 73.81 | 10000 |
| 15 | 1068 | 88.56 | 10000 |
| 16 | 565.1 | 97.91 | 10000 |
| 17a | 1872 | 90.63 | 10000 |
| 17b | 523.6 | 95.61 | 10000 |
| 18a | 492.6 | 99.99 | 10000 |
| 18b | 414.1 | 99.08 | 10000 |
| 19 | 425.4 | 82.74 | 16000 |
| 20a | >10000 | 0 | 10000 |
| 20b | 22.24 | 101.4 | 10000 |
| 20c | >10000 | 9.533 | 10000 |
| 20d | 1345 | 91.36 | 10000 |
| 20e | 2136 | 87.48 | 10000 |
| 20f | 435.8 | 99.19 | 10000 |
| 21a | 15.41 | 99.76 | 10000 |
| 21b | 1977 | 79.08 | 10000 |
| 21c | 641.8 | 90.97 | 10000 |
| 21d | >10000 | 25.98 | 10000 |
| 21e | 335.7 | 90.35 | 10000 |
| 21f | 13.66 | 99.63 | 10000 |
| 21g | >10000 | 30.26 | 10000 |
| 21h | >10000 | 6 | 10000 |
| 21i | 454.3 | 93.24 | 10000 |
| 21j | 274.7 | 95.2 | 10000 |
| 22 | 850.3 | 93.88 | 10000 |
| 23a | 737.4 | 86.52 | 10000 |
| 23b | >10000 | 38.83 | 10000 |
| 24 | 2149 | 95.89 | 100000 |
| 25a | 1135 | 91.11 | 10000 |
| 25b | >10000 | 7.702 | 10000 |
| 25c | >10000 | 5.589 | 10000 |
| 25d | 427.3 | 97.09 | 10000 |
| 26 | 4016 | 45.22 | 10000 |
| 27a | >10000 | 43.75 | 10000 |
| 27b | 67.22 | 97.74 | 10000 |
| 28 | 252 | 90.36 | 10000 |
| 29a | >10000 | 19.44 | 10000 |
| 29b | 42.92 | 100.1 | 10000 |
| 29c | >10000 | 32.49 | 10000 |
| 29d | >10000 | 48.1 | 10000 |
| 30 | 1443 | 87.28 | 10000 |
| 31a | 80.82 | 89.94 | 10000 |
| 31b | 1212 | 70.02 | 10000 |
| 32 | 122.5 | 97.19 | 10000 |
| 33a | 4435 | 62.7 | 10000 |
| 34a | >10000 | 22.21 | 10000 |
| 34b | >10000 | 6.973 | 10000 |
| 34c | 2630 | 81.9 | 10000 |
| 34d | >10000 | 2.002 | 10000 |
| 35a | 237 | 99.73 | 10000 |
| 35c | 2095 | 82.29 | 10000 |
| 36a | 4805 | 93 | 10000 |
| 36b | 3123 | 47.43 | 10000 |
| 37a | 26.42 | 97.95 | 10000 |
| 37b | >10000 | 8.327 | 10000 |
| 37c | 1550 | 90.45 | 10000 |
| 37d | 2.141 | 99.85 | 10000 |
| 37e | 559.6 | 97.07 | 10000 |
| 37f | 24 | 10000 | 10000 |
| 37g | 50 | 103 | 10000 |
| 37h | 1846 | 86.89 | 10000 |
| 37i | 138.3 | 98.61 | 10000 |
| 38a | 4435 | 63.01 | 10000 |
| 39 | 270.9 | 94.67 | 10000 |
| 40 | 1035 | 91.44 | 10000 |
| 41 | 42.25 | 97.71 | 10000 |
| 42 | 52 | 98 | 10000 |
| 43a | 1172 | 96 | 10000 |
| 43b | >10000 | 24 | 10000 |
| 44a | 259.1 | 97.06 | 10000 |
| 44b | 178 | 97.4 | 10000 |
| 45 | 3.854 | 99.38 | 10000 |
| 46 | 528.6 | 96.82 | 10000 |
| 47 | 522.2 | 94.18 | 10000 |
| 48 | 49.57 | 98.36 | 10000 |
| 49 | 1299 | 85.91 | 10000 |
| 50 | 27.16 | 97.85 | 10000 |
| 51a | 32.97 | 99.59 | 10000 |
| 51b | 20.47 | 98.67 | 10000 |
| 52a | 219.9 | 96.25 | 10000 |
| 52b | 37 | 99.46 | 10000 |
| 52c | 4.561 | 99.64 | 10000 |
| 53b | 6.93 | 100 | 10000 |
| 54a | 14.16 | 101.1 | 10000 |
| 54b | 42.55 | 100.1 | 10000 |
| 55a | 23.23 | 103.1 | 10000 |
| 55b | 14.29 | 101.7 | 10000 |

What is claimed is:

1. A compound of Formula I:

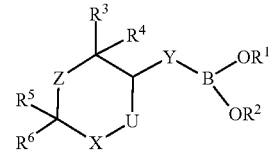

or a pharmaceutically acceptable salt thereof, wherein:

Y is a straight or branched ($C_2$-$C_5$)alkylene, wherein one or more —$CH_2$— groups in Y are optionally and independently replaced with a moiety selected from the group consisting of O, S and NH;

U is a bond, O, $NR^{15}$ or $CR^7R^8$;

X is O, $NR^{15}$ or $CR^9R^{10}$, wherein U and X cannot be simultaneously O and $NR^{15}$, respectively;

Z is a bond or $CR^{11}R^{12}$;

$R^1$ is hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^2$ is hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is unsubstituted or substituted with one to four substituents selected from the group consisting of halogen, $C_1$-$C_6$alkyl or OH;

$R^3$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, $N(R^{13})(R^{14})$, $C_1$-$C_6$alkylN$(R^{13})(R^{14})$, $C_1$-$C_6$alkoxy or COO$C_1$-$C_6$alkyl;

$R^4$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, $N(R^{13})(R^{14})$, $C_1$-$C_6$alkylN$(R^{13})(R^{14})$, $C_1$-$C_6$alkoxy or COO$C_1$-$C_6$alkyl;

$R^5$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, $N(R^{13})(R^{14})$, $C_1$-$C_6$alkylN$(R^{13})(R^{14})$, $C_1$-$C_6$alkoxy or COO$C_1$-$C_6$alkyl or when taken with $R^6$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and $COOC_1$-$C_6$alkyl;

$R^6$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC_1$-$C_6$alkyl, COOH, N($R^{13}$)($R^{14}$), $C_1$-$C_6$alkylN($R^{13}$)($R^{14}$), $C_1$-$C_6$alkoxy or $COOC_1$-$C_6$alkyl or when taken with $R^5$ forms a $C_3$-$C_6$cycloalkyl or heterocycle, or taken with $R^7$ forms a $C_1$-$C_6$alkyl bridge, or taken with $R^{10}$ or $R^{12}$ forms an aryl, heteroaryl, $C_3$-$C_6$cycloalkyl or heterocycle or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy or $COOC_1$-$C_6$alkyl;

$R^7$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC_1$-$C_6$alkyl, COOH, N($R^{13}$)($R^{14}$), $C_1$-$C_6$alkylN($R^{13}$)($R^{14}$), $C_1$-$C_6$alkoxy or $COOC_1$-$C_6$alkyl or when taken with $R^6$, $R^{11}$ or $R^{12}$ forms a $C_1$-$C_6$alkyl bridge or when taken with $R^8$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), —$C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and $COOC_1$-$C_6$alkyl;

$R^8$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC_1$-$C_6$alkyl, COOH, N($R^{13}$)($R^{14}$), $C_1$-$C_6$alkylN($R^{13}$)($R^{14}$), $C_1$-$C_6$alkoxy or $COOC_1$-$C_6$alkyl or when taken with $R^{11}$ or $R^{12}$ forms a $C_1$-$C_6$alkyl bridge or when taken with $R^7$ forms a $C_3$-$C_6$cycloalkyl or heterocycle, or when taken with $R^{10}$ forms an aryl, heteroaryl, $C_3$-$C_6$cycloalkyl or heterocycle or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), —$C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and $COOC_1$-$C_6$alkyl;

$R^9$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC_1$-$C_6$alkyl, COOH, N($R^{13}$)($R^{14}$), $C_1$-$C_6$alkylN($R^{13}$)($R^{14}$), $C_1$-$C_6$alkoxy or $COOC_1$-$C_6$alkyl or when taken with $R^{10}$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, $C_1$-$C_6$alkylOC_1$-$C_6$alkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), $C_1$-$C_6$alkylN($R^{13}$)($R^{14}$), —$C_1$-$C_6$alkylaryl, —$C_1$-$C_6$alkylhaloaryl, C(NH)N($R^{13}$)($R^{14}$), heteroaryl, $C_1$-$C_6$alkoxy and $COOC_1$-$C_6$alkyl;

$R^{10}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC_1$-$C_6$alkyl, COOH, N($R^{13}$)($R^{14}$), $C_1$-$C_6$alkylN($R^{13}$)($R^{14}$), $C_1$-$C_6$alkoxy or $COOC_1$-$C_6$alkyl or when taken with $R^6$ or $R^8$ forms an aryl, heteroaryl, $C_3$-$C_6$cycloalkyl or heterocycle, or taken with $R^9$ forms $C_3$-$C_6$cycloalkyl or heterocycle, or when taken with $R^{15}$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, $C_1$-$C_6$alkylOC_1$-$C_6$alkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), $C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), $C_1$-$C_6$alkoxy and $COOC_1$-$C_6$alkyl;

$R^{11}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC_1$-$C_6$alkyl, COOH, N($R^{13}$)($R^{14}$), $C_1$-$C_6$alkylN($R^{13}$)($R^{14}$), $C_1$-$C_6$alkoxy or $COOC_1$-$C_6$alkyl or when taken with $R^7$ or $R^8$ forms a $C_1$-$C_6$alkyl bridge or when taken with $R^{12}$ forms a $C_3$-$C_6$cycloalkyl or heterocycle, wherein the $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, $C_1$-$C_6$alkylOC_1$-$C_6$alkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-$C_6$alkyl, $SO_2$N($R^{13}$)($R^{14}$), N($R^{13}$)($R^{14}$), —$C_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), heteroaryl, $C_1$-$C_6$alkoxy and $COOC_1$-$C_6$alkyl;

$R^{12}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylOC_1$-$C_6$alkyl, COOH, N($R^{13}$)($R^{14}$), $C_1$-$C_6$alkylN($R^{13}$)($R^{14}$), $C_1$-$C_6$alkoxy or $COOC_1$-$C_6$alkyl or when taken with $R^7$ or $R^8$ forms a $C_1$-$C_6$alkyl bridge or when taken with $R^6$ forms an aryl, heteroaryl, $C_3$-$C_6$cycloalkyl or heterocycle or when taken with $R^{11}$ forms a $C_3$-$C_6$cycloalkyl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, $C_1$-$C_6$alkylOC_1$-$C_6$alkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), CON($R^{13}$)($R^{14}$), $SO_2C_1$-

$C_6$alkyl, $SO_2N(R^{13})(R^{14})$, $N(R^{13})(R^{14})$, —$C_1$-$C_6$alkyl$N(R^{13})(R^{14})$, $C_1$-$C_6$alkylaryl, $C_1$-$C_6$alkylhaloaryl, $C(NH)N(R^{13})(R^{14})$, heteroaryl, $C_1$-$C_6$alkoxy and $COOC_1$-$C_6$alkyl;

$R^{13}$ is hydrogen, $C_3$-$C_6$cycloalkyl, $C_1$-$C_6$alkyl, $COC_1$-$C_6$alkyl$NH_2$, $COC_1$-$C_6$alkylNH($C_1$-$C_6$alkyl), $COC_1$-$C_6$alkylN($C_1$-$C_6$alkyl)$_2$, $C_1$-$C_6$haloalkyl, $C_1$-$C_6$alkylOH or $COC_1$-$C_6$alkyl;

$R^{14}$ is hydrogen, $C_3$-$C_6$cycloalkyl, $C_1$-$C_6$alkyl, $COC_1$-$C_6$alkyl$NH_2$, $COC_1$-$C_6$alkylNH($C_1$-$C_6$alkyl), $COC_1$-$C_6$alkylN($C_1$-$C_6$alkyl)$_2$, $C_1$-$C_6$haloalkyl, $C_1$-$C_6$alkylOH or $COC_1$-$C_6$alkyl; and $R^{15}$ is hydrogen, $C_3$-$C_6$cycloalkyl, $C_1$-$C_6$alkyl, $COC_1$-$C_6$alkylN($R^{13}$)($R^{14}$) or $COC_1$-$C_6$alkyl or when taken with $R^6$ or $R^8$ forms a heteroaryl or heterocycle, wherein the aryl, heteroaryl, $C_3$-$C_6$cycloalkyl or heterocycle is unsubstituted or substituted with 1 to 3 substituents selected from the group consisting of halogen, OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), $CON(R^{13})(R^{14})$, $SO_2C_1$-$C_6$alkyl, $SO_2N(R^{13})(R^{14})$, $N(R^{13})(R^{14})$, —$C_1$-$C_6$alkyl$N(R^{13})(R^{14})$, $C_1$-$C_6$alkylaryl, $C_1$-$C_6$alkylhaloaryl, $C(NH)N(R^{13})(R^{14})$, heteroaryl, $C_1$-$C_6$alkoxy and $COOC_1$-$C_6$alkyl;

wherein the structure of Formula I comprises a bridged ring or multiple rings.

2. The compound of claim 1, or a pharmaceutically acceptable salt thereof, wherein $R^1$ and $R^2$ are both hydrogen.

3. The compound of claim 1, or a pharmaceutically acceptable salt thereof, wherein Y is propylenyl.

4. The compound of claim 1, or a pharmaceutically acceptable salt thereof, wherein $R^3$ is COOH.

5. The compound of claim 1, or a pharmaceutically acceptable salt thereof, wherein $R^4$ is $NH_2$ or $NHCH_3$.

6. The compound of claim 1, or a pharmaceutically acceptable salt thereof, wherein U is a bond.

7. The compound of claim 1, or a pharmaceutically acceptable salt thereof, wherein $R^5$ is hydrogen and $R^6$, when taken with $R^{10}$, forms a heterocycle.

8. The compound of claim 1, or a pharmaceutically acceptable salt thereof, wherein $R^6$, when taken with $R^{10}$, forms

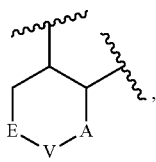

wherein
A is NH or $CH_2$;
E is a bond, NH or $CHR^{21}$;
V is $NR^{22}$ or $CHR^{23}$, wherein A and V cannot be simultaneously NH and $NR^{22}$, and wherein E and V cannot be simultaneously NH and $NR^{22}$;
$R^{21}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, $N(R^{13})(R^{14})$, $C_1$-$C_6$alkylN($R^{13}$)($R^{14}$), $C_1$-$C_6$alkoxy, $COOC_1$-$C_6$alkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), $CON(R^{13})(R^{14})$, $SO_2C_1$-$C_6$alkyl, $SO_2N(R^{13})(R^{14})$, $C_1$-$C_6$alkylaryl, $C_1$-$C_6$alkylhaloaryl, $C(NH)N(R^{13})(R^{14})$ or heteroaryl;

$R^{22}$ hydrogen, $C_3$-$C_6$cycloalkyl, $C_1$-$C_6$alkyl, halo$C_1$-$C_6$alkyl, $C_1$-$C_6$alkylOH, $C_1$-$C_6$alkylO$C_1$-$C_6$alkyl, COOH, $C_1$-$C_6$alkylN($R^{13}$)($R^{14}$), $COOC_1$-$C_6$alkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), $CON(R^{13})(R^{14})$, $SO_2C_1$-$C_6$alkyl, $SO_2N(R^{13})(R^{14})$, $C_1$-$C_6$alkylaryl, $C_1$-$C_6$alkylhaloaryl, $C(NH)N(R^{13})(R^{14})$ or heteroaryl; and $R^{23}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, $N(R^{13})(R^{14})$, $C_1$-$C_6$alkylN($R^{13}$)($R^{14}$), $C_1$-$C_6$alkoxy, $COOC_1$-$C_6$alkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), $CON(R^{13})(R^{14})$, $SO_2C_1$-$C_6$alkyl, $SO_2N(R^{13})(R^{14})$, $C_1$-$C_6$alkylaryl, $C_1$-$C_6$alkylhaloaryl, $C(NH)N(R^{13})(R^{14})$ or heteroaryl.

9. The compound of claim 1, or a pharmaceutically acceptable salt thereof, wherein $R^8$, when taken with $R^{10}$, forms

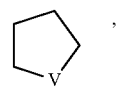

wherein
V is $NR^{22}$ or $CHR^{23}$;
$R^{22}$ is hydrogen, $C_3$-$C_6$cycloalkyl, $C_1$-$C_6$alkyl, halo$C_1$-$C_6$alkyl, $C_1$-$C_6$alkylOH, $C_1$-$C_6$alkylO$C_1$-$C_6$alkyl, COOH, $C_1$-$C_6$alkylN($R^{13}$)($R^{14}$), $COOC_1$-$C_6$alkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), $CON(R^{13})(R^{14})$, $SO_2C_1$-$C_6$alkyl, $SO_2N(R^{13})(R^{14})$, $C_1$-$C_6$alkylaryl, $C_1$-$C_6$alkylhaloaryl, $C(NH)N(R^{13})(R^{14})$ or heteroaryl; and $R^{23}$ is hydrogen, halogen, $C_3$-$C_6$cycloalkyl, $C_1$-$C_6$alkyl, halo$C_1$-$C_6$alkyl, OH, $C_1$-$C_6$alkylOH, $C_1$-$C_6$alkylO$C_1$-$C_6$alkyl, COOH, $N(R^{13})(R^{14})$, $C_1$-$C_6$alkylN($R^{13}$)($R^{14}$), $C_1$-$C_6$alkoxy, $COOC_1$-$C_6$alkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), $CON(R^{13})(R^{14})$, $SO_2C_1$-$C_6$alkyl, $SO_2N(R^{13})(R^{14})$, $C_1$-$C_6$alkylaryl, $C_1$-$C_6$alkylhaloaryl, $C(NH)N(R^{13})(R^{14})$ or heteroaryl.

10. The compound of claim 1, or a pharmaceutically acceptable salt thereof, wherein $R^5$ is hydrogen and $R^6$, when taken with $R^{10}$, forms a pyrrolidine.

11. The compound of claim 1, or a pharmaceutically acceptable salt thereof, wherein X is $CR^9R^{10}$ and wherein $R^{10}$, when taken with $R^9$, forms a heterocycle.

12. The compound of claim 1, or a pharmaceutically acceptable salt thereof, wherein X is $CR^9R^{10}$ and wherein $R^{10}$, when taken with $R^9$, forms a pyrrolidine.

13. The compound of claim 10, or a pharmaceutically acceptable salt thereof, wherein the pyrrolidine is substituted with a substituent selected from the group consisting of halogen, OH, $C_1$-$C_6$alkylOH, $C_3$-$C_6$cycloalkyl, $C_1$-$C_6$alkylO$C_1$-$C_6$alkyl, oxo, $C_1$-$C_6$alkyl, $C_1$-$C_6$haloalkyl, $COC_1$-$C_6$alkyl, $COC_1$-$C_6$alkylN($R^{13}$)($R^{14}$), $COC_1$-$C_6$alkyl(OH)N($R^{13}$)($R^{14}$), $C_1$-$C_6$alkylCON($R^{13}$)($R^{14}$), $CON(R^{13})(R^{14})$, $SO_2C_1$-$C_6$alkyl, $SO_2N(R^{13})(R^{14})$, $N(R^{13})(R^{14})$, $C_1$-$C_6$alkylN($R^{13}$)($R^{14}$), $C_1$-$C_6$alkylaryl, $C_1$-$C_6$alkylhaloaryl, $C(NH)N(R^{13})(R^{14})$, $C_1$-$C_6$alkoxy or $COOC_1$-$C_6$alkyl.

14. The compound of claim 1, or a pharmaceutically acceptable salt thereof, wherein X is $CR^9R^{10}$ and wherein $R^9$ is hydrogen and $R^{10}$ when taken with $R^8$ forms a heterocycle.

15. The compound of claim 1, or a pharmaceutically acceptable salt thereof, wherein X is $CR^9R^{10}$ and wherein $R^9$ is hydrogen and $R^{10}$ when taken with $R^8$ forms a pyrrolidine.

16. The compound of claim 15, or a pharmaceutically acceptable salt thereof, wherein the pyrrolidine is substituted with a substituent selected from the group consisting of halogen, OH, $C_1$-$C_6$alkylOH, $C_3$-$C_6$cycloalkyl, $C_1$-$C_6$alkylOC$_1$-$C_6$alkyl, oxo, $C_1$-$C_6$alkyl, $C_1$-$C_6$haloalkyl, COC$_1$-$C_6$alkyl, COC$_1$-$C_6$alkylN($R^{13}$)($R^{14}$), COC$_1$-$C_6$alkyl(OH)N($R^{13}$)($R^{14}$), $C_1$-$C_6$alkylCON($R^{13}$)($R^{14}$), CON($R^{13}$)($R^{14}$), SO$_2$C$_1$-$C_6$alkyl, SO$_2$N($R^{13}$)($R^{14}$), N($R^{13}$)($R^{14}$), —C$_1$-$C_6$alkylN($R^{13}$)($R^{14}$), $C_1$-$C_6$alkylaryl, $C_1$-$C_6$alkylhaloaryl, C(NH)N($R^{13}$)($R^{14}$), $C_1$-$C_6$alkoxy and COOC$_1$-$C_6$alkyl, wherein $R^{13}$ is hydrogen, $C_3$-$C_6$cycloalkyl, $C_1$-$C_6$alkyl or COC$_1$-$C_6$alkyl; and $R^{14}$ is hydrogen, $C_3$-$C_6$cycloalkyl or $C_1$-$C_6$alkyl.

17. A compound which is:

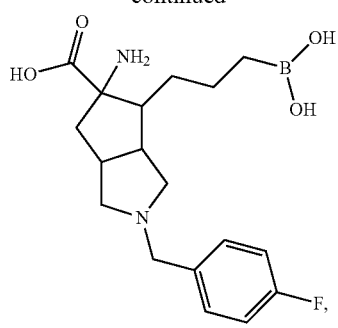

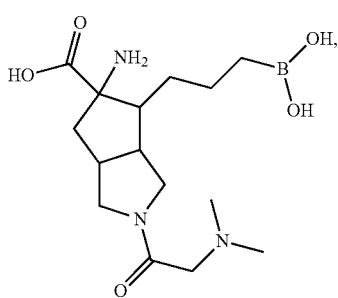

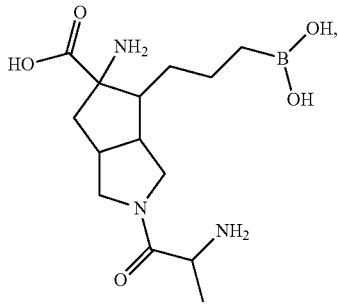

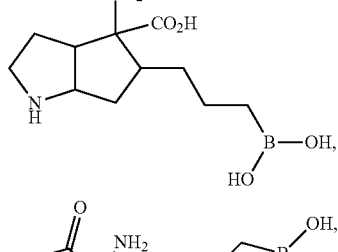

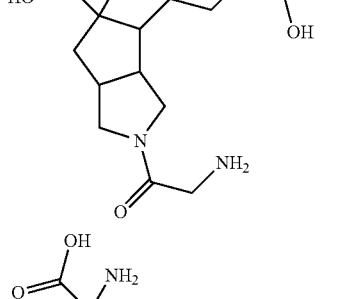

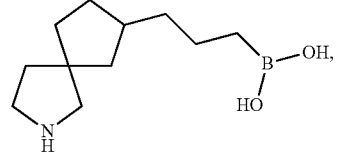

309
-continued
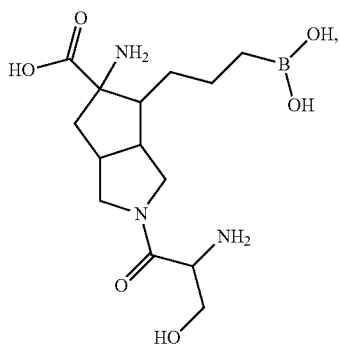
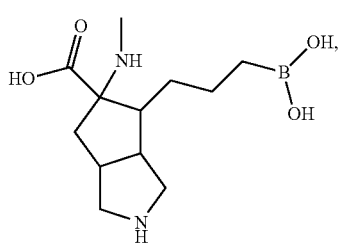
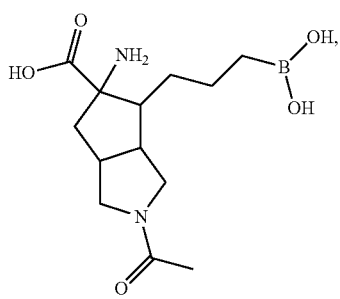
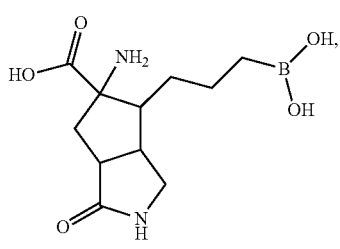
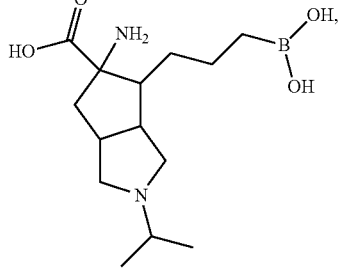
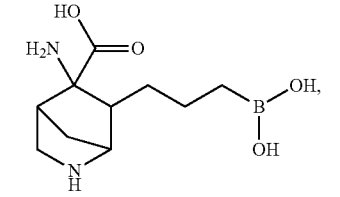
310
-continued
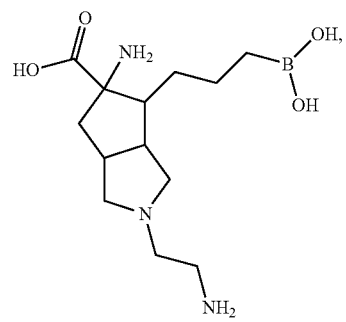
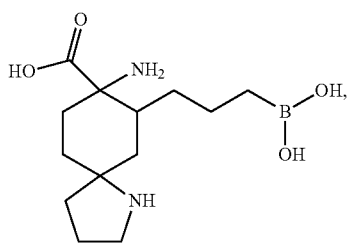
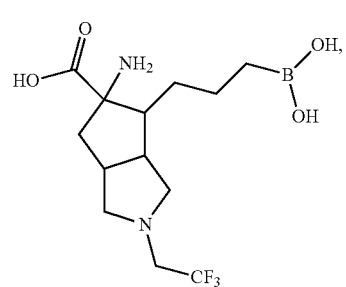
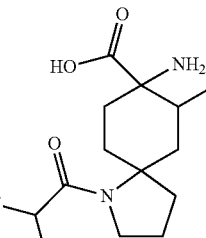
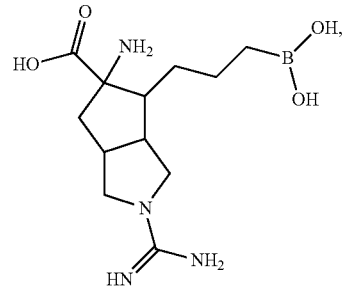
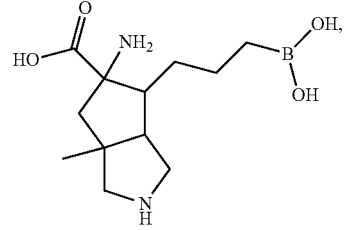

311
-continued
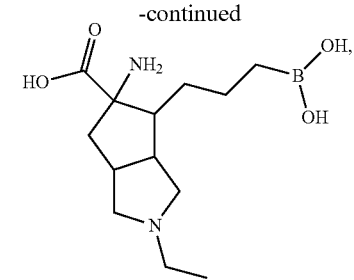
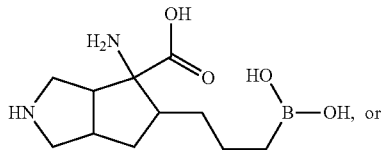
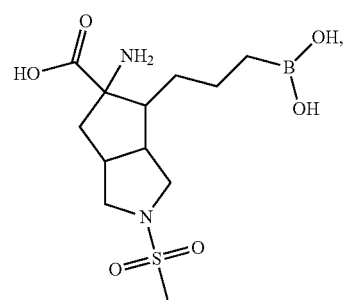
312
-continued
or a pharmaceutically acceptable salt thereof.
18. A pharmaceutical composition comprising a compound of claim 1, or a pharmaceutically acceptable salt thereof, and a pharmaceutically acceptable carrier.
19. A pharmaceutical composition comprising a compound of claim 1 and a pharmaceutically acceptable carrier.
* * * * *